United States Patent
Kim et al.

(10) Patent No.: US 11,581,496 B2
(45) Date of Patent: Feb. 14, 2023

(54) BENZOCARBAZOLE-BASED COMPOUND AND ORGANIC LIGHT-EMITTING DEVICE COMPRISING SAME

(71) Applicant: LG CHEM, LTD, Seoul (KR)

(72) Inventors: Minjun Kim, Daejeon (KR); Hyok Joon Kwon, Daejeon (KR); Young Seok Kim, Daejeon (KR); Donghee Kim, Daejeon (KR); Kongkyeom Kim, Daejeon (KR); Min Woo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 449 days.

(21) Appl. No.: 16/339,284

(22) PCT Filed: Mar. 27, 2018

(86) PCT No.: PCT/KR2018/003608
§ 371 (c)(1),
(2) Date: Apr. 3, 2019

(87) PCT Pub. No.: WO2018/182294
PCT Pub. Date: Oct. 4, 2018

(65) Prior Publication Data
US 2019/0237680 A1 Aug. 1, 2019

(30) Foreign Application Priority Data
Mar. 27, 2017 (KR) .......... 10-2017-0038526

(51) Int. Cl.
*H01L 51/00* (2006.01)
*H01L 51/50* (2006.01)
(Continued)

(52) U.S. Cl.
CPC ........ *H01L 51/0072* (2013.01); *C07D 209/56* (2013.01); *C07D 209/82* (2013.01);
(Continued)

(58) Field of Classification Search
CPC ............... C07D 209/56; C07D 209/82; C07D 403/04; C09K 11/06; H01L 51/00;
(Continued)

(56) References Cited

U.S. PATENT DOCUMENTS

2006/0273714 A1\* 12/2006 Forrest ............... H01L 51/5044
313/504
2012/0217485 A1 8/2012 Lee et al.
(Continued)

FOREIGN PATENT DOCUMENTS

JP 2014-183315 A 9/2014
JP 2017-155033 A 9/2017
(Continued)

OTHER PUBLICATIONS

Dyes and Pigments, vol. 123, (2015), pp. 196-203. (Year: 2015).\*
(Continued)

*Primary Examiner* — Dawn L Garrett
(74) *Attorney, Agent, or Firm* — Dentons US LLP

(57) ABSTRACT

The present specification provides a benzocarbazole-based compound of chemical formula 1 and an organic light-emitting device comprising same. The benzocarbazole-based compound as a material of an organic material layer of the organic light emitting device provides enhanced efficiency, low driving voltage and increased lifetime.

(Continued)

[Chemical Formula 1]

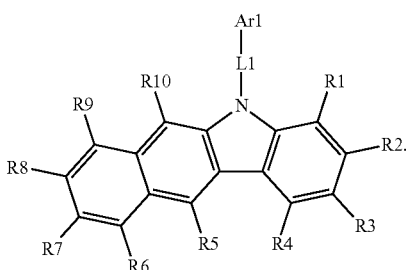

7 Claims, 3 Drawing Sheets

(51) Int. Cl.
*C07D 209/82* (2006.01)
*C07D 209/56* (2006.01)
*C07D 403/04* (2006.01)
*C09K 11/06* (2006.01)

(52) U.S. Cl.
CPC ............ *C07D 403/04* (2013.01); *C09K 11/06* (2013.01); *H01L 51/00* (2013.01); *H01L 51/50* (2013.01); *H01L 51/5012* (2013.01); *H01L 51/5048* (2013.01); *H01L 51/5072* (2013.01); *H01L 51/5088* (2013.01); *H01L 51/5092* (2013.01); *H01L 51/5056* (2013.01)

(58) Field of Classification Search
CPC ............. H01L 51/0072; H01L 51/5012; H01L 51/5056; H01L 51/5092; H01L 51/50
See application file for complete search history.

(56) References Cited

U.S. PATENT DOCUMENTS

2016/0225992 A1* 8/2016 Ito .......................... C09B 57/001
2016/0248024 A1* 8/2016 Shin .................... H01L 51/0074

FOREIGN PATENT DOCUMENTS

| | | |
|---|---|---|
| KR | 2000-0051826 A | 8/2000 |
| KR | 10-2011-0013220 A | 9/2011 |
| KR | 10-2012-0050557 A | 5/2012 |
| KR | 10-2014-0120089 A | 10/2014 |
| KR | 10-2017-0119291 A | 10/2014 |
| KR | 10-2012-0030009 A | 12/2014 |
| KR | 10-2015-0036982 A | 4/2015 |
| KR | 10-1595697 B1 | 2/2016 |
| KR | 10-2016-0089033 A | 7/2016 |
| KR | 10-1778359 B1 | 9/2017 |
| WO | WO-2013032284 A1 * | 3/2013 ........... C07D 403/04 |
| WO | 2017/183859 A1 | 10/2017 |
| WO | 2017183859 A1 | 10/2017 |

OTHER PUBLICATIONS

Journal of Materials Chemistry C, (2017), vol. 5, pp. 9072-9079. (Year: 2017).*

Zhang et al., Dyes and Pigments, vol. 125, (2016), pp. 299-308. (Year: 2016).*

* cited by examiner

【FIG. 1】
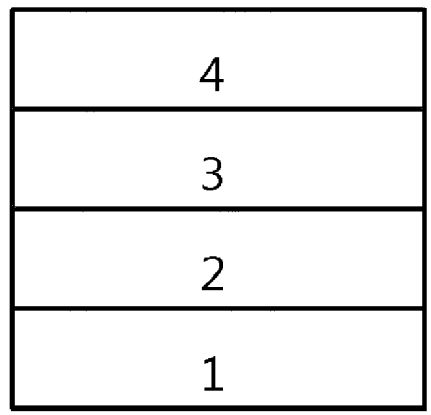
【FIG. 2】
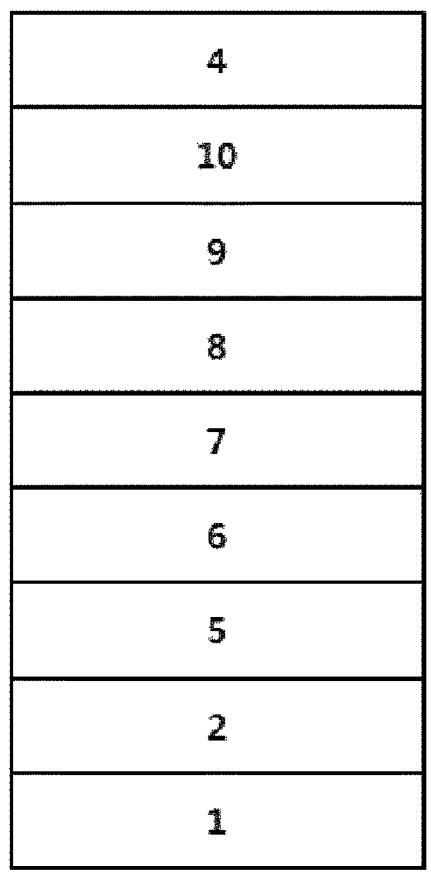

[FIG 3]
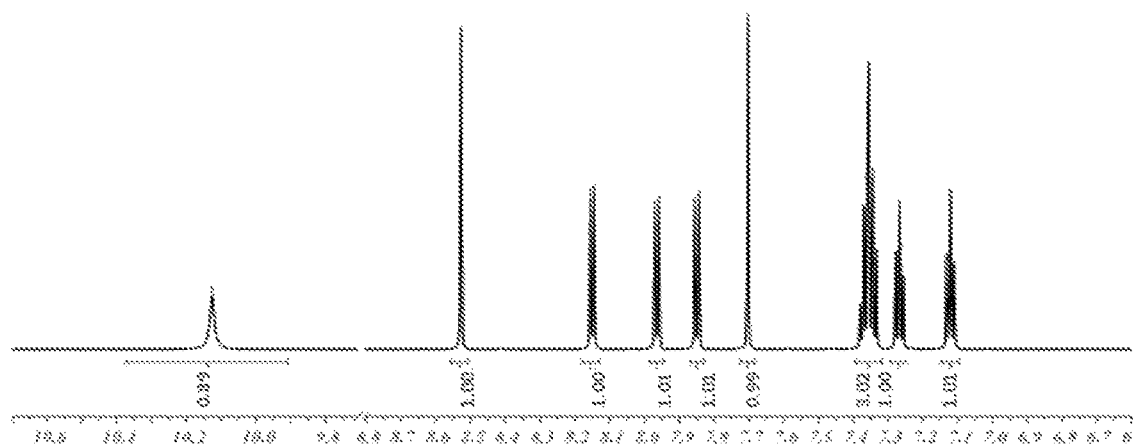
[FIG 4]
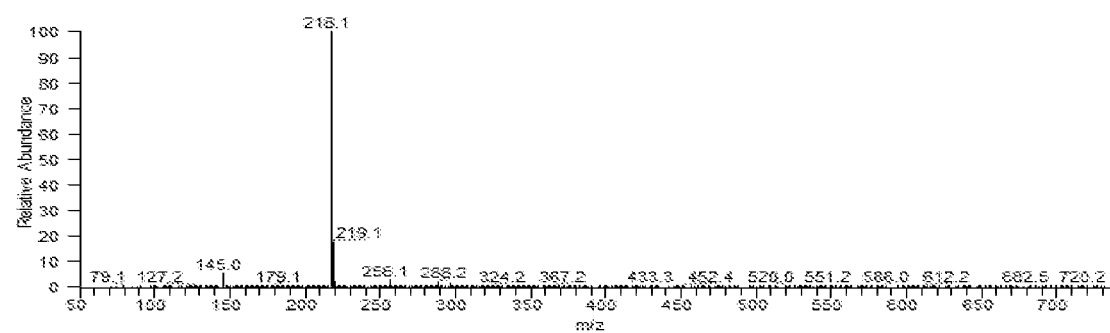

[FIG. 5]
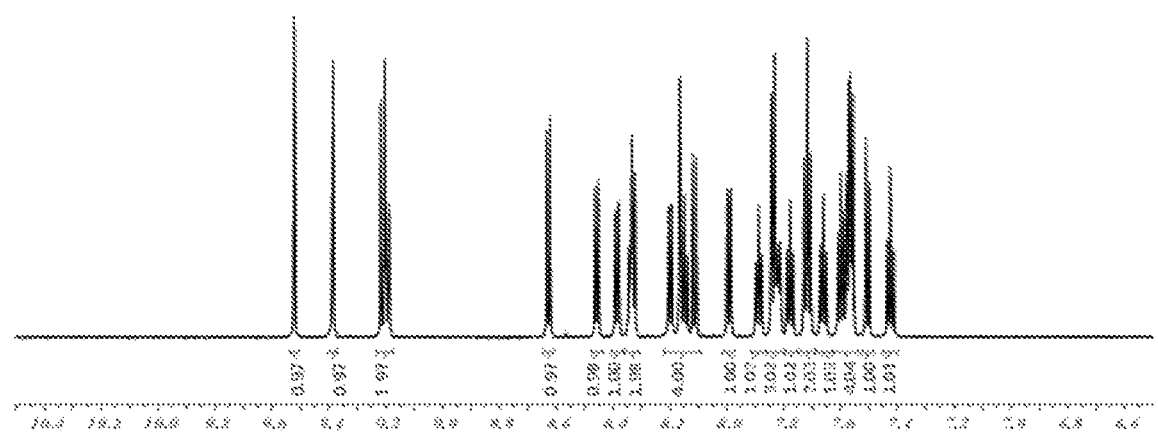

BENZOCARBAZOLE-BASED COMPOUND AND ORGANIC LIGHT-EMITTING DEVICE COMPRISING SAME

TECHNICAL FIELD

This application is a National Stage Entry of International Application No. PCT/KR2018/003608, filed on Mar. 27, 2018, and claims the benefit of and priority to Korean Application No. 10-2017-0038526, filed on Mar. 27, 2017, all of which are hereby incorporated by reference in their entirety for all purposes as if fully set forth herein.

The present specification relates to a benzocarbazole-based compound and an organic light emitting device comprising the same.

Background Art

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a benzocarbazole-based compound and an organic light emitting device comprising the same.

Technical Solution

One embodiment of the present specification provides a benzocarbazole-based compound represented by the following Chemical Formula 1.

[Chemical Formula 1]

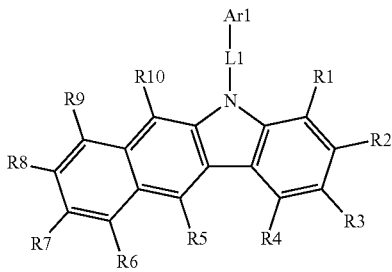

In Chemical Formula 1,

R1 to R10 are each independently hydrogen or deuterium, or

R1 and R2, R2 and R3, or R3 and R4 of R1 to R10 bond to each other to form a benzene ring, and the rest are each independently hydrogen or deuterium, L1 is a direct bond; or a substituted or unsubstituted arylene group having 6 to 40 carbon atoms, and Ar1 is a fused bicyclic heteroaryl group having 2 to 40 carbon atoms and two or more ‖N‖ N atoms substituted with one or more selected from the group consisting of a substituted or unsubstituted aryl group having 6 to 40 carbon atoms and a substituted or unsubstituted heteroaryl group having 2 to 40 carbon atoms.

Another embodiment of the present specification provides an organic light emitting device comprising a first electrode; a second electrode provided opposite to the first electrode; and one or more organic material layers provided between the first electrode and the second electrode, wherein one or more layers of the organic material layers comprise the benzocarbazole-based compound represented by Chemical Formula 1.

Advantageous Effects

A compound described in the present specification can be used as a material of an organic material layer of an organic light emitting device. A compound according to at least one embodiment is capable of enhancing efficiency, obtaining low driving voltage and/or enhancing lifetime properties in an organic light emitting device. Particularly, a compound described in the present specification can be used as a material of hole injection, hole transfer, hole injection and hole transfer, electron blocking, light emitting, hole blocking, electron transfer or electron injection.

Mode for Disclosure

Hereinafter, the present specification will be described in more detail.

The present specification provides a benzocarbazole-based compound represented by Chemical Formula 1. When using the benzocarbazole-based compound represented by Chemical Formula 1 in an organic material layer of an organic light emitting device, efficiency of the organic light emitting device is enhanced, and a low driving voltage and excellent lifetime properties are obtained as well.

In the present specification,

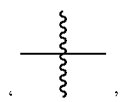

means a site linking to other substituents or Chemical Formula 1.

In the present specification, a description of a certain part "comprising" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

Examples of the substituents are described below, however, the substituents are not limited thereto.

The term "substituted or unsubstituted" in the present specification means being substituted with one, two or more substituents selected from the group consisting of deuterium; a halogen group; a nitrile group; a hydroxyl group; a carbonyl group; an ester group; a silyl group; a boron group; a substituted or unsubstituted alkyl group; a substituted or unsubstituted cycloalkyl group; a substituted or unsubstituted alkoxy group; a substituted or unsubstituted alkenyl group; a substituted or unsubstituted alkylamine group; a substituted or unsubstituted heteroarylamine group; a substituted or unsubstituted arylamine group; a substituted or unsubstituted aryl group; and a substituted or unsubstituted heterocyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification, examples of the halogen group may include fluorine (F), chlorine (Cl), bromine (Br) or iodine (I).

In the present specification, the number of carbon atoms of the carbonyl group is not particularly limited, but is preferably from 1 to 40. Specifically, compounds having structures as below may be included, however, the carbonyl group is not limited thereto.

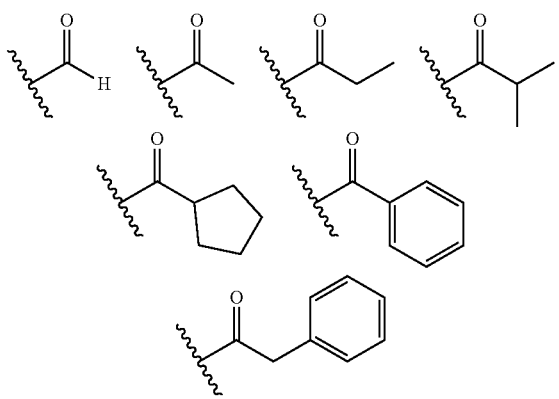

In the present specification, in the ester group, the oxygen of the ester group may be substituted with a linear, branched or cyclic alkyl group having 1 to 40 carbon atoms or an aryl group having 6 to 30 carbon atoms. Specifically, compounds having the following structural formulae may be included, however, the ester group is not limited thereto.

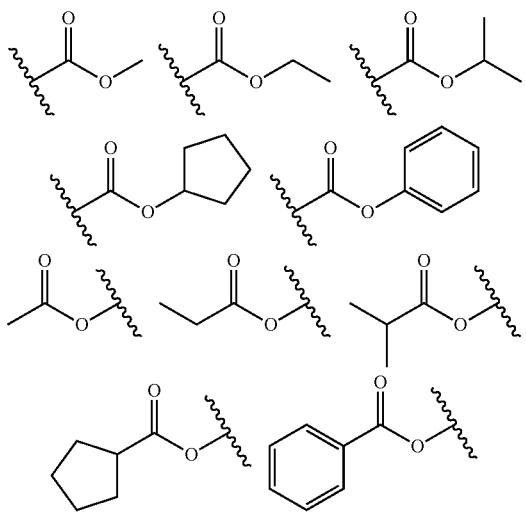

In the present specification, the silyl group may be represented by a chemical formula of $-SiY_aY_bY_c$, and $Y_a$, $Y_b$ and $Y_c$ may each be hydrogen; a substituted or unsubstituted alkyl group; or a substituted or unsubstituted aryl group. Specific examples of the silyl group may include a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not limited thereto.

In the present specification, the boron group may be represented by a chemical formula of $-BY_dY_e$, and $Y_d$ and $Y_e$ may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group may include a methyl group, an ethyl group, a propyl group, an n-propyl group, an isopropyl group, a butyl group, an n-butyl group, an isobutyl group, a tert-butyl group, a sec-butyl group, a 1-methylbutyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 4-methylhexyl group, a 5-methylhexyl group and the like, but are not limited thereto.

In the present specification, the alkoxy group may be linear, branched or cyclic. The number of carbon atoms of the alkoxy group is not particularly limited, but is preferably from 1 to 40. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

The alkyl group, the alkoxy group and other substituents including an alkyl group part described in the present specification include both linear and branched forms.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of carbon atoms of the cycloalkyl group is from 3 to 20. According to another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkylamine group preferably has, although not particularly limited thereto, 1 to 40 carbon atoms. Specific examples of the alkylamine group may include a methylamine group, a dimethylamine group, an ethylamine group, a diethylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include monocyclic aryl groups, polycyclic aryl groups, or both monocyclic aryl groups and polycyclic aryl groups.

Specific examples of the arylamine group may include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, examples of the heteroarylamine group may include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a polycyclic heterocyclic group. The heteroarylamine group including two or more heterocyclic groups may include monocyclic heterocyclic groups, polycyclic heterocyclic groups, or both monocyclic heterocyclic groups and polycyclic heterocyclic groups.

In the present specification, the aryl group is not particularly limited, but preferably has 6 to 60 carbon atoms, and may be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. Examples of the polycyclic aryl group may include a naphthyl group, an anthracenyl group, a phenanthryl group, a pyrenyl group, a perylenyl group, a triphenyl group, a chrysenyl group, a fluorenyl group, a benzofluorenyl group, a phenanthrenyl group, a triphenylene group and the like, but are not limited thereto.

In the present specification, the fluorenyl group may be substituted, and two substituents may bond to each other to form a spiro structure.

When the fluorenyl group is substituted, spirofluorenyl groups such as

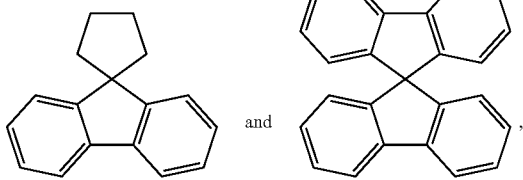

and and substituted fluorenyl groups such as

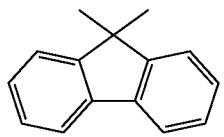

(9,9-dimethylfluorenyl group) and

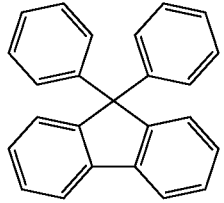 [SMILES: c1ccc(C2(c3ccccc3)c3ccccc3-c3ccccc32)cc1]

(9,9-diphenylfluorenyl group) may be included. However, the structure is not limited thereto.

In the present specification, the heterocyclic group is a heterocyclic group including one or more of N, O, P, S, Si and Se as a heteroatom, and although not particularly limited thereto, the number of carbon atoms is preferably from 2 to 60. According to one embodiment, the number of carbon atoms of the heterocyclic group is from 2 to 30. Examples of the heterocyclic group may include a pyridyl group, a pyrrole group, a pyrimidyl group, a pyridazinyl group, a furanyl group, a thiophenyl group, an imidazole group, a pyrazole group, an oxozole group, an isoxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophenyl group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a naphthobenzofuranyl group, a naphthobenzothiophenyl group, a benzimidazophenanthridine group or the like, but are not limited thereto.

In the present specification, descriptions on the heterocyclic group provided above may be applied to the heteroaryl group except for being aromatic.

In the present specification, descriptions on the aryl group provided above may be applied to the arylene group except for being divalent.

In one embodiment of the present specification, L1 is a direct bond; or a substituted or unsubstituted arylene group having 6 to 40 carbon atoms.

In another embodiment, L1 is a direct bond; or a substituted or unsubstituted arylene group having 6 to 20 carbon atoms.

According to another embodiment, L1 is a direct bond; or an arylene group having 6 to 40 carbon atoms unsubstituted or substituted with deuterium or a nitrile group.

In another embodiment, L1 is a direct bond; or an arylene group having 6 to 20 carbon atoms unsubstituted or substituted with deuterium or a nitrile group.

According to another embodiment, L1 is a direct bond; or a substituted or unsubstituted phenylene group; a substituted or unsubstituted biphenylene group; or a substituted or unsubstituted naphthylene group.

In another embodiment, L1 is a direct bond; a phenylene group unsubstituted or substituted with deuterium or a nitrile group; a biphenylene group unsubstituted or substituted with deuterium or a nitrile group; or a naphthylene group unsubstituted or substituted with deuterium or a nitrile group.

In another embodiment, L1 is a direct bond; a phenylene group unsubstituted or substituted with deuterium or a nitrile group; or a naphthylene group unsubstituted or substituted with deuterium or a nitrile group.

According to one embodiment of the present specification, Ar1 is a fused bicyclic heteroaryl group having 2 to 40 carbon atoms and two or more N atoms substituted with one or more selected from the group consisting of a substituted or unsubstituted aryl group having 6 to 40 carbon atoms and a substituted or unsubstituted heteroaryl group having 2 to 40 carbon atoms.

In another embodiment, Ar1 is a dicyclic fused bicyclic heteroaryl group having 2 to 30 carbon atoms and two or more N atoms substituted with one or more selected from the group consisting of a substituted or unsubstituted aryl group having 6 to 30 carbon atoms and a substituted or unsubstituted heteroaryl group having 2 to 30 carbon atoms.

In one embodiment of the present specification, Ar1 is represented by the following Chemical Formula 2.

[Chemical Formula 2]

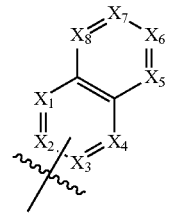

In Chemical Formula 2, $X_1$ to $X_8$ are N, CH or CR, two or more of $X_1$ to $X_8$ are N, and one or more of $X_1$ to $X_8$ are CR, and R is a substituted or unsubstituted aryl group having 6 to 40 carbon atoms, or a substituted or unsubstituted heteroaryl group having 2 to 40 carbon atoms.

In one embodiment of the present specification, $X_1$ to $X_8$ are N, CH or CR, two to four of $X_1$ to $X_8$ are N, one to four of $X_1$ to $X_8$ are CR, and R is a substituted or unsubstituted aryl group having 6 to 40 carbon atoms; or a substituted or unsubstituted heteroaryl group having 2 to 40 carbon atoms.

According to another embodiment, R is a substituted or unsubstituted aryl group having 6 to 30 carbon atoms; or a substituted or unsubstituted heteroaryl group having 2 to 30 carbon atoms.

In one embodiment of the present specification, Ar1 is represented by any one of the following Chemical Formula 3 to Chemical Formula 18.

[Chemical Formula 3]

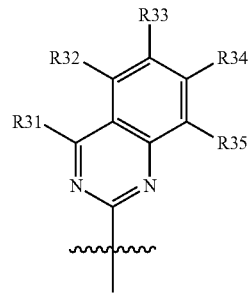

[Chemical Formula 4]

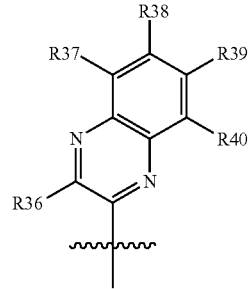

[Chemical Formula 5]
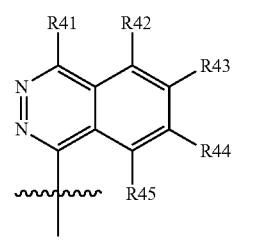
[Chemical Formula 6]
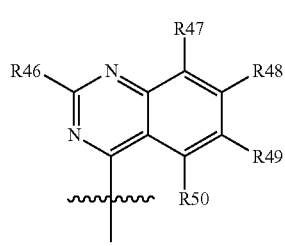
[Chemical Formula 7]
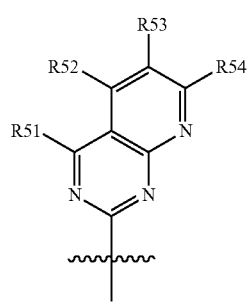
[Chemical Formula 8]
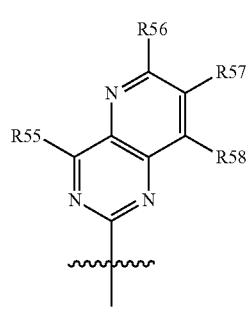
[Chemical Formula 9]
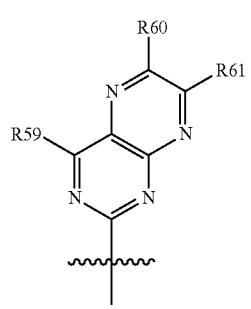
[Chemical Formula 10]
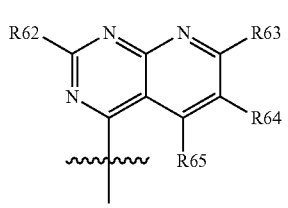
[Chemical Formula 11]
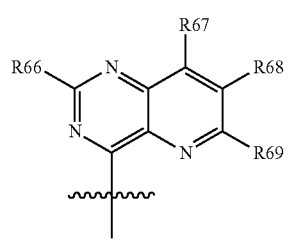
[Chemical Formula 12]
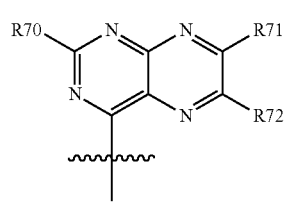
[Chemical Formula 13]
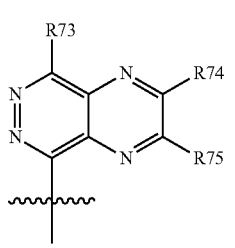
[Chemical Formula 14]
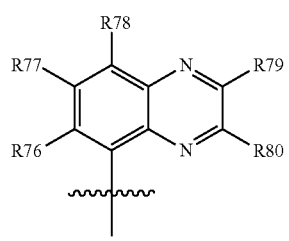
[Chemical Formula 15]
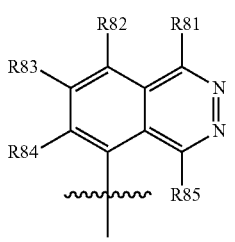
[Chemical Formula 16]
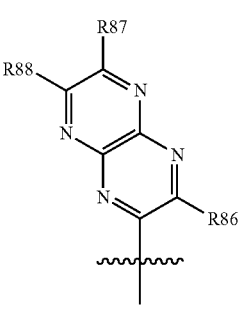

[Chemical Formula 17]

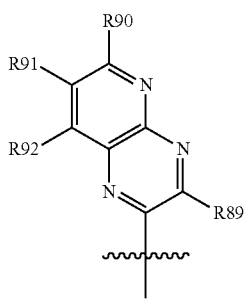

[Chemical Formula 18]

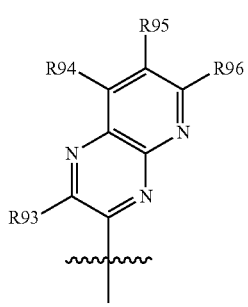

In Chemical Formulae 3 to 18,

R31 to R96 are the same as or different from each other, and each independently hydrogen; a substituted or unsubstituted aryl group having 6 to 40 carbon atoms; or a substituted or unsubstituted heteroaryl group having 2 to 40 carbon atoms, at least one of R31 to R35; at least one of R36 to R40; at least one of R41 to R45; at least one of R46 to R50; at least one of R51 to R54; at least one of R55 to R58; at least one of R59 to R61; at least one of R62 to R65; at least one of R66 to R69; at least one of R70 to R72; at least one of R73 to R75; at least one of R76 to R80; at least one of R81 to R85; at least one of R86 to R88; at least one of R89 to R92; and at least one of R93 to R96 are a substituted or unsubstituted aryl group having 6 to 40 carbon atoms; or a substituted or unsubstituted heteroaryl group having 2 to 40 carbon atoms.

According to one embodiment of the present specification, R31 to R96 are the same as or different from each other, and each independently hydrogen; an aryl group having 6 to 40 carbon atoms unsubstituted or substituted with deuterium, a nitrile group, an alkyl group having 1 to 30 carbon atoms, an aryl group having 6 to 60 carbon atoms unsubstituted or substituted with deuterium or a nitrile group, or a heteroaryl group having 2 to 60 carbon atoms; or a heteroaryl group having to 40 carbon atoms unsubstituted or substituted with deuterium, a nitrile group, an alkyl group having 1 to 30 carbon atoms, an aryl group having 6 to 60 carbon atoms unsubstituted or substituted with deuterium or a nitrile group, or a heteroaryl group having 2 to 60 carbon atoms, however, at least one of R31 to R35; at least one of R36 to R40; at least one of R41 to R45; at least one of R46 to R50; at least one of R51 to R54; at least one of R55 to R58; at least one of R59 to R61; at least one of R62 to R65; at least one of R66 to R69; at least one of R70 to R72; at least one of R73 to R75; at least one of R76 to R80; at least one of R81 to R85; at least one of R86 to R88; at least one of R89 to R92; and at least one of R93 to R96 are an aryl group having 6 to 40 carbon atoms unsubstituted or substituted with deuterium, a nitrile group, an alkyl group having 1 to 30 carbon atoms, an aryl group having 6 to 60 carbon atoms unsubstituted or substituted with deuterium or a nitrile group, or a heteroaryl group having 2 to 60 carbon atoms; or a heteroaryl group having 2 to 40 carbon atoms unsubstituted or substituted with deuterium, a nitrile group, an alkyl group having 1 to 30 carbon atoms, an aryl group having 6 to 60 carbon atoms unsubstituted or substituted with deuterium or a nitrile group, or a heteroaryl group having 2 to 60 carbon atoms.

In one embodiment of the present specification, R31 to R35 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R31 to R35 is a substituted or unsubstituted aryl group having 6 to 30 carbon atoms; or a substituted or unsubstituted heteroaryl group having 2 to 30 carbon atoms.

In another embodiment, R31 to R35 are the same as or different from each other, and each independently hydrogen; an aryl group having 6 to 30 carbon atoms unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; or a heteroaryl group having 2 to 30 carbon atoms unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms, and at least one of R31 to R35 is an aryl group having 6 to 30 carbon atoms unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; or a heteroaryl group having 2 to 30 carbon atoms unsubstituted or substituted with deuterium, a nitrile group, or an aryl group having 6 to 60 carbon atoms unsubstituted or substituted with deuterium, a hetoroaryl group having 2 to 60 carbon atoms, or an alkyl group having 1 to 30 carbon atoms.

According to another embodiment, at least one of R31 to R35 is a substituted or unsubstituted phenyl group; a substituted or unsubstituted naphthyl group; a substituted or unsubstituted biphenyl group; a substituted or unsubstituted phenanthrenyl group; a substituted or unsubstituted triphenylene group; a substituted or unsubstituted terphenyl group; a substituted or unsubstituted fluorenyl group; a substituted or unsubstituted benzofluorenyl group; a substituted or unsubstituted carbazole group; a substituted or unsubstituted dibenzofuranyl group; a substituted or unsubstituted dibenzothiophenyl group; a substituted or unsubstituted benzocarbazole group; a substituted or unsubstituted pyridyl group; a substituted or unsubstituted naphthobenzofuranyl group; or a substituted or unsubstituted naphthobenzothiophenyl group.

In another embodiment, at least one of R31 to R35 is a phenyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a naphthyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a biphenyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a phenanthrenyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a triphenylene group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a terphenyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a fluorenyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a benzofluorenyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a carbazole group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a dibenzofuranyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a dibenzothiophenyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a benzocarbazole group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a pyridyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; a naphthobenzofuranyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms; or a naphthobenzothiophenyl group unsubstituted or substituted with deuterium, a nitrile group, an aryl group having 6 to 60 carbon atoms unsubstituted or substituted with deuterium, a hetoroaryl group having 2 to 60 carbon atoms, or an alkyl group having 1 to 30 carbon atoms.

According to another embodiment, at least one of R31 to R35 is a phenyl group unsubstituted or substituted with deuterium, a nitrile group, a naphthyl group, a pyridyl group or a quinoline group; a naphthyl group unsubstituted or substituted with deuterium or a phenyl group; a biphenyl group unsubstituted or substituted with a nitrile group; a phenanthrenyl group; a triphenylene group; a terphenyl group; a fluorenyl group substituted with a methyl group; a benzofluorenyl group substituted with a methyl group; a carbazole group substituted with a phenyl group unsubstituted or substituted with deuterium, a biphenyl group unsubstituted or substituted with deuterium, or a naphthyl group unsubstituted or substituted with deuterium; a dibenzofuranyl group; a dibenzothiophenyl group; a benzocarbazole group substituted with a phenyl group unsubstituted or substituted with deuterium; a pyridyl group unsubstituted or substituted with a naphthyl group, a quinoline group or a pyridyl group; a naphthobenzofuranyl group; or a naphthobenzothiophenyl group.

In one embodiment of the present specification, R36 to R40 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R36 to R40 is a substituted or unsubstituted aryl group having 6 to 40 carbon atoms; or a substituted or unsubstituted heteroaryl group having 2 to 40 carbon atoms.

In one embodiment of the present specification, R36 to R40 are the same as or different from each other, and each independently hydrogen; an aryl group having 6 to 40 carbon atoms unsubstituted or substituted with deuterium, a nitrile group, an alkyl group having 1 to 30 carbon atoms, an aryl group having 6 to 60 carbon atoms or a hetoroaryl group having 2 to 60 carbon atoms; or a heteroaryl group having 2 to 40 carbon atoms unsubstituted or substituted with deuterium, a nitrile group, an alkyl group having 1 to 30 carbon atoms, an aryl group having 6 to 60 carbon atoms or a heteroaryl group having 2 to 30 carbon atoms, and at least one of R36 to R40 is an aryl group having 6 to 40 carbon atoms unsubstituted or substituted with deuterium, a nitrile group, an alkyl group having 1 to 30 carbon atoms, an aryl group having 6 to 60 carbon atoms or a hetoroaryl group having 2 to 60 carbon atoms; or a heteroaryl group having 2 to 40 carbon atoms unsubstituted or substituted with deuterium, a nitrile group, an alkyl group having 1 to 30 carbon atoms, an aryl group having 6 to 60 carbon atoms or a hetoroaryl group having 2 to 60 carbon atoms.

In one embodiment of the present specification, R36 to R40 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R36 to R40 is a substituted or unsubstituted aryl group having 6 to 30 carbon atoms; or a substituted or unsubstituted heteroaryl group having 2 to 30 carbon atoms.

According to another embodiment, at least one of R36 to R40 is a substituted or unsubstituted phenyl group; a substituted or unsubstituted biphenyl group; a substituted or unsubstituted naphthyl group; a substituted or unsubstituted phenanthrenyl group; a substituted or unsubstituted triphenylene group; a substituted or unsubstituted pyridyl group; a substituted or unsubstituted quinoline group; a substituted or unsubstituted fluorenyl group; a substituted or unsubstituted dibenzofuranyl group; a substituted or unsubstituted dibenzothiophenyl group; a substituted or unsubstituted carbazole group; or a substituted or unsubstituted benzocarbazole group.

According to another embodiment, at least one of R36 to R40 is a phenyl group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a biphenyl group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a naphthyl group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a phenanthrenyl group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a triphenylene group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a pyridyl group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a quinoline group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a fluorenyl group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a dibenzofuranyl group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a dibenzothiophenyl group unsubstituted or substituted with deuterium, a nitrile group, an alkyl group having 1 to 30 carbon atoms, an aryl group having 6 to 60 carbon atoms or a hetoroaryl group having 2 to 60 carbon atoms; a carbazole group unsubstituted or substituted with deuterium, a nitrile group, an alkyl group having 1 to 30 carbon atoms, an aryl group having 6 to 60 carbon atoms or a hetoroaryl group having 2 to 60 carbon atoms; or a benzocarbazole group unsubstituted or substituted with deuterium, a nitrile group, an alkyl group having 1 to 30 carbon atoms, an aryl group having 6 to 60 carbon atoms or a hetoroaryl group having 2 to 60 carbon atoms.

In another embodiment, at least one of R36 to R40 is a phenyl group unsubstituted or substituted with deuterium, a nitrile group or a naphthyl group; a biphenyl group; a naphthyl group unsubstituted or substituted with a nitrile group or a phenyl group; a phenanthrenyl group; a triphenylene group; a pyridyl group; a quinoline group; a fluorenyl group substituted with a methyl group; a dibenzofuranyl group; a dibenzothiophenyl group; a carbazole group substituted with a phenyl group unsubstituted or substituted with deuterium; or a benzocarbazole group substituted with a phenyl group unsubstituted or substituted with deuterium.

In one embodiment of the present specification, R41 to R45 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R41 to R45 is a substituted or unsubstituted aryl group having 6 to 40 carbon atoms; or a substituted or unsubstituted heteroaryl group having 2 to 40 carbon atoms.

In one embodiment of the present specification, R41 to R45 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R41 to R45 is a substituted or unsubstituted aryl group having 6 to 30 carbon atoms; or a substituted or unsubstituted heteroaryl group having 2 to 30 carbon atoms.

According to another embodiment, at least one of R41 to R45 is a substituted or unsubstituted phenyl group; a substituted or unsubstituted biphenyl group; a substituted or unsubstituted naphthyl group; a substituted or unsubstituted phenanthrenyl group; a substituted or unsubstituted triphenylene group; a substituted or unsubstituted terphenyl group; a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R41 to R45 is a phenyl group unsubstituted or substituted with a nitrile group; a biphenyl group; a naphthyl group unsubstituted or substituted with a phenyl group unsubstituted or substituted with a nitrile group; a phenanthrenyl group; a triphenylene group; a terphenyl group; a fluorenyl group substituted with a methyl group; a dibenzofuranyl group; a dibenzothiophenyl group; or a carbazole group substituted with a phenyl group unsubstituted or substituted with deuterium.

In one embodiment of the present specification, R46 to R50 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R46 to R50 is a substituted or unsubstituted aryl group having 6 to 40 carbon atoms; or a substituted or unsubstituted heteroaryl group having 2 to 40 carbon atoms.

In one embodiment of the present specification, R46 to R50 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R46 to R50 is a substituted or unsubstituted aryl group having 6 to 30 carbon atoms; or a substituted or unsubstituted heteroaryl group having 2 to 30 carbon atoms.

According to another embodiment, at least one of R46 to R50 is a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted triphenylene group; a substituted or unsubstituted fluorenyl group; a substituted or unsubstituted pyridyl group; a substituted or unsubstituted quinoline group; a substituted or unsubstituted dibenzofuranyl group; a substituted or unsubstituted dibenzothiophenyl group; a substituted or unsubstituted carbazole group; or a substituted or unsubstituted benzocarbazole group.

In another embodiment, at least one of R46 to R50 is a phenyl group unsubstituted or substituted with deuterium, a nitrile group, a naphthyl group, a quinoline group, deuterium and a quinoline group, deuterium and a pyridyl group, or a pyridyl group; a biphenyl group unsubstituted or substituted with deuterium; a terphenyl group; a naphthyl group unsubstituted or substituted with deuterium or a phenyl group; a phenanthrenyl group; a triphenylene group; a fluorenyl group substituted with a methyl group; a pyridyl group unsubstituted or substituted with a quinoline group; a quinoline group; a dibenzofuranyl group; a dibenzothiophenyl group; a carbazole group substituted with a phenyl group unsubstituted or substituted with deuterium, a biphenyl group or a naphthyl group; or a benzocarbazole group unsubstituted or substituted with a phenyl group unsubstituted or substituted with deuterium.

In one embodiment of the present specification, R51 to R54 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R51 to R54 is a substituted or unsubstituted aryl group having 6 to 40 carbon atoms; or a substituted or unsubstituted heteroaryl group having 2 to 40 carbon atoms.

In one embodiment of the present specification, R51 to R54 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R51 to R54 is a substituted or unsubstituted aryl group having 6 to 30 carbon atoms; or a substituted or unsubstituted heteroaryl group having 2 to 30 carbon atoms.

According to another embodiment, at least one of R51 to R54 is a substituted or unsubstituted phenyl group; a substituted or unsubstituted biphenyl group; a substituted or unsubstituted naphthyl group; a substituted or unsubstituted fluorenyl group; or a substituted or unsubstituted carbazole group.

According to another embodiment, at least one of R51 to R54 is a phenyl group unsubstituted or substituted with deuterium; a biphenyl group unsubstituted or substituted with a nitrile group; a naphthyl group; or a fluorenyl group substituted with a methyl group; a carbazole group substituted with a phenyl group.

In one embodiment of the present specification, R55 to R58 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R55 to R58 is a substituted or unsubstituted aryl group having 6 to 40 carbon atoms; or a substituted or unsubstituted heteroaryl group having 2 to 40 carbon atoms.

In one embodiment of the present specification, R55 to R58 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R55 to R58 is a substituted or unsubstituted aryl group having 6 to 30 carbon atoms; or a substituted or unsubstituted heteroaryl group having 2 to 30 carbon atoms.

In another embodiment, at least one of R55 to R58 is a substituted or unsubstituted phenyl group; a substituted or unsubstituted naphthyl group; a substituted or unsubstituted fluorenyl group; or a substituted or unsubstituted carbazole group.

In another embodiment, at least one of R55 to R58 is a phenyl group unsubstituted or substituted with deuterium; a naphthyl group; a fluorenyl group substituted with a methyl group; or a carbazole group substituted with a phenyl group.

In one embodiment of the present specification, R59 to R61 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R59 to R61 is a substituted or unsubstituted aryl group having 6 to 40 carbon atoms; or a substituted or unsubstituted heteroaryl group having 2 to 40 carbon atoms.

In one embodiment of the present specification, R59 to R61 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R59 to R61 is a substituted or unsubstituted aryl group having 6 to 30 carbon atoms; or a substituted or unsubstituted heteroaryl group having 2 to 30 carbon atoms.

In another embodiment, at least one of R59 to R61 is a substituted or unsubstituted phenyl group; a substituted or unsubstituted naphthyl group; a substituted or unsubstituted fluorenyl group; or a substituted or unsubstituted carbazole group.

In another embodiment, at least one of R59 to R61 is a phenyl group unsubstituted or substituted with a nitrile group; a naphthyl group; a fluorenyl group substituted with a methyl group; or a carbazole group substituted with a phenyl group unsubstituted or substituted with deuterium.

In one embodiment of the present specification, R62 to R65 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R62 to R65 is a substituted or unsubstituted aryl group having 6 to 40 carbon atoms; or a substituted or unsubstituted heteroaryl group having 2 to 40 carbon atoms.

In one embodiment of the present specification, R62 to R65 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R62 to R65 is a substituted or unsubstituted aryl group having 6 to 30 carbon atoms; or a substituted or unsubstituted heteroaryl group having 2 to 30 carbon atoms.

In another embodiment, at least one of R62 to R65 is a substituted or unsubstituted phenyl group; a substituted or unsubstituted biphenyl group; a substituted or unsubstituted naphthyl group; a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R62 to R65 is a phenyl group; a biphenyl group unsubstituted or substituted with deuterium; a naphthyl group; a fluorenyl group substituted with a methyl group; a dibenzofuranyl group; a dibenzothiophenyl group; or a carbazole group substituted with a phenyl group unsubstituted or substituted with deuterium.

In one embodiment of the present specification, R66 to R69 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R66 to R69 is a substituted or unsubstituted aryl group having 6 to 40 carbon atoms; or a substituted or unsubstituted heteroaryl group having 2 to 40 carbon atoms.

In one embodiment of the present specification, R66 to R69 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R66 to R69 is a substituted or unsubstituted aryl group having 6 to 30 carbon atoms; or a substituted or unsubstituted heteroaryl group having 2 to 30 carbon atoms.

In another embodiment, at least one of R66 to R69 is a substituted or unsubstituted phenyl group; a substituted or unsubstituted biphenyl group; a substituted or unsubstituted naphthyl group; a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R66 to R69 is a phenyl group substituted with a nitrile group; a biphenyl group; a naphthyl group; a fluorenyl group substituted with a methyl group; a dibenzofuranyl group; a dibenzothiophenyl group; or a carbazole group substituted with a phenyl group unsubstituted or substituted with deuterium.

In one embodiment of the present specification, R70 to R72 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R70 to R72 is a substituted or unsubstituted aryl group having 6 to 40 carbon atoms; or a substituted or unsubstituted heteroaryl group having 2 to 40 carbon atoms.

In one embodiment of the present specification, R70 to R72 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R70 to R72 is a substituted or unsubstituted aryl group having 6 to 30 carbon atoms; or a substituted or unsubstituted heteroaryl group having 2 to 30 carbon atoms.

In another embodiment, at least one of R70 to R72 is a substituted or unsubstituted phenyl group; a substituted or unsubstituted biphenyl group; a substituted or unsubstituted naphthyl group; a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R70 to R72 is a phenyl group; a biphenyl group; a naphthyl group; a fluorenyl group substituted with a methyl group; a dibenzofuranyl group; a dibenzothiophenyl group; or a carbazole group substituted with a phenyl group.

In one embodiment of the present specification, R73 to R75 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R73 to R75 is a substituted or unsubstituted aryl group having 6 to 40 carbon atoms; or a substituted or unsubstituted heteroaryl group having 2 to 40 carbon atoms.

In one embodiment of the present specification, R73 to R75 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R73 to R75 is a substituted or unsubstituted aryl group having 6 to 30 carbon atoms; or a substituted or unsubstituted heteroaryl group having 2 to 30 carbon atoms.

In another embodiment, at least one of R73 to R75 is a substituted or unsubstituted phenyl group; a substituted or unsubstituted biphenyl group; a substituted or unsubstituted naphthyl group; a substituted or unsubstituted phenanthrenyl group; a substituted or unsubstituted triphenylene group; a substituted or unsubstituted terphenyl group; a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R73 to R75 is a phenyl group unsubstituted or substituted with deuterium, a nitrile group or a naphthyl group; a biphenyl group; a naphthyl group unsubstituted or substituted with a phenyl group; a phenanthrenyl group; a triphenylene group; a terphenyl group; a fluorenyl group substituted with a methyl group; a dibenzofuranyl group; a dibenzothiophenyl group; or a carbazole group substituted with a phenyl group.

In one embodiment of the present specification, R76 to R80 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R76 to R80 is a substituted or unsubstituted aryl group having 6 to 40 carbon atoms; or a substituted or unsubstituted heteroaryl group having 2 to 40 carbon atoms.

In one embodiment of the present specification, R76 to R80 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R76 to R80 is a substituted or unsubstituted aryl group having 6 to 30 carbon atoms; or a substituted or unsubstituted heteroaryl group having 2 to 30 carbon atoms.

In another embodiment, at least one of R76 to R80 is a substituted or unsubstituted phenyl group; a substituted or unsubstituted biphenyl group; a substituted or unsubstituted naphthyl group; a substituted or unsubstituted phenanthrenyl group; a substituted or unsubstituted triphenylene group; a substituted or unsubstituted terphenyl group; a substituted or unsubstituted fluorenyl group; a substituted or unsubstituted dibenzofuranyl group; a substituted or unsubstituted dibenzothiophenyl group; or a substituted or unsubstituted carbazole group.

In another embodiment, at least one of R76 to R80 is a phenyl group unsubstituted or substituted with deuterium, a nitrile group or a naphthyl group; a biphenyl group; a naphthyl group unsubstituted or substituted with a phenyl group; a phenanthrenyl group; a triphenylene group; a terphenyl group; a fluorenyl group substituted with a methyl group; a dibenzofuranyl group; a dibenzothiophenyl group; or a carbazole group substituted with a phenyl group.

In one embodiment of the present specification, R81 to R85 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R81 to R85 is a substituted or unsubstituted aryl group having 6 to 40 carbon atoms; or a substituted or unsubstituted heteroaryl group having 2 to 40 carbon atoms.

In one embodiment of the present specification, R81 to R85 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R81 to R85 is a substituted or unsubstituted aryl group having 6 to 30 carbon atoms; or a substituted or unsubstituted heteroaryl group having 2 to 30 carbon atoms.

According to another embodiment, at least one of R81 to R85 is a substituted or unsubstituted phenyl group; a substituted or unsubstituted biphenyl group; a substituted or unsubstituted naphthyl group; a substituted or unsubstituted phenanthrenyl group; a substituted or unsubstituted terphenyl group; a substituted or unsubstituted triphenylene group; a substituted or unsubstituted fluorenyl group; a substituted or unsubstituted dibenzofuranyl group; a substituted or unsubstituted dibenzothiophenyl group; or a substituted or unsubstituted carbazole group.

According to another embodiment, at least one of R81 to R85 is a phenyl group unsubstituted or substituted with a naphthyl group; a biphenyl group; a naphthyl group unsubstituted or substituted with a phenyl group; a phenanthrenyl group; a terphenyl group; a triphenylene group; a fluorenyl group substituted with a methyl group; a dibenzofuranyl group; a dibenzothiophenyl group; or a carbazole group substituted with a phenyl group unsubstituted or substituted with deuterium.

In one embodiment of the present specification, R86 to R88 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R86 to R88 is a substituted or unsubstituted aryl group having 6 to 40 carbon atoms; or a substituted or unsubstituted heteroaryl group having 2 to 40 carbon atoms.

In one embodiment of the present specification, R86 to R88 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R86 to R88 is a substituted or unsubstituted aryl group having 6 to 30 carbon atoms; or a substituted or unsubstituted heteroaryl group having 2 to 30 carbon atoms.

In another embodiment, at least one of R86 to R88 is a substituted or unsubstituted phenyl group; a substituted or unsubstituted naphthyl group; a substituted or unsubstituted dibenzofuranyl group; a substituted or unsubstituted benzocarbazole group; a substituted or unsubstituted quinoline group; or a substituted or unsubstituted pyridyl group.

In another embodiment, at least one of R86 to R88 is a phenyl group; a naphthyl group; a dibenzofuranyl group; a benzocarbazole group substituted with a phenyl group; a quinoline group; or a pyridyl group.

In one embodiment of the present specification, R89 to R92 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R89 to R92 is a substituted or unsubstituted aryl group having 6 to 40 carbon atoms; or a substituted or unsubstituted heteroaryl group having 2 to 40 carbon atoms.

In one embodiment of the present specification, R89 to R92 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R89 to R92 is a substituted or unsubstituted aryl group having 6 to 30 carbon atoms; or a substituted or unsubstituted heteroaryl group having 2 to 30 carbon atoms.

In another embodiment, at least one of R89 to R92 is a substituted or unsubstituted phenyl group; a substituted or unsubstituted biphenyl group; a substituted or unsubstituted naphthyl group; a substituted or unsubstituted phenanthrenyl group; a substituted or unsubstituted fluorenyl group; a substituted or unsubstituted dibenzofuranyl group; a substituted or unsubstituted dibenzothiophenyl group; a substituted or unsubstituted carbazole group; or a substituted or unsubstituted pyridyl group.

In another embodiment, at least one of R89 to R92 is a phenyl group substituted with deuterium or a quinoline group; a biphenyl group unsubstituted or substituted with deuterium; a naphthyl group substituted with a phenyl group; a phenanthrenyl group; a fluorenyl group substituted with a methyl group; a dibenzofuranyl group; a dibenzothiophenyl group; a carbazole group substituted with a phenyl group; or a pyridyl group.

In one embodiment of the present specification, R93 to R96 are the same as or different from each other, and each independently hydrogen; a substituted or unsubstituted aryl group having 6 to 40 carbon atoms; or a substituted or unsubstituted heteroaryl group having 2 to 40 carbon atoms, and at least one of R93 to R96 is a substituted or unsubstituted aryl group having 6 to 40 carbon atoms; or a substituted or unsubstituted heteroaryl group having 2 to 40 carbon atoms.

In one embodiment of the present specification, R93 to R96 are the same as or different from each other, and each independently hydrogen; a substituted or unsubstituted aryl group having 6 to 30 carbon atoms; or a substituted or unsubstituted heteroaryl group having 2 to 30 carbon atoms, and at least one of R93 to R96 is a substituted or unsubstituted aryl group having 6 to 30 carbon atoms; or a substituted or unsubstituted heteroaryl group having 2 to 30 carbon atoms.

In another embodiment, at least one of R93 to R96 is a substituted or unsubstituted phenyl group; a substituted or unsubstituted triphenylene group; a substituted or unsubstituted fluorenyl group; a substituted or unsubstituted carbazole group; a substituted or unsubstituted pyridyl group; or a substituted or unsubstituted dibenzofuranyl group.

In another embodiment, at least one of R93 to R96 is a phenyl group substituted with a nitrile group, a naphthyl group or a quinoline group; a triphenylene group; a fluorenyl group substituted with a methyl group; a carbazole group substituted with a phenyl group unsubstituted or substituted with deuterium; a pyridyl group; or a dibenzofuranyl group.

According to one embodiment of the present disclosure, R1 to R10 are each independently hydrogen or deuterium, or R1 and R2, R2 and R3, or R3 and R4 of R1 to R10 bond to each other to form a benzene ring, and the rest are each independently hydrogen or deuterium.

According to another embodiment, R1 to R10 are each independently hydrogen or deuterium.

In another embodiment, R1 to R10 are hydrogen.

According to another embodiment, R1 and R2, R2 and R3, or R3 and R4 of R1 to R10 bond to each other to form a benzene ring, and the rest are each independently hydrogen or deuterium.

In another embodiment, R1 and R2 of R1 to R10 bond to each other to form a benzene ring, R2 and R3 thereof bond to each other to form a benzene ring, or R3 and R4 thereof bond to each other to form a benzene ring, and the rest are each independently hydrogen or deuterium.

In another embodiment, R1 and R2 of R1 to R10 bond to each other to form a benzene ring, R2 and R3 thereof bond to each other to form a benzene ring, or R3 and R4 thereof bond to each other to form a benzene ring, and the rest are hydrogen.

In one embodiment of the present specification, Chemical Formula 1 is represented by any one of the following Chemical Formulae 19 to 22.

[Chemical Formula 19]

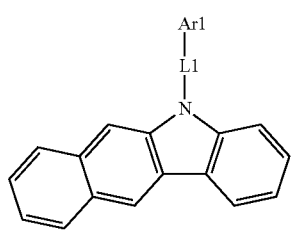

[Chemical Formula 20]

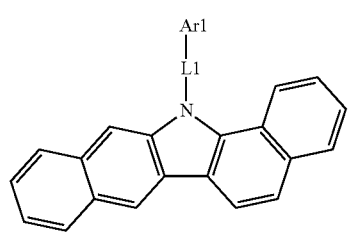

[Chemical Formula 21]

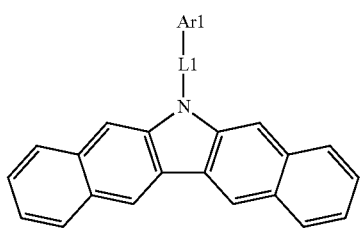

[Chemical Formula 22]

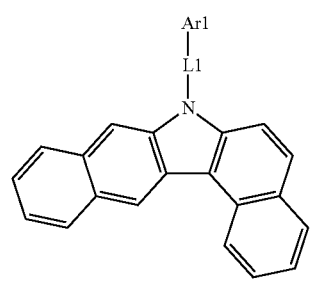

In Chemical Formulae 19 to 22,

Ar1 and L1 have the same definitions as in Chemical Formula 1.

In one embodiment of the present specification, Chemical Formula 1 may be any one selected from among the following compounds.

1

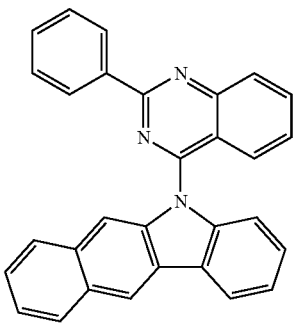

2

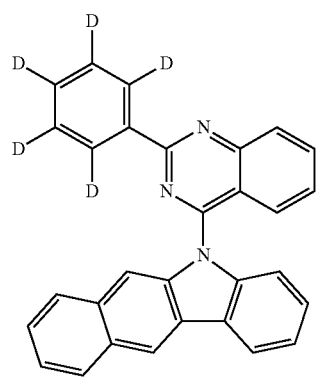

3

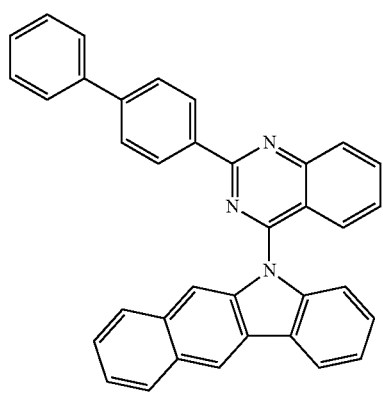

4

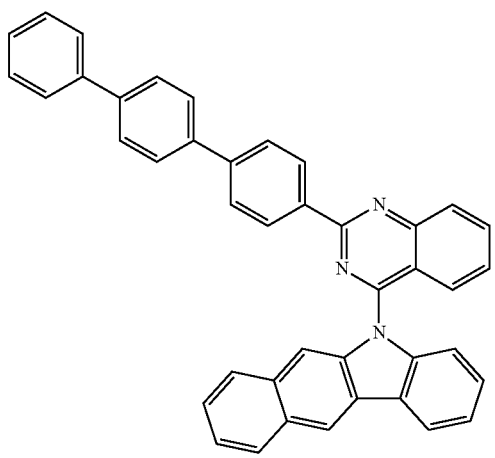

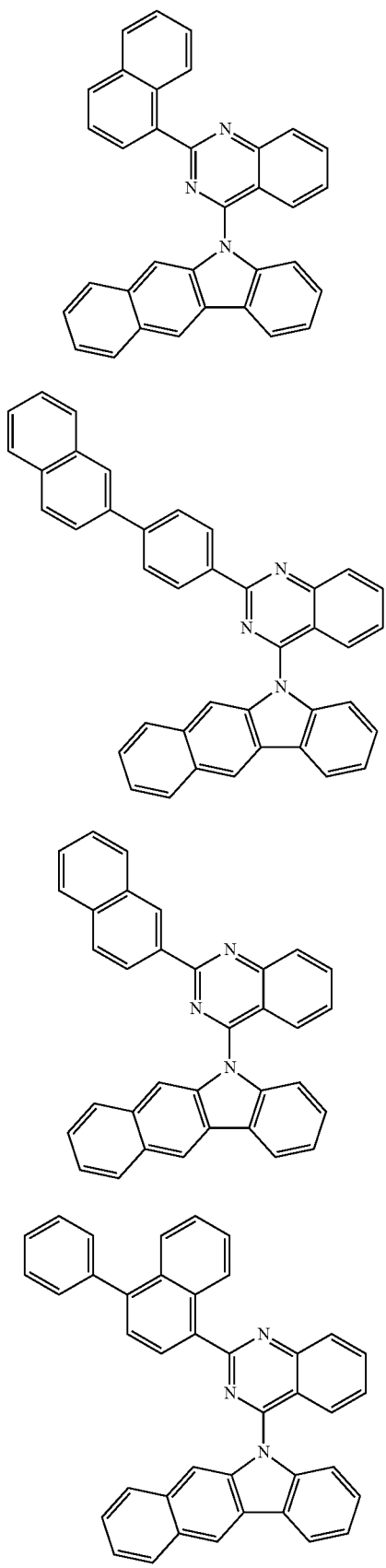
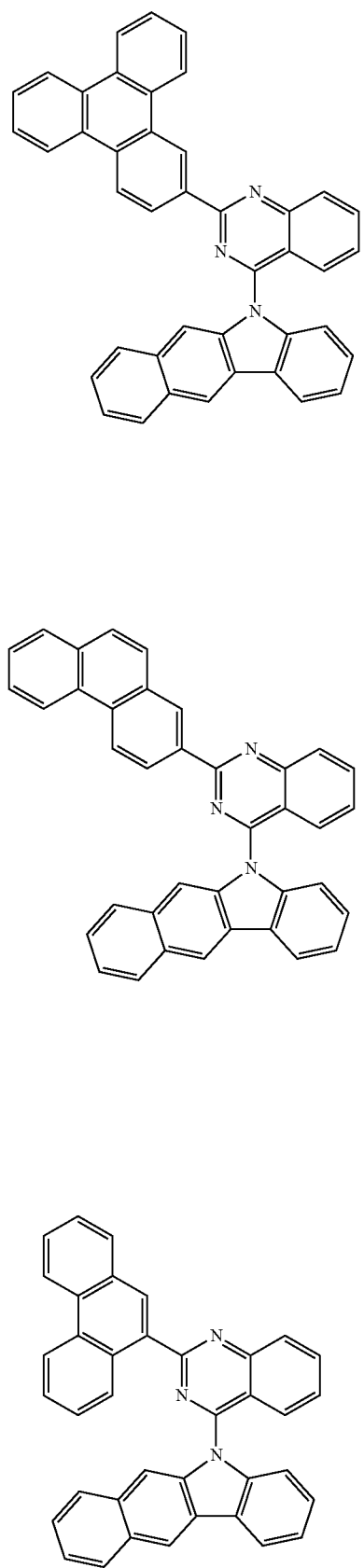

-continued
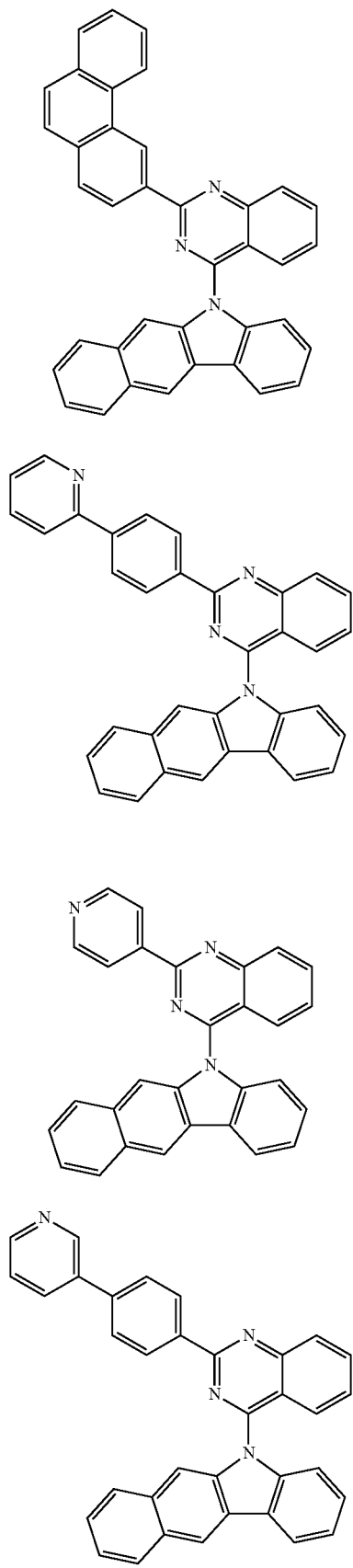
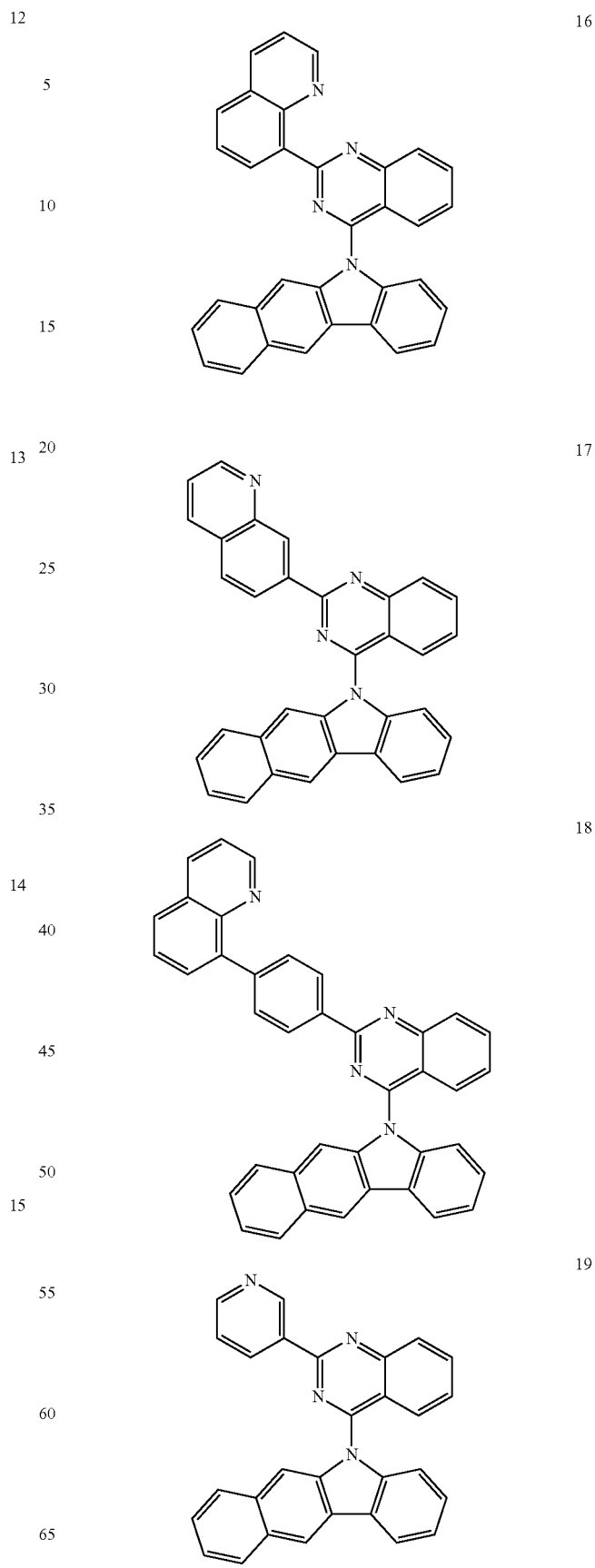

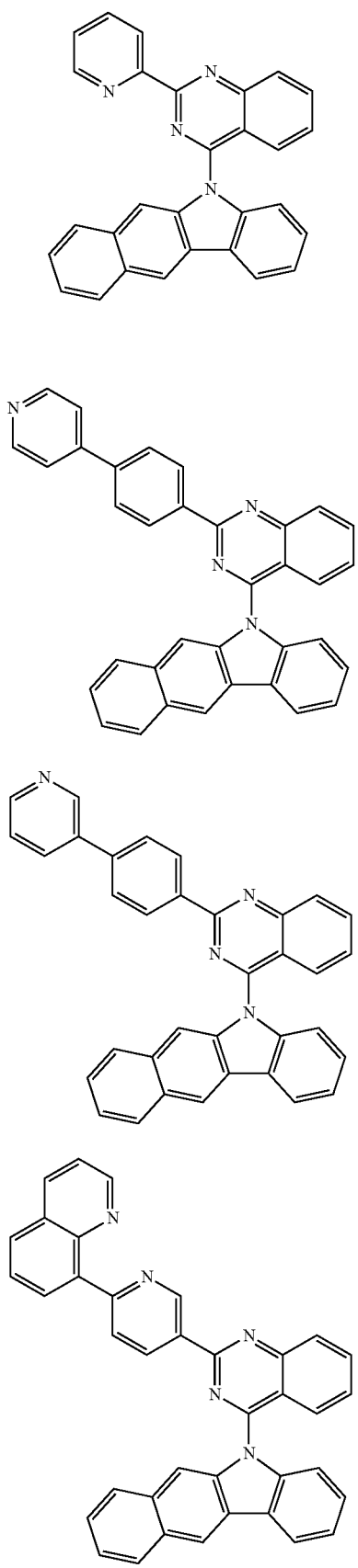
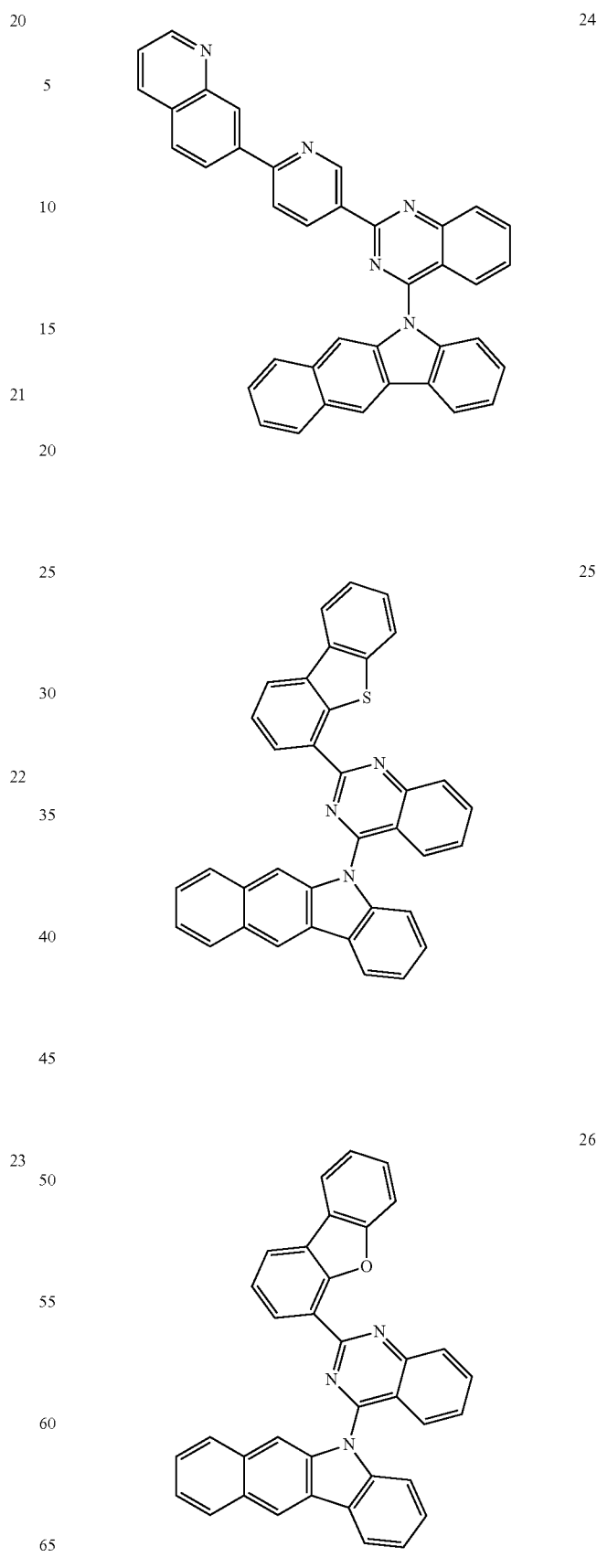

27
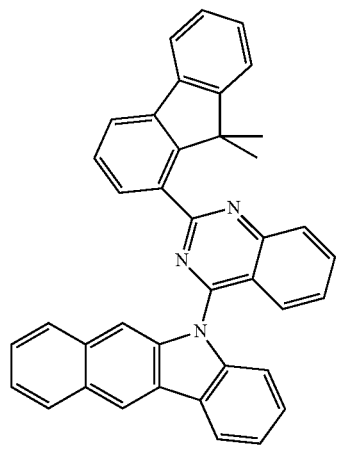
28
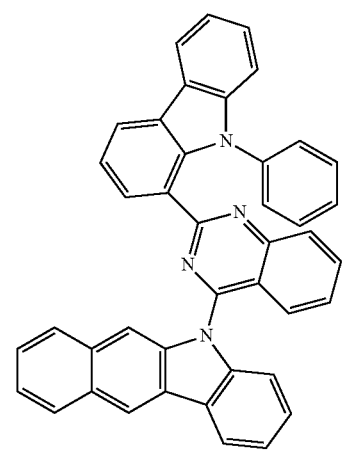
29
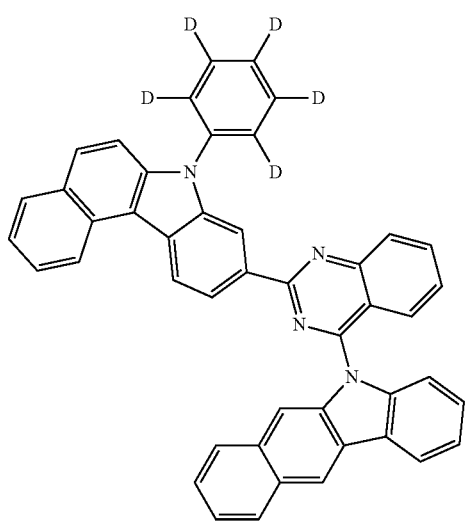
30
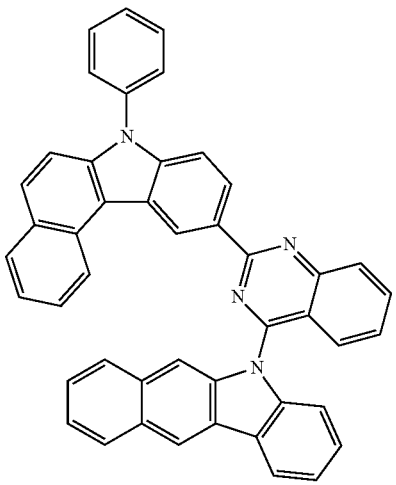
31
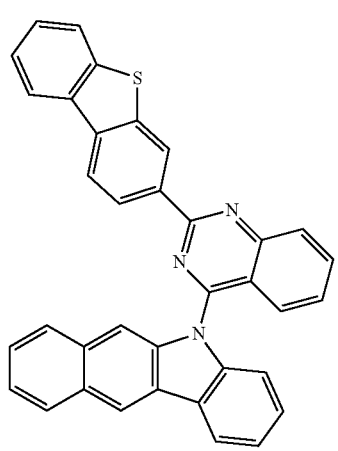
32
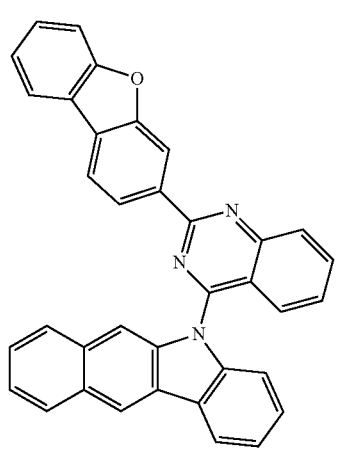

33
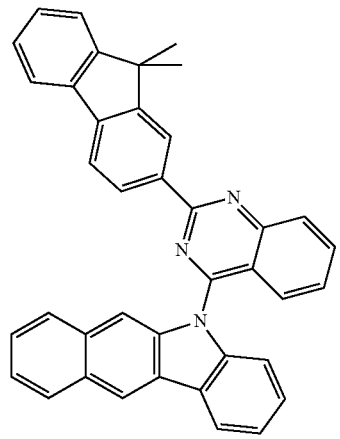
34
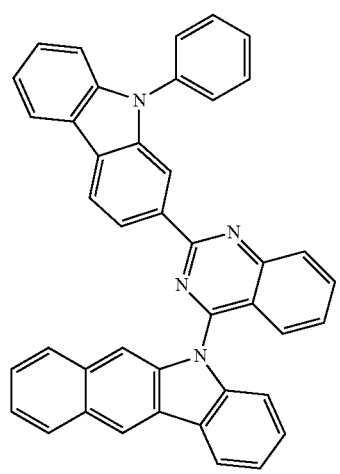
36
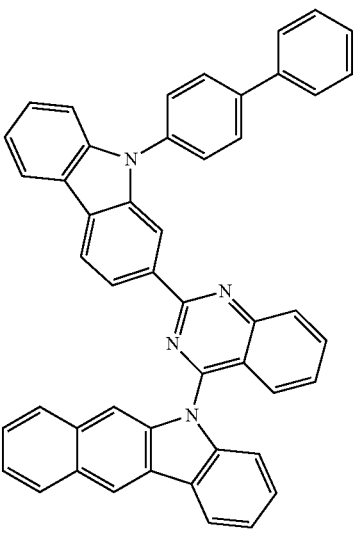
37
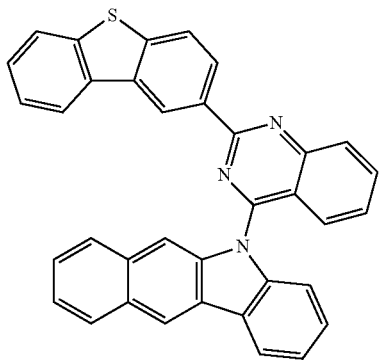
38
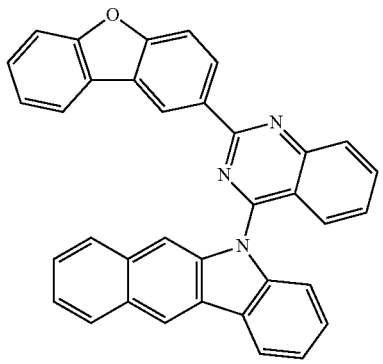
39
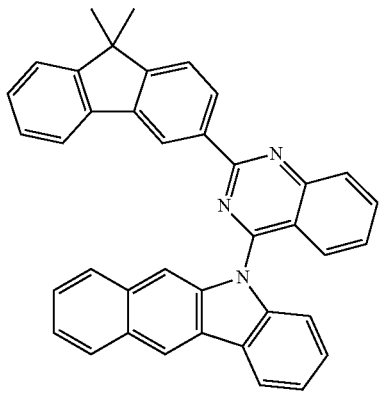

40
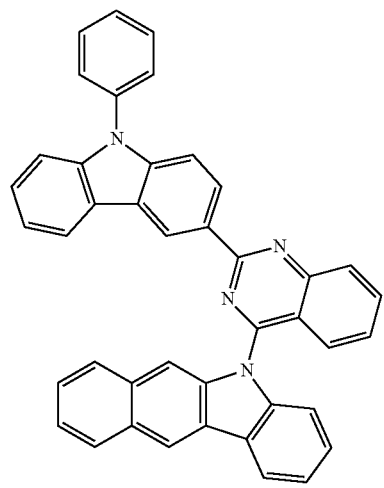
41
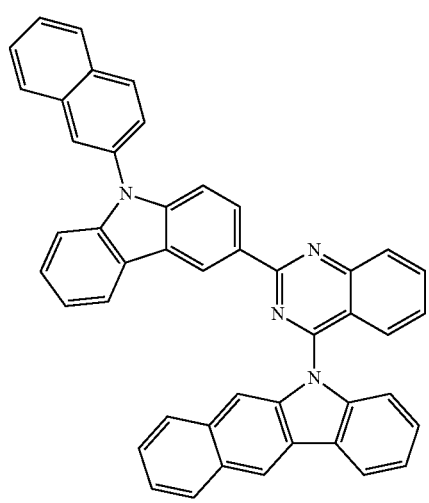
42
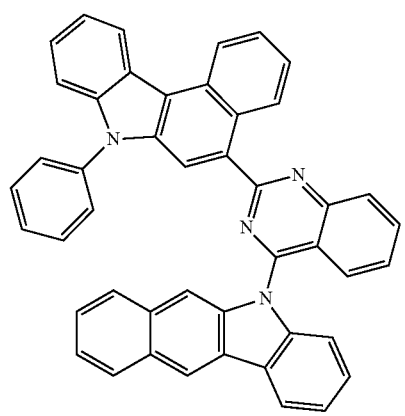
43
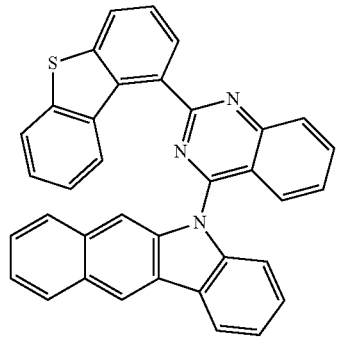
44
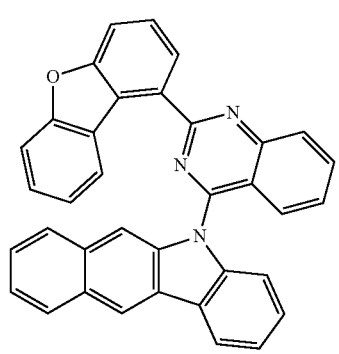
45
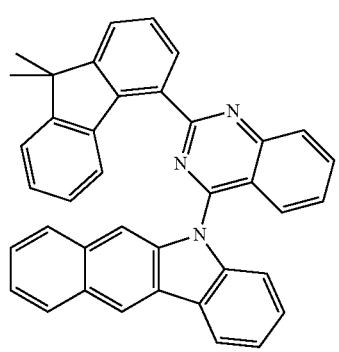
46
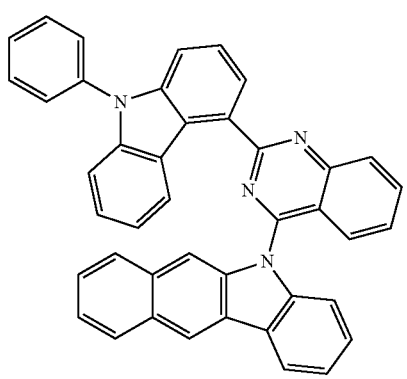

47
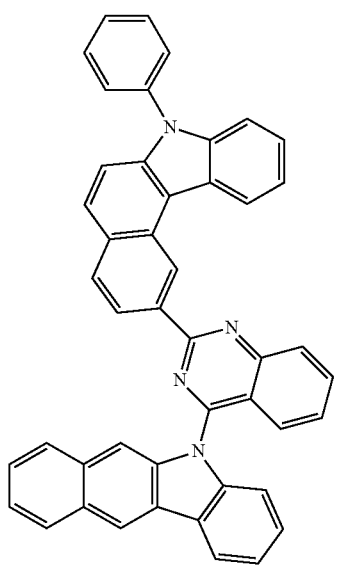
48
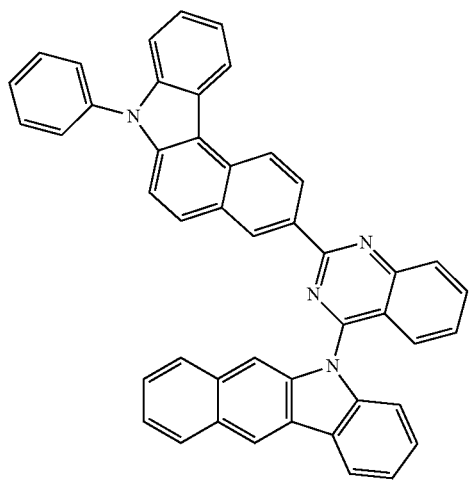
49
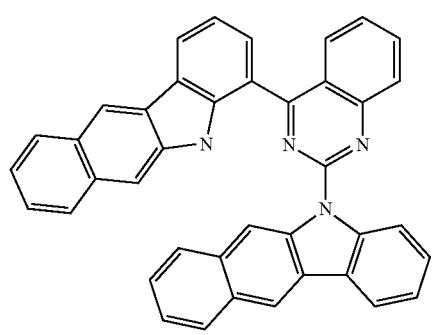
50
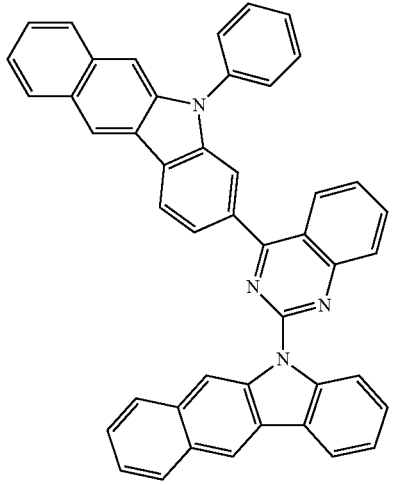
51
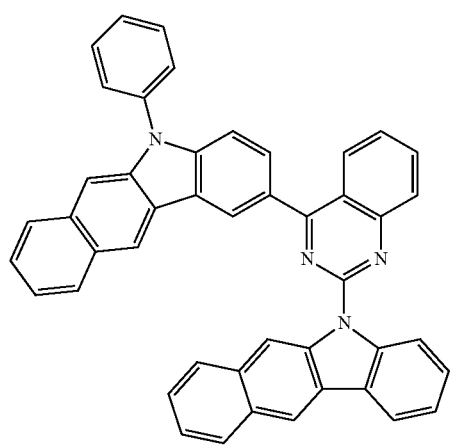
52
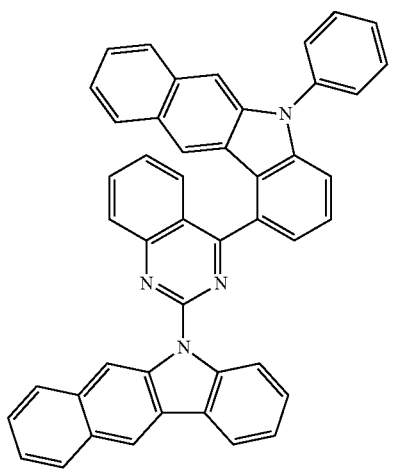

53
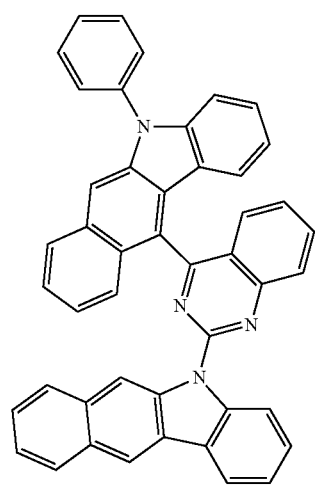
54
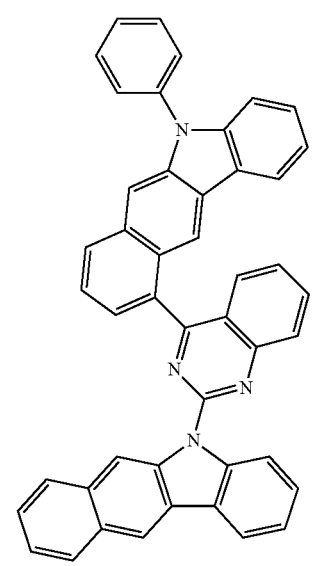
55
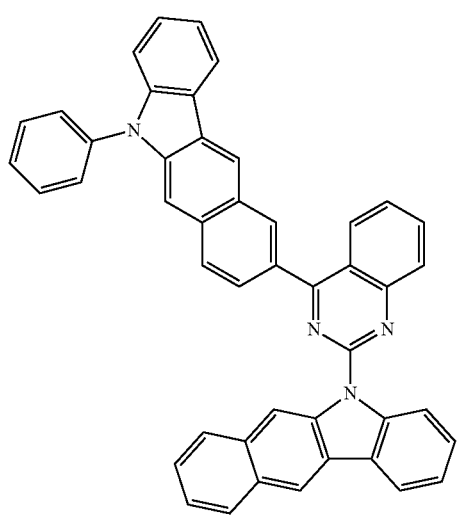
56
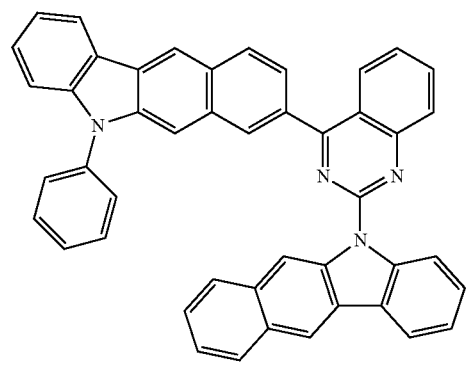
57
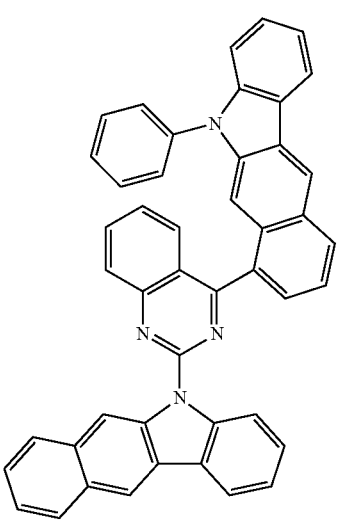
58
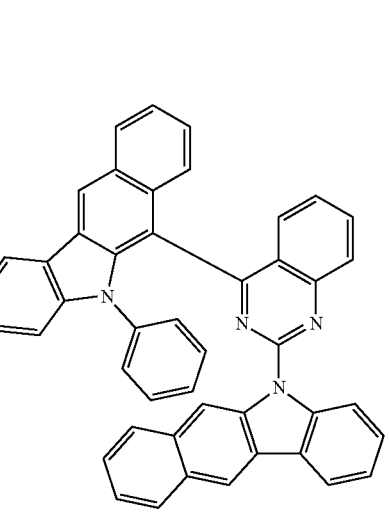

59
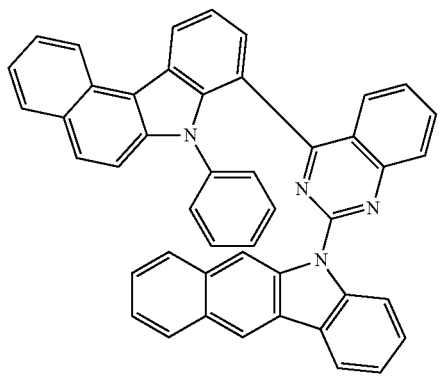
60
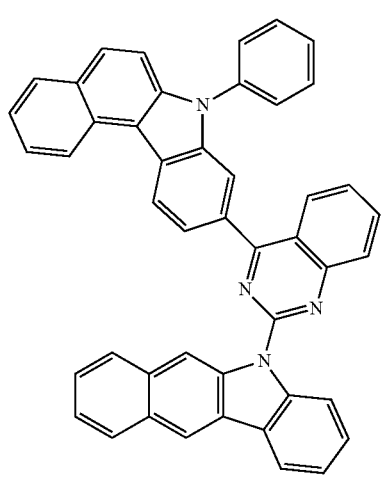
61
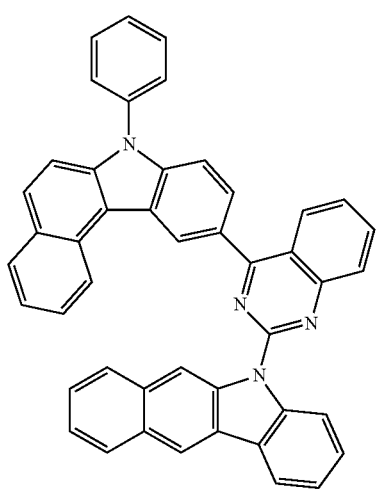
62
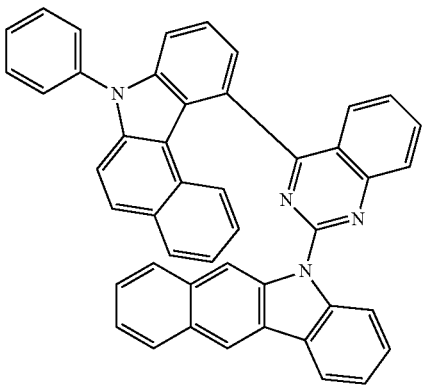
63
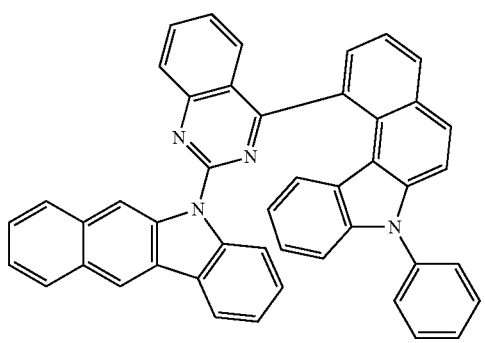
64
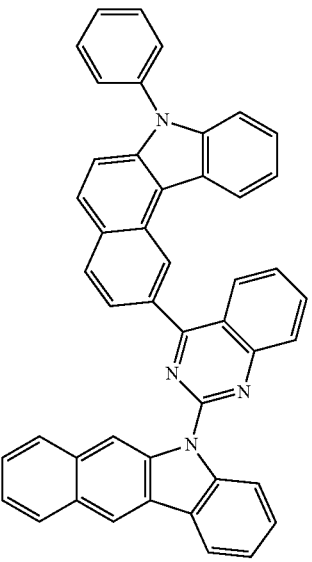

65
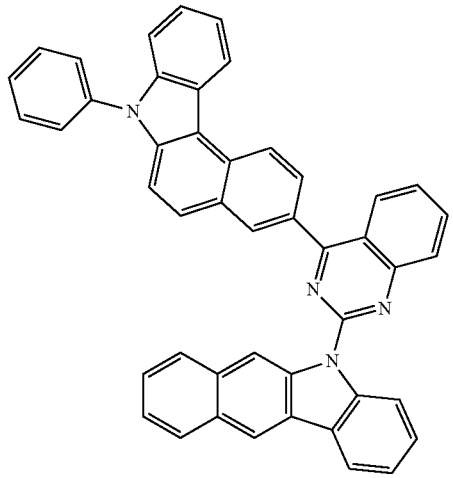
66
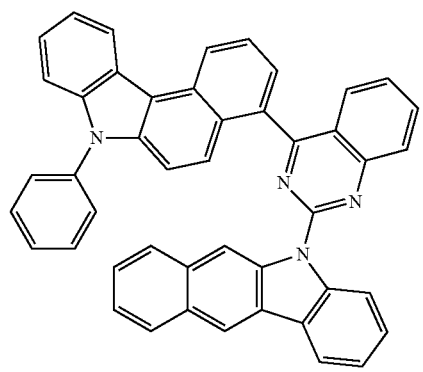
67
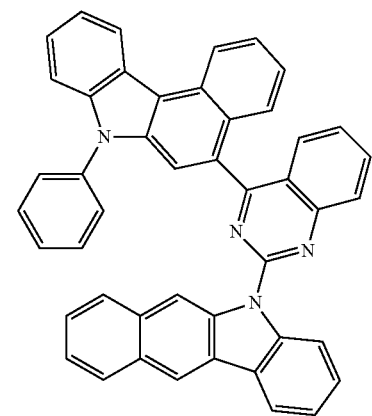
68
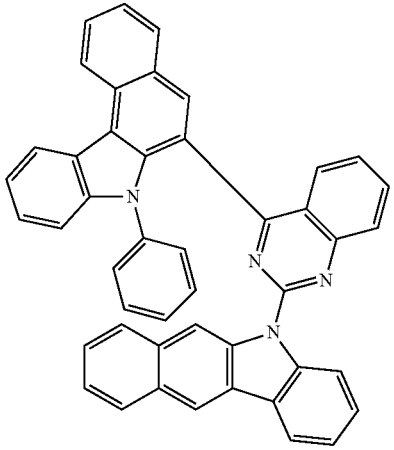
69
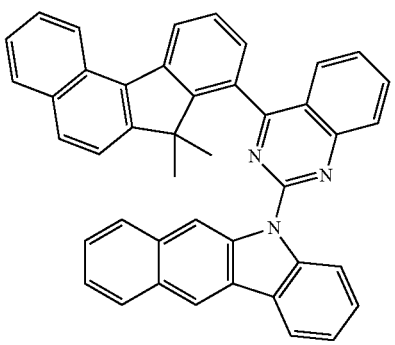
70
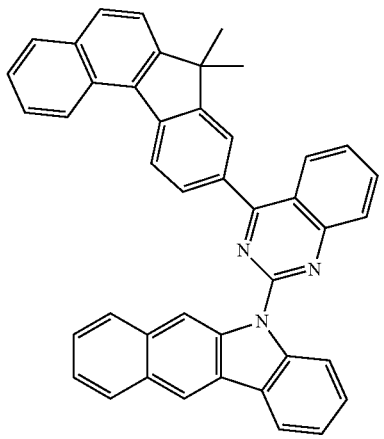
71
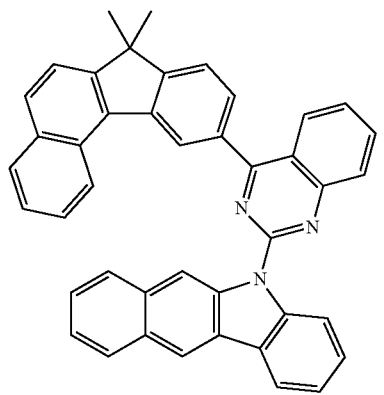

-continued

72

73

74

75

-continued

76

77

78

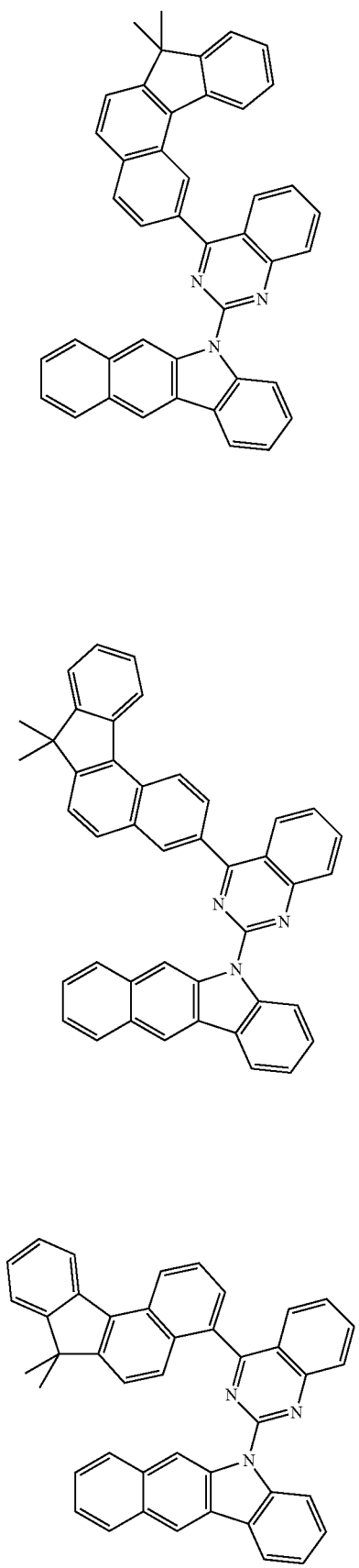
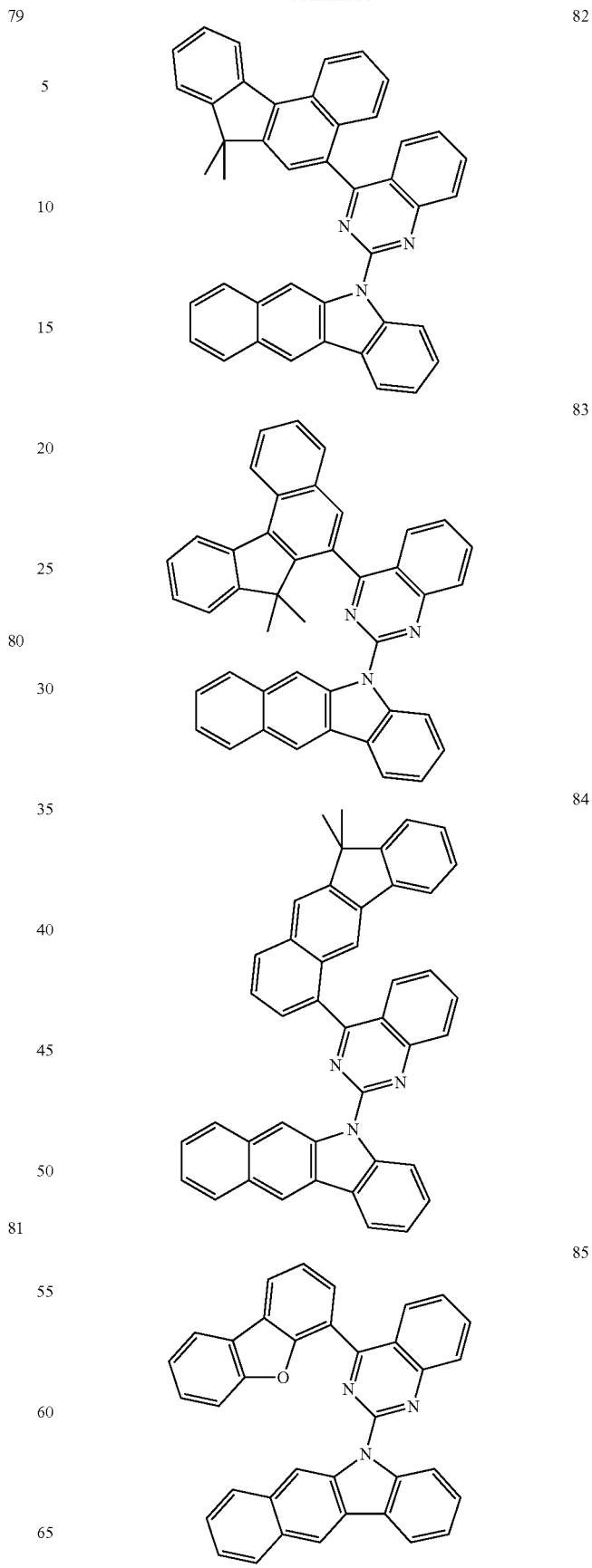

86 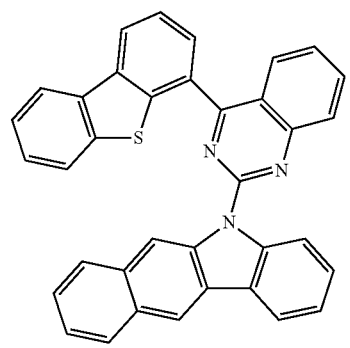
87 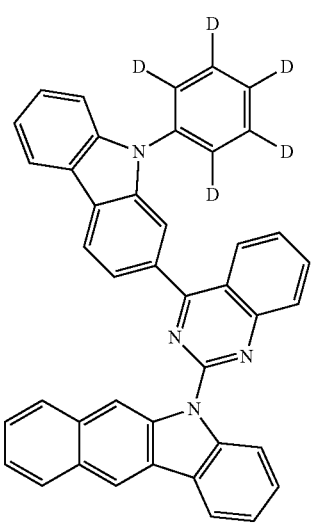
88 
89 
90 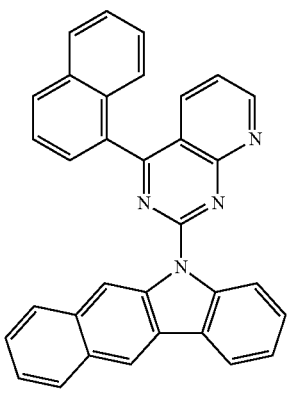
91 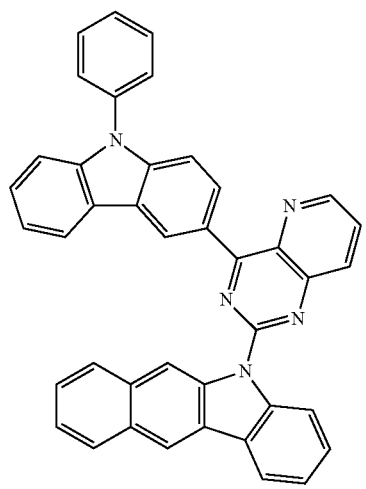
92 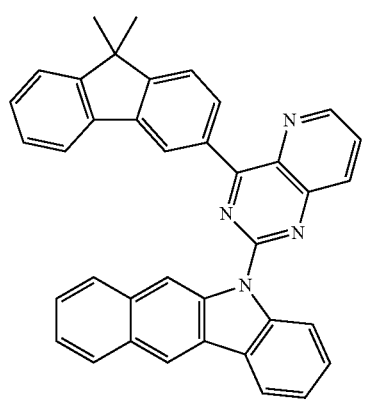

93
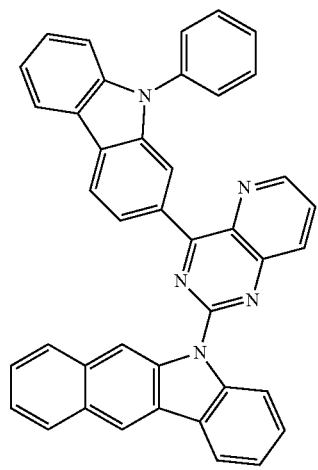
94
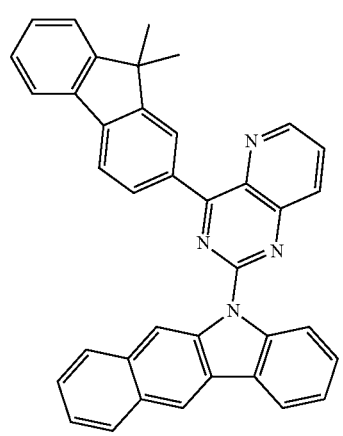
95
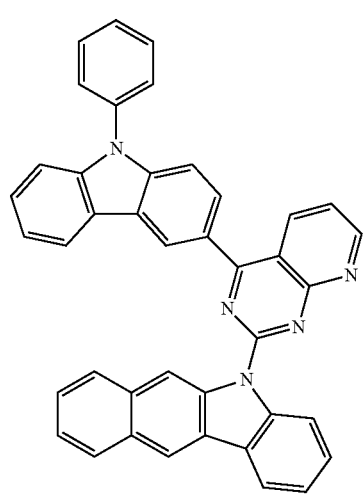
96
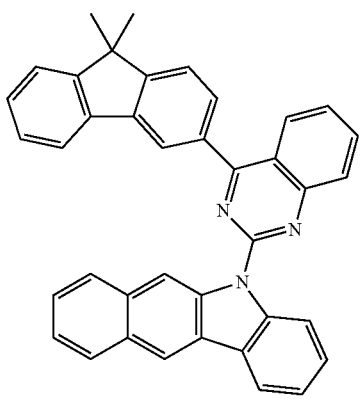
97
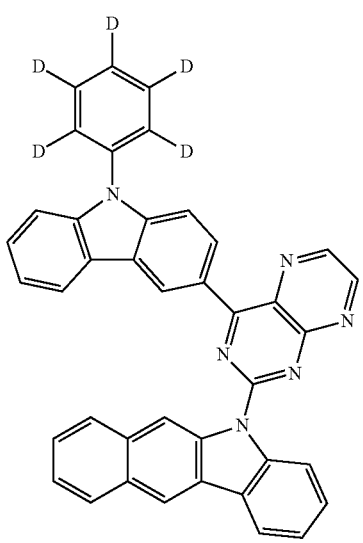
98
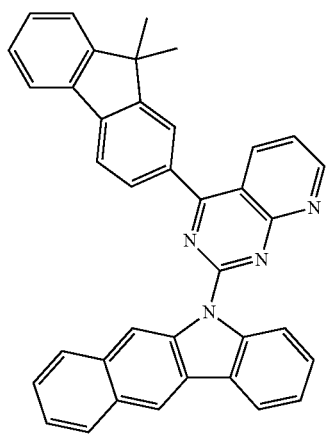

99
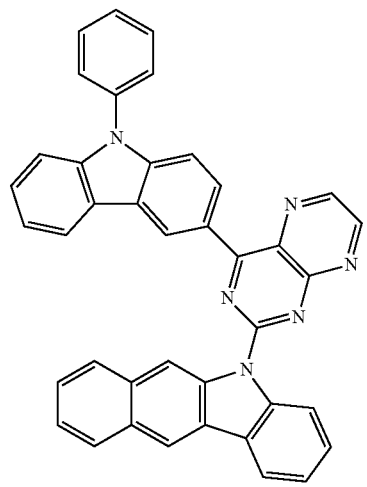
100
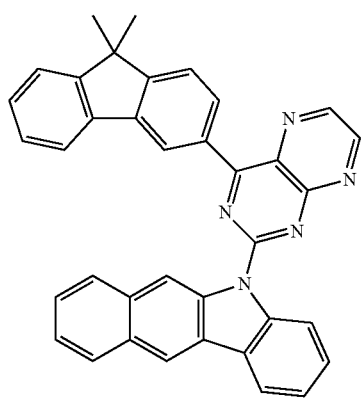
101
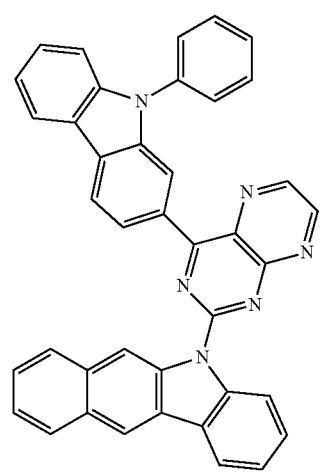
102
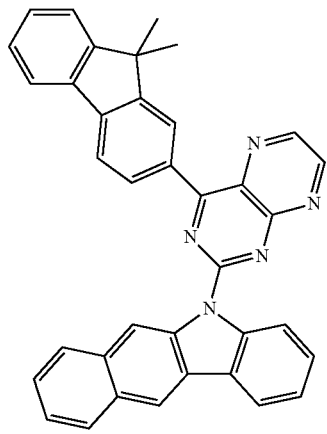
103
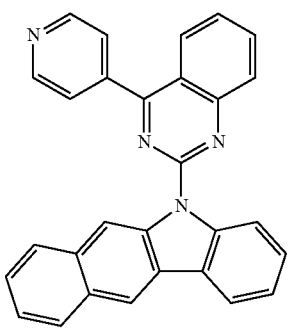
104
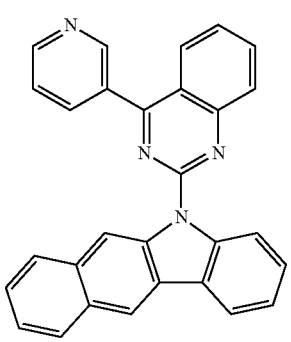
105
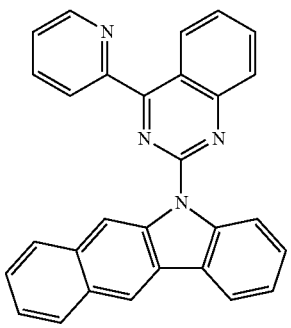

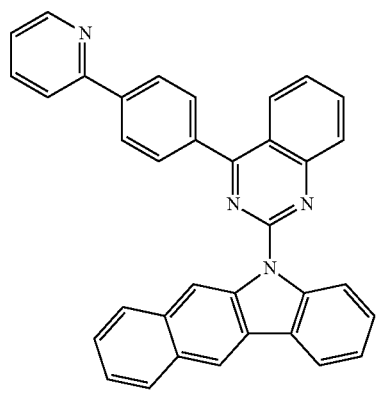
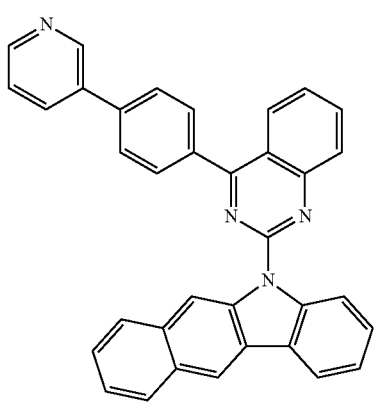

112
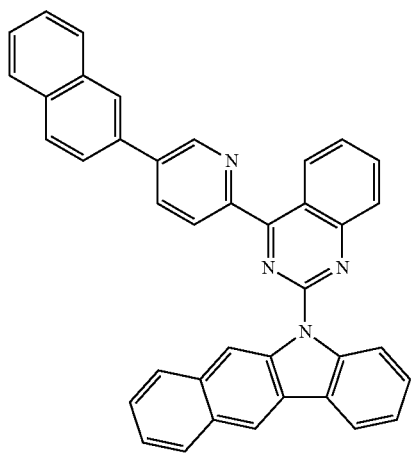
113
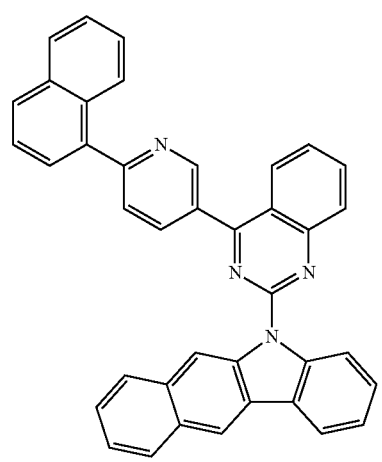
114
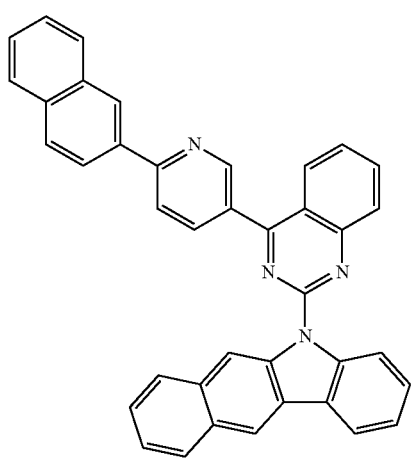
115
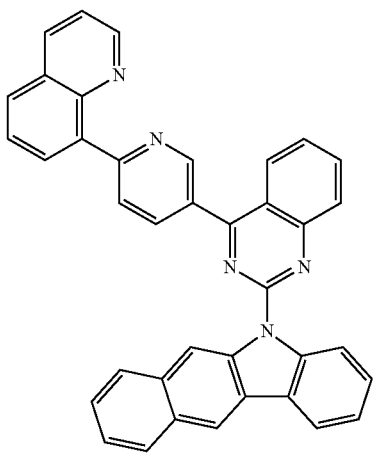
116
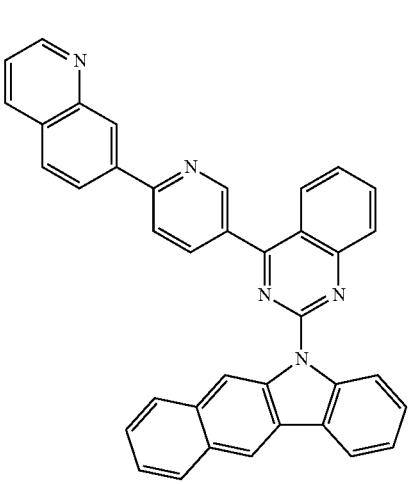
117
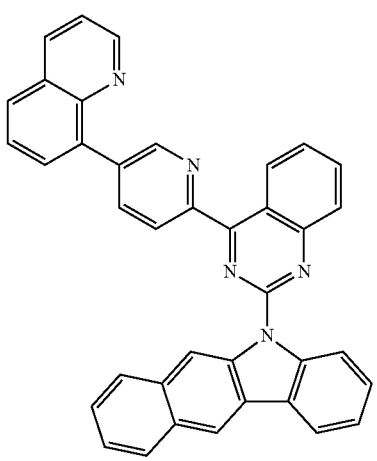

118
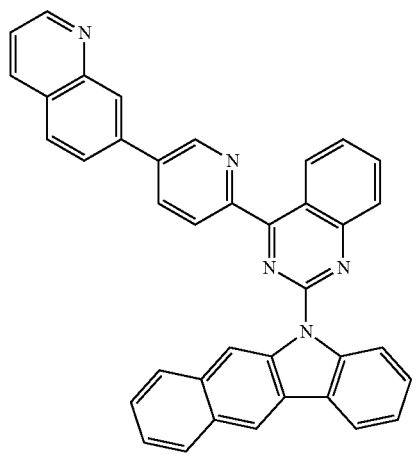
119
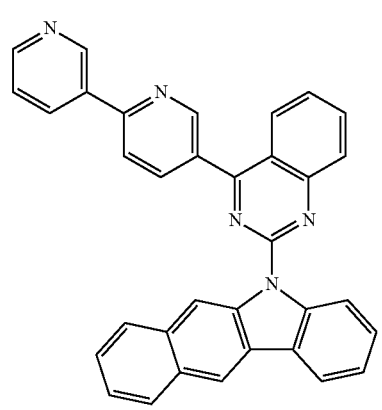
120
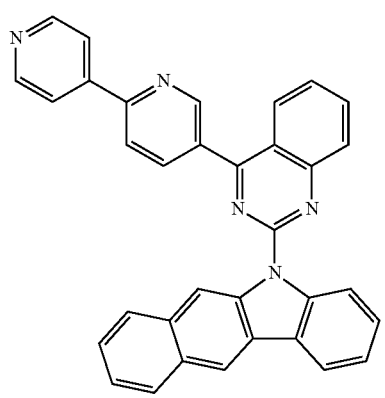
121
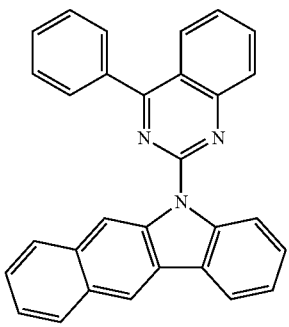
122
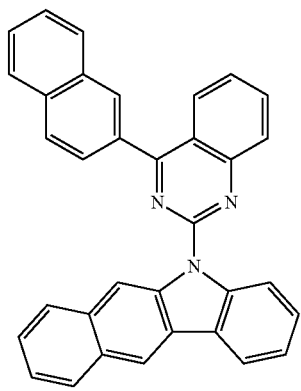
123
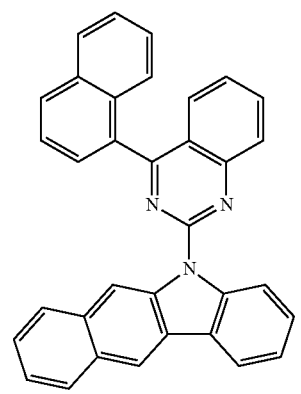
124
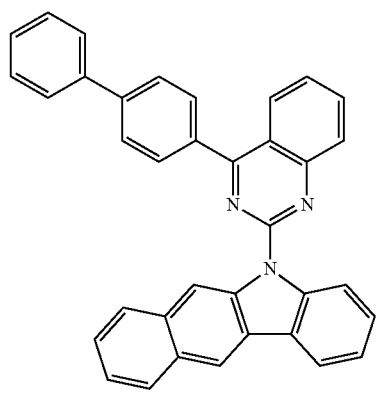
125
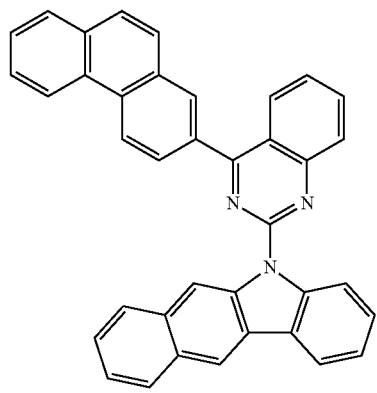

126
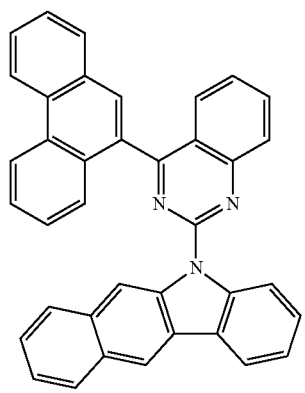
127
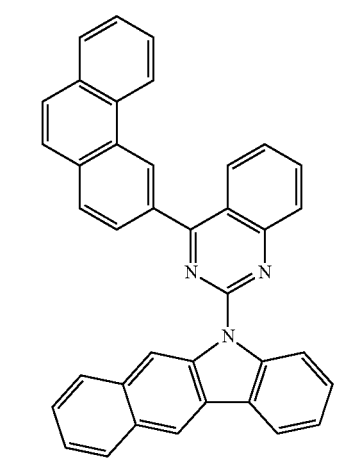
128
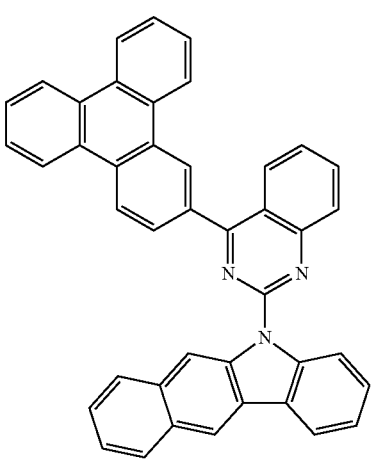
129
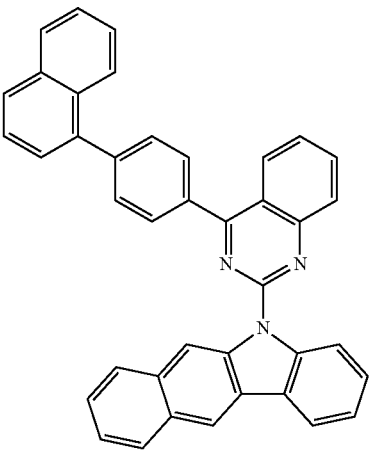
130
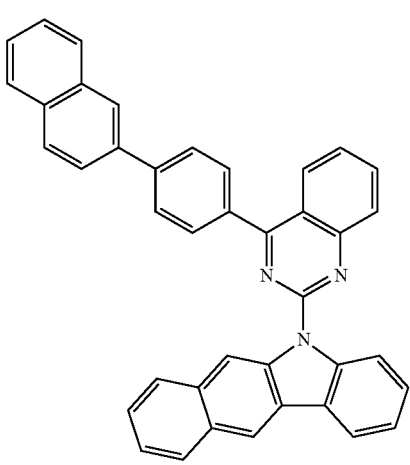
131
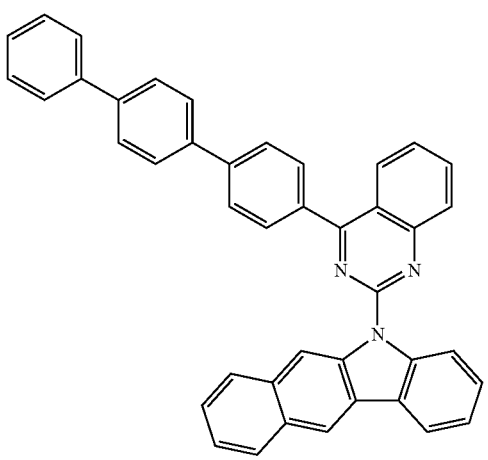

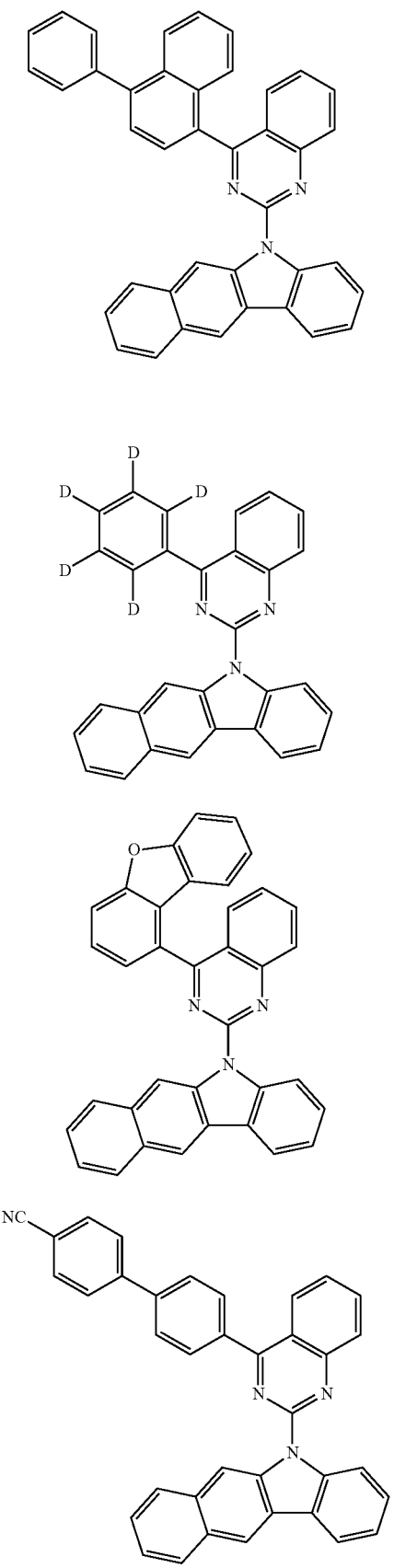
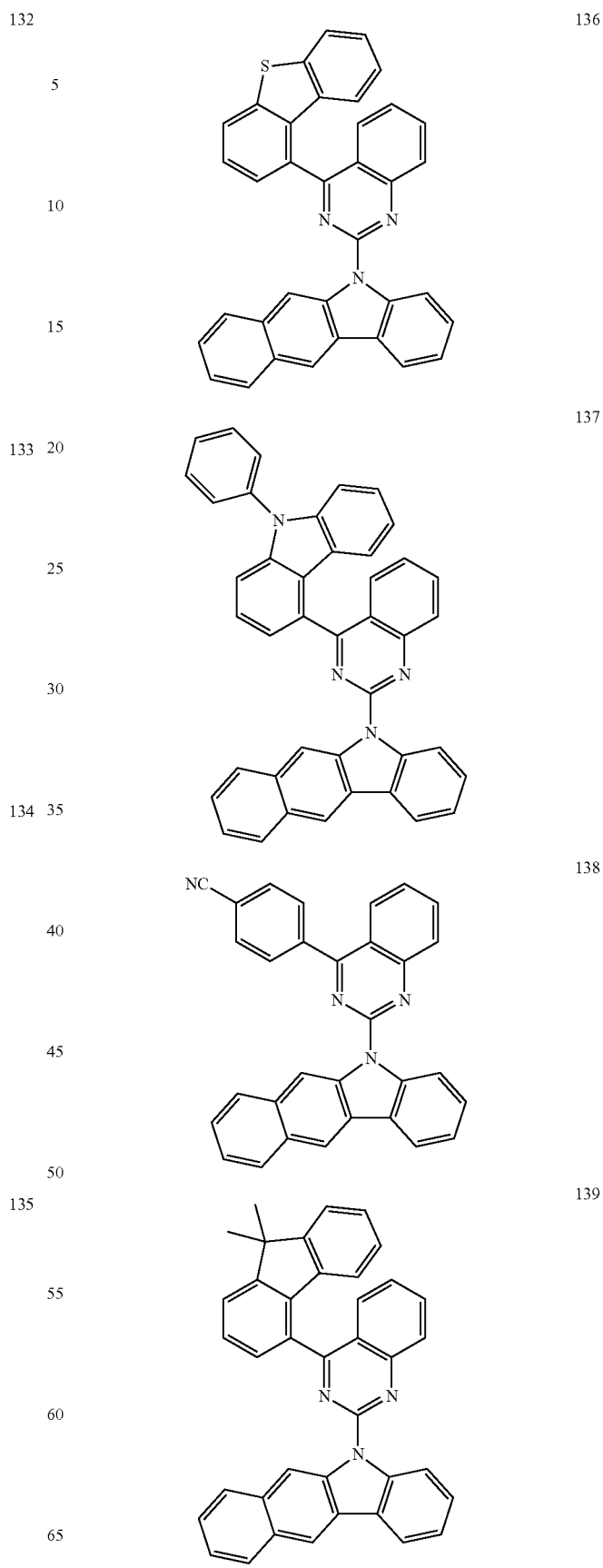

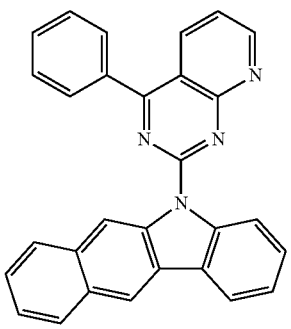
140
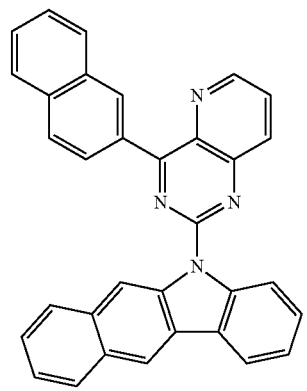
144
141
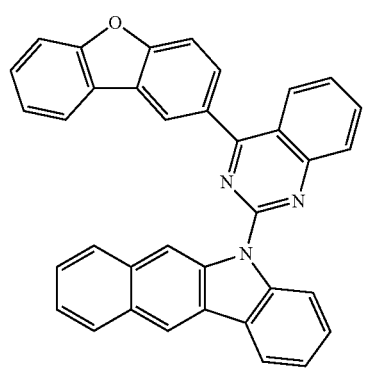
145
142
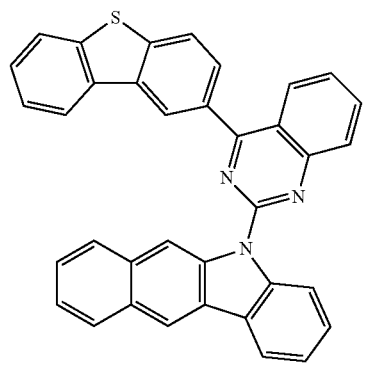
146
143
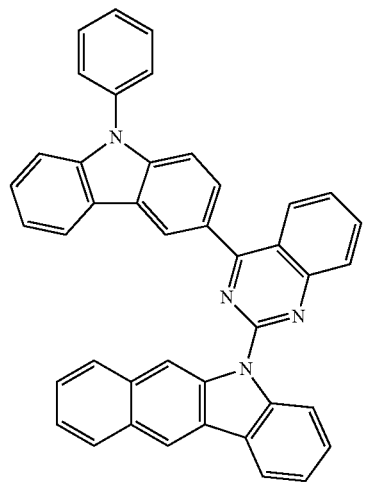
147

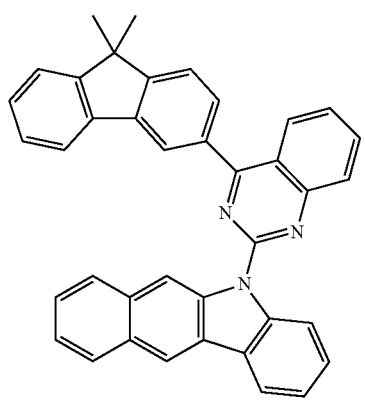
148
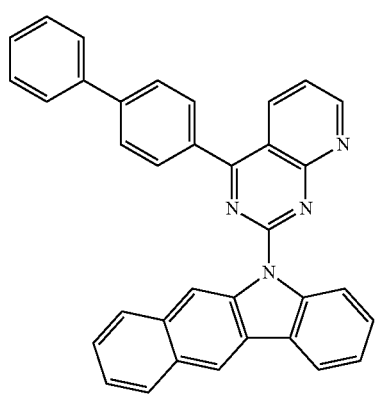
149
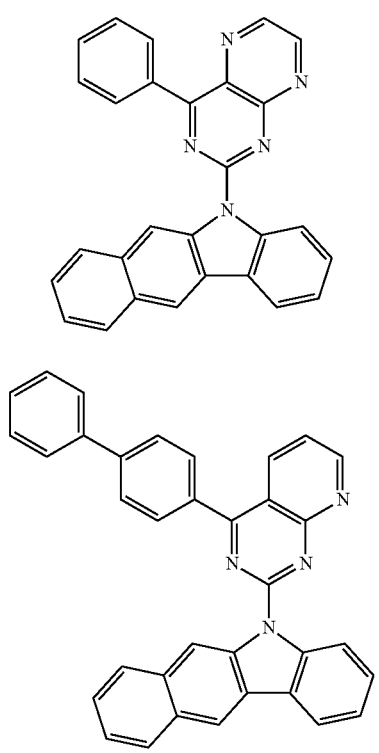
150
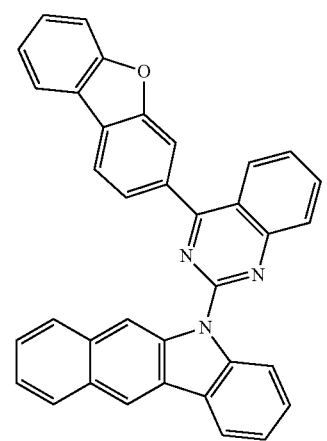
151
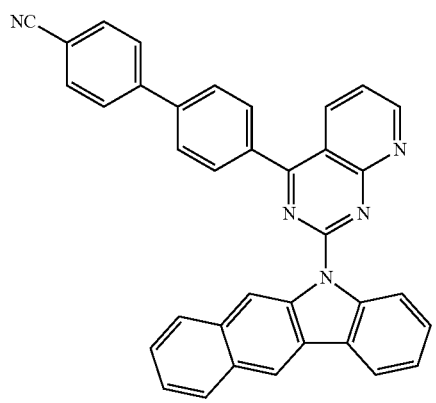
152
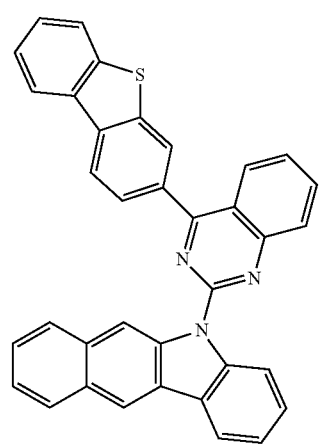
153
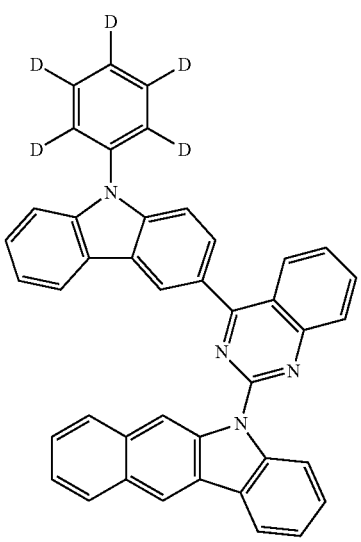
154

155
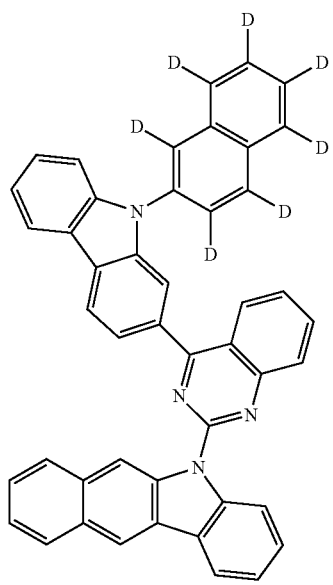
156
157
158
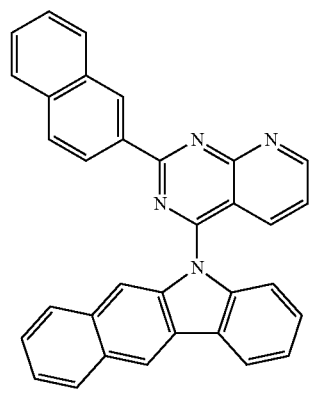
159
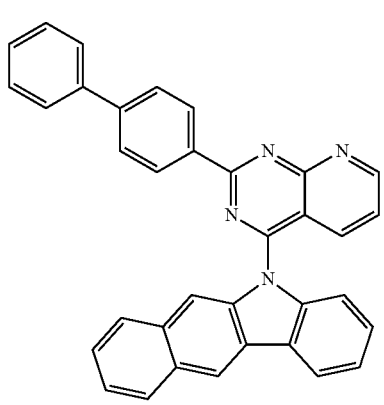
160
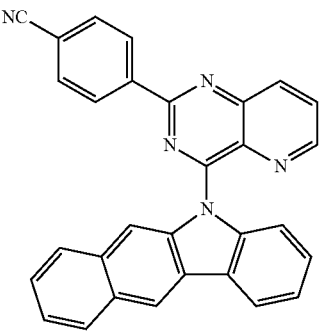
161
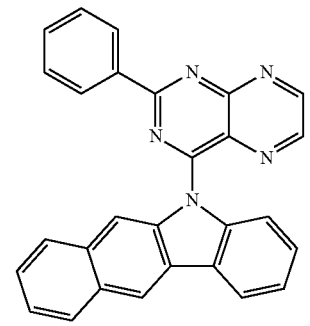

162
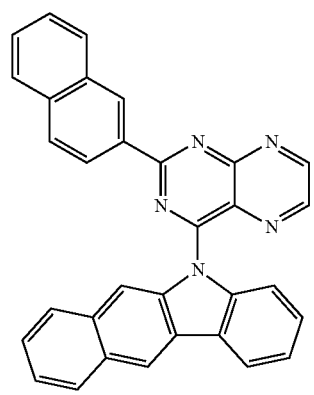
163
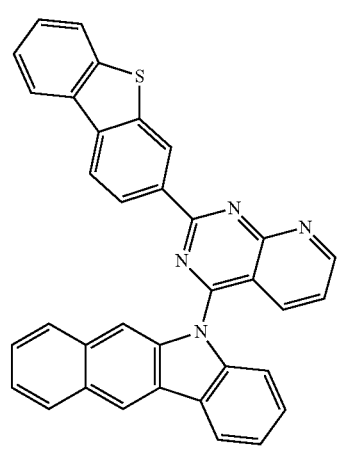
164
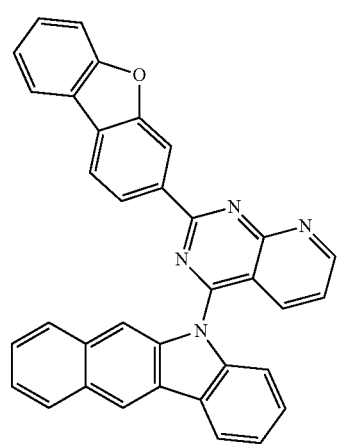
165
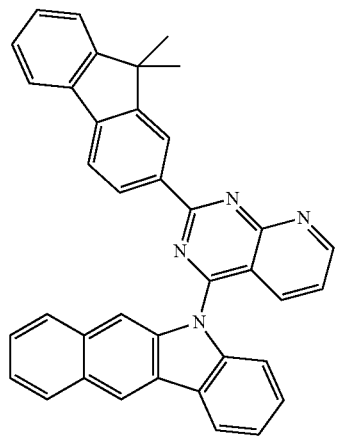
166
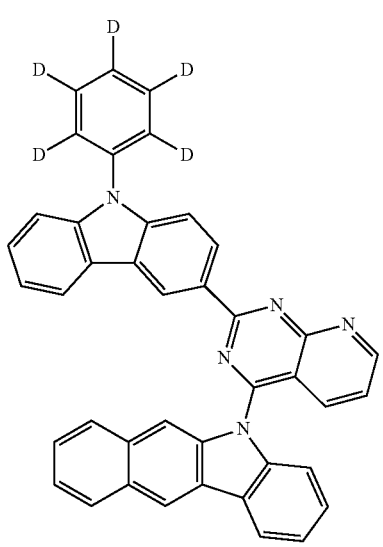
167
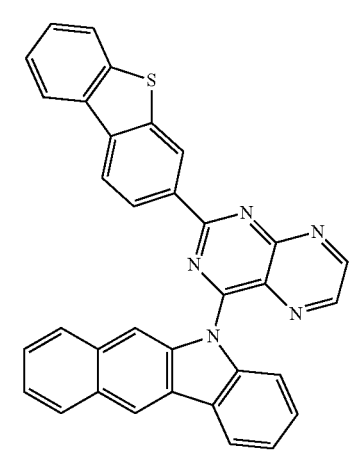

168
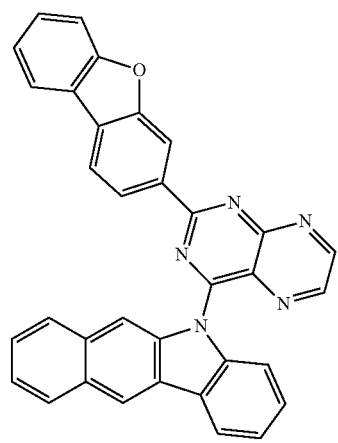
169
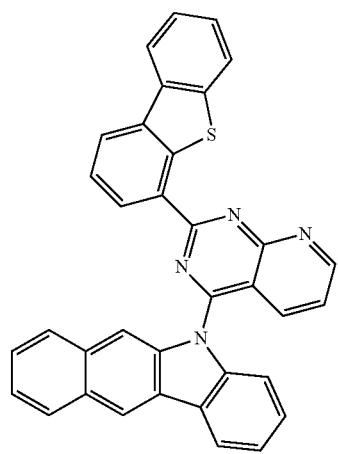
170
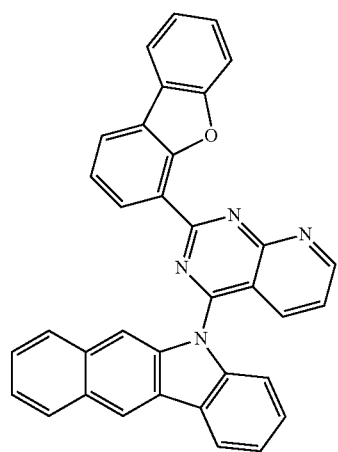
171
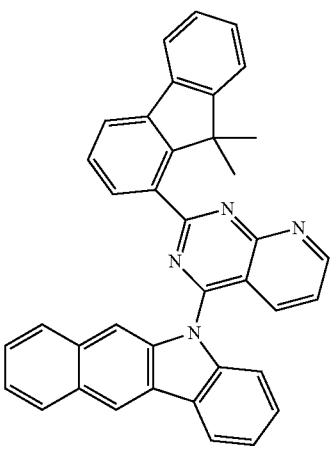
172
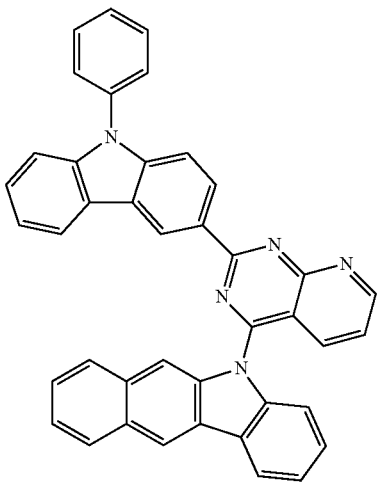
173
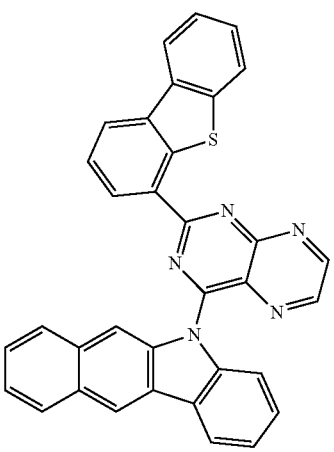

174 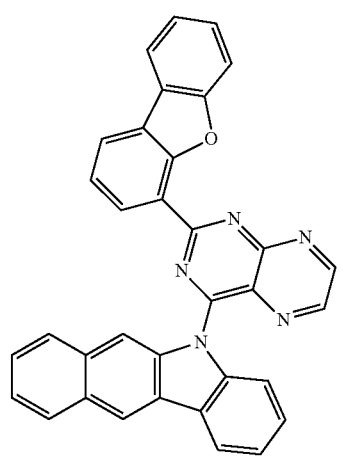
175 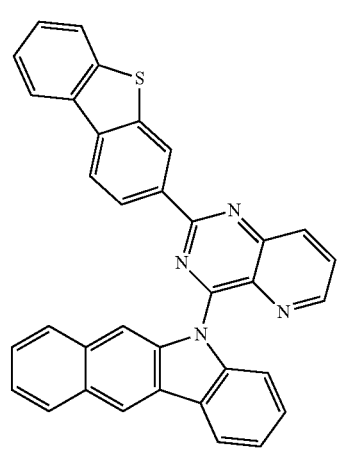
176 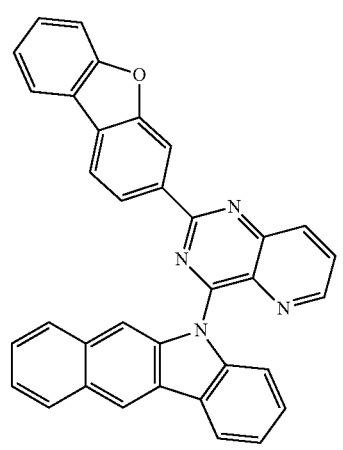
177 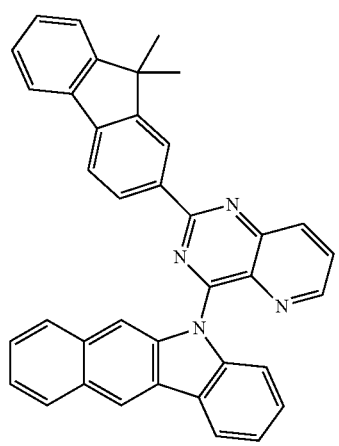
178 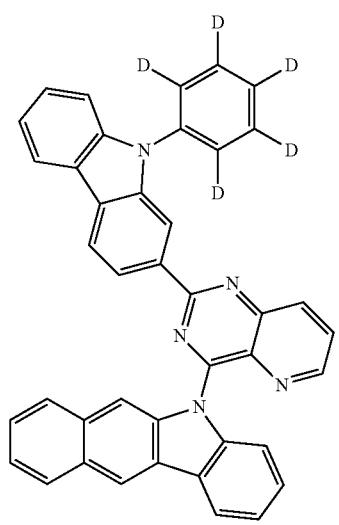
179 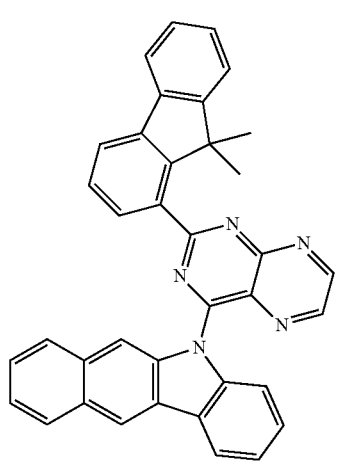

180
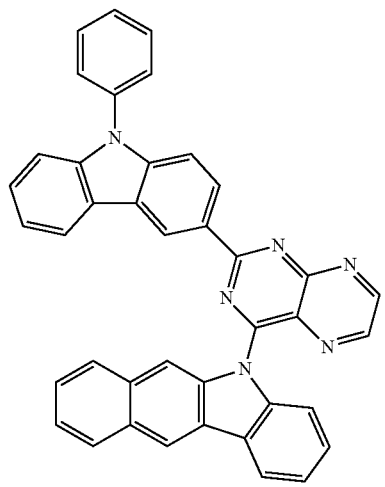
181
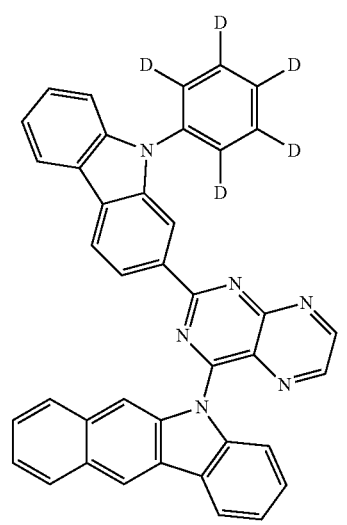
182
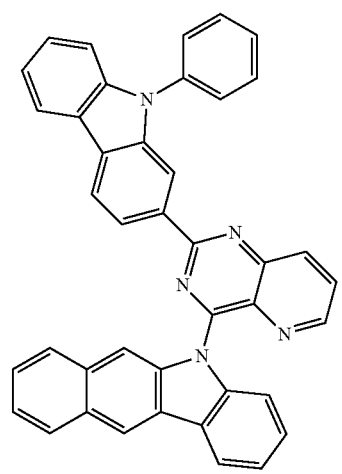
183
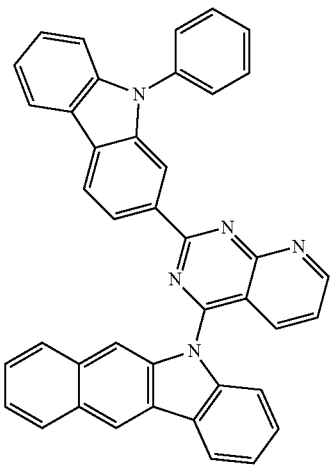
184
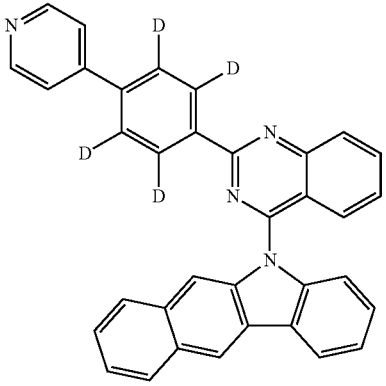
185
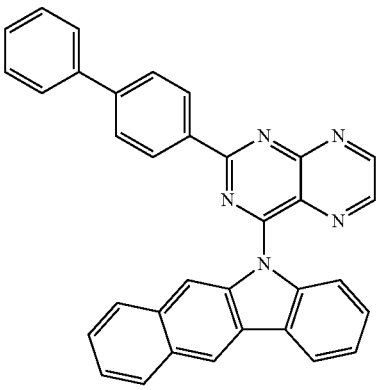

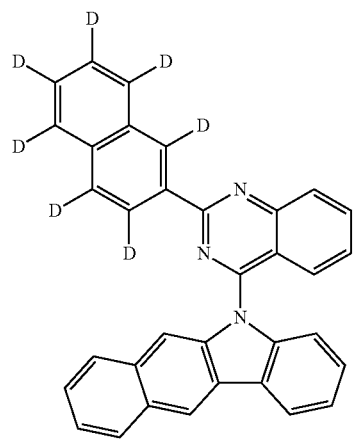
186
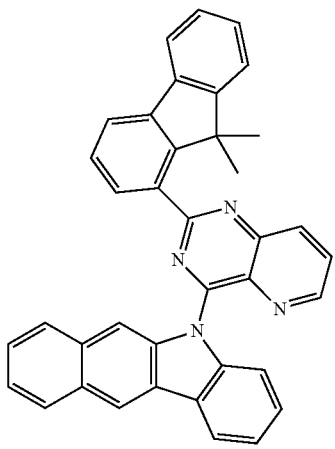
189
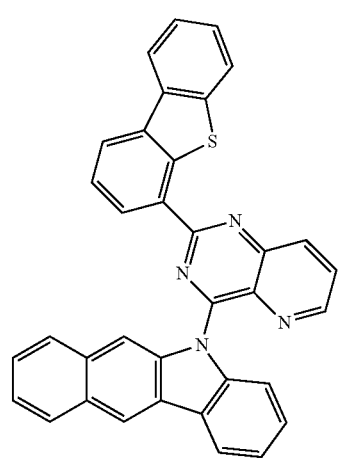
187
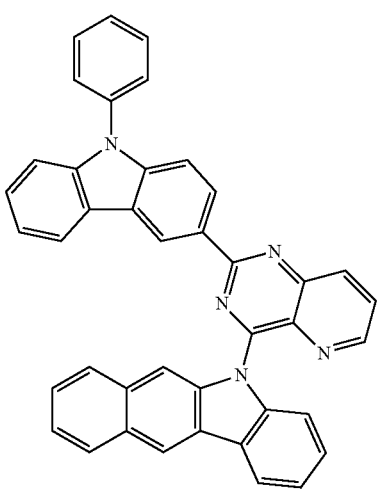
190
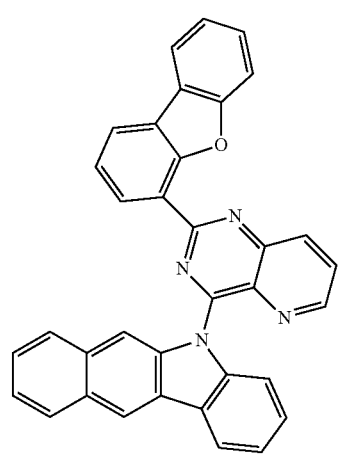
188
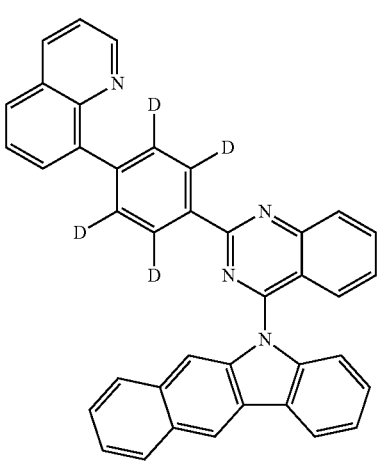
191

192 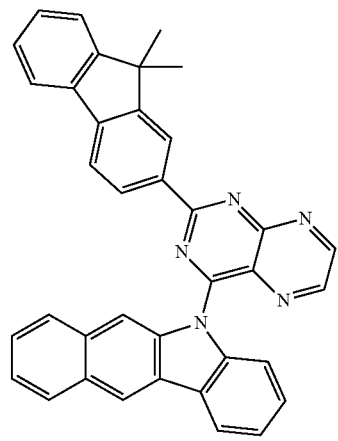
193 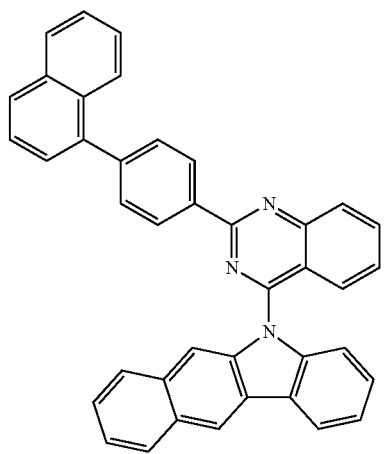
194 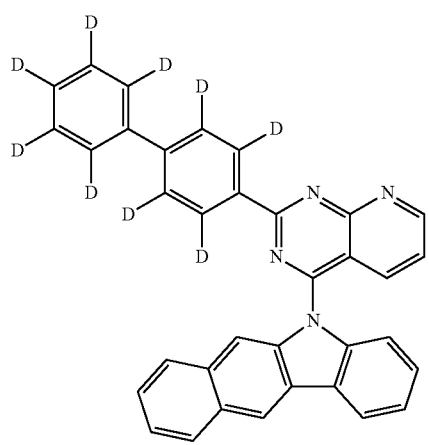
195 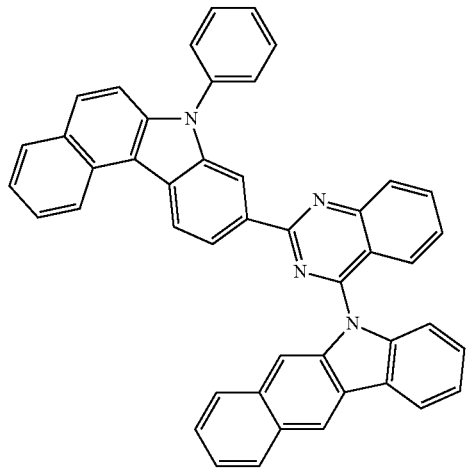
196 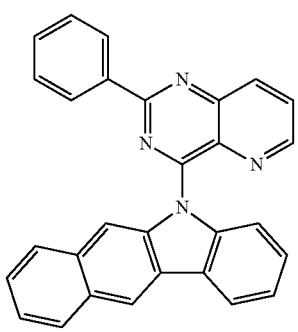
197 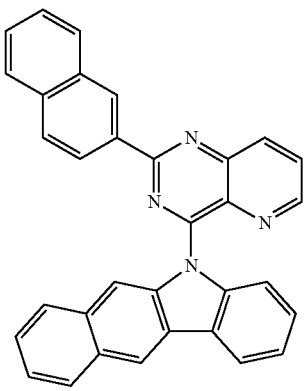
198 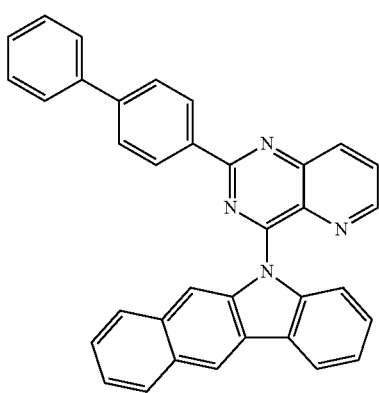

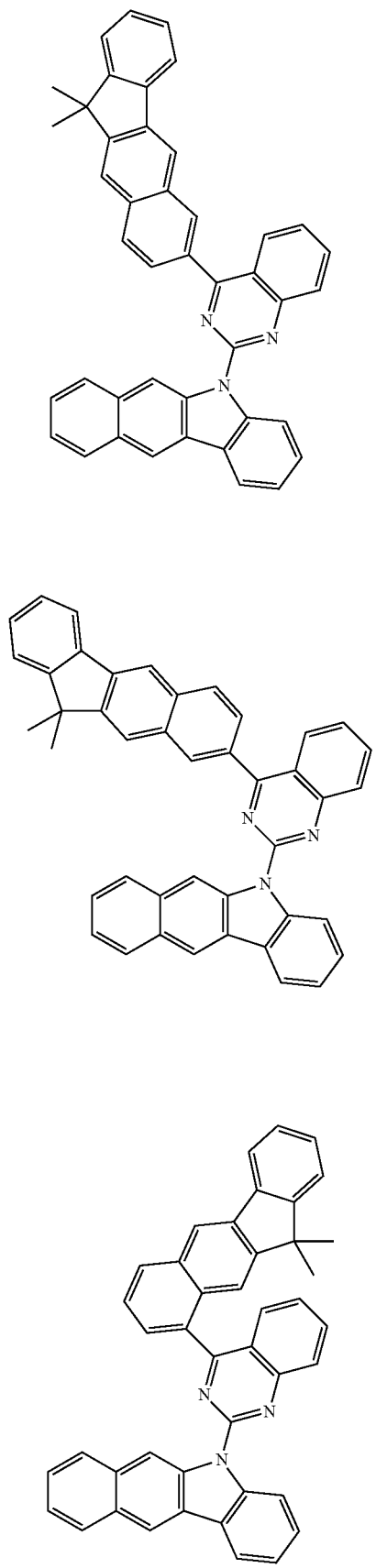
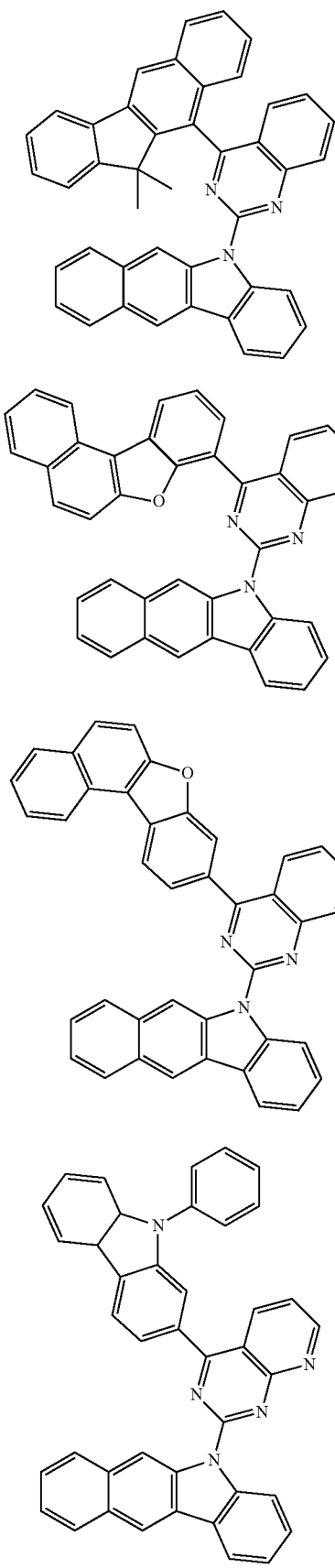

206
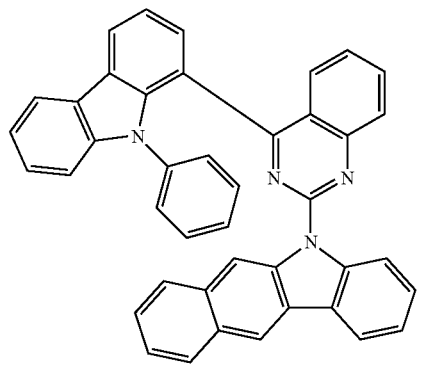
207
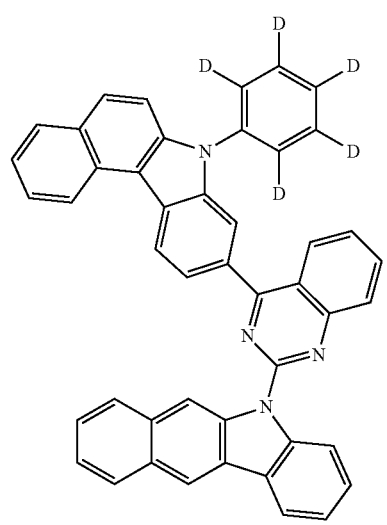
208
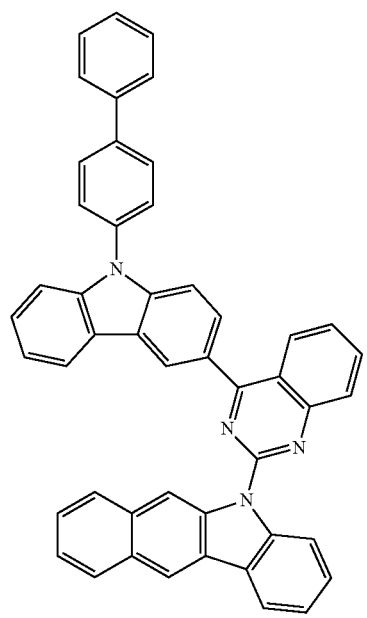
209
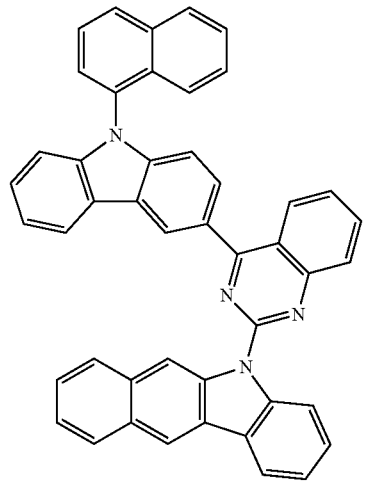
210
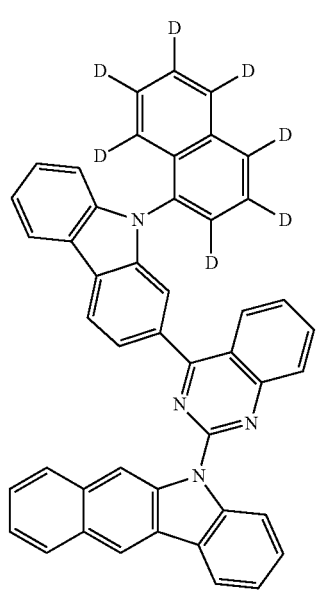
211
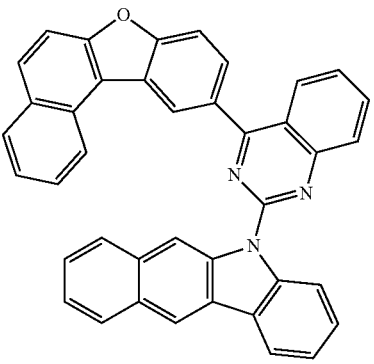

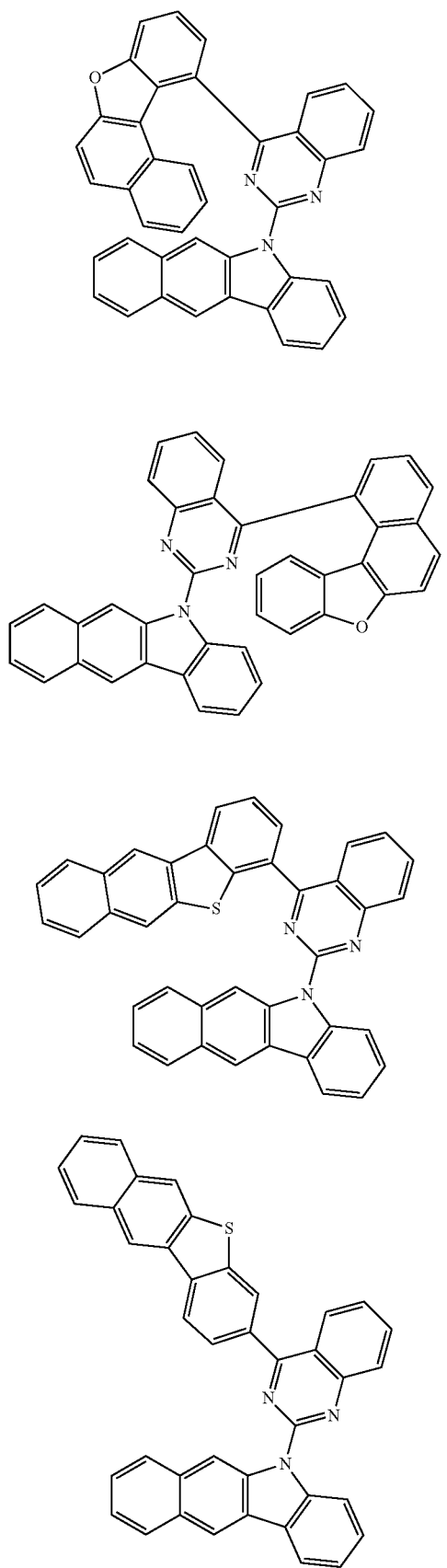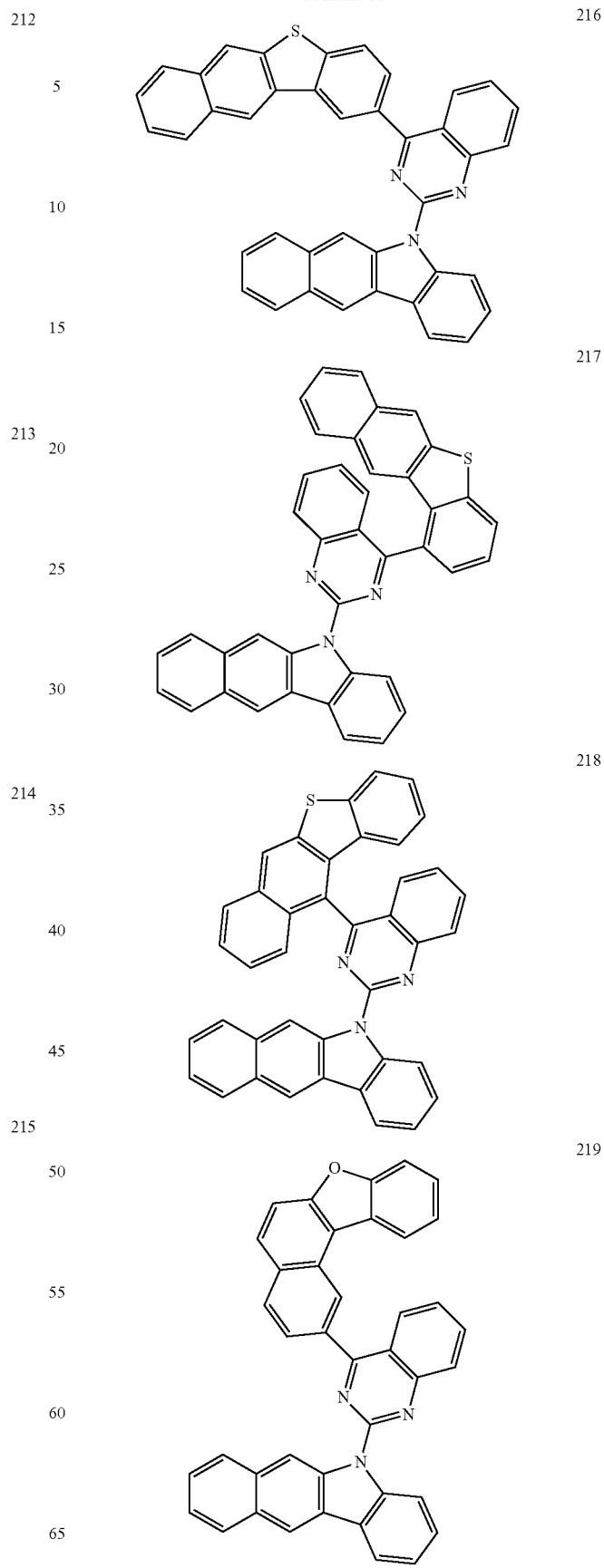

89
-continued
220
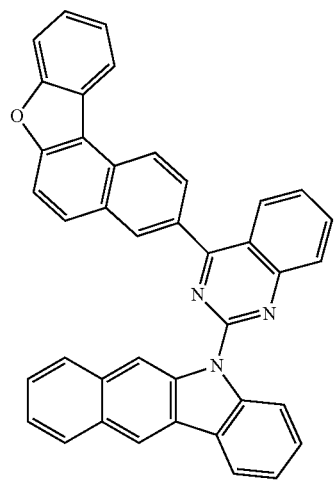
221
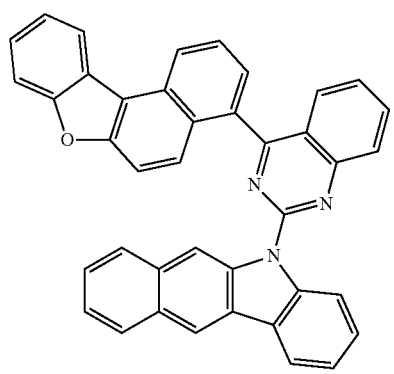
222
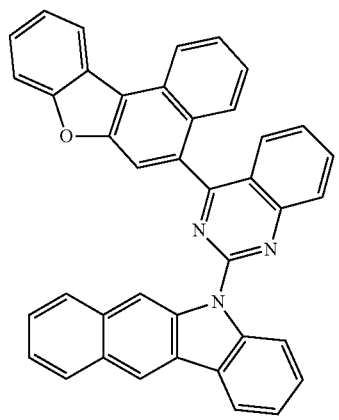
90
-continued
223
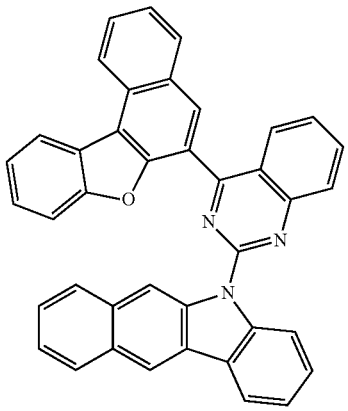
224
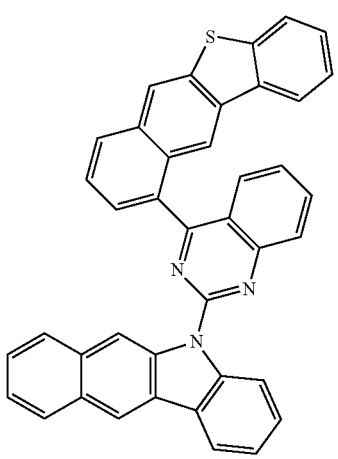
225
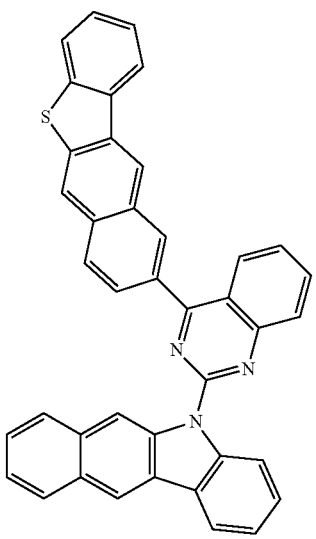

91
-continued
226
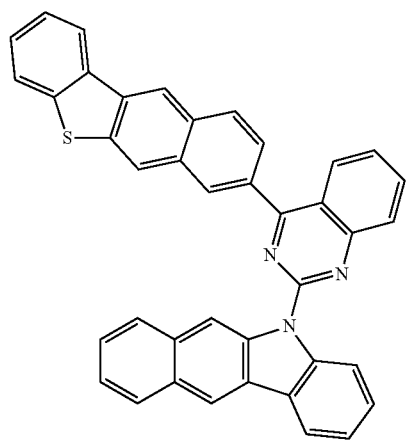
227
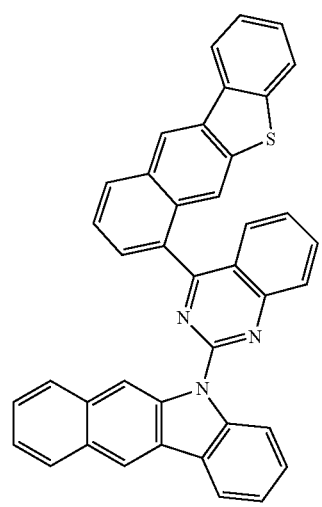
228
92
-continued
229
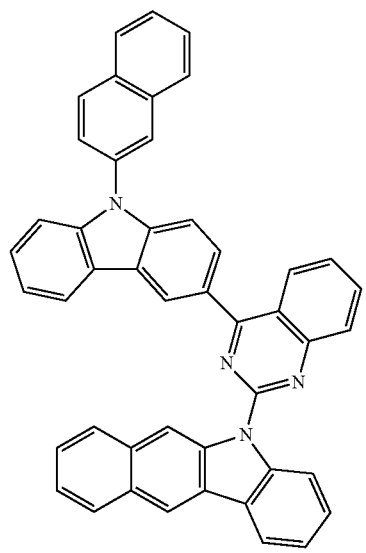
230
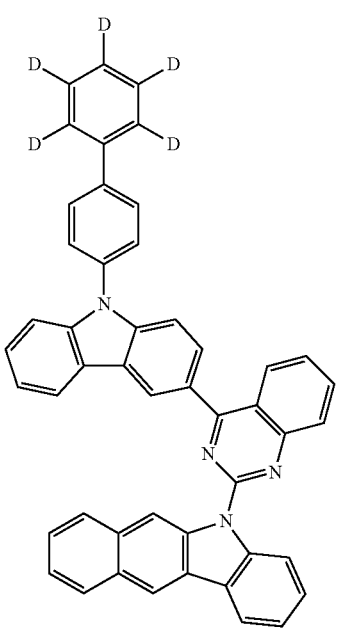

231
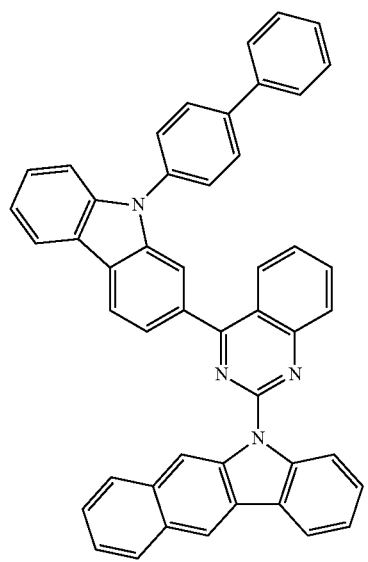
232
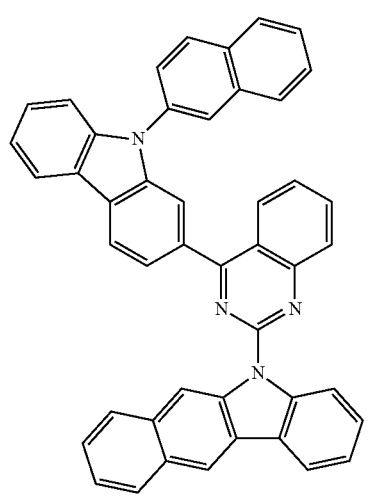
233
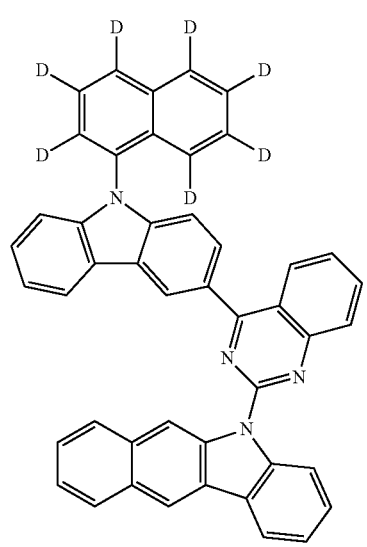
234
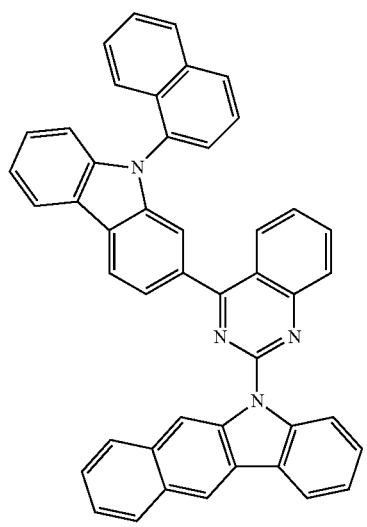
235
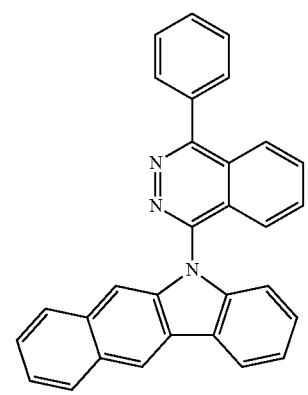
236
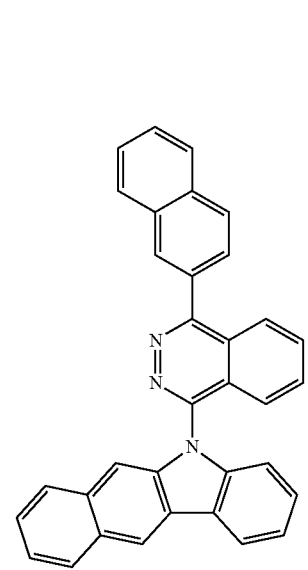

237 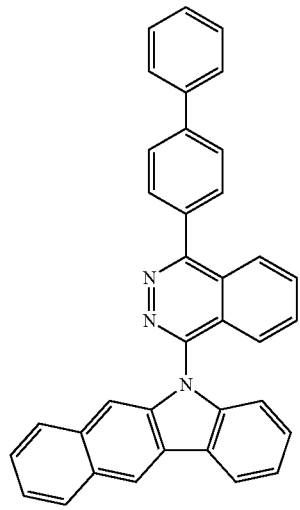
238 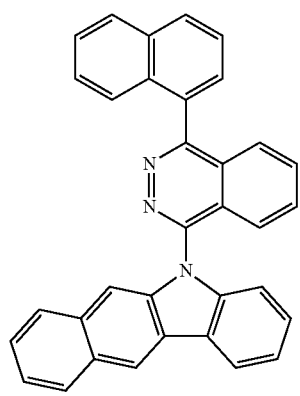
239 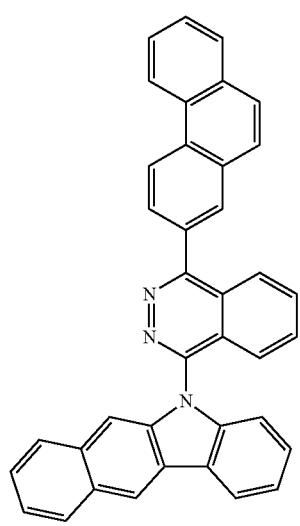
240 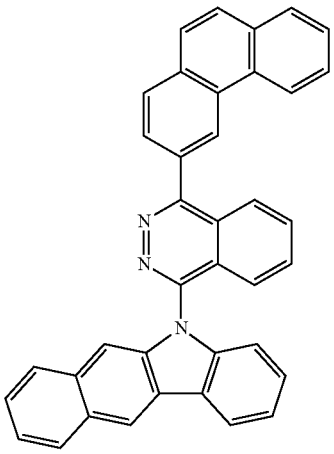
241 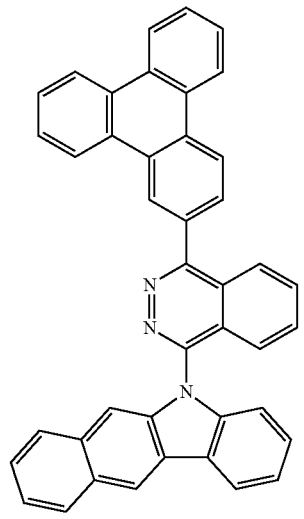
242 

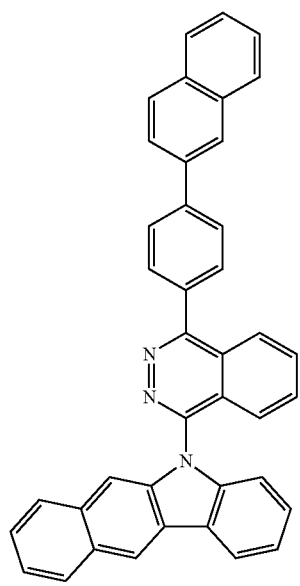
243
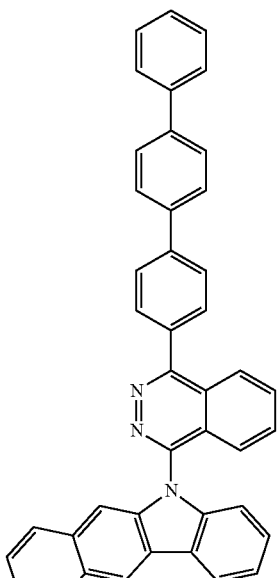
245
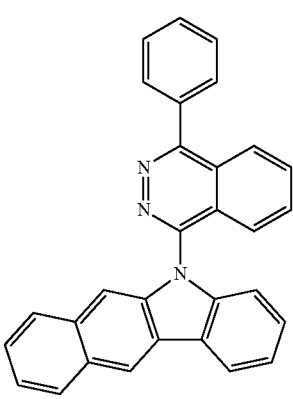
246
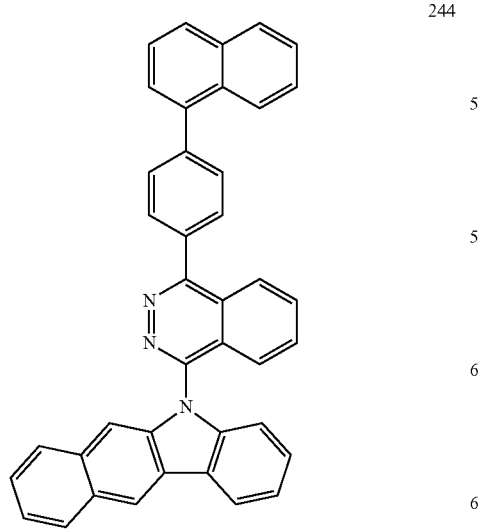
244
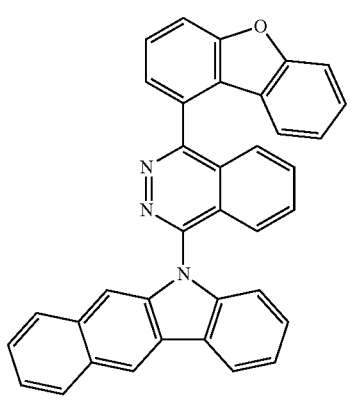
247

248
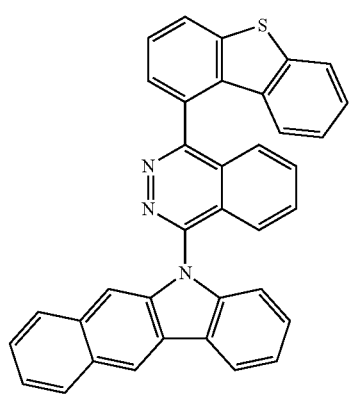
249
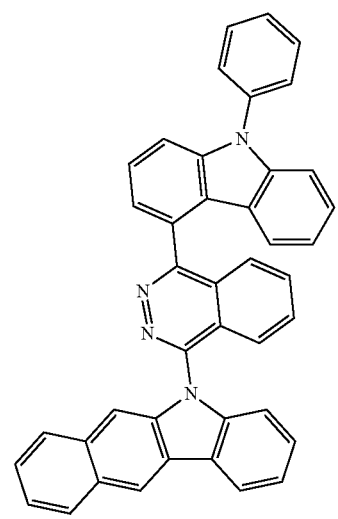
250
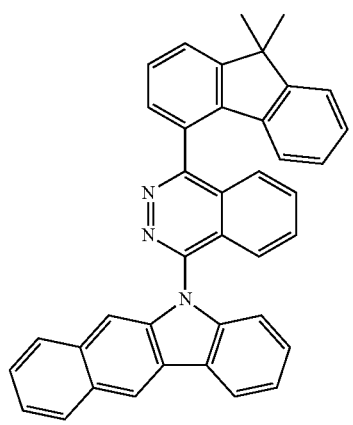
251
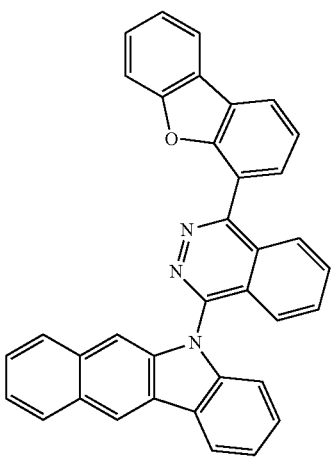
252
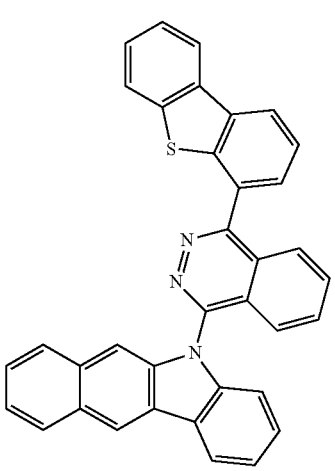
253
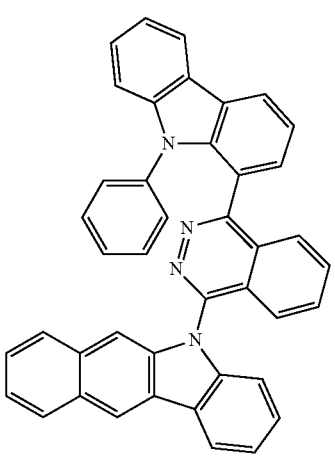

254
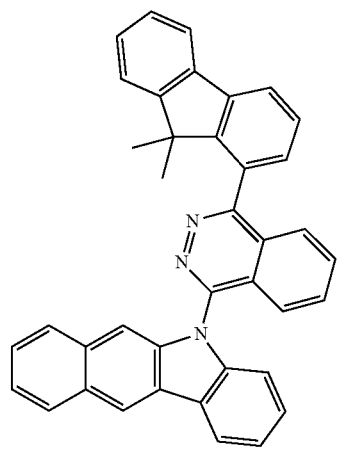
255
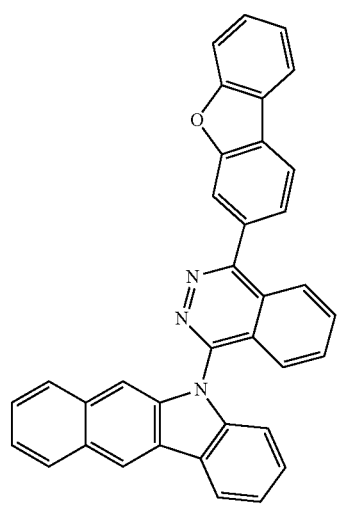
256
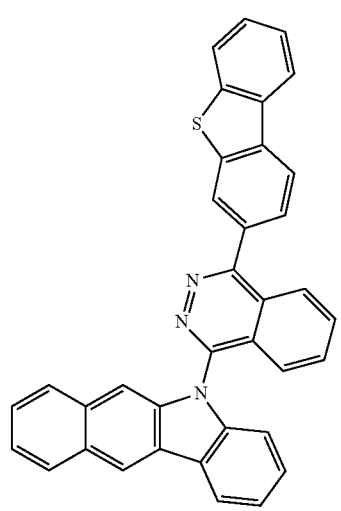
257
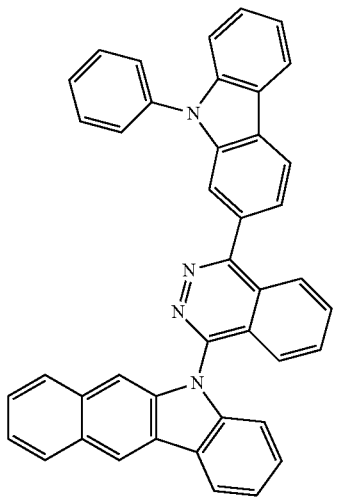
258
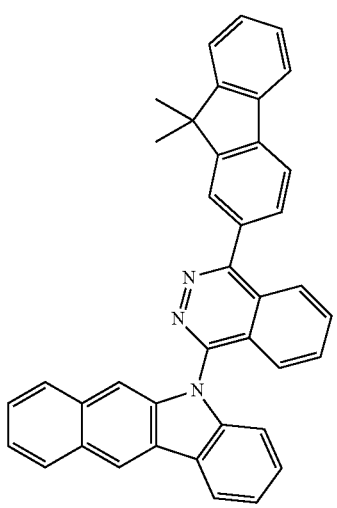
259
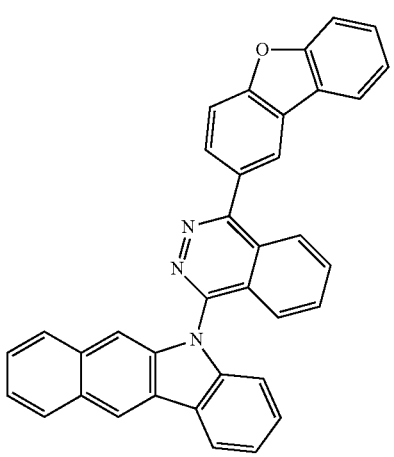

| 103 | 104 |
|---|---|
| 260 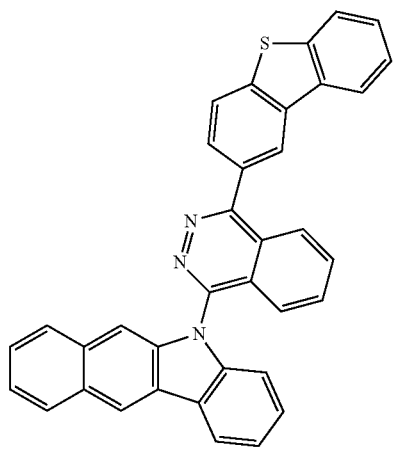 | 263 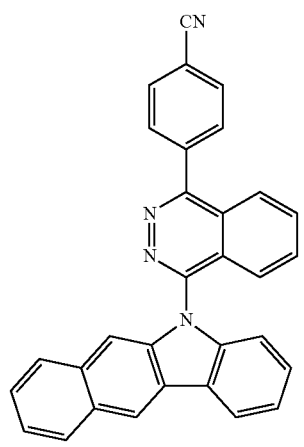 |
| 261 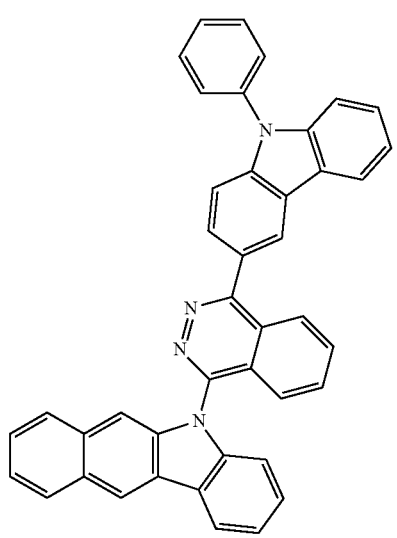 | 264 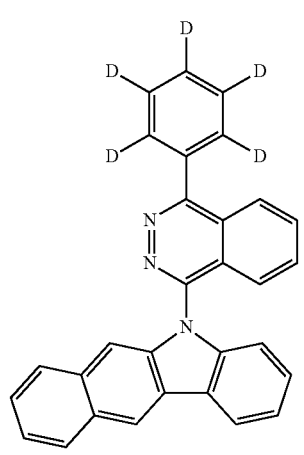 |
| 262 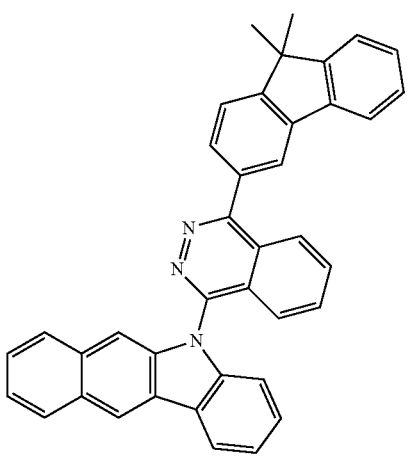 | 265 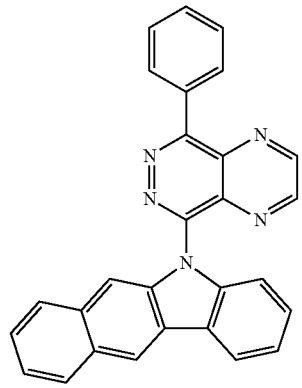 |

266
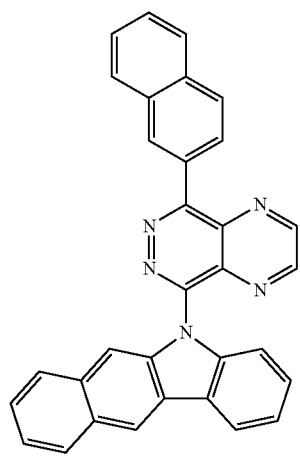
267
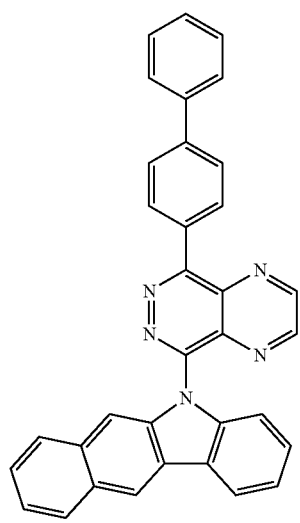
268
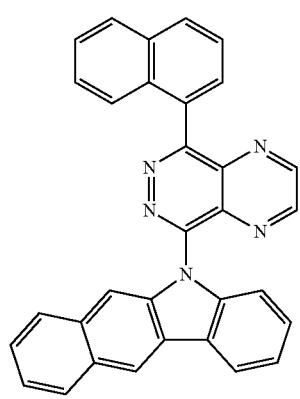
269
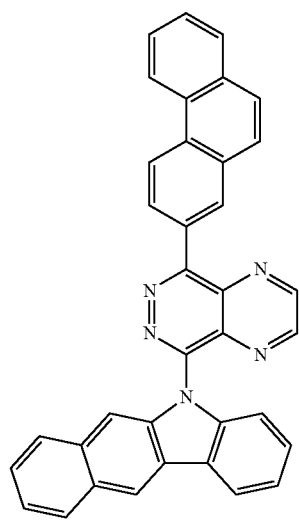
270
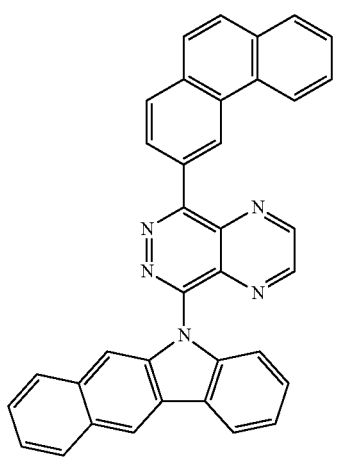
271
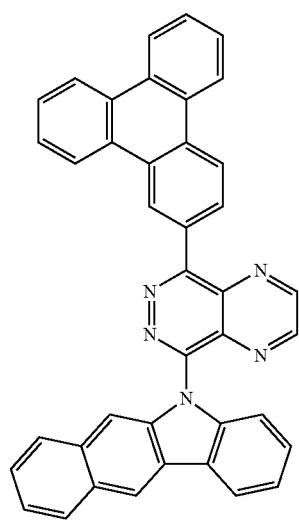

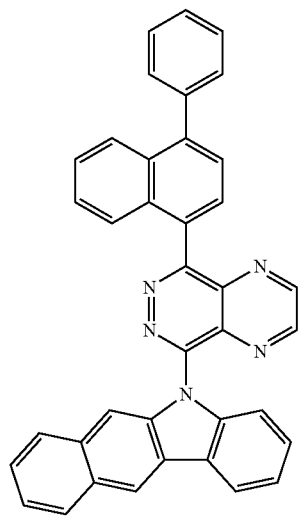
272
273
274
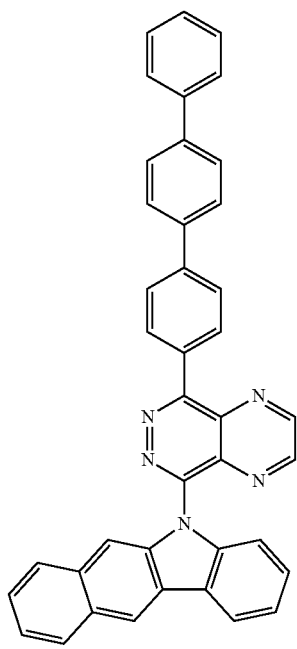
275
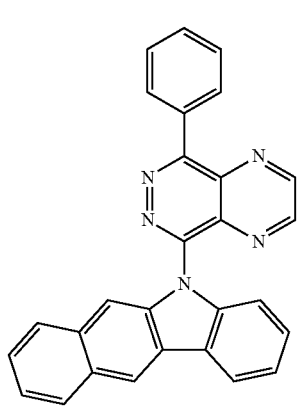
276
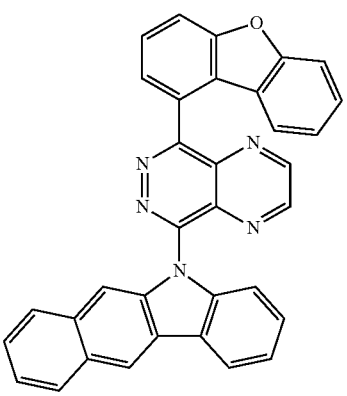
277

278
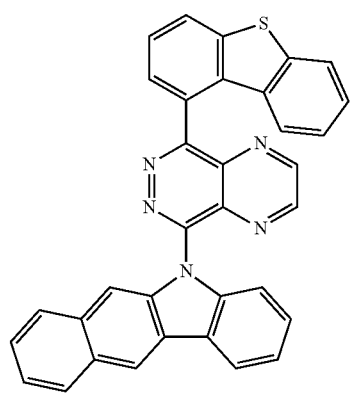
279
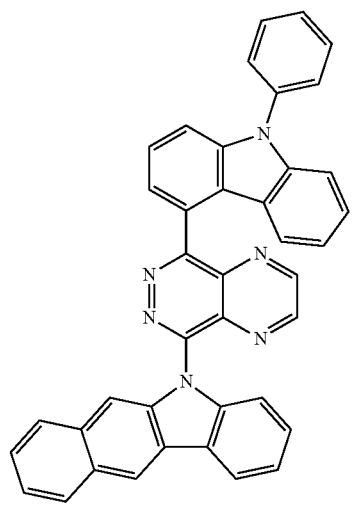
280
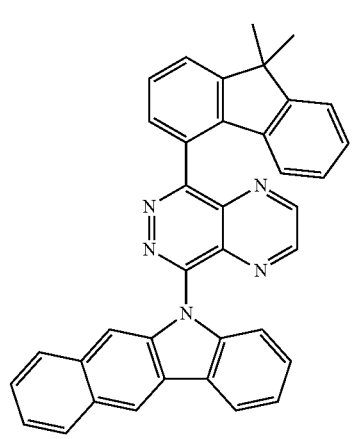
281
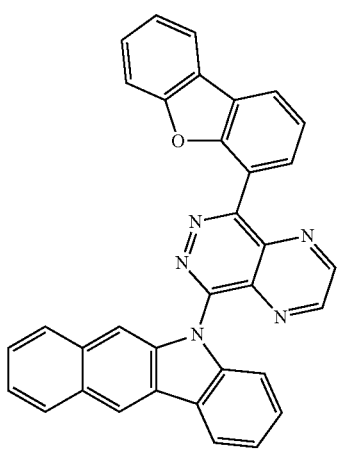
282
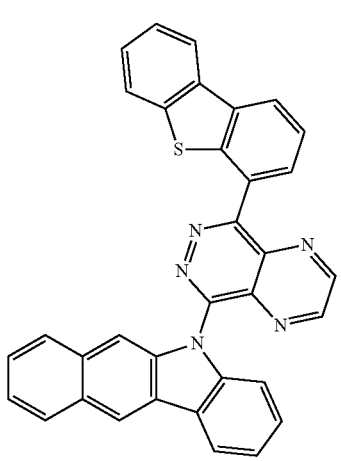
283
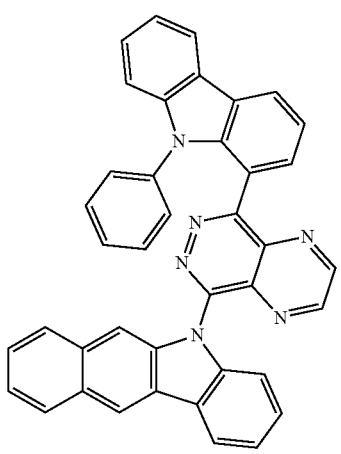

284 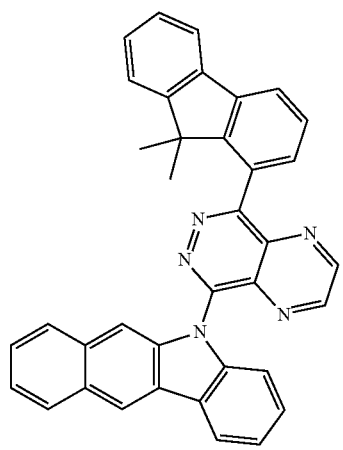
285 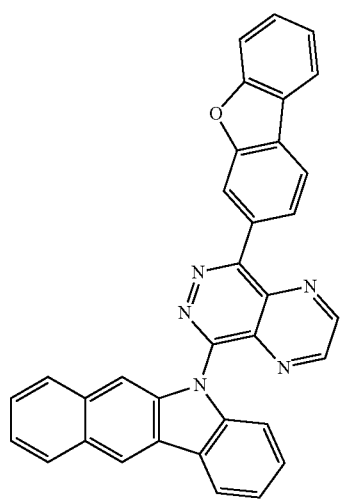
286 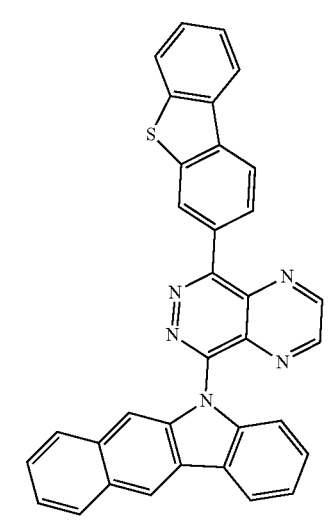
287 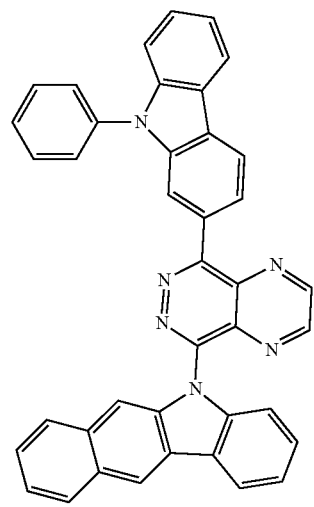
288 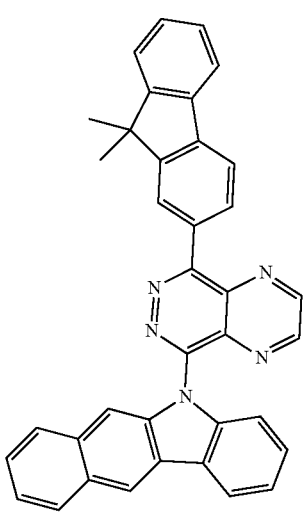
289 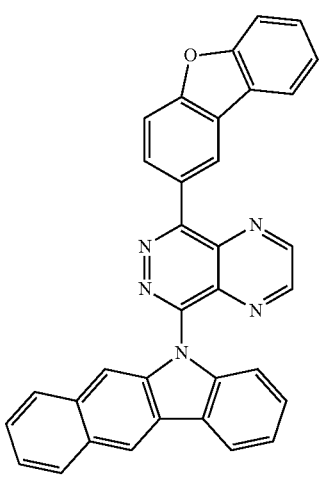

290
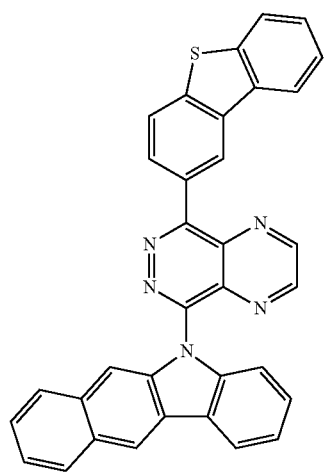
291
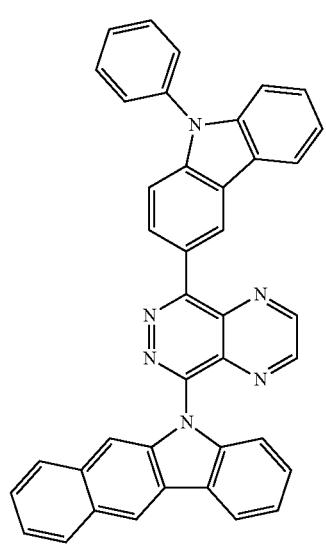
292
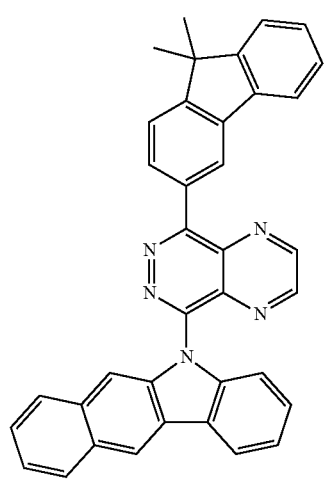
293
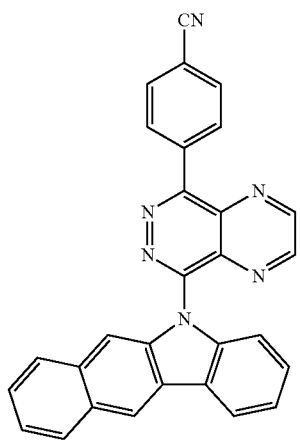
294
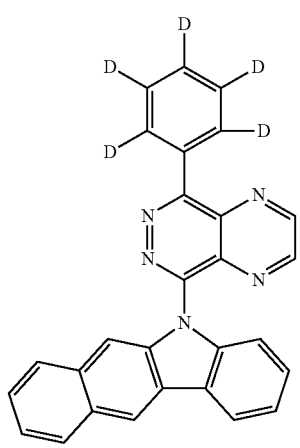
295
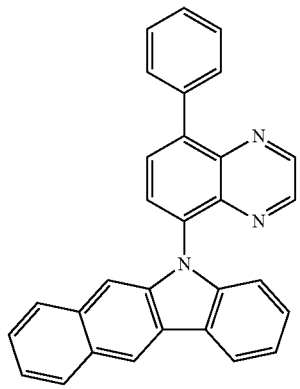

296
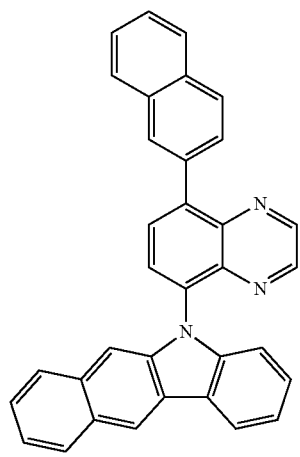
297
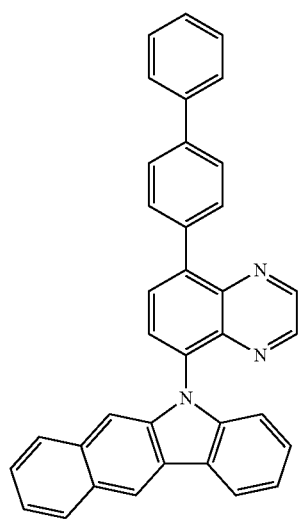
298
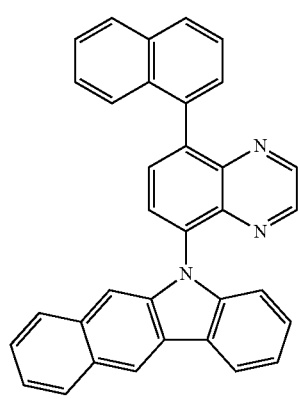
299
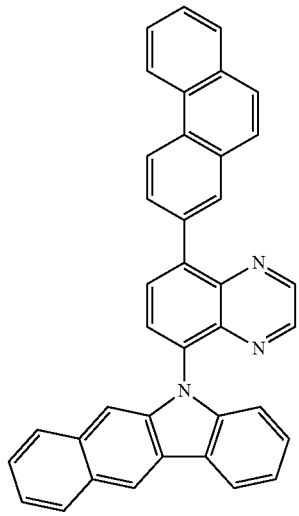
300
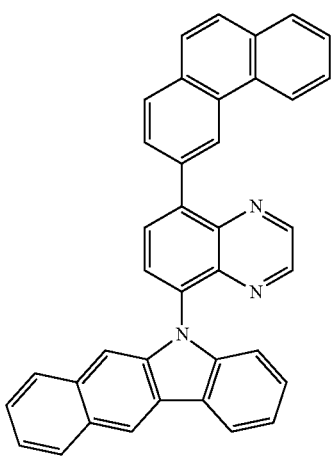
301
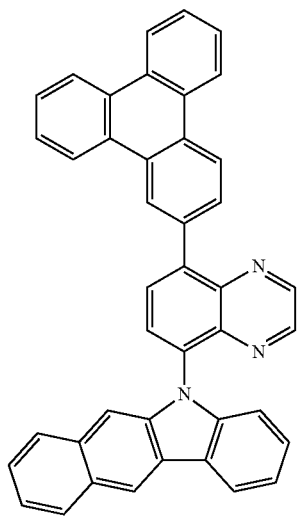

117
-continued
302
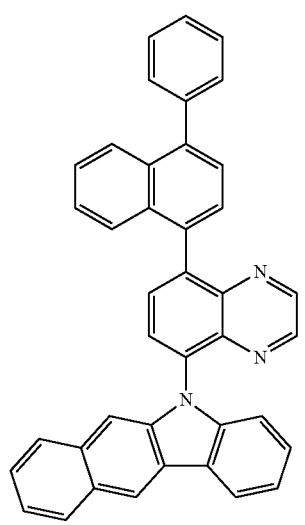
303
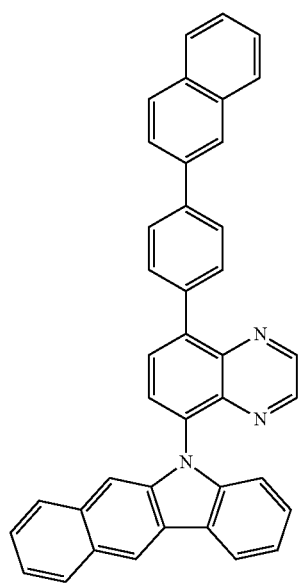
304
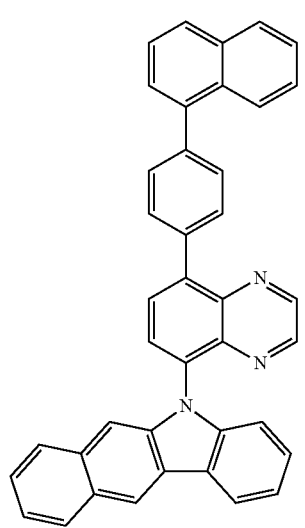
118
-continued
305
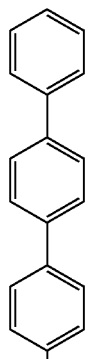
306
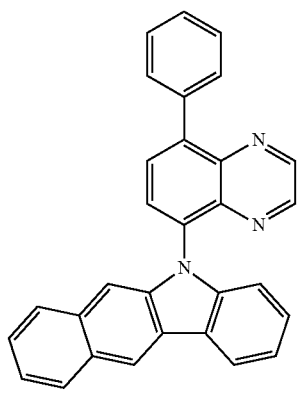
307
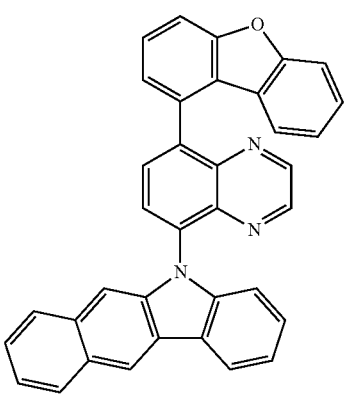

119
-continued
308
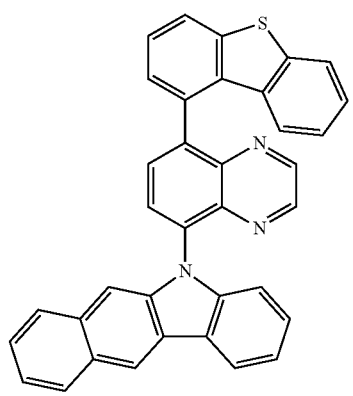
309
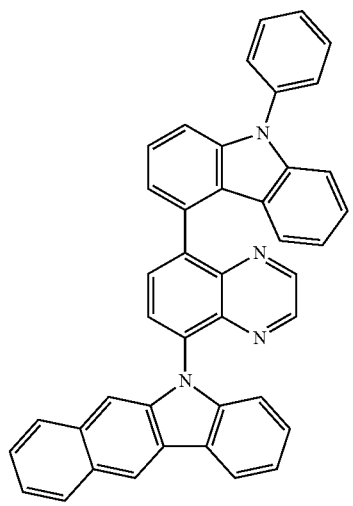
310
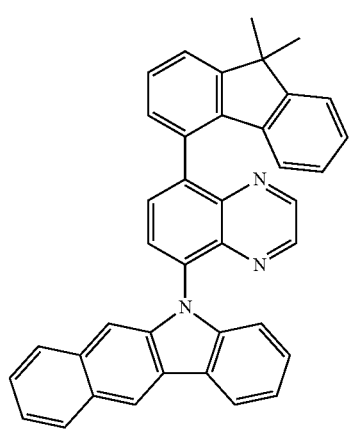
120
-continued
311
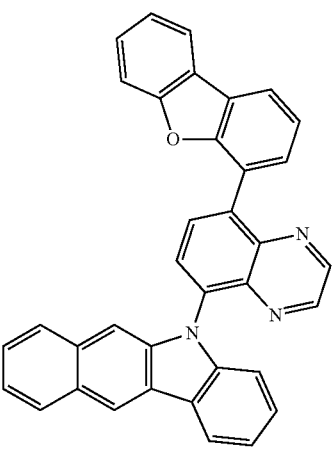
312
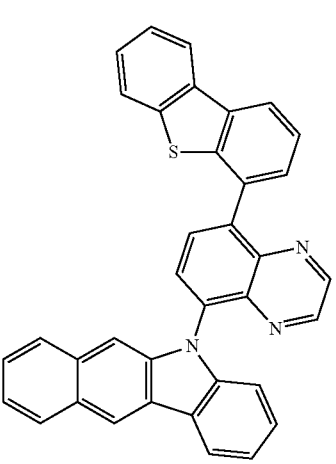
313
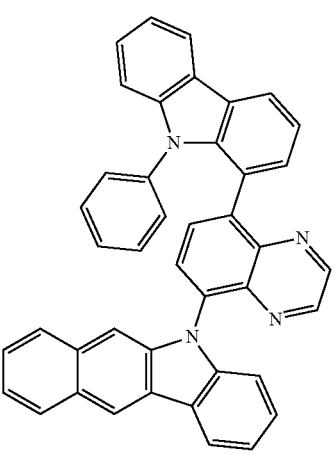

314
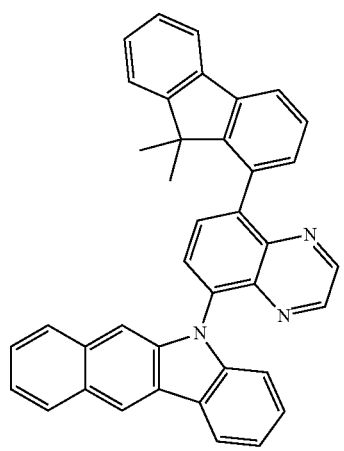
315
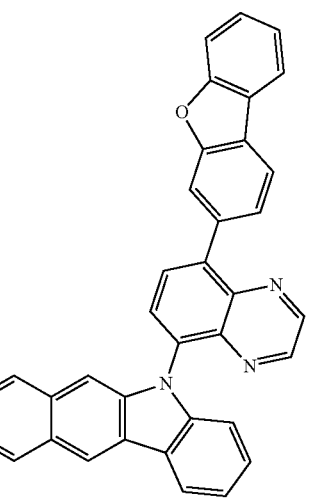
316
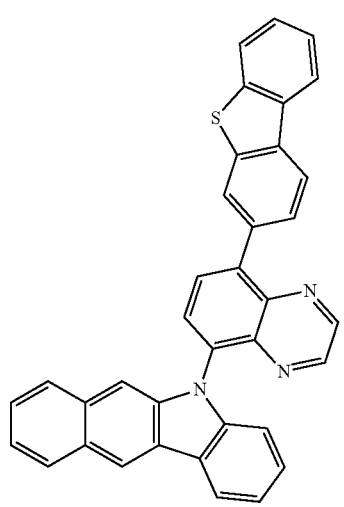
317
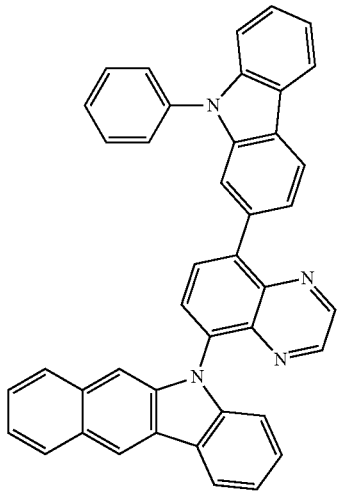
318
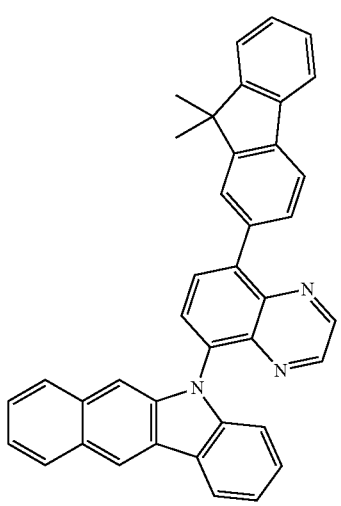
319
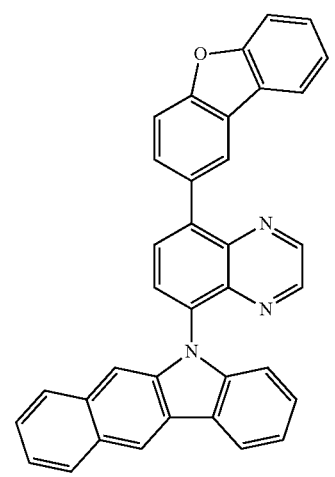

US 11,581,496 B2
123
-continued
320
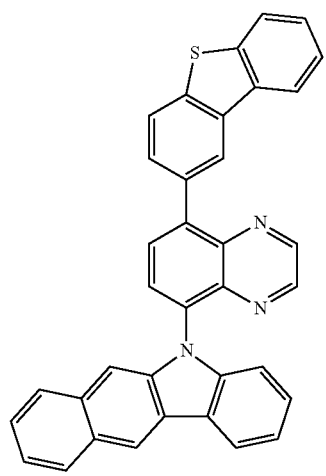
321
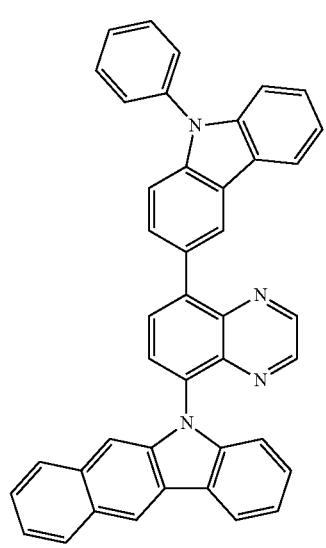
322
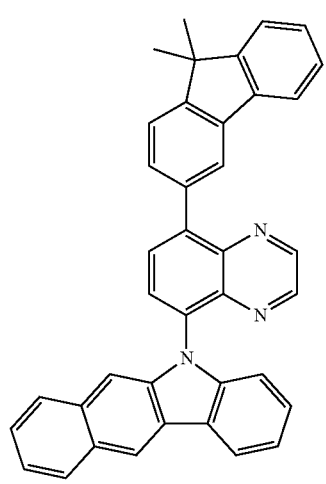
124
-continued
323
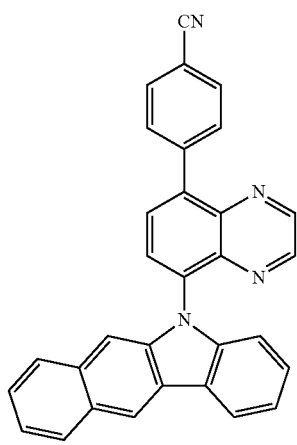
324
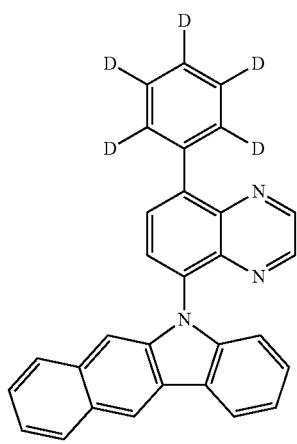
325
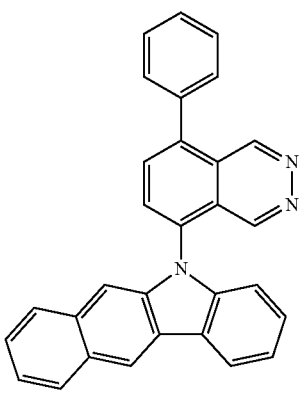

-continued
326
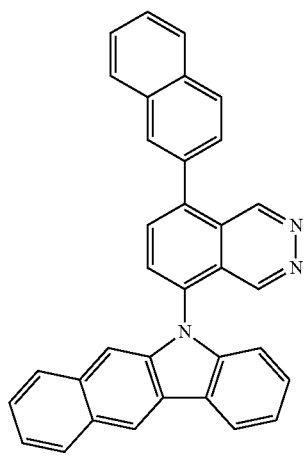
327
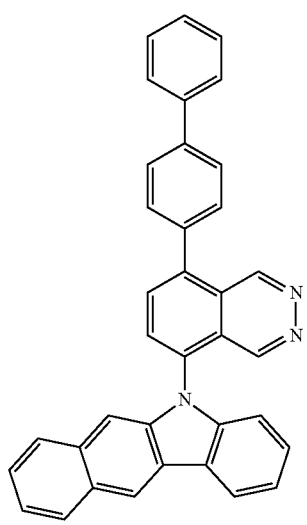
328
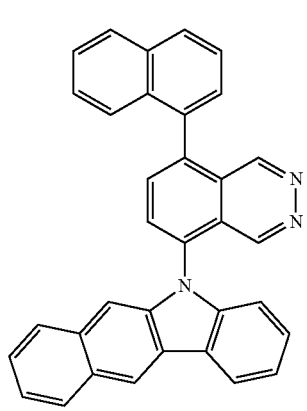
-continued
329
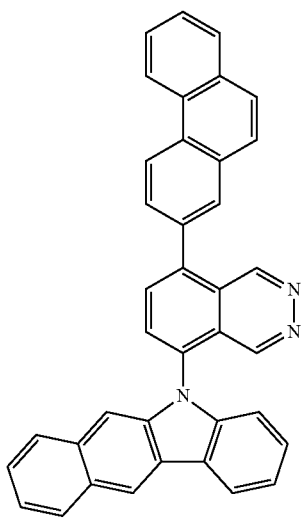
330
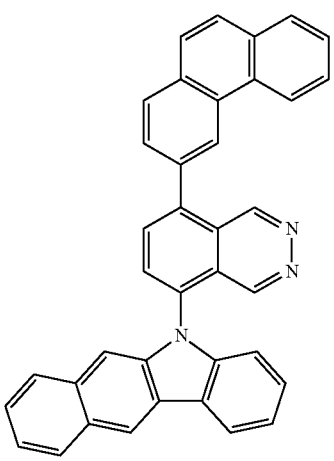
331
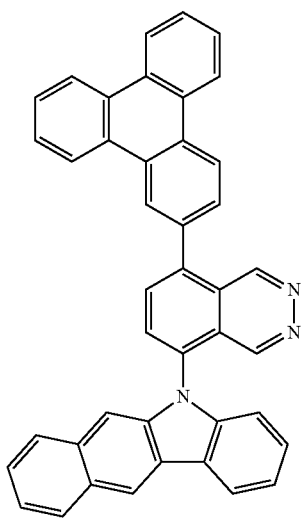

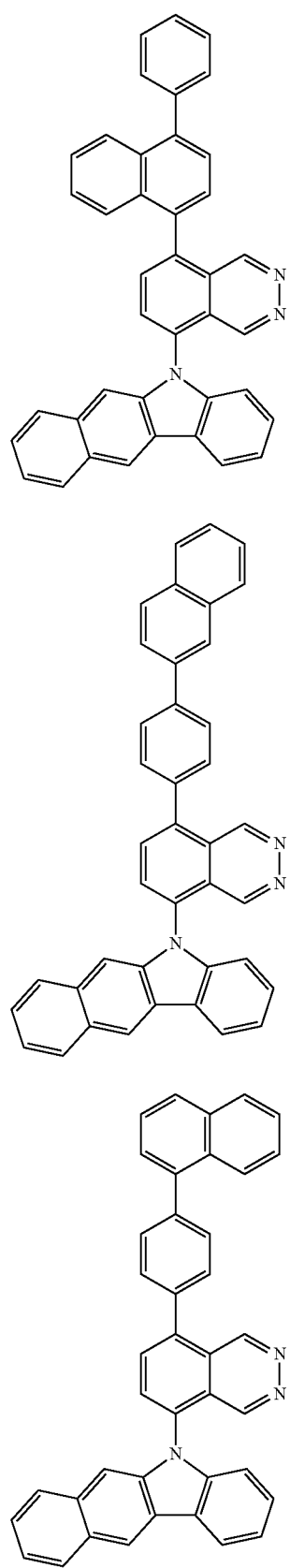
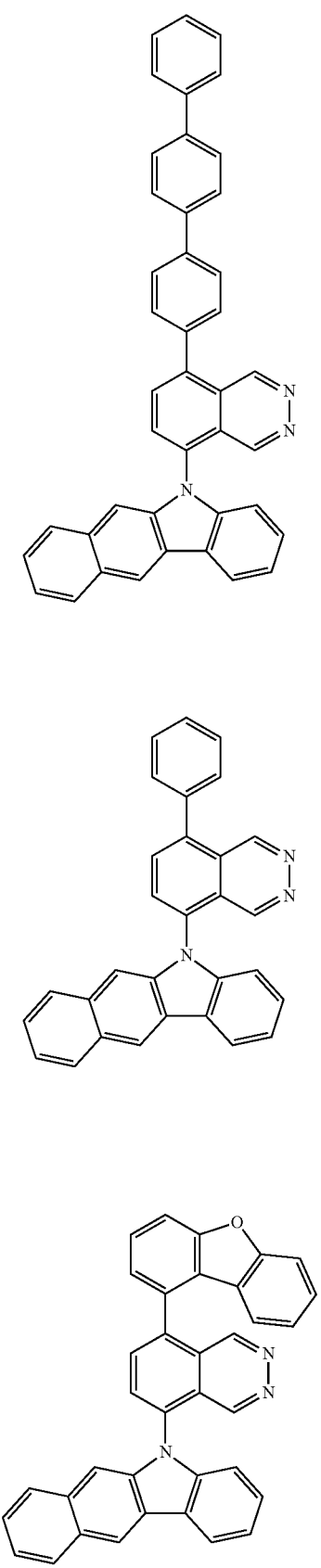

-continued
338
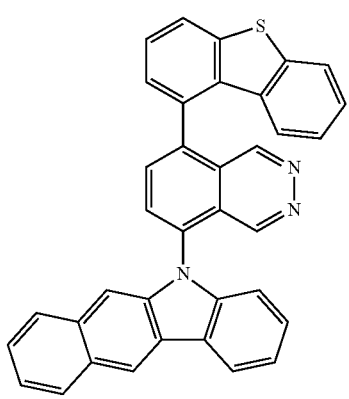
339
340
341
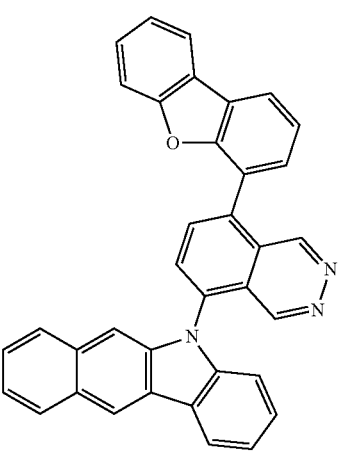
342
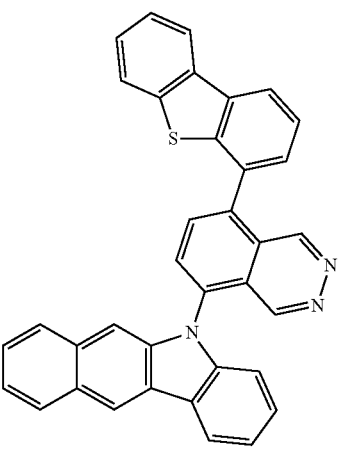
343
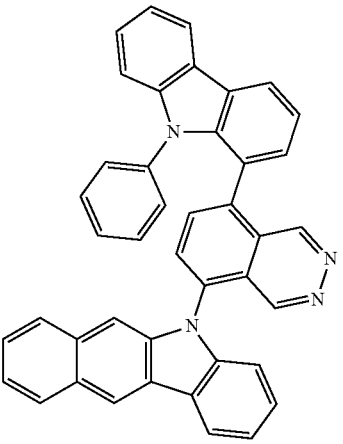

-continued
344
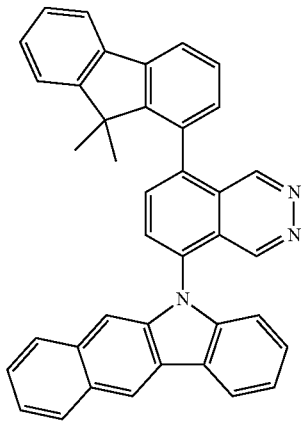
345
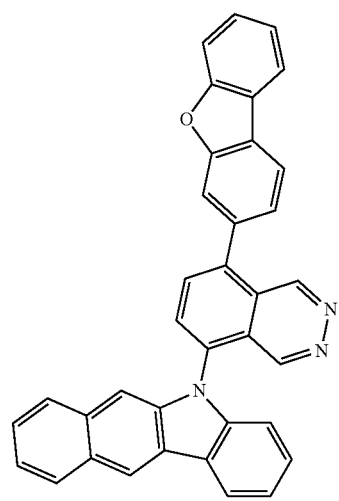
346
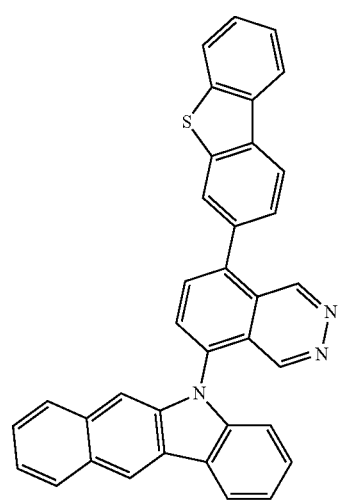
-continued
347
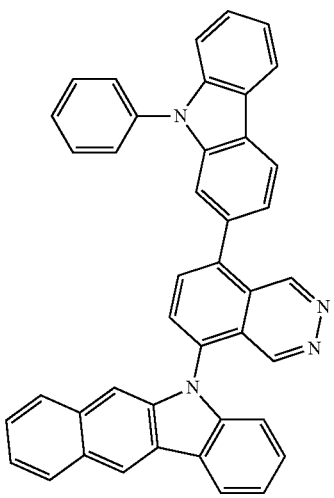
348
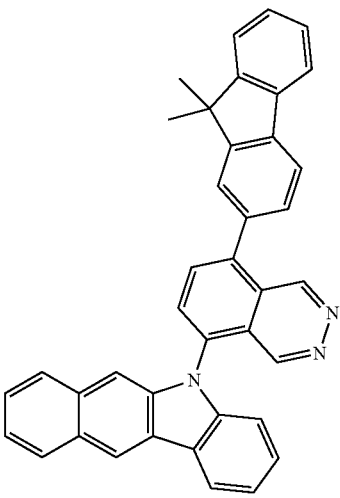
349
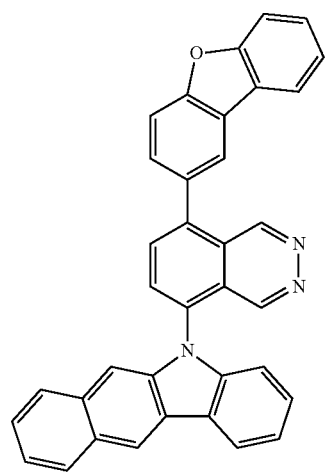

| 133 | 134 |
|---|---|
| -continued | -continued |
| 350 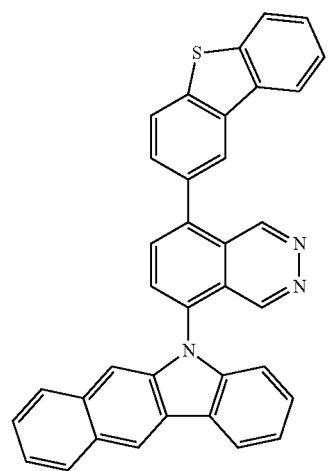 | 353 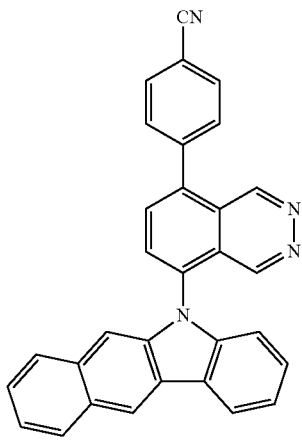 |
| 351 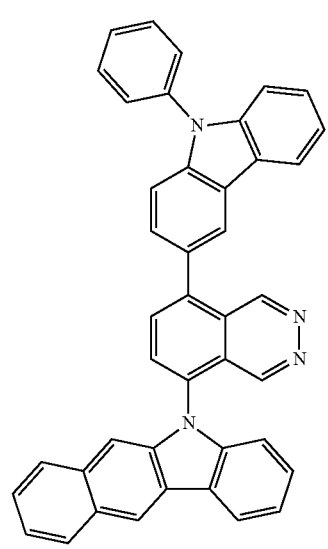 | 354 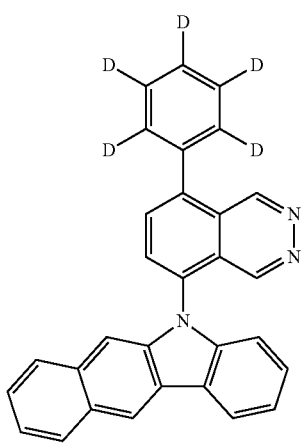 |
| | 355 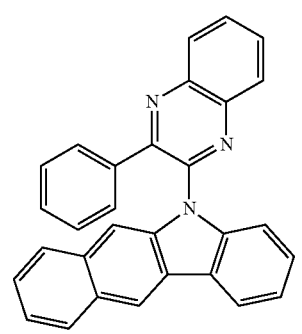 |
| 352 | 356 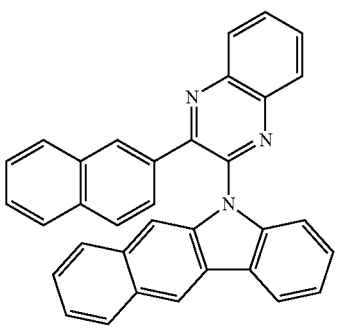 |

357
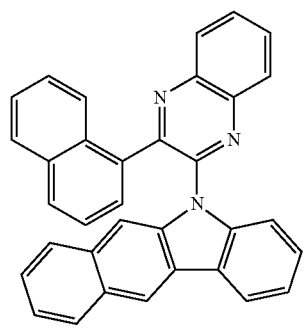
358
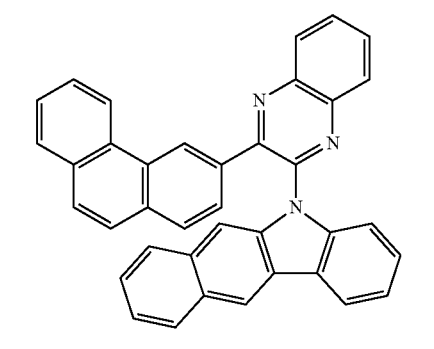
359
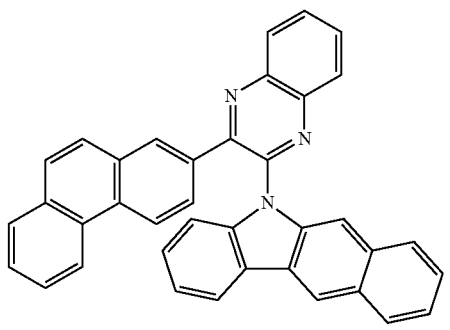
360
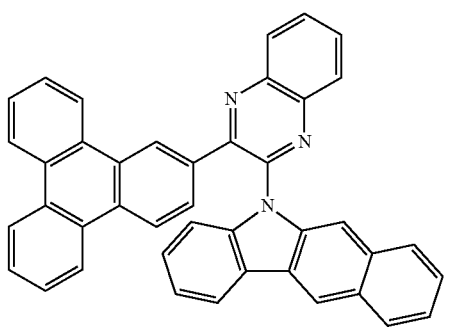
361
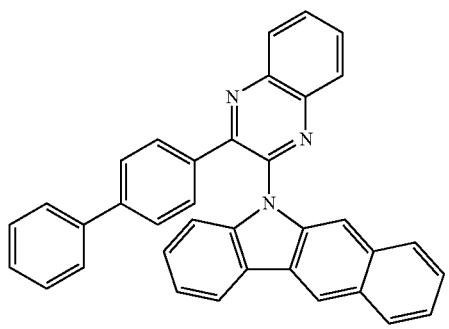
362
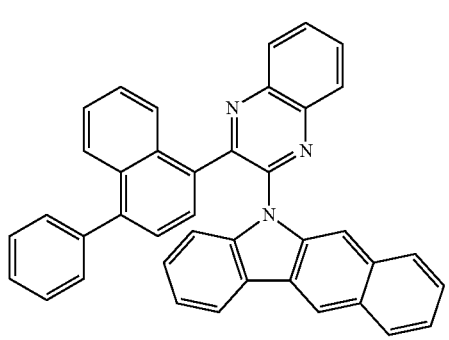
363
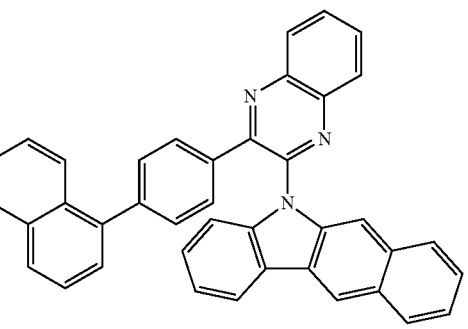
364
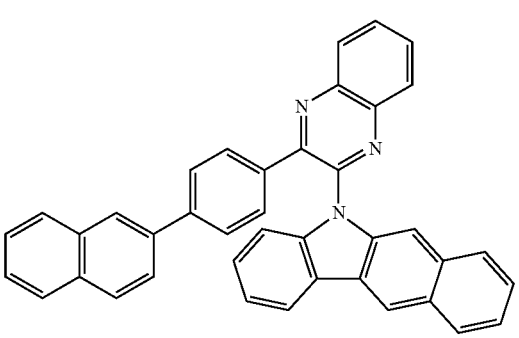

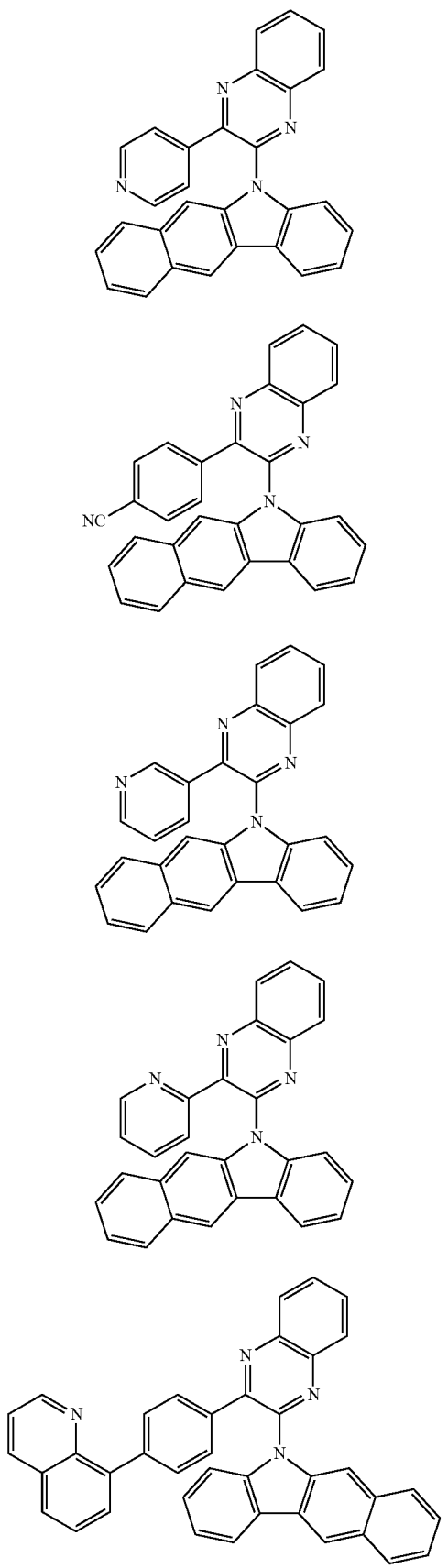
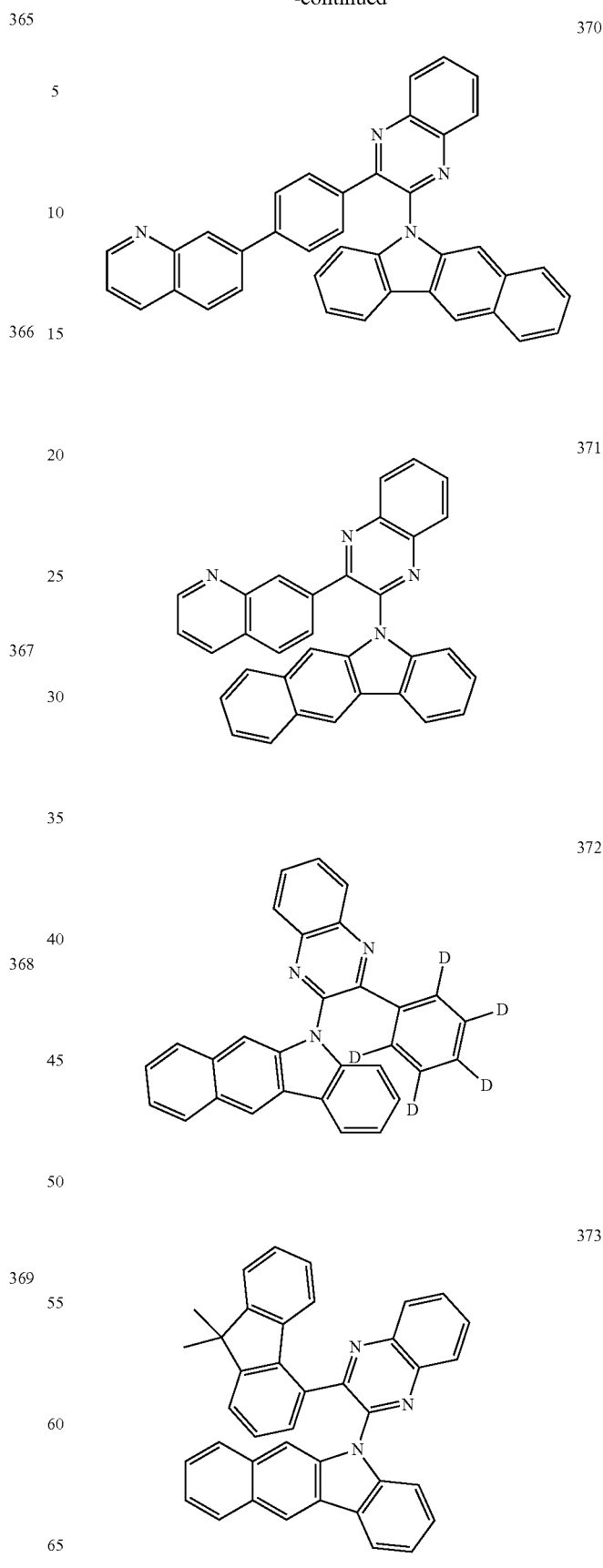

374
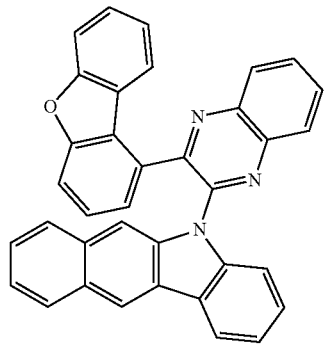
375
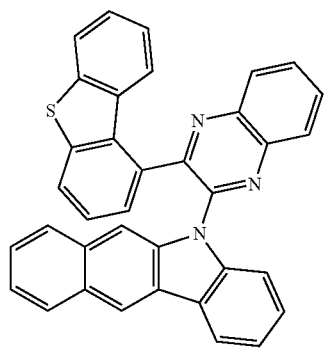
376
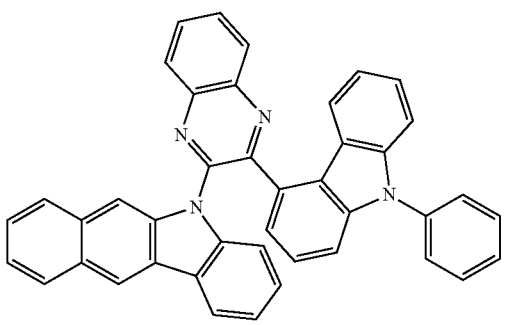
377
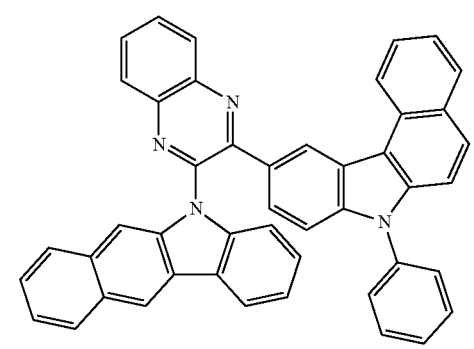
378
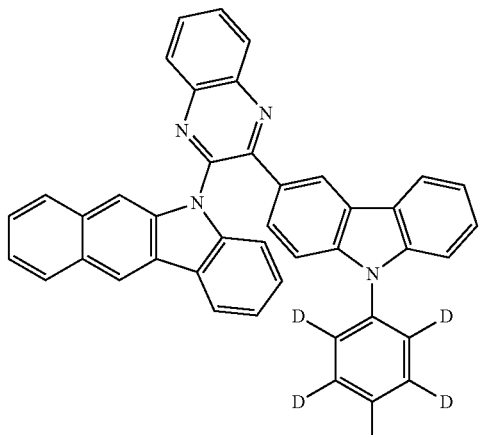
379
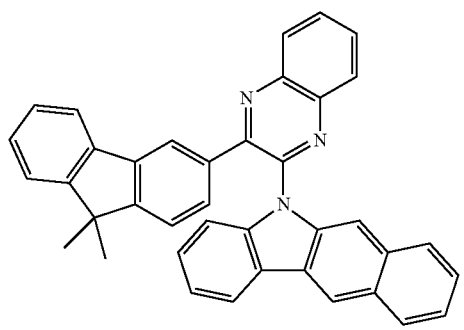
380
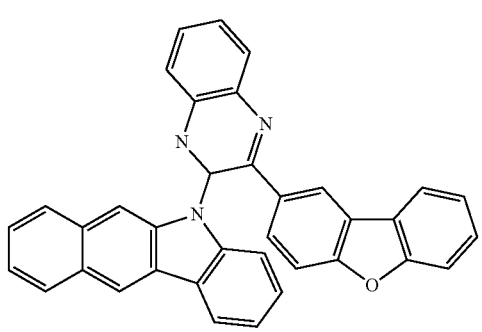
381
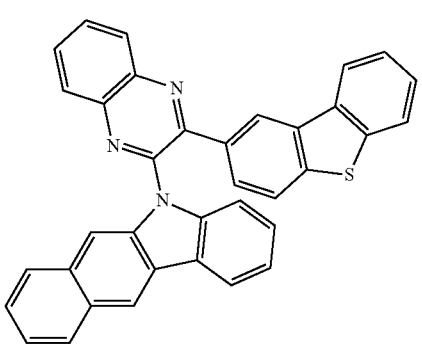

-continued
382
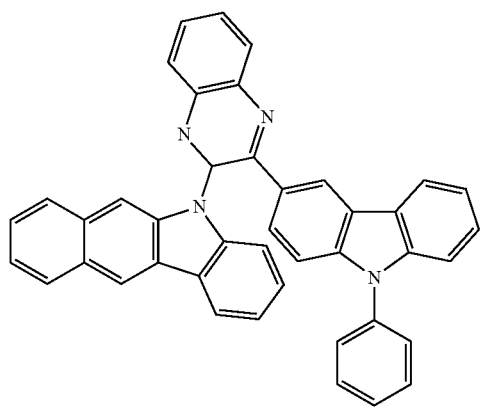
383
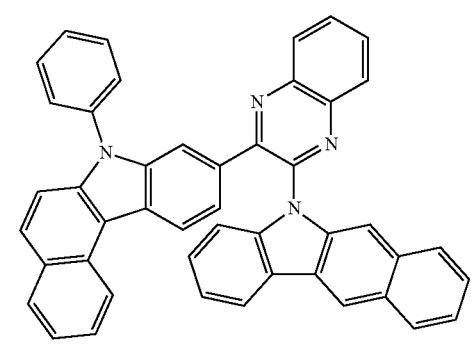
384
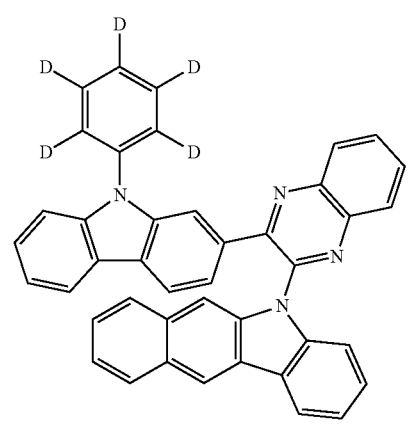
385
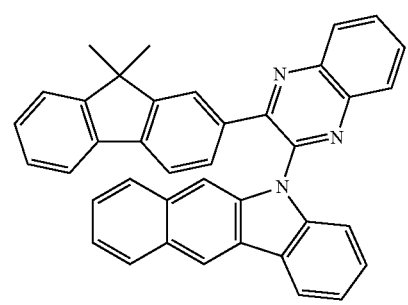
-continued
386
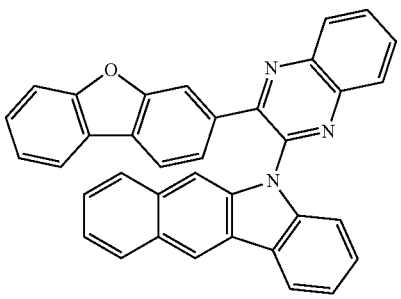
387
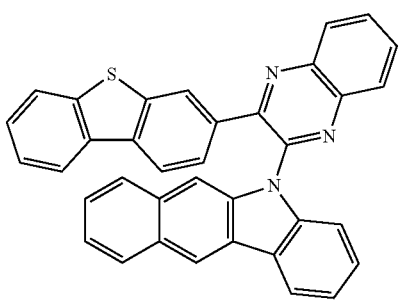
388
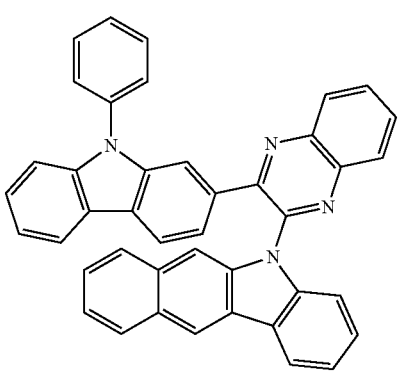
389
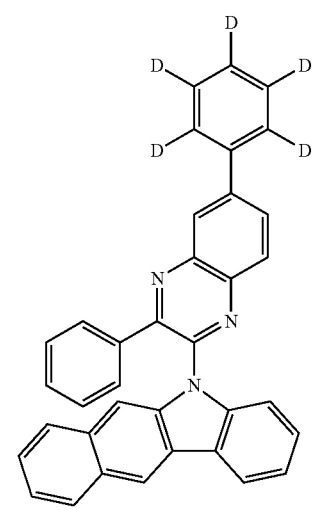

390
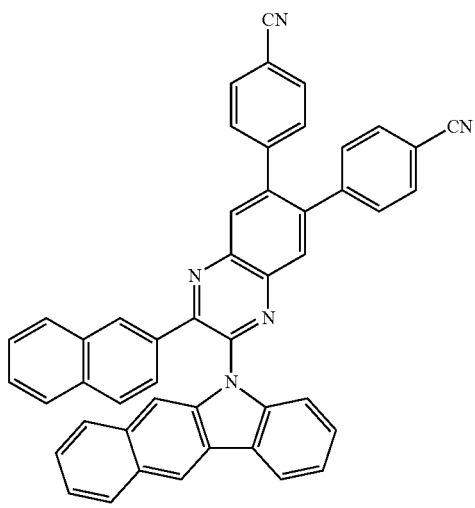
391
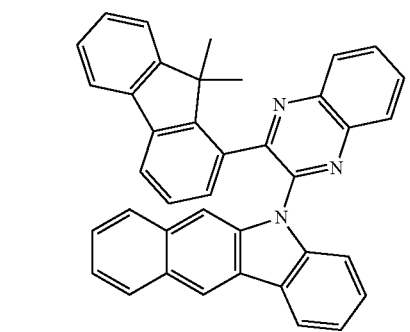
392
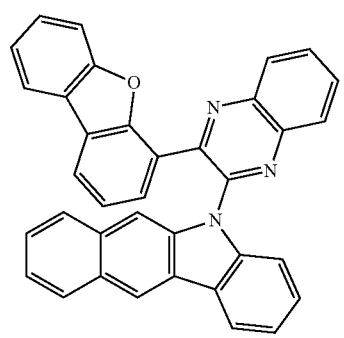
393
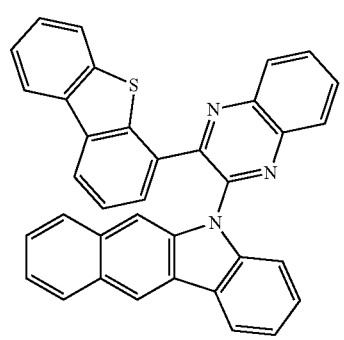
394
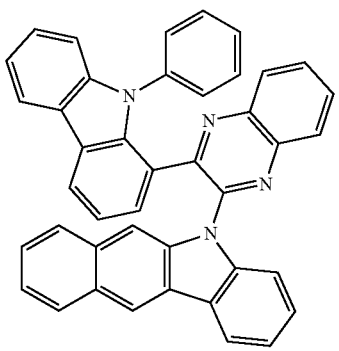
395
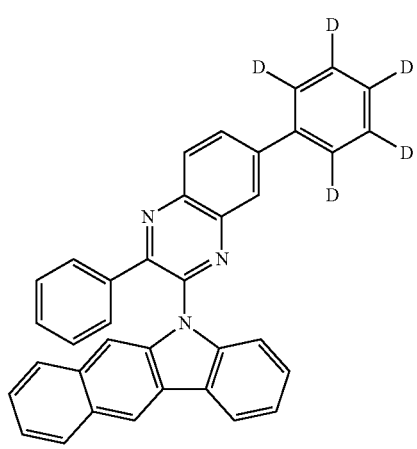
396

397
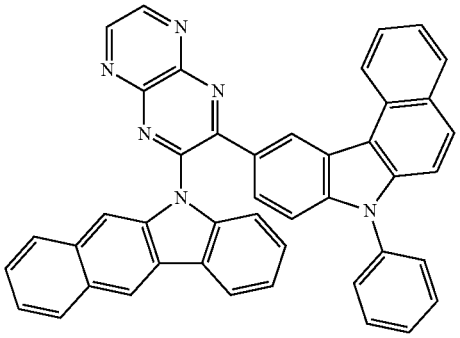

398 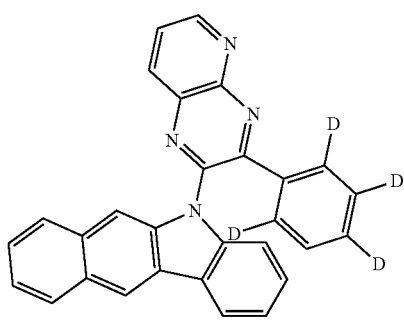
399 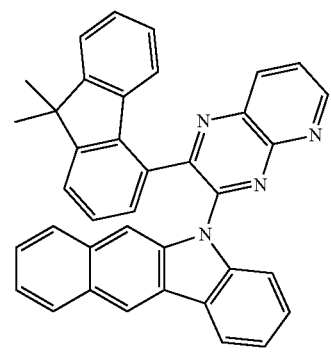
400 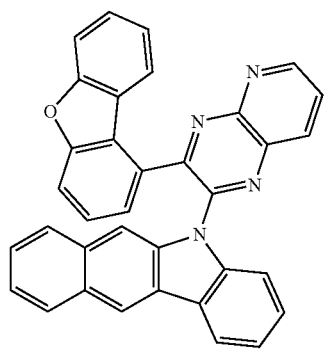
401 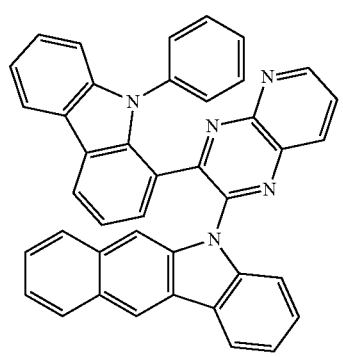
402 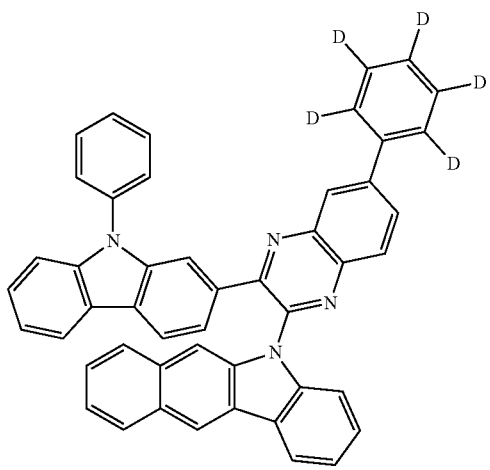
403 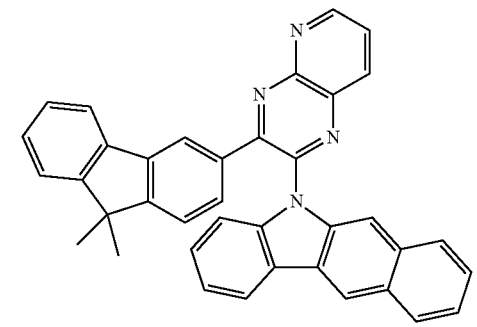
404 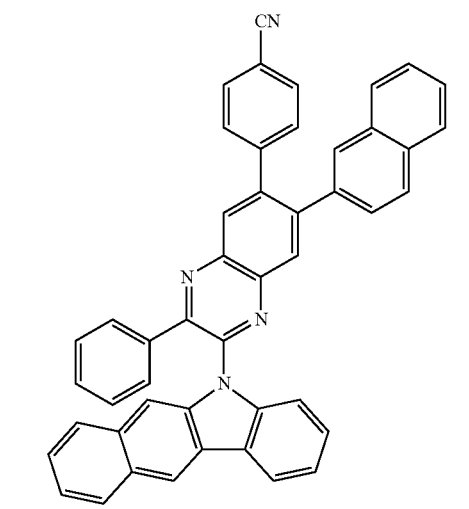
405 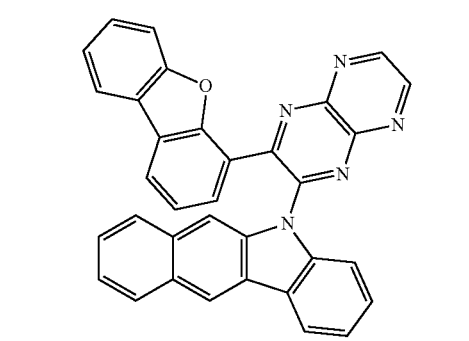

-continued
406
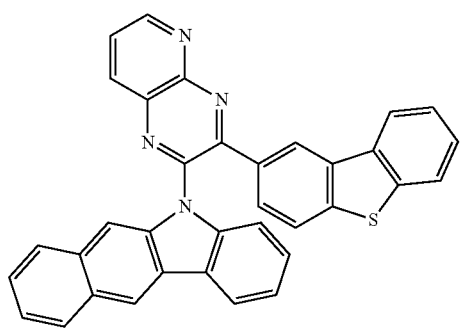
407
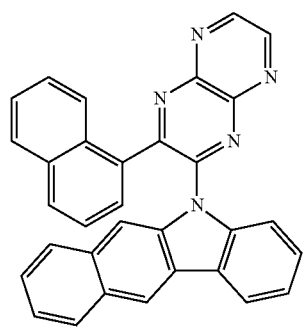
408
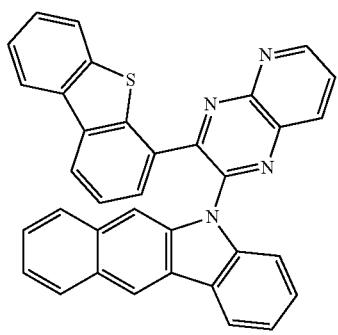
409
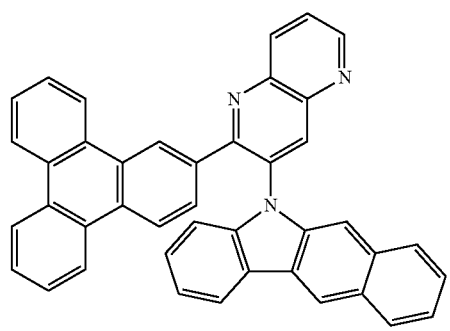
-continued
410
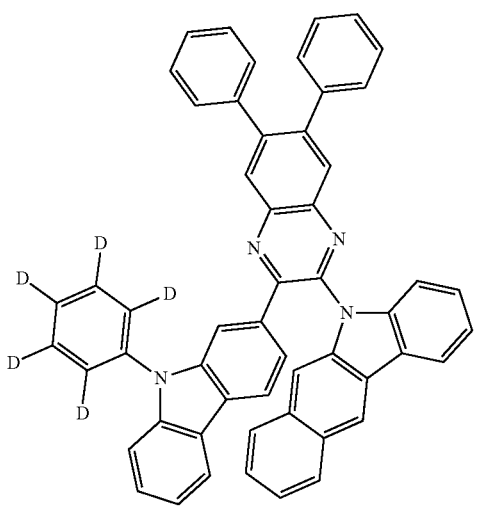
411
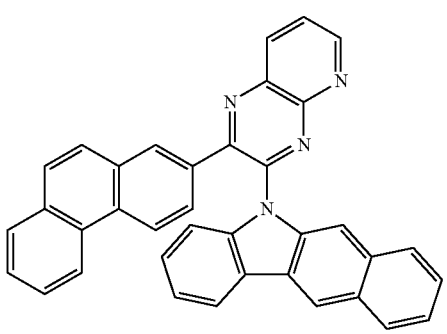
412
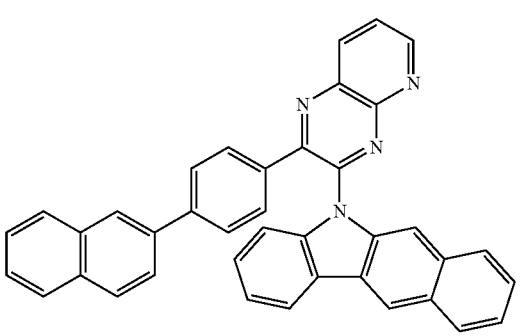
413
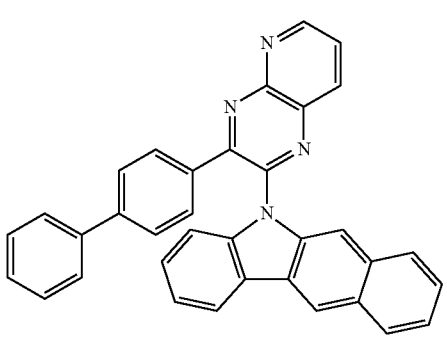

149
-continued
414
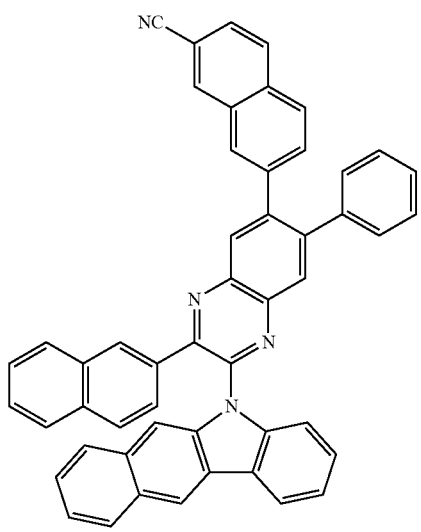
415
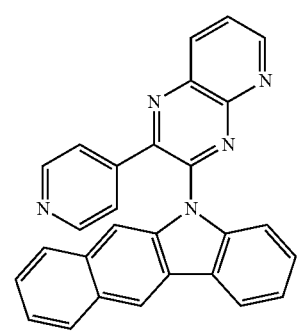
416
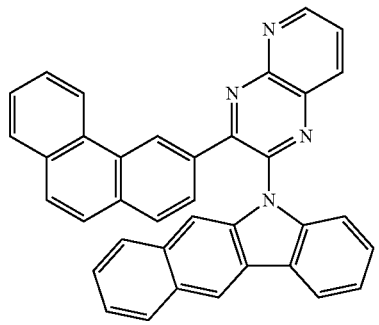
417
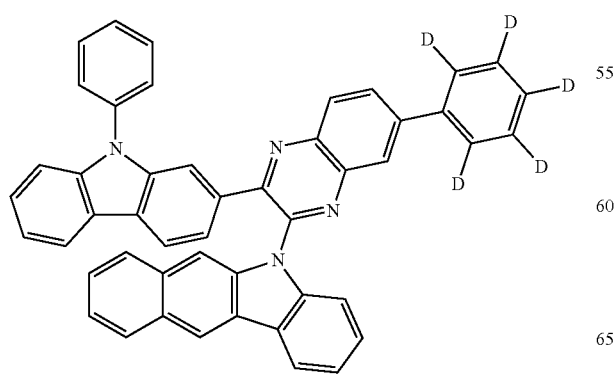
150
-continued
418
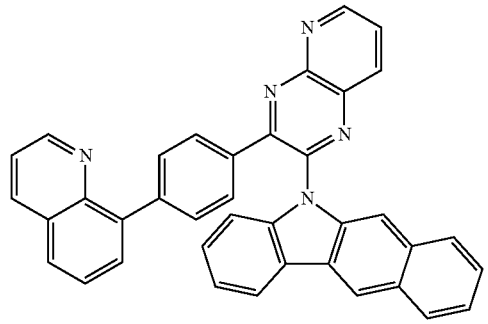
419
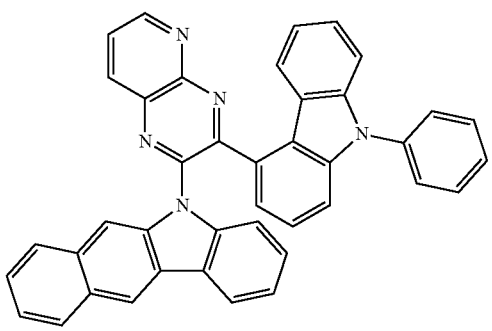
420
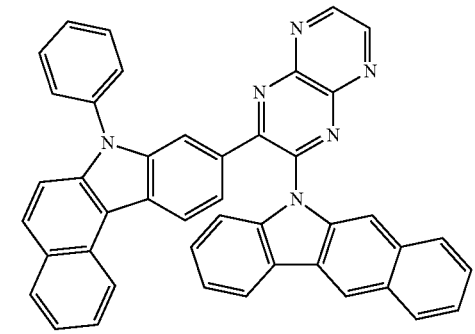
421
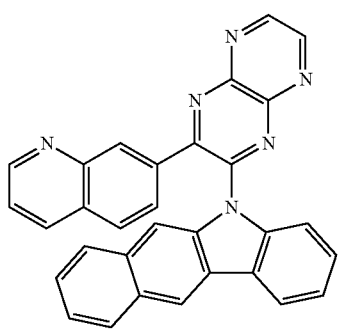

-continued
422
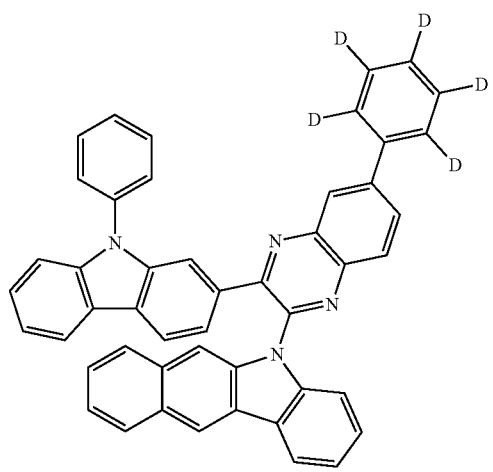
423
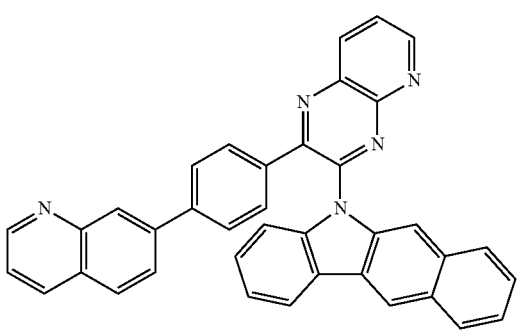
424
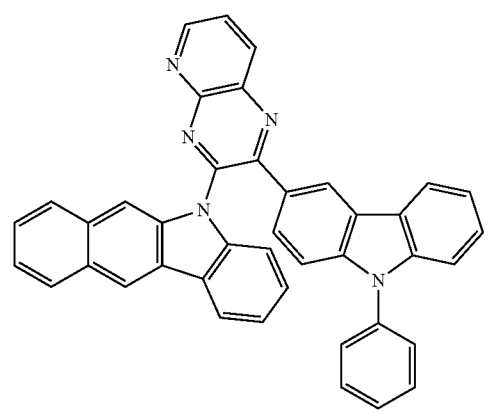
425
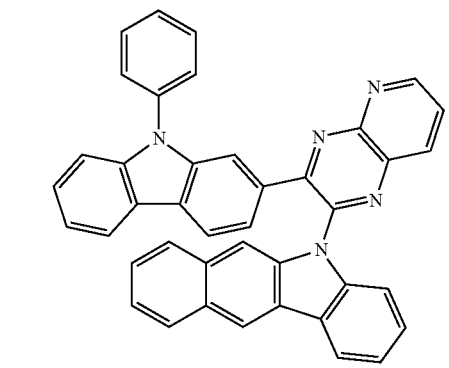
-continued
426
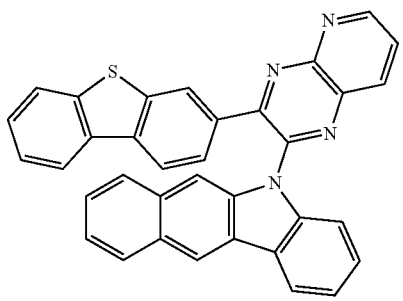
427
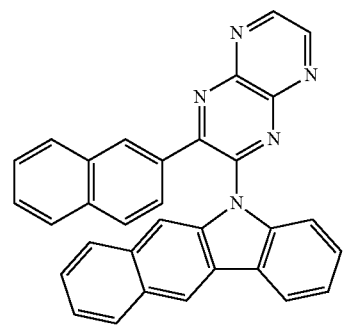
428
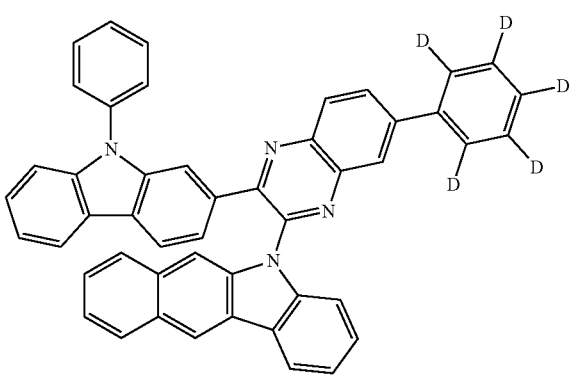
429
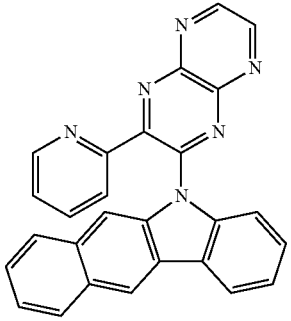
430
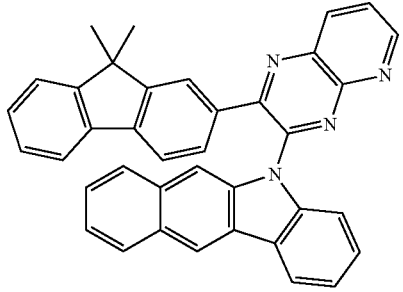

431 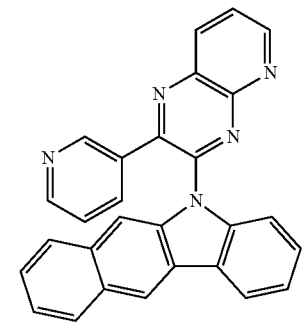
432 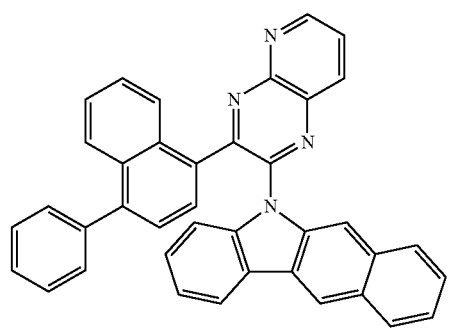
433 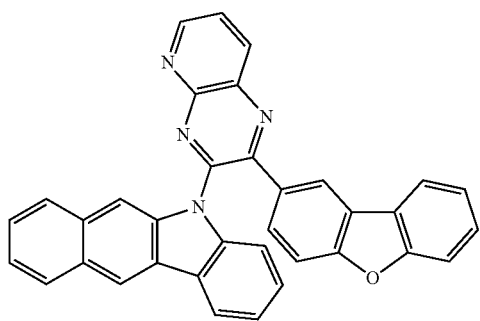
434 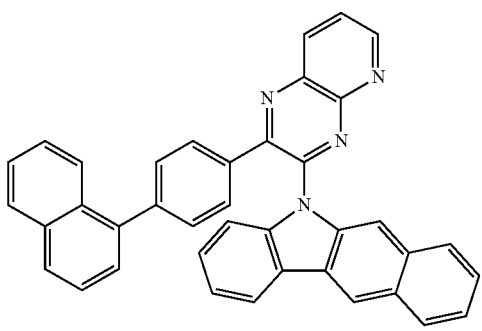
435 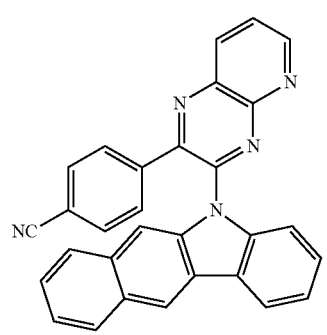
436 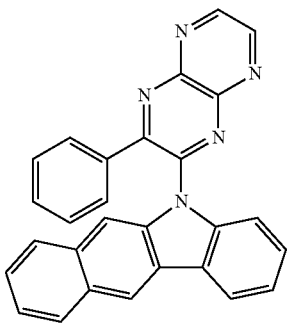
437 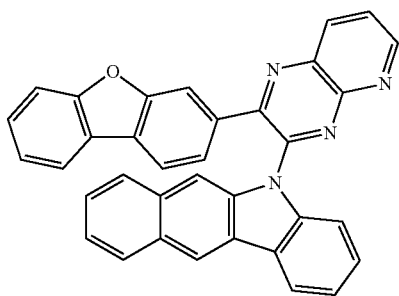
438 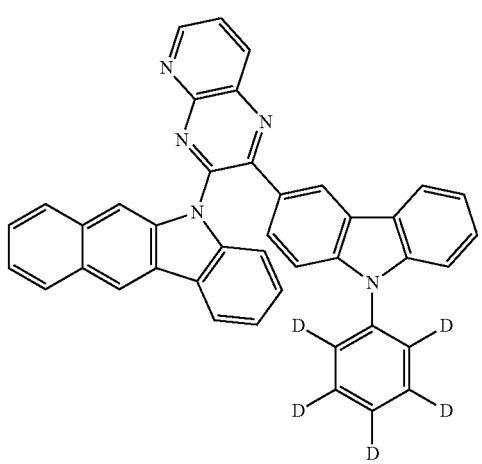
439 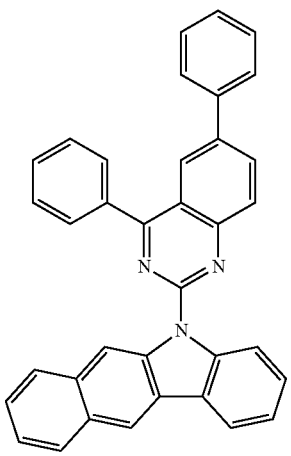

-continued
440
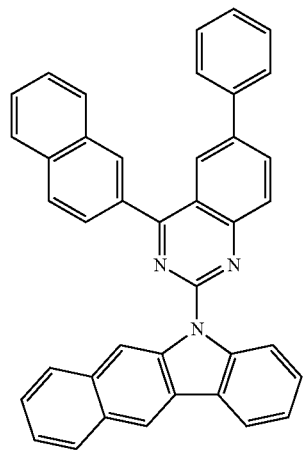
441
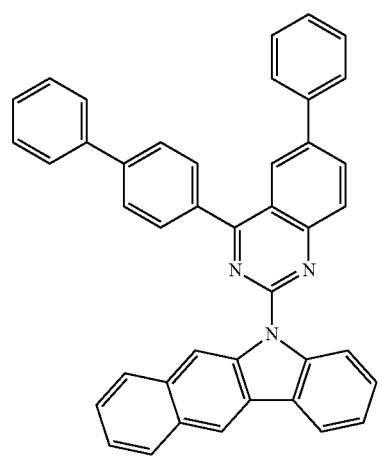
442
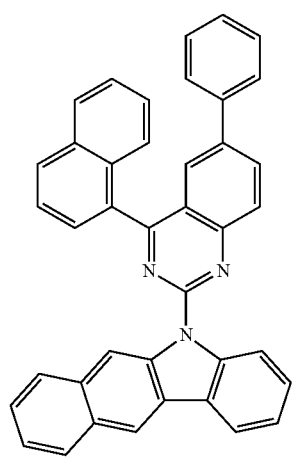
-continued
443
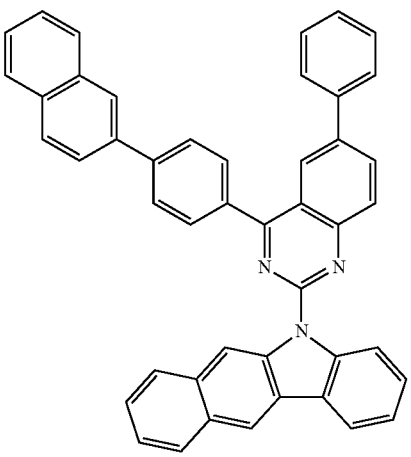
444
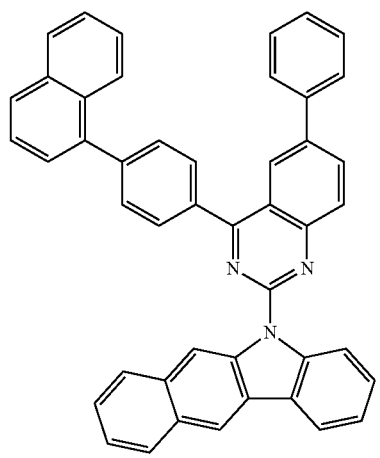
445
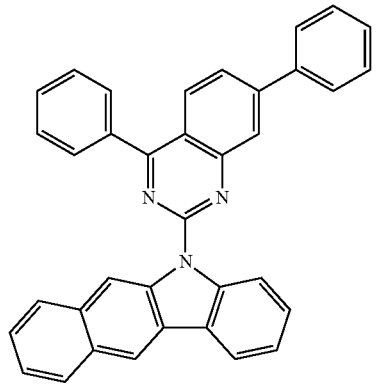

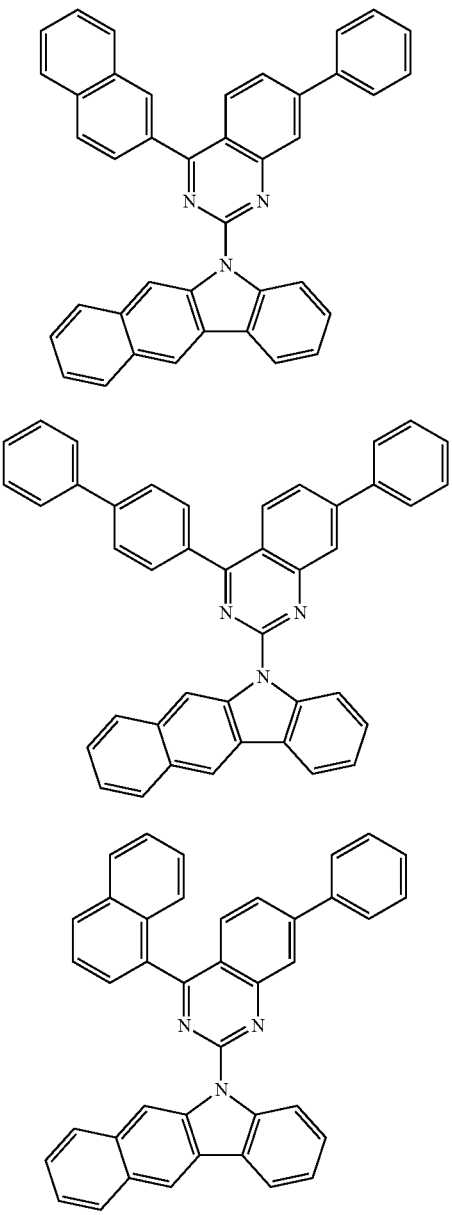
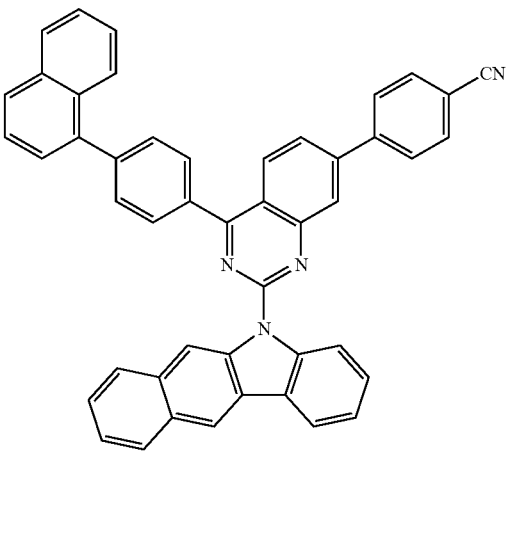
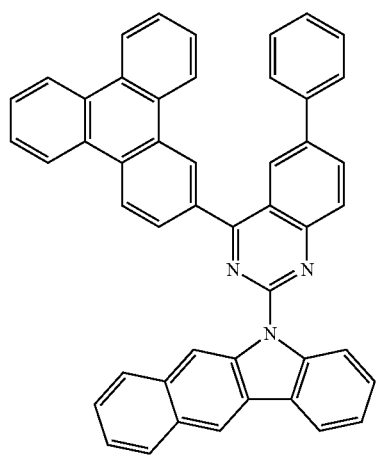
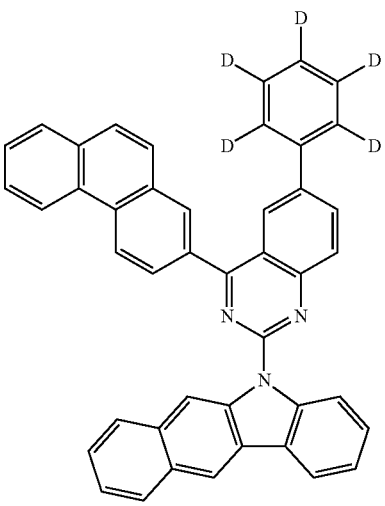

453
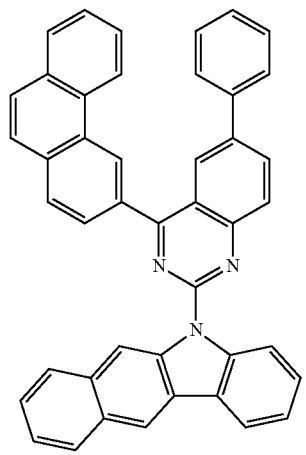
454
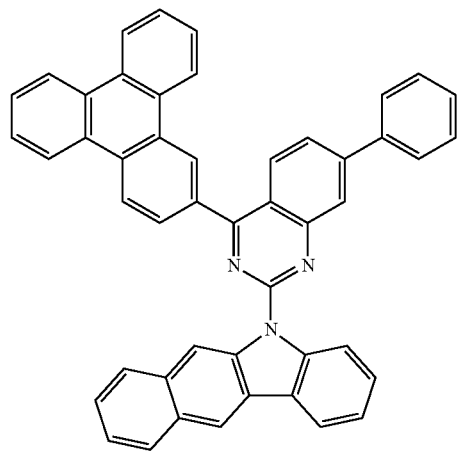
455
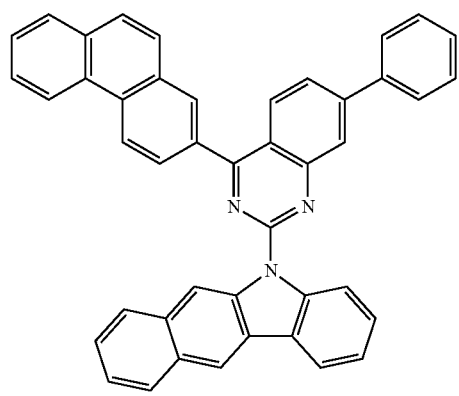
456
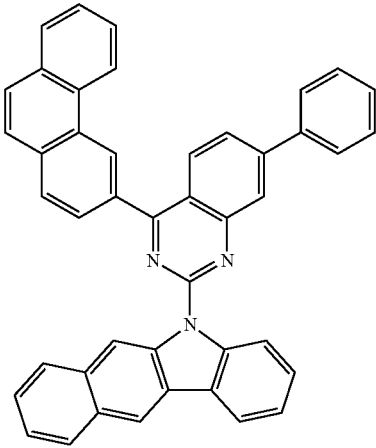
457
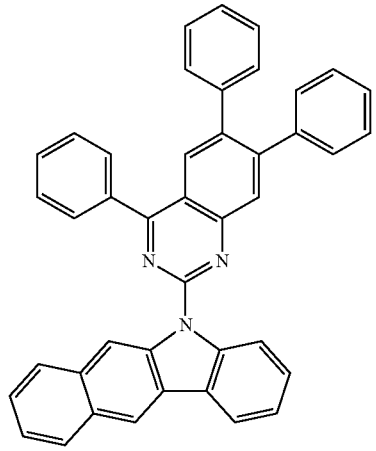
458
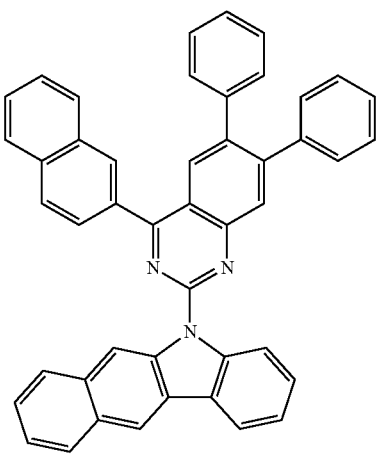

-continued
459
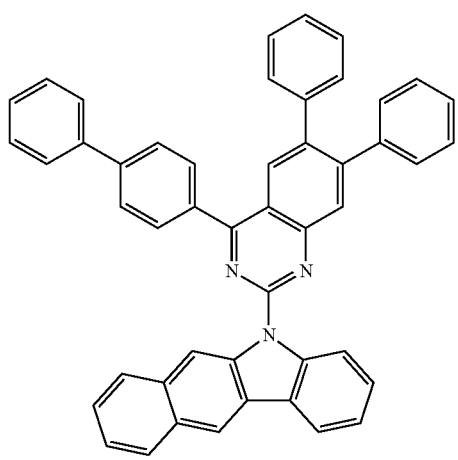
460
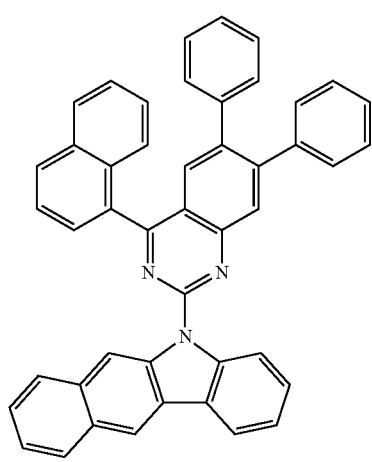
461
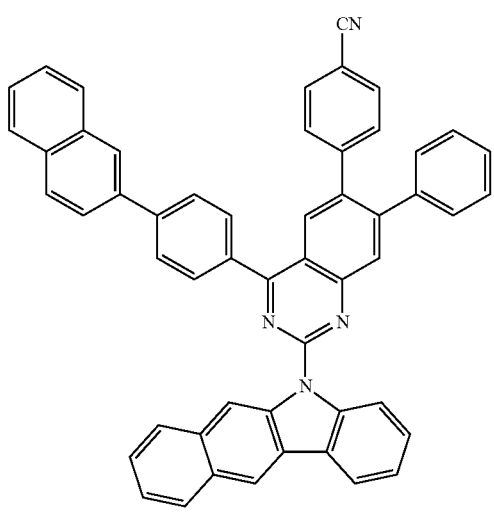
-continued
462
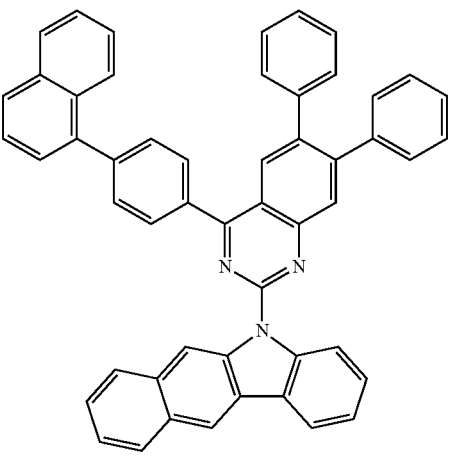
463
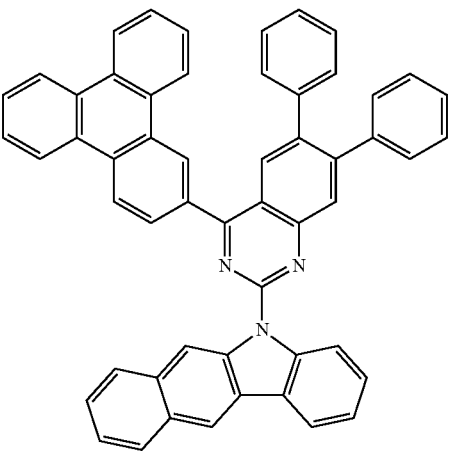
464
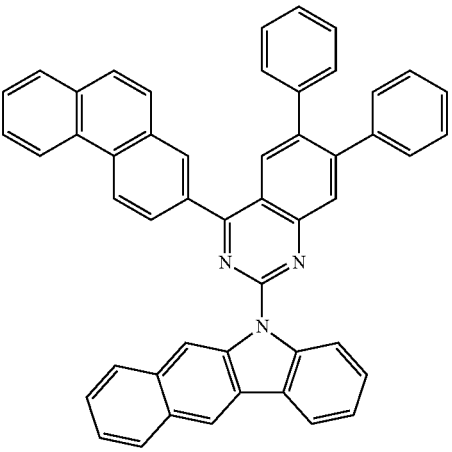

163
-continued
465
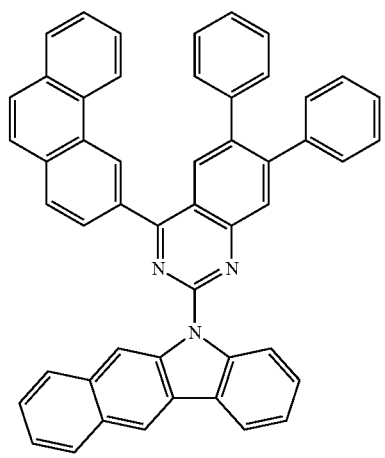
466
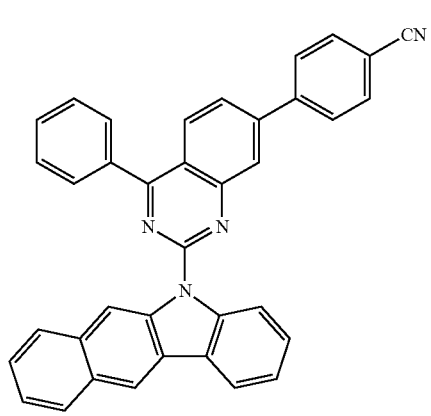
467
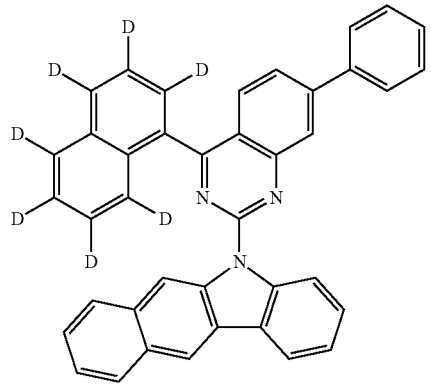
164
-continued
468
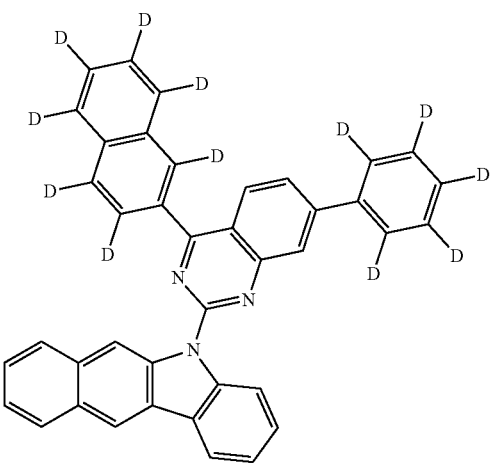
469
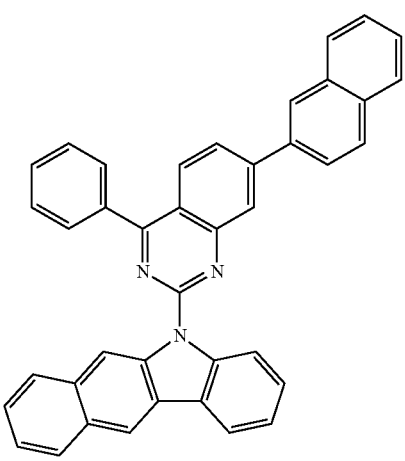
470
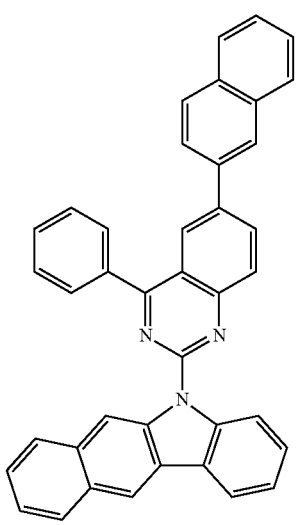

471
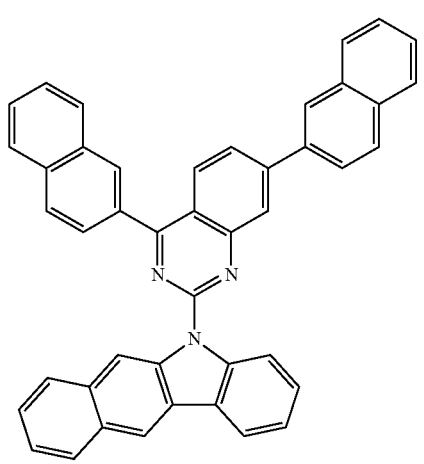
472
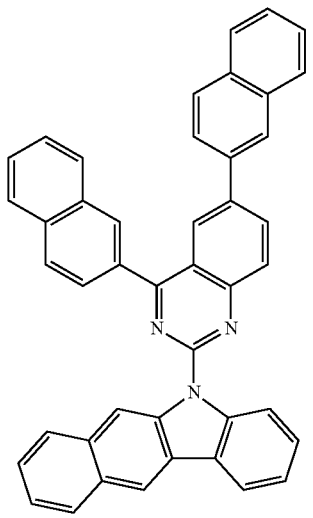
473
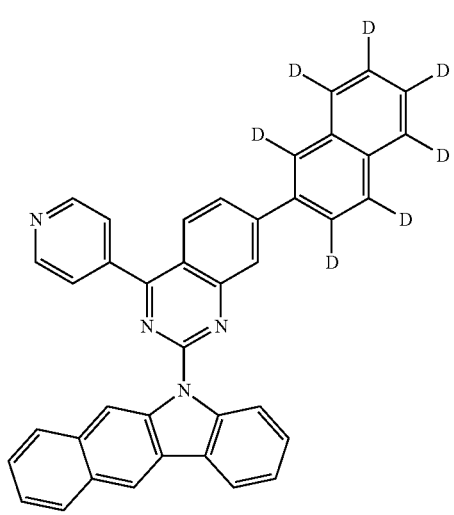
474
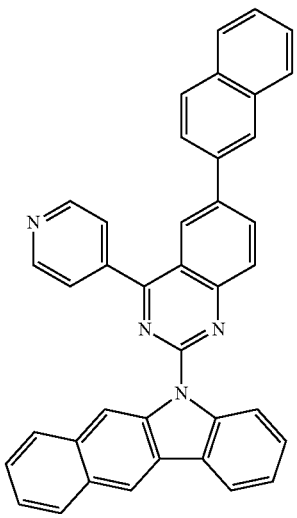
475
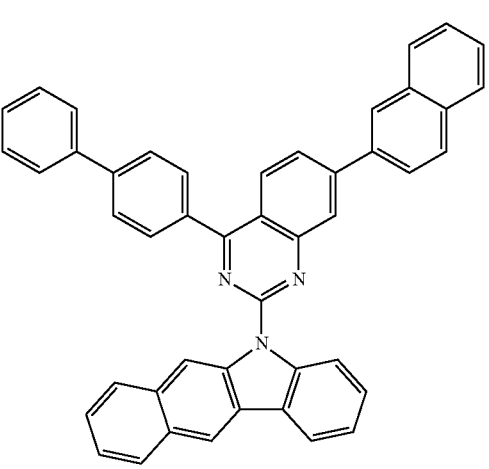
476
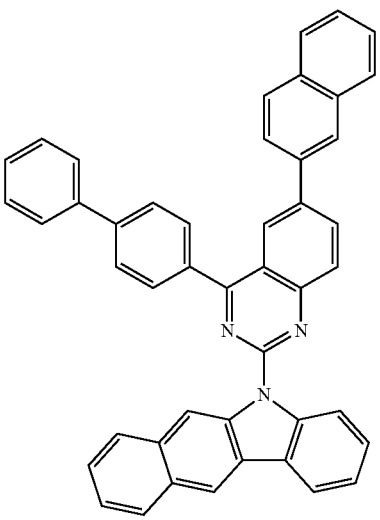

477 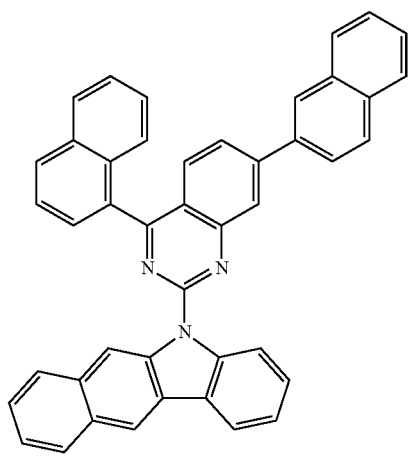
478 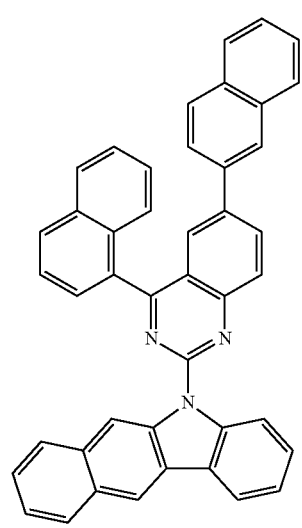
479 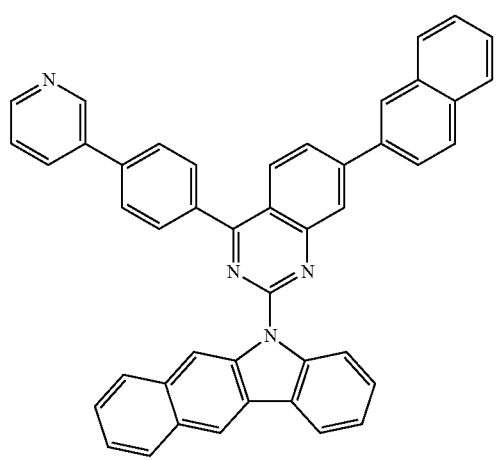
480 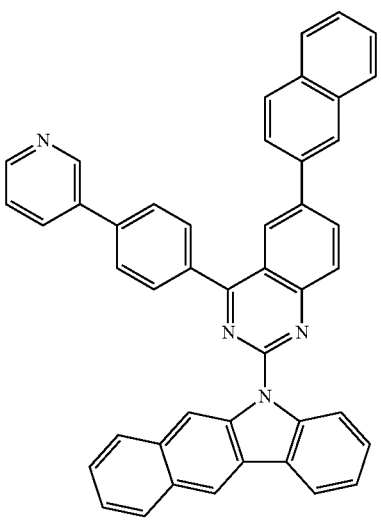
481 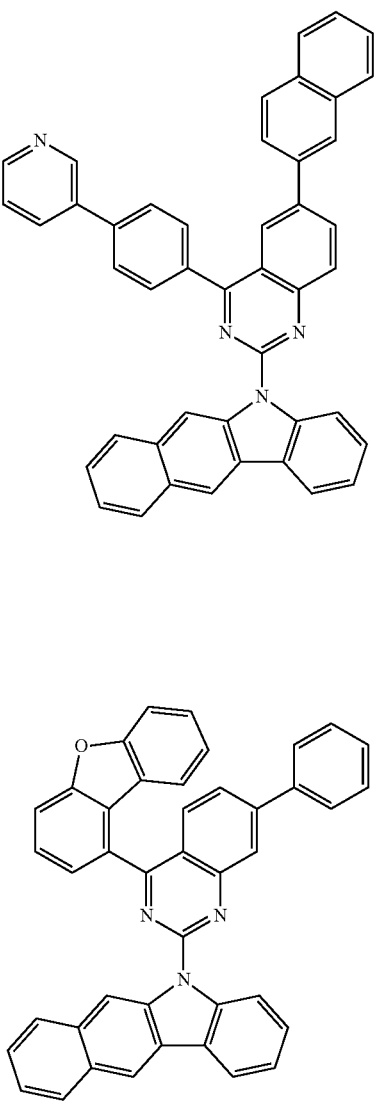
482 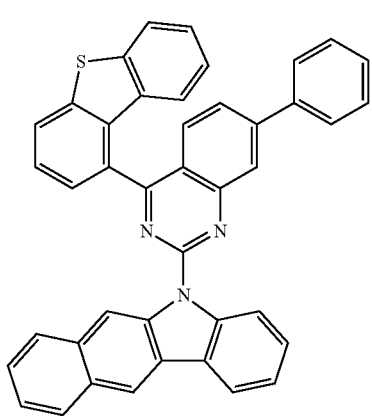

483
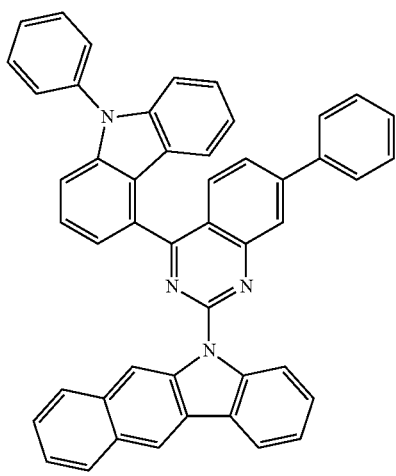
484
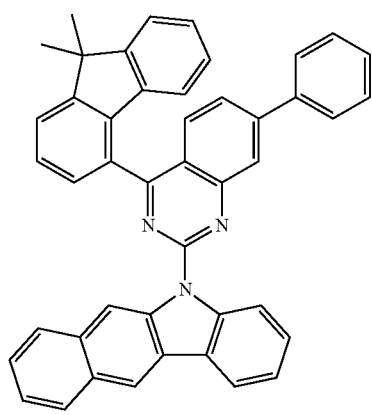
485
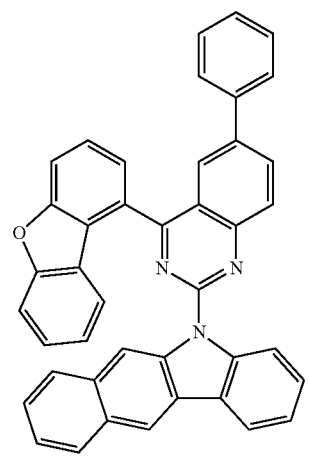
486
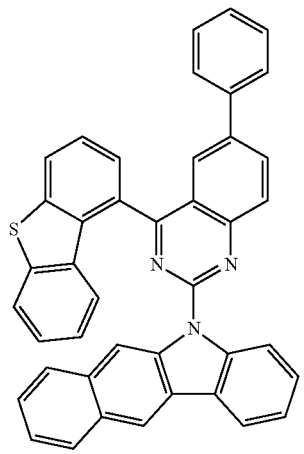
487
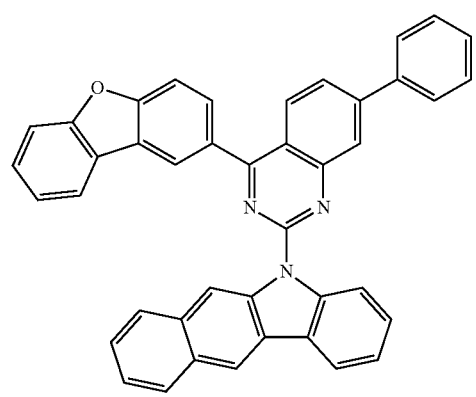
488
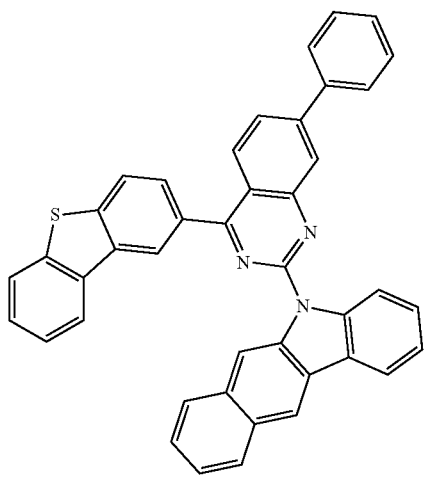

489
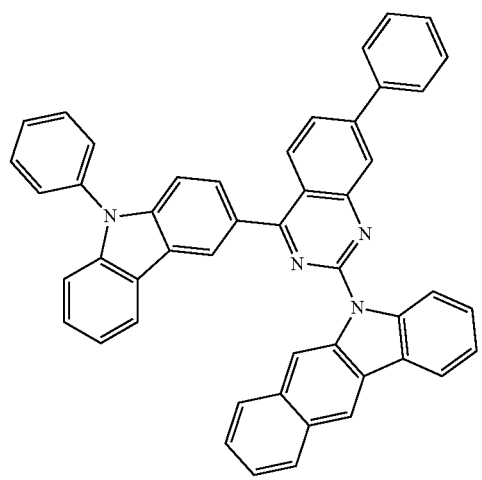
490
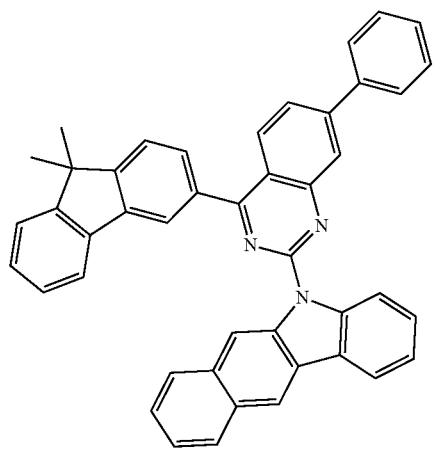
491
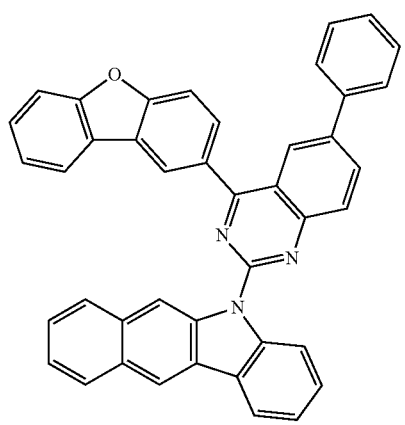
492
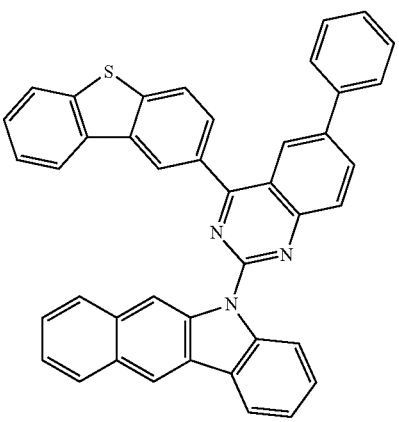
493
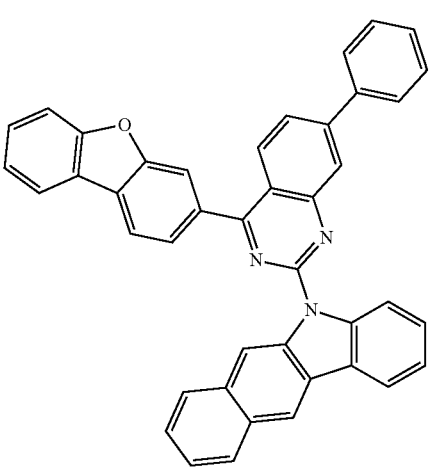
494
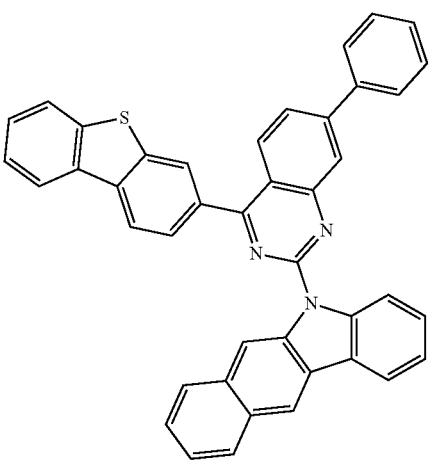

495
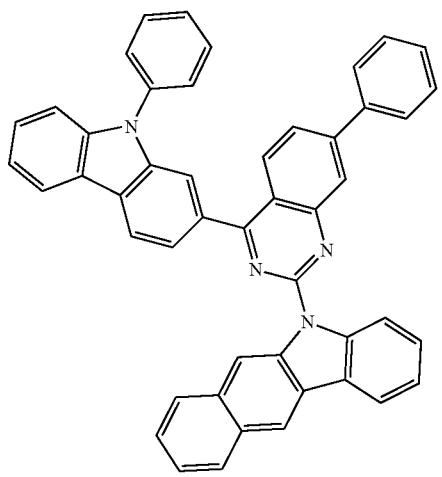
496
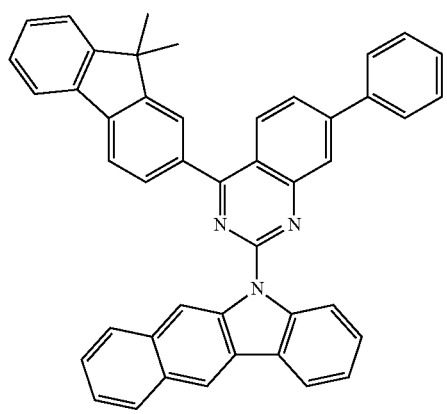
497
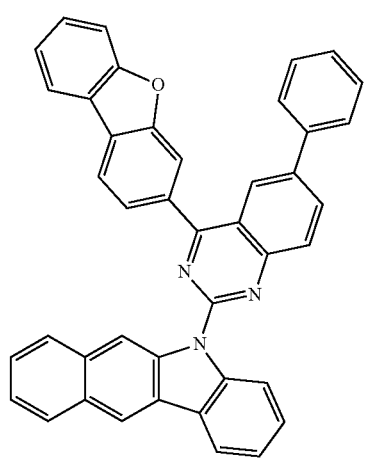
498
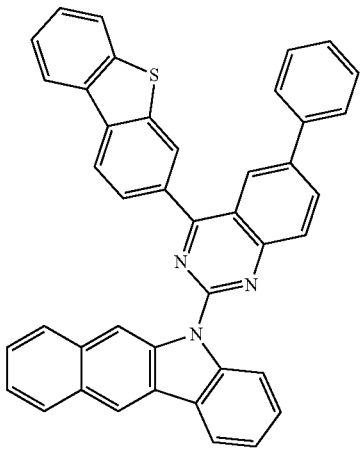
499
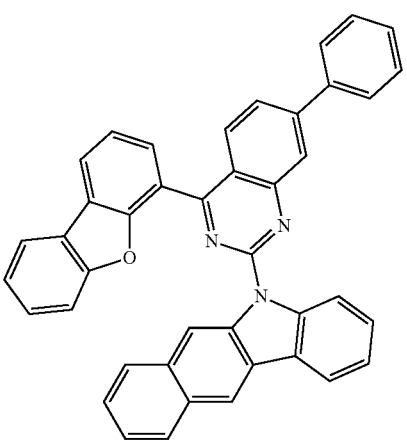
500
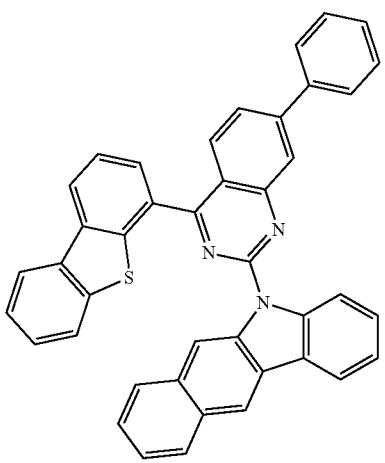

501
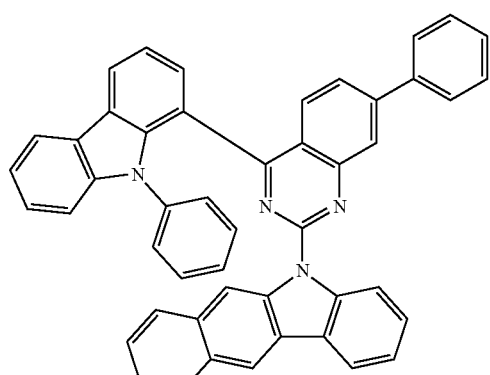
502
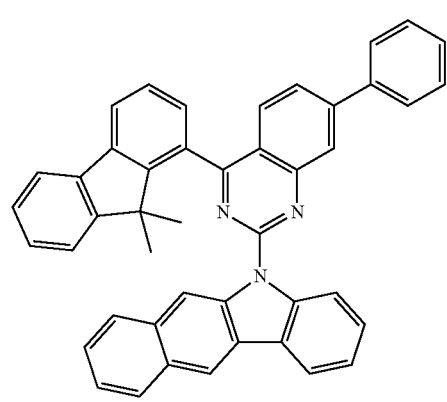
503
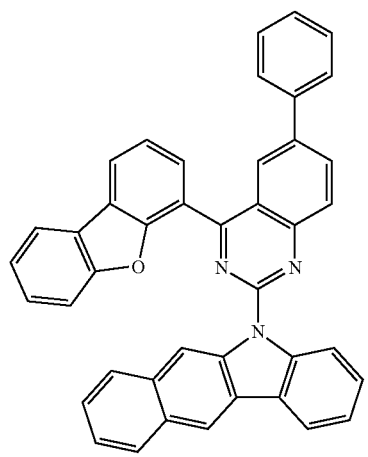
504
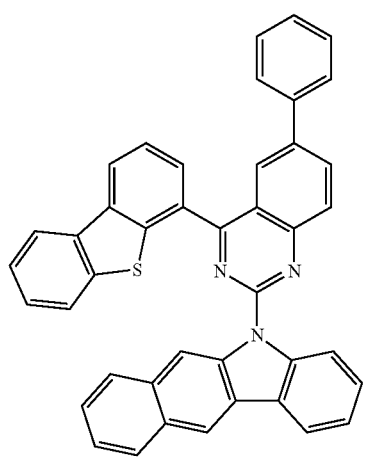
505
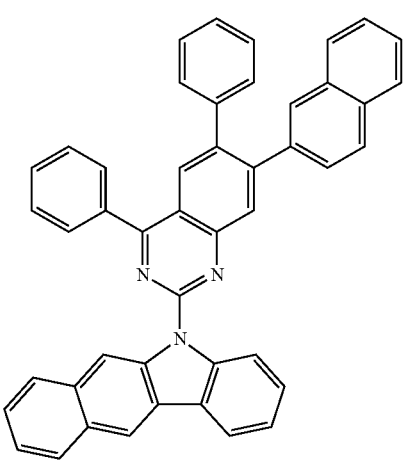
506
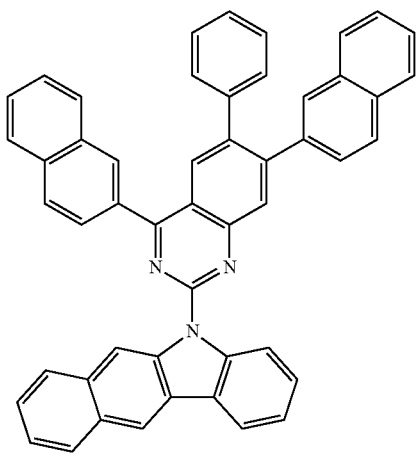

507
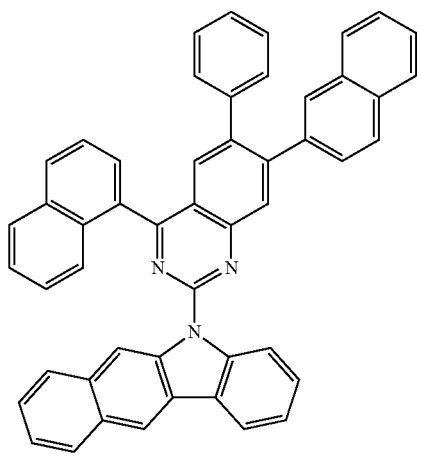
508
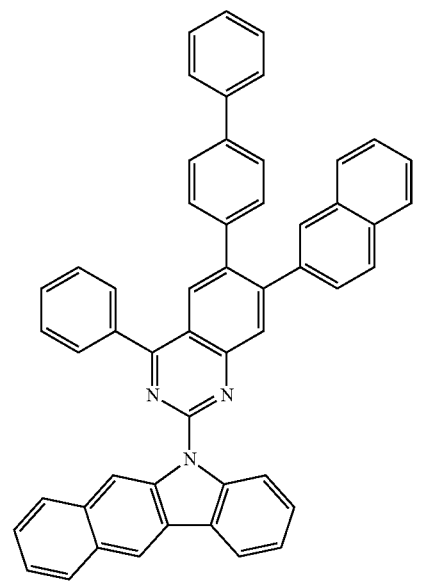
509
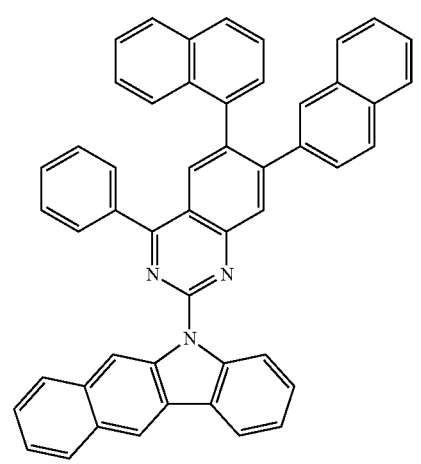
510
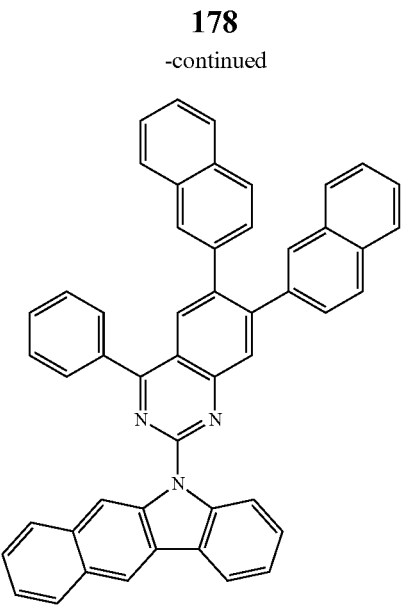
511
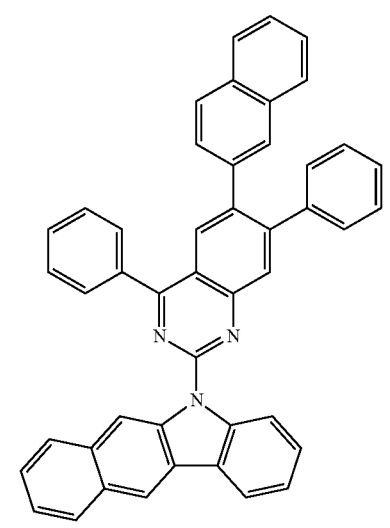
512
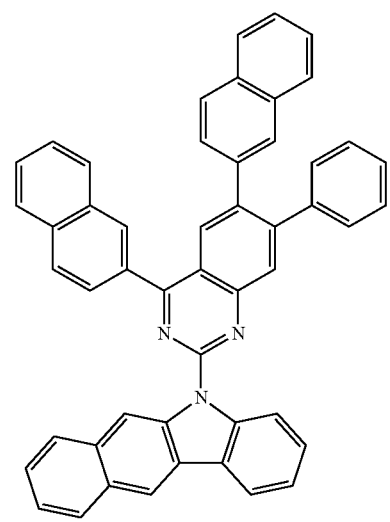

-continued
513
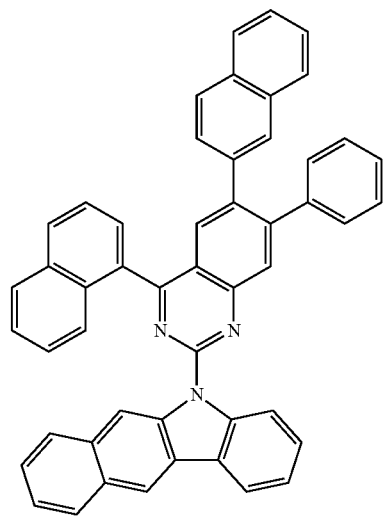
514
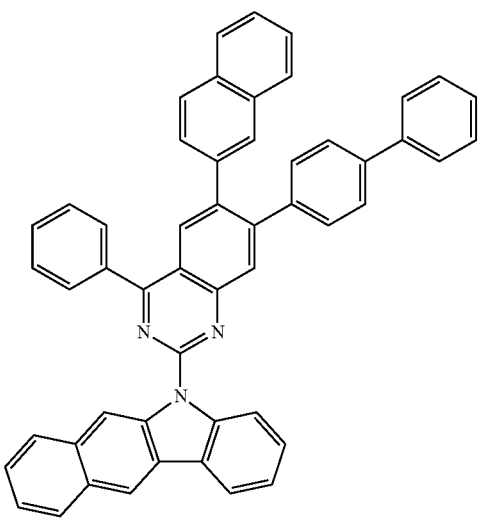
515
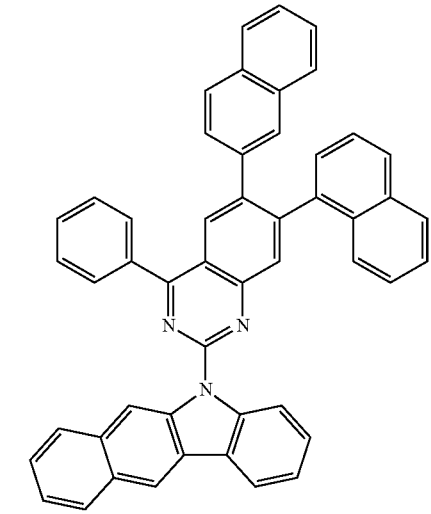
-continued
516
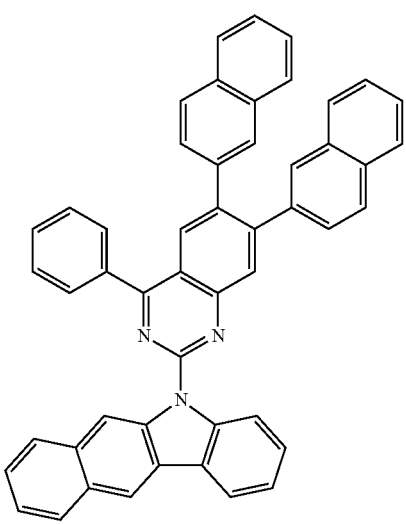
517
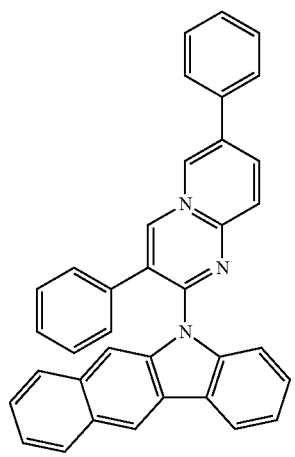
518

519
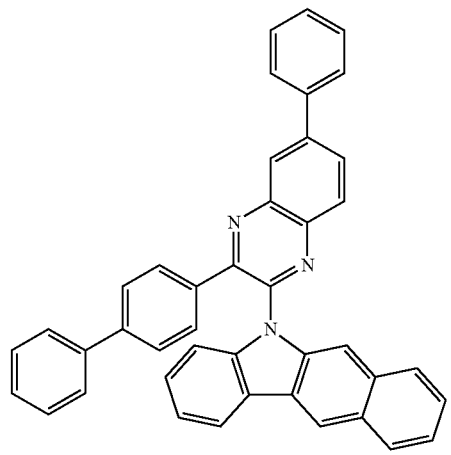
520
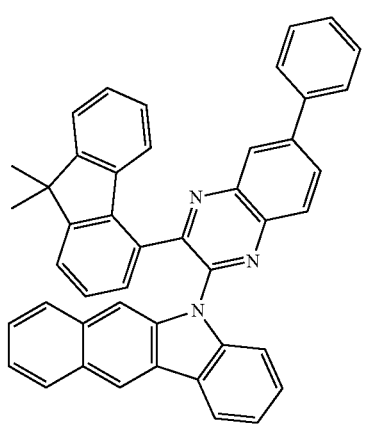
521
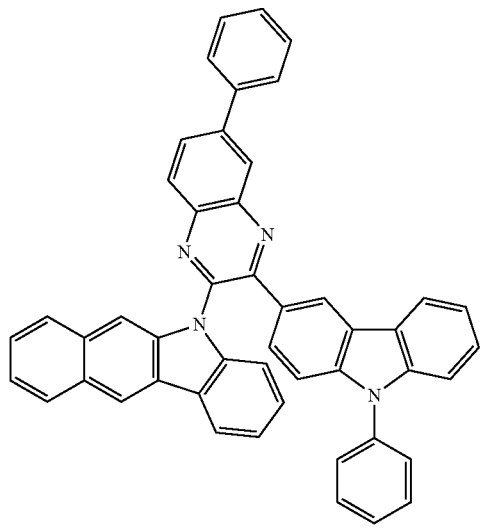
522
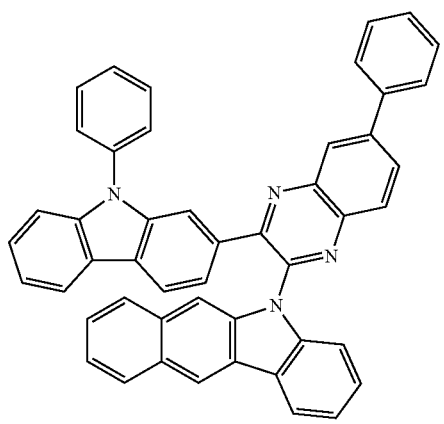
523
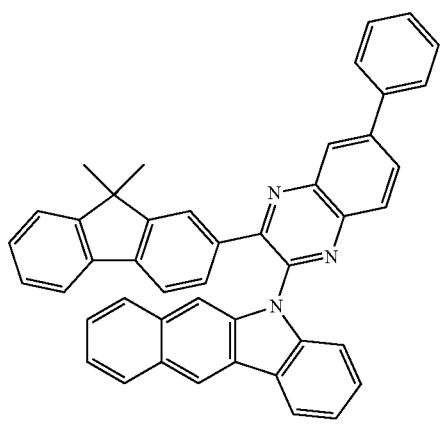
524
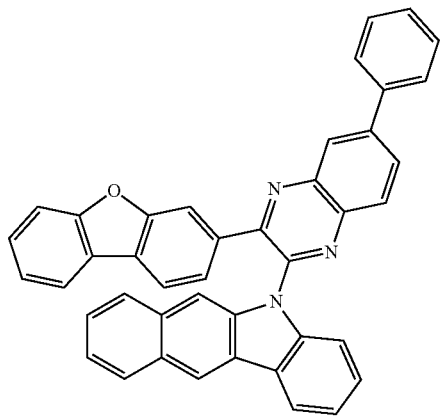

525
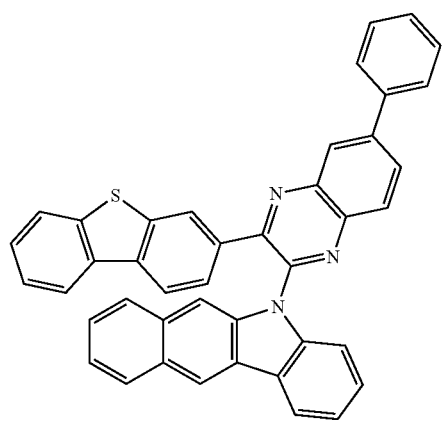
526
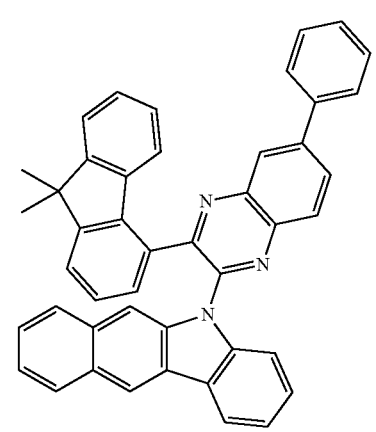
527
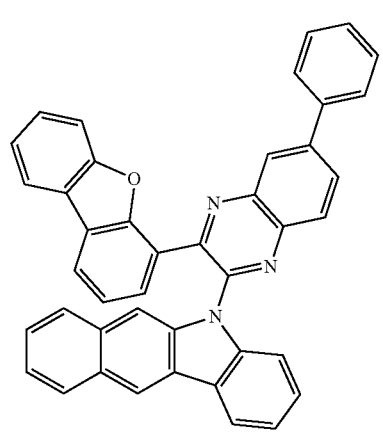
528
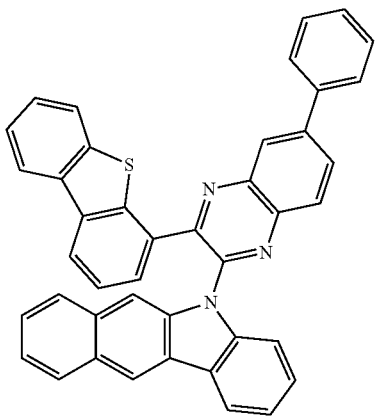
529
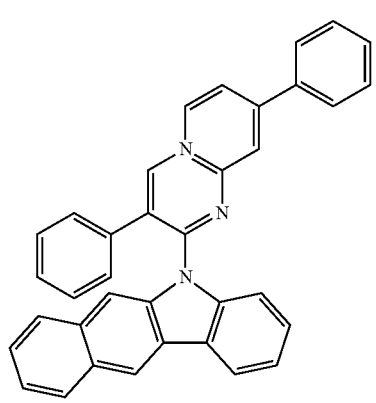
530
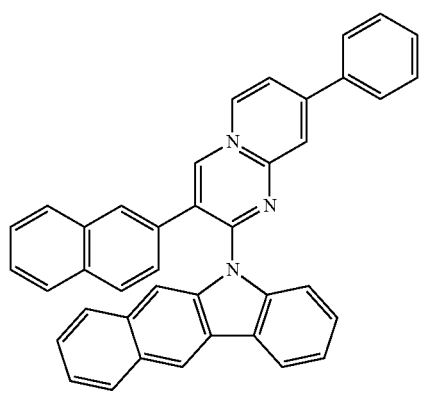
531
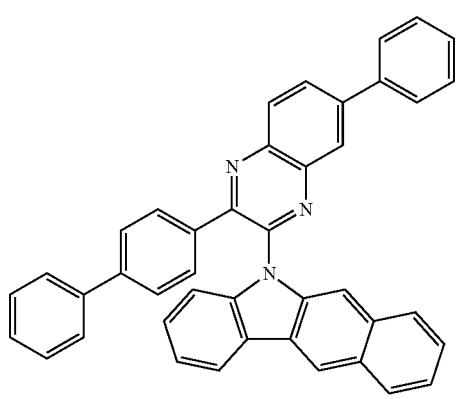

532
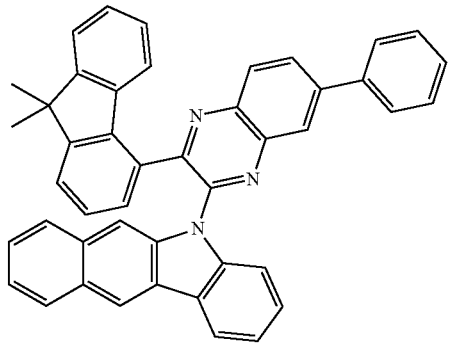
533
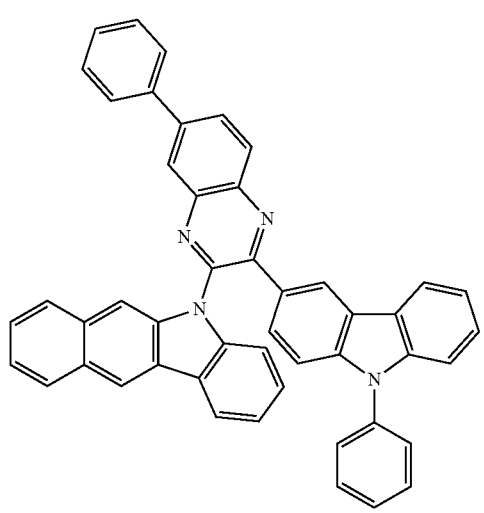
534
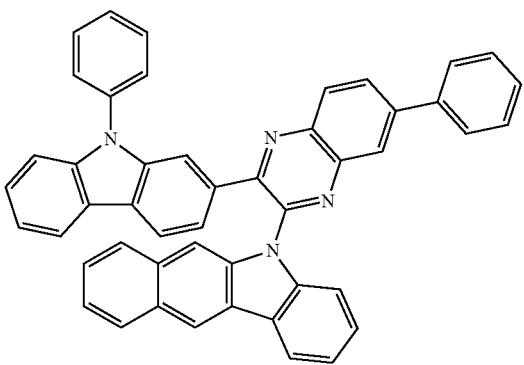
535
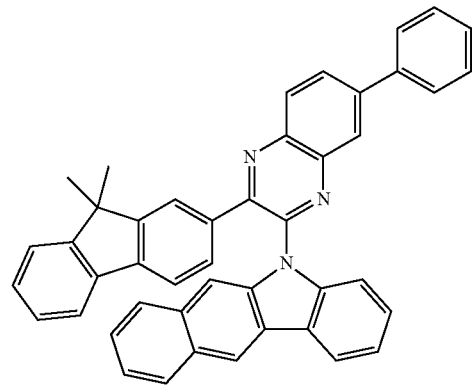
536
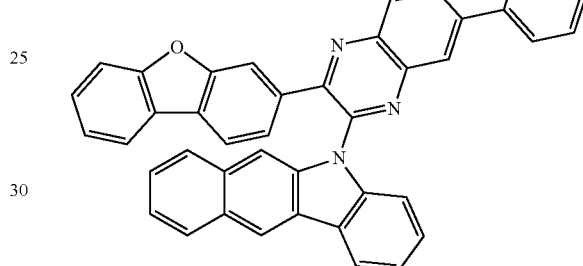
537
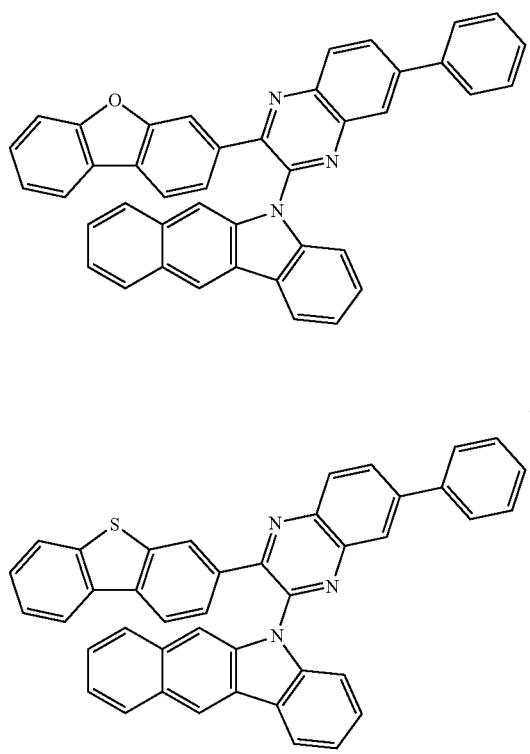
538
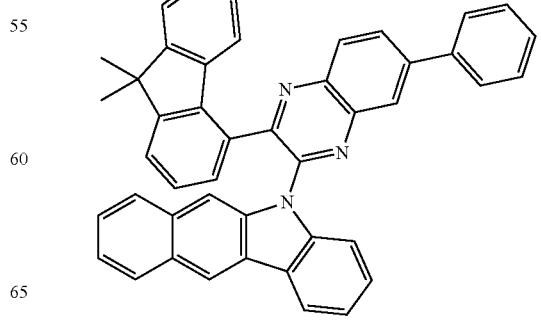

539
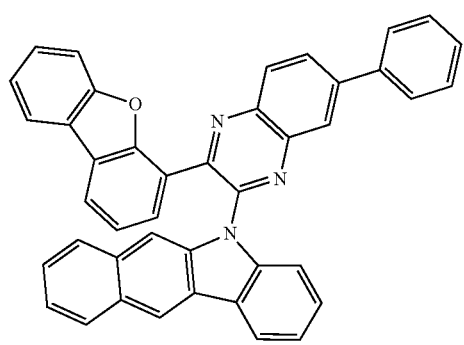
540
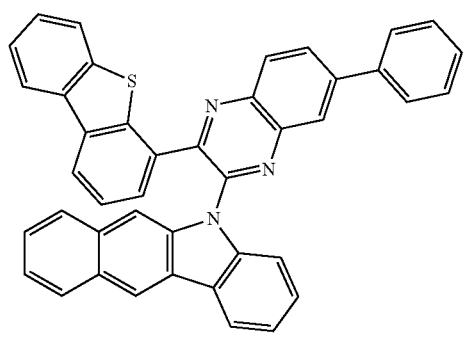
541
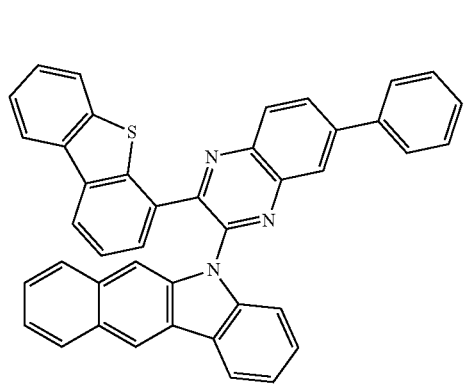
542
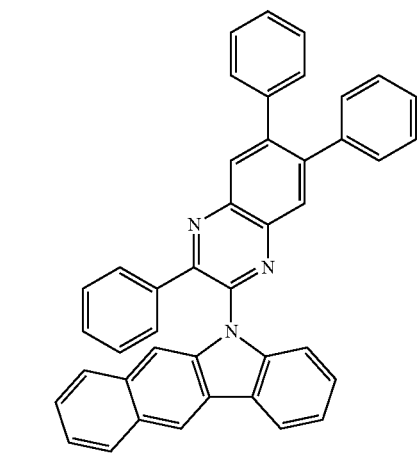
543
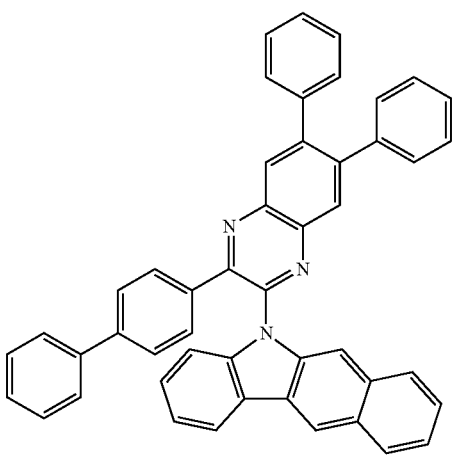
544
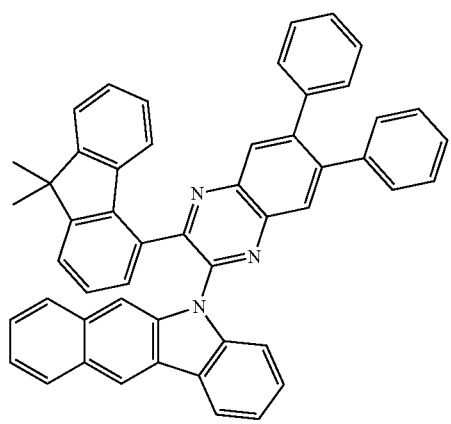
545
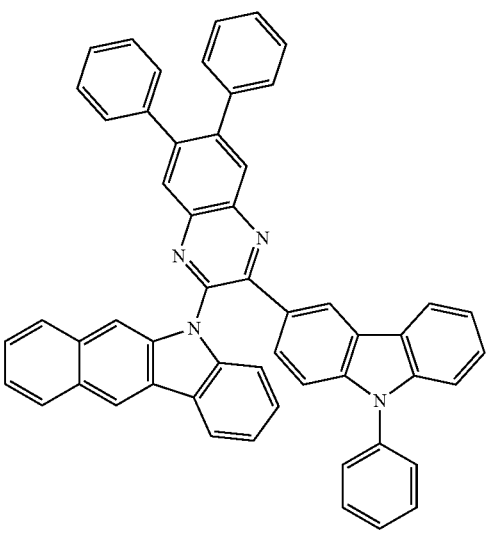

546
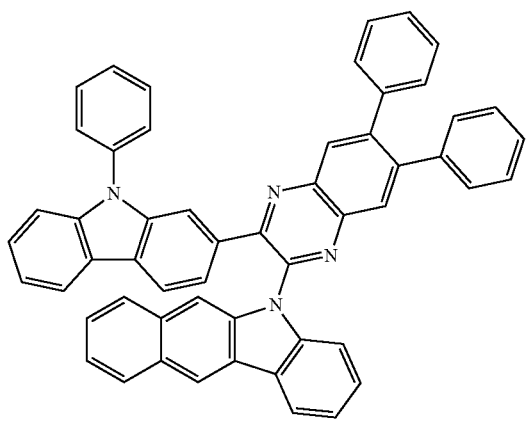
547
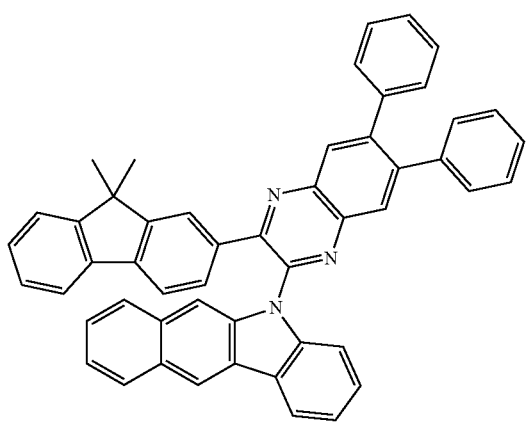
548
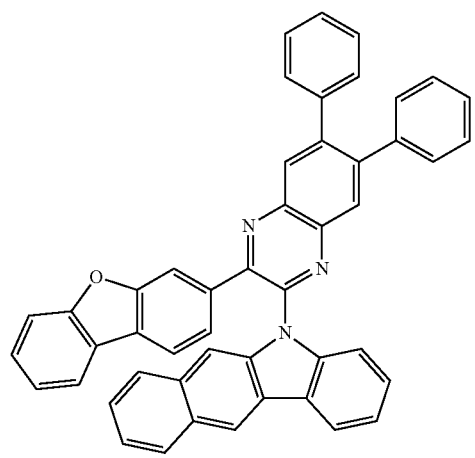
549
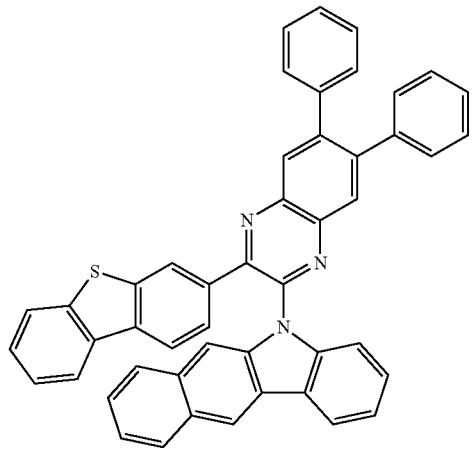
550
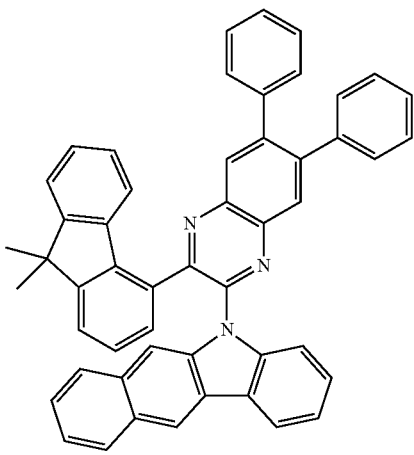
551
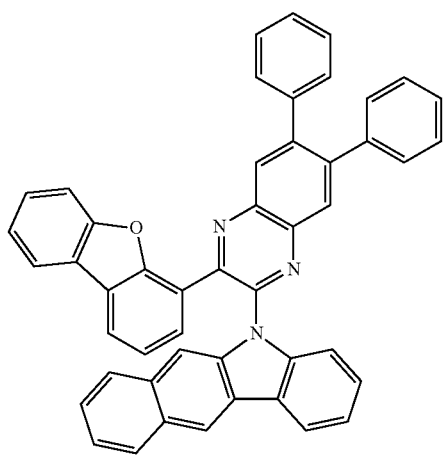

552
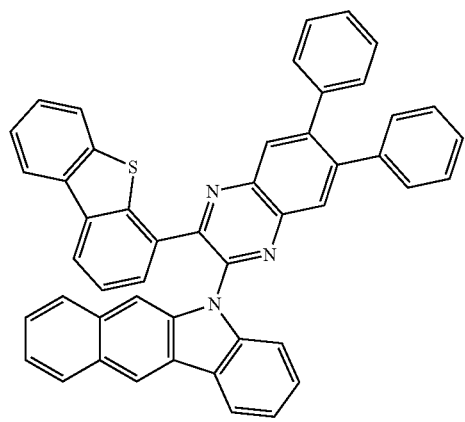
553
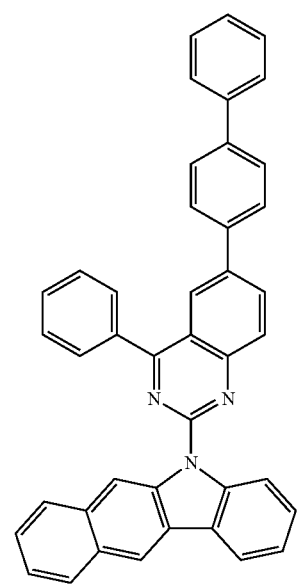
554
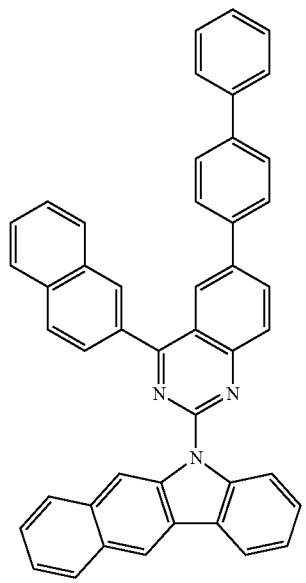
555
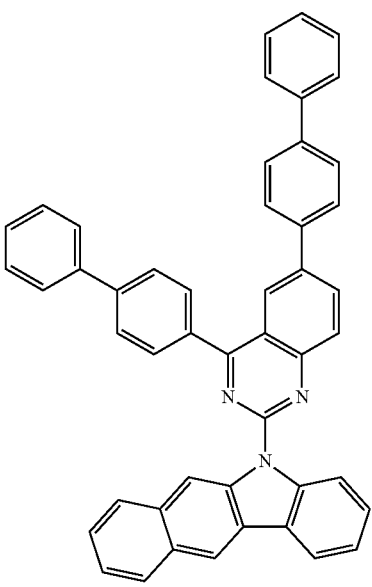
556
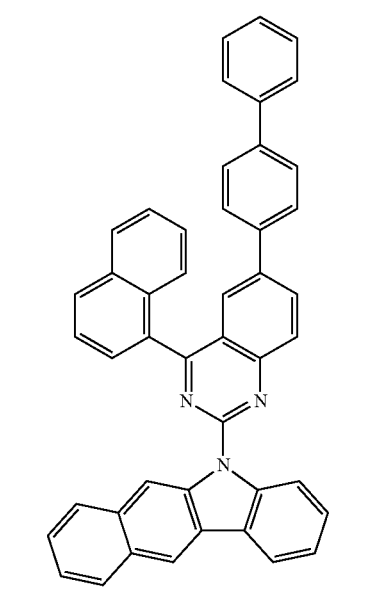
587
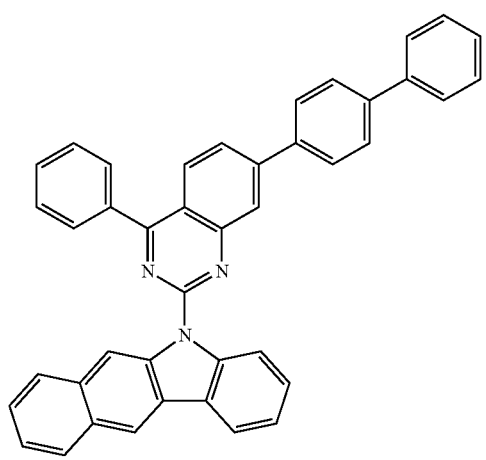

588
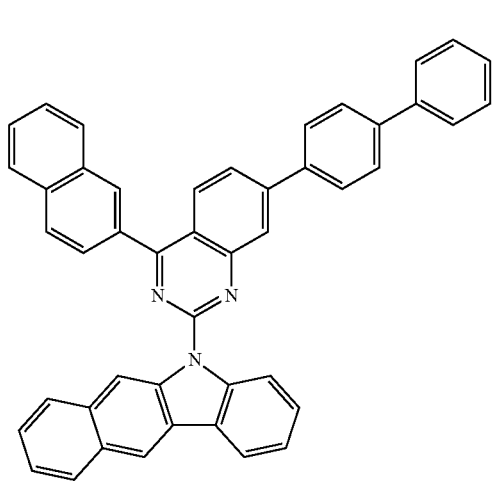
589
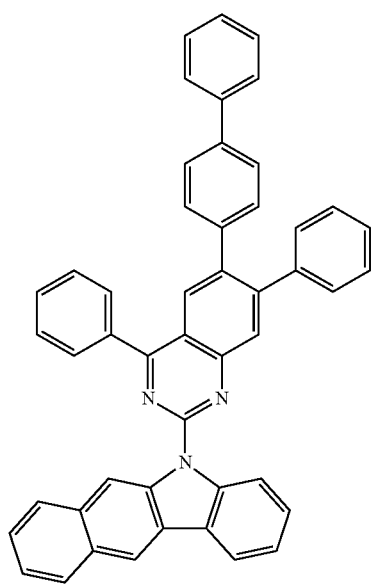
560
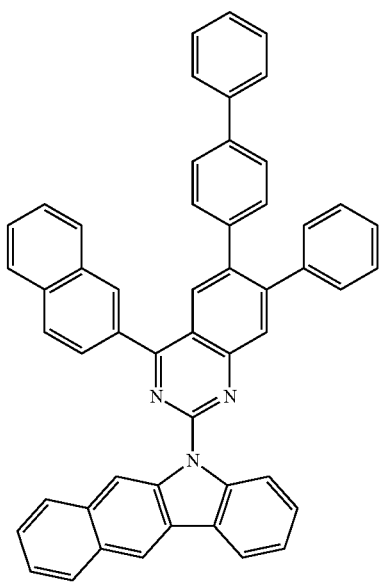
561
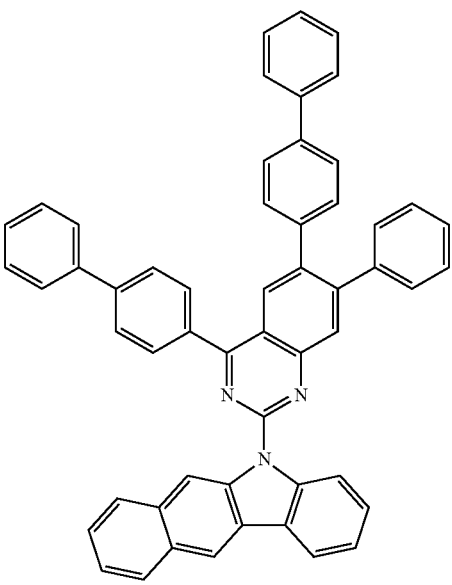
562
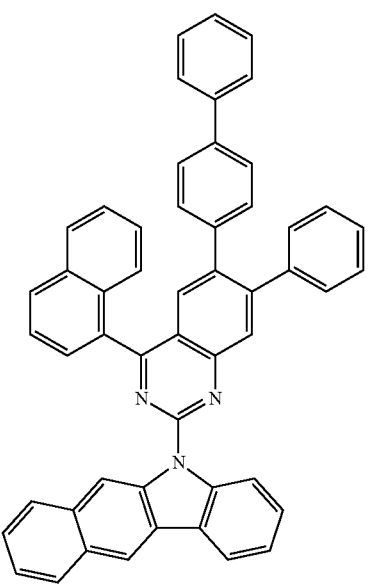
563
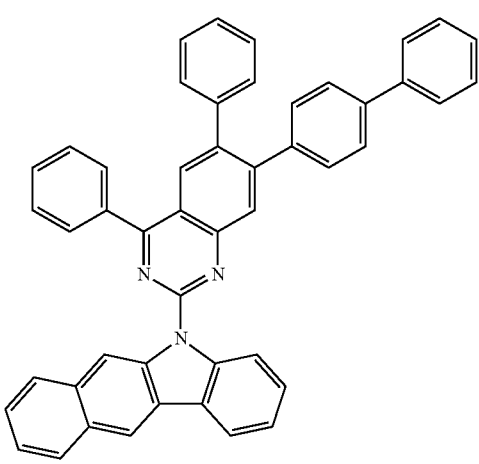

564
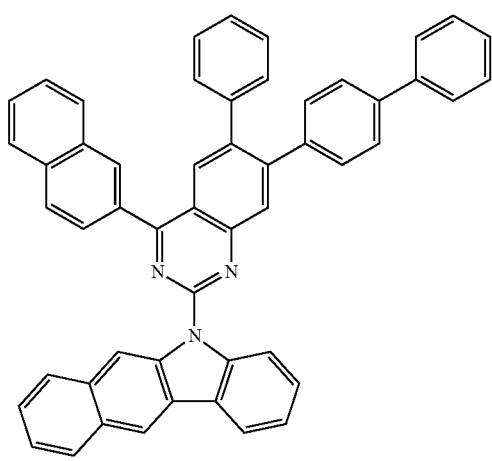
565
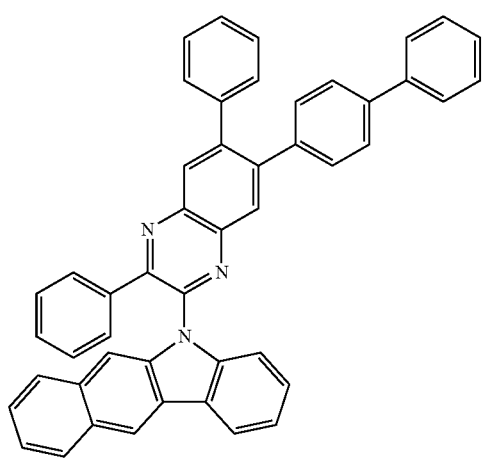
566
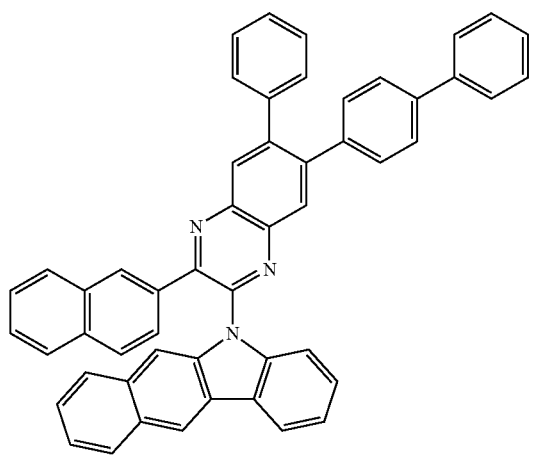
567
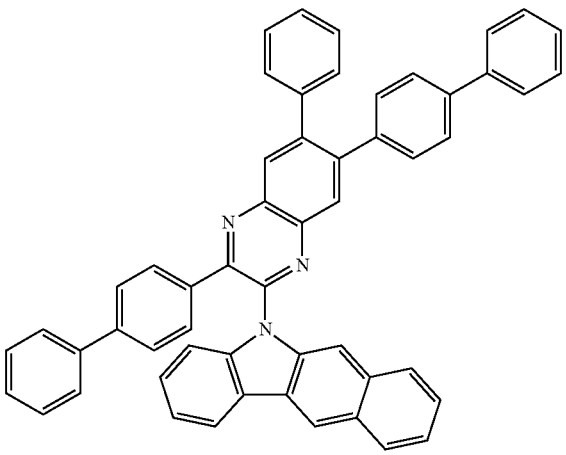
568
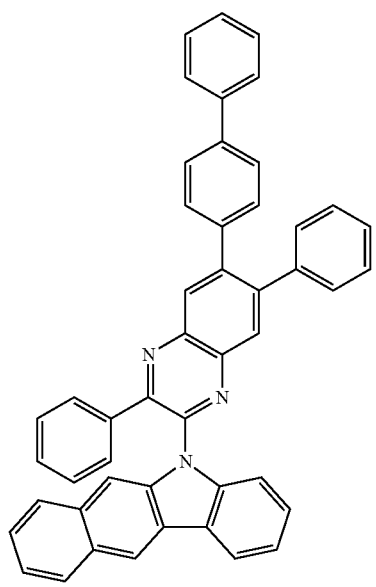
569
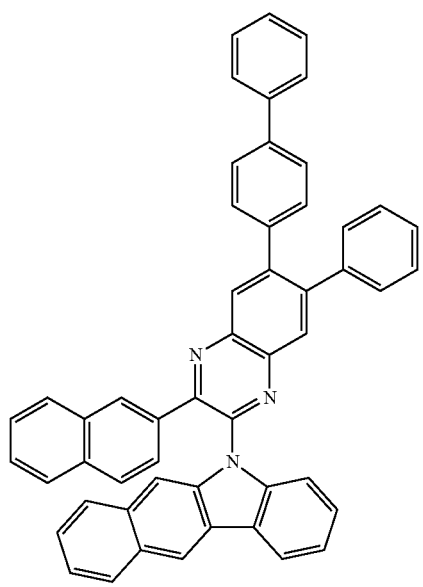

570
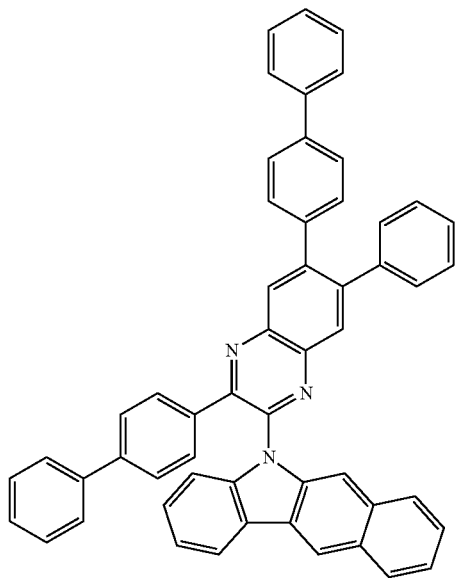
571
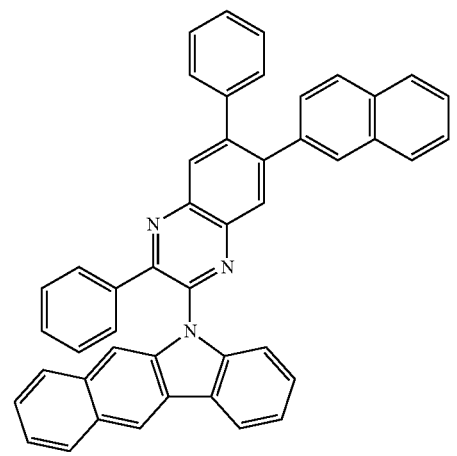
572
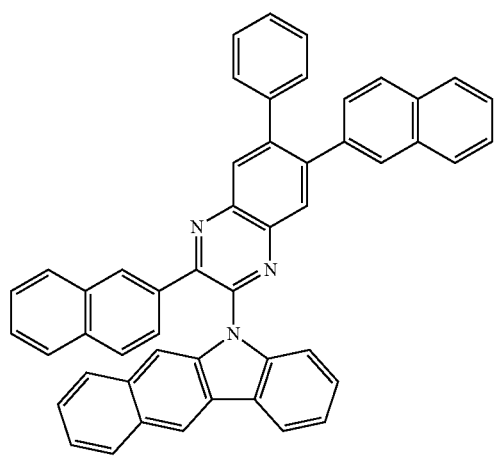
573
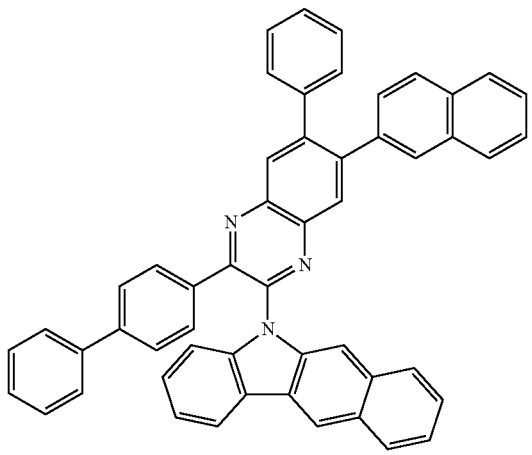
574
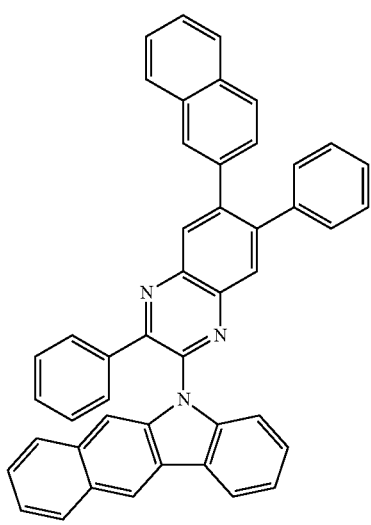
575
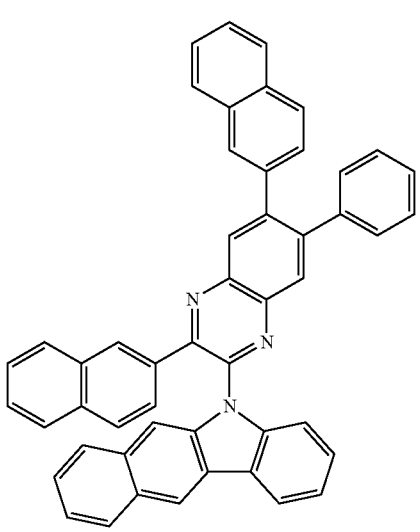

576
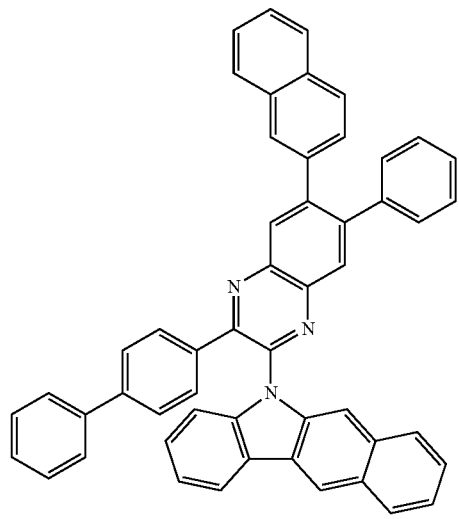
577
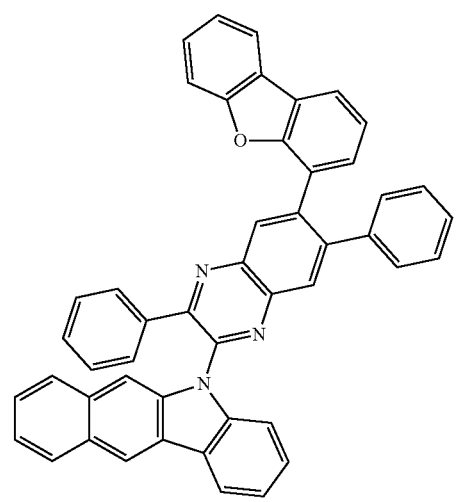
578
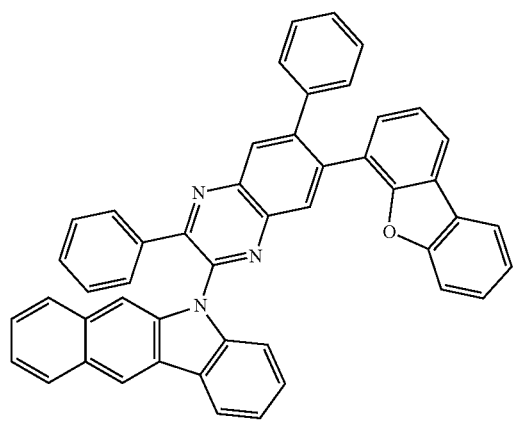
579
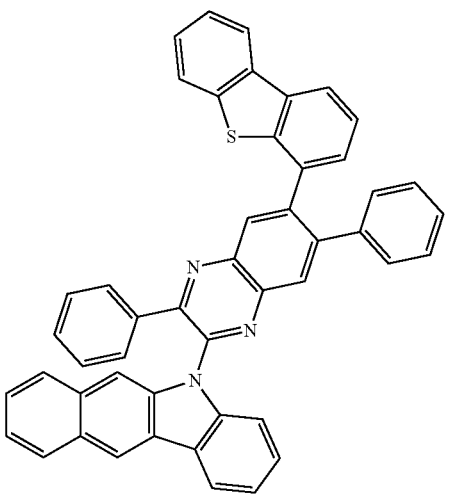
580
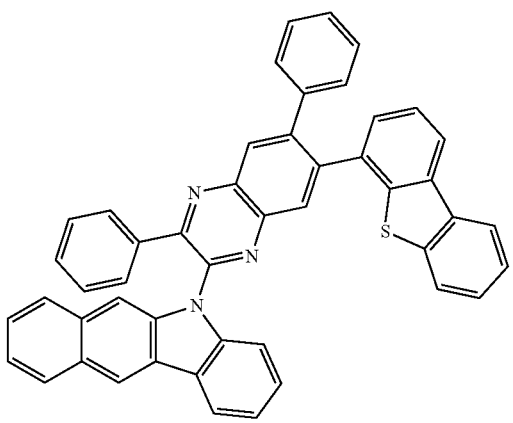
581
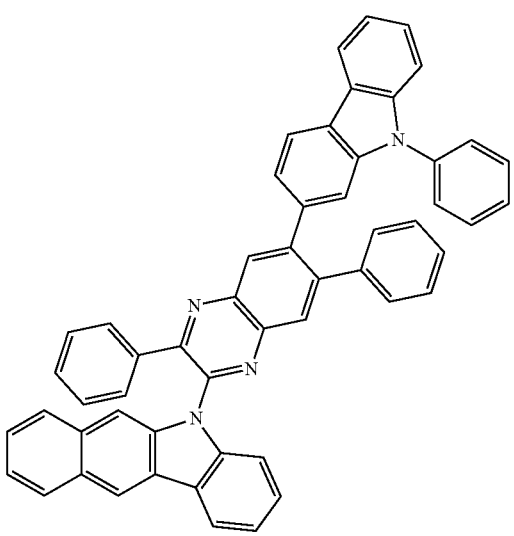

201
-continued
582
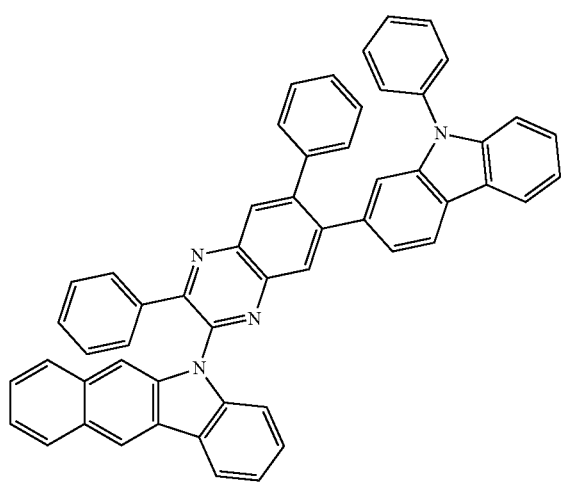
583
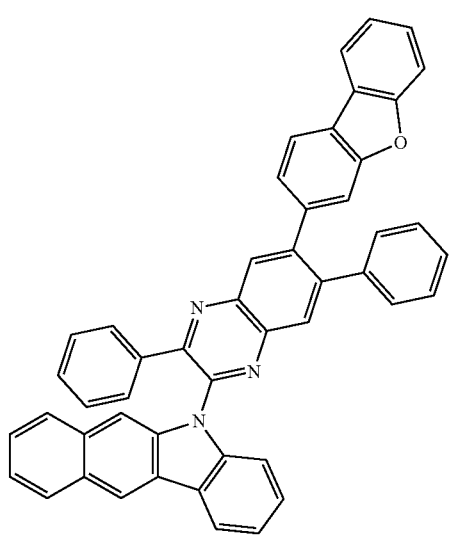
584
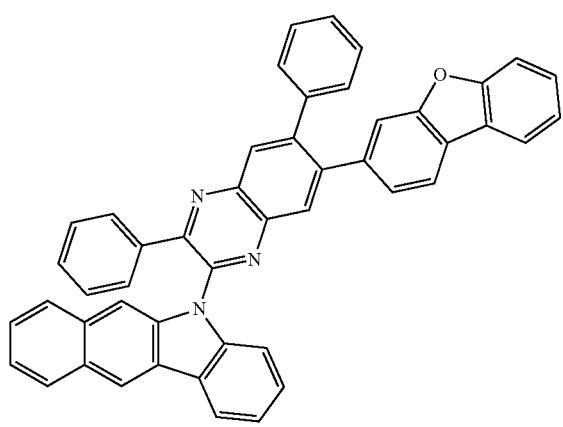
202
-continued
585
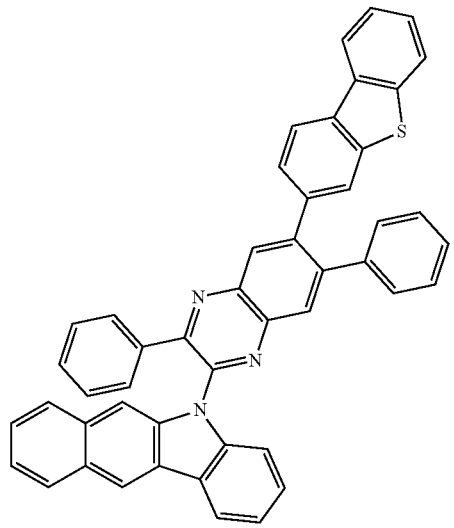
586
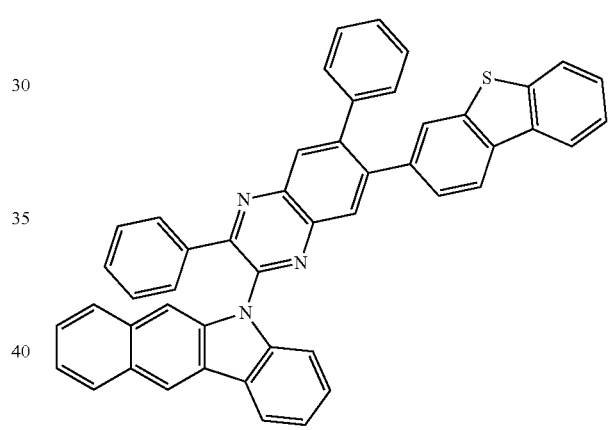
587
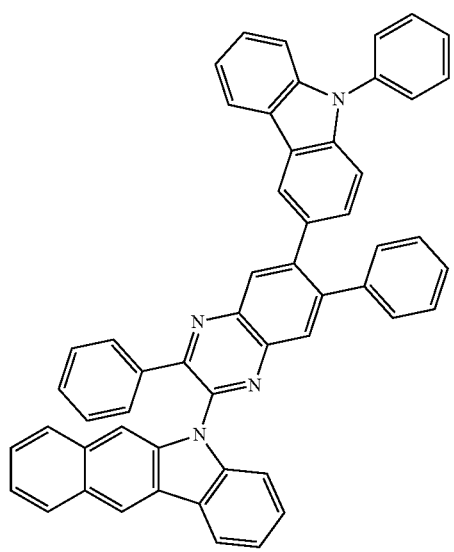

203
-continued
588
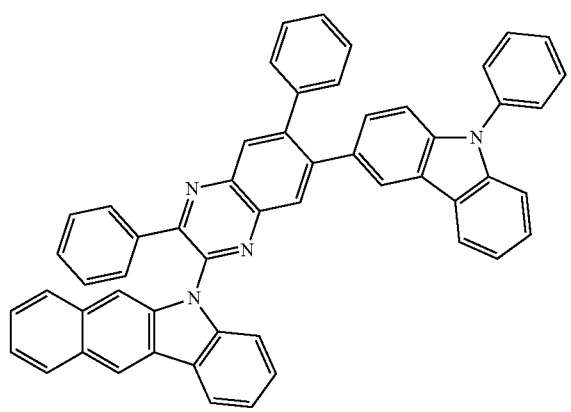
589
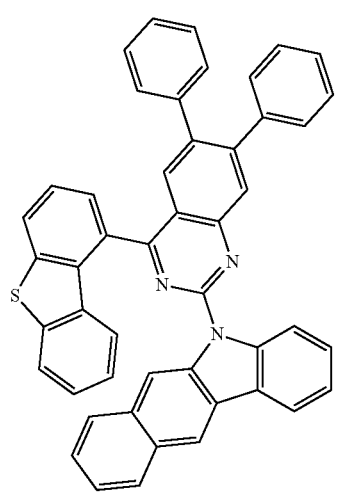
590
591
-continued
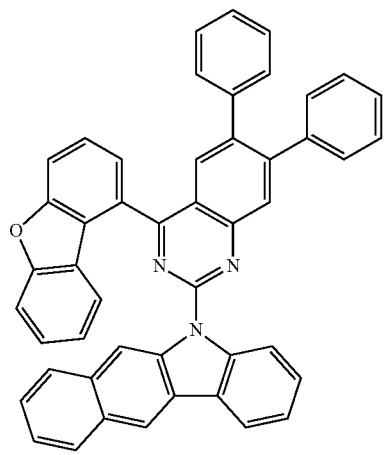
592
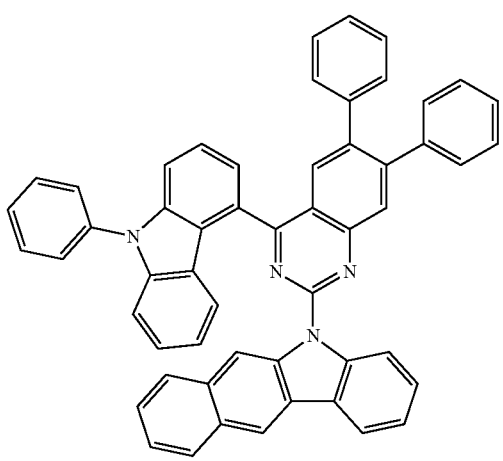
593

594 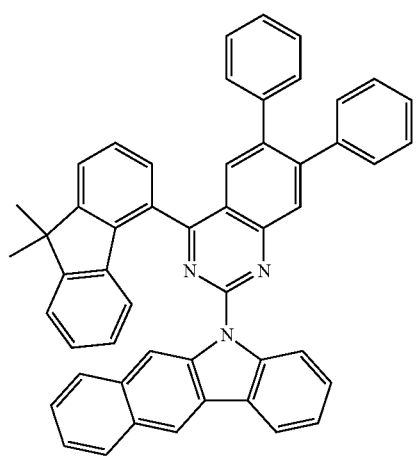
595 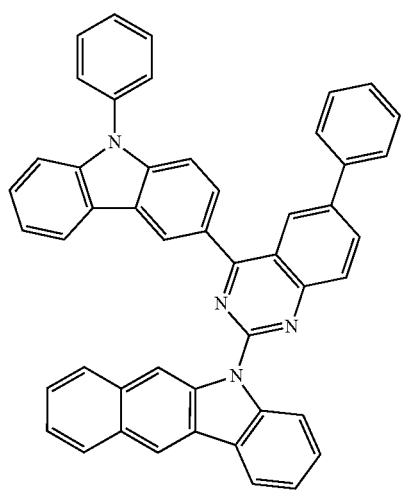
596 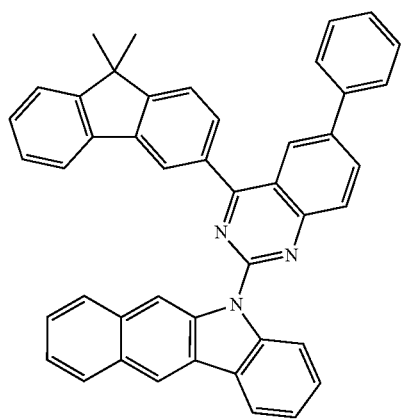
597 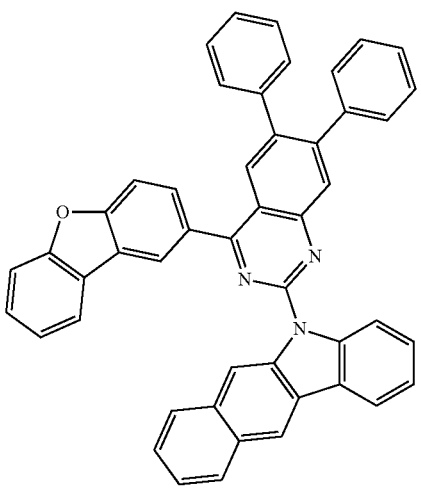
598 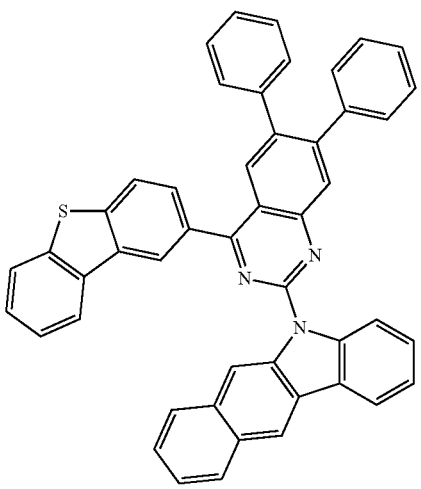
599 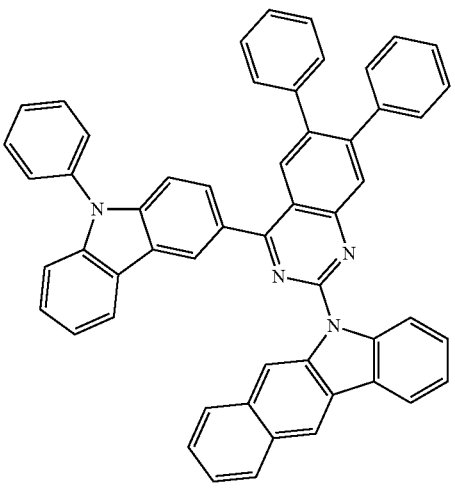

| 600 | 603 |
|---|---|
| 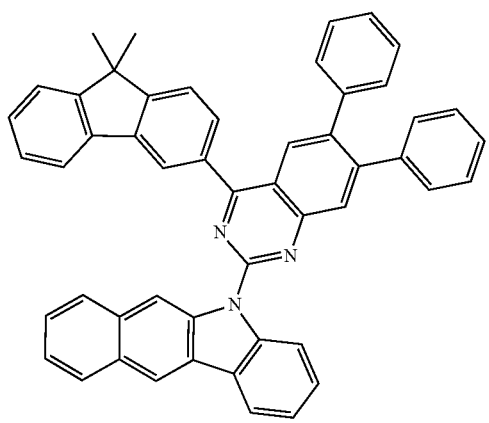 | 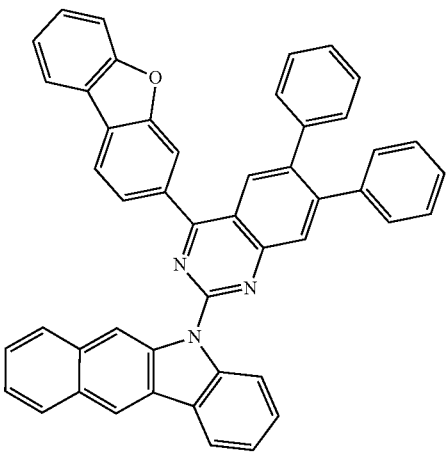 |
| 601 | 604 |
| 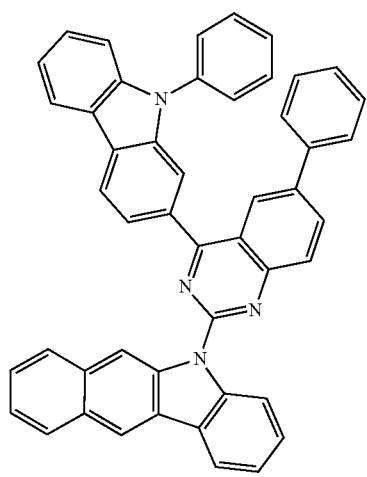 | 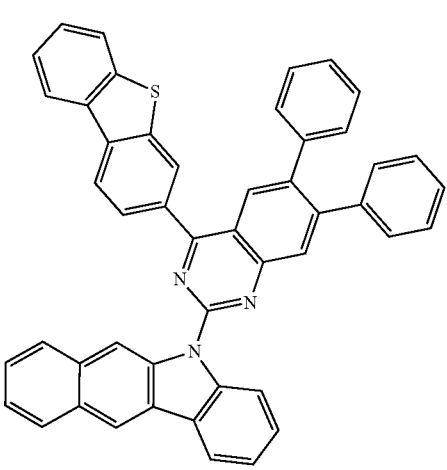 |
| 602 | 605 |
| 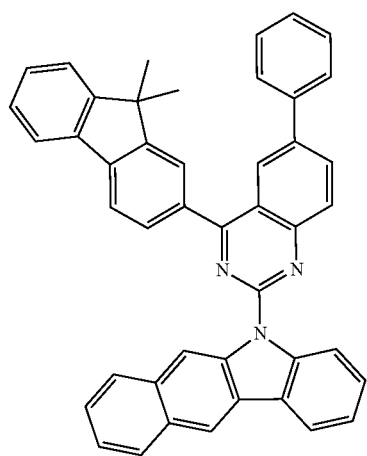 | 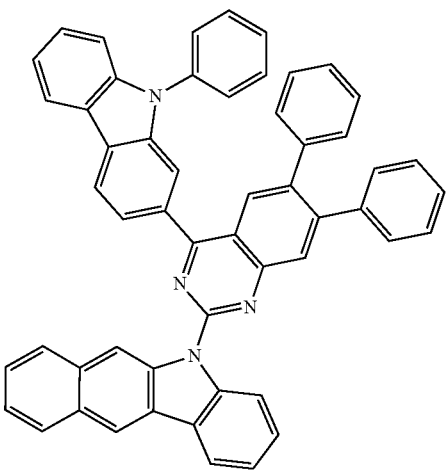 |

209
-continued
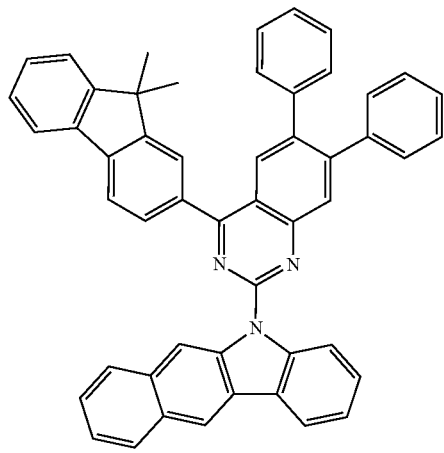
606
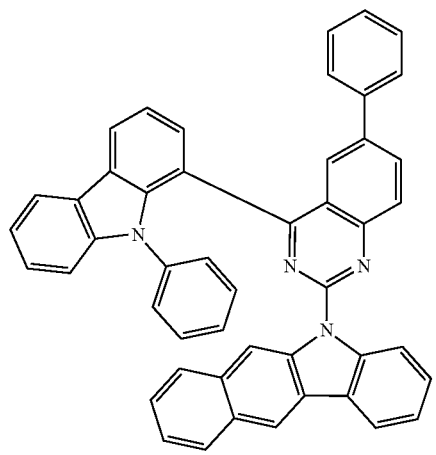
607
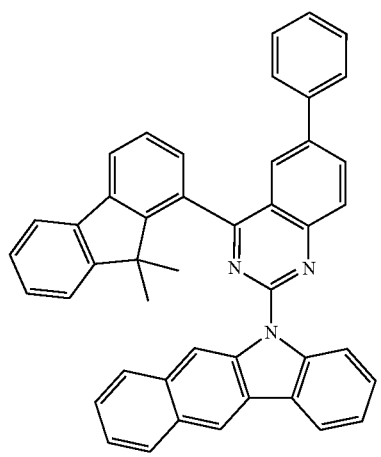
608
210
-continued
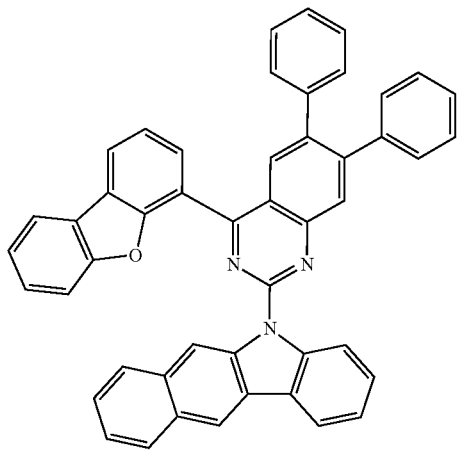
609
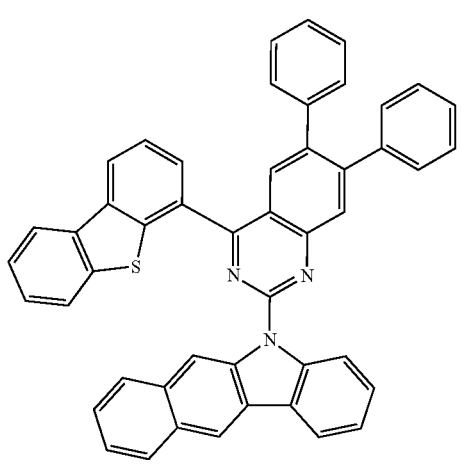
610
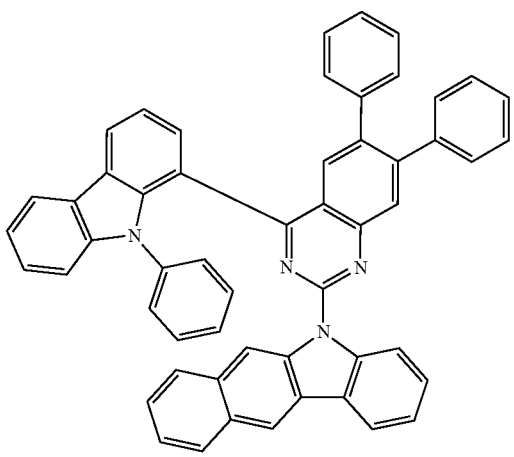
611

211
-continued
612
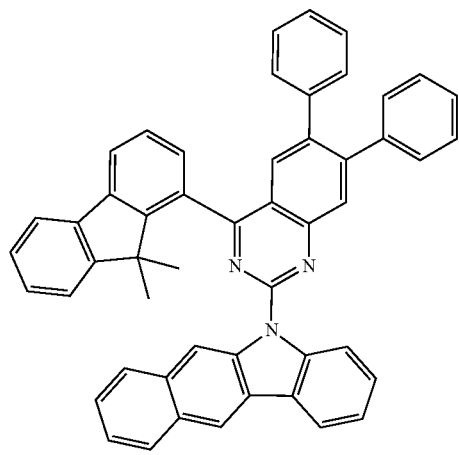
613
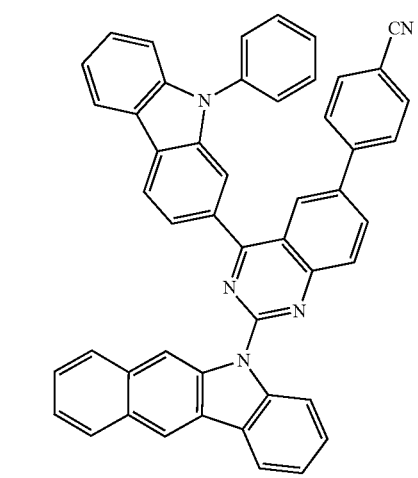
614
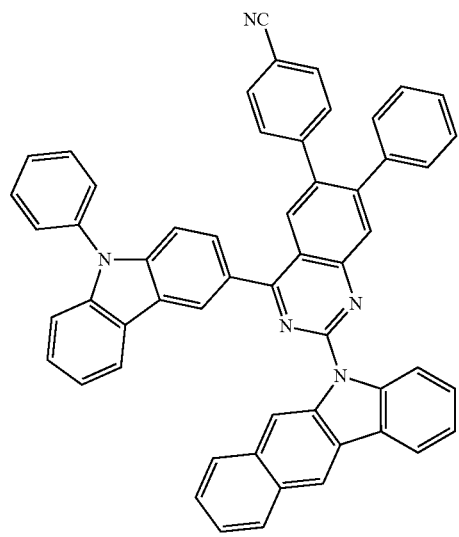
212
-continued
615
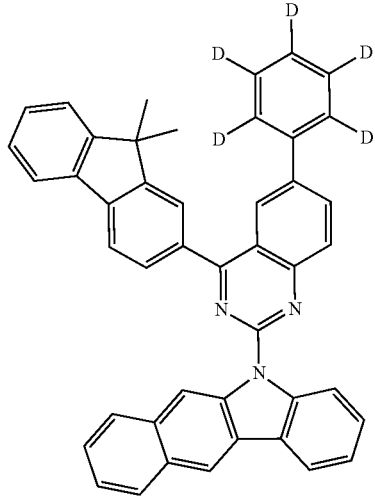
616
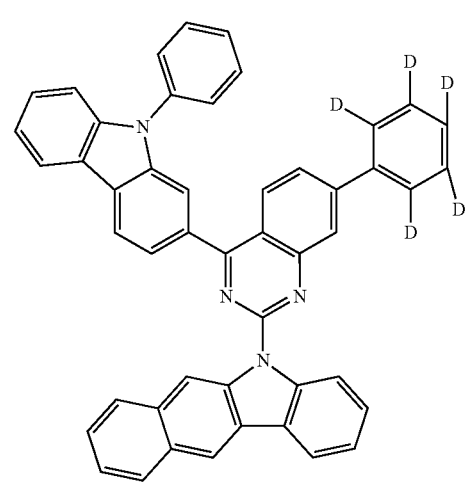
617
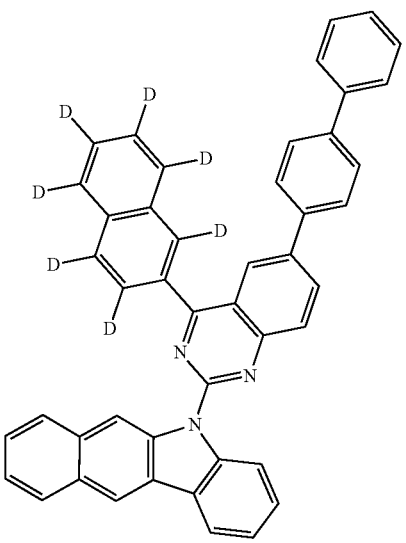

| 213 -continued | 214 -continued |
|---|---|
| 618 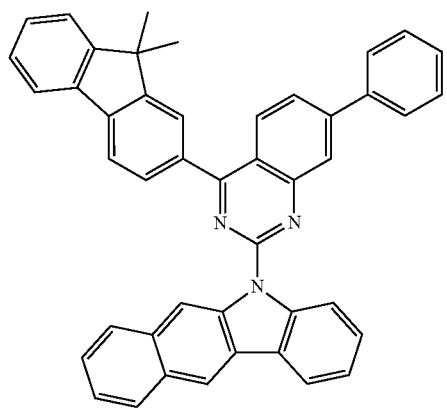 | 621 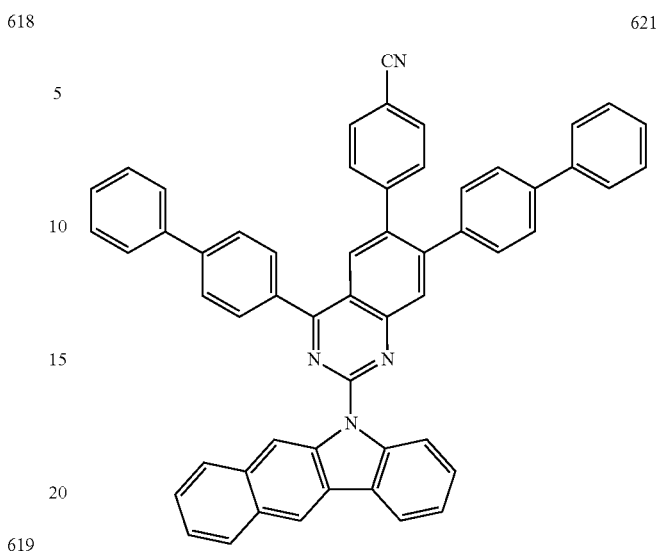 |
| 619 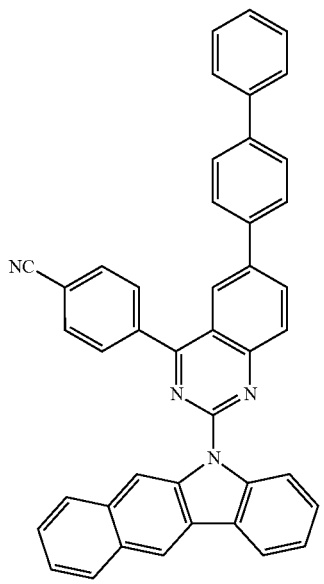 | 622 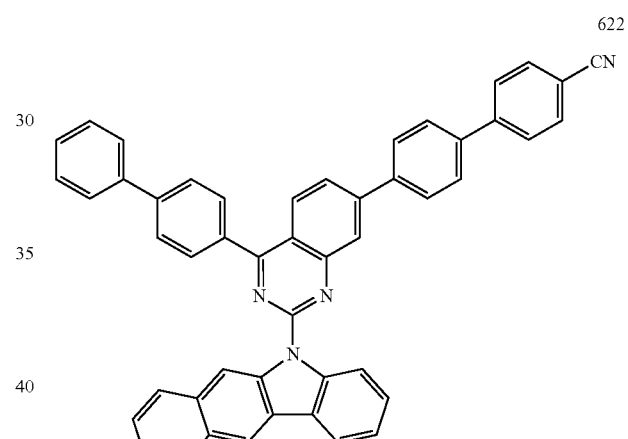 |
| 620 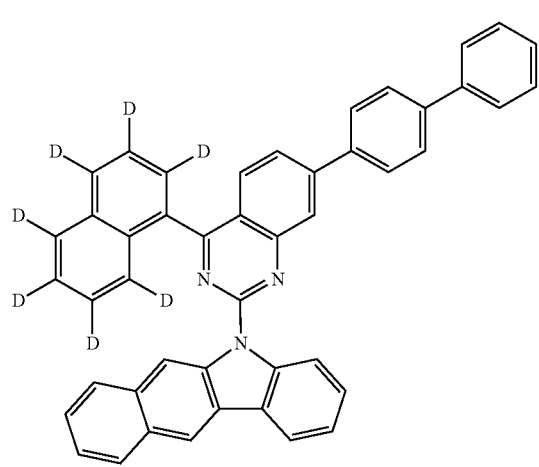 | 623 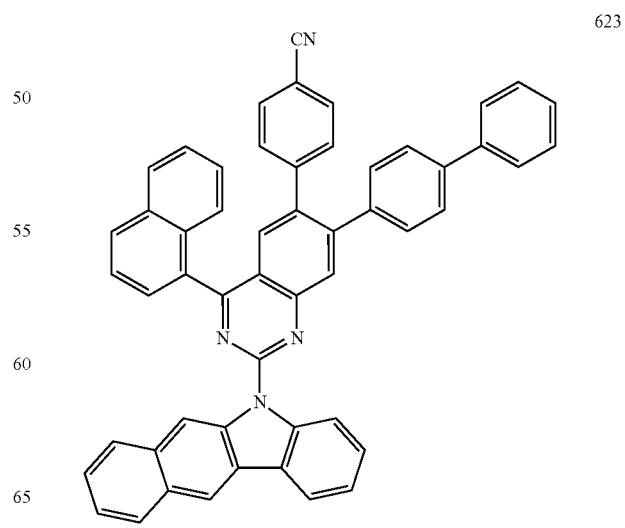 |

215
-continued
624
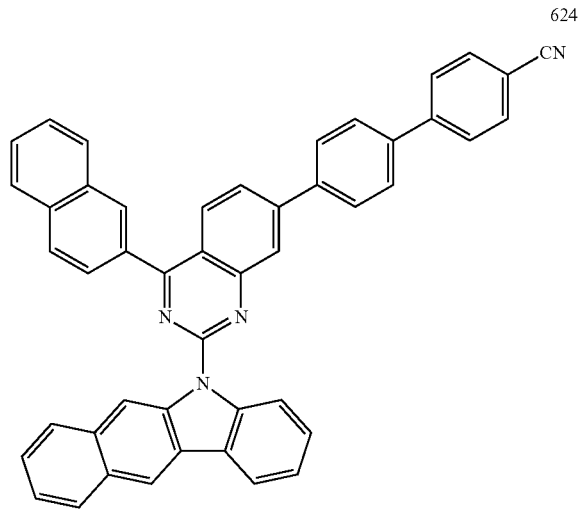
625
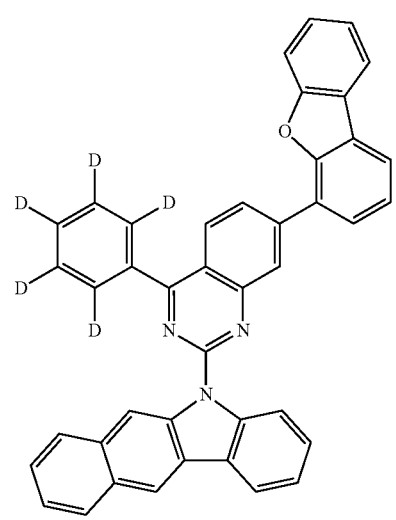
626
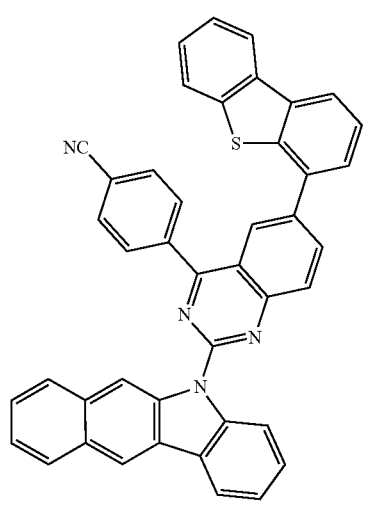
216
-continued
627
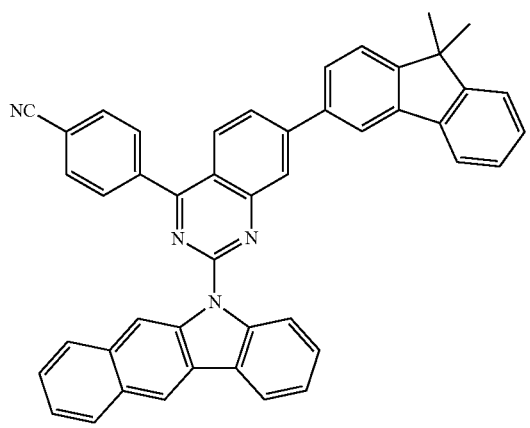
628
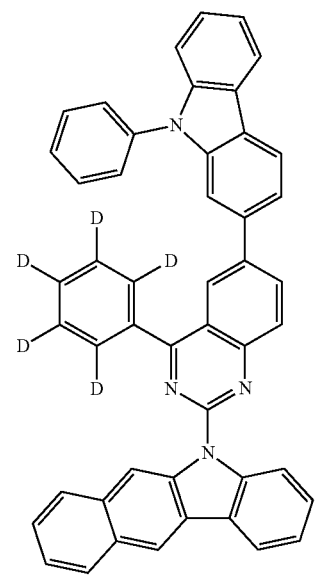
629
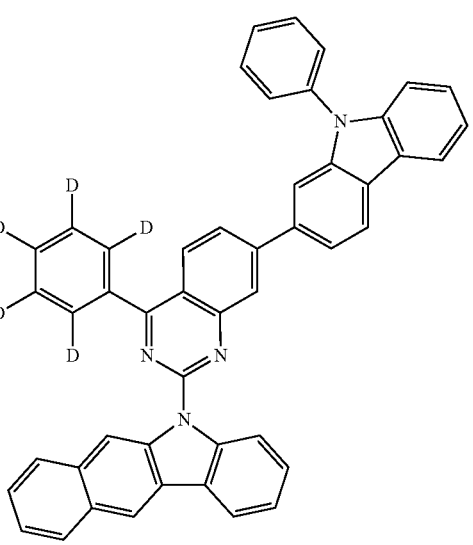

630
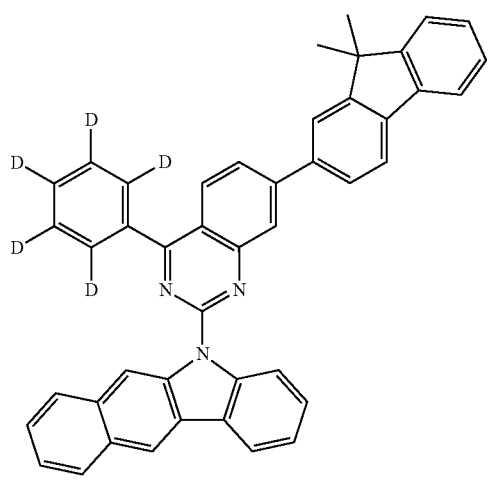
833
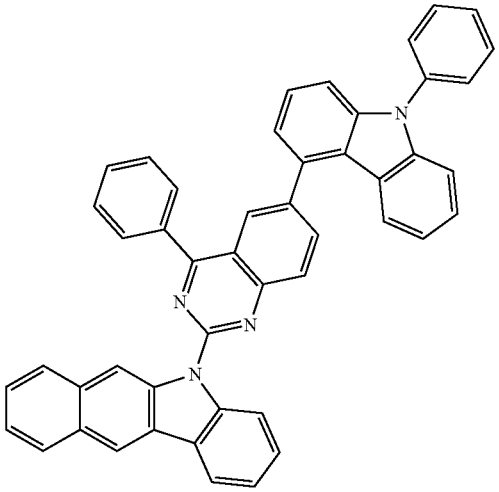
831
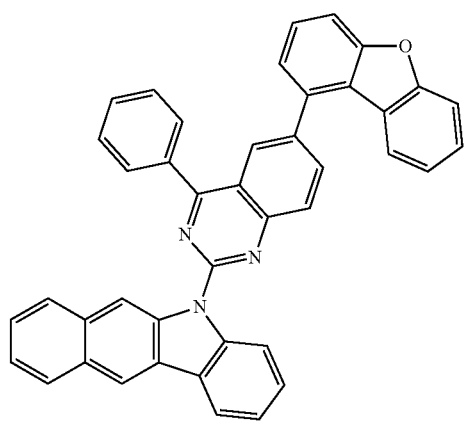
634
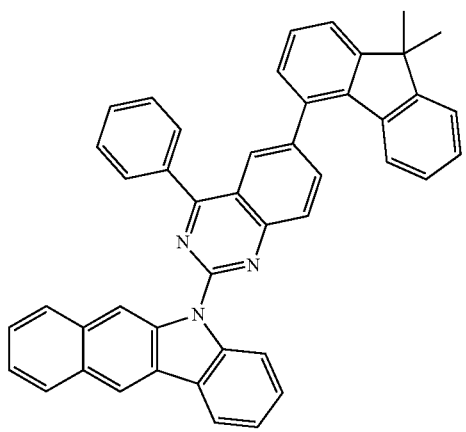
832
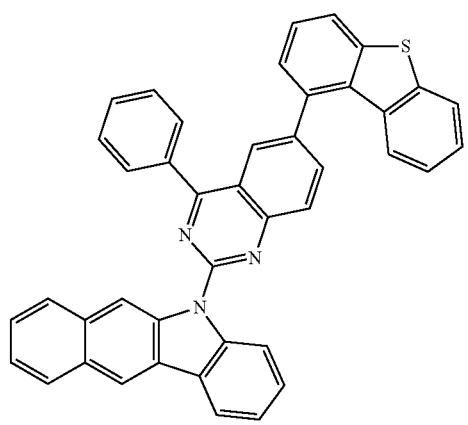
635
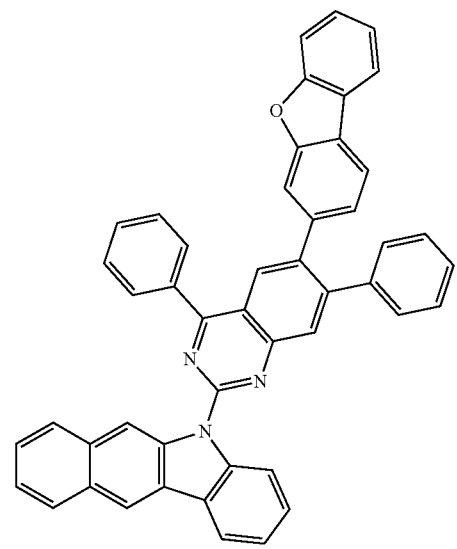

219
-continued
636
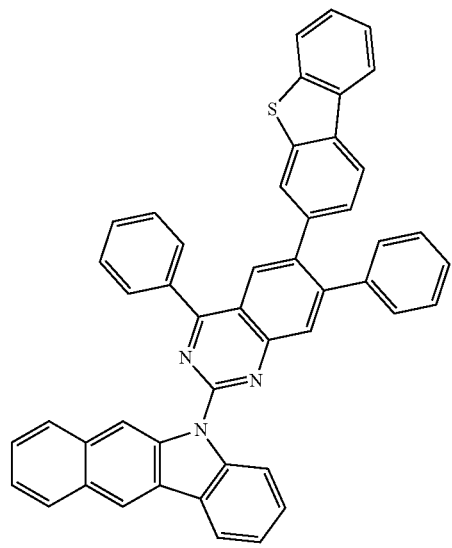
637
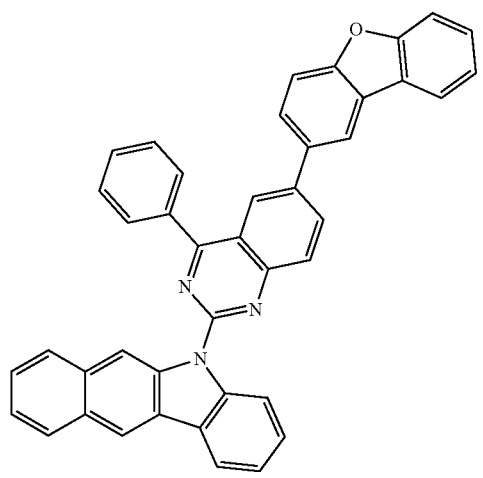
638
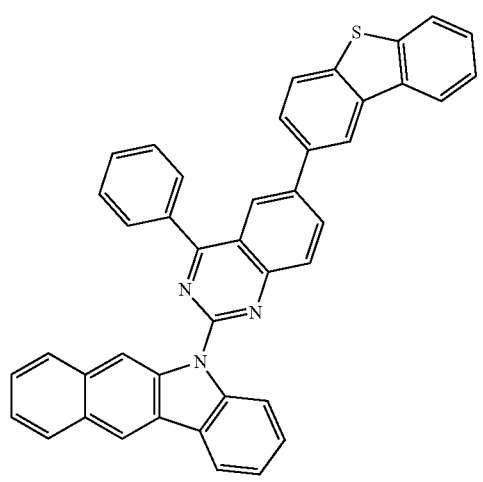
220
-continued
639
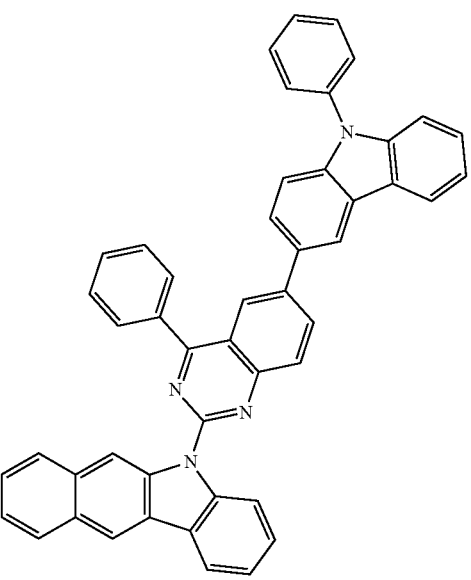
640
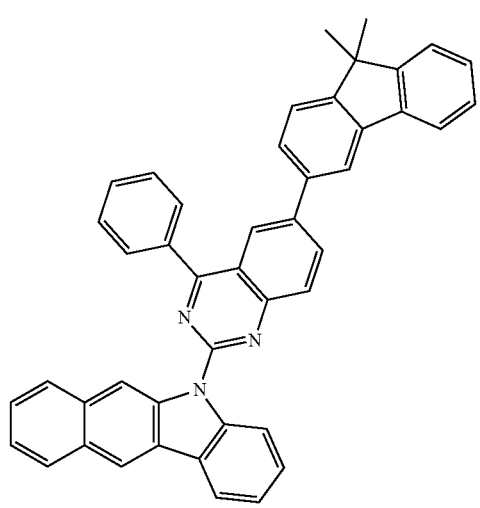
641
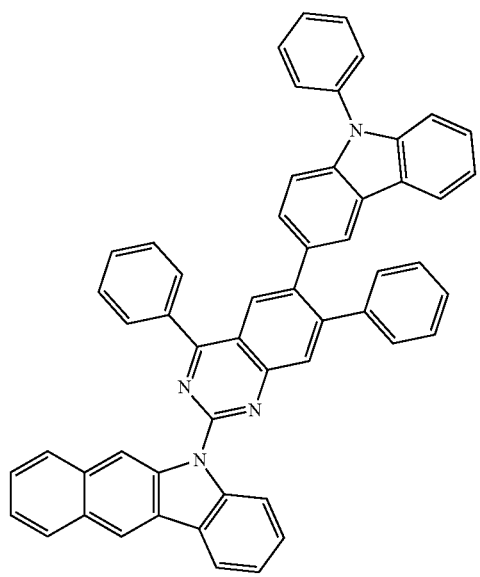

642
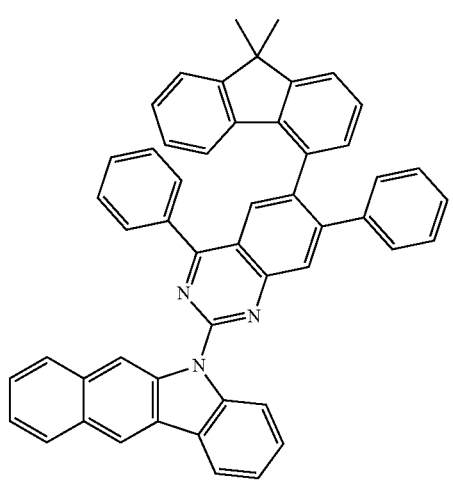
643
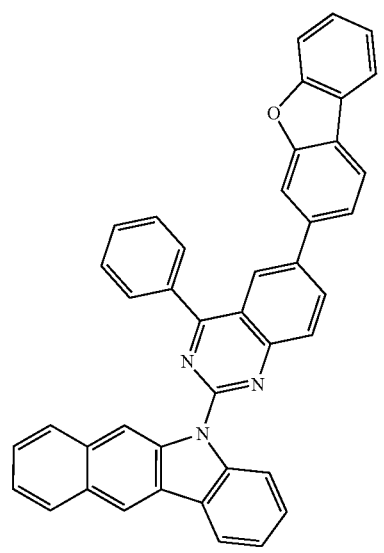
644
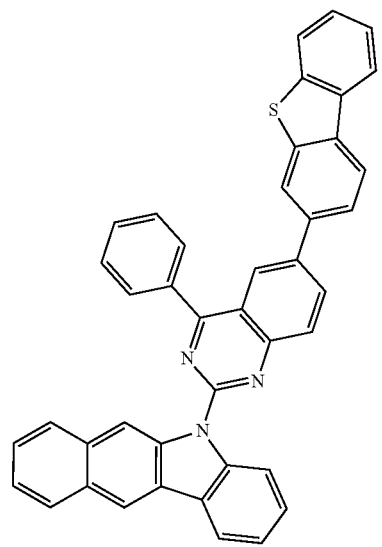
645
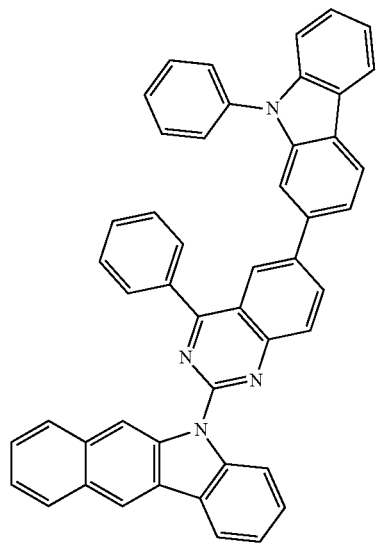
646
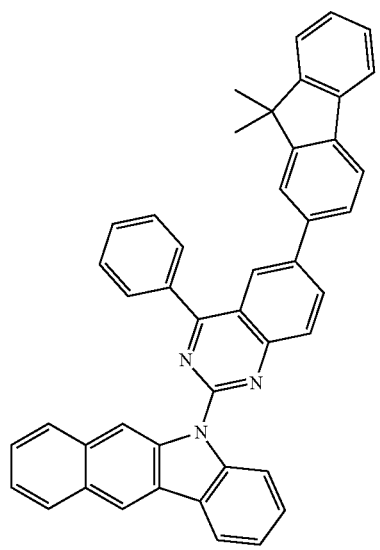
647
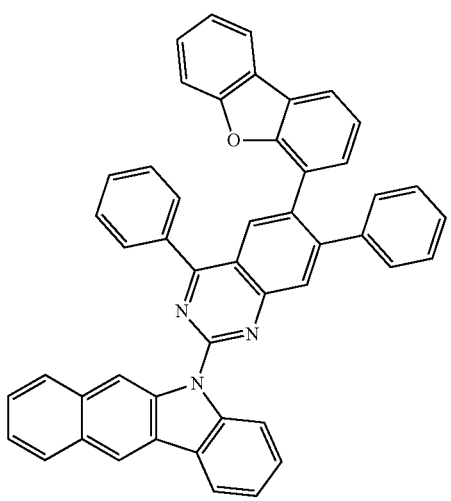

223
-continued
648
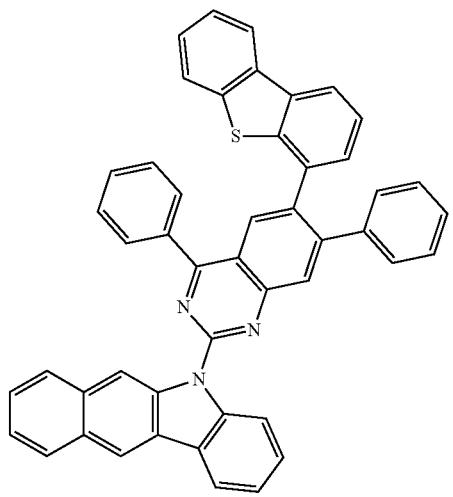
649
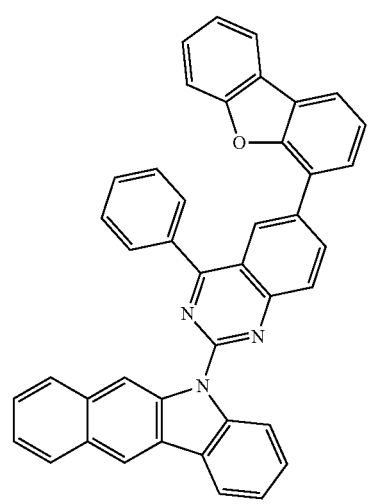
650
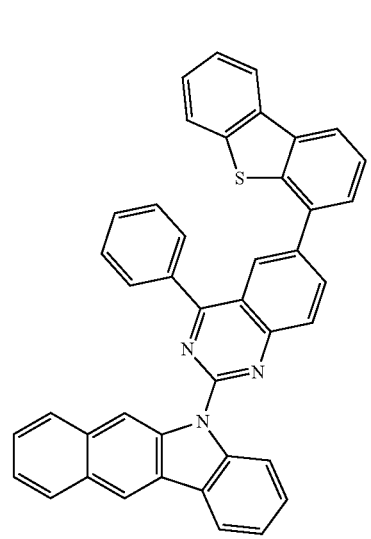
224
-continued
651
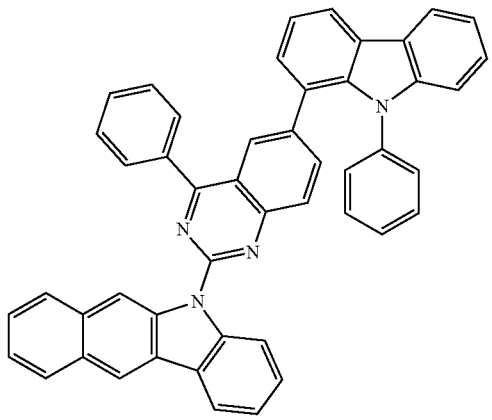
652
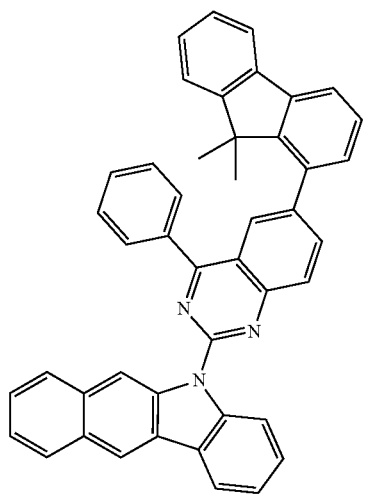
653
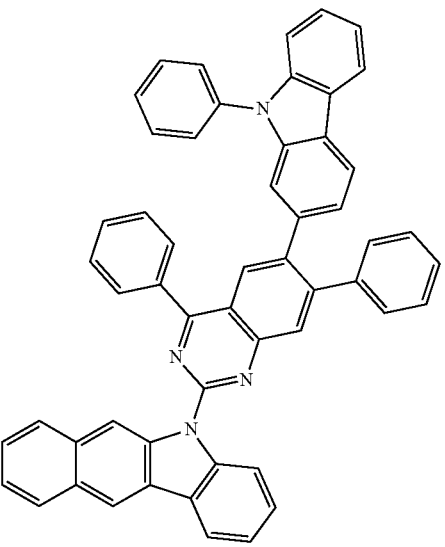

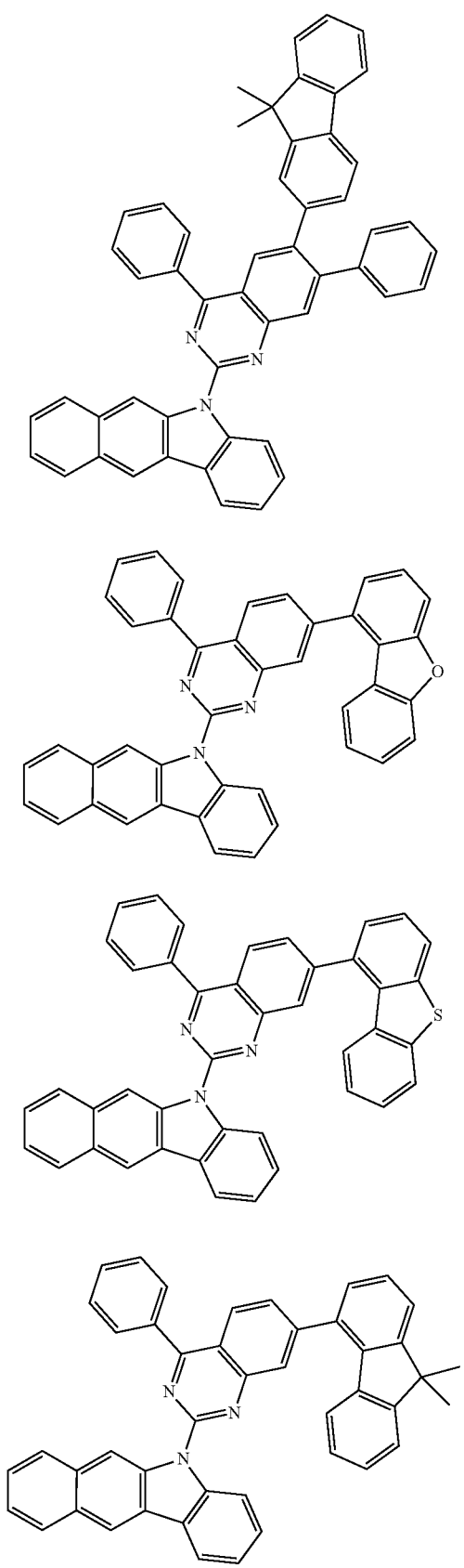
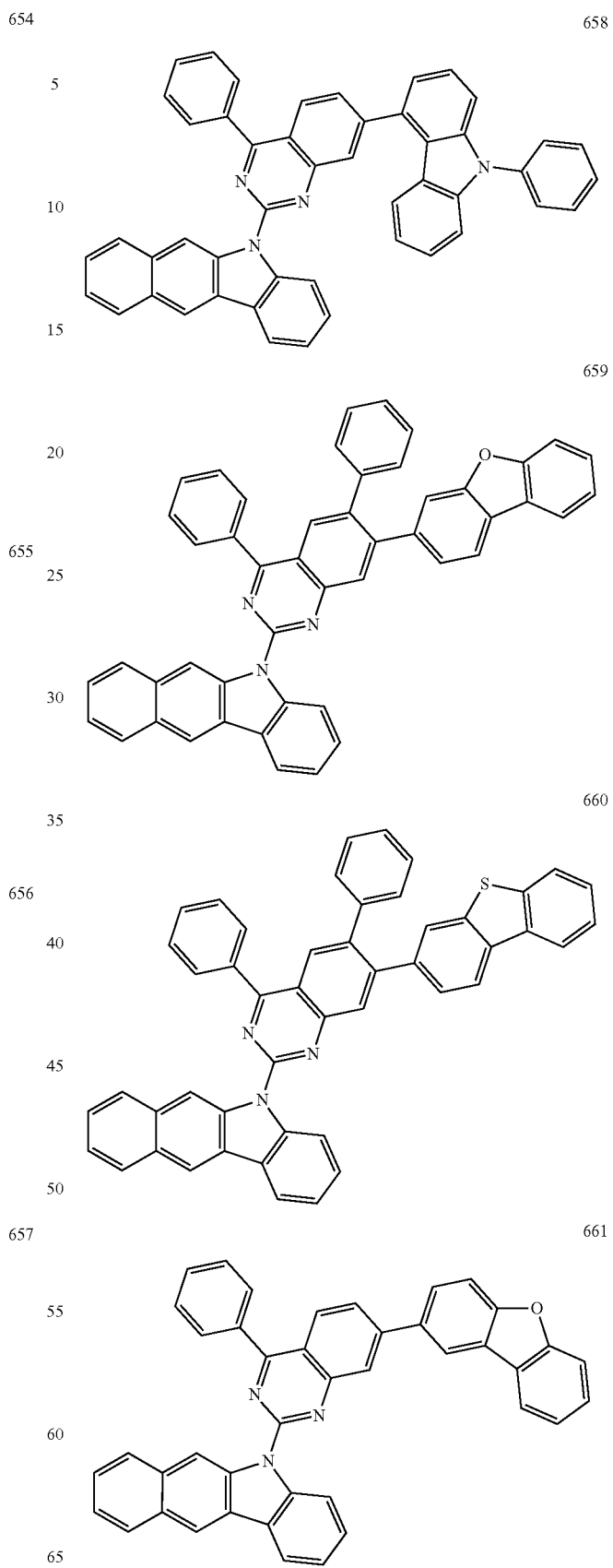

227
-continued
662
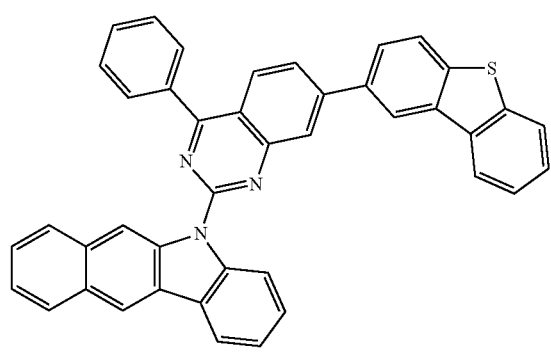
663
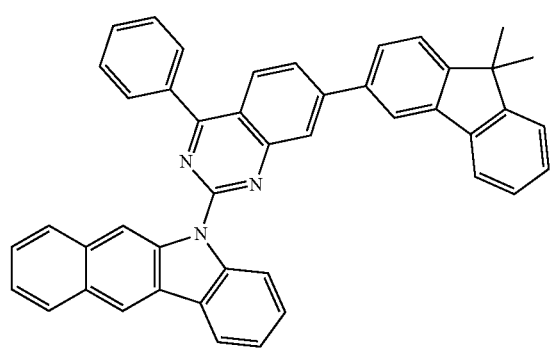
664
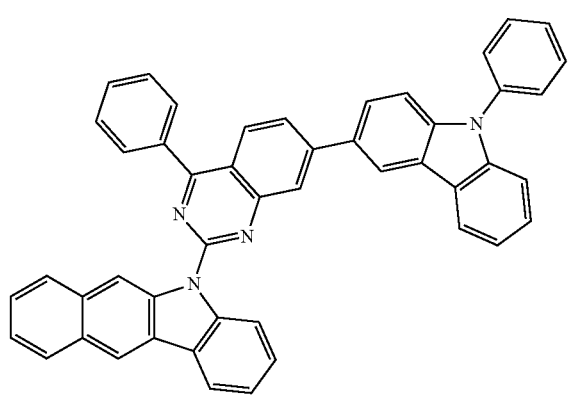
665
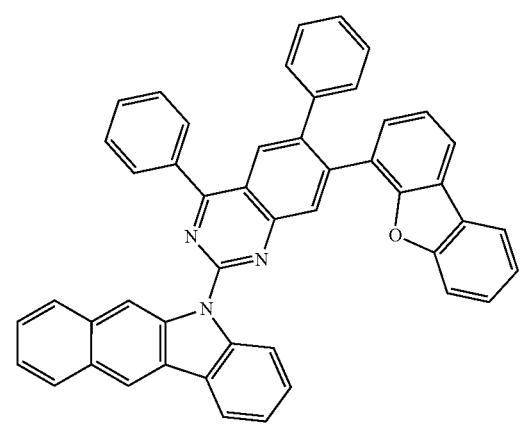
228
-continued
666
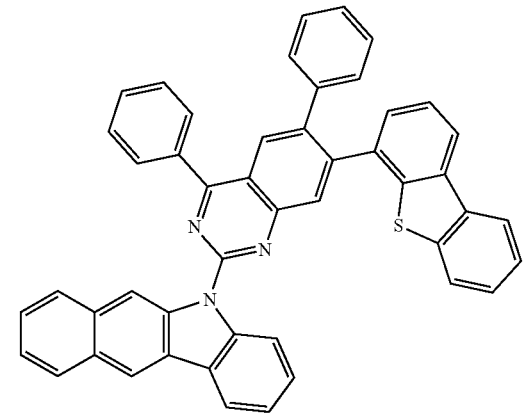
667
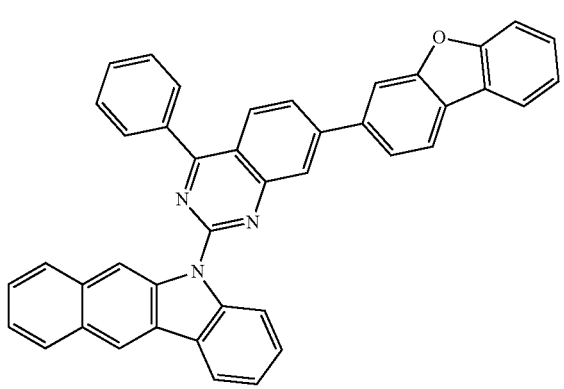
668
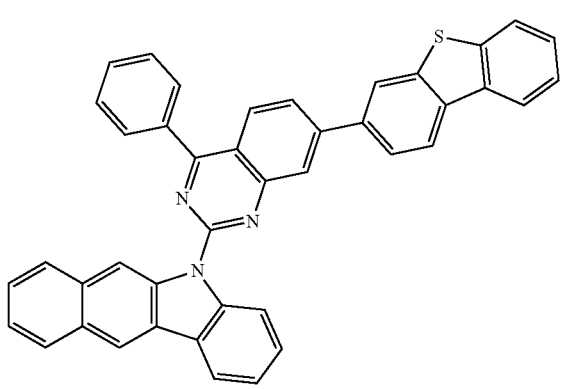
669
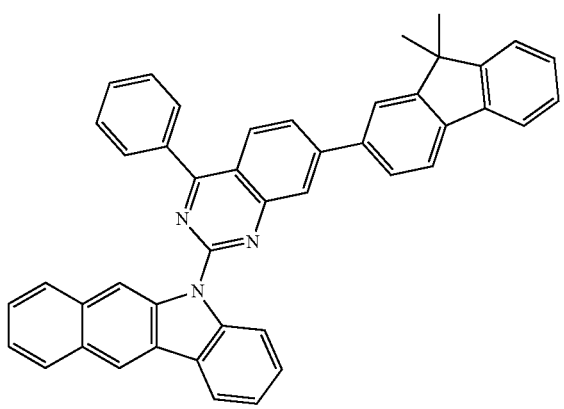

229
-continued
670
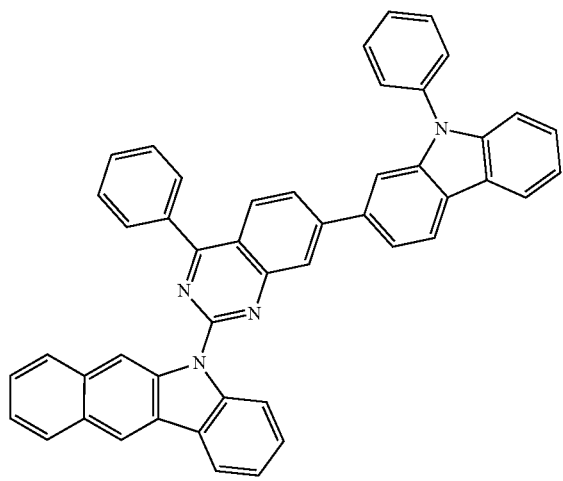
671
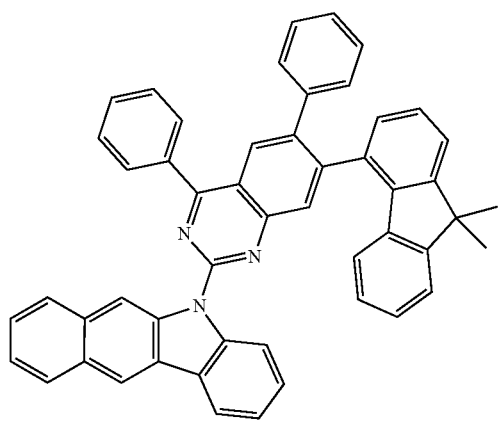
672
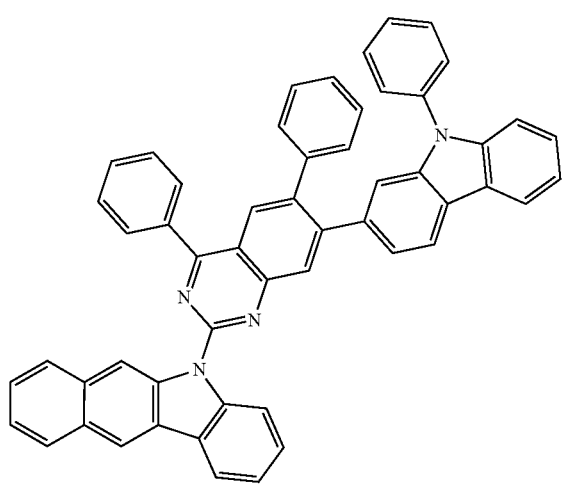
230
-continued
673
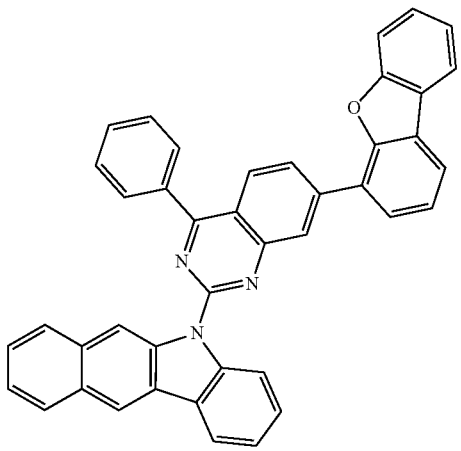
674
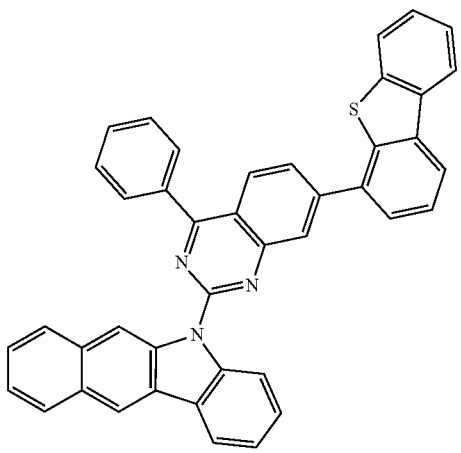
675
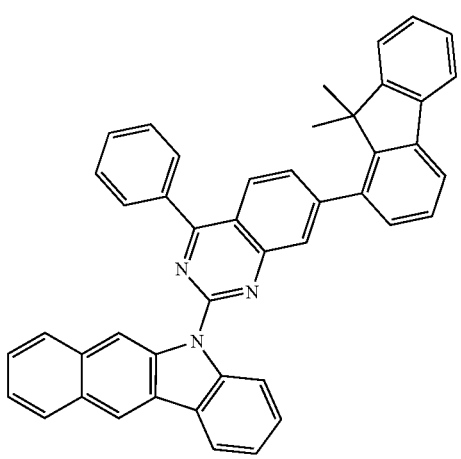

-continued
676
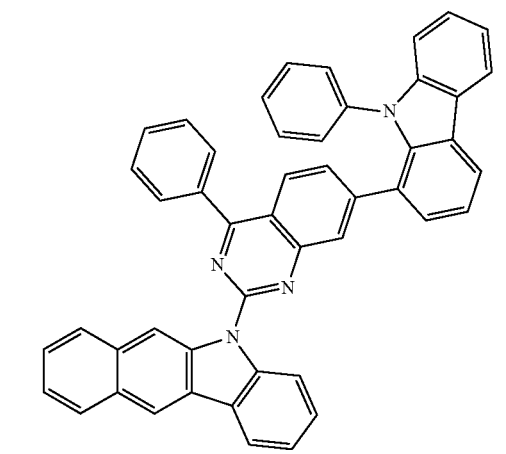
677
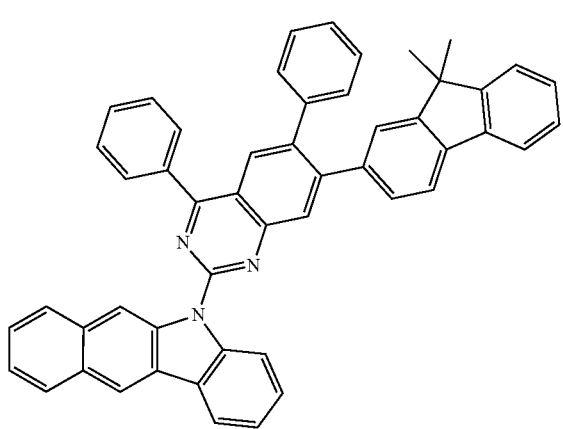
678
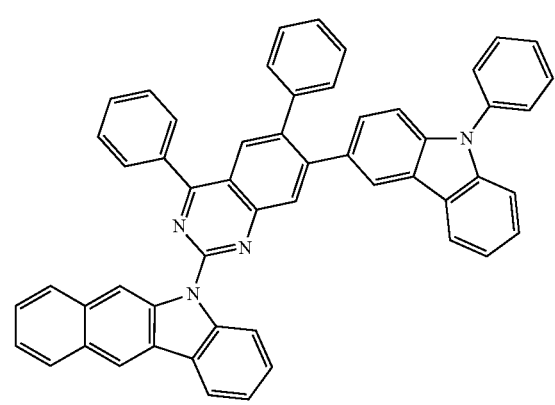
679
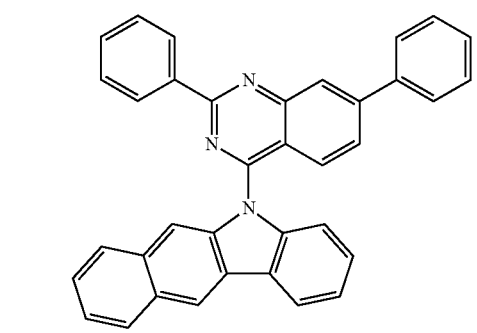
-continued
680
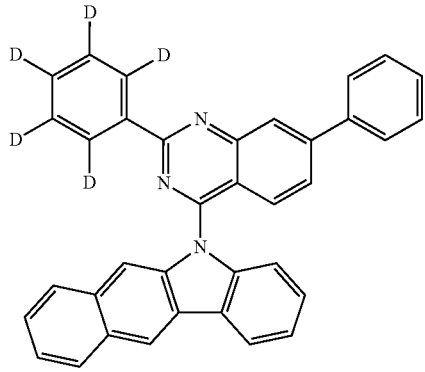
681
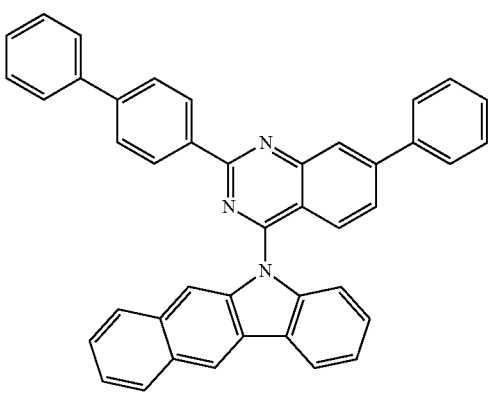
682
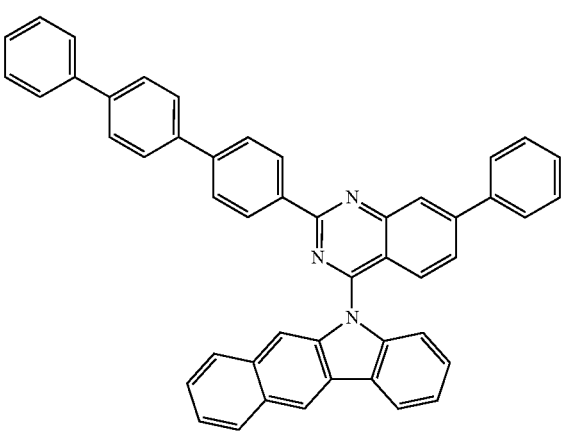
683
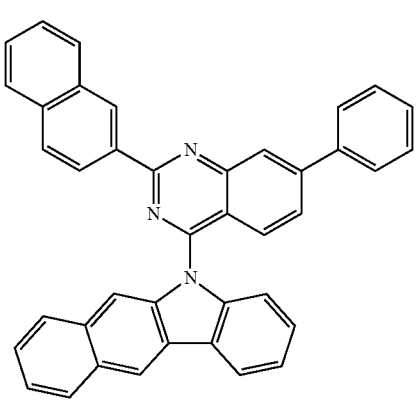

684
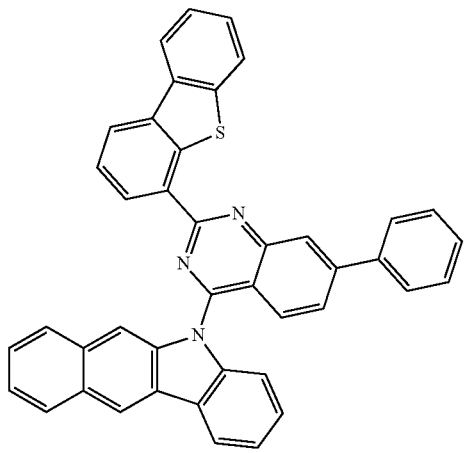
685
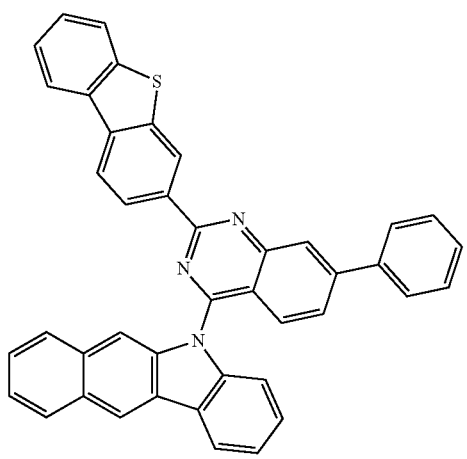
686
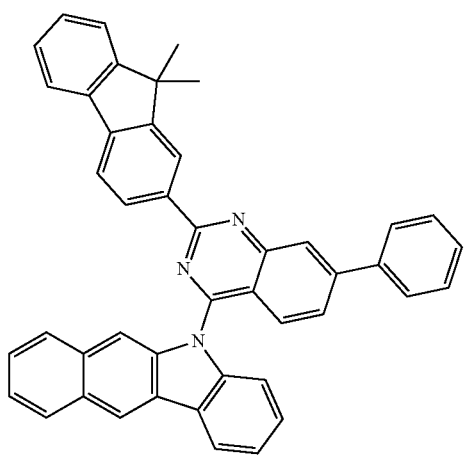
687
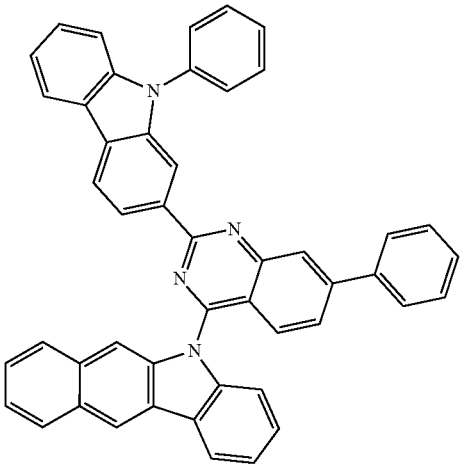
688
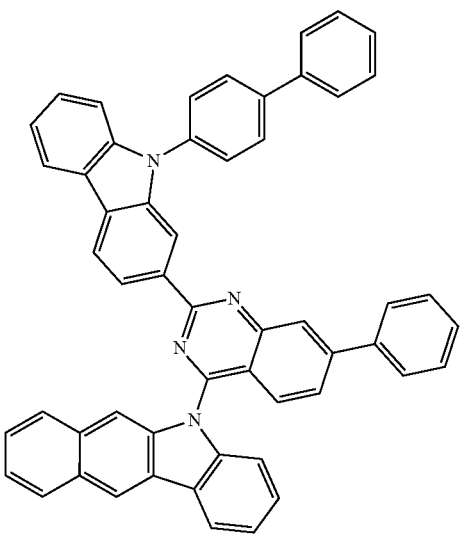
689
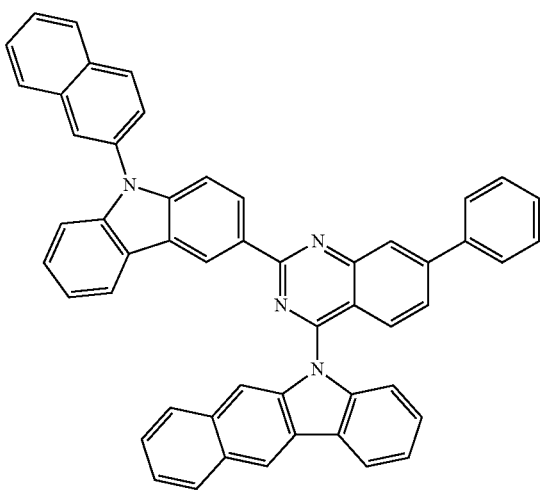

690
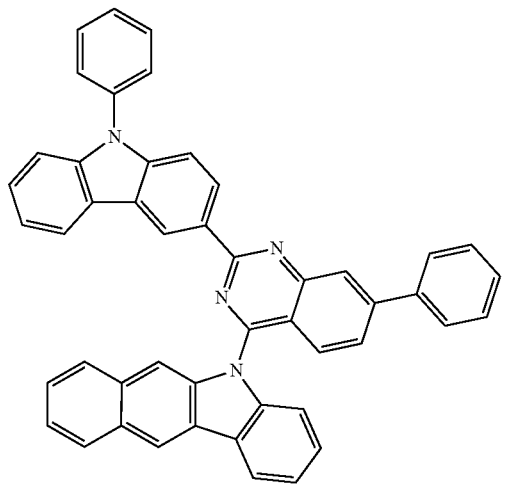
691
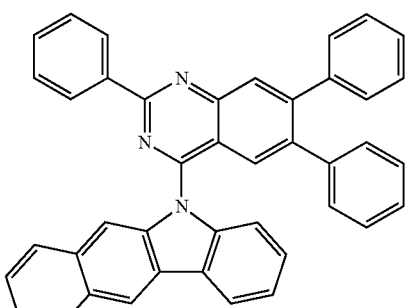
692
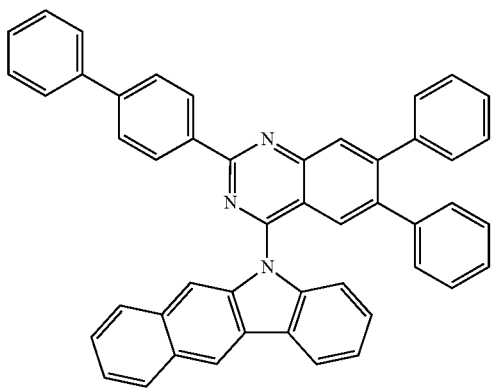
693
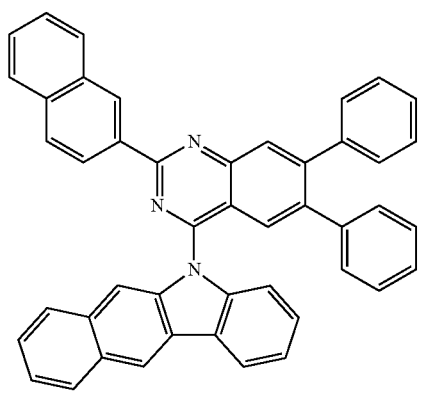
694
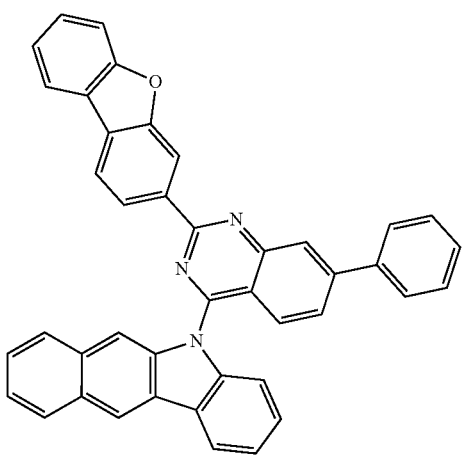
695
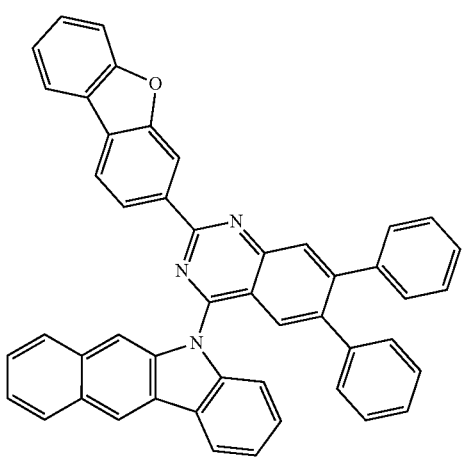
696
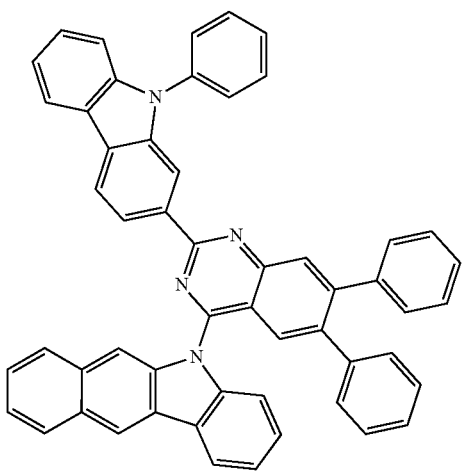

697
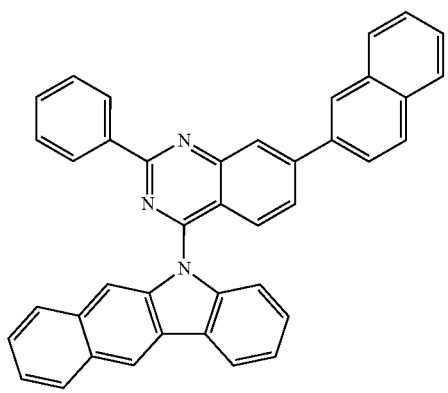
698
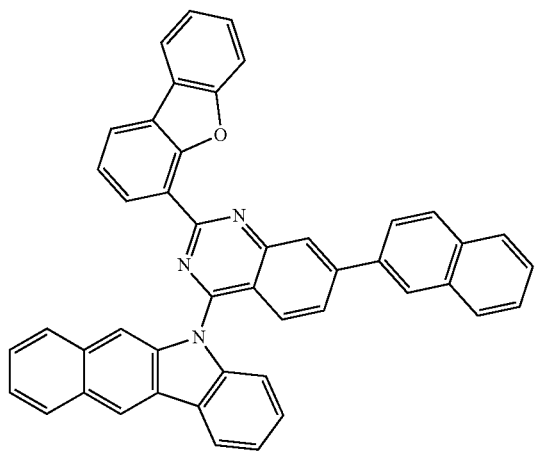
699
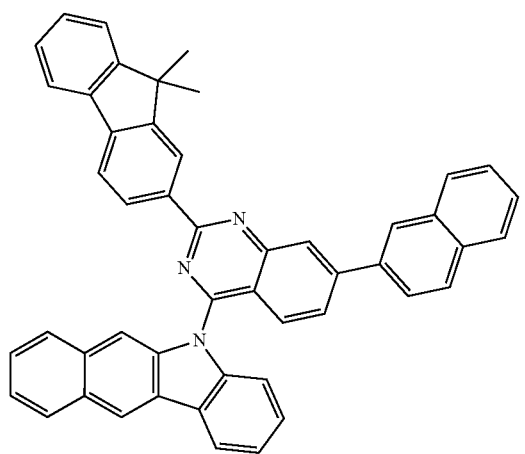
700
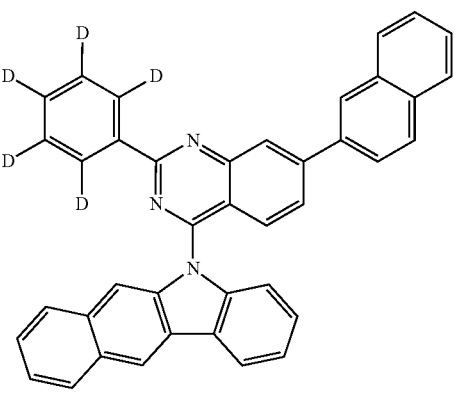
701
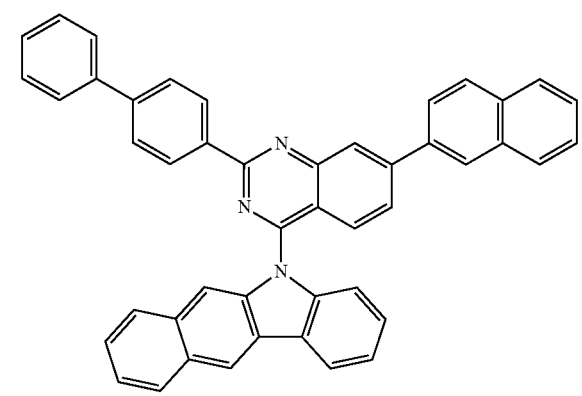
702
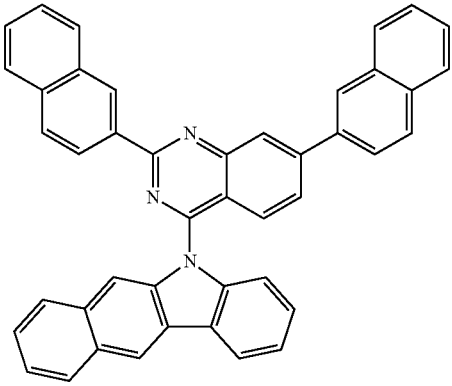

703
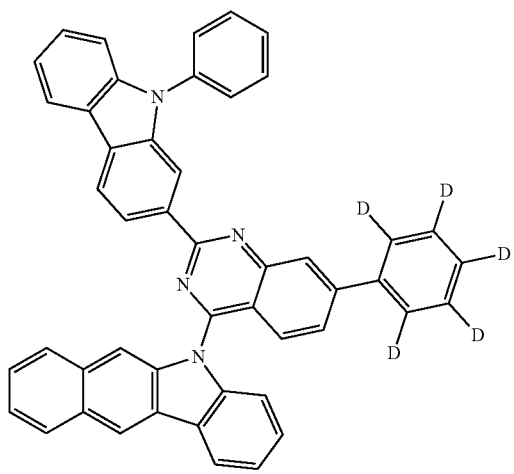
704
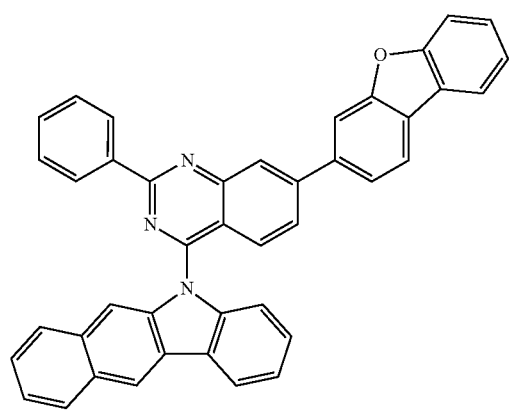
705
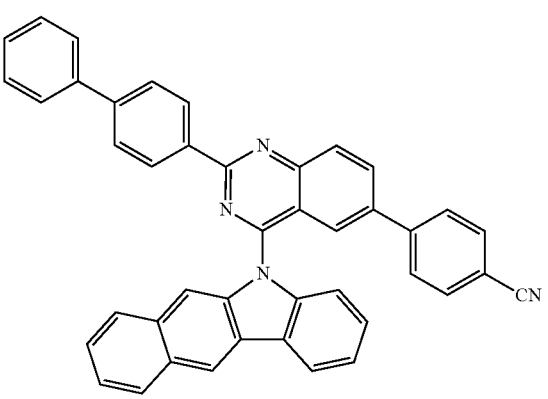
706
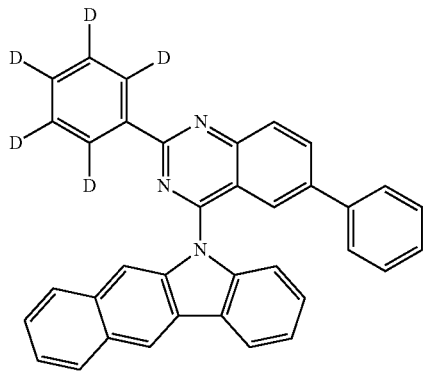
707
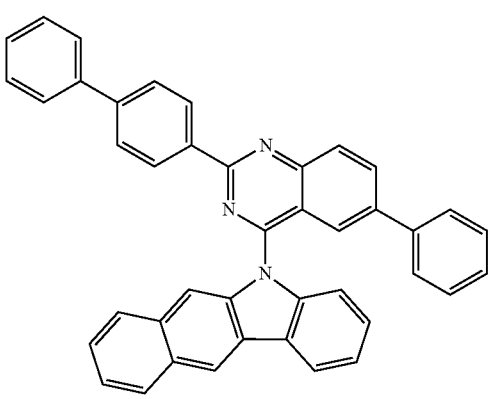
708
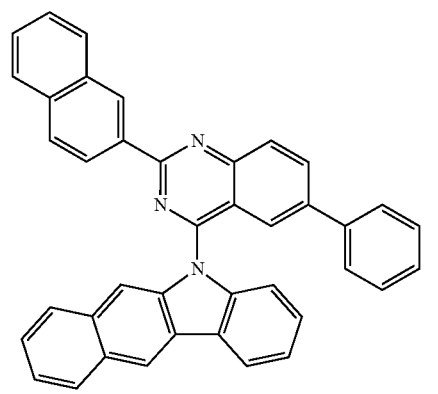
709
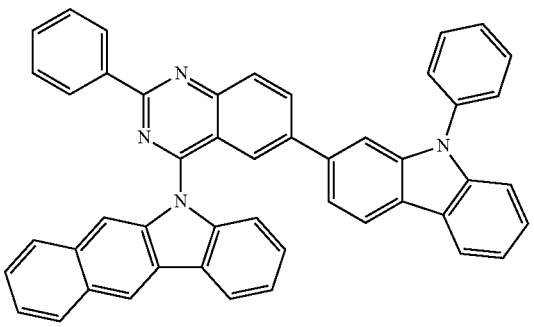

710
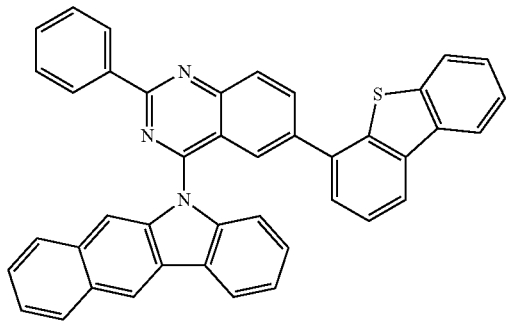
711
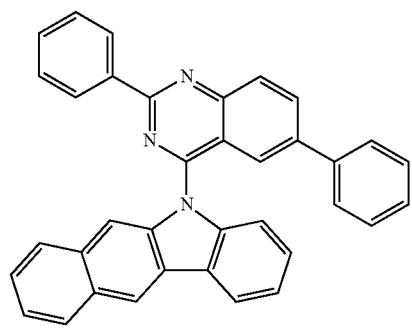
712
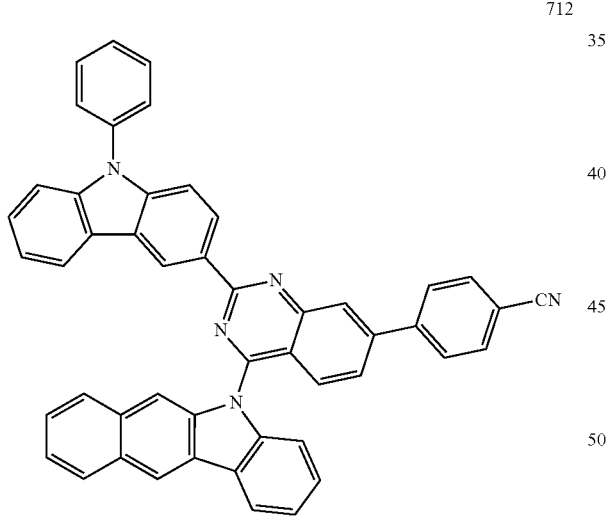
713
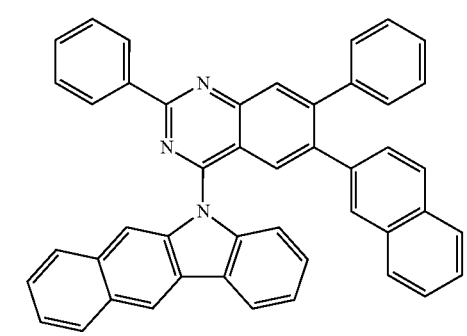
714
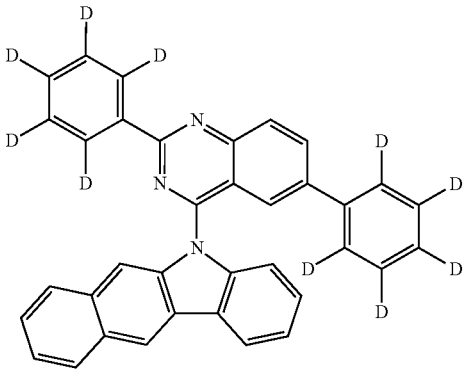
715
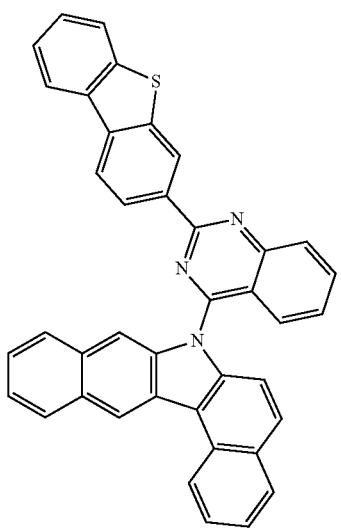
716
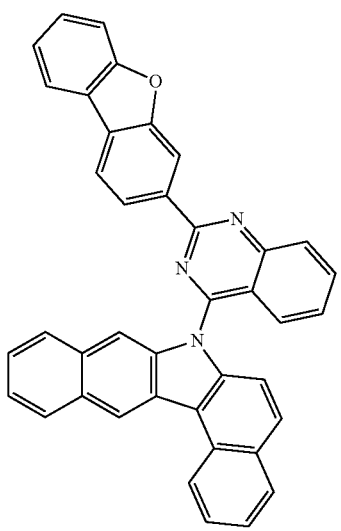

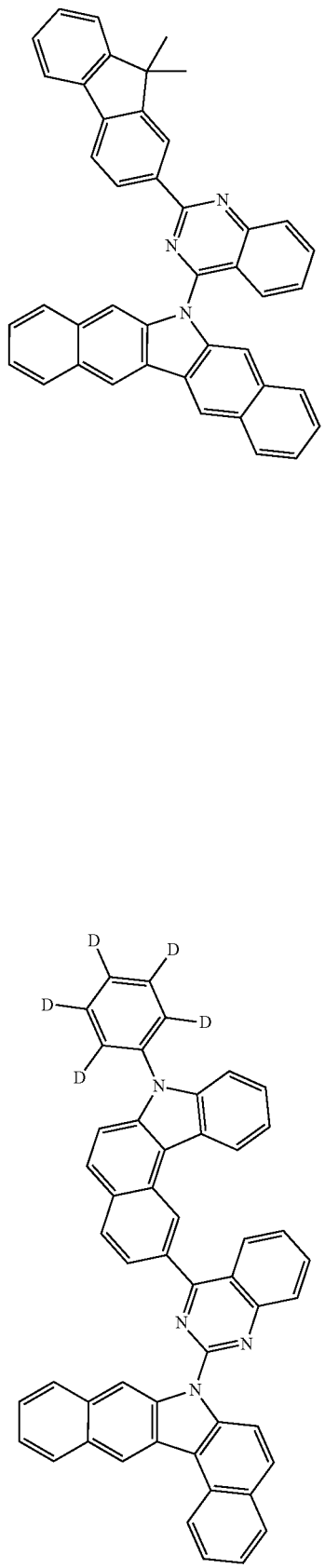
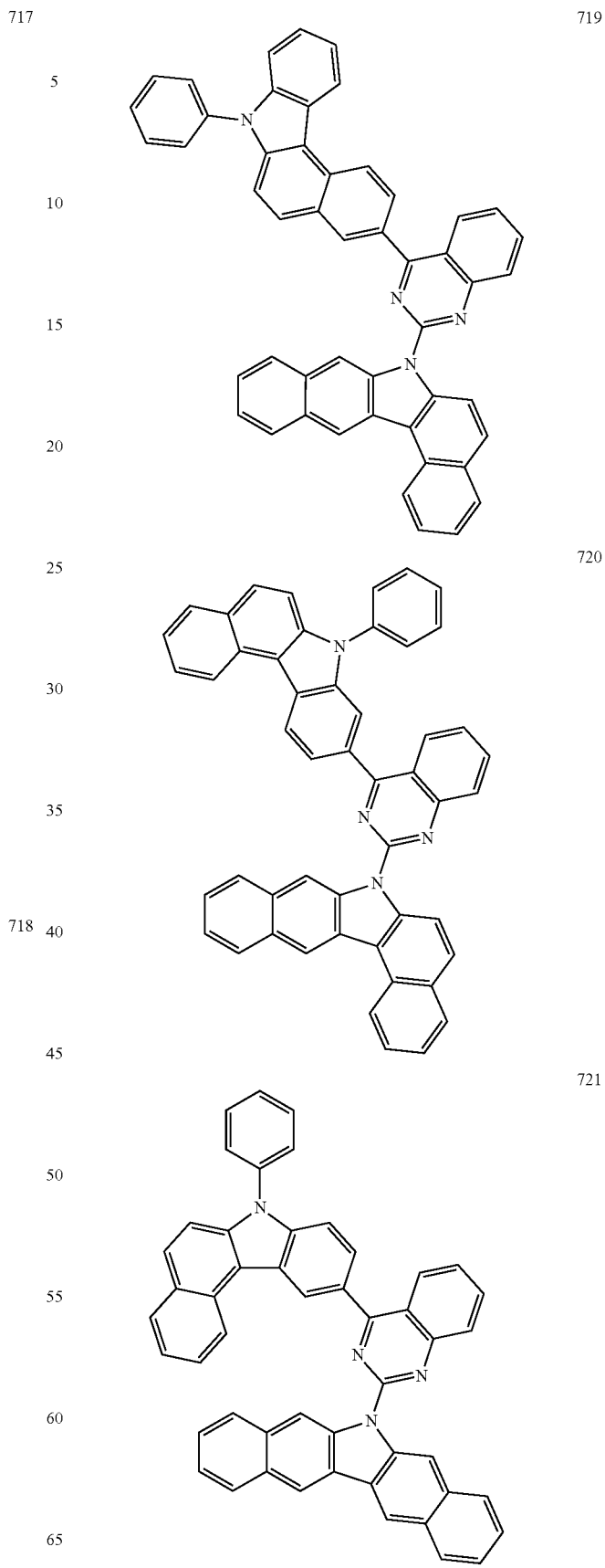

245
-continued
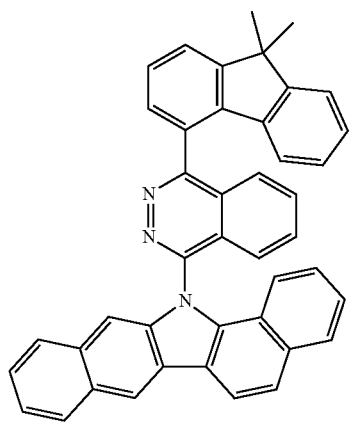
722
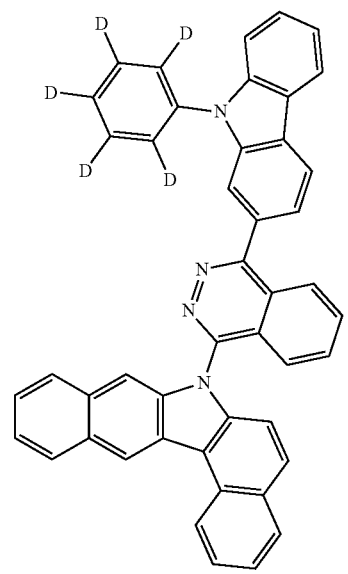
723
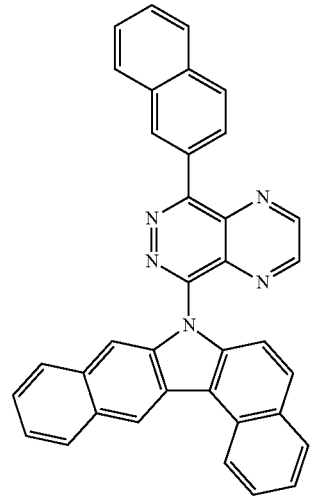
724
246
-continued
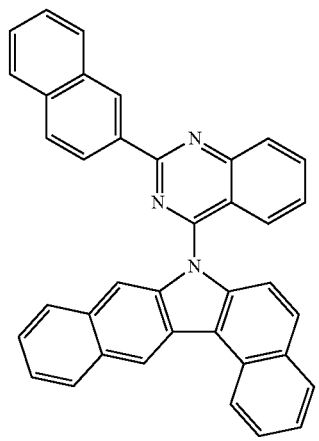
725
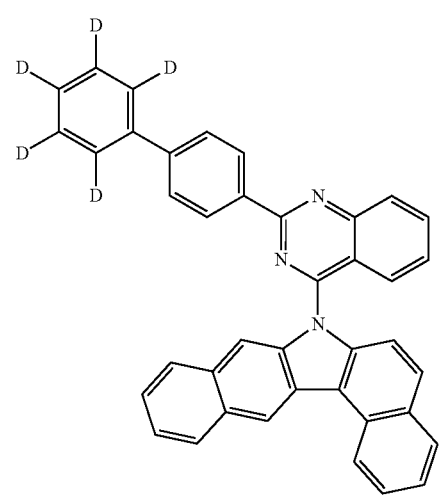
726
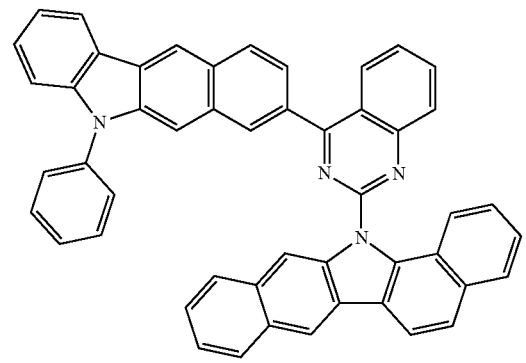
727

728
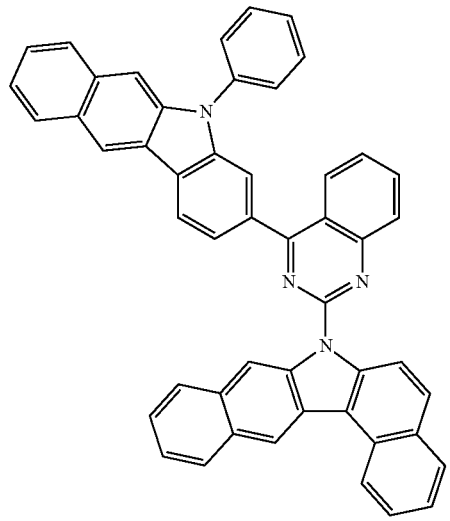
729
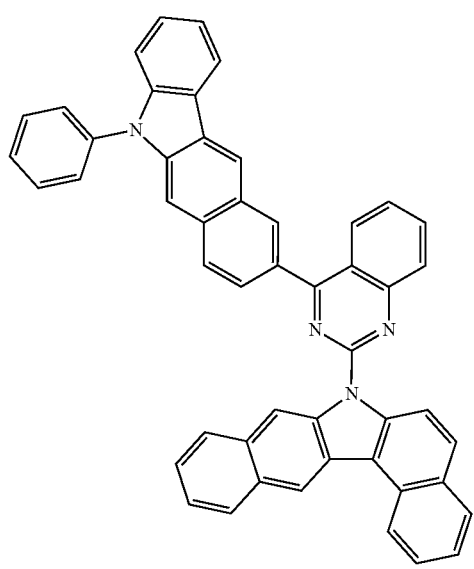
730
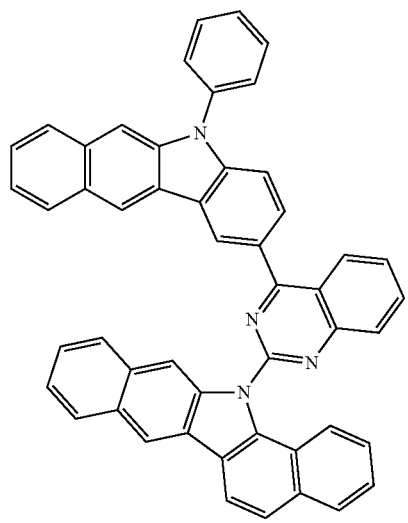
731
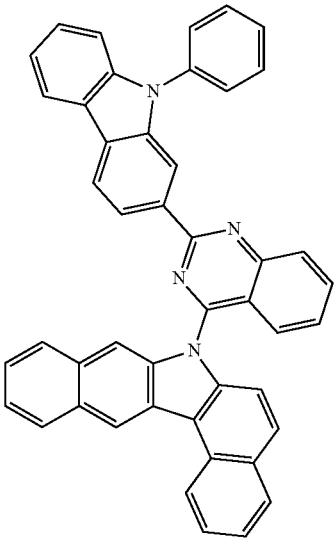
732
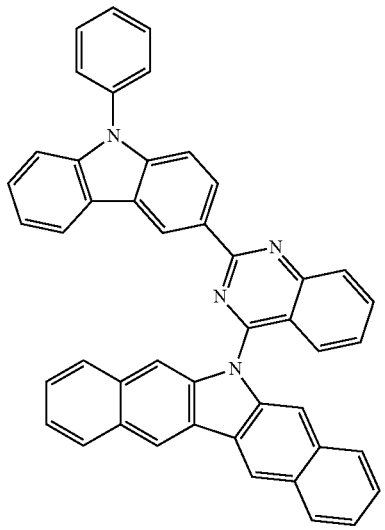
733
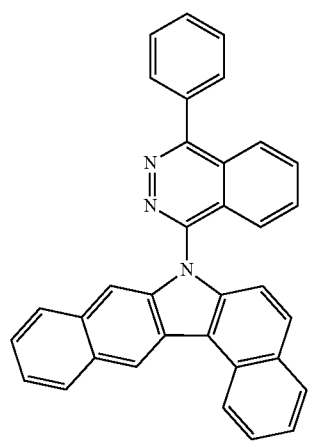

249
-continued
734
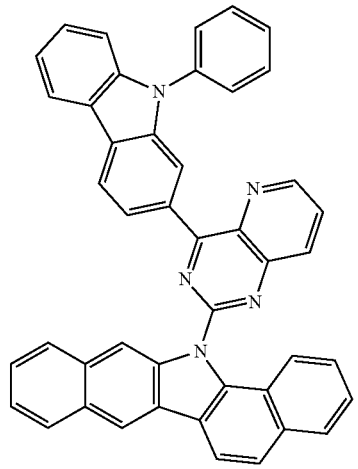
735
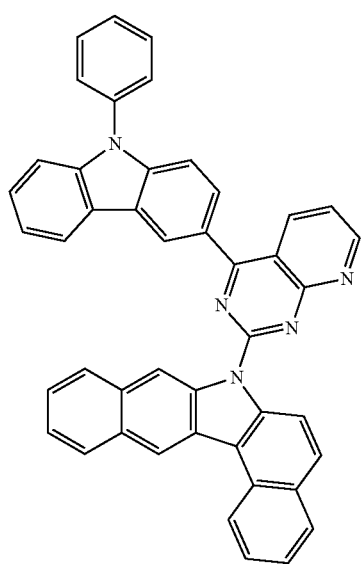
736
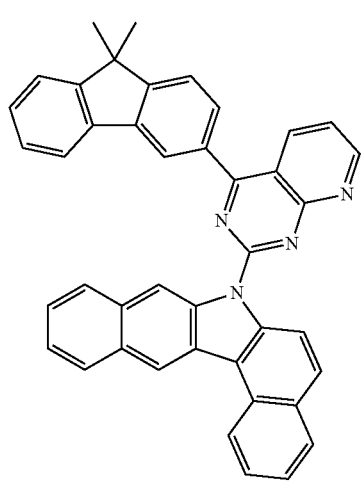
250
-continued
737
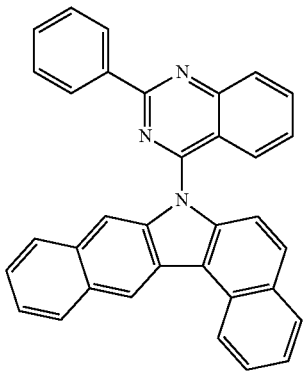
738
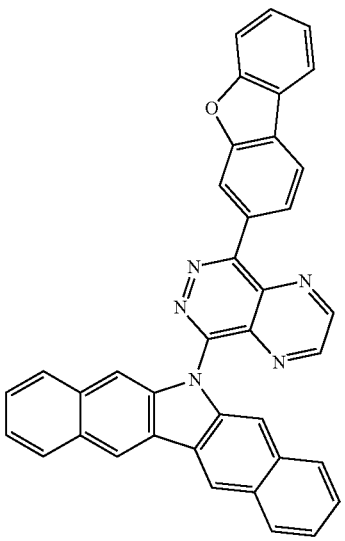
739
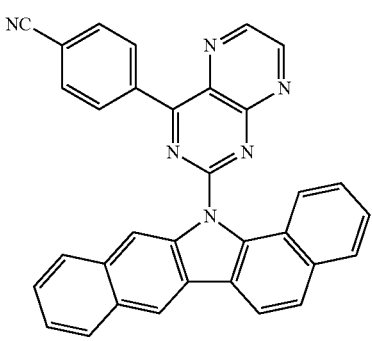
740
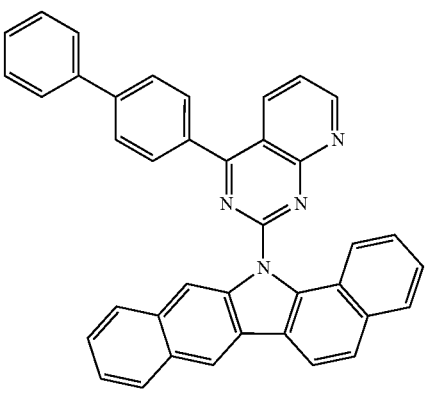

-continued
741
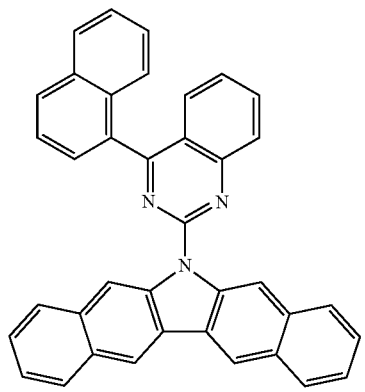
742
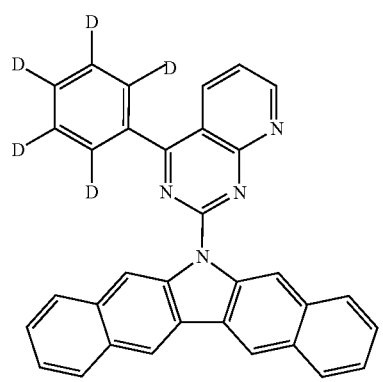
743
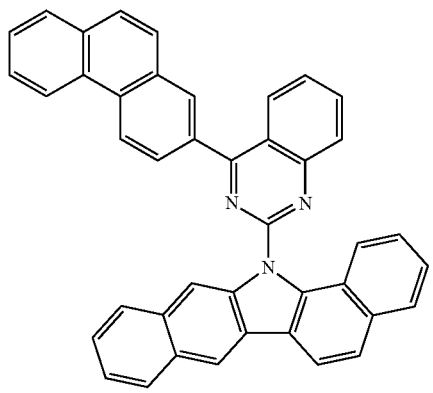
744
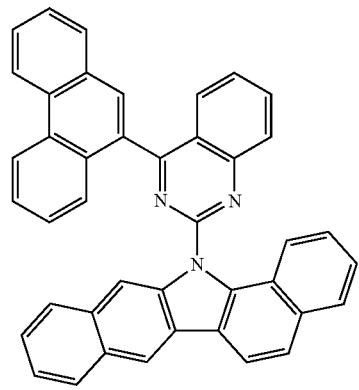
-continued
745
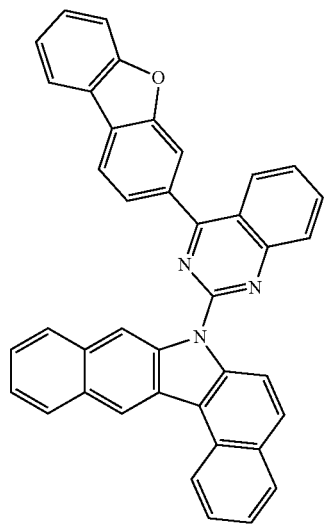
746
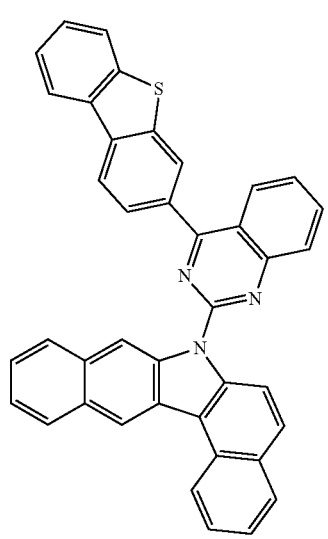
747
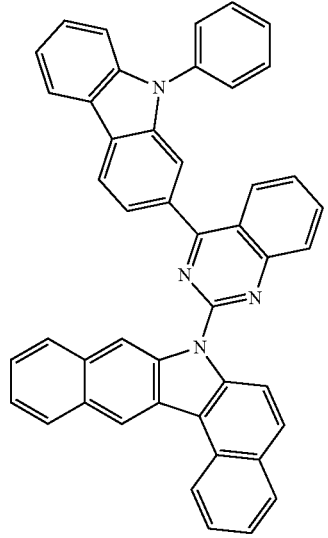

748
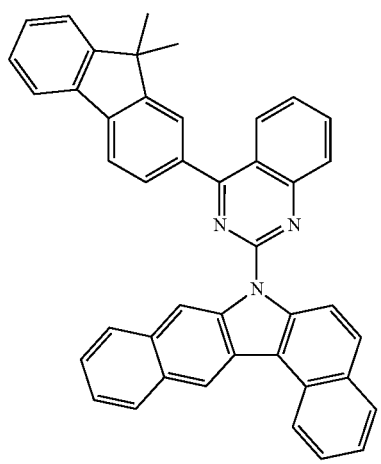
749
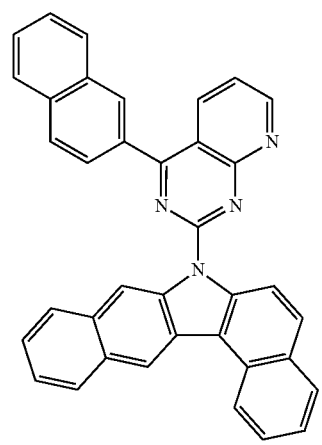
750
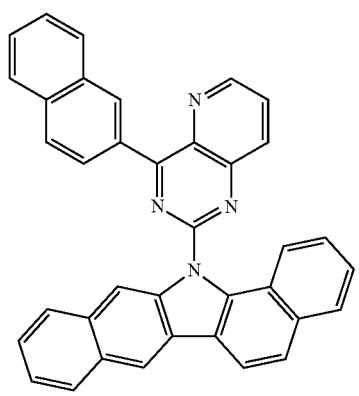
751
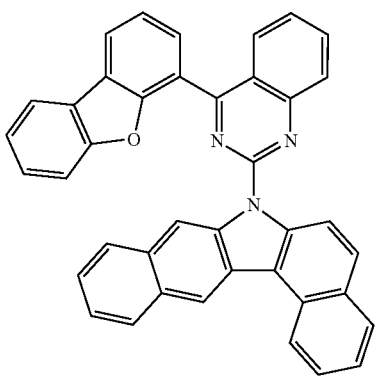
752
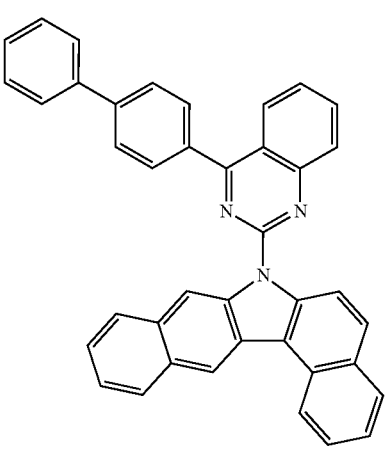
753
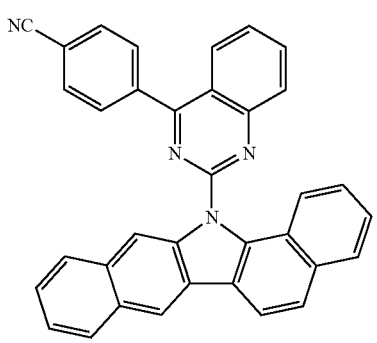

754 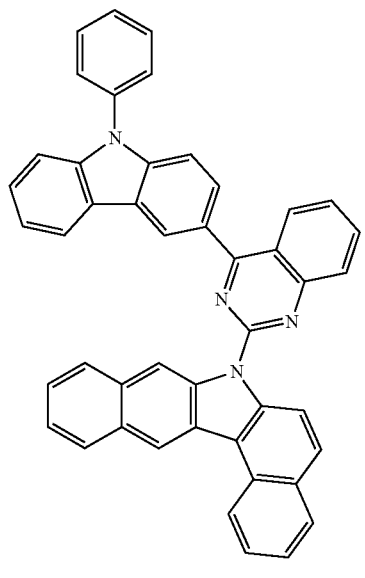
755 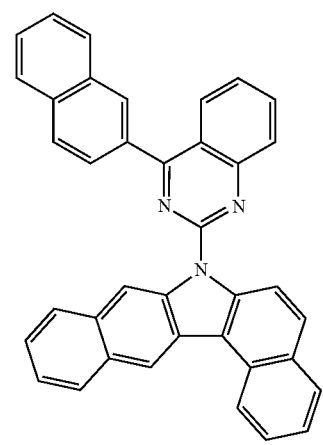
756 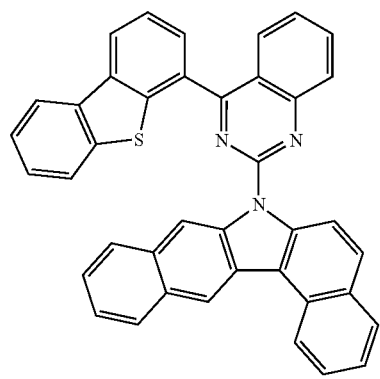
757 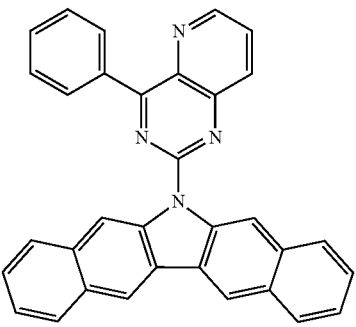
758 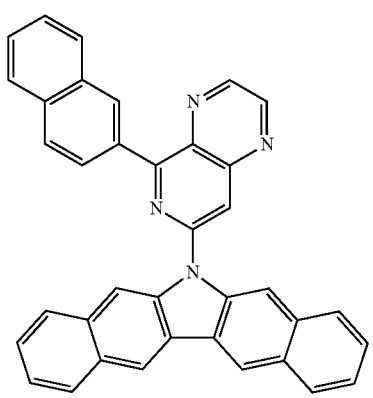
759 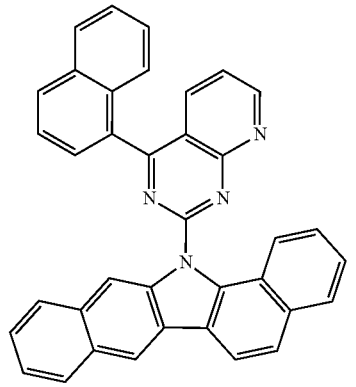
760 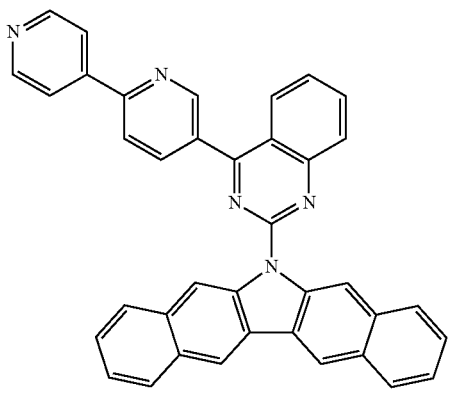

257
-continued
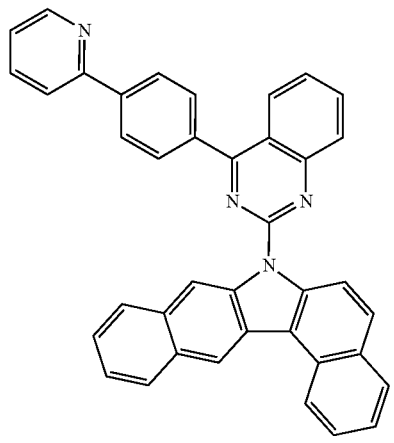
761
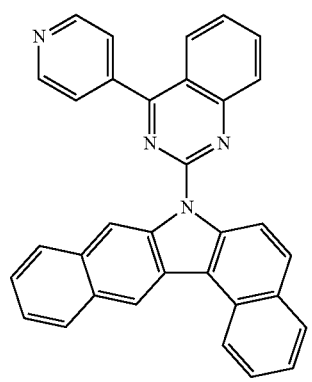
762
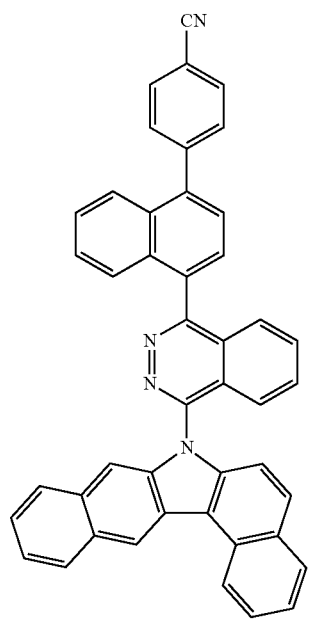
763
258
-continued
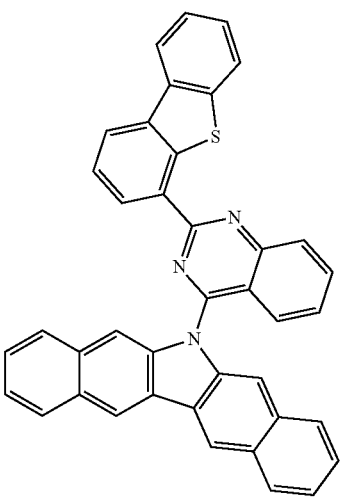
764
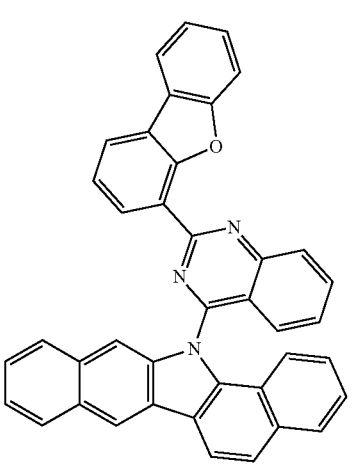
765
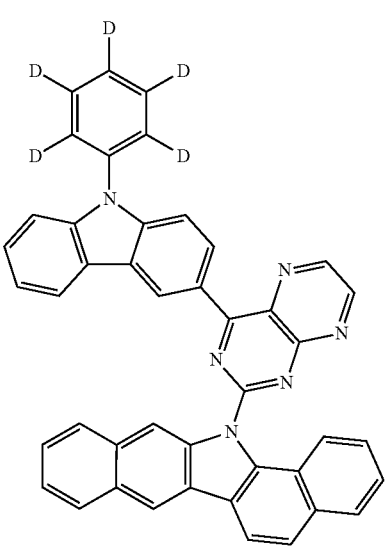
766

259
-continued
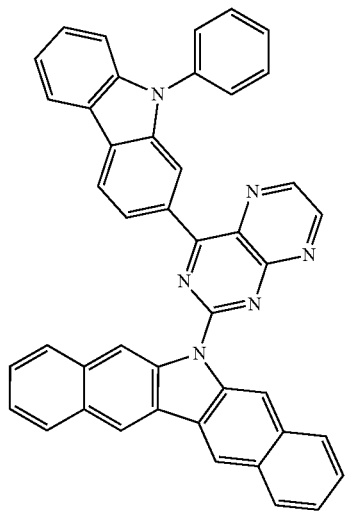
767
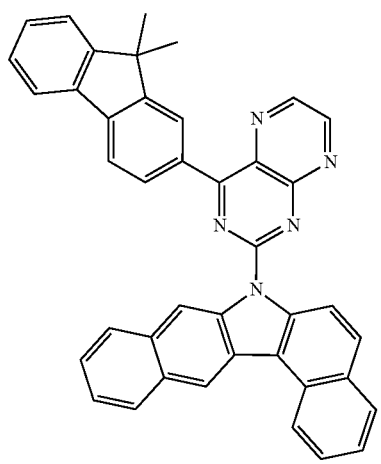
768
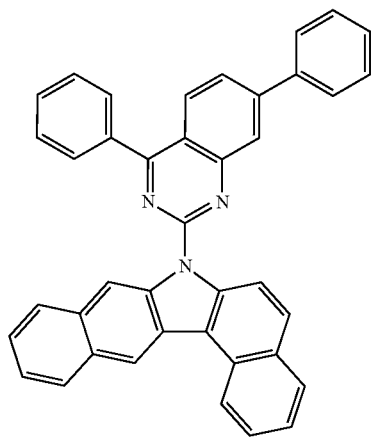
769
260
-continued
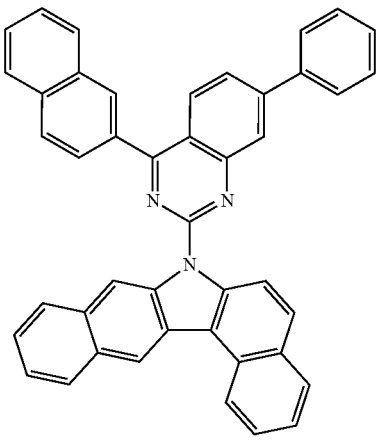
770
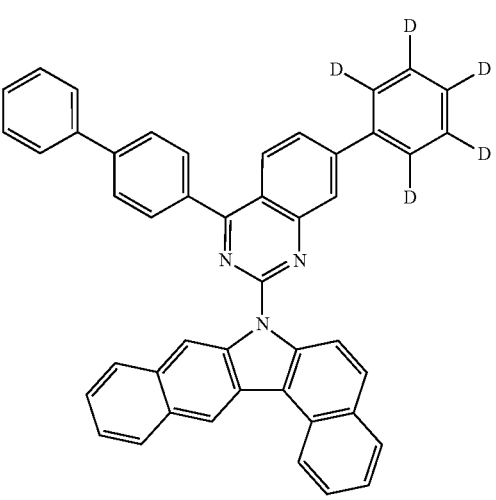
771
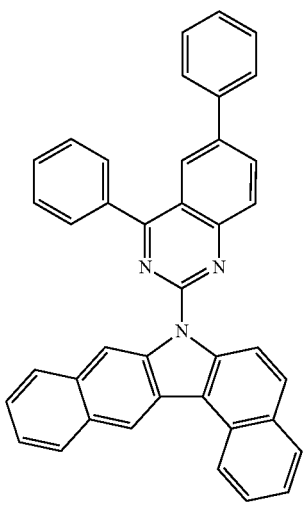
772

773
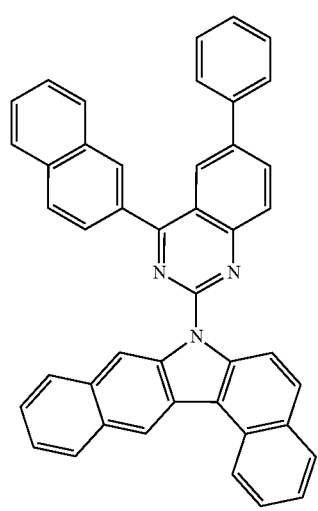
774
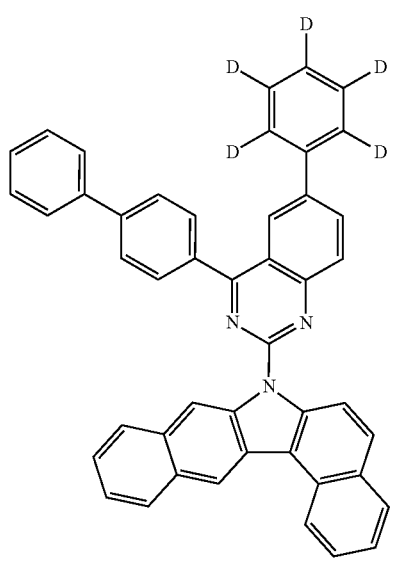
775
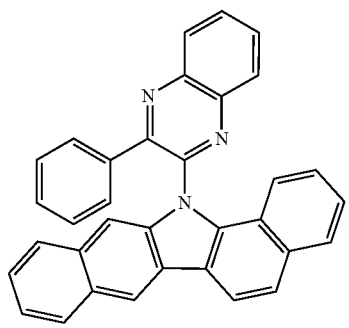
776
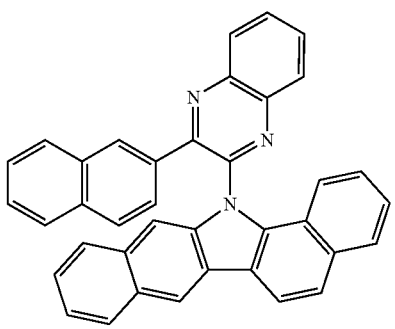
777
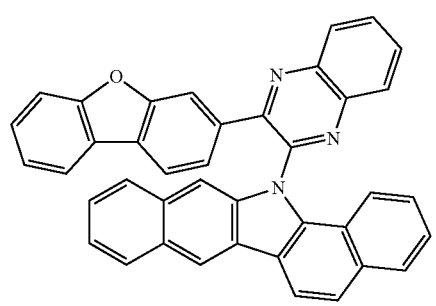
778
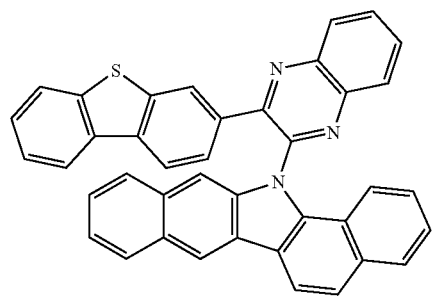
779
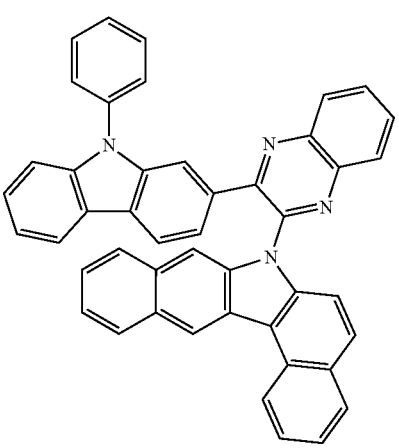

780
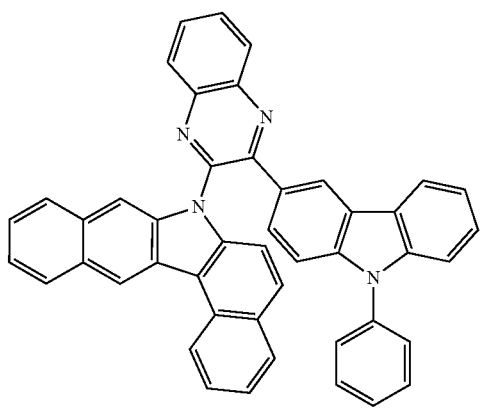
781
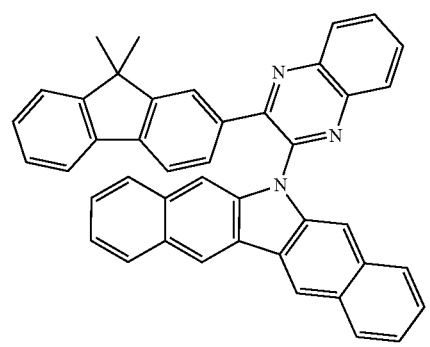
782
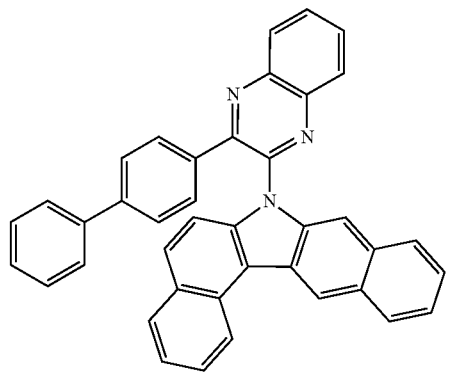
783
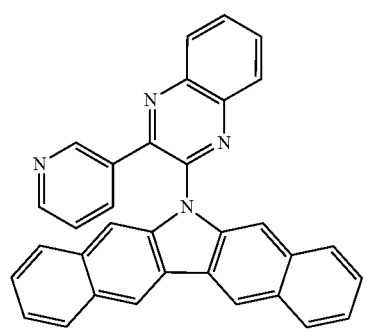
784
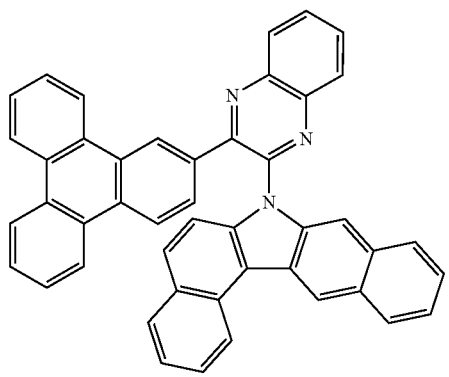
785
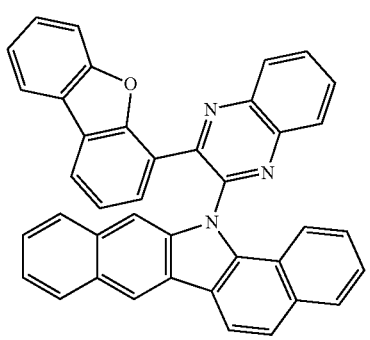
786
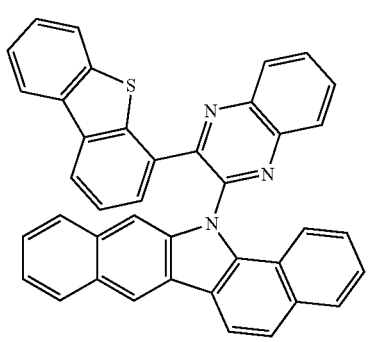
787
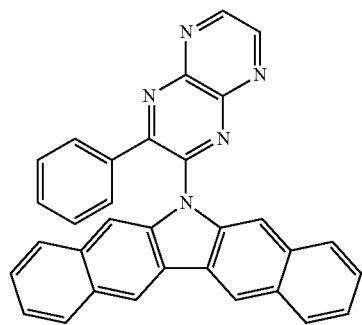

265
-continued
788
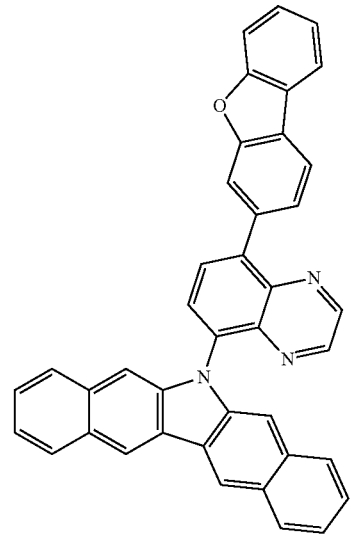
789
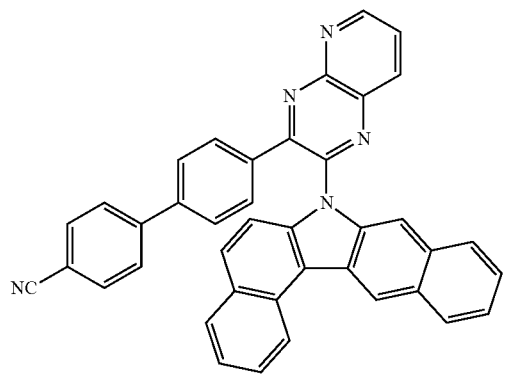
790
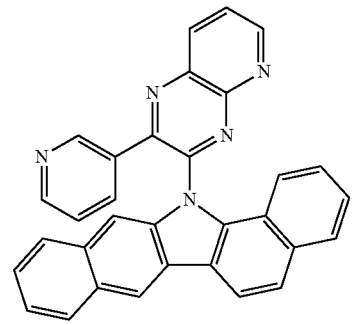
266
-continued
791
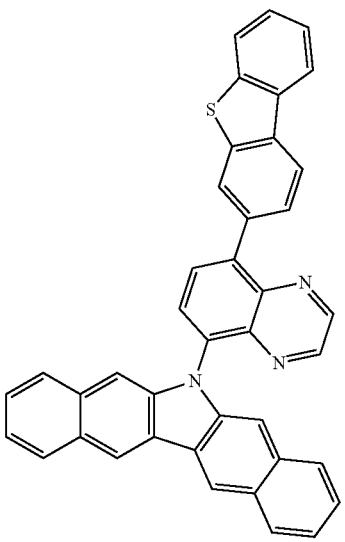
792
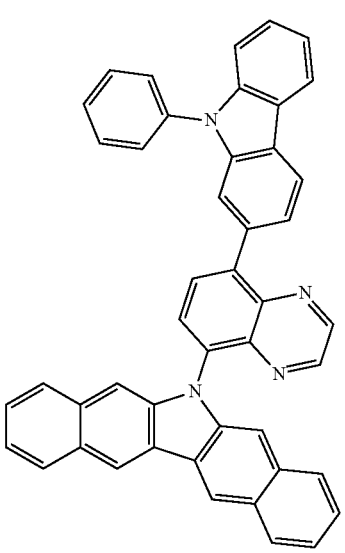
793
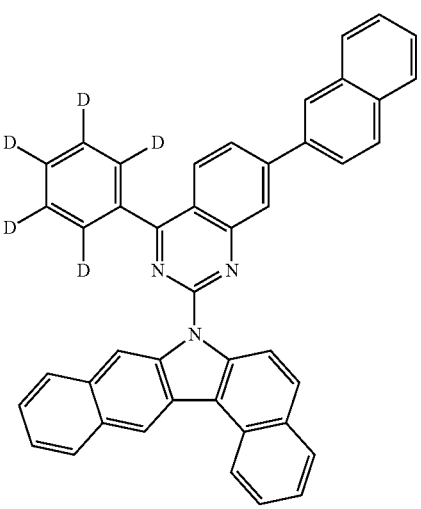

267
-continued
794
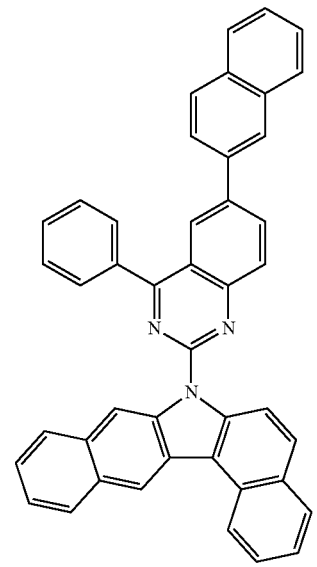
795
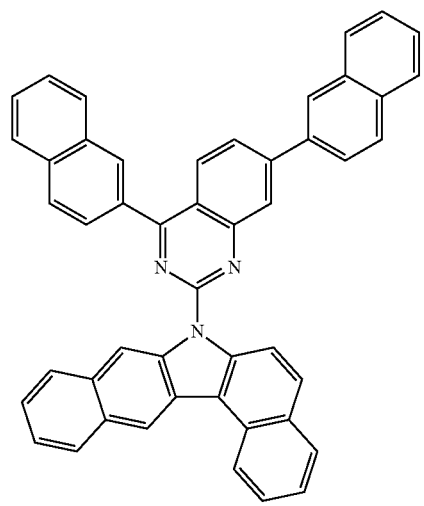
796
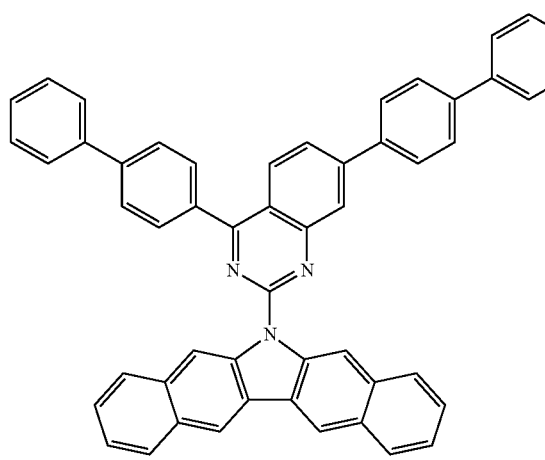
268
-continued
797
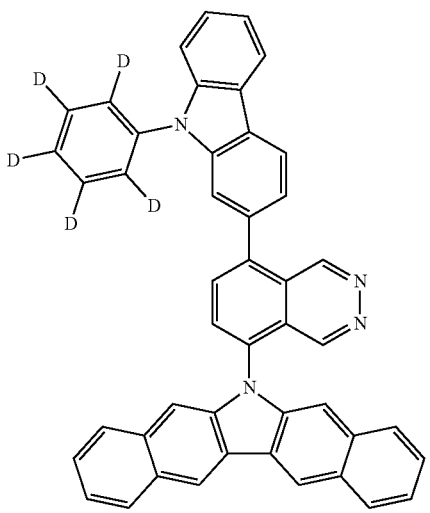
798
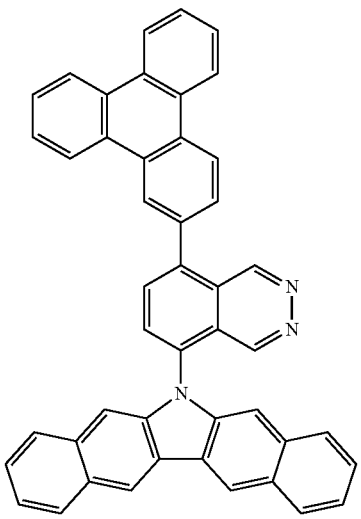
799
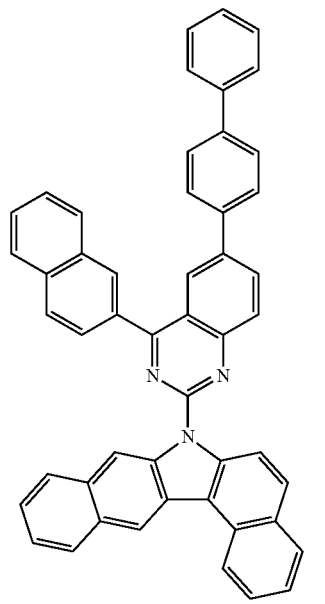

800
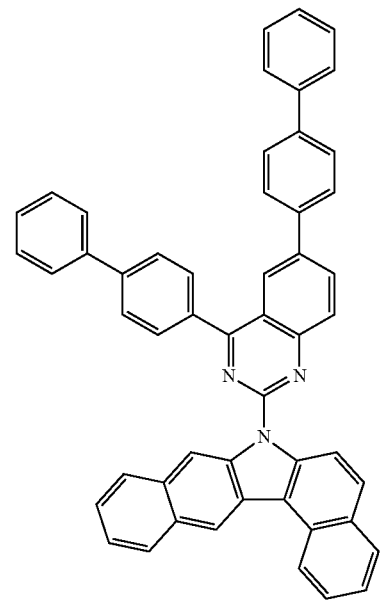
801
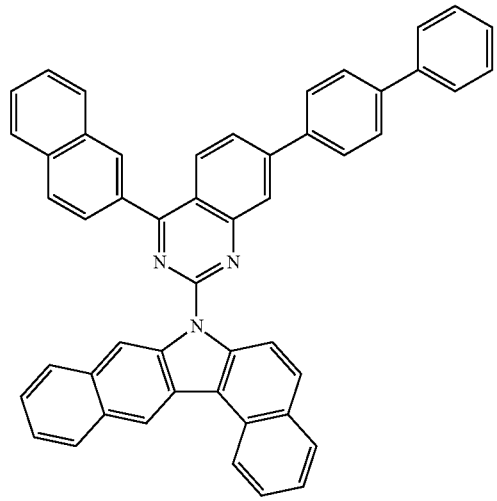
802
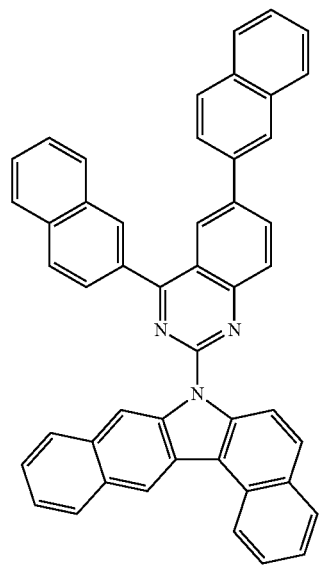
803
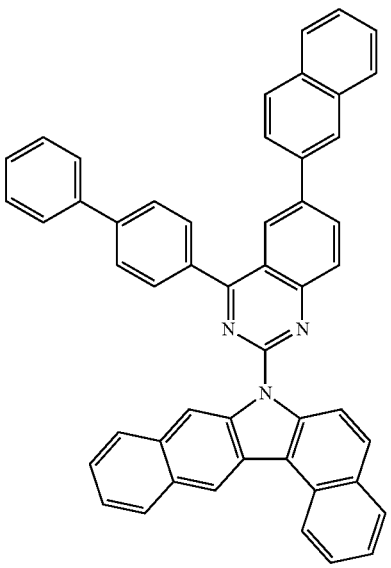
804

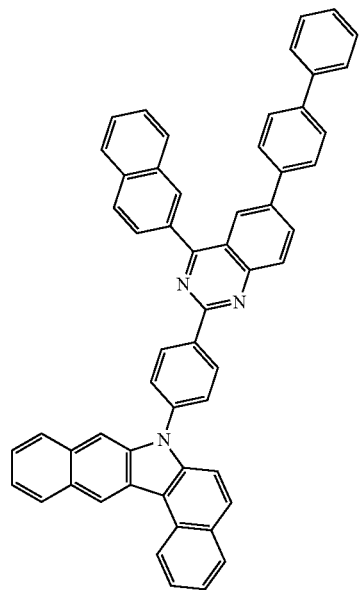
805
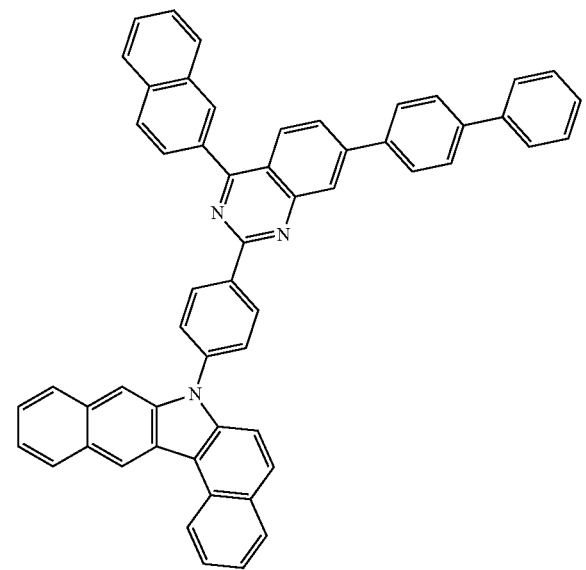
807
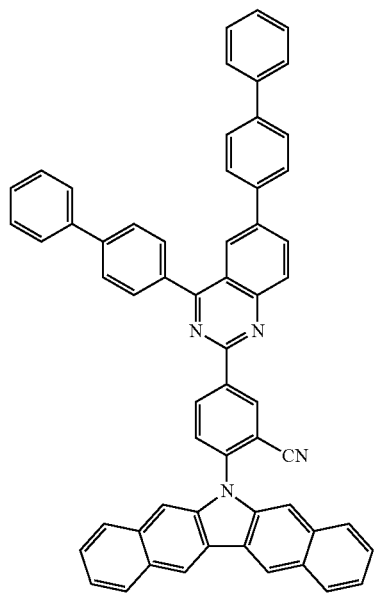
806
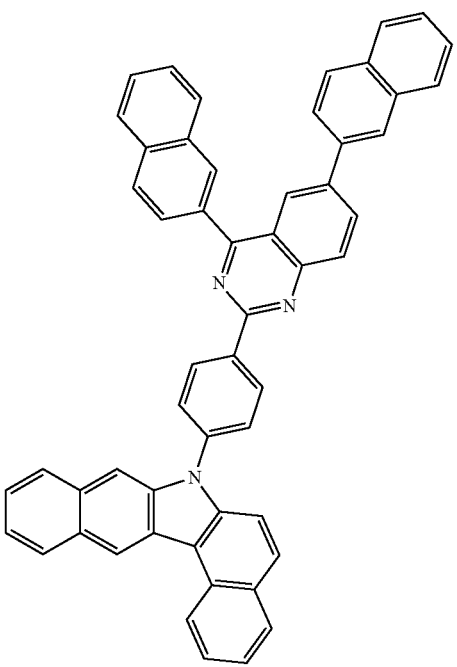
808

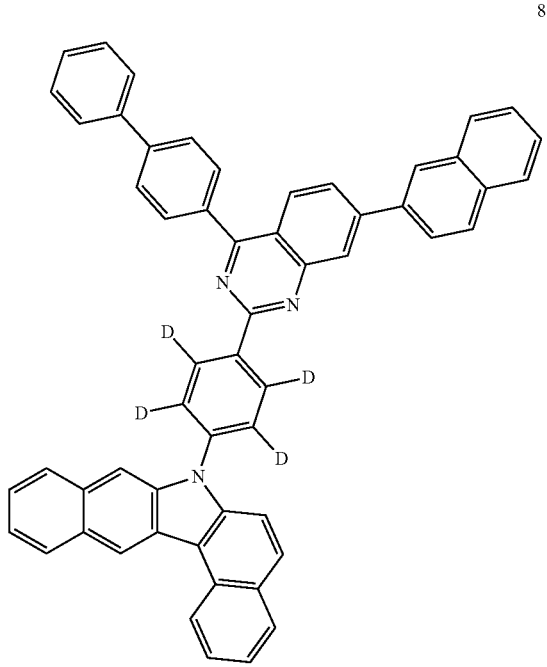
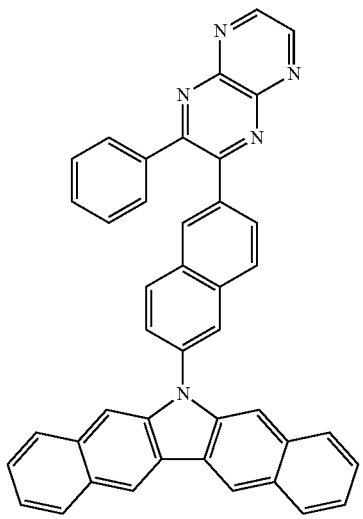

275
-continued
814
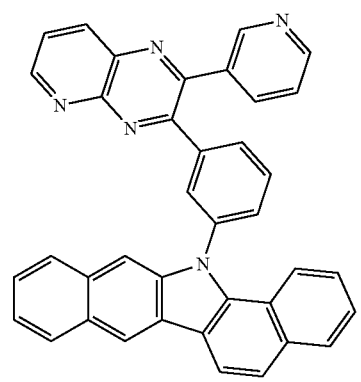
815
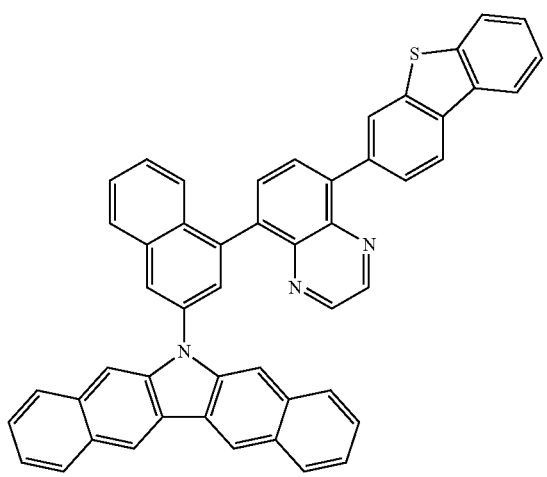
816
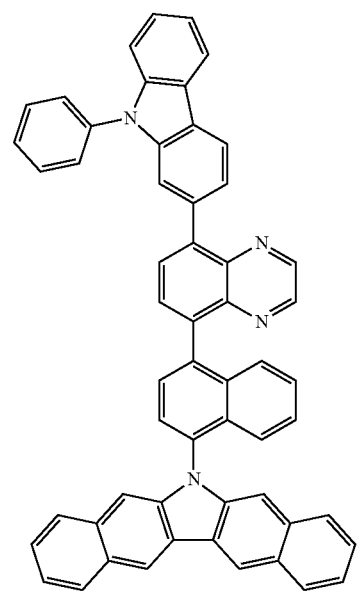
276
-continued
817
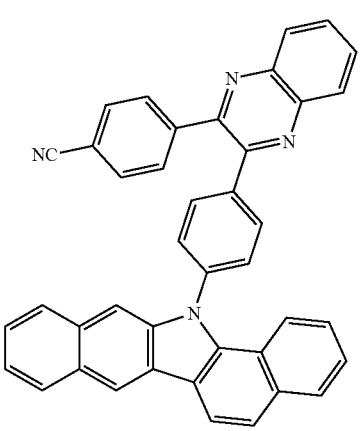
818
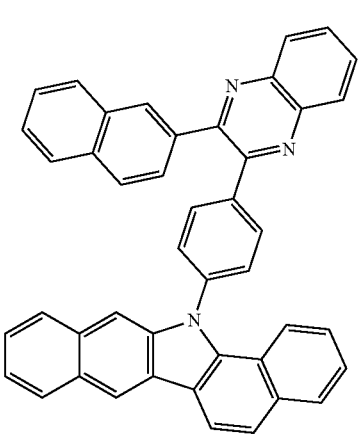
819
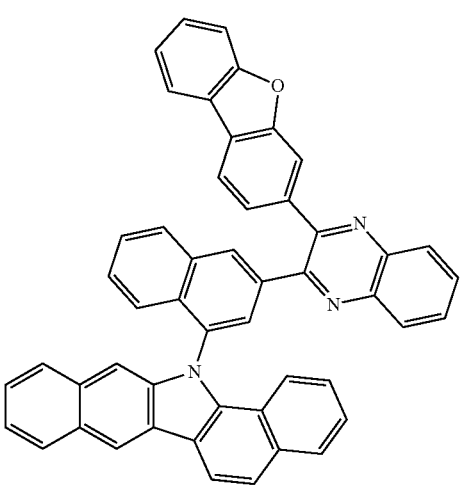

277
-continued
820
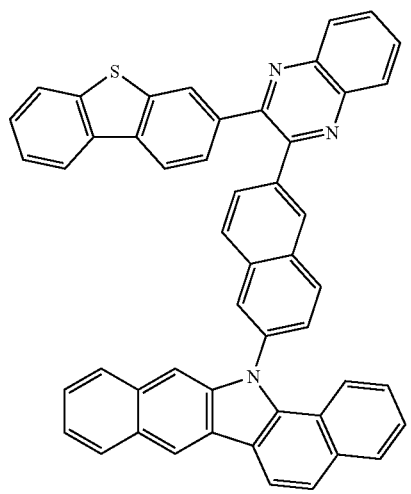
821
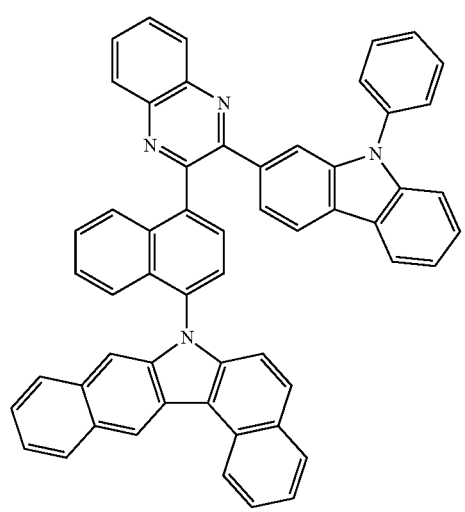
822
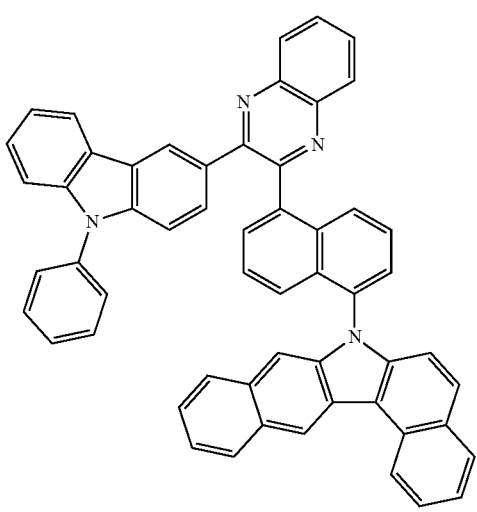
278
-continued
823
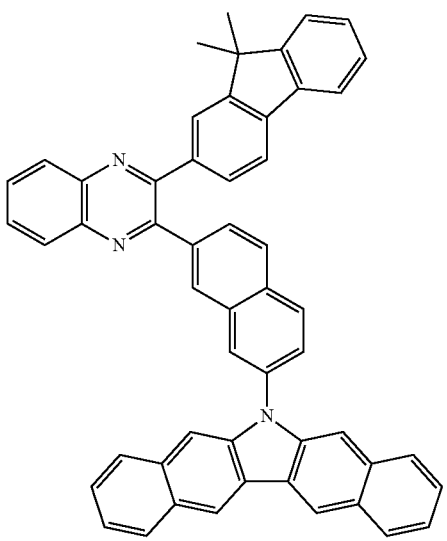
824
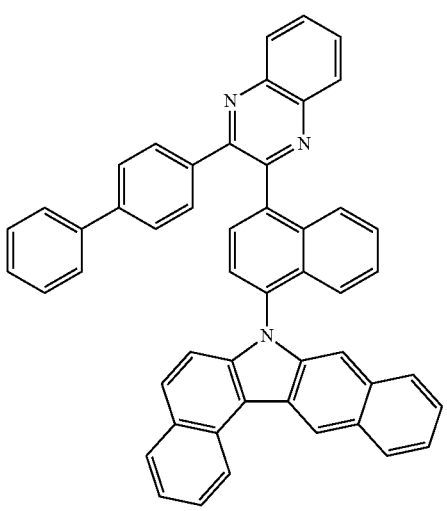
825
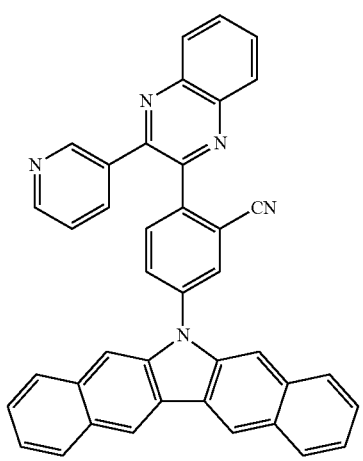

279
-continued
826
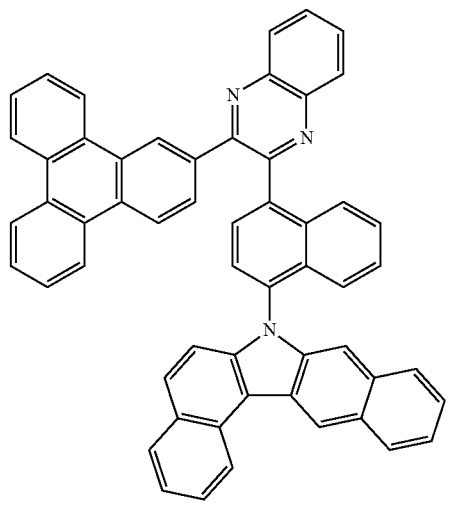
827
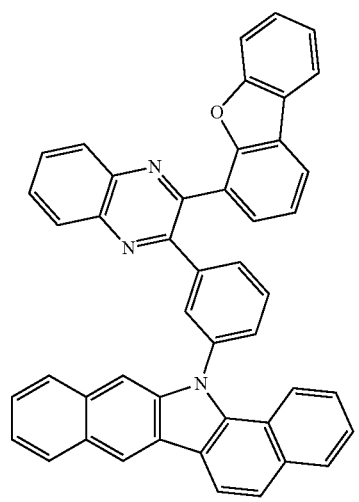
828
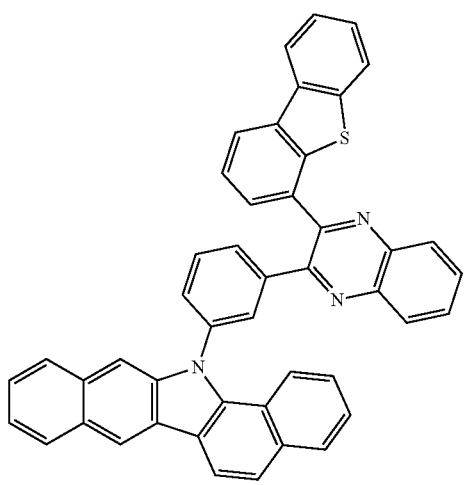
280
-continued
829
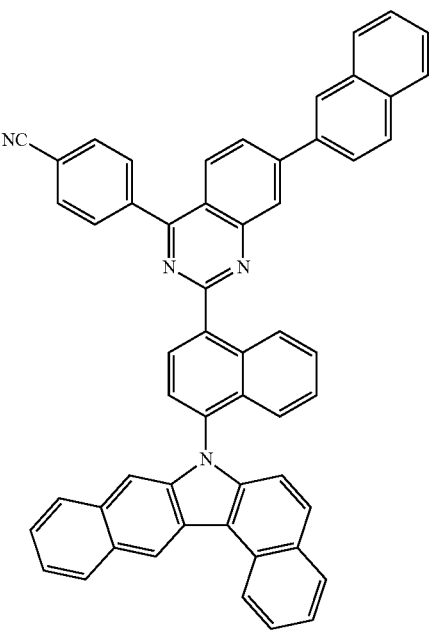
830
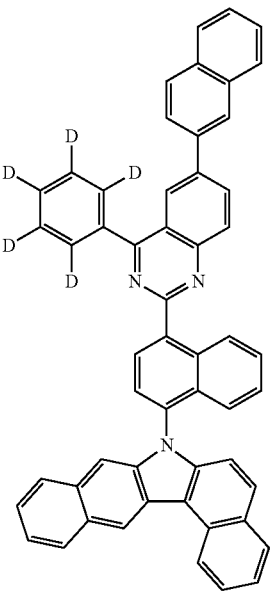

281
-continued
833
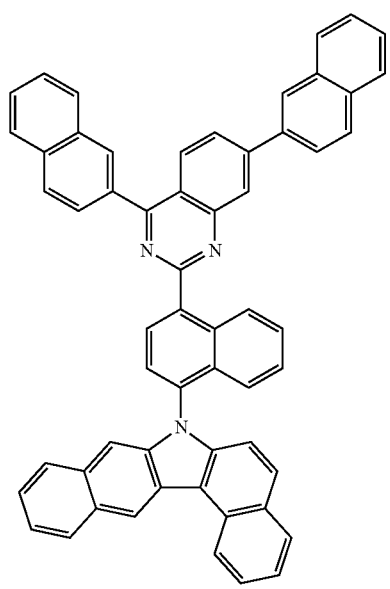
282
-continued
831
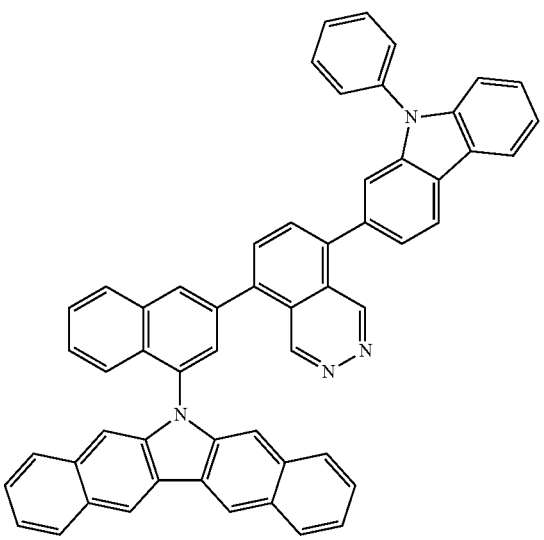
832
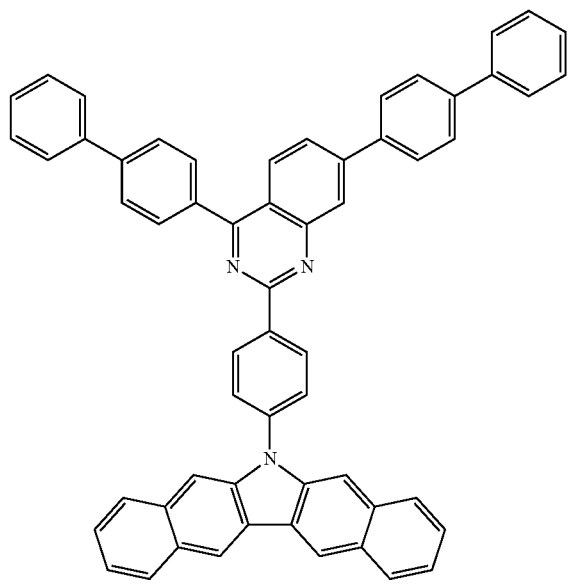
834
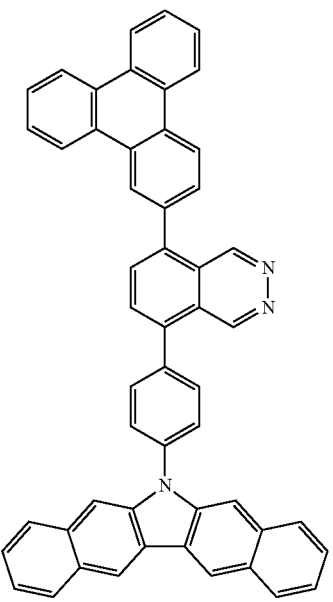

283 -continued
835
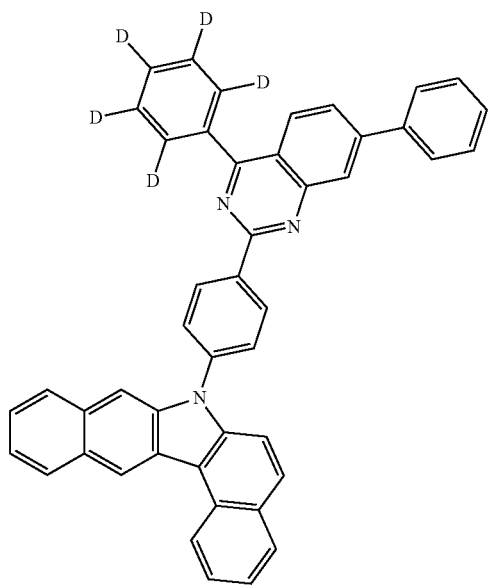
284 -continued
837
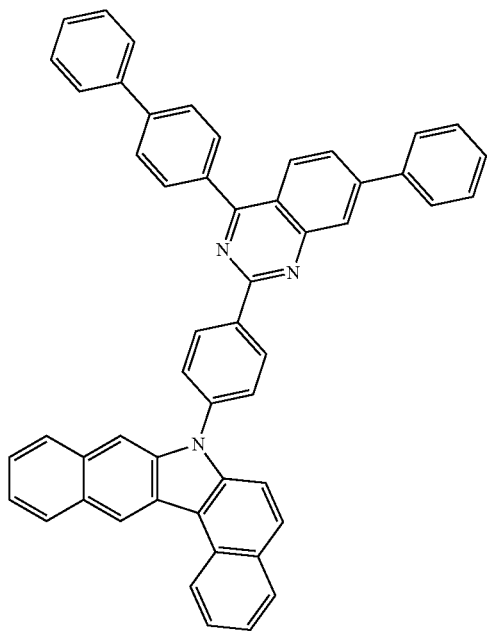
836
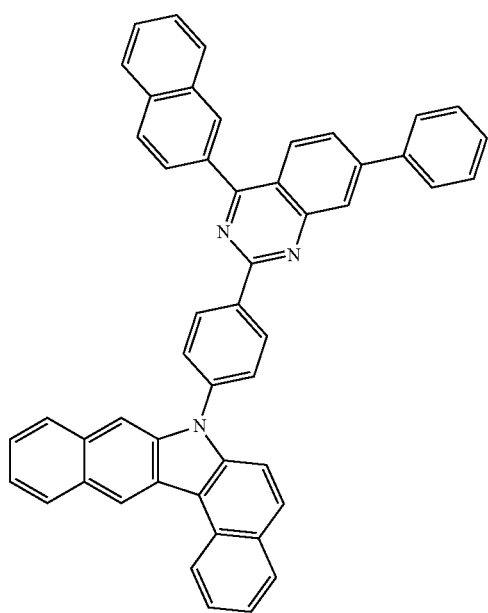
838
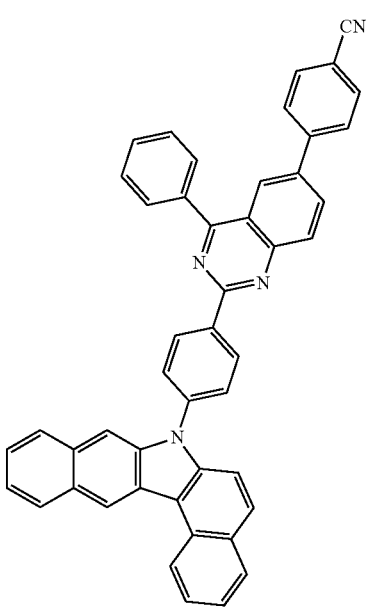

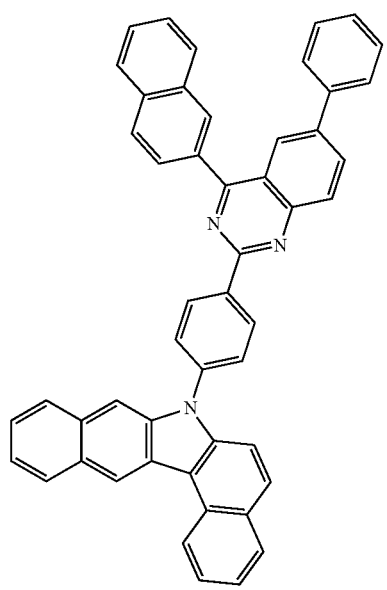
839
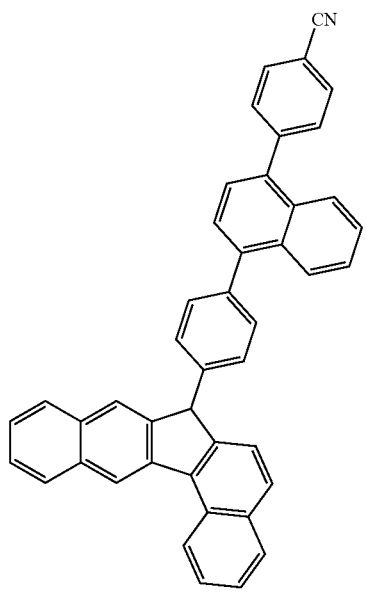
841
840
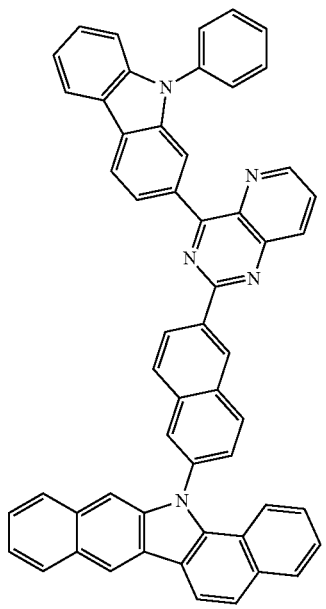
842

US 11,581,496 B2
287
-continued
843
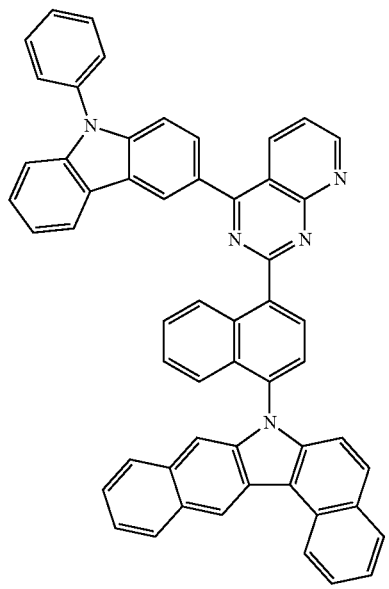
844
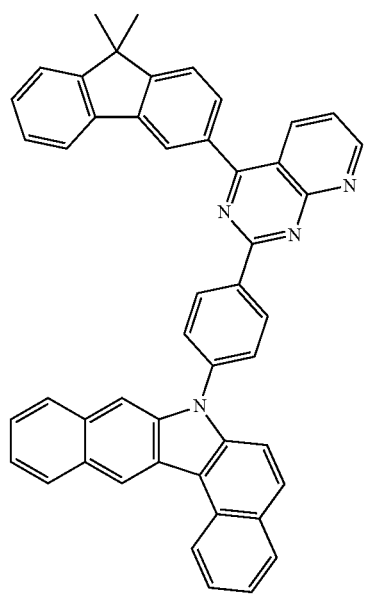
288
-continued
845
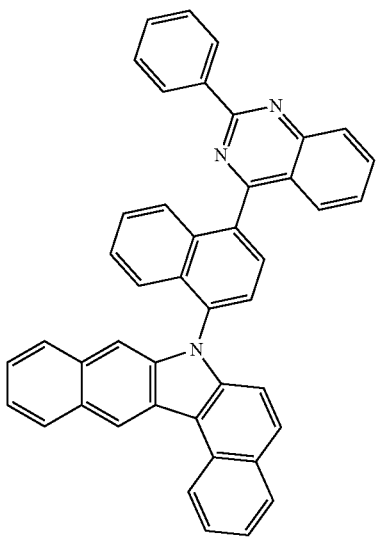
846
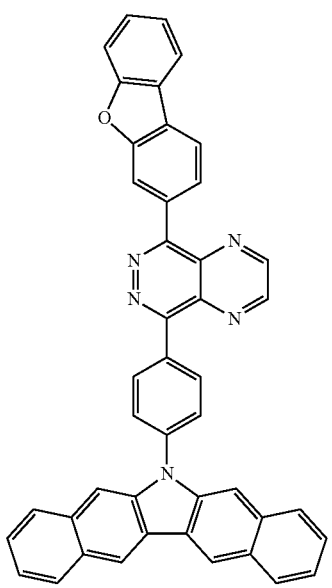
847
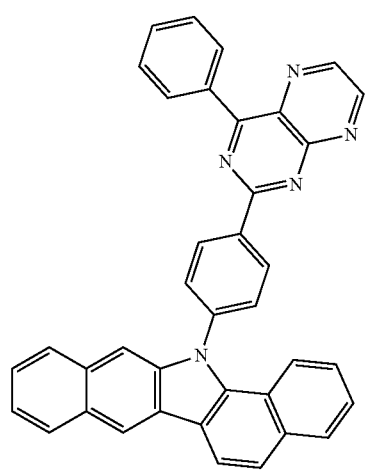

289
-continued
848
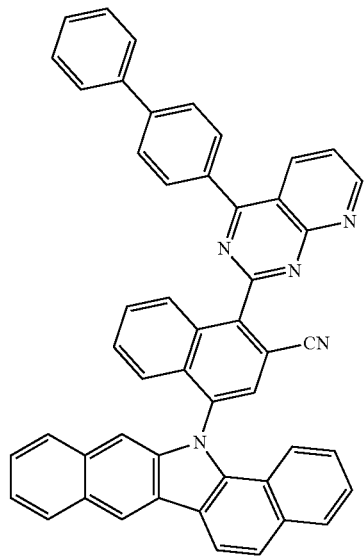
849
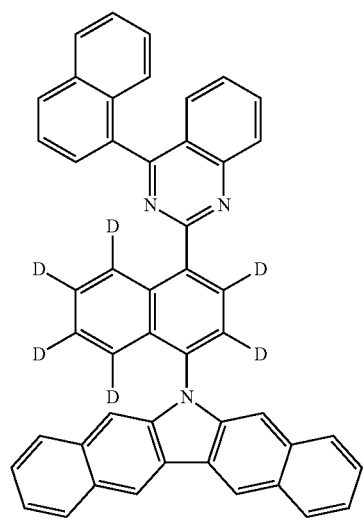
850
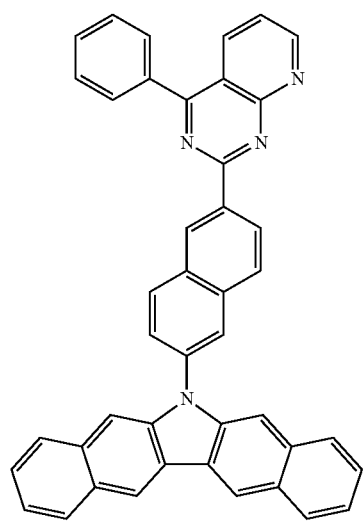
290
-continued
851
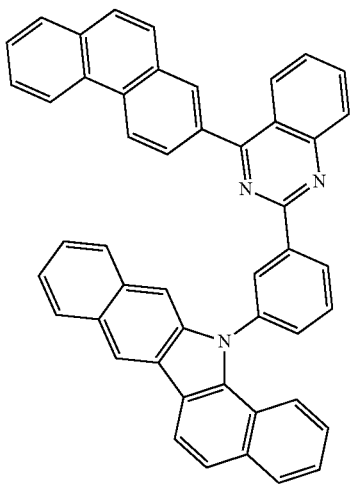
852
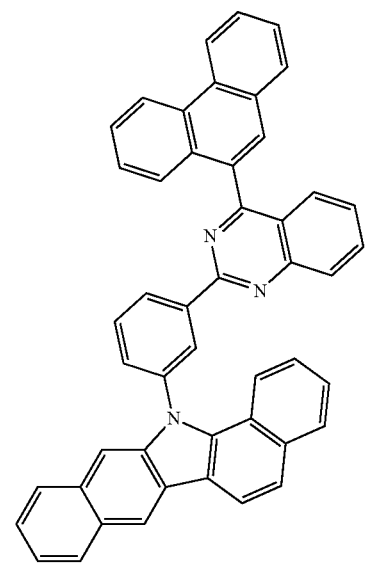
853

291
-continued
854
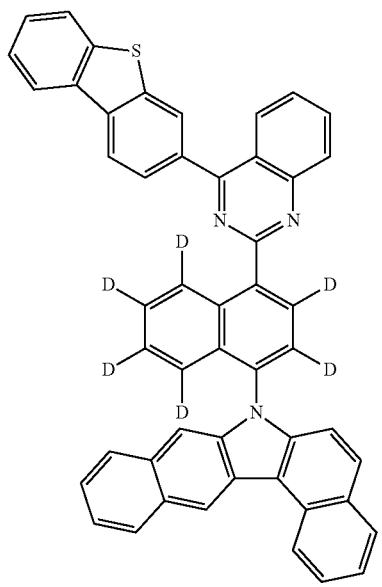
855
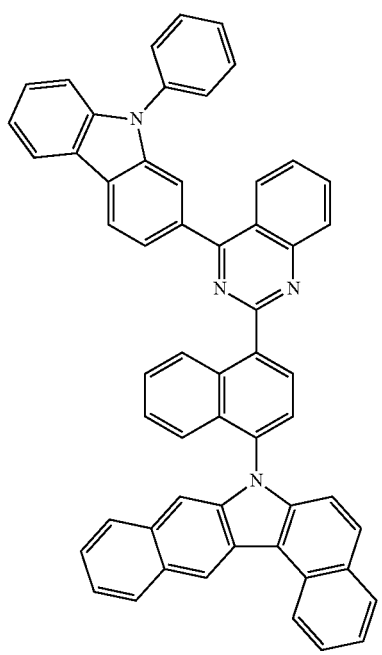
292
-continued
856
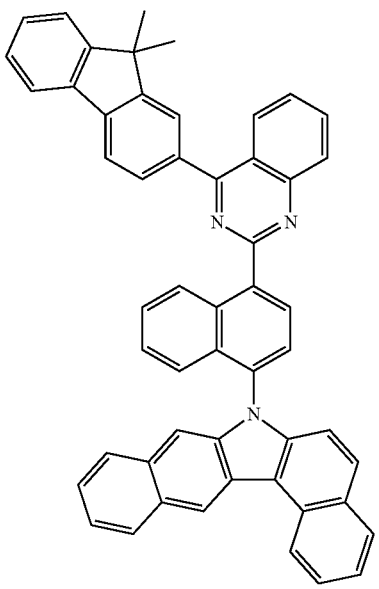
857
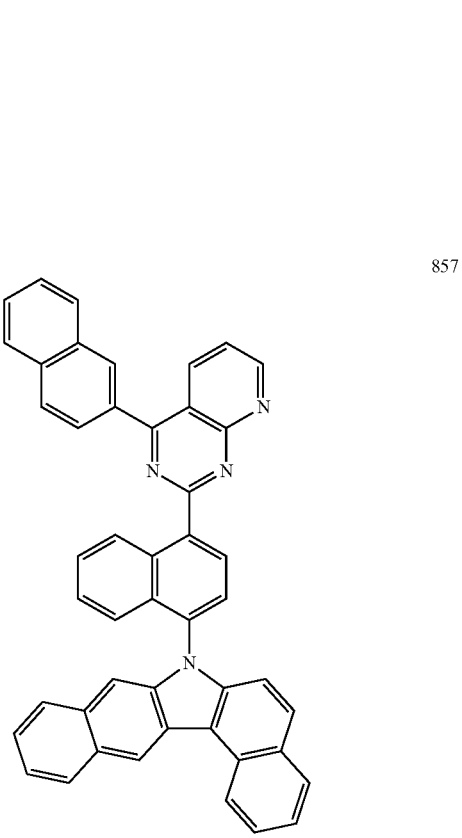

293
-continued
858
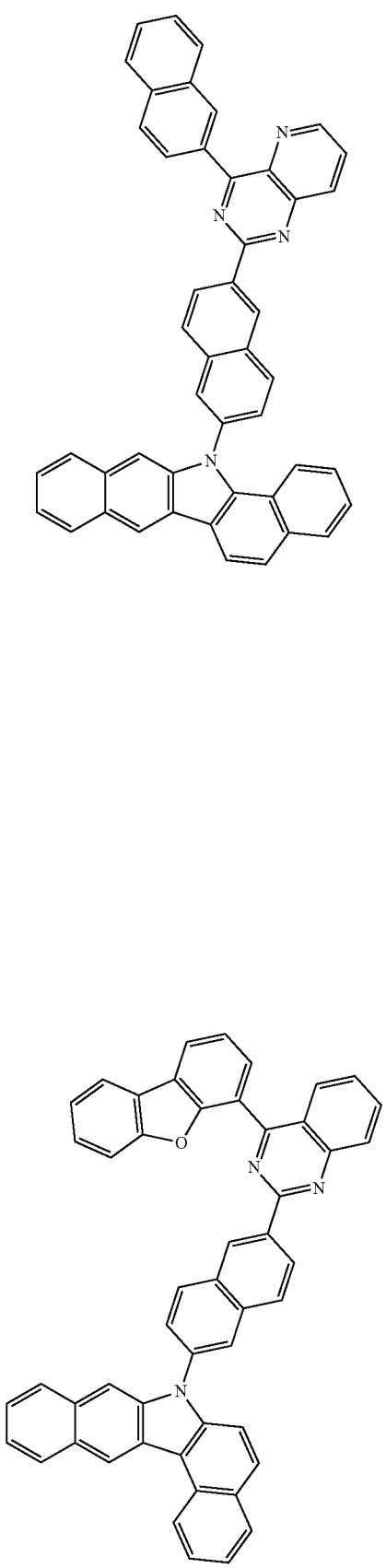
859
294
-continued
860
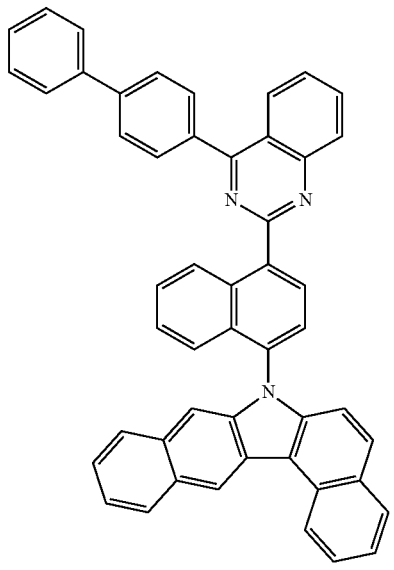
861
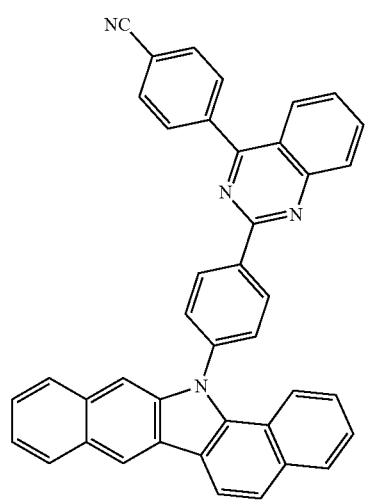
862
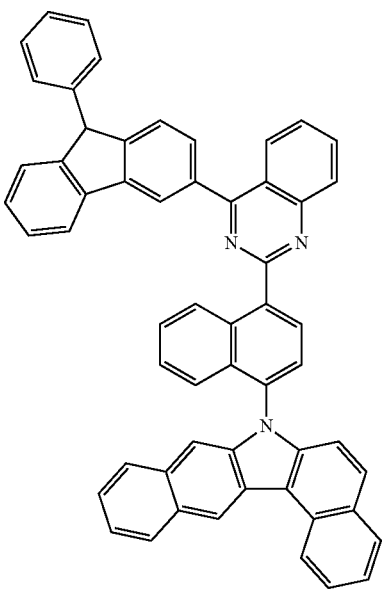

295
-continued
863
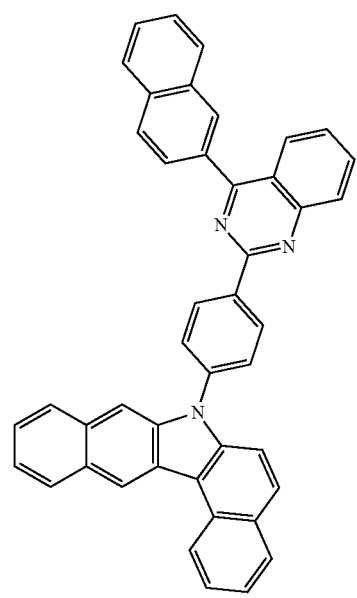
864
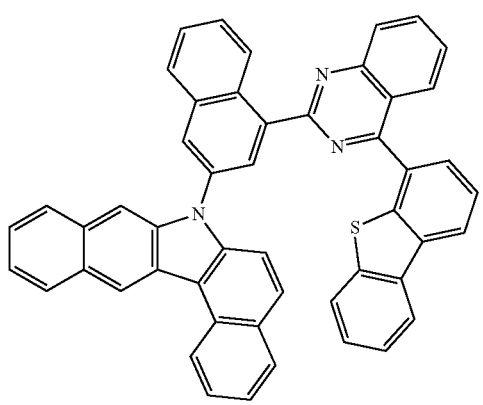
865
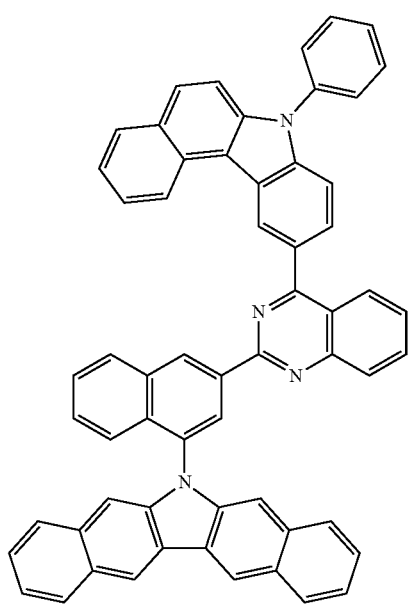
296
-continued
866
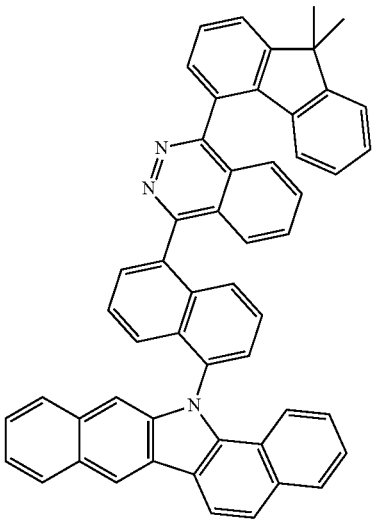
867
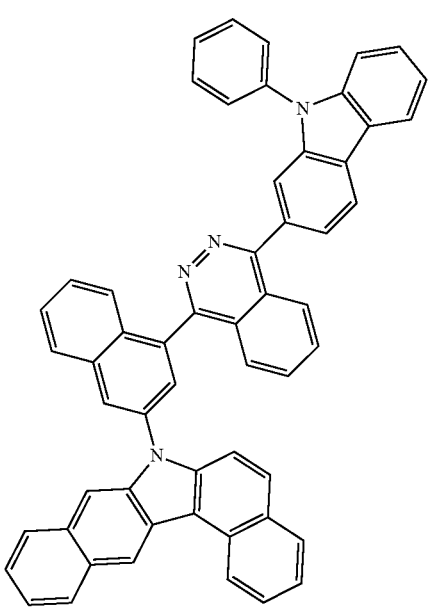

-continued
868
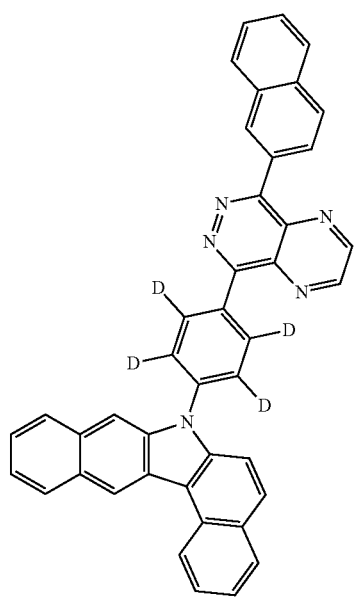
870
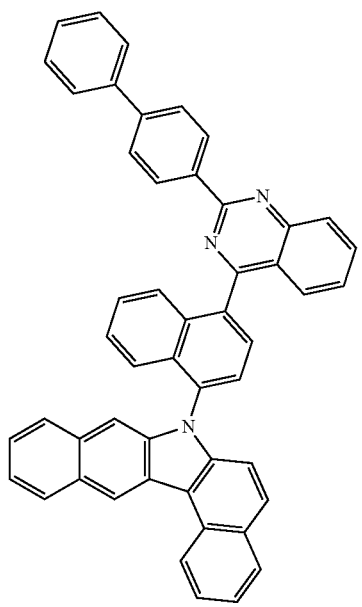
871
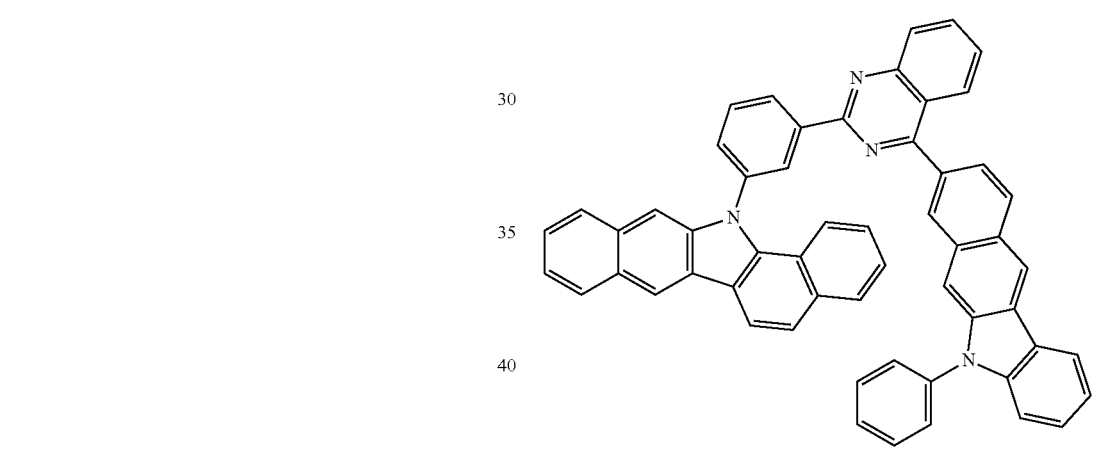
869
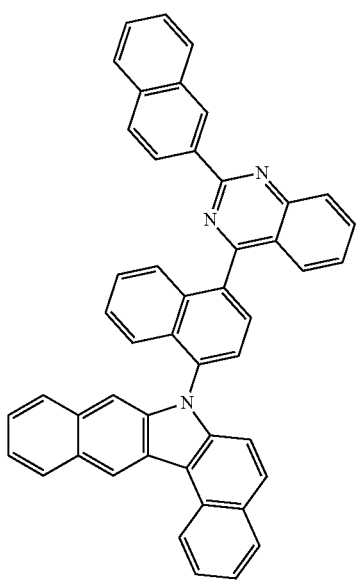
872
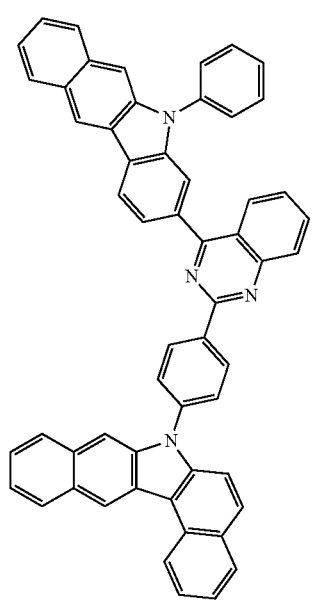

299
-continued
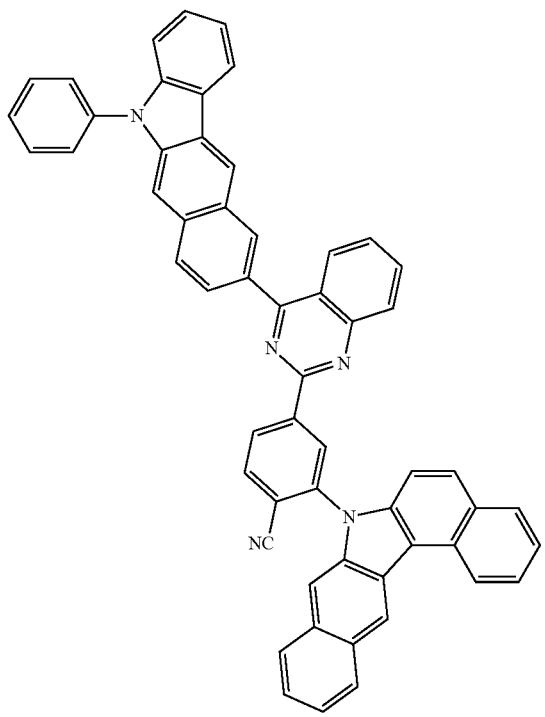
873
300
-continued
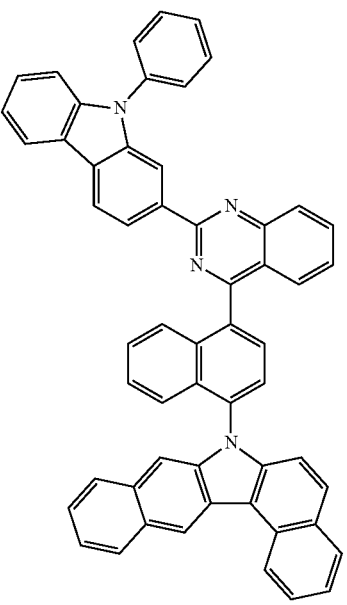
875
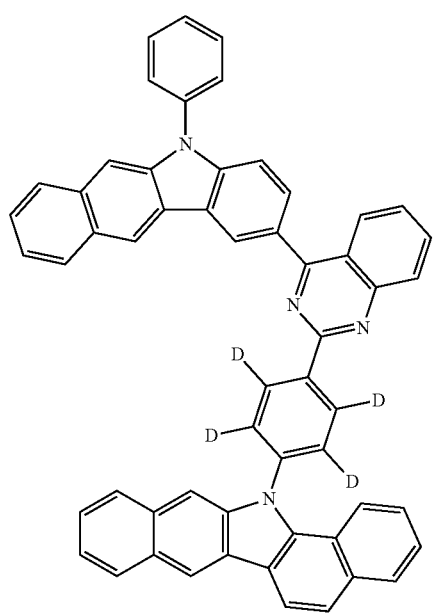
874
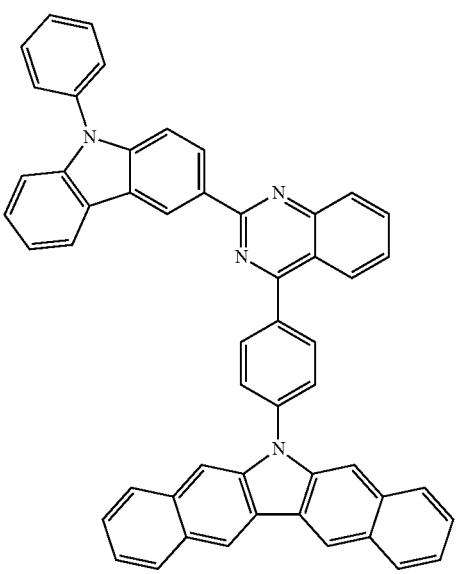
876

301
-continued
877
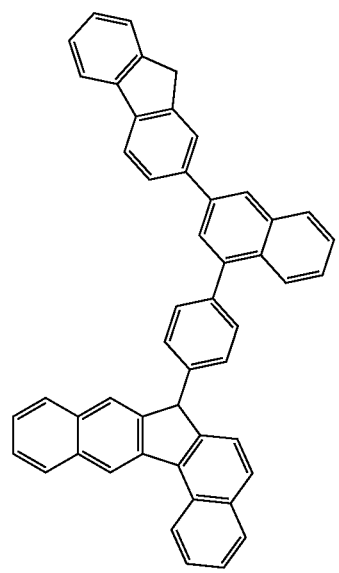
302
-continued
879
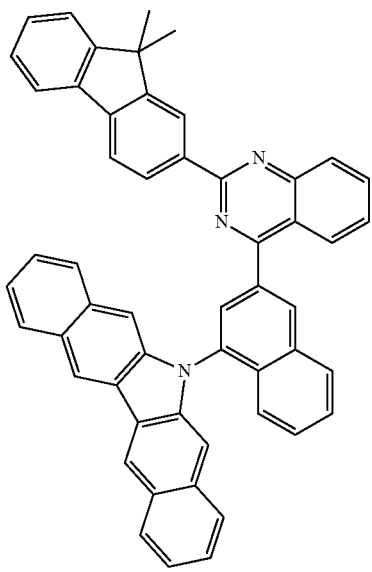
878
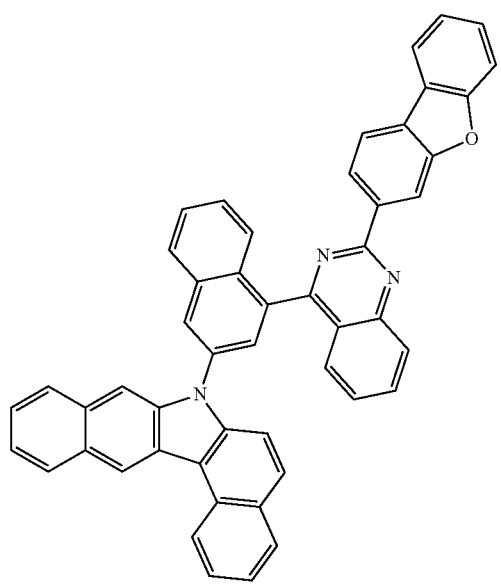
880
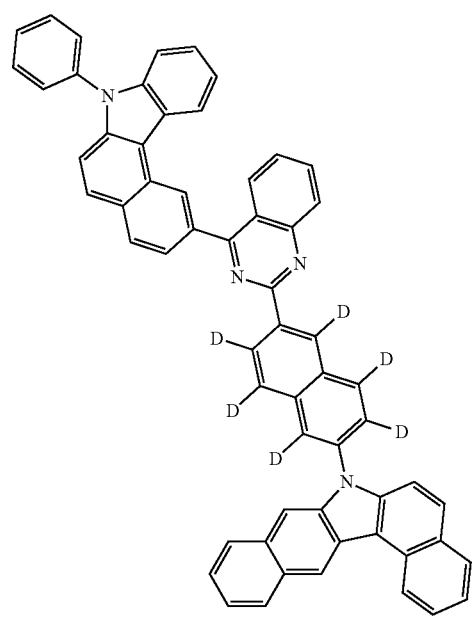

-continued
881
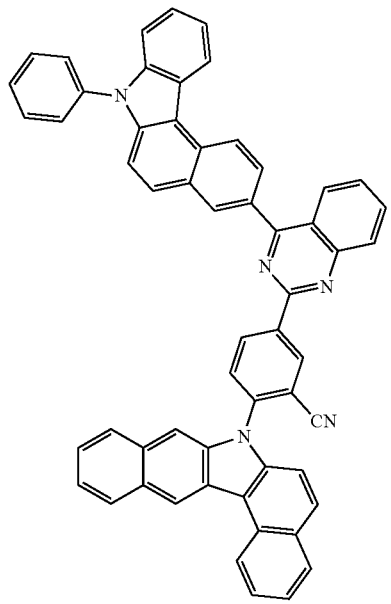
882
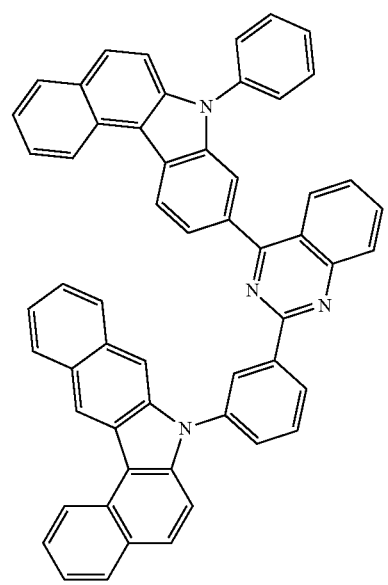
883
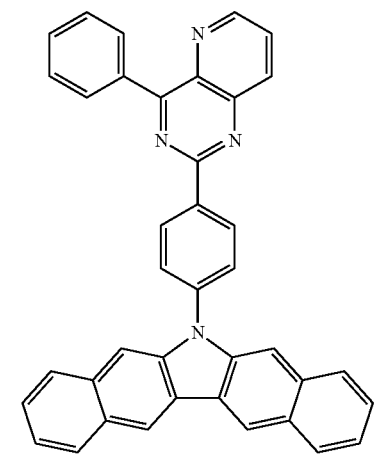
-continued
884
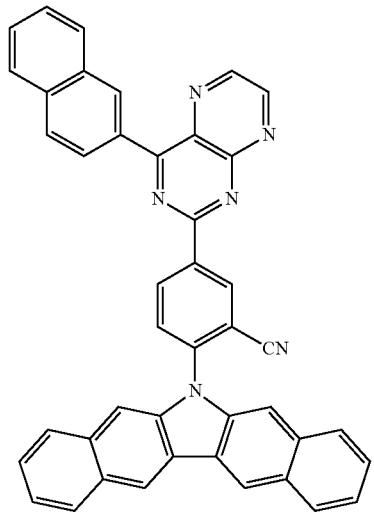
885
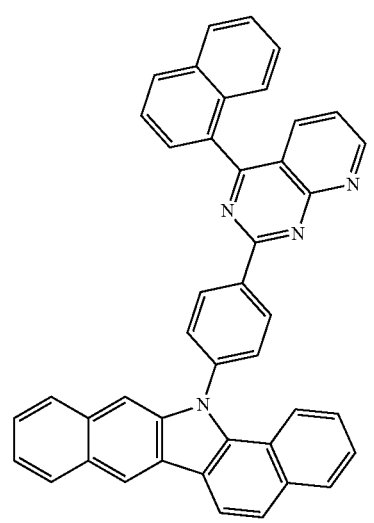
886
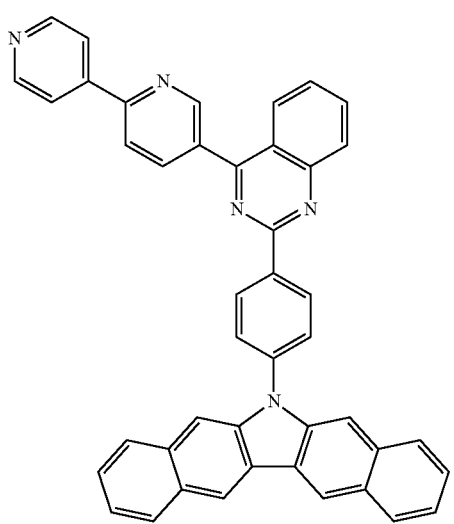

305
-continued
887
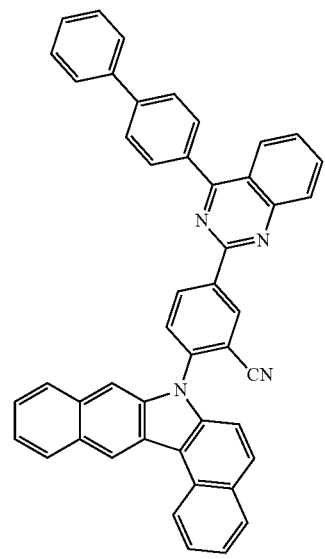
888
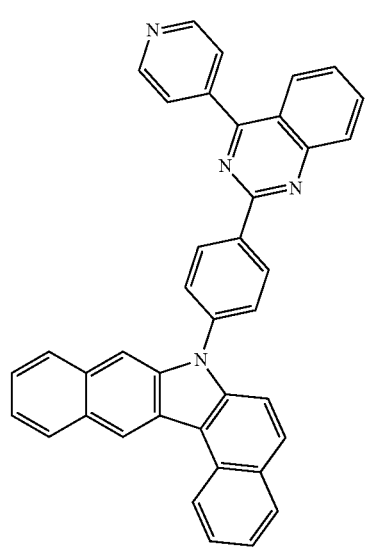
306
-continued
889
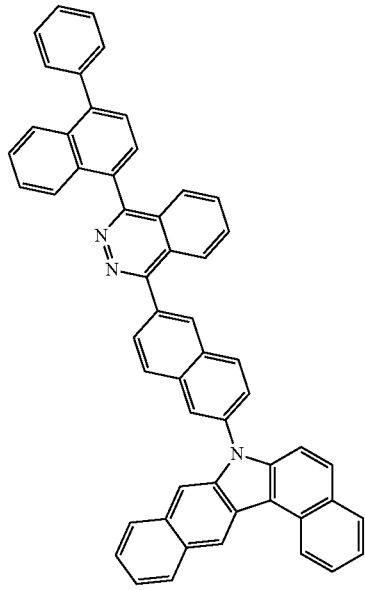
890
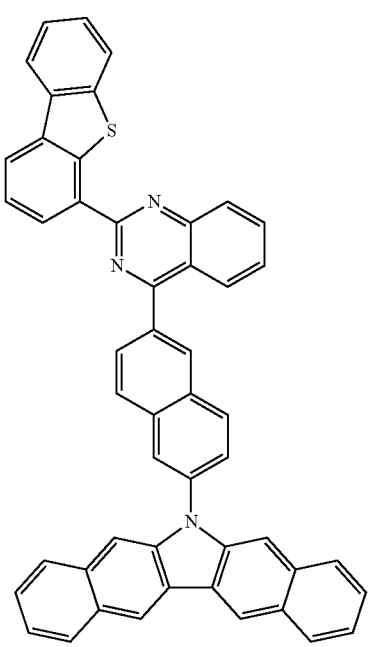

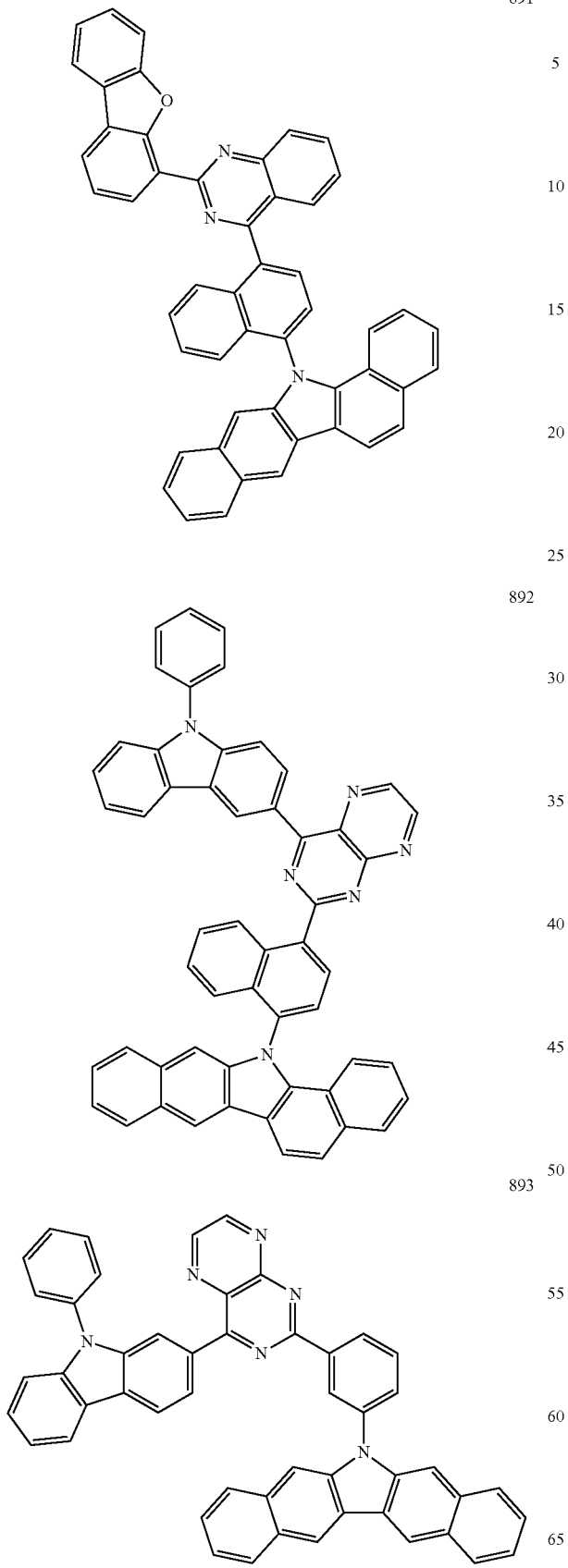
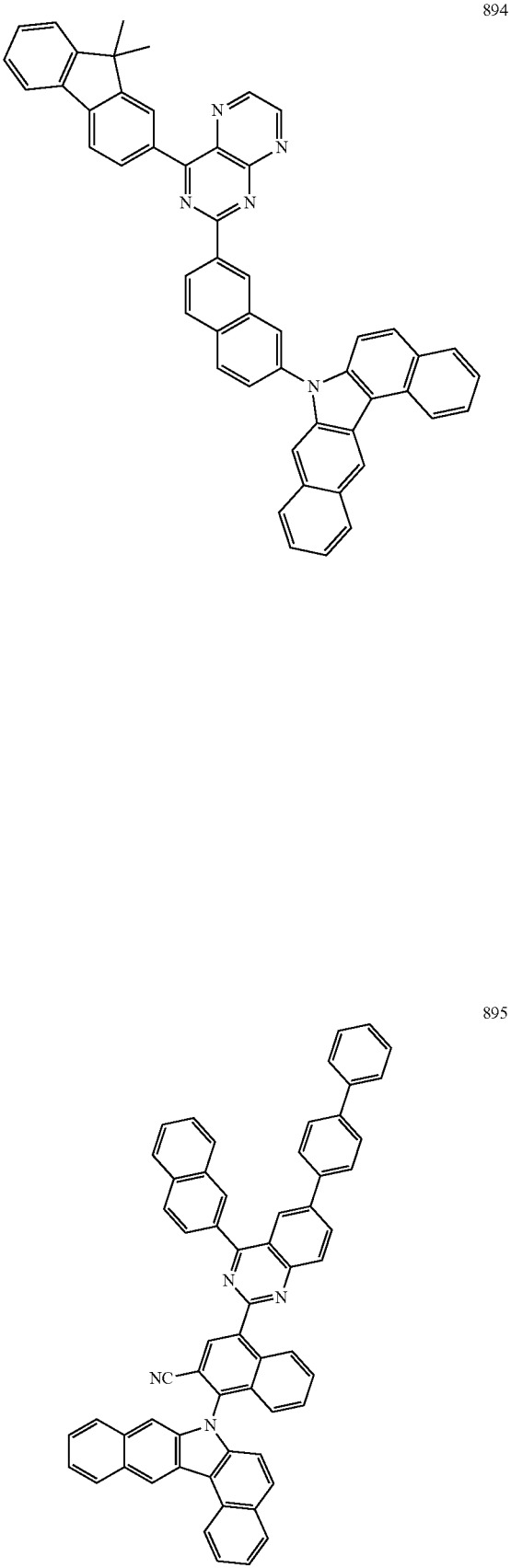

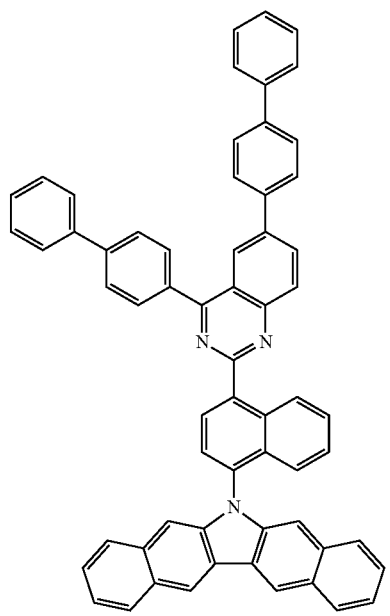
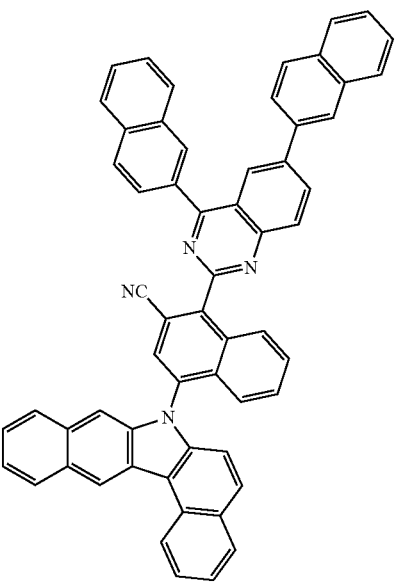
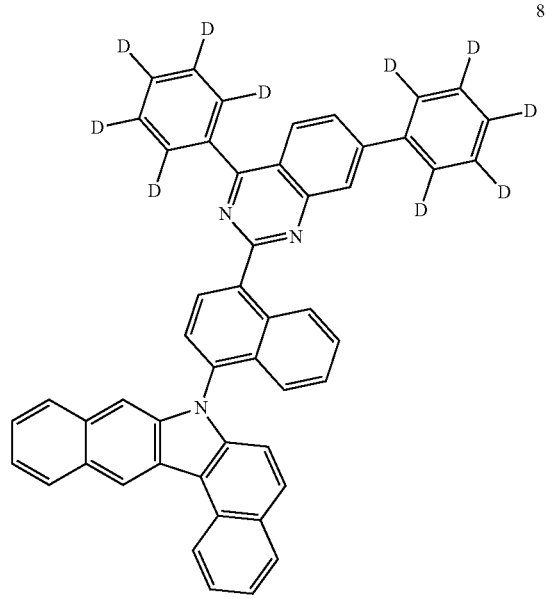

311
-continued
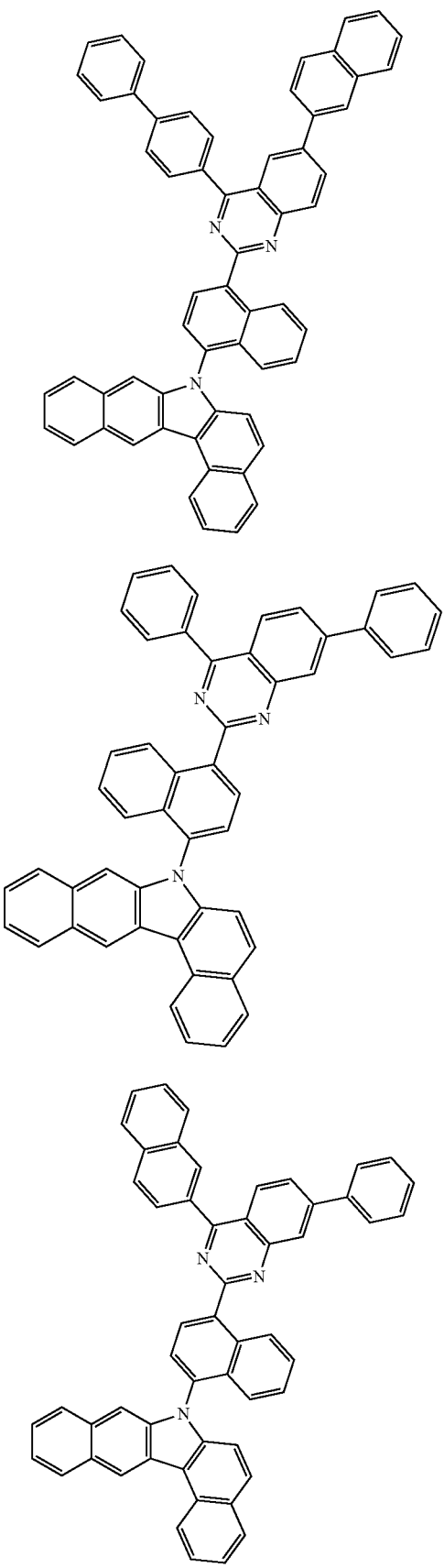
312
-continued
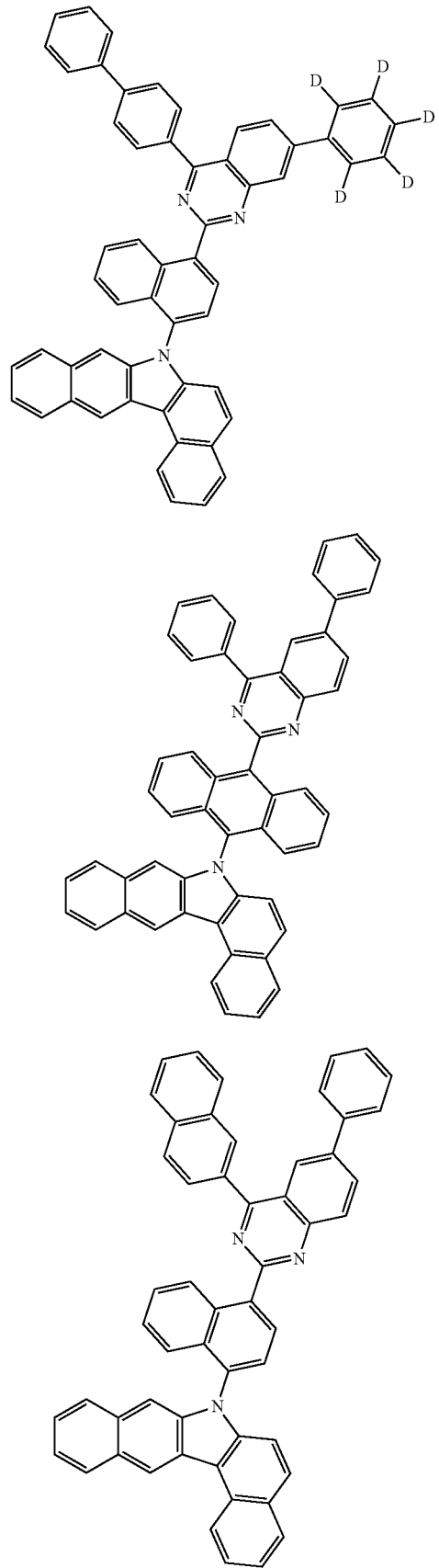

313
-continued
314
-continued
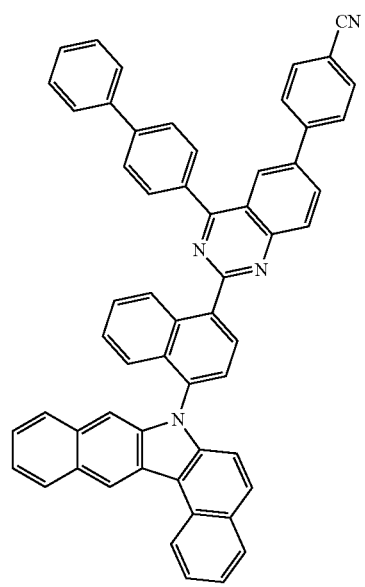
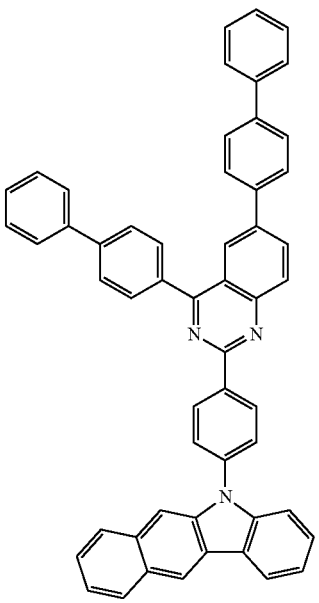

315
-continued
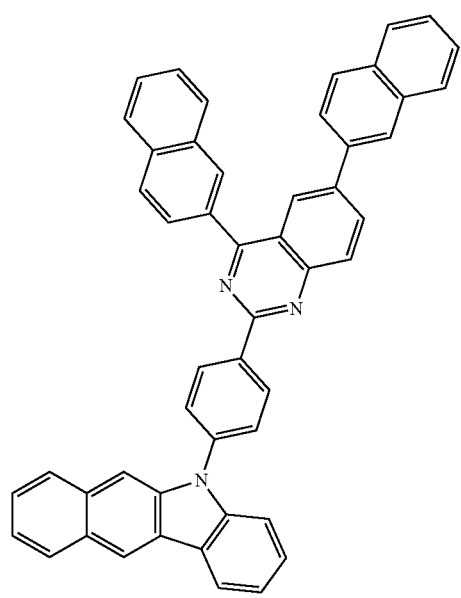
910
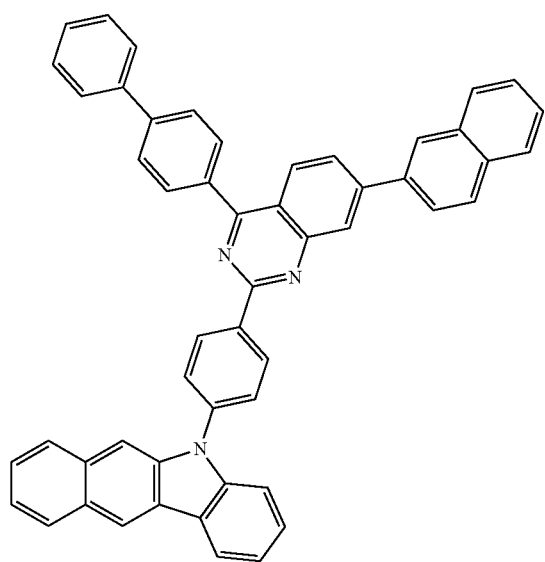
911
316
-continued
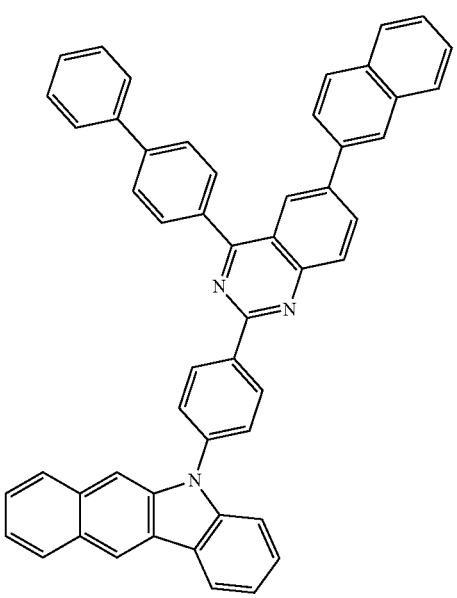
912
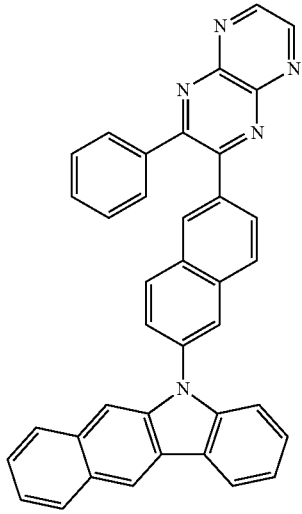
913

-continued
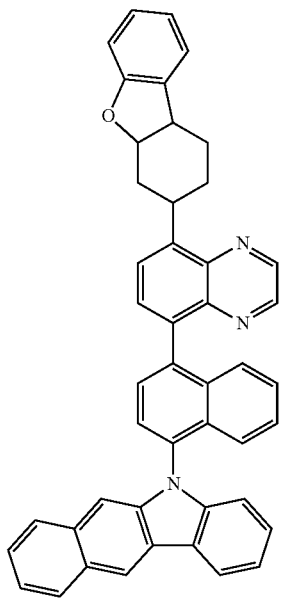
914
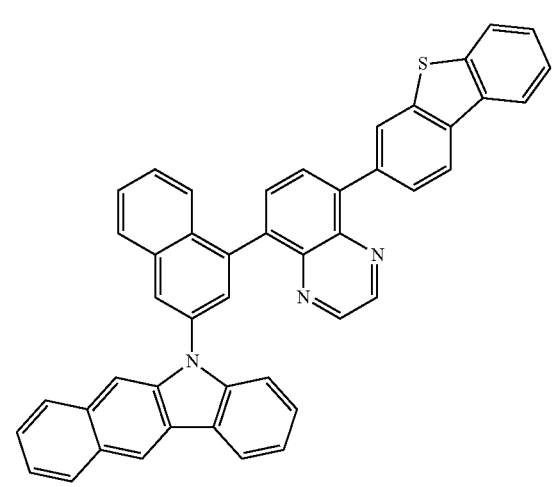
917
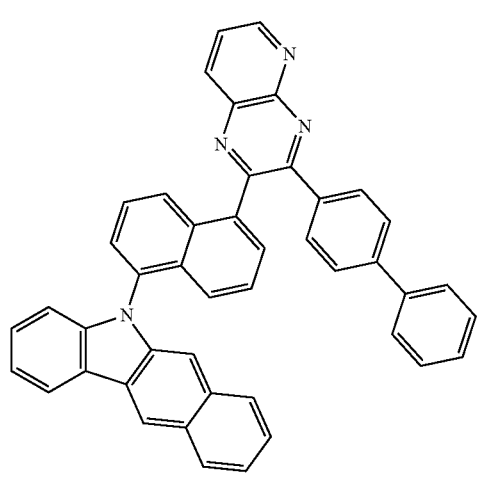
915
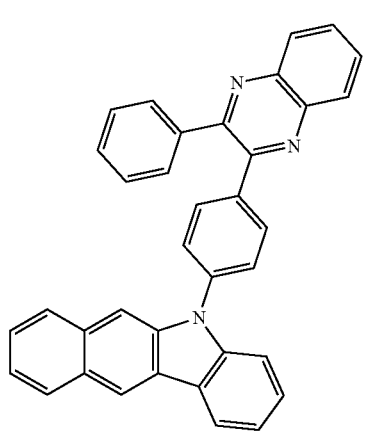
918
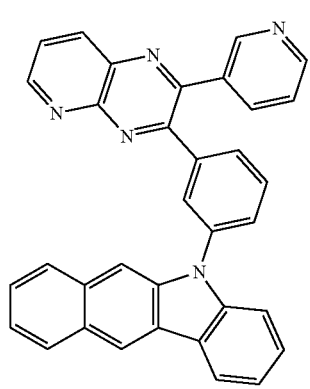
916
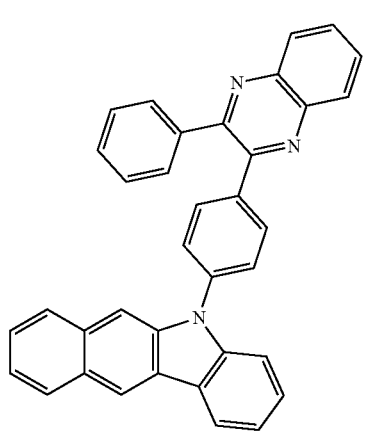
919

-continued
920
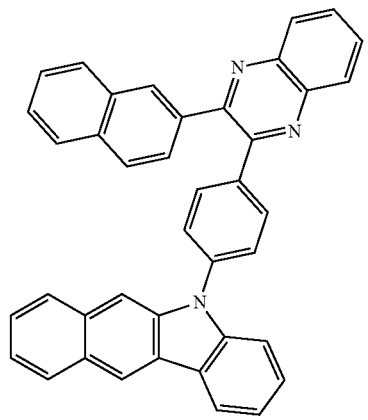
921
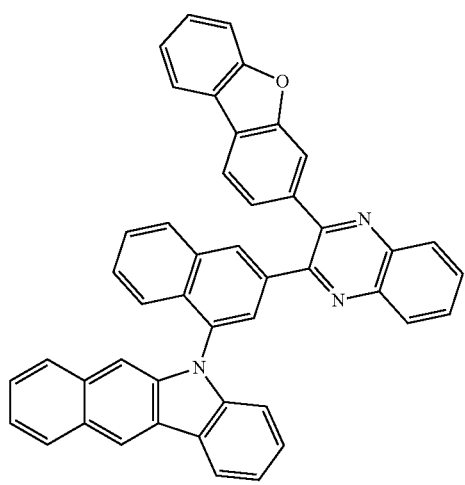
922
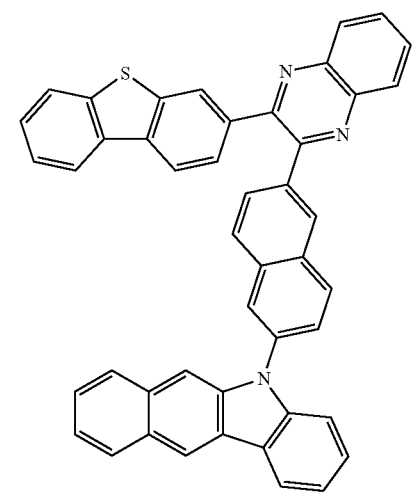
-continued
923
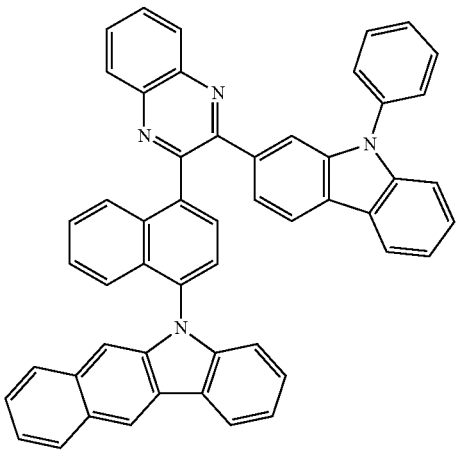
924
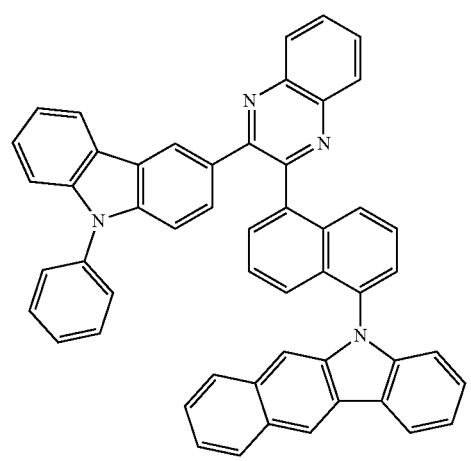
925
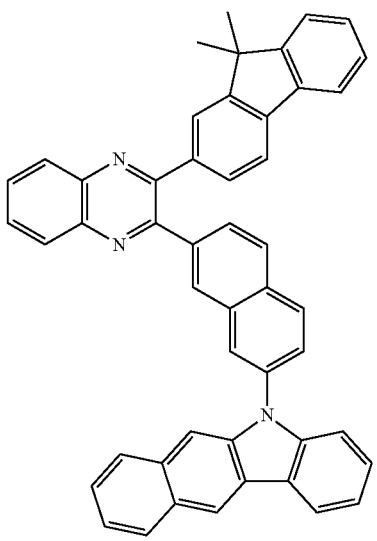

-continued
926
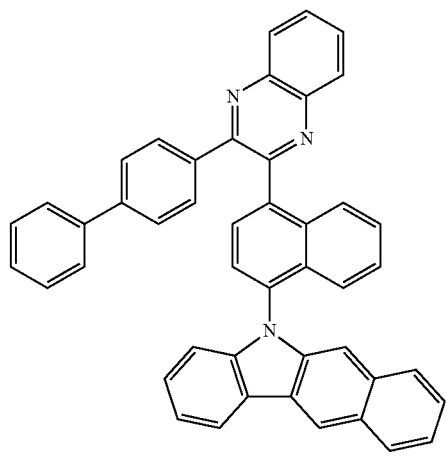
927
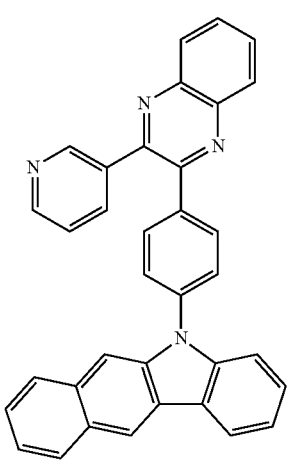
928
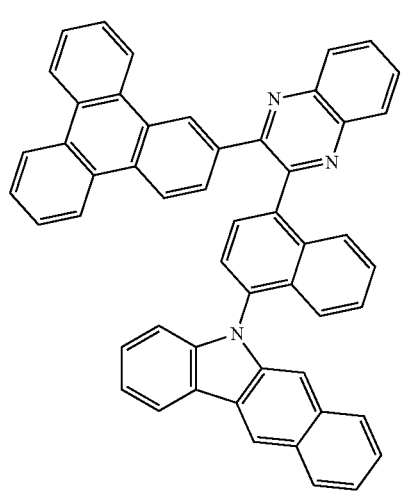
-continued
929
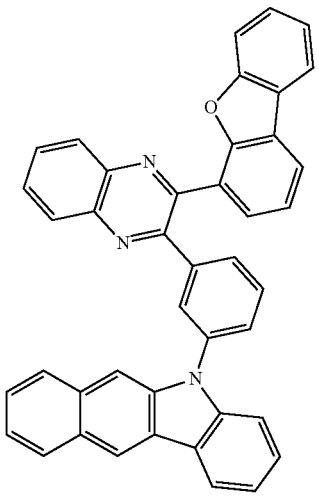
930
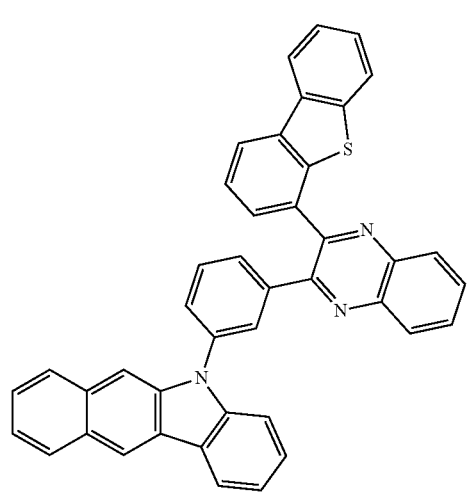
931
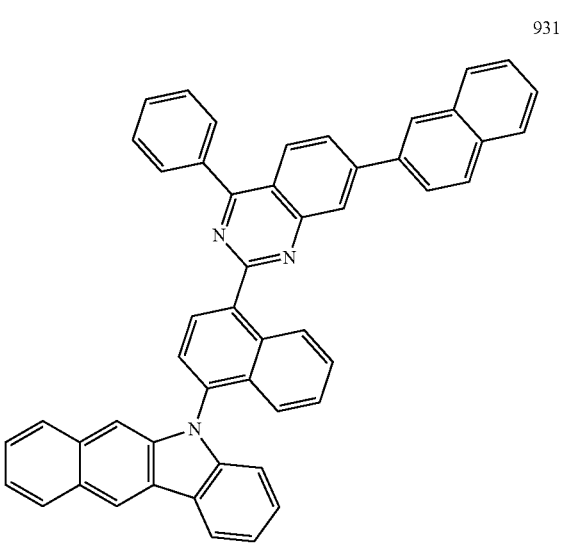

323
-continued
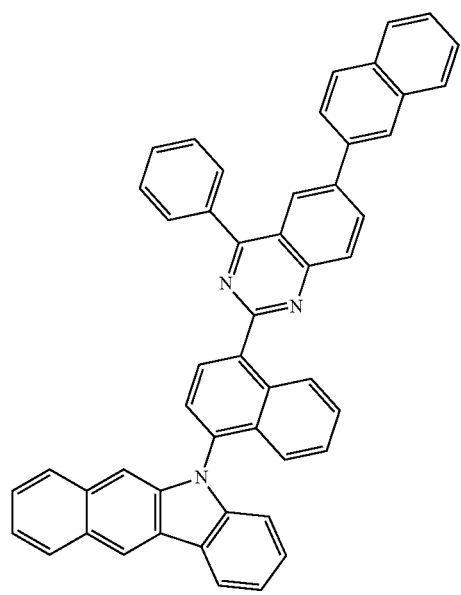
932
324
-continued
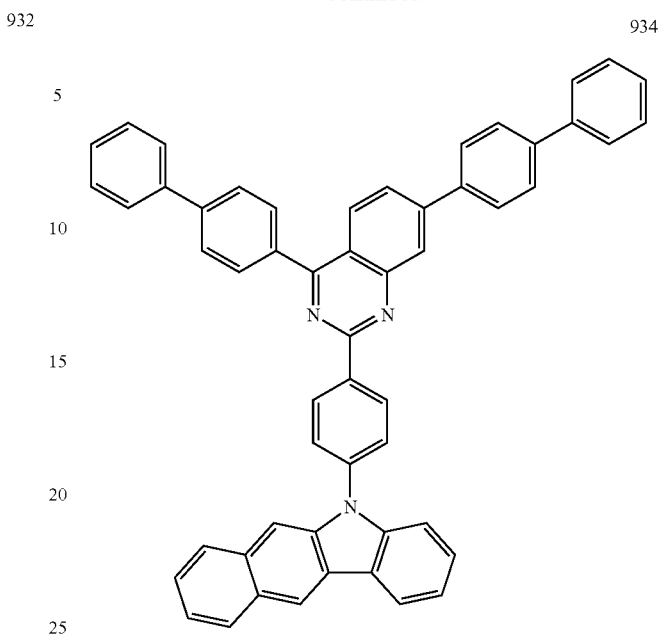
934
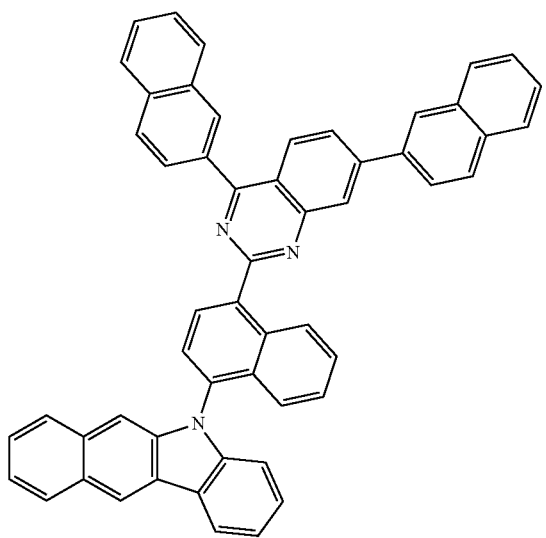
933
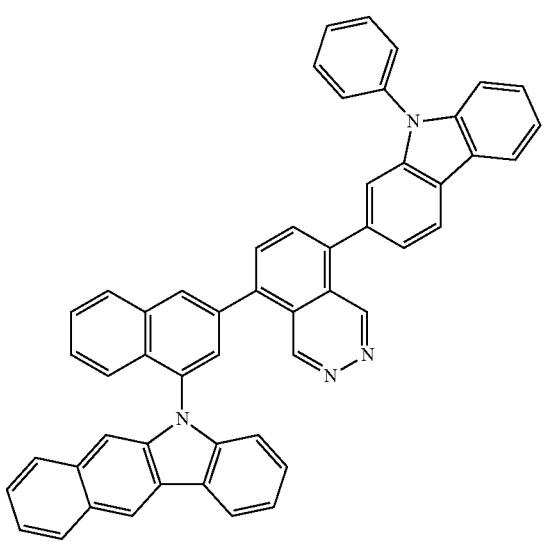
935

325
-continued
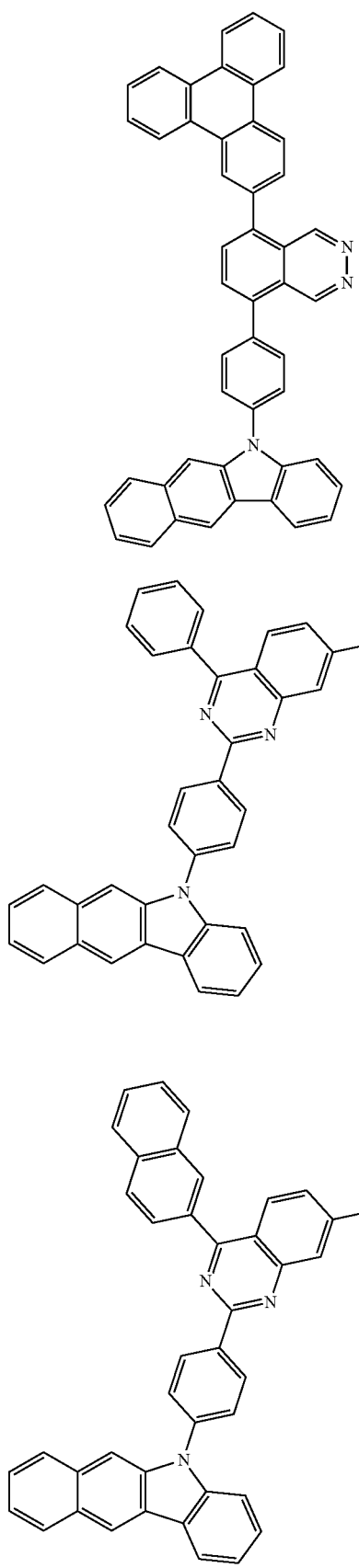
326
-continued
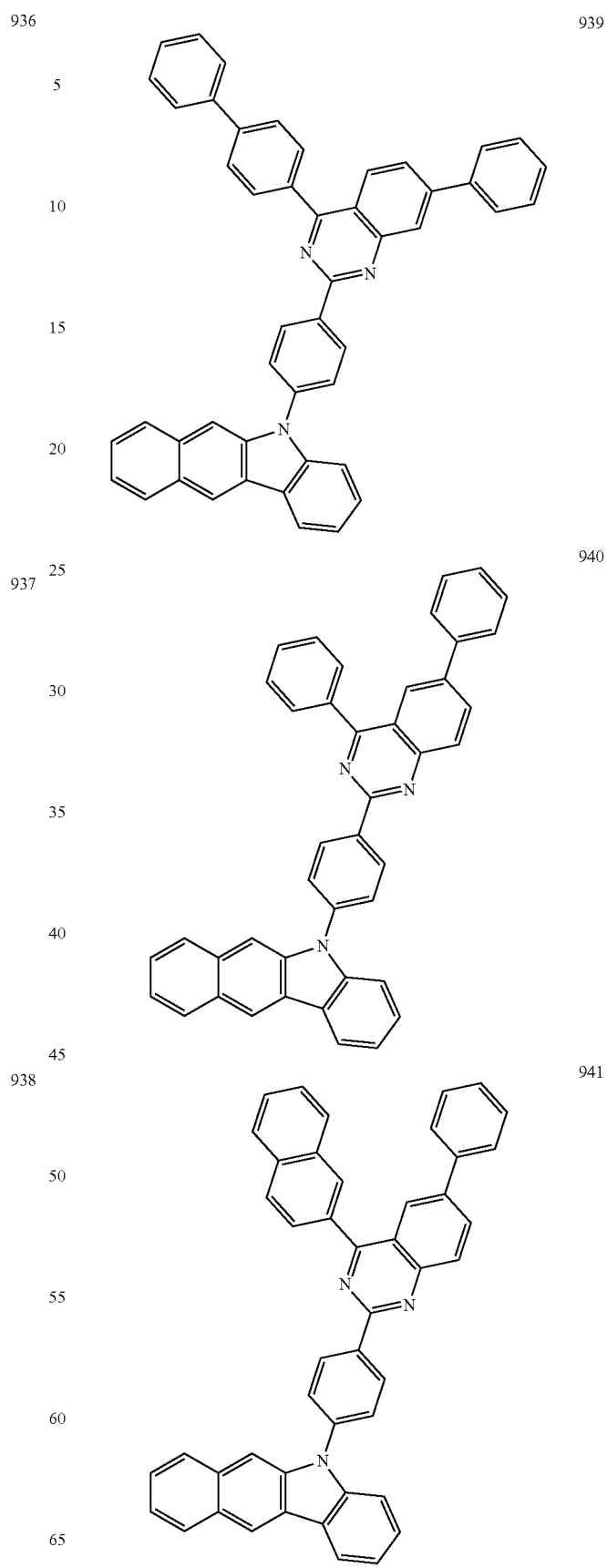

327
-continued
942
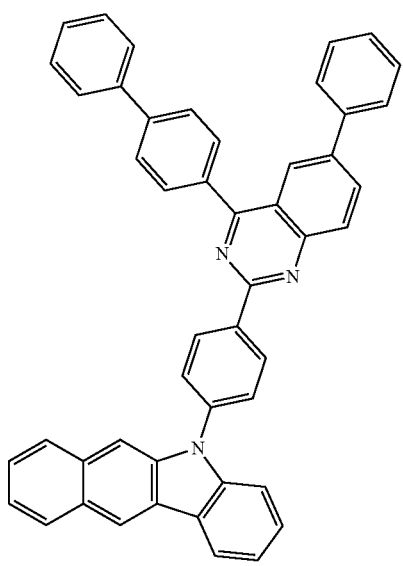
943
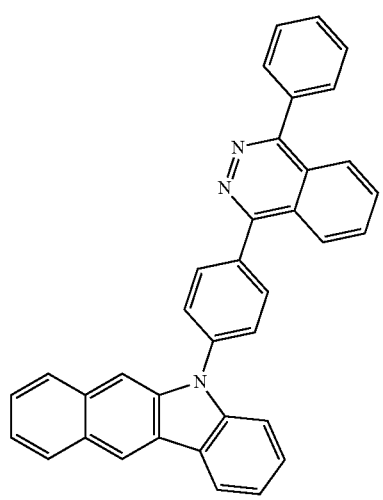
944
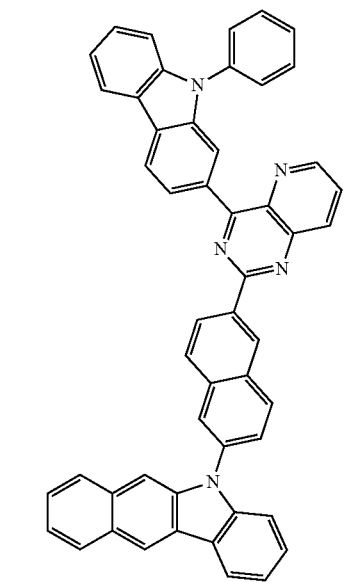
328
-continued
945
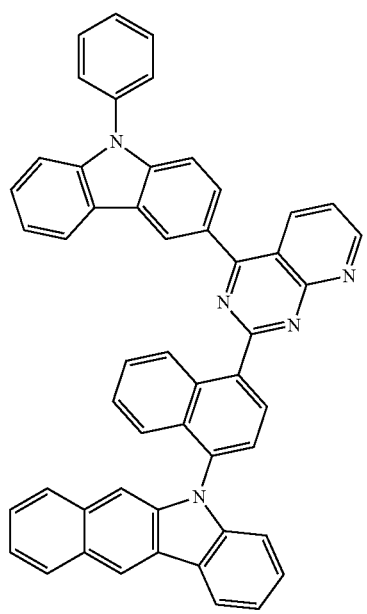
946
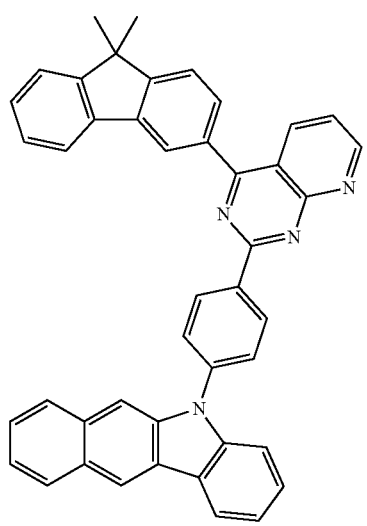
947
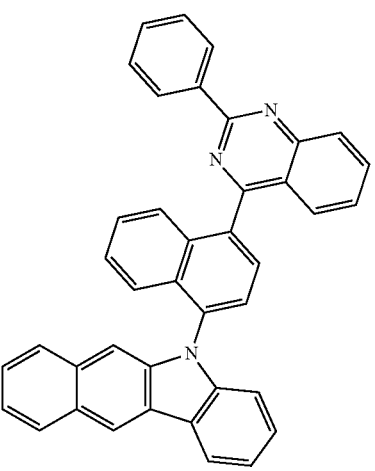

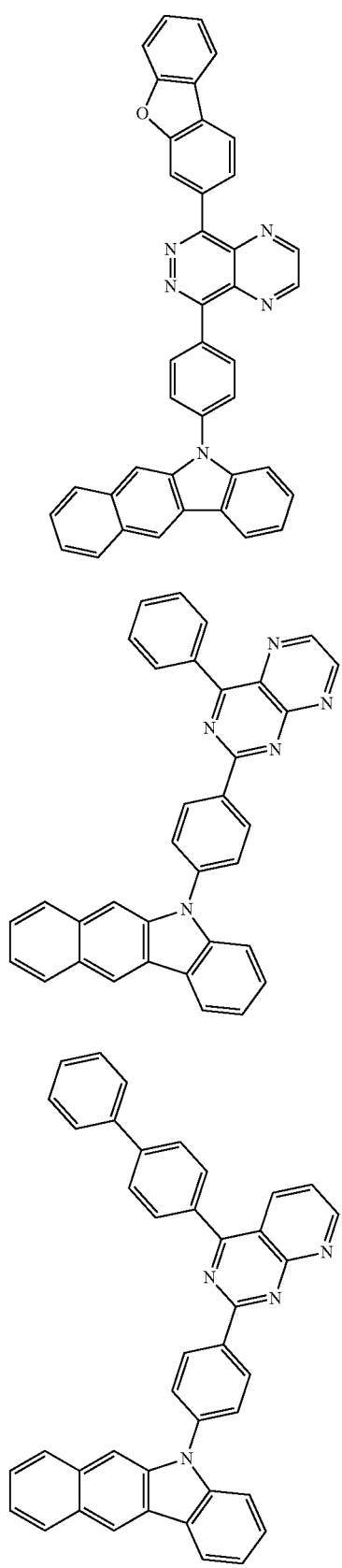
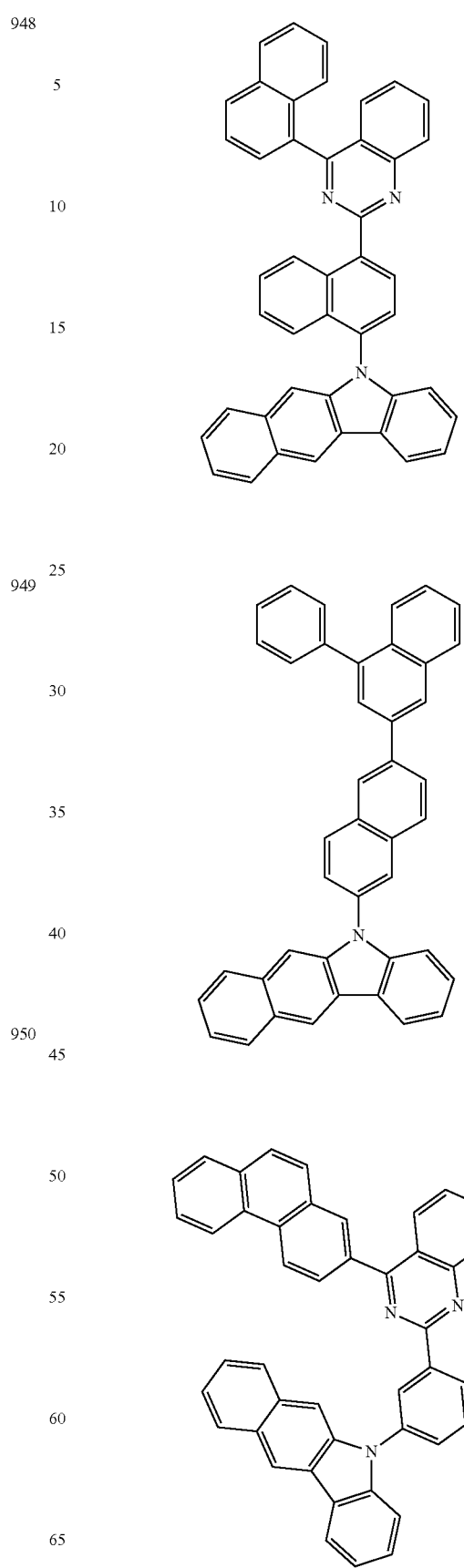

331
-continued
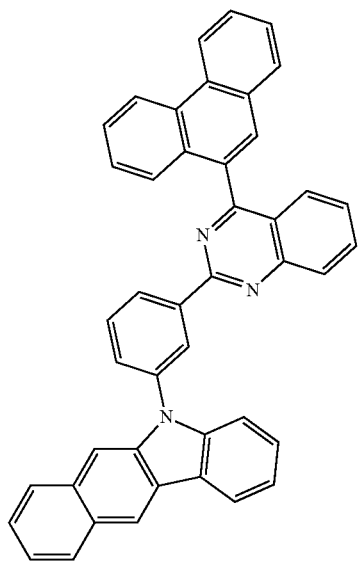
954
332
-continued
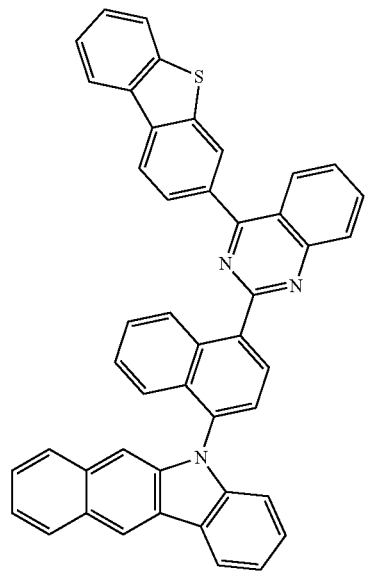
956
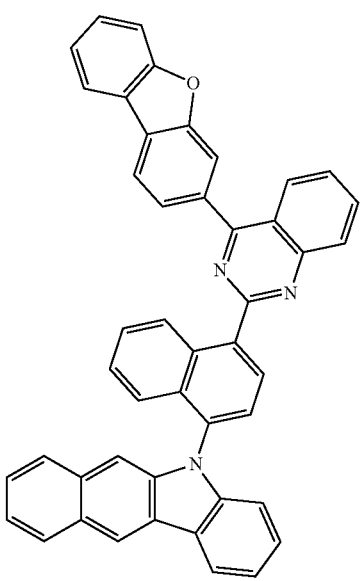
955
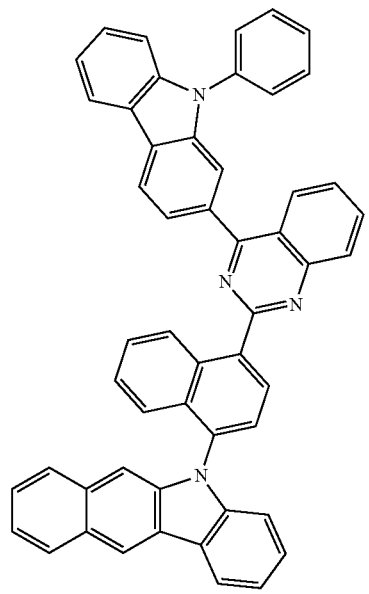
957

333
-continued
958
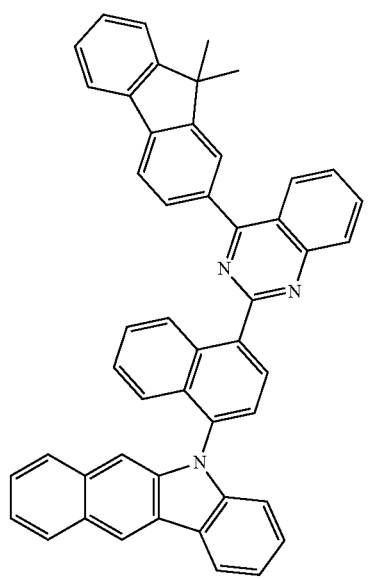
959
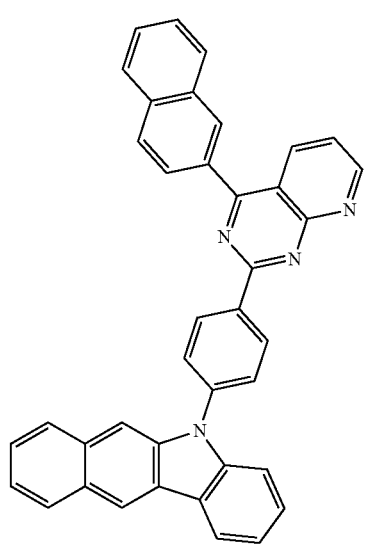
334
-continued
960
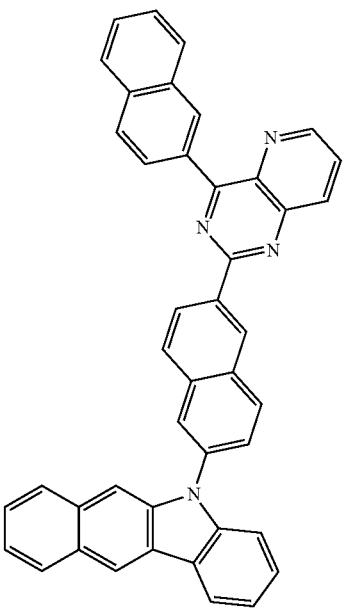
961
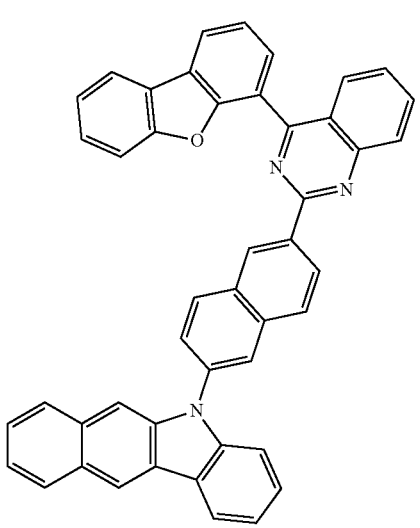

335
-continued
962
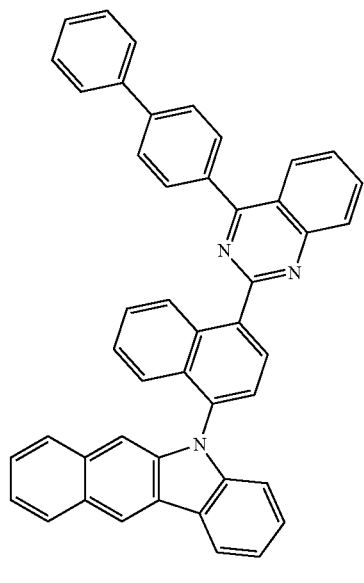
963
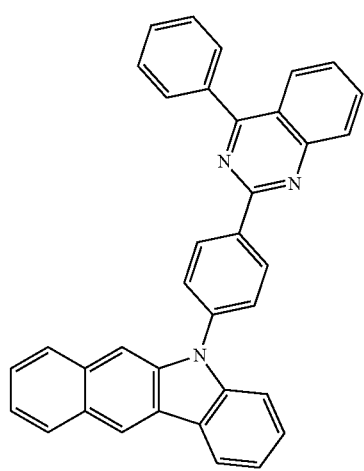
964
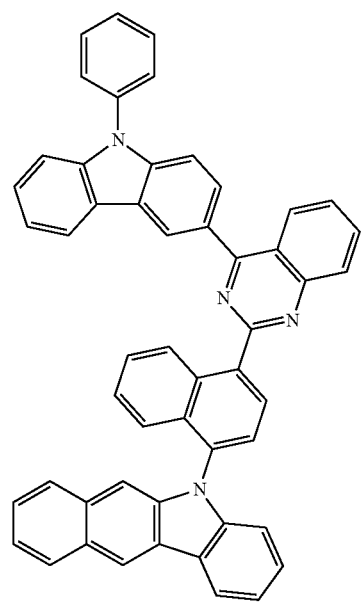
336
-continued
965
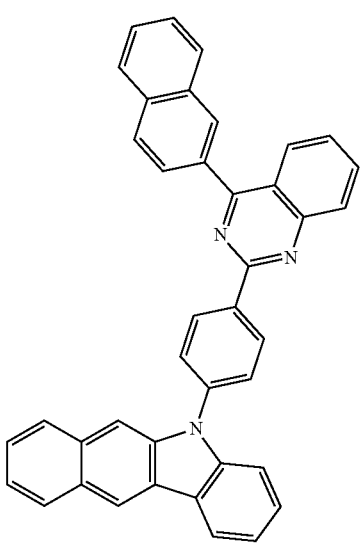
966
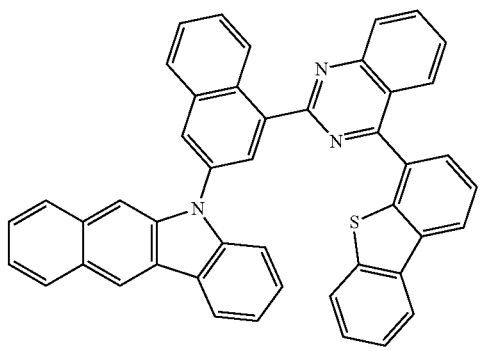
967
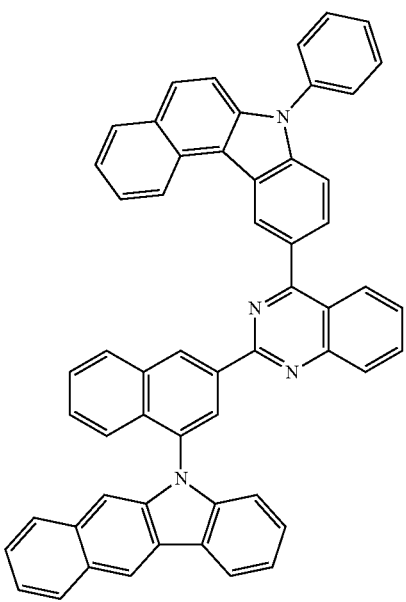

337
-continued
338
-continued
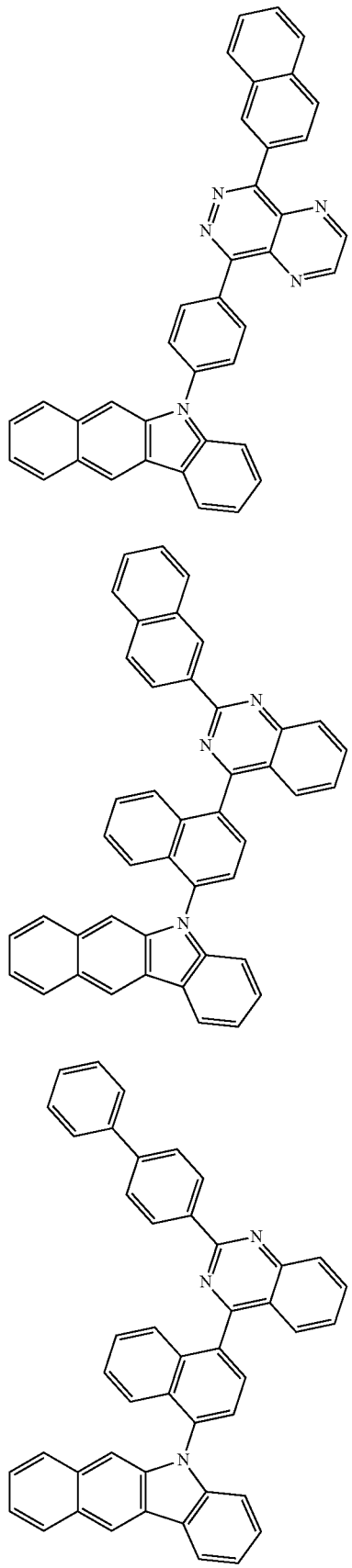

-continued
973
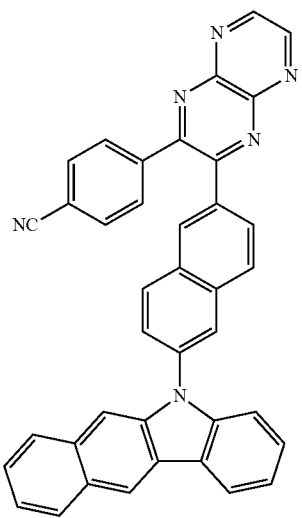
974
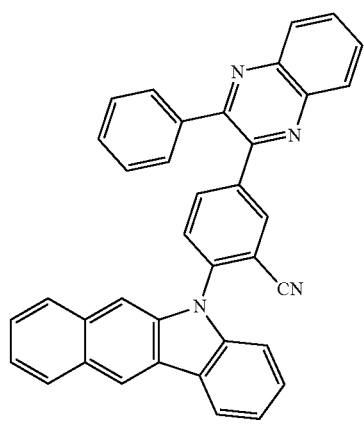
975
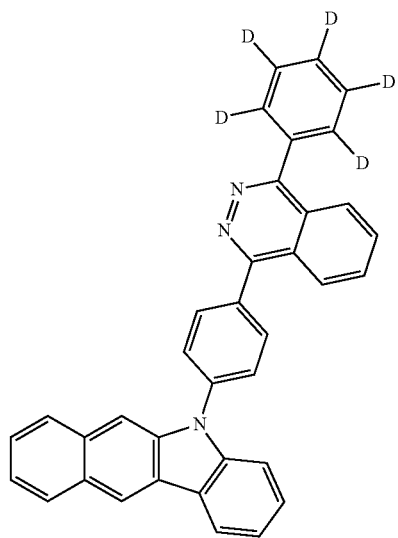
-continued
976
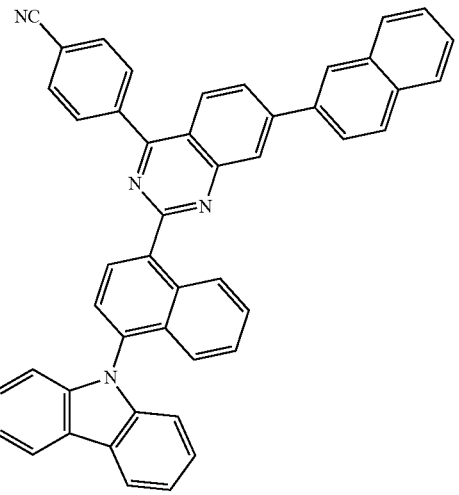
977
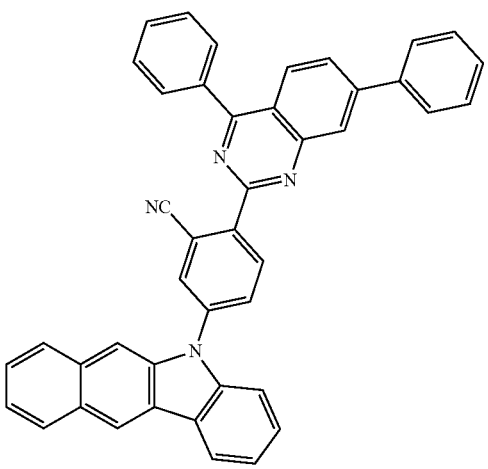
978
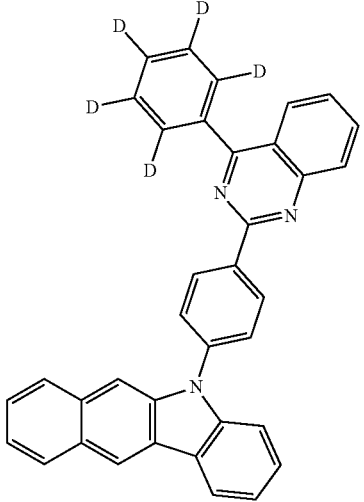

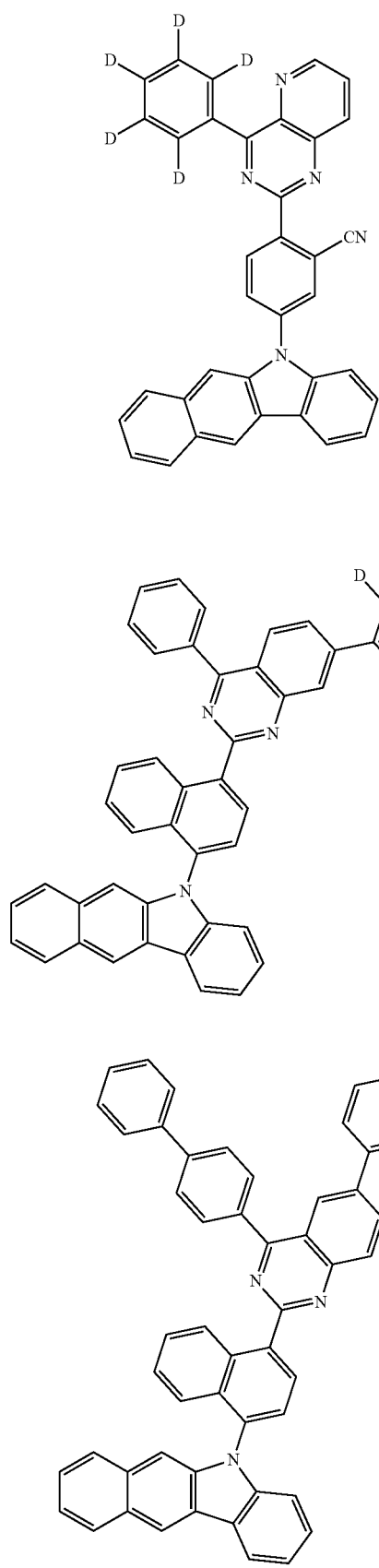
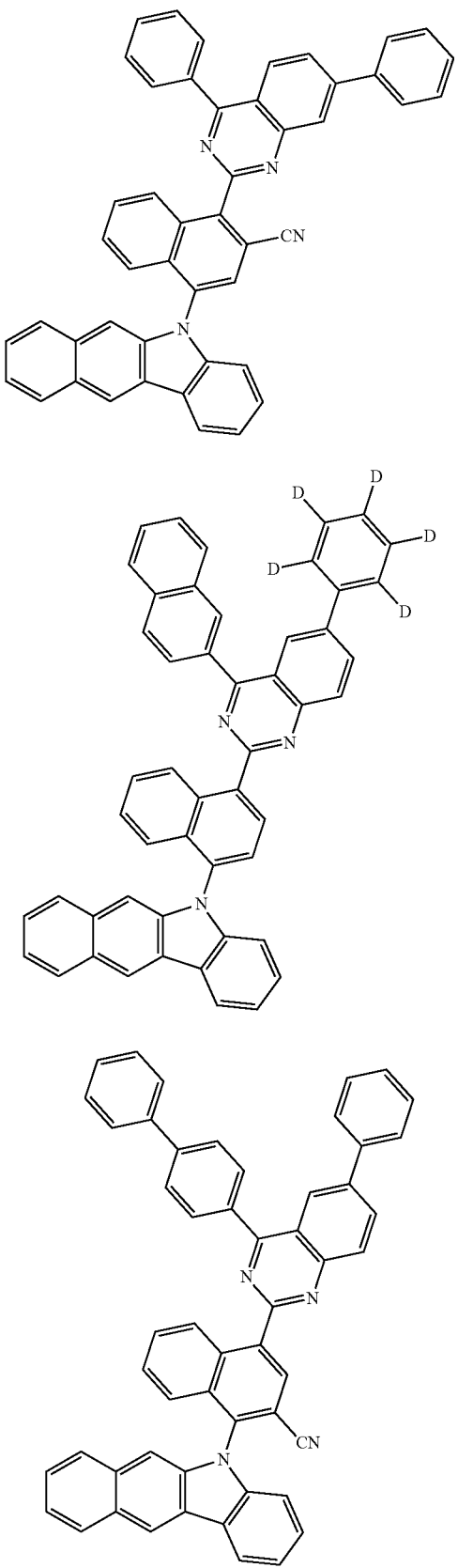

-continued
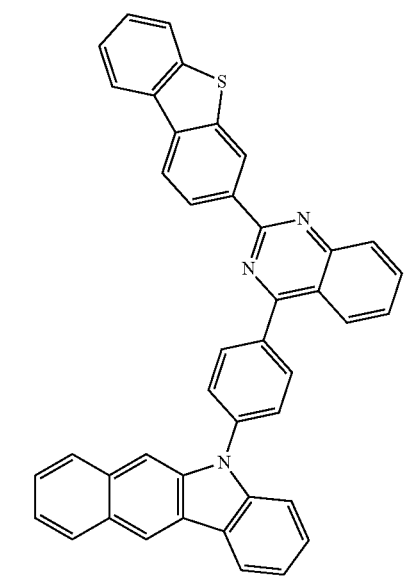
985
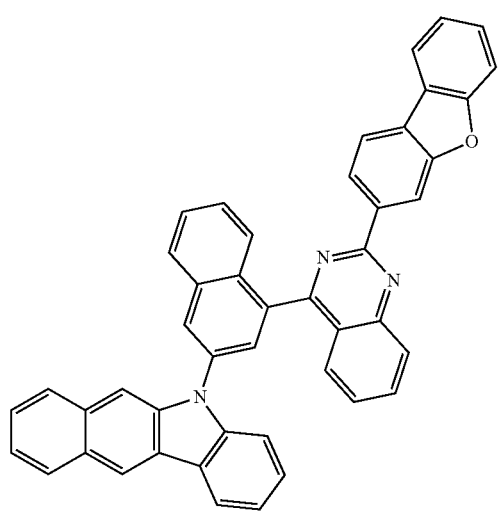
986
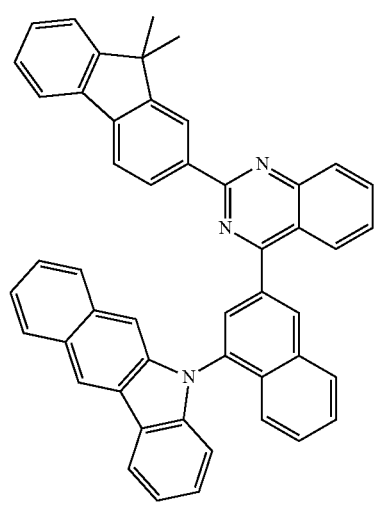
987
-continued
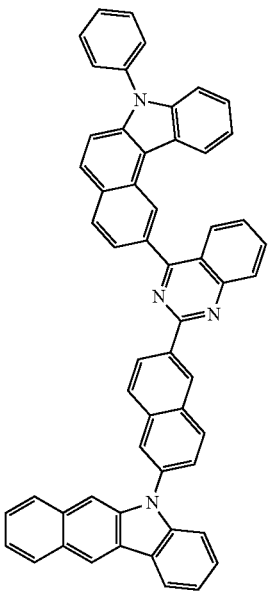
988
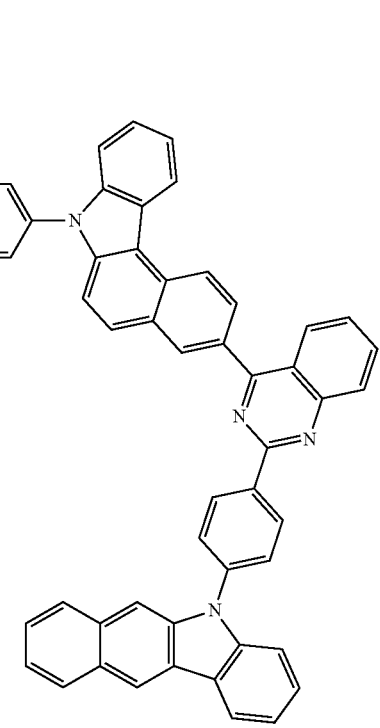
989

345
-continued
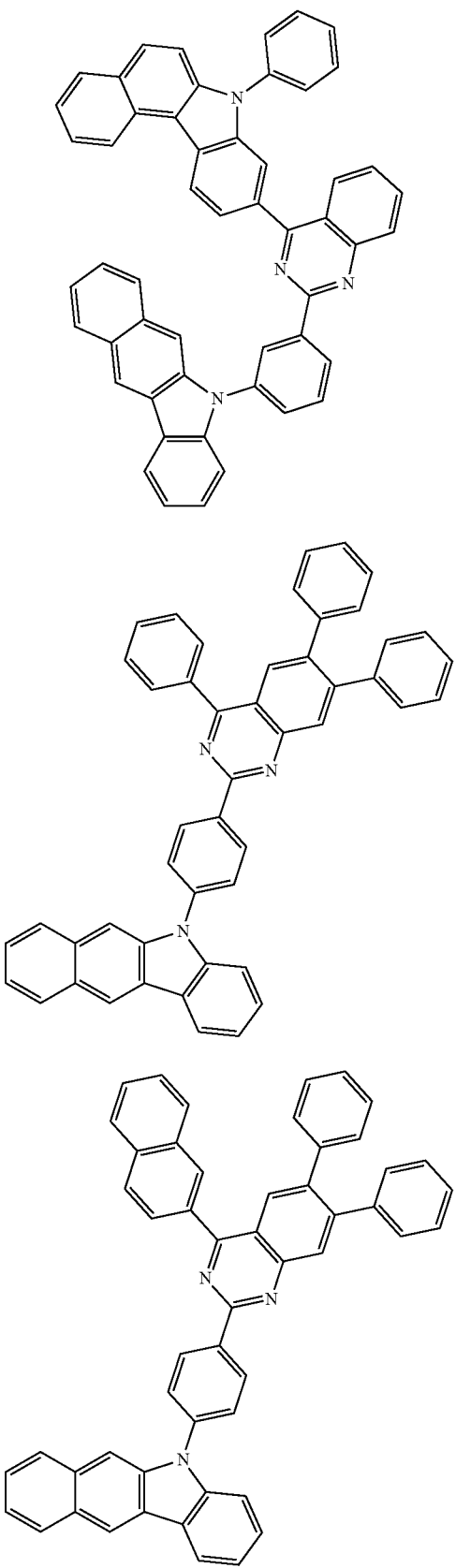
346
-continued
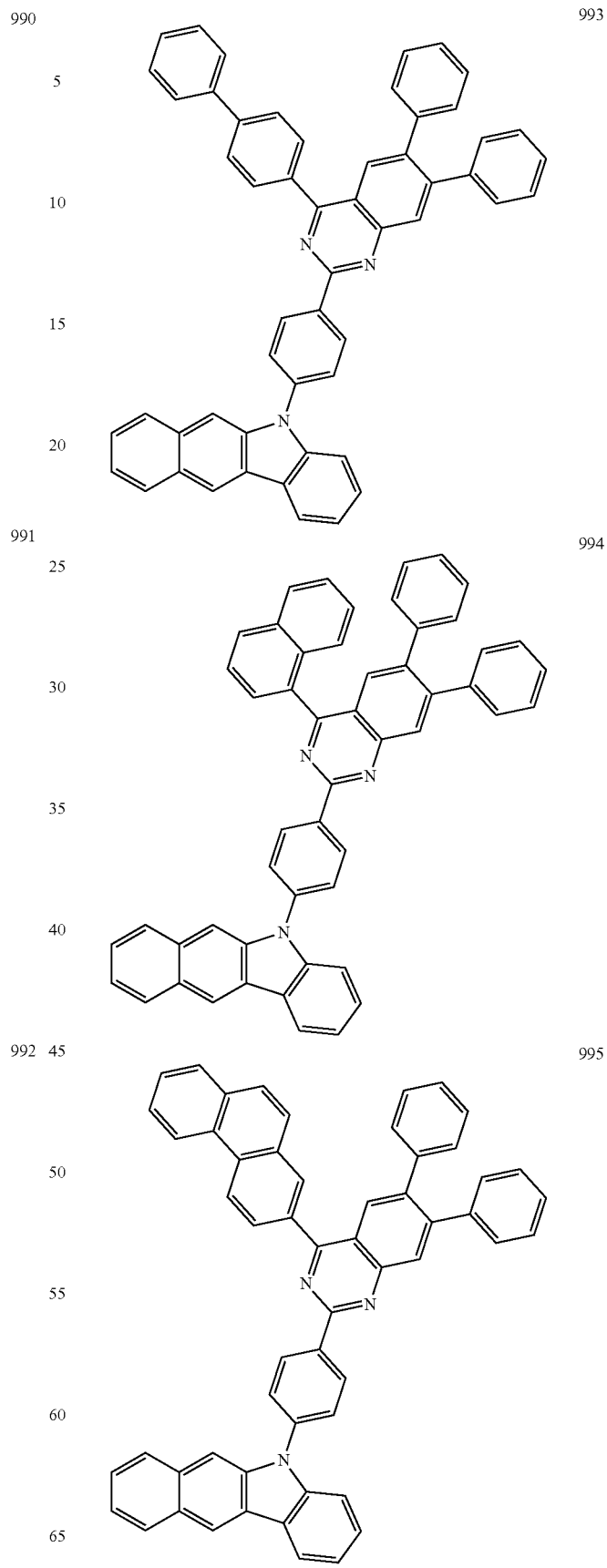

347
-continued
996
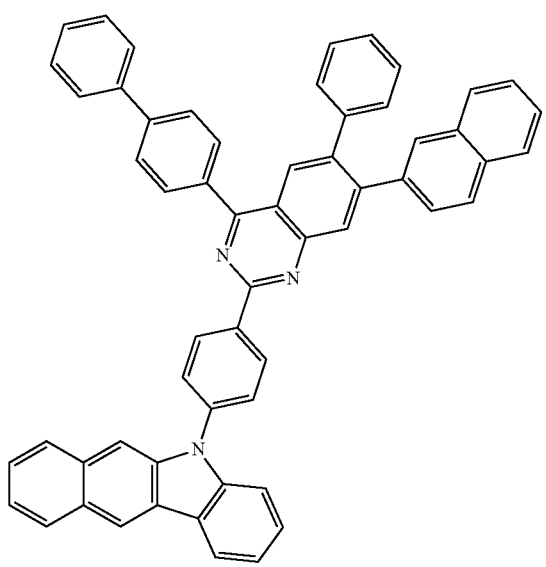
348
-continued
998
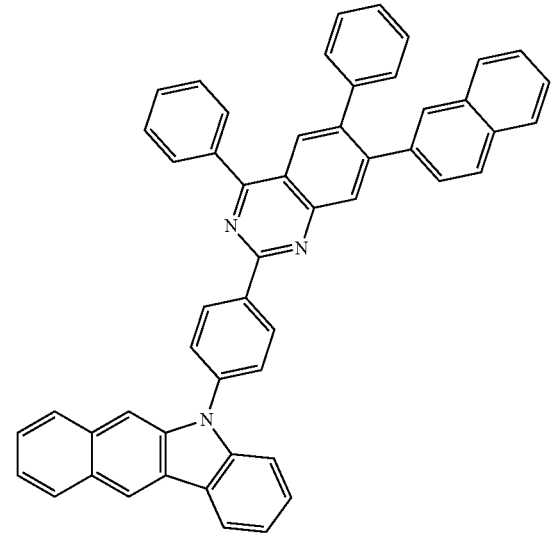
997
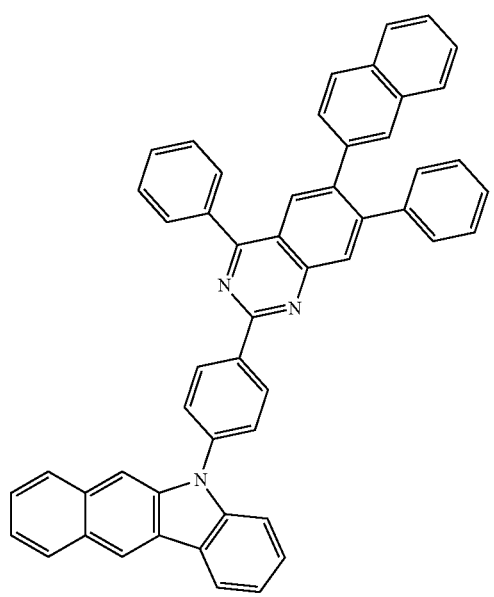
999
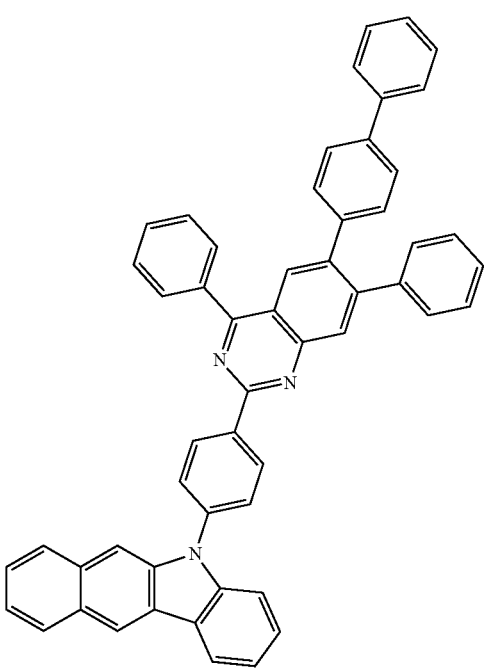

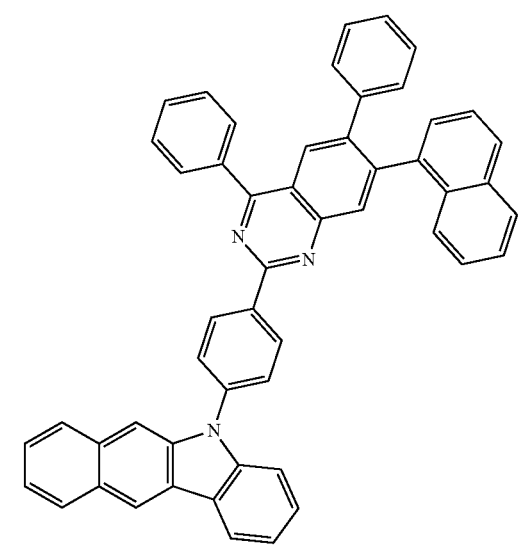
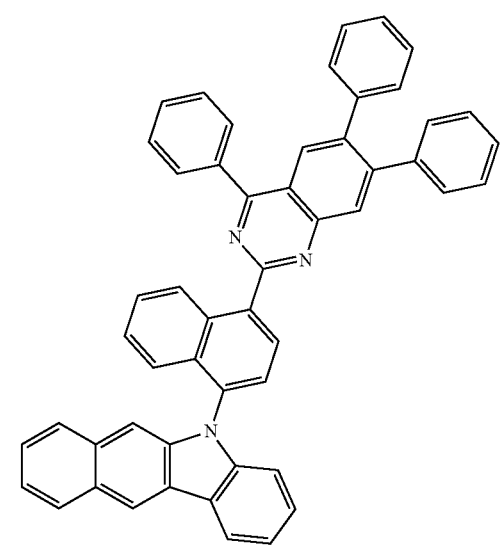

351
-continued
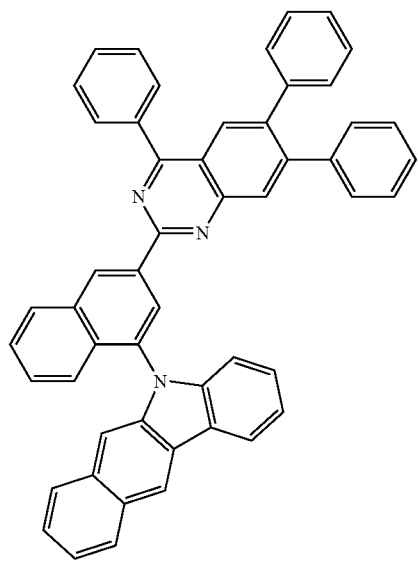
1006
352
-continued
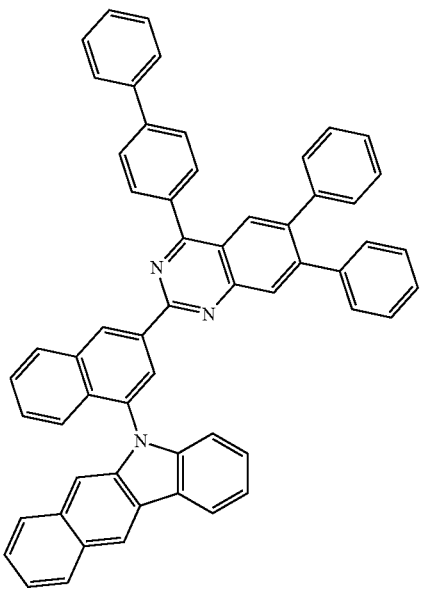
1008
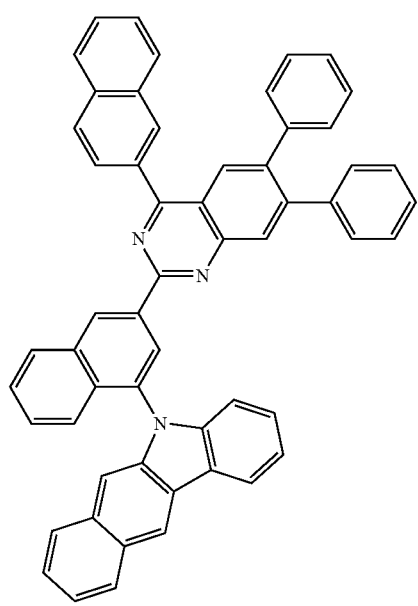
1007
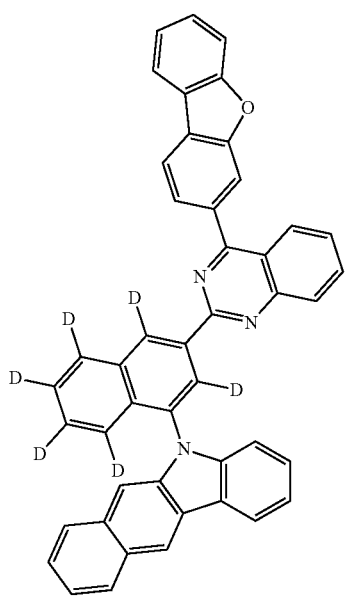
1009

1010
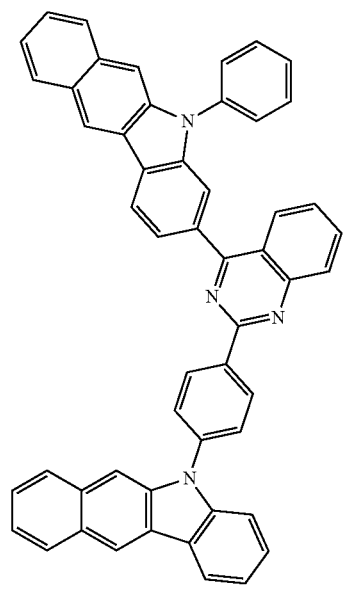
1011
1012
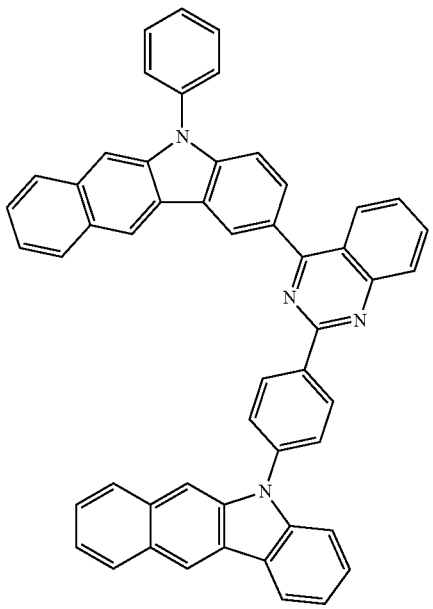
1013
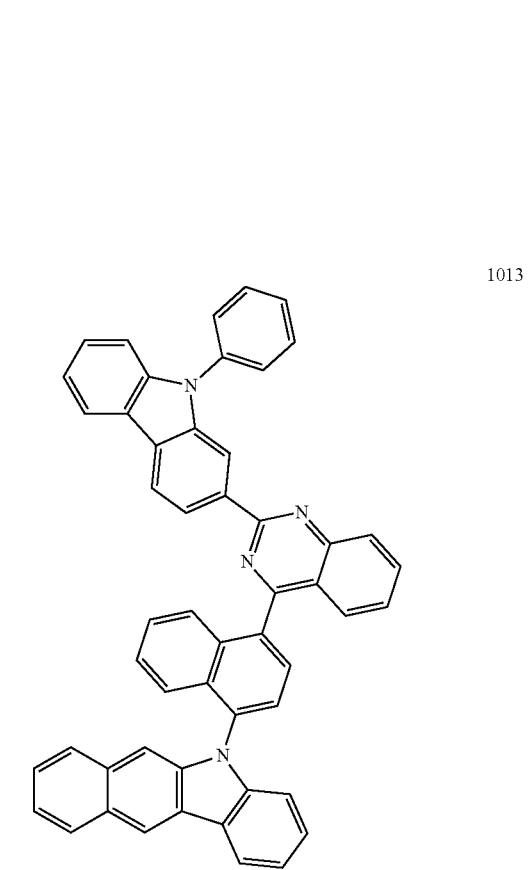

355
-continued
1014
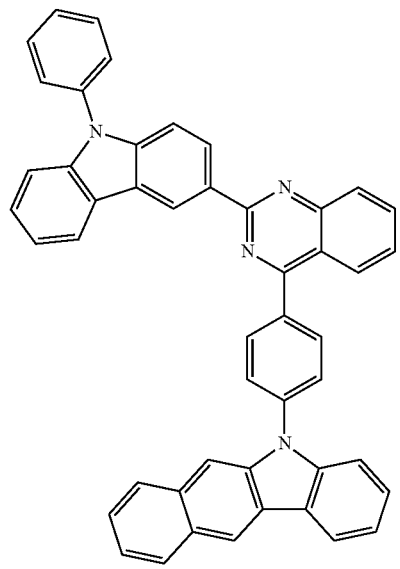
1015
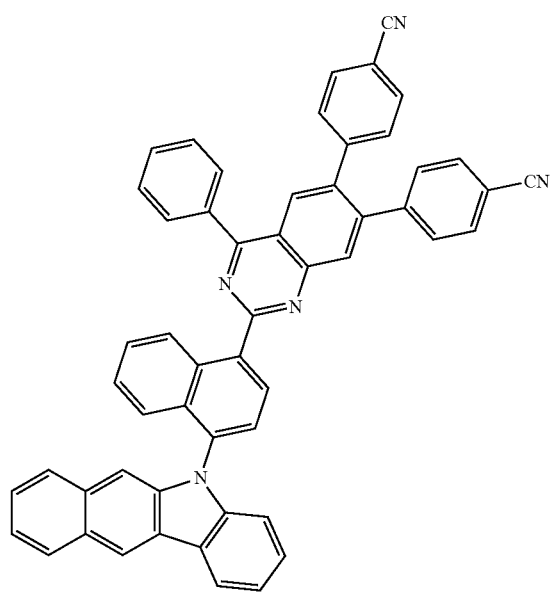
356
-continued
1016
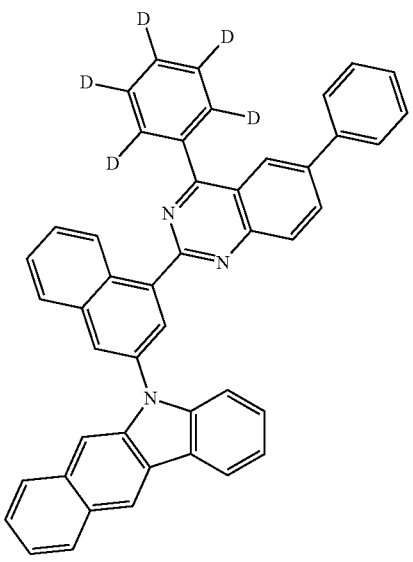
1017
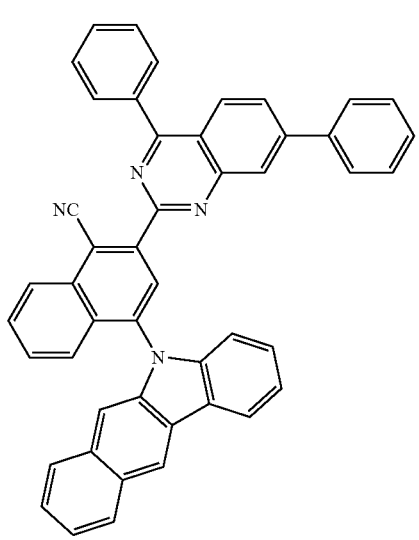
1018
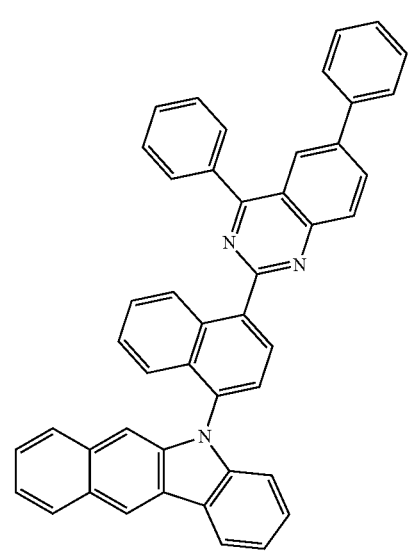

357 -continued
1019
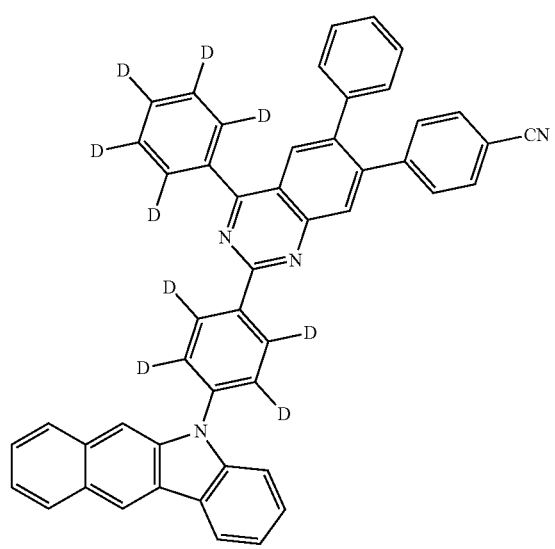
1020
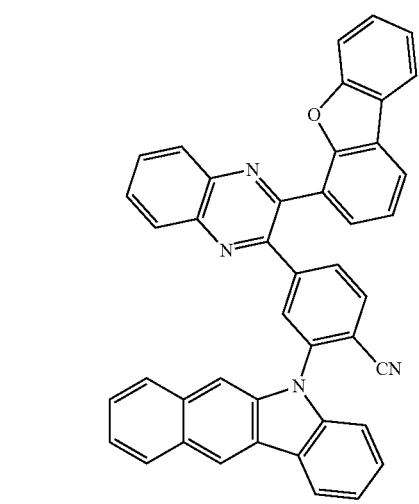
1021
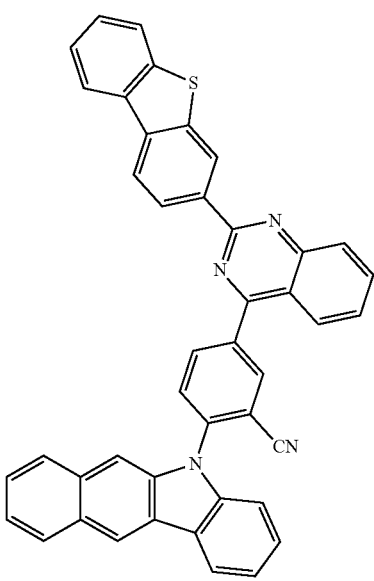
358 -continued
1022
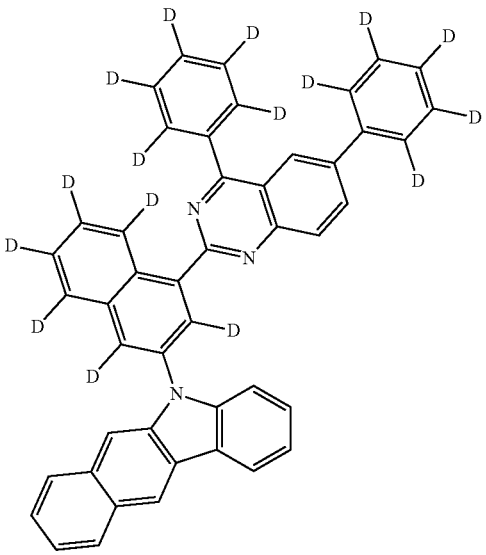
1023
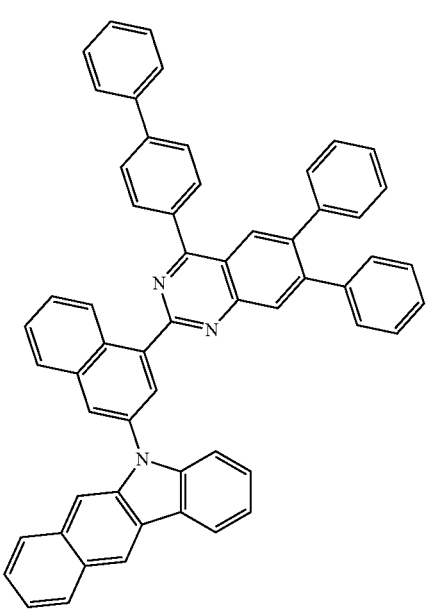
1024
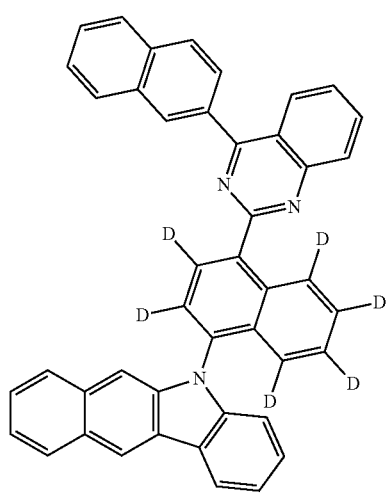

359
-continued
1025
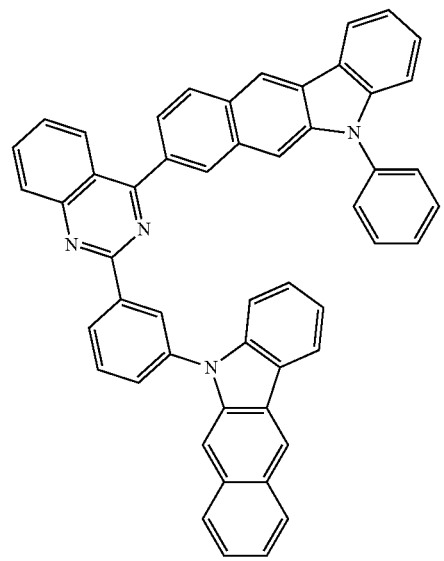
1026
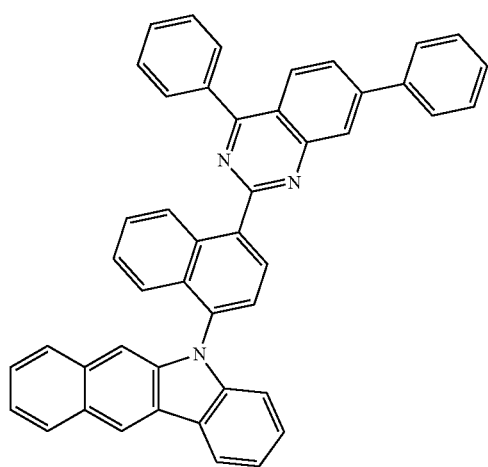
1027
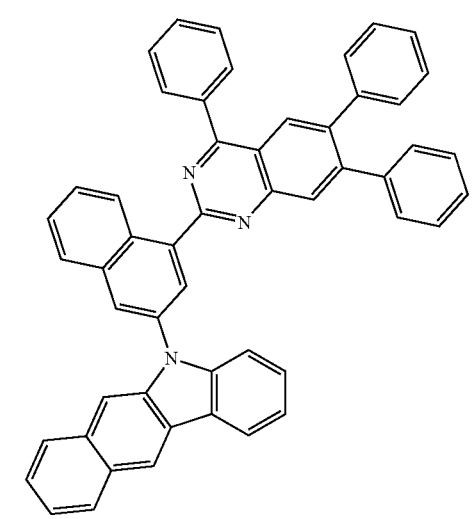
360
-continued
1028
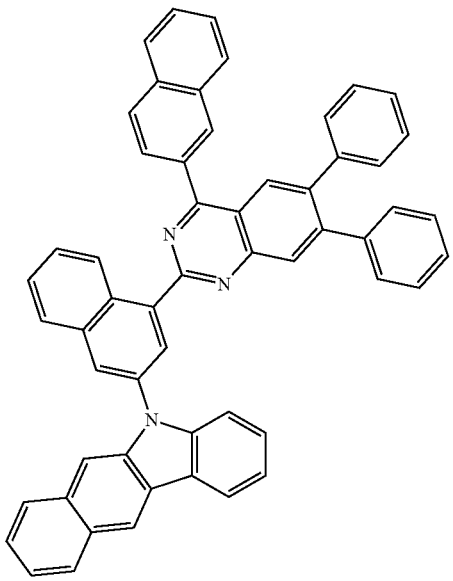
1029
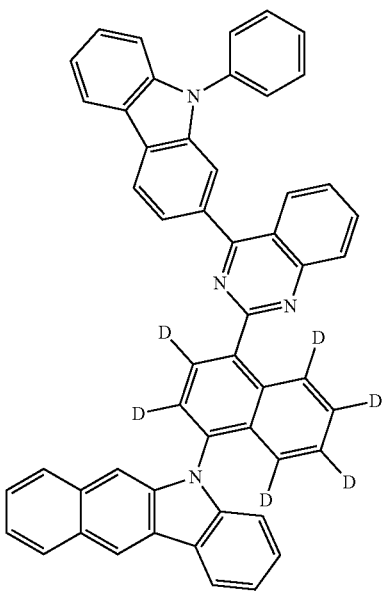

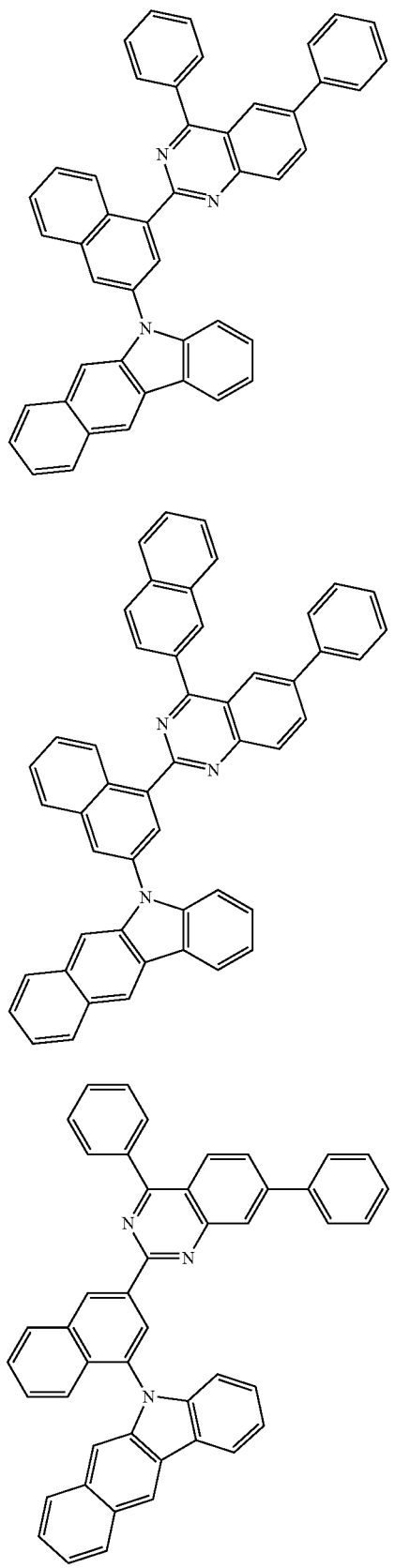
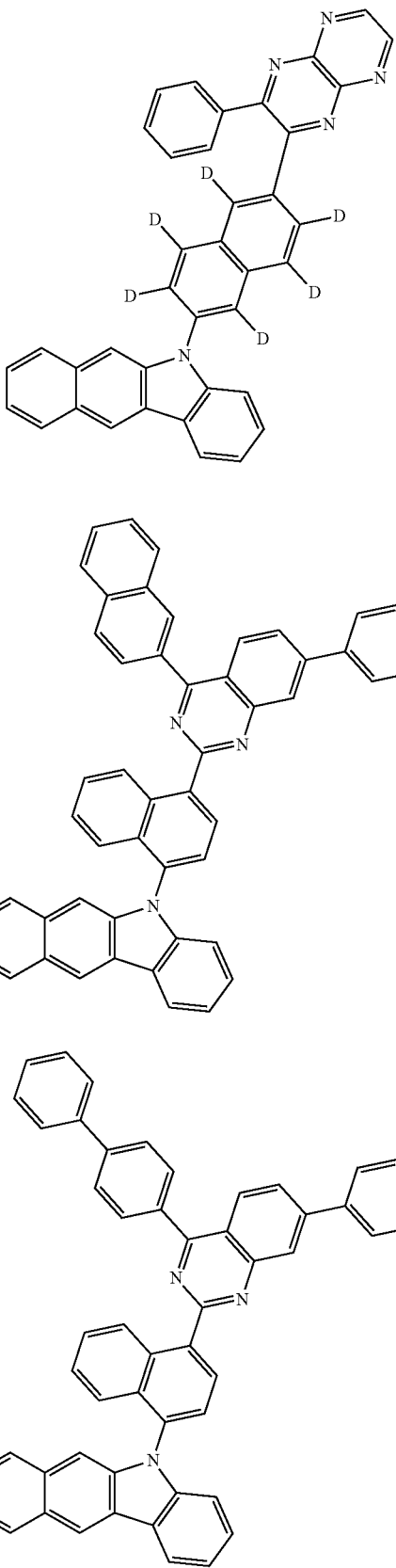

-continued
1036
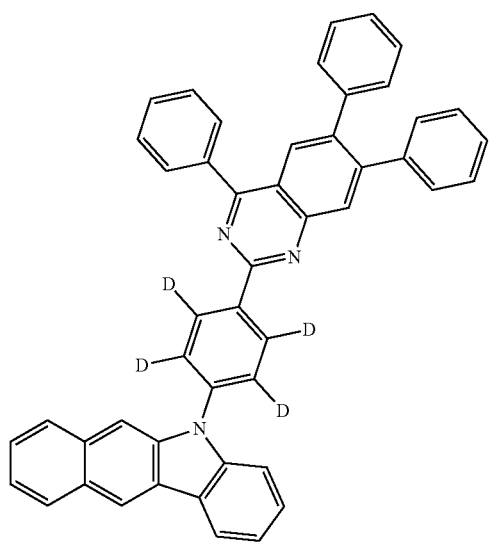
1038
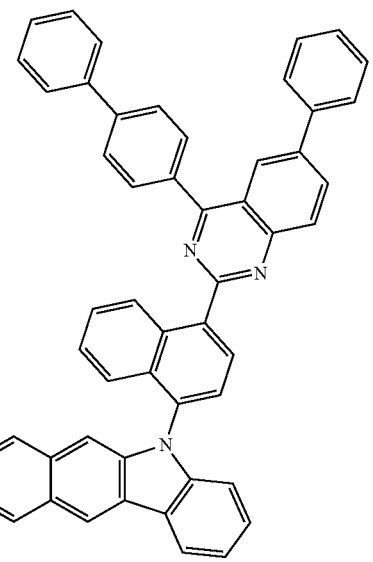
1039
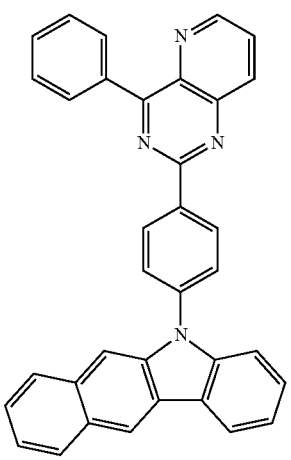
1037
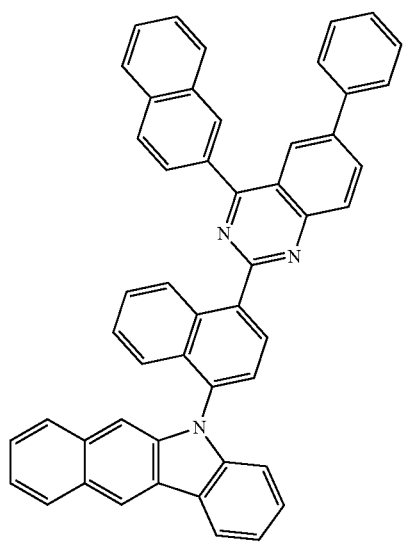
1040
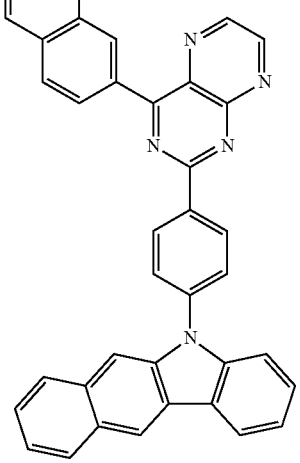

1041
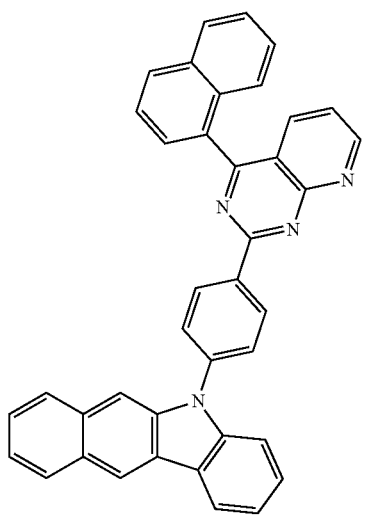
1042
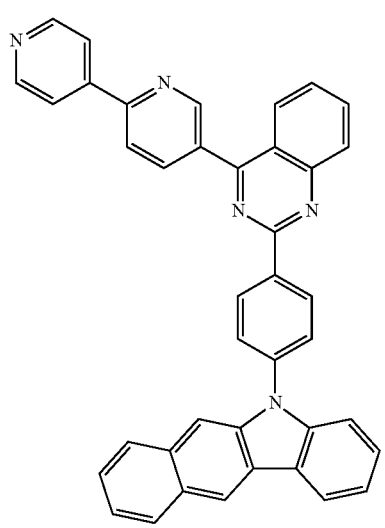
1043
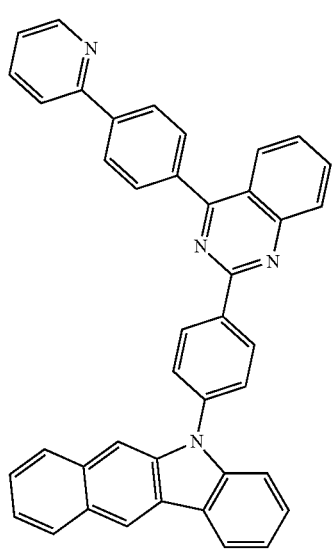
1044
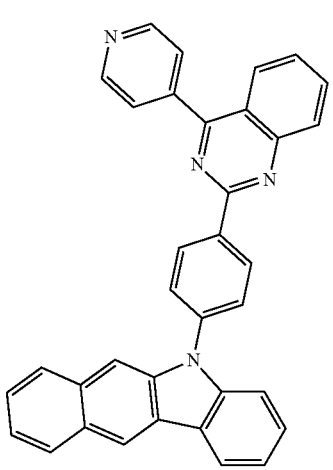
1045
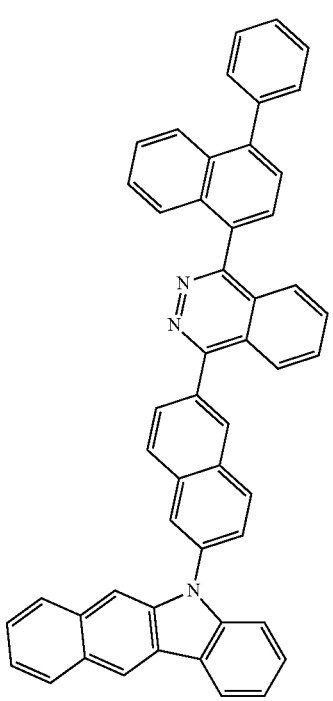

1046
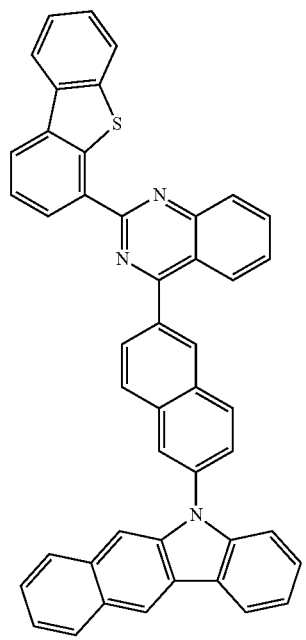
1048
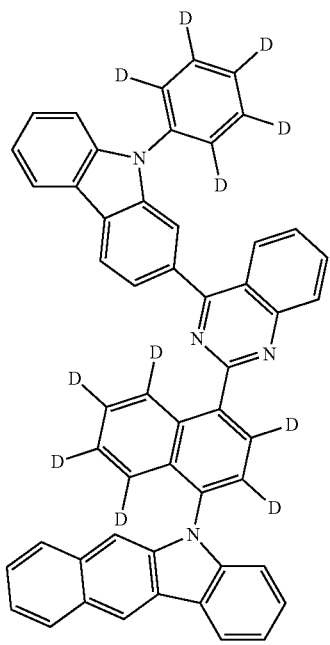
1047
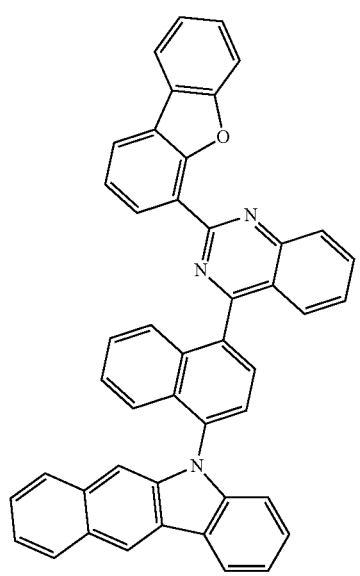
1049
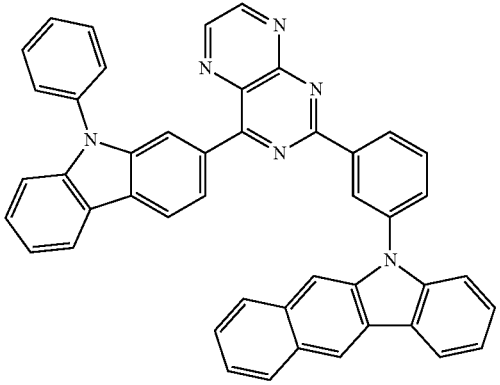

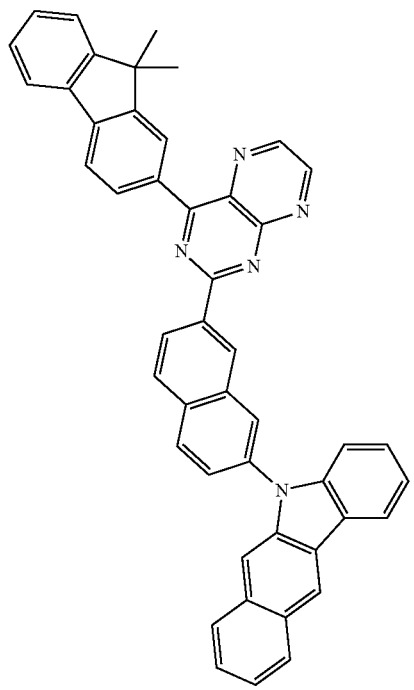
1050
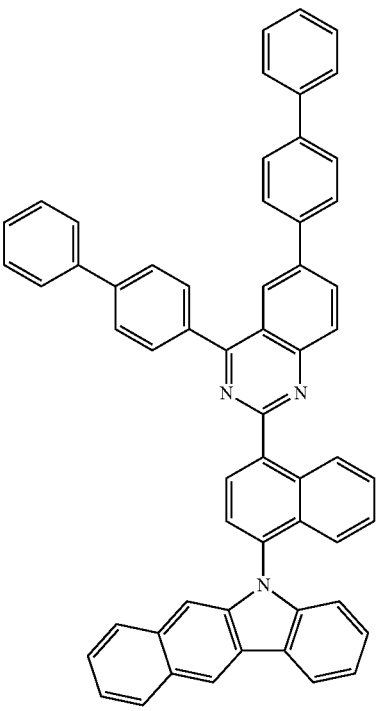
1052
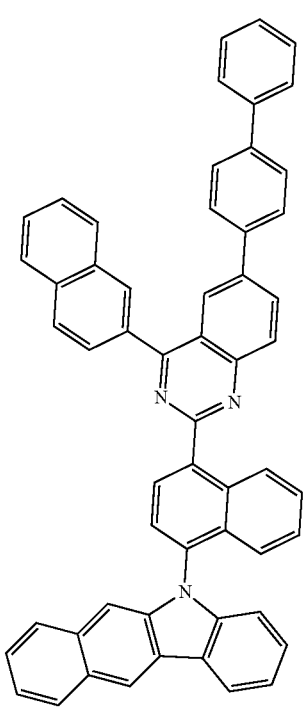
1051
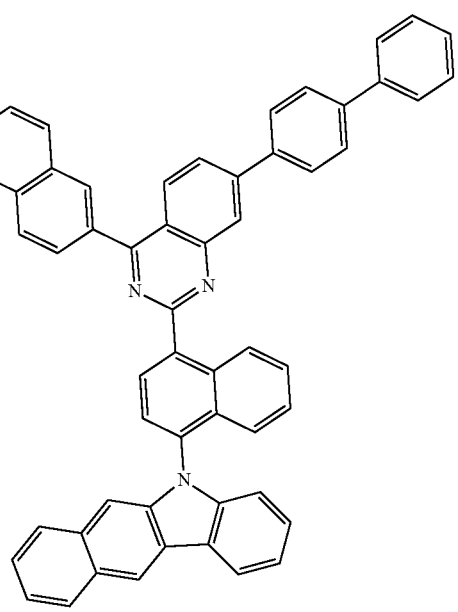
1053

371
-continued
1054
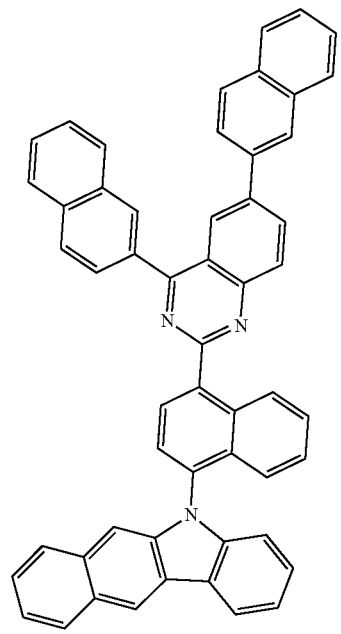
1055
372
-continued
1056
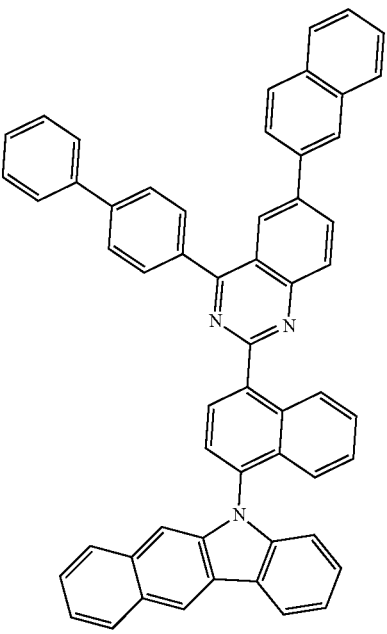
1057
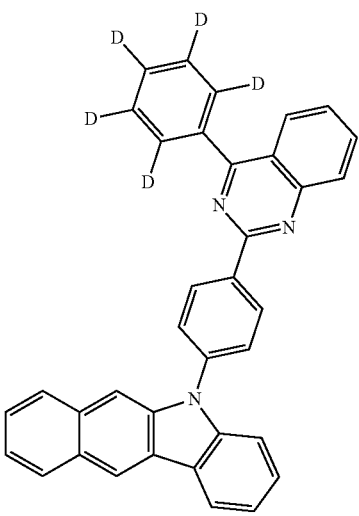

373
-continued
1058
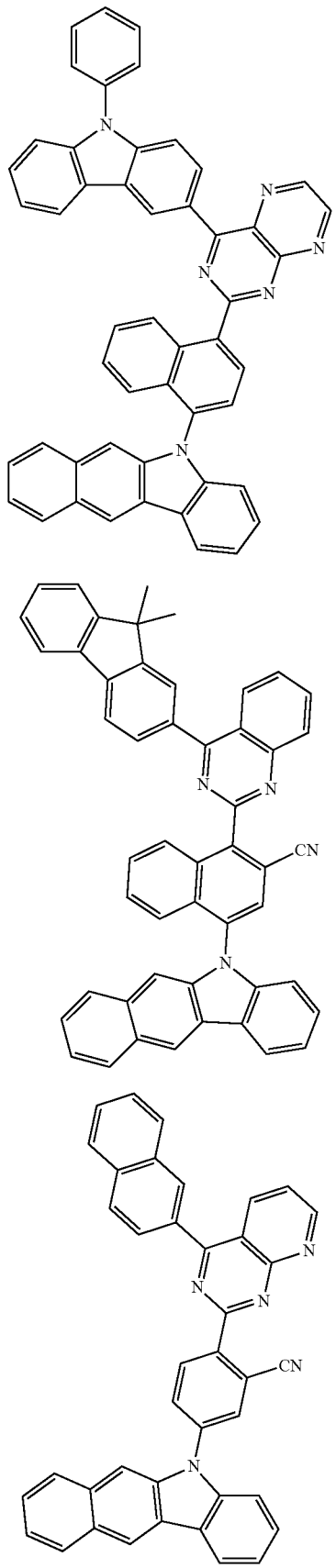
1059
1060
374
-continued
1061
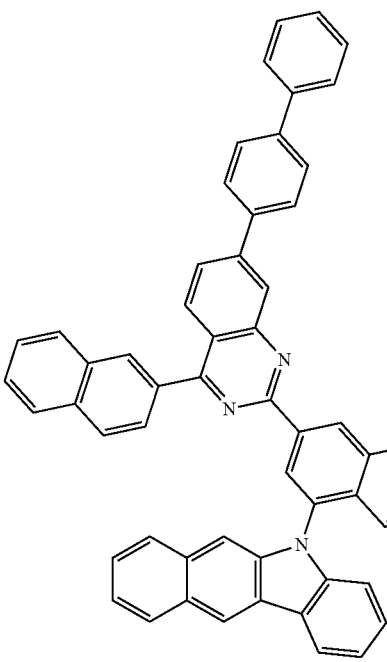
1062
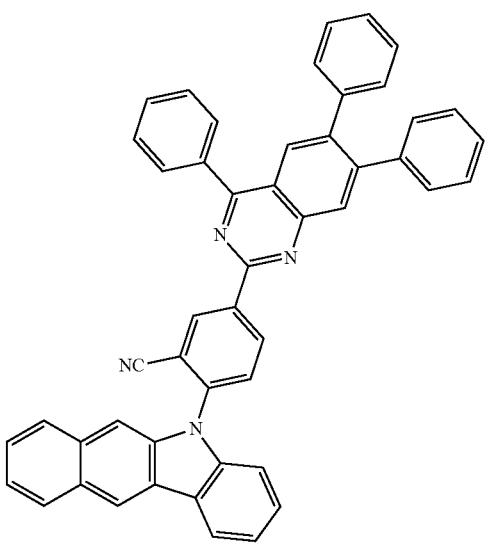

375
-continued
1063
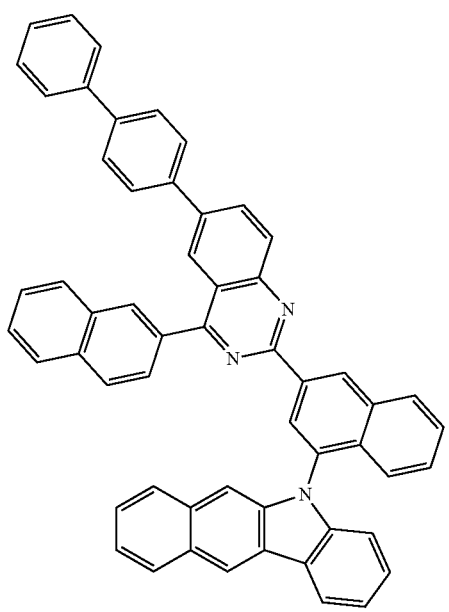
1064
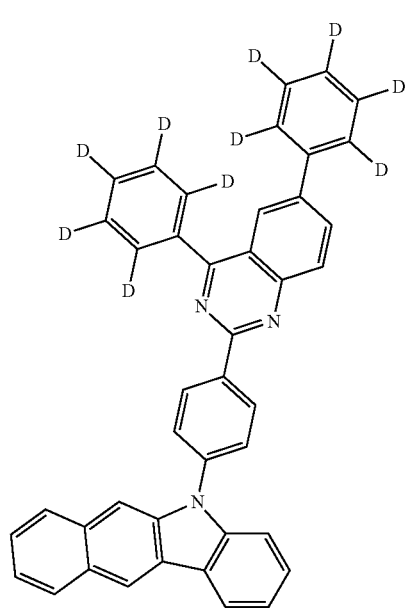
376
-continued
1065
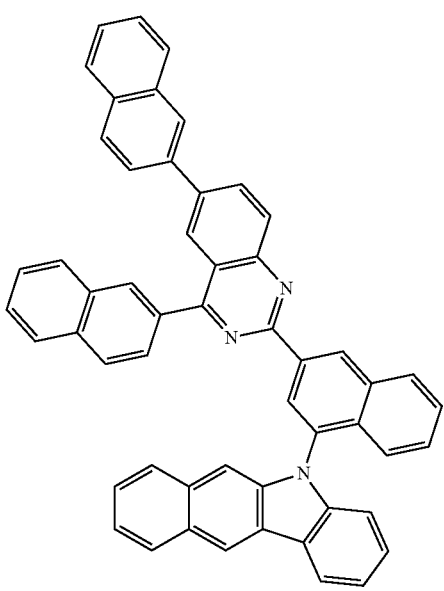
1066
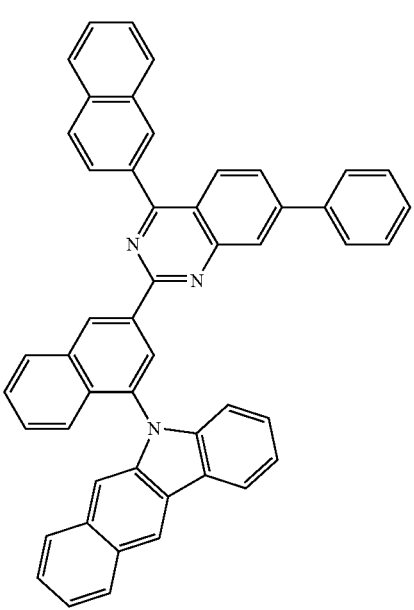

-continued

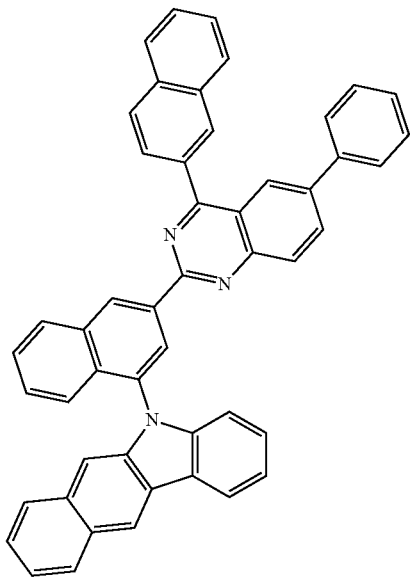

1067

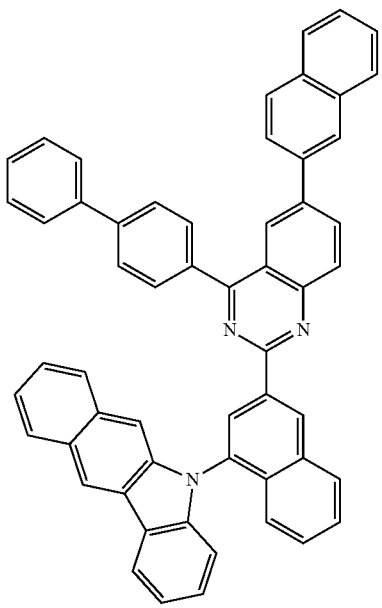

1068

The benzocarbazole-based compound of Chemical Formula 1 according to one embodiment of the present specification may be prepared using a preparation method to describe below.

For example, the benzocarbazole-based compound of Chemical Formula 1 may have its core structure prepared as in the following reaction formula. Substituents may bond using methods known in the art, and types, positions or the number of the substituents may vary depending on technologies known in the art.

The benzocarbazole-based compound of the present disclosure may be prepared using as typical reactions, a Buchwald-Hartwig coupling reaction, a Heck coupling reaction, a Suzuki coupling reaction and the like.

<Reaction Formula>

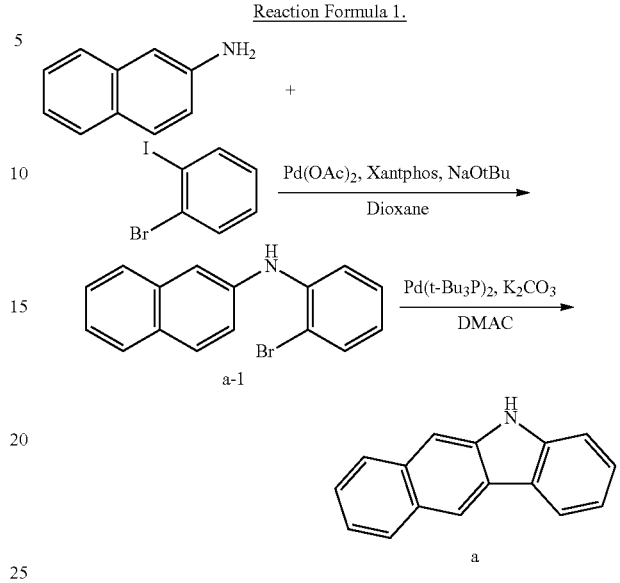

1) Preparation of Chemical Formula a-1

Naphthalen-2-amine (300.0 g, 1.0 eq.), 1-bromo-2-iodobenzene (592.7 g, 1.0 eq.), NaOtBu (302.0 g, 1.5 eq.), Pd(OAc)$_2$ (4.70 g, 0.01 eq.) and Xantphos (12.12 g, 0.01 eq.) are dissolved in 1,4-dioxane (5 L), and the result is stirred under reflux. When the reaction is terminated after 3 hours, the solvent is removed under vacuum. After that, the result is completely dissolved in ethyl acetate, washed with water, and approximately 70% of the solvent is removed under vacuum again. Under reflux again, crystals are dropped while adding hexane thereto, and the result is cooled and then filtered. This goes through column chromatography to obtain Compound a-1 (443.5 g, yield 71%). [M+H]=299

2) Preparation of Chemical Formula a (5H-benzo[b]carbazole)

Pd(t-Bu$_3$P)$_2$ (8.56 g, 0.01 eq.) and K$_2$CO$_3$ (463.2 g, 2.00 eq.) are added to Chemical Formula a-1 (443.5 g, 1.0 eq.) in dimethylacetamide (4 L), and the result is stirred under reflux. After 3 hours, the reaction material is poured into water to drop crystals, and the result is filtered. The filtered solids are completely dissolved in 1,2-dichlorobenzene, then washed with water, and the solution in which a product is dissolved is vacuum concentrated to drop crystals, and the result is cooled and filtered. This is purified using column chromatography to obtain Chemical Formula a (5H-benzo[b]carbazole) (174.8 g, yield 48%). [M+H]=218

A graph measuring 1H-NMR of Chemical Formula a is shown in FIG. 3, and a graph measuring LC/MS of Chemical Formula a is shown in FIG. 4.

Reaction Formula 2. Preparation of Chemical Formula b (7H-dibenzo[b,g]carbazole)

7H-Dibenzo[b,g]carbazole is synthesized in the same manner as in the method preparing Chemical Formula a using 1-bromo-2-iodonaphthalene instead of 1-bromo-2-iodobenzene.

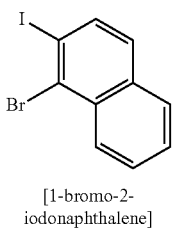

[1-bromo-2-iodonaphthalene]

[Chemical Formula b]

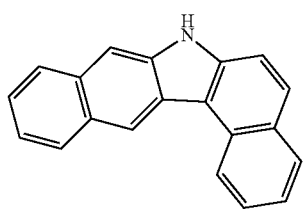

Reaction Formula 3. Preparation of Chemical Formula c (6H-dibenzo[b,h]carbazole)

6H-Dibenzo[b,h]carbazole is synthesized in the same manner as in the method preparing Chemical Formula a using 2,3-dibromonaphthalene instead of 1-bromo-2-iodobenzene.

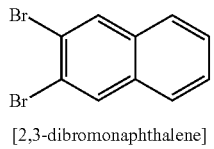

[2,3-dibromonaphthalene]

[Chemical Formula c]

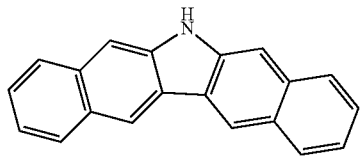

Reaction Formula 4. Preparation of Chemical Formula d (13H-dibenzo[a,h]carbazole)

13H-Dibenzo[a,h]carbazole is synthesized in the same manner as in the method preparing Chemical Formula a using 2-bromo-1-iodonaphthalene instead of 1-bromo-2-iodobenzene.

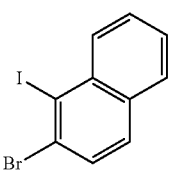

[2-bromo1-iodonaphthalene

[Chemical Formula d]

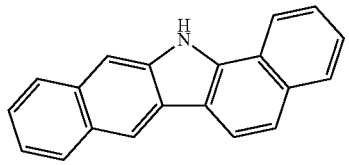

A conjugation length of a compound and an energy band gap thereof are closely related. Specifically, as a conjugation length of a compound increases, an energy band gap thereof decreases.

By introducing various substituents to the core structure as above, compounds having various energy band gaps may be synthesized in the present disclosure. In addition, by introducing various substituents to the core structure having structures as above, HOMO and LUMO energy levels of the compound may also be controlled in the present disclosure.

In addition, by introducing various substituents to the core structure having structures as above, compounds having unique properties of the introduced substituents may be synthesized. For example, by introducing substituents normally used as a hole injection layer material, a material for hole transfer, a light emitting layer material and an electron transfer layer material used for manufacturing an organic light emitting device to the core structure, materials satisfying needs required from each organic material layer may be synthesized.

In addition, an organic light emitting device according to the present disclosure comprises a first electrode; a second electrode provided opposite to the first electrode; and one or more organic material layers provided between the first electrode and the second electrode, wherein one or more layers of the organic material layers include the benzocarbazole-based compound of Chemical Formula 1.

The organic light emitting device of the present disclosure may be prepared using common methods and materials for preparing an organic light emitting device except that one or more organic material layers are formed using the benzocarbazole-based compound described above.

The benzocarbazole-based compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising a hole injection layer, a hole transfer layer, a hole injection and transfer layer, an electron blocking layer, a light emitting layer, an electron transfer layer, an electron injection layer, a hole blocking layer, an electron injection and transfer layer and the like as the organic material layer. However, the structure of the organic light emitting device is not limited thereto, and may include less numbers of organic material layers or more numbers of organic material layers.

In the organic light emitting device of the present disclosure, the organic material layer may comprise an electron transfer layer or an electron injection layer, and the electron transfer layer or the electron injection layer may comprise the benzocarbazole-based compound represented by Chemical Formula 1.

In the organic light emitting device of the present disclosure, the organic material layer may comprise a hole injection layer or a hole transfer layer, and the hole injection layer or the hole transfer layer may comprise the benzocarbazole-based compound represented by Chemical Formula 1.

In another embodiment, the organic material layer comprises a light emitting layer, and the light emitting layer comprises the benzocarbazole-based compound represented by Chemical Formula 1. As one example, the compound represented by Chemical Formula 1 may be included as a dopant of the light emitting layer.

In one embodiment of the present specification, the organic light emitting device is a green organic light emitting device in which the light emitting layer comprises the benzocarbazole-based compound represented by Chemical Formula 1.

According to one embodiment of the present specification, the organic light emitting device is a red organic light emitting device in which the light emitting layer comprises the benzocarbazole-based compound represented by Chemical Formula 1.

In another embodiment, the organic light emitting device is a blue organic light emitting device in which the light emitting layer comprises the benzocarbazole-based compound represented by Chemical Formula 1.

As another example, the organic material layer comprising the benzocarbazole-based compound represented by Chemical Formula 1 comprises the benzocarbazole-based compound represented by Chemical Formula 1 as a dopant, and may comprise a fluorescent host or a phosphorescent host.

In another embodiment, the organic material layer comprising the benzocarbazole-based compound represented by Chemical Formula 1 comprises the benzocarbazole-based compound represented by Chemical Formula 1 as a dopant, includes a fluorescent host or a phosphorescent host, and may comprise other organic compounds, metals or metal compounds as a dopant.

As another example, the organic material layer comprising the benzocarbazole-based compound represented by Chemical Formula 1 comprises the benzocarbazole-based compound represented by Chemical Formula 1 as a dopant, comprises a fluorescent host or a phosphorescent host, and may be used together with an iridium (Ir)-based dopant.

According to one embodiment of the present disclosure, the organic light emitting device comprises a light emitting layer, and the light emitting layer may comprise the benzocarbazole-based compound represented by Chemical Formula 1 as a host of the light emitting layer.

According to another embodiment, the organic light emitting device comprises the benzocarbazole-based compound represented by Chemical Formula 1 as a host of the light emitting layer, and may further comprise a dopant.

In another embodiment, the organic light emitting device includes the benzocarbazole-based compound represented by Chemical Formula 1 as a host of the light emitting layer, and may further include an iridium (Ir)-based dopant. Herein, a weight ratio of the host and the dopant (host: dopant) may be from 90:10 to 99:1, but is not limited thereto.

The structure of the organic light emitting device of the present disclosure may be as illustrated in FIG. 1 and FIG. 2, but is not limited thereto.

FIG. 1 illustrates a structure of the organic light emitting device in which an anode (2), a light emitting layer (3) and a cathode (4) are consecutively laminated on a substrate (1). In such a structure, the compound may be included in the light emitting layer (3).

The organic light emitting device may have, for example, a laminated structure as below, however, the structure is not limited thereto.

(1) Anode/hole transfer layer/light emitting layer/cathode (2) Anode/hole injection layer/hole transfer layer/light emitting layer/cathode (3) Anode/hole injection layer/hole buffer layer/hole transfer layer/light emitting layer/cathode (4) Anode/hole transfer layer/light emitting layer/electron transfer layer/cathode (5) Anode/hole transfer layer/light emitting layer/electron transfer layer/electron injection layer/cathode (6) Anode/hole injection layer/hole transfer layer/light emitting layer/electron transfer layer/cathode (7) Anode/hole injection layer/hole transfer layer/light emitting layer/electron transfer layer/electron injection layer/cathode (8) Anode/hole injection layer/hole buffer layer/hole transfer layer/light emitting layer/electron transfer layer/cathode (9) Anode/hole injection layer/hole buffer layer/hole transfer layer/light emitting layer/electron transfer layer/electron injection layer/cathode

(10) Anode/hole transfer layer/electron blocking layer/light emitting layer/electron transfer layer/cathode

(11) Anode/hole transfer layer/electron blocking layer/light emitting layer/electron transfer layer/electron injection layer/cathode

(12) Anode/hole injection layer/hole transfer layer/electron blocking layer/light emitting layer/electron transfer layer/cathode

(13) Anode/hole injection layer/hole transfer layer/electron blocking layer/light emitting layer/electron transfer layer/electron injection layer/cathode

(14) Anode/hole transfer layer/light emitting layer/hole blocking layer/electron transfer layer/cathode

(15) Anode/hole transfer layer/light emitting layer/hole blocking layer/electron transfer layer/electron injection layer/cathode

(16) Anode/hole injection layer/hole transfer layer/light emitting layer/hole blocking layer/electron transfer layer/cathode

(17) Anode/hole injection layer/hole transfer layer/light emitting layer/hole blocking layer/electron transfer layer/electron injection layer/cathode

(18) Anode/hole injection layer/hole transfer layer/electron blocking layer/light emitting layer/hole blocking layer/electron injection and transfer layer/cathode FIG. 2 illustrates a structure of the organic light emitting device in which an anode (2), a hole injection layer (5), a hole transfer layer (6), an electron blocking layer (7), a light emitting layer (8), a hole blocking layer (9), an electron injection and transfer layer (10) and a cathode (4) are consecutively laminated on a substrate (1). In such a structure, the compound may be included in the hole injection layer (5), the hole transfer layer (6) or the light emitting layer (8).

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer comprising a hole injection layer, a hole transfer layer, an electron blocking layer, a light emitting layer, a hole blocking layer, and an electron injection and transfer layer thereon, and then depositing a material capable of being used as a cathode thereon. In addition to such a method, the organic light emitting device may also be manufactured by consecutively depositing a cathode material, an organic material layer and an anode material on a substrate.

The organic material layer may have a multilayer structure comprising a hole injection layer, a hole transfer layer, a light emitting layer, an electron transfer layer and the like, however, the structure is not limited thereto, and the organic material layer may have a single layer structure. In addition, the organic material layer may be prepared to have less numbers of layers through a solvent process such as spin coating, dip coating, doctor blading, screen printing, inkjet printing or a thermal transfer method instead of a deposition method using various polymer materials.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material favorably receiving holes from an anode at a low voltage, and the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto, and additional compounds capable of p-doping may be further included.

The hole transfer material is a material capable of receiving holes from an anode or a hole injection layer and transferring the holes to a light emitting layer, and materials having high mobility for the holes are suited. Specific examples thereof include arylamine-based organic materials, conductive polymers, block copolymers having conjugated parts and non-conjugated parts together, and the like, but are not limited thereto.

An electron blocking layer may be provided between the hole transfer layer and the light emitting layer. As the electron blocking layer, materials known in the art such as arylamine-based organic materials may be used.

The light emitting layer may emit light of red, green or blue, and may be formed with phosphorescent materials or fluorescent materials. The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The host material of the light emitting layer includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The iridium-based complex used as a dopant of the light emitting layer is as follows, but is not limited thereto.

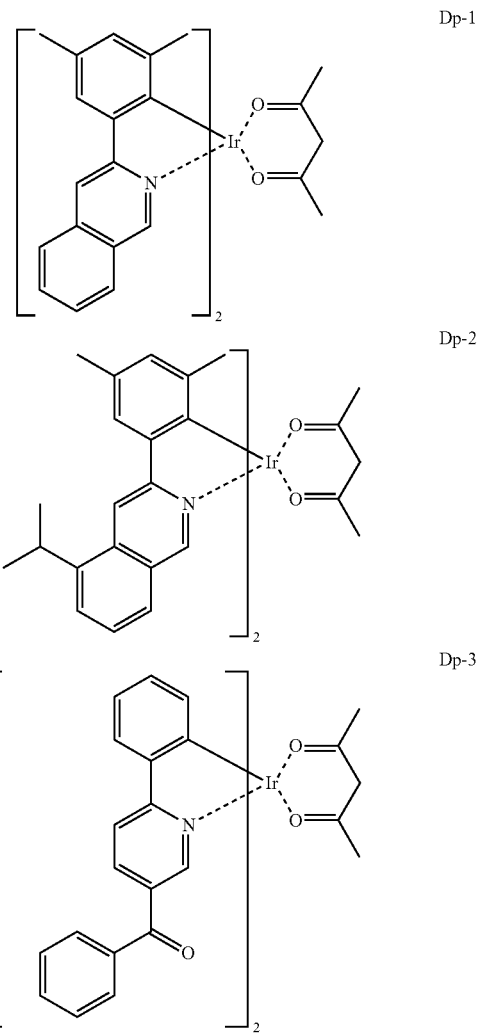

-continued
Dp-4
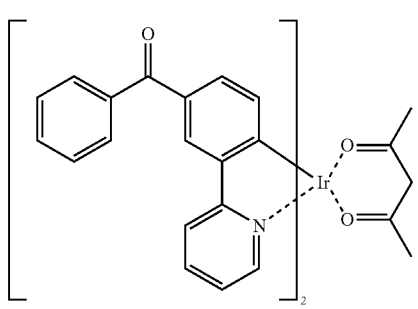
Dp-5
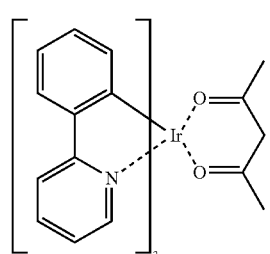
Dp-6
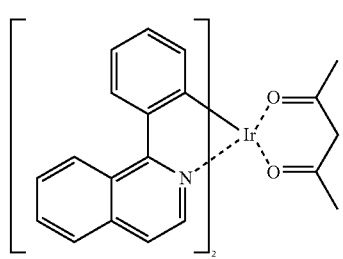
Dp-7
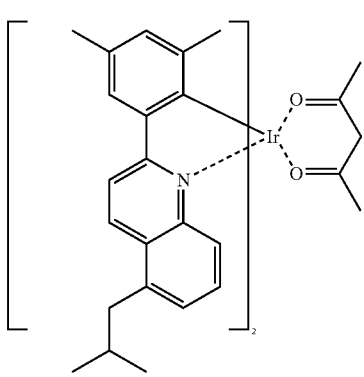
Dp-8
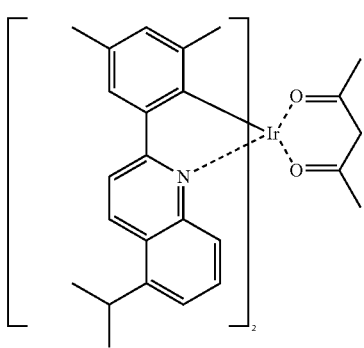
-continued
Dp-9
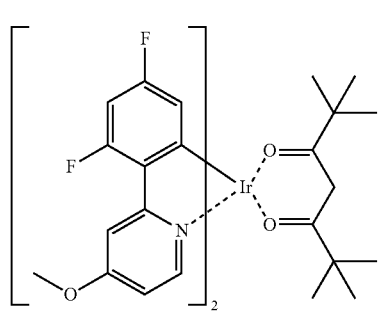
Dp-10
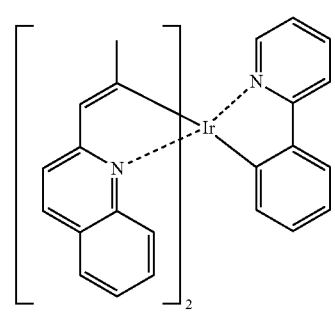
Dp-11
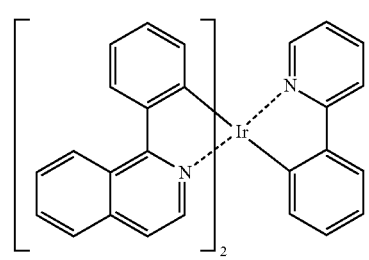
Dp-12
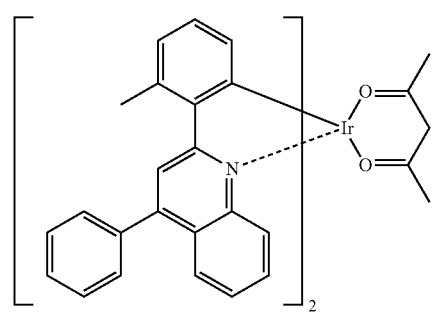
Dp-13
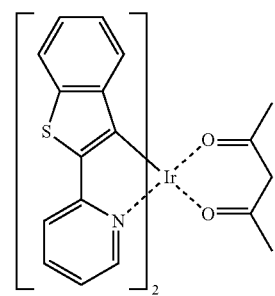

Dp-14
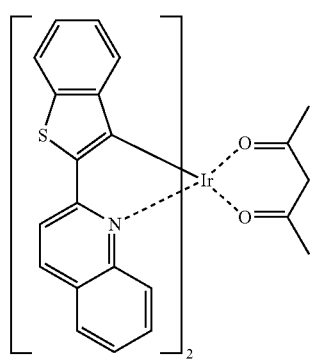
Dp-15
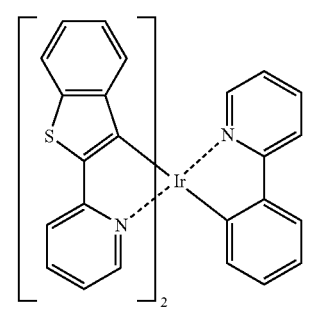
Dp-16
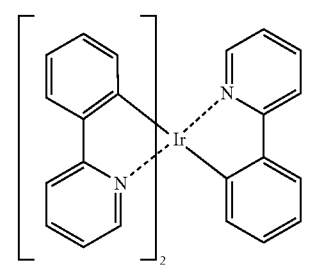
Dp-17
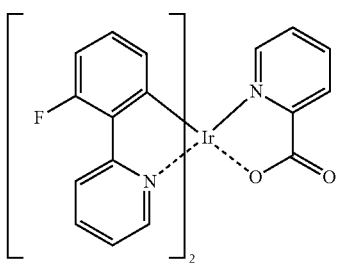
Dp-18
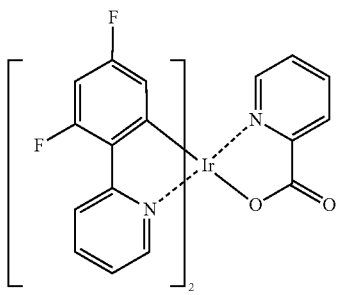
Dp-19
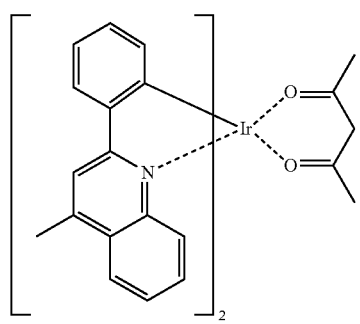
Dp-20
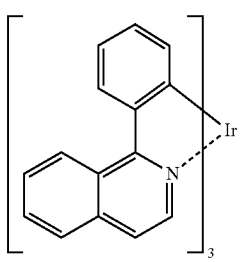
Dp-21
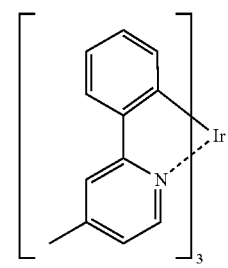
Dp-22
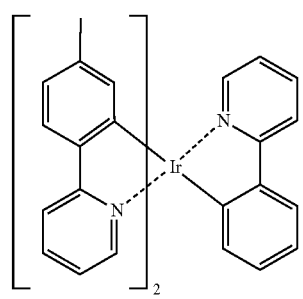
Dp-23
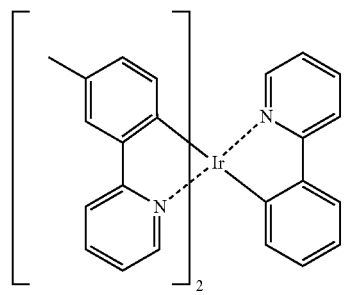

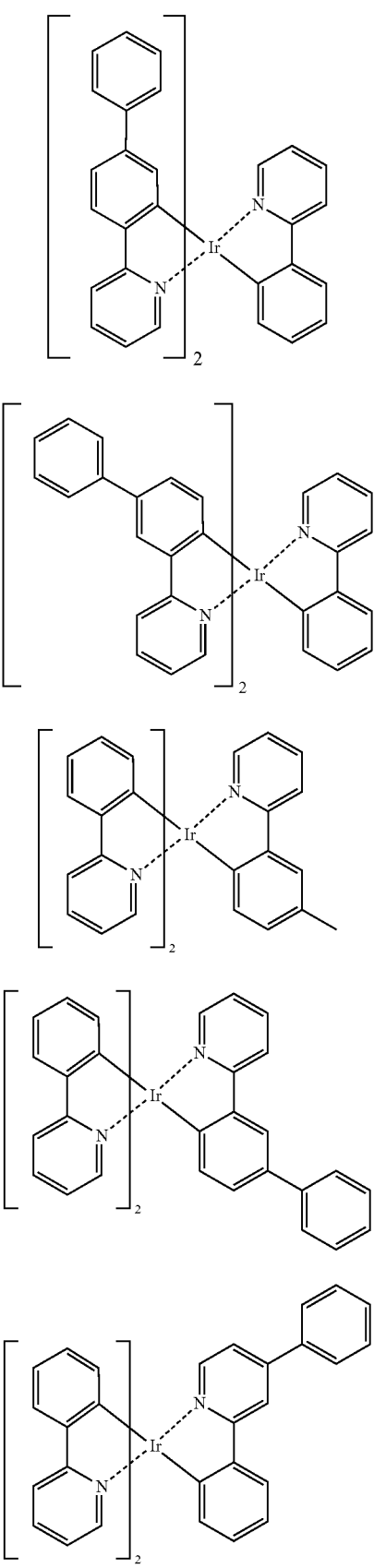
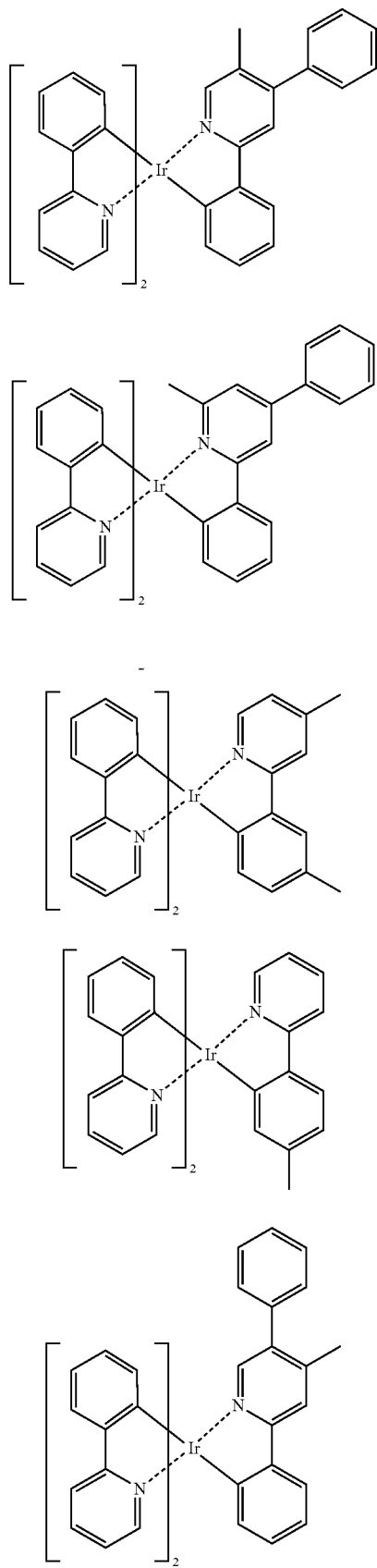

Dp-34 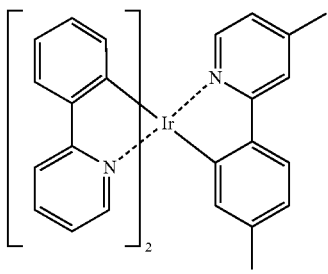

Dp-35 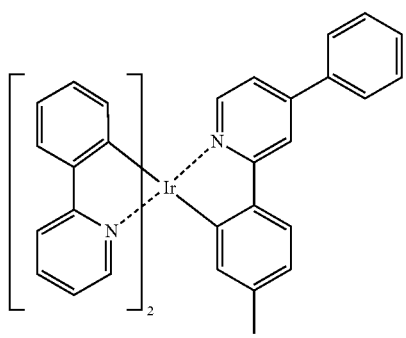

Dp-36 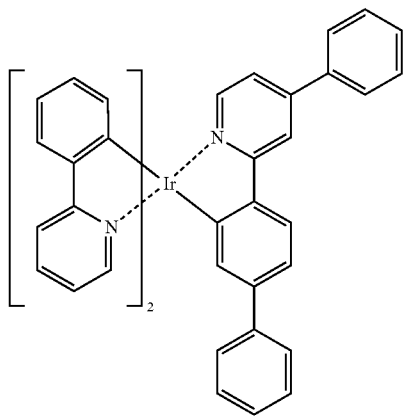

Dp-37 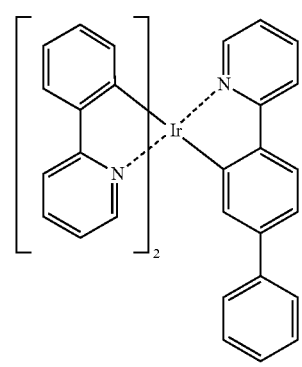

Dp-38 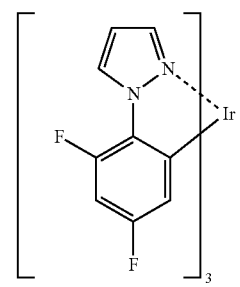

A hole blocking layer may be provided between the electron transfer layer and the light emitting layer, and materials known in the art such as triazine-based compounds may be used.

The electron transfer layer may perform a role of facilitating electron transfer. The electron transfer material is a material favorably receiving electrons from a cathode and transferring the electrons to a light emitting layer, materials having high mobility for the electrons are suited. Specific examples thereof include Al complexes of 8-hydroxyquinoline; complexes including Alga; organic radical compounds; hydroxyflavon-metal complexes, and the like, but are not limited thereto. The electron transfer layer may have a thickness of 1 nm to 50 nm. The electron transfer layer having a thickness of 1 nm or greater has an advantage of preventing decline in the electron transfer properties, and the thickness being 50 nm or less has an advantage of preventing an increase in the driving voltage for enhancing electron migration caused by the electron transfer layer being too thick.

The electron injection layer may perform a role of facilitating electron injection. The electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The organic light emitting device according to the present specification may be a top-emission type, a bottom-emission type or a dual-emission type depending on the materials used.

Hereinafter, the present specification will be described in detail with reference to examples in order to specifically describe the present specification. However, examples according to the present specification may be modified to various different forms, and the scope of the present specification is not to be construed as being limited to the examples described below. Examples of the present specification are provided in order to more fully describe the present specification to those having average knowledge in the art.

SYNTHESIS EXAMPLE

Synthesis Example 1

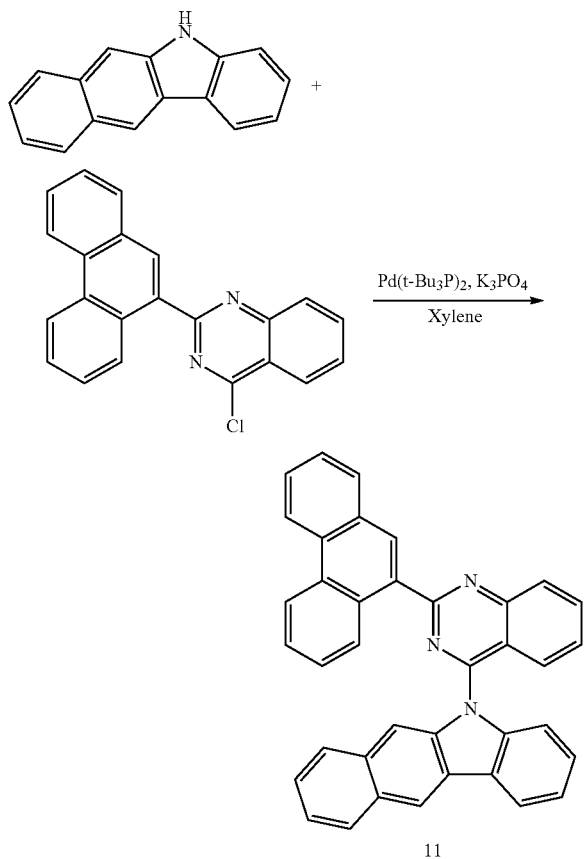

11

Chemical Formula a (10.0 g, 1.0 eq.), 4-chloro-2-(phenanthren-9-yl)quinazoline (17.25 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 11 (17.52 g, yield 73%). [M+H]=522

Synthesis Example 2

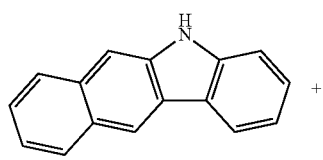

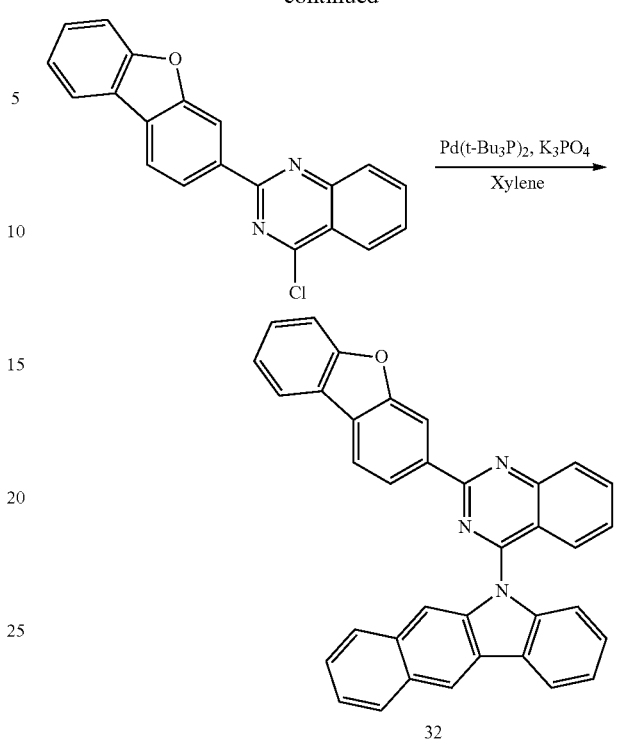

32

Chemical Formula a (10.0 g, 1.0 eq.), 4-chloro-2-(dibenzo[b,d]furan-3-yl)quinazoline (16.74 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 32 (16.48 g, yield 70%). [M+H]=512

Synthesis Example 3

-continued

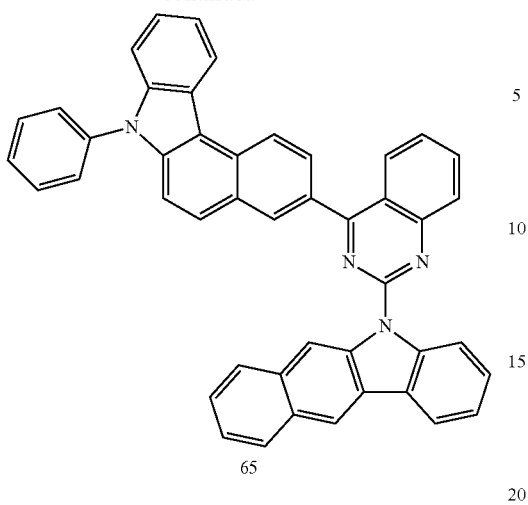

65

Chemical Formula a (10.0 g, 1.0 eq.), 3-(2-chloroquinazo-lin-4-yl)-7-phenyl-7H-benzo[c]carbazole (23.08 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 65 (22.85 g, yield 78%). [M+H]=634

Synthesis Example 4

-continued

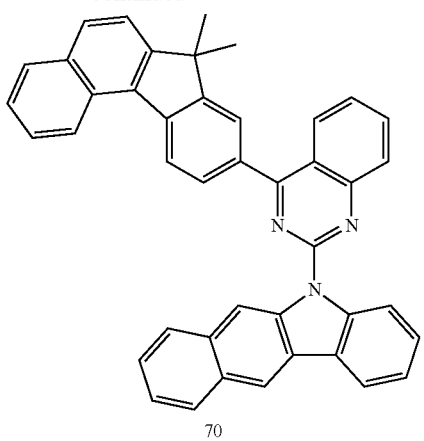

70

Chemical Formula a (10.0 g, 1.0 eq.), 2-chloro-4-(7,7-dimethyl-7H-benzo[c]fluoren-9-yl)quinazoline (20.60 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 70 (18.66 g, yield 69%). [M+H]=588

Synthesis Example 5

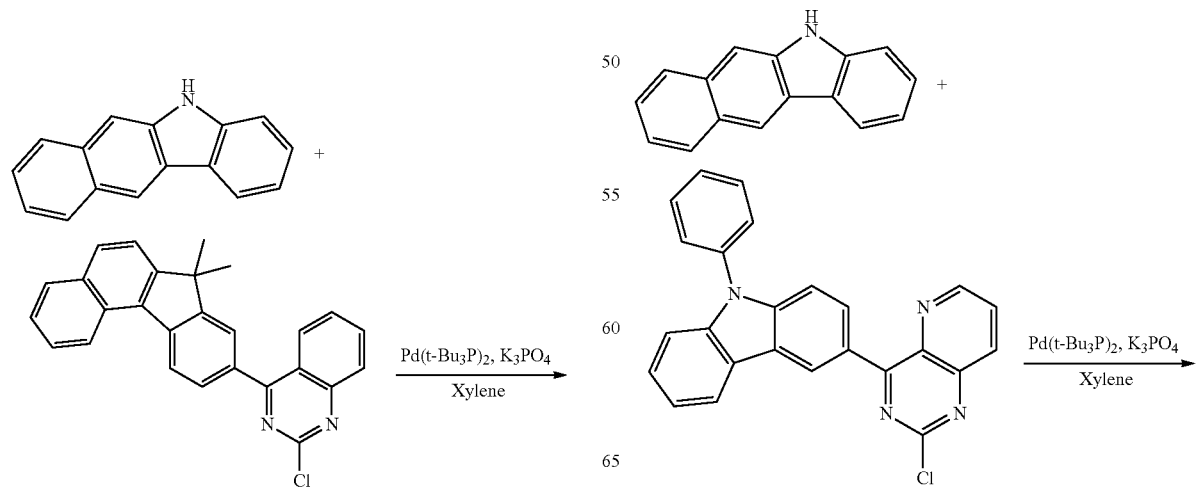

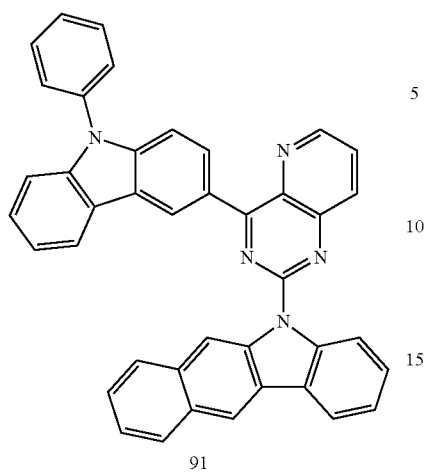

91

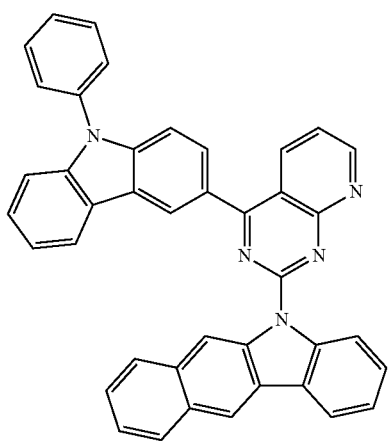

95

Chemical Formula a (10.0 g, 1.0 eq.), 3-(2-chloropyrido [3, 2-d]pyrimidin-4-yl)-9-phenyl-9H-carbazole (20.59 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 91 (20.55 g, yield 76%). [M+H]=588

Synthesis Example 6

Chemical Formula a (10.0 g, 1.0 eq.), 3-(2-chloropyrido [2,3-d]pyrimidin-4-yl)-9-phenyl-9H-carbazole (20.59 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 95 (19.20 g, yield 71%). [M+H]=588

Synthesis Example 7

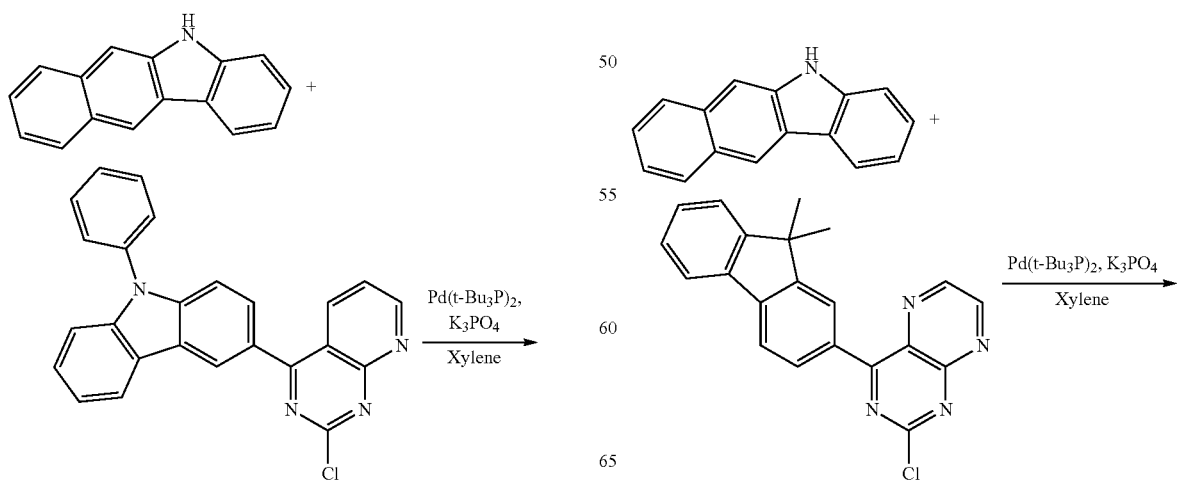

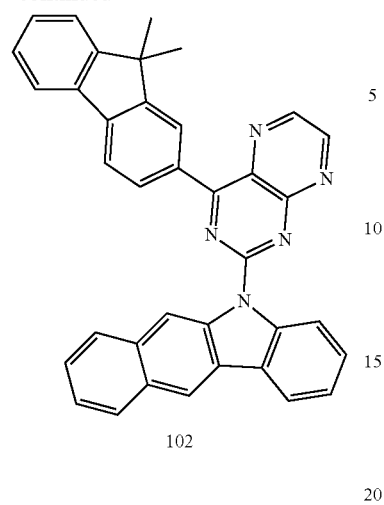

102

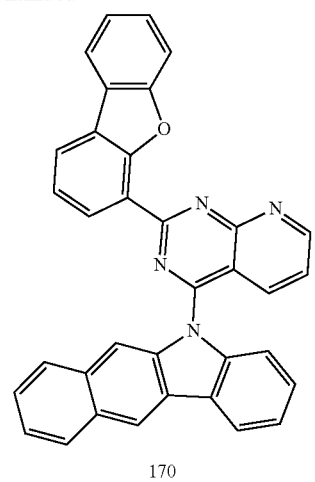

170

Chemical Formula a (10.0 g, 1.0 eq.), 2-chloro-4-(9,9-dimethyl-9H-fluoren-2-yl)pteridine (18.16 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 102 (18.37 g, yield 74%). [M+H]=540

Synthesis Example 8

Chemical Formula a (10.0 g, 1.0 eq.), 4-chloro-2-(dibenzo[b,d]furan-4-yl)pyrido[2,3-d]pyrimidine (16.79 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 170 (16.51 g, yield 70%). [M+H]=513

Synthesis Example 9

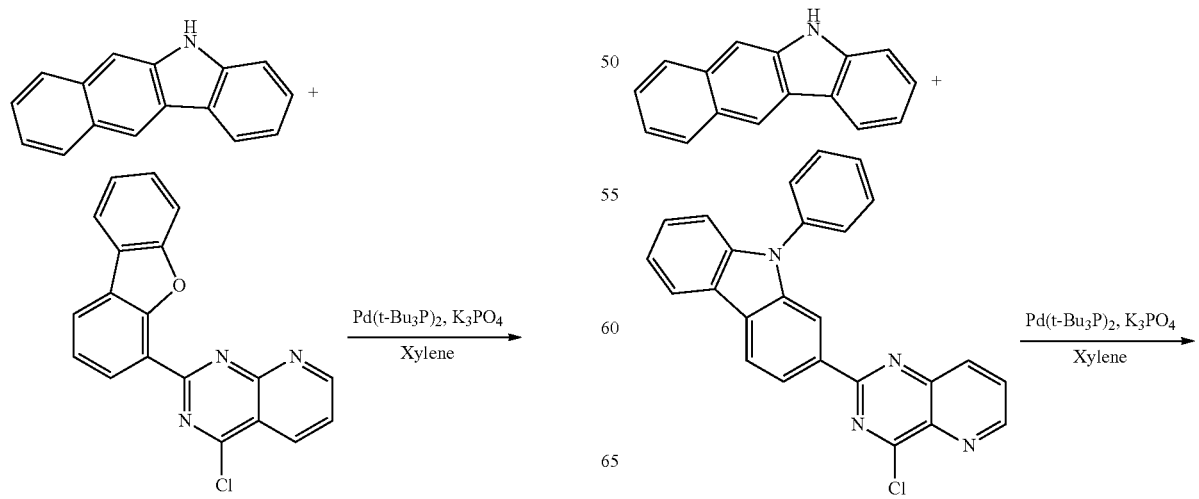

-continued

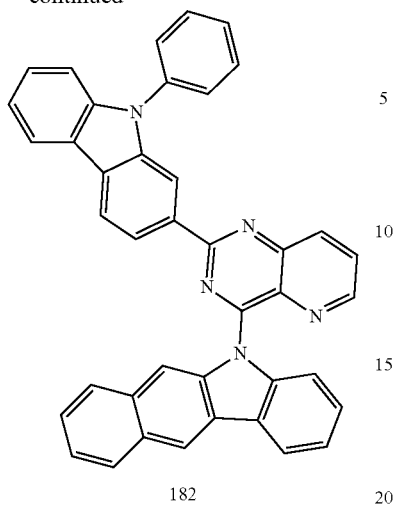

182

-continued

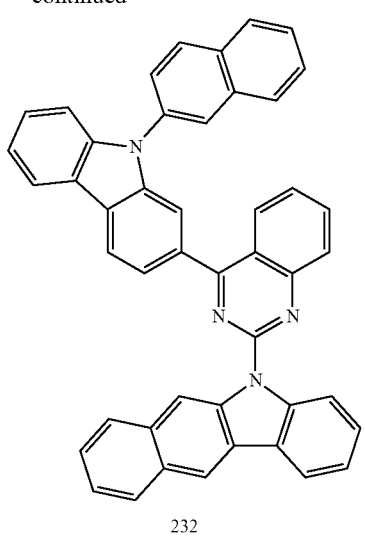

232

Chemical Formula a (10.0 g, 1.0 eq.), 2-(4-chloropyrido[3,2-d]pyrimidin-2-yl)-9-phenyl-9H-carbazole (20.59 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 182 (18.12 g, yield 67%). [M+H]=588

Chemical Formula a (10.0 g, 1.0 eq.), 2-(2-chloroquinazolin-4-yl)-9-(naphthalen-2-yl)-9H-carbazole (23.08 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 232 (20.22 g, yield 69%). [M+H]=637

Synthesis Example 10

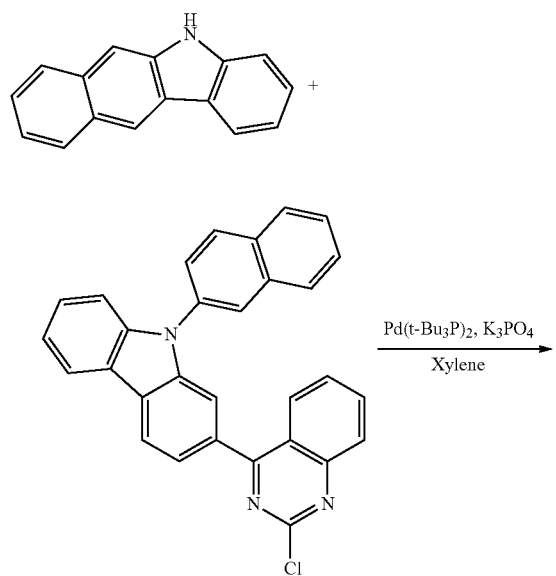

Synthesis Example 11

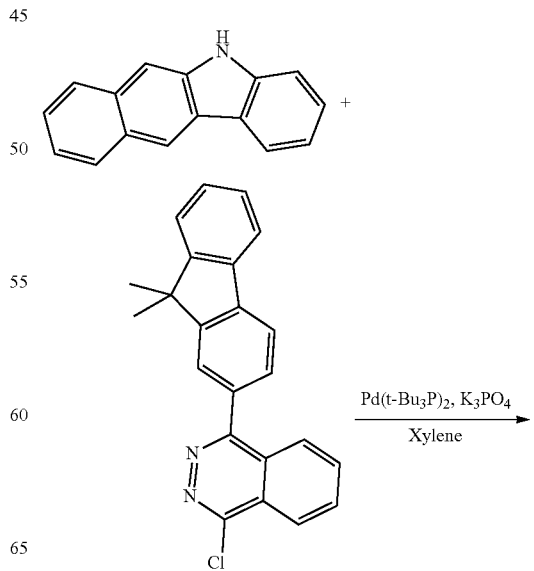

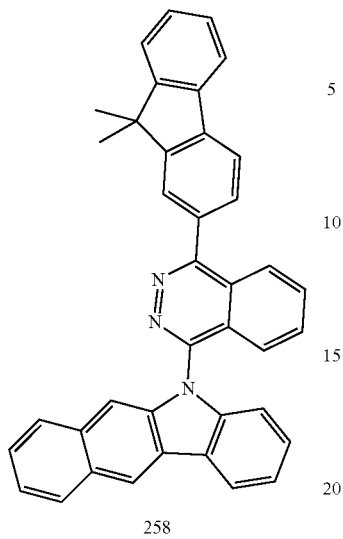

258

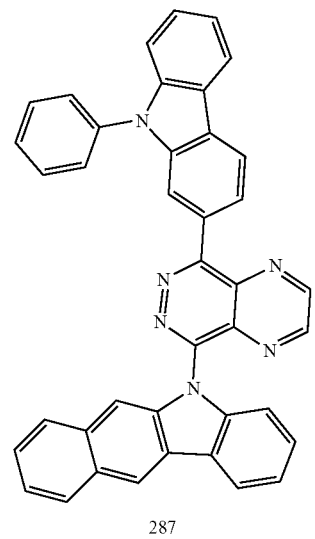

287

Chemical Formula a (10.0 g, 1.0 eq.), 1-chloro-4-(9,9-dimethyl-9H-fluoren-2-yl)phthalazine (18.06 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 258 (18.31 g, yield 74%). [M+H]=538

Synthesis Example 12

Chemical Formula a (10.0 g, 1.0 eq.), 2-(8-chloropyrazino[2,3-d]pyridazin-5-yl)-9-phenyl-9H-carbazole (20.64 g, 1.1 eq.), K$_3$PO$_4$ (19.53 g, 2.0 eq.) and Pd(t-Bu$_3$N2 (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 287 (18.96 g, yield 70%). [M+H]=589

Synthesis Example 13

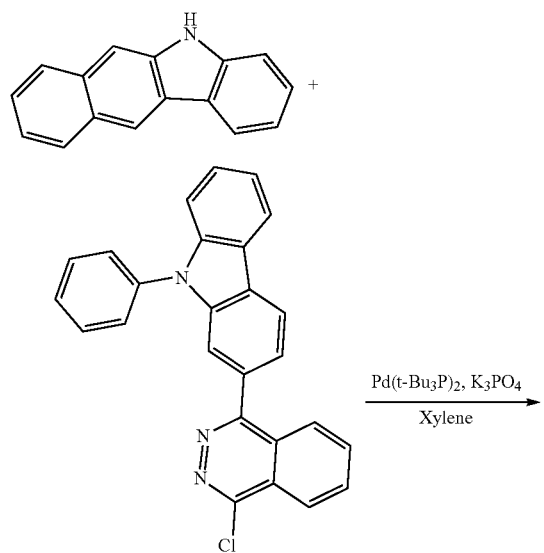

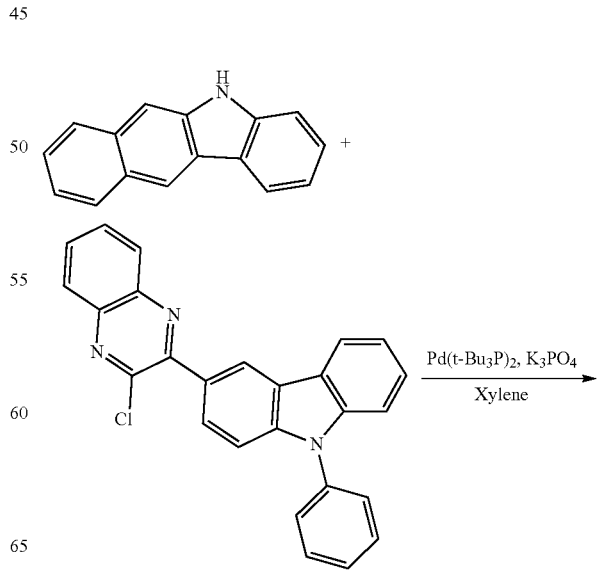

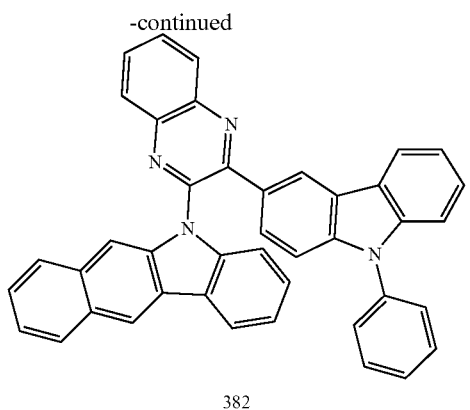

382

Chemical Formula a (10.0 g, 1.0 eq.), 3-(3-chloroquinoxalin-2-yl)-9-phenyl-9H-carbazole (20.54 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 382 (16.74 g, yield 62%). [M+H]=587

Synthesis Example 14

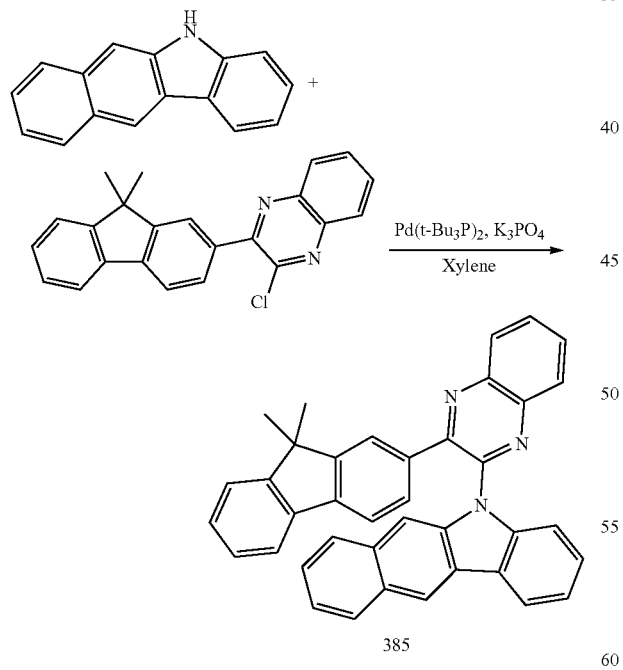

385

Chemical Formula a (10.0 g, 1.0 eq.), 2-chloro-3-(9,9-dimethyll-9H-fluoren-2-yl)quinoxaline (18.06 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 385 (15.83 g, yield 64%). [M+H]=538

Synthesis Example 15

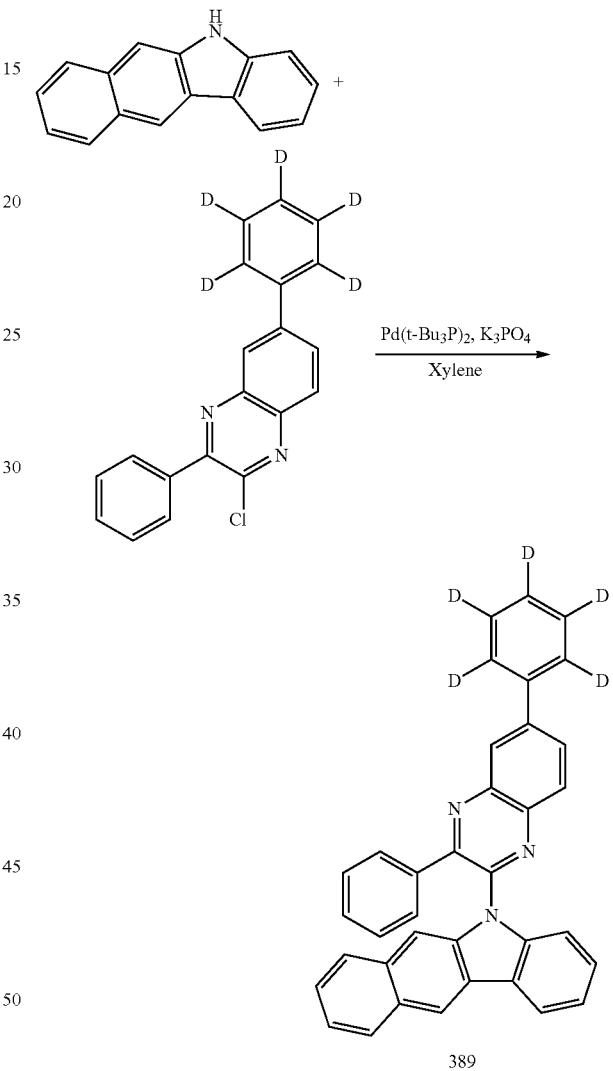

389

Chemical Formula a (10.0 g, 1.0 eq.), 2-chloro-3-phenyl-6-(phenyl-d5)quinoxaline (19.53 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 389 (15.96 g, yield 69%). [M+H]=503

407
Synthesis Example 16

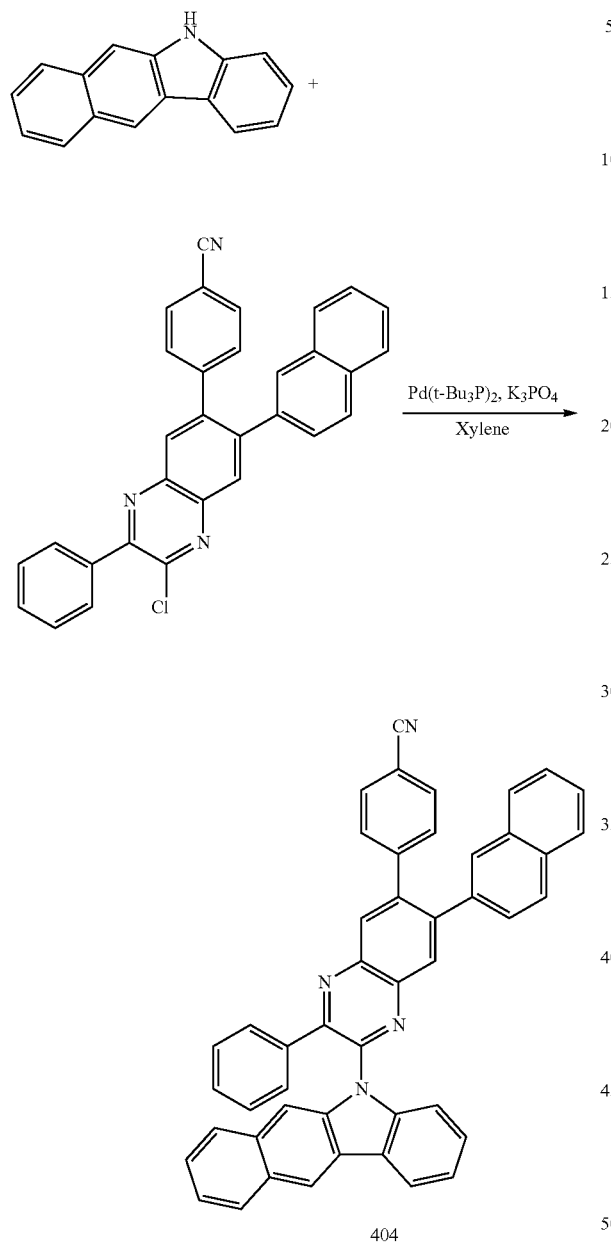

404

Chemical Formula a (10.0 g, 1.0 eq.), 4-(2-chloro-7-(naphthalen-2-yl)-3-phenylquinoxalin-6-yl)benzonitrile (23.69 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 404 (19.40 g, yield 65%). [M+H]=649

408
Synthesis Example 17

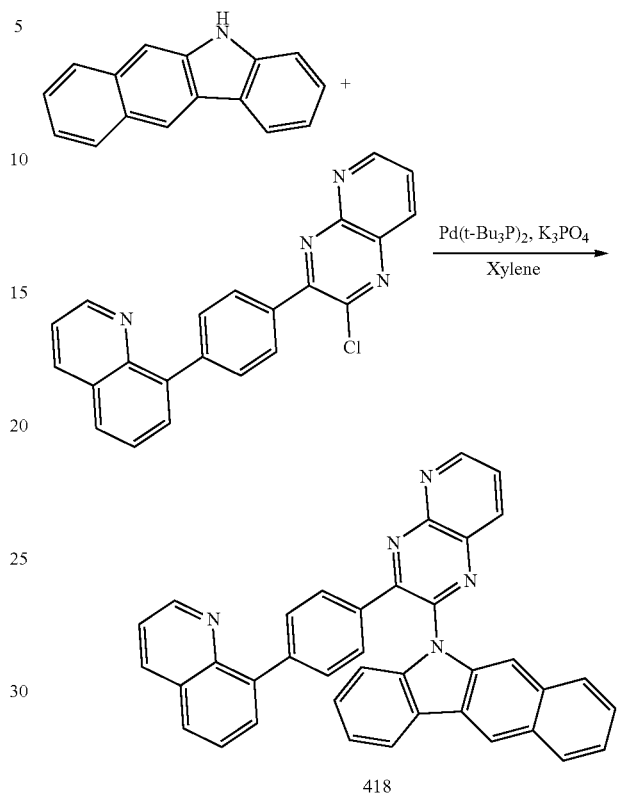

418

Chemical Formula a (10.0 g, 1.0 eq.), 2-chloro-3-(4-(quinolin-8-yl)phenyl)pyrido[2,3-b]pyrazine (18.67 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 418 (17.18 g, yield 68%). [M+H]=550

Synthesis Example 18

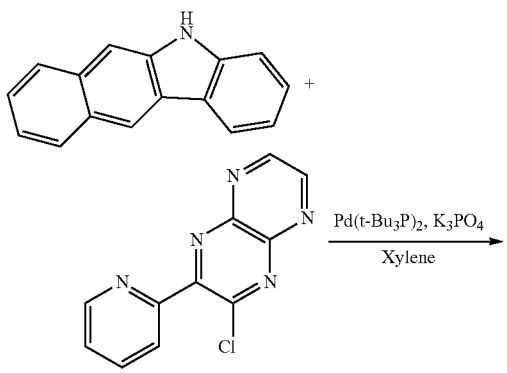

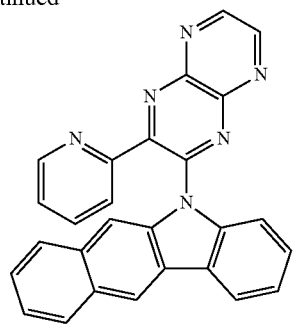

429

Chemical Formula a (10.0 g, 1.0 eq.), 2-chloro-3-(pyridin-2-yl)pyrazino[2,3-b]pyrazine (12.33 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 429 (12.68 g, yield 65%). [M+H]=425

Synthesis Example 19

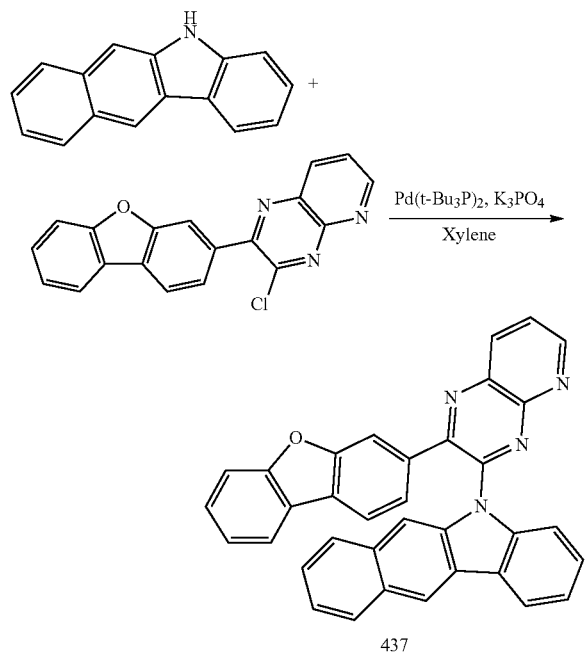

437

Chemical Formula a (10.0 g, 1.0 eq.), 3-chloro-2-(dibenzo[b,d]furan-3-yl)pyrido[2,3-b]pyrazine (16.79 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 437 (15.80 g, yield 67%). [M+H]=513

Synthesis Example 20

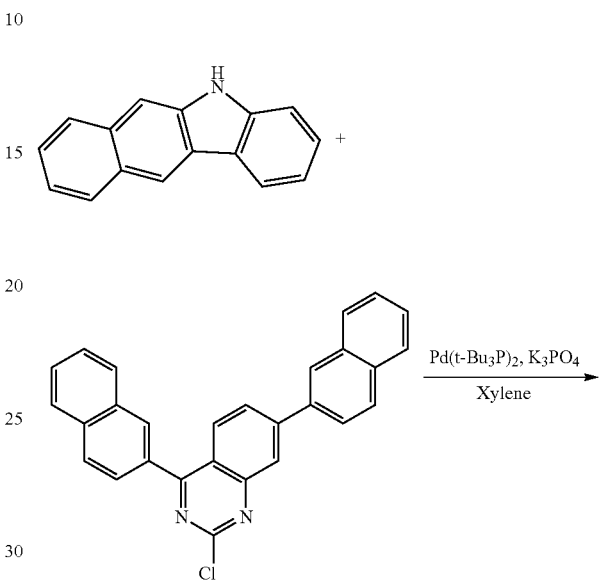

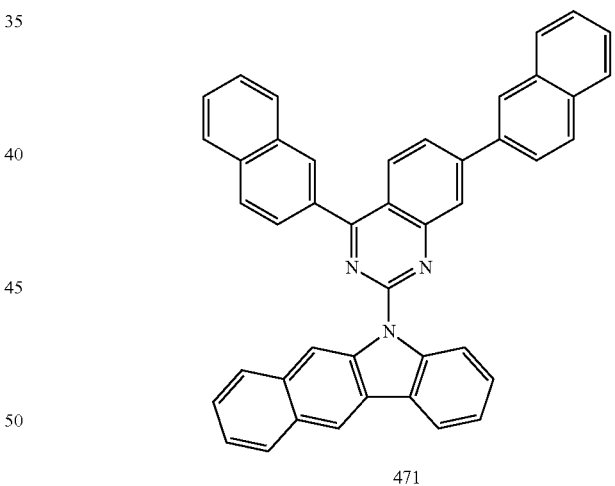

471

Chemical Formula a (10.0 g, 1.0 eq.), 2-chloro-4,7-di(naphthalen-2-yl)quinazoline (21.10 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 471 (20.63 g, yield 75%). [M+H]=598

Synthesis Example 21

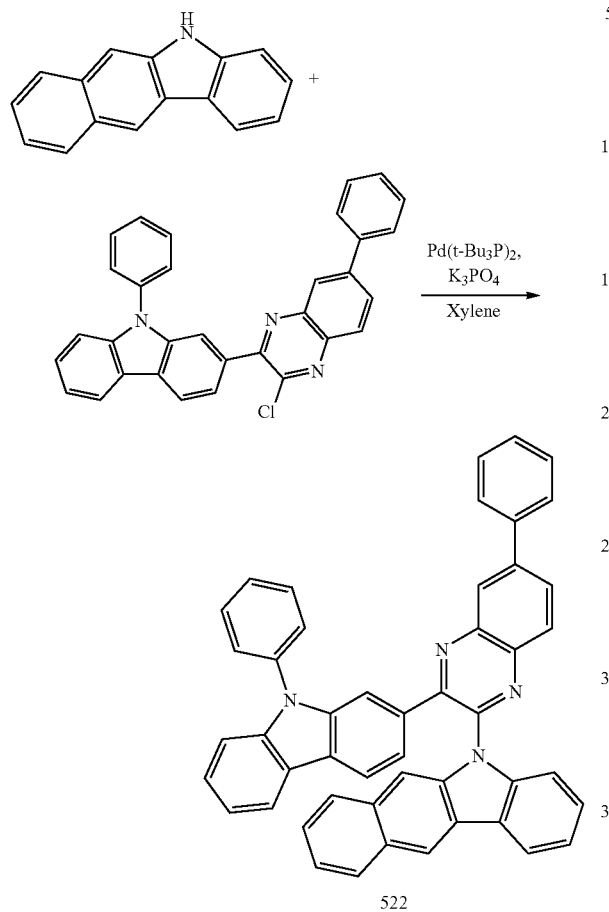

522

Chemical Formula a (10.0 g, 1.0 eq.), 2-(3-chloro-7-phenylquinoxalin-2-yl)-9-phenyl-9H-carbazole (24.40 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 522 (22.26 g, yield 72%). [M+H]=663

Synthesis Example 22

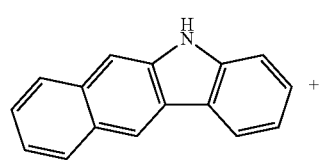

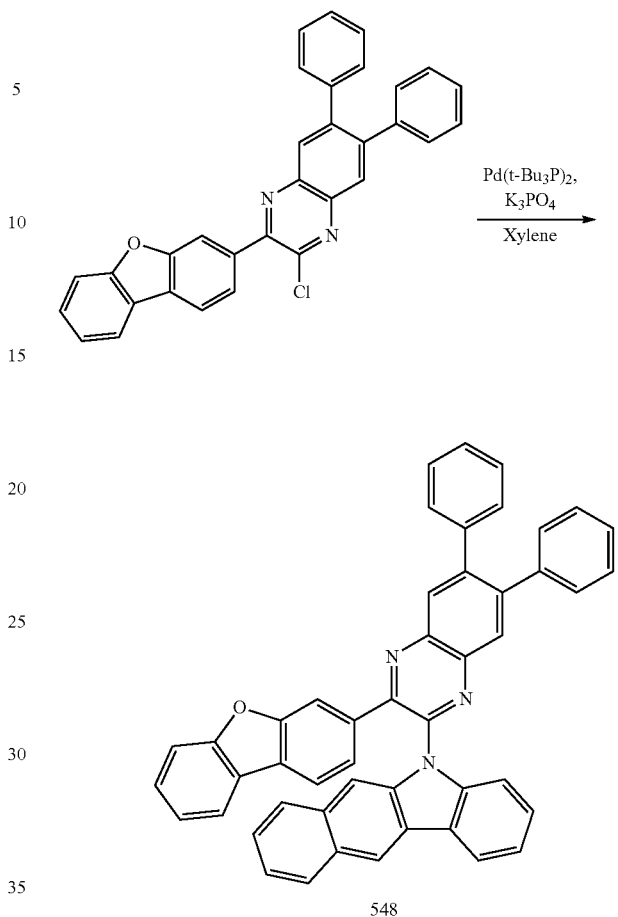

548

Chemical Formula a (10.0 g, 1.0 eq.), 2-chloro-3-(dibenzo[b,d]furan-3-yl)-6,7-diphenylquinoxaline (24.45 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 548 (21.38 g, yield 70%). [M+H]=664

Synthesis Example 23

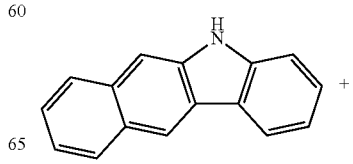

413

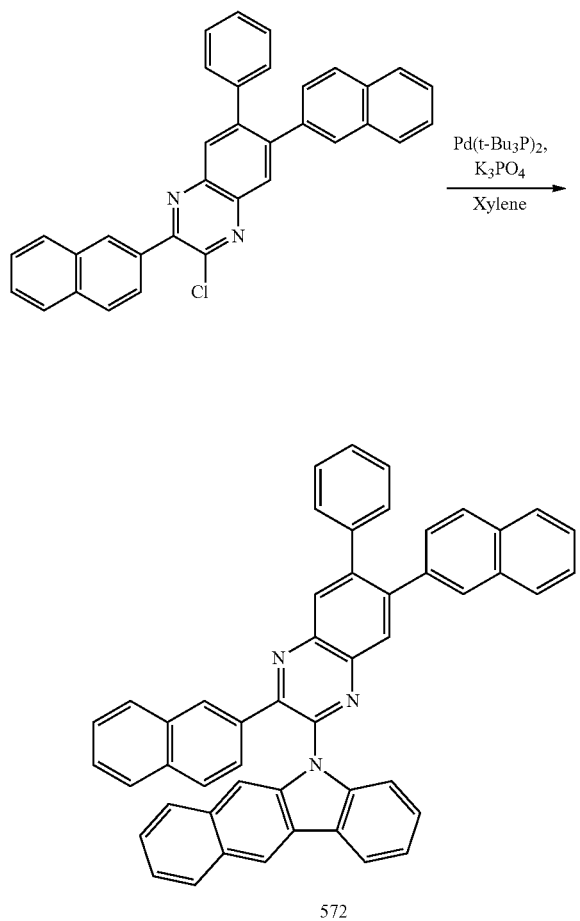

414

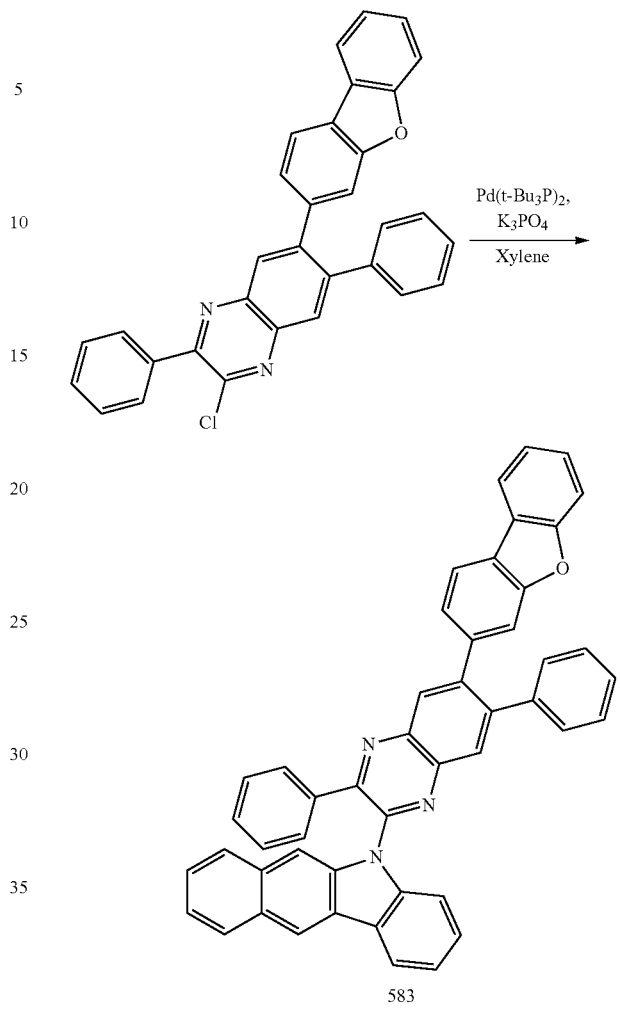

Chemical Formula a (10.0 g, 1.0 eq.), 2-chloro-3,7-di(naphthalen-2-yl)-6-phenylquinoxaline (24.96 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 572 (20.77 g, yield 67%). [M+H]=674

Synthesis Example 24

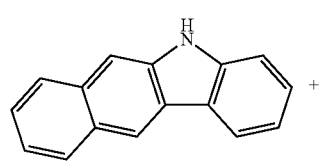

Chemical Formula a (10.0 g, 1.0 eq.), 2-chloro-6-(dibenzo[b,d]furan-3-yl)-3,7-diphenylquinoxaline (24.45 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 583 (19.55 g, yield 64%). [M+H]=664

Synthesis Example 25

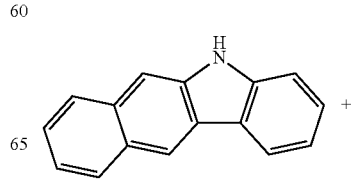

415
-continued

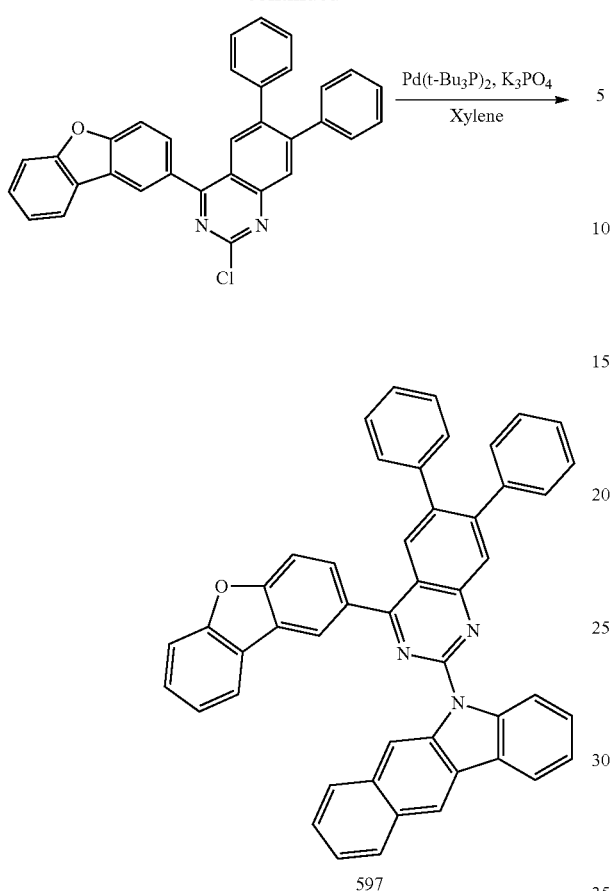

597

416
-continued

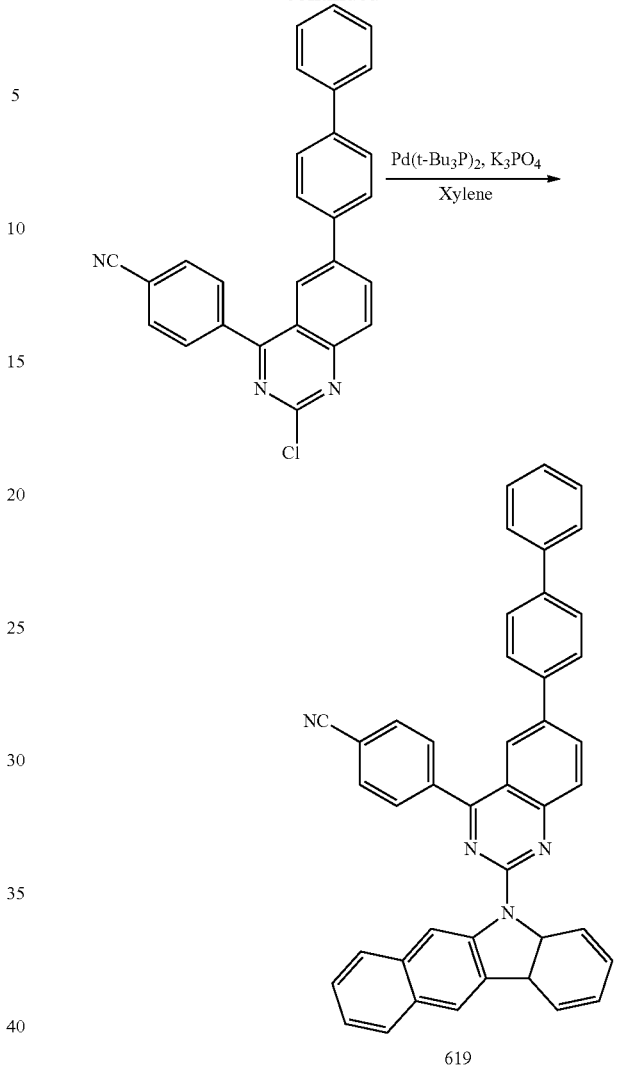

619

Chemical Formula a (10.0 g, 1.0 eq.), 2-chloro-4-(dibenzo[b,d]furan-2-yl)-6,7-diphenylquinazoline (24.45 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 597 (20.46 g, yield 67%). [M+H]=664

Synthesis Example 26

Chemical Formula a (10.0 g, 1.0 eq.), 4-(6-([1,1'-biphenyl]-4-yl)-2-chloroquinazolin-4-yl)benzonitrile (21.15 g, 1.1 eq.), K$_3$PO$_4$ (19.53 g, 2.0 eq.) and Pd(t-Bu$_3$P)$_2$ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 619 (19.84 g, yield 72%). [M+H]=599

Synthesis Example 27

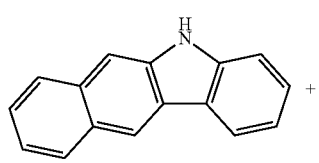 +

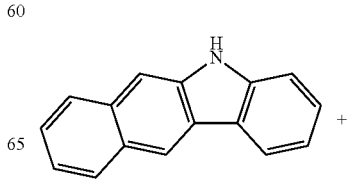 +

417

-continued

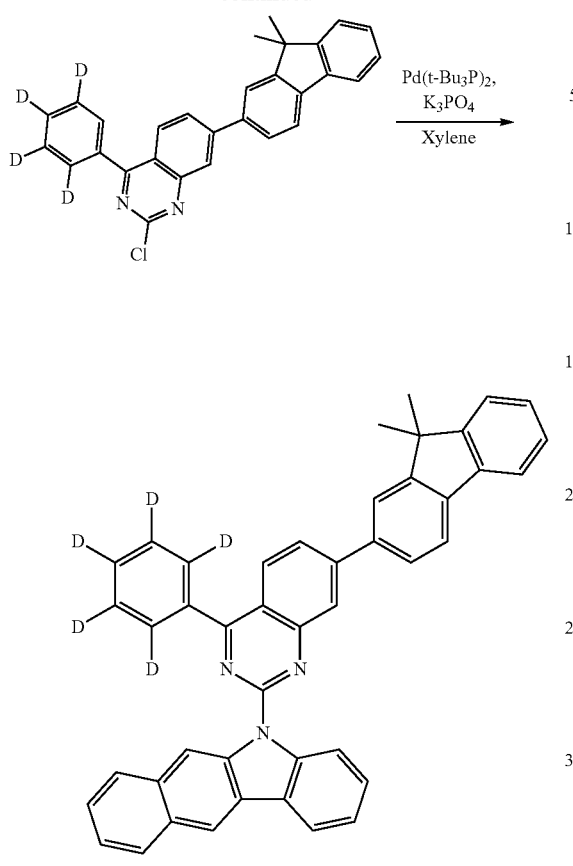

630

418

-continued

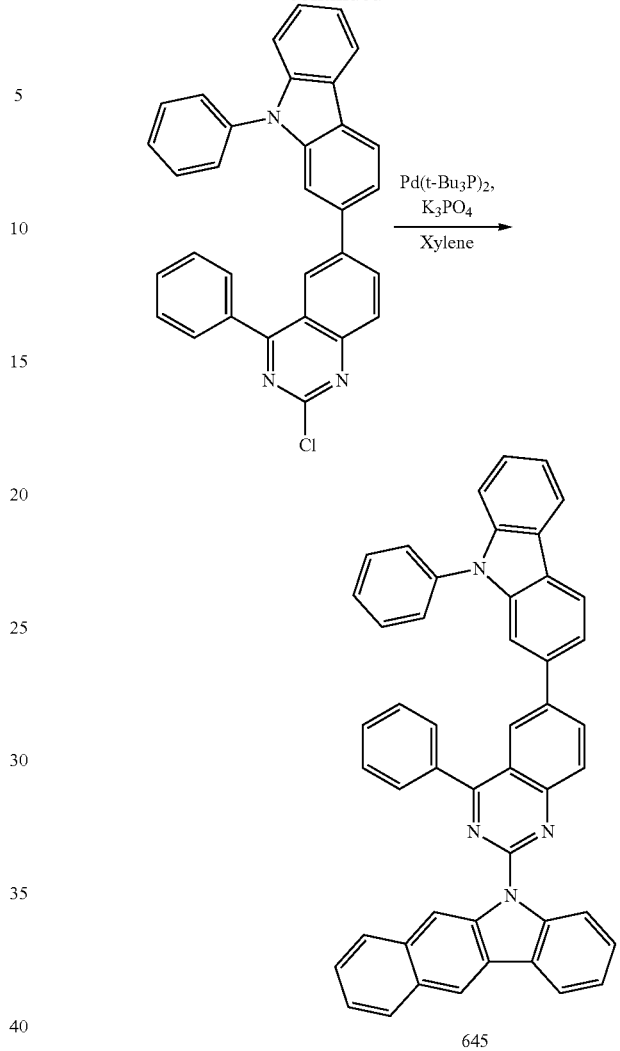

645

Chemical Formula a (10.0 g, 1.0 eq.), 2-chloro-7-(9,9-dimethyl-9H-fluoren-2-yl)-4-(phenyl-d5)quinazoline (22.17 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 630 (20.22 g, yield 71%). [M+H]=619

Synthesis Example 28

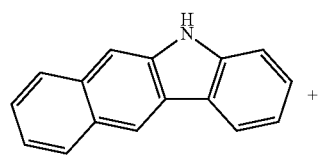

Chemical Formula a (10.0 g, 1.0 eq.), 2-(2-chloro-4-phenylquinazolin-6-yl)-9-phenyl-9H-carbazole (24.40 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 645 (22.57 g, yield 74%). [M+H]=663

Synthesis Example 29

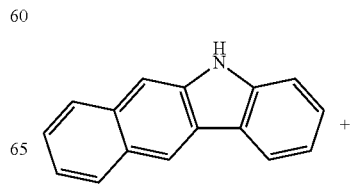

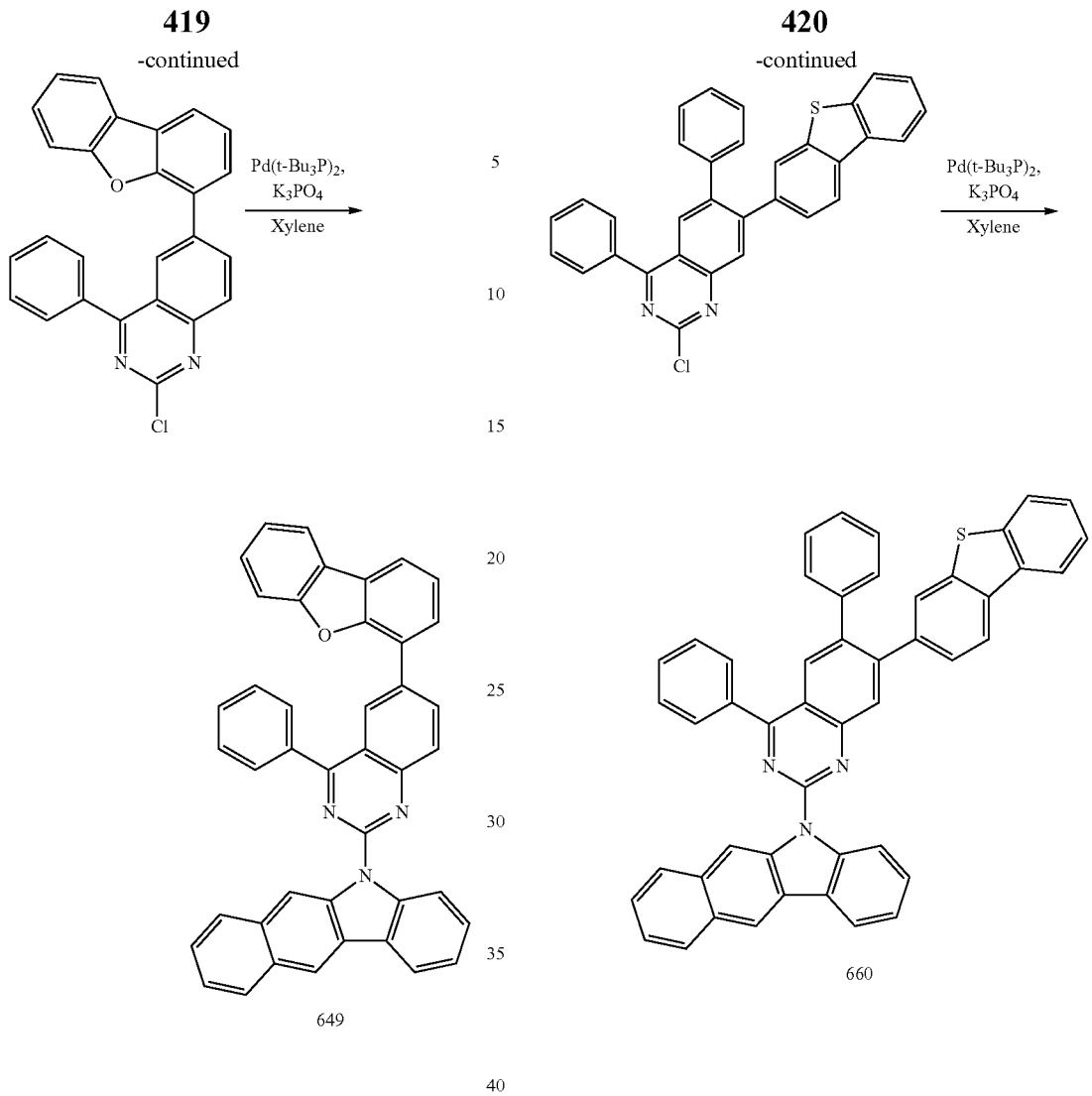

Chemical Formula a (10.0 g, 1.0 eq.), 2-chloro-6-(dibenzo[b,d]furan-4-yl)-4-phenylquinazoline (20.59 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 649 (19.20 g, yield 71%). [M+H]=588

Chemical Formula a (10.0 g, 1.0 eq.), 2-chloro-7-(dibenzo[b,d]thiophen-3-yl)-4,6-diphenylquinazoline (25.26 g, 1.1 eq.), $K_3PO_4$ (19.53 g, 2.0 eq.) and $Pd(t-Bu_3P)_2$ (0.12 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 660 (23.15 g, yield 74%). [M+H]=680

Synthesis Example 30

Synthesis Example 31

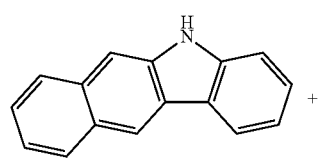

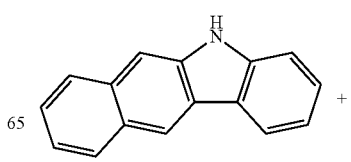

-continued

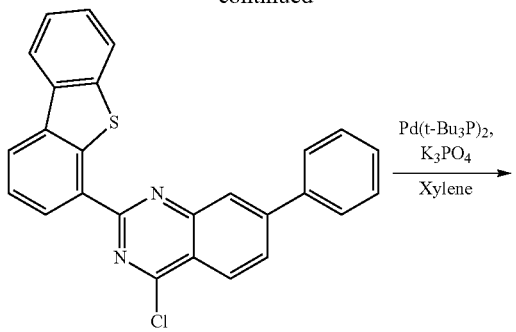

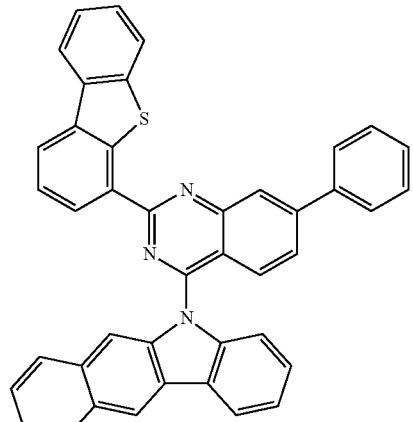
684

Chemical Formula a (10.0 g, 1.0 eq.), 4-chloro-2-(dibenzo[b,d]thiophen-4-yl)-7-phenylquinazoline (21.41 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 684 (18.61 g, yield 67%). [M+H]=604

Synthesis Example 32

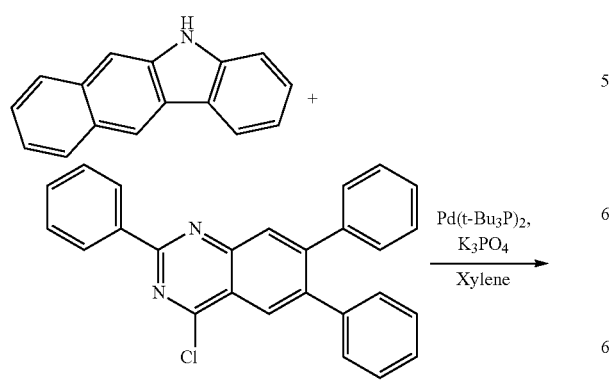

-continued

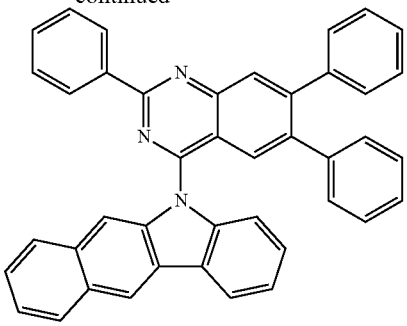
691

Chemical Formula a (10.0 g, 1.0 eq.), 4-chloro-2,6,7-triphenylquinazoline (19.89 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 691 (18.48 g, yield 70%). [M+H]=574

Synthesis Example 33

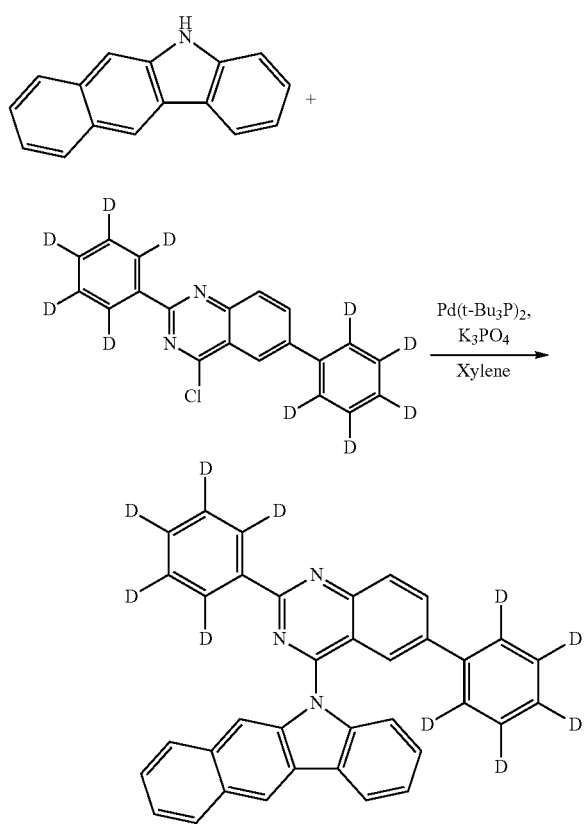
714

Chemical Formula a (10.0 g, 1.0 eq.), 4-chloro-2,6-bis(phenyl-d5)quinazoline (16.54 g, 1.1 eq.), K₃PO₄ (19.53 g, 2.0 eq.) and Pd(t-Bu₃P)₂ (0.12 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 714 (15.88 g, yield 68%). [M+H]=508

Synthesis Example 34

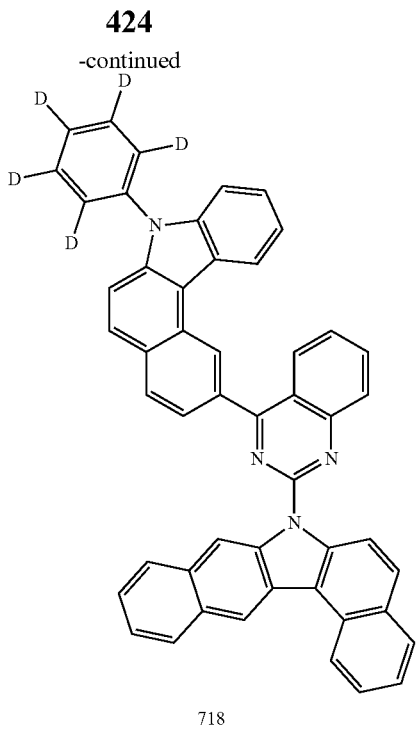

718

Chemical Formula b (10.0 g, 1.0 eq.), 2-(2-chloroquinazolin-4-yl)-7-(phenyl-d5)-7H-benzo[c]carbazole (18.96 g, 1.1 eq.), K₃PO₄ (15.88 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 718 (18.89 g, yield 73%). [M+H]=692

Synthesis Example 35

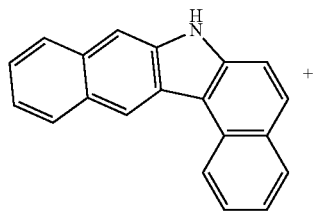

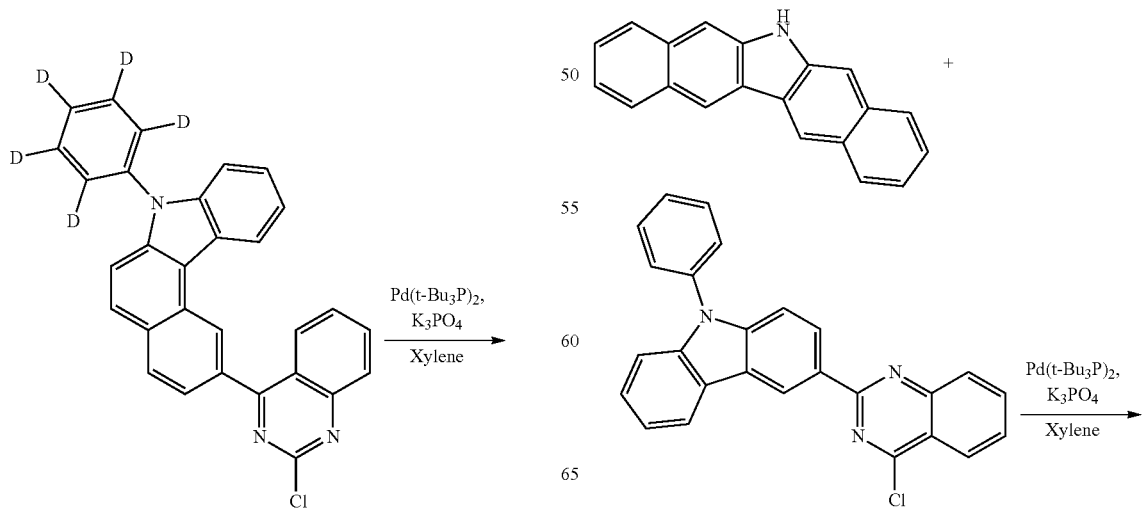

-continued

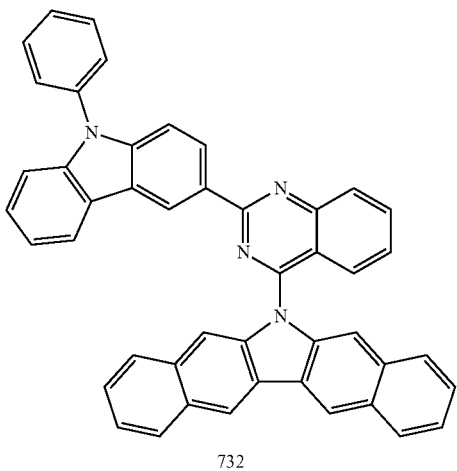

732

Chemical Formula c (10.0 g, 1.0 eq.), 3-(4-chloroquinazolin-2-yl)-9-phenyl-9H-carbazole (16.70 g, 1.1 eq.), $K_3PO_4$ (15.88 g, 2.0 eq.) and $Pd(t-Bu_3P)_2$ (0.10 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 732 (17.38 g, yield 73%). [M+H]=637

Synthesis Example 36

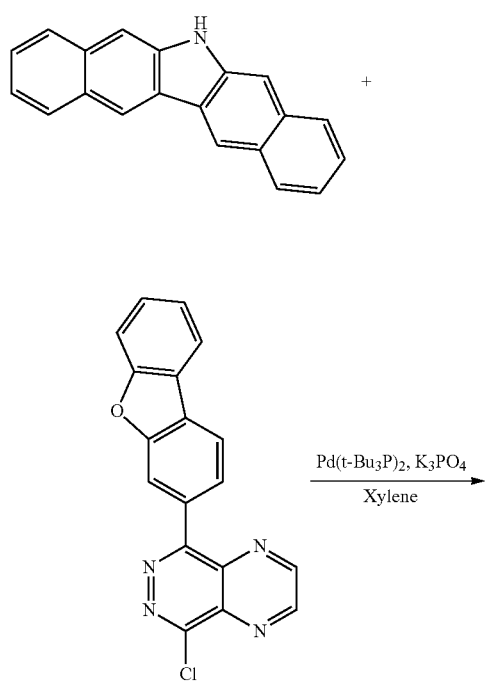

-continued

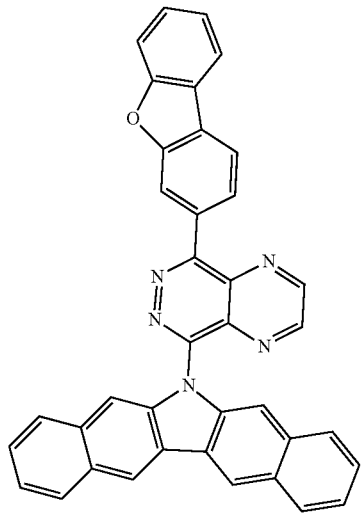

738

Chemical Formula c (10.0 g, 1.0 eq.), 5-chloro-8-(dibenzo[b,d]furan-3-yl)pyrazino[2,3-d]pyridazine (13.69 g, 1.1 eq.), $K_3PO_4$ (15.88 g, 2.0 eq.) and $Pd(t-Bu_3P)_2$ (0.10 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 738 (14.75 g, yield 70%). [M+H]=564

Synthesis Example 37

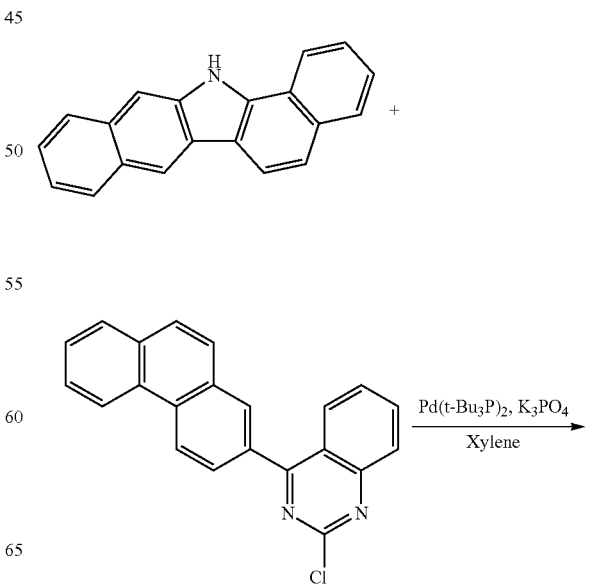

427
-continued

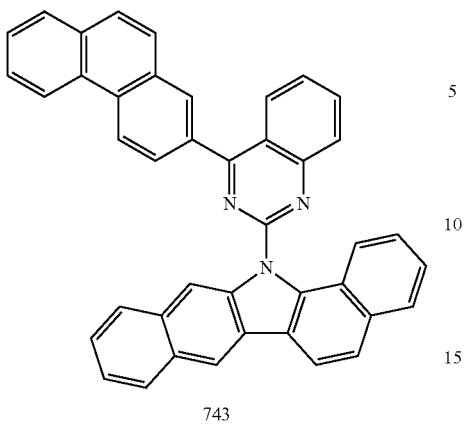

743

Chemical Formula d (10.0 g, 1.0 eq.), 2-chloro-4-(phenanthren-2-yl)quinazoline (14.02 g, 1.1 eq.), K₃PO₄ (15.88 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 743 (14.96 g, yield 70%). [M+H]=572

Synthesis Example 38

428
-continued

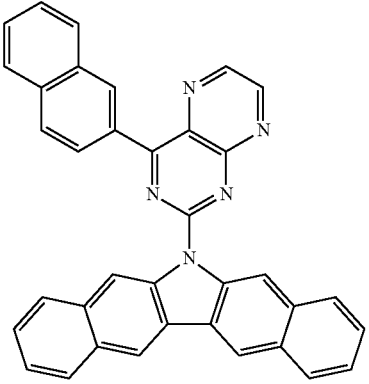

758

Chemical Formula c (10.0 g, 1.0 eq.), 2-chloro-4-(naphthalen-2-yl)pteridine (12.04 g, 1.1 eq.), K₃PO₄ (15.88 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 758 (14.29 g, yield 73%). [M+H]=524

Synthesis Example 39

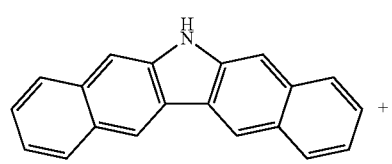 +

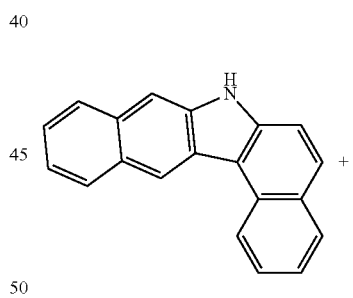 +

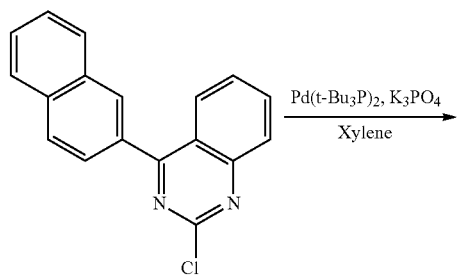

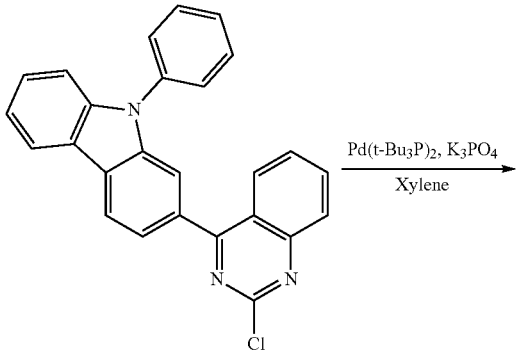

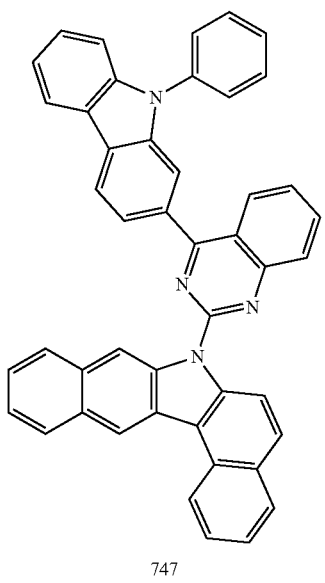

747

Chemical Formula b (10.0 g, 1.0 eq.), 2-(2-chloroquinazolin-4-yl)-9-phenyl-9H-carbazole (16.70 g, 1.1 eq.), $K_3PO_4$ (15.88 g, 2.0 eq.) and $Pd(t-Bu_3P)_2$ (0.10 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 747 (17.14 g, yield 72%). A graph measuring 1H-NMR of Compound 747 is shown in FIG. 5. [M+H]=637

Synthesis Example 40

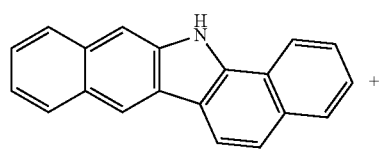

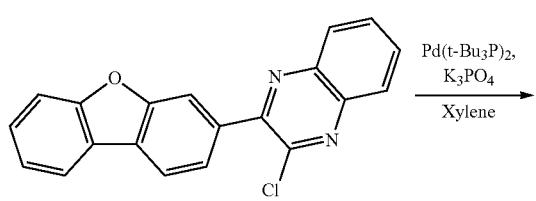

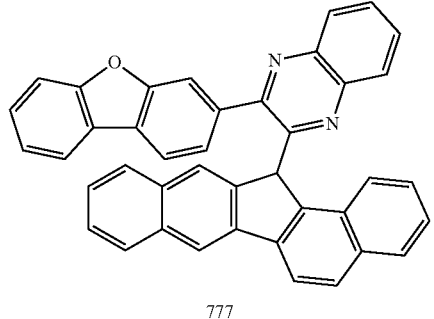

777

Chemical Formula c (10.0 g, 1.0 eq.), 2-chloro-3-(dibenzo[b,d]furan-3-yl)quinoxaline (13.61 g, 1.1 eq.), $K_3PO_4$ (15.88 g, 2.0 eq.) and $Pd(t-Bu_3P)_2$ (0.10 g, 0.005 eq.) were dissolved in xylene (250 ml), and the result was stirred under reflux. When the reaction was terminated after 3 hours, the solvent was removed under vacuum. After that, the result was completely dissolved in $CHCl_3$, washed with water, and approximately 50% of the solvent was removed under vacuum again. Under reflux again, crystals were dropped while adding ethyl acetate thereto, and the result was cooled and then filtered. This went through column chromatography to obtain Compound 777 (13.44 g, yield 64%). [M+H]=562

Synthesis Example 41

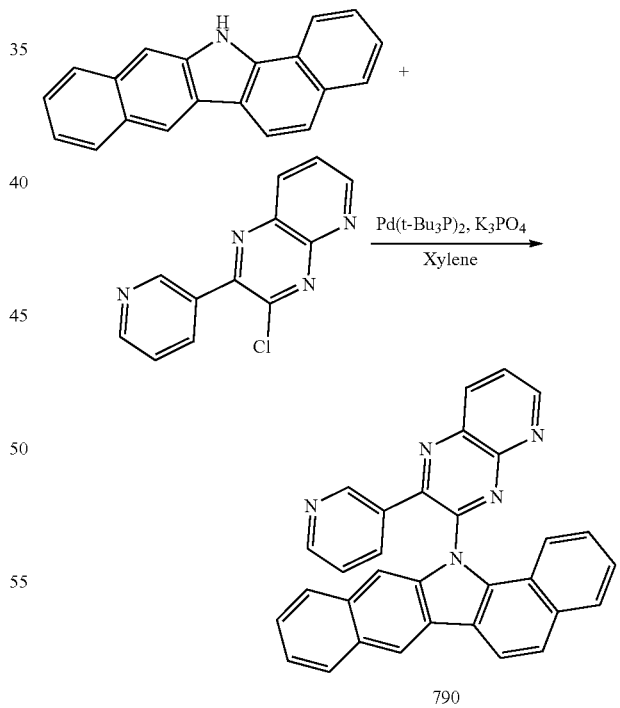

790

Chemical Formula d (10.0 g, 1.0 eq.), 3-chloro-2-(pyridin-3-yl)pyrido[2,3-b]pyrazine (9.98 g, 1.1 eq.), $K_3PO_4$ (15.88 g, 2.0 eq.) and $Pd(t-Bu_3P)_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 790 (10.62 g, yield 60%). [M+H]=474

Synthesis Example 42

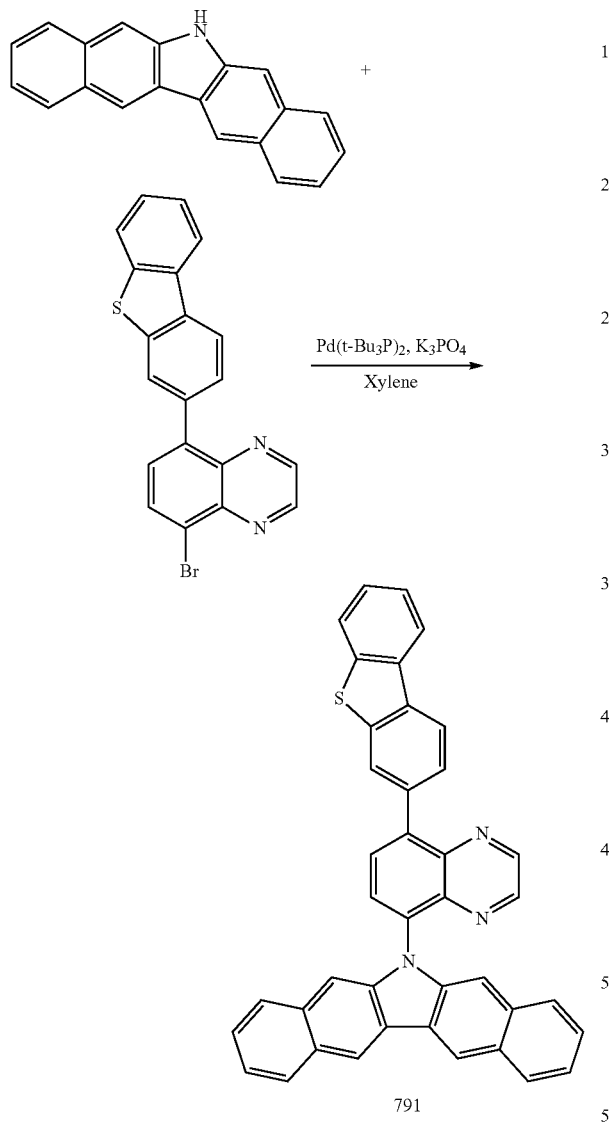

791

Chemical Formula d (10.0 g, 1.0 eq.), 5-bromo-8-(dibenzo[b,d]thiophen-3-yl)quinoxaline (16.10 g, 1.1 eq.), K$_3$PO$_4$ (15.88 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 791 (15.77 g, yield 73%). [M+H]=578

Synthesis Example 43

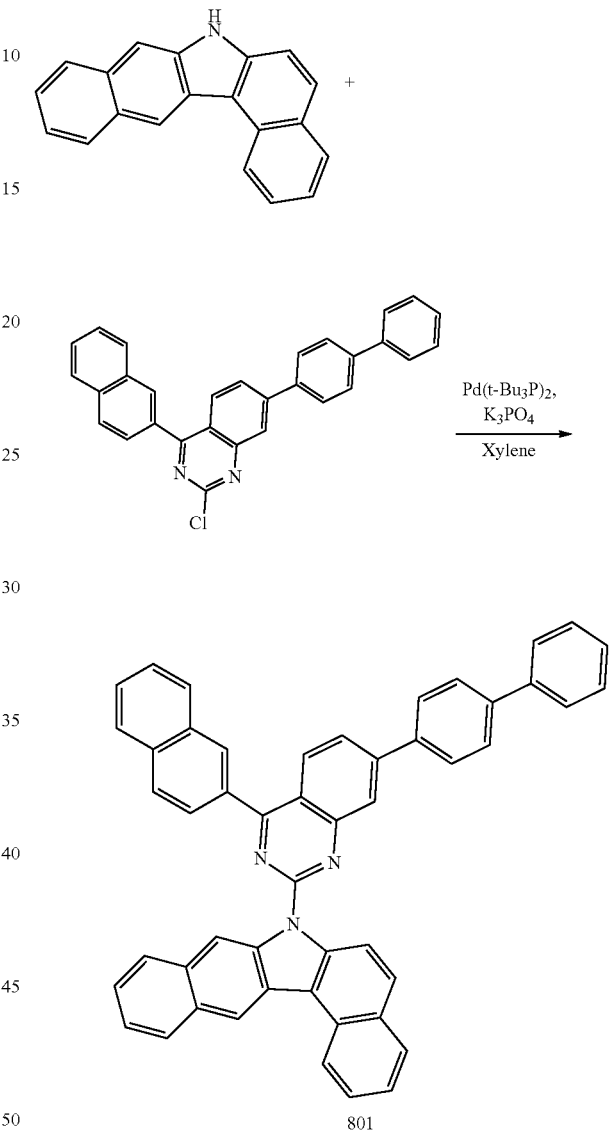

801

Chemical Formula b (10.0 g, 1.0 eq.), 7-([1,1'-biphenyl]-4-yl)-2-chloro-4-(naphthalen-2-yl)quinazoline (18.22 g, 1.1 eq.), K$_3$PO$_4$ (15.88 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 801 (17.71 g, yield 70%). [M+H]=674

Synthesis Example 44

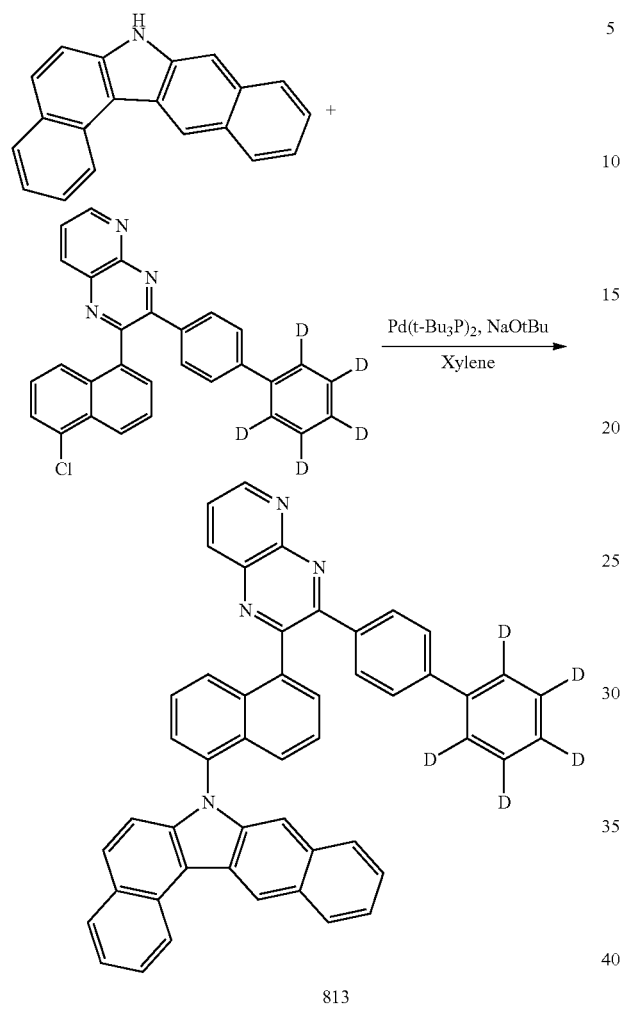

813

Chemical Formula b (10.0 g, 1.0 eq.), 3-([1,1'-biphenyl]-4-yl-2',3',4',5',6'-d5)-2-(5-chloronaphthalen-1-yl)pyrido[2,3-b]pyrazine (18.47 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 813 (19.51 g, yield 77%). [M+H]=680

Synthesis Example 45

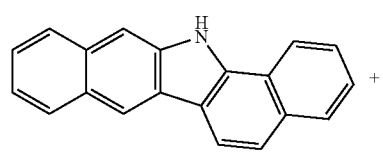

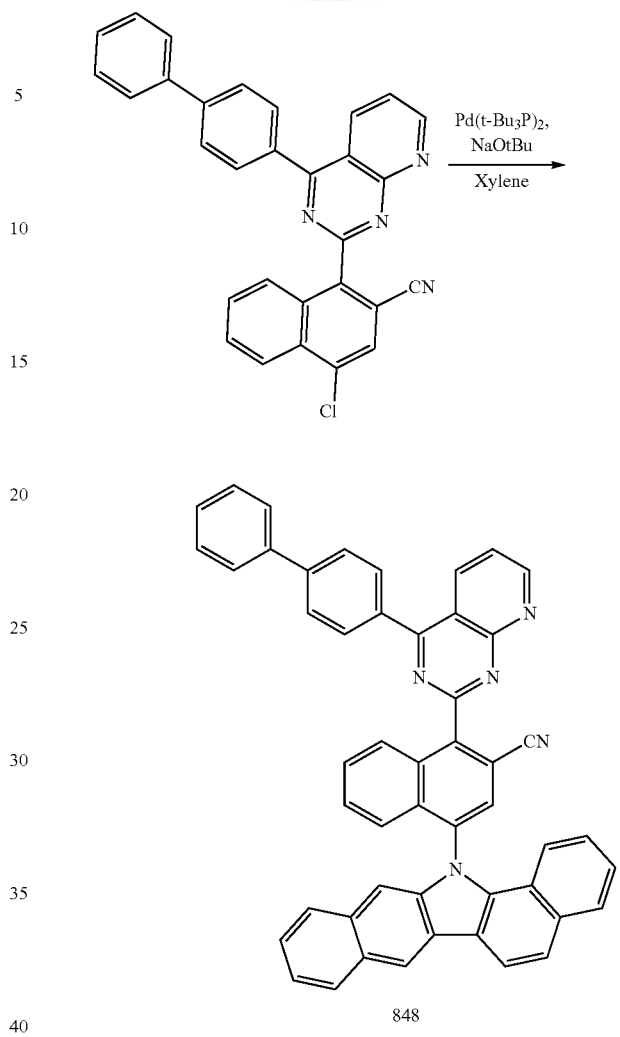

848

Chemical Formula d (10.0 g, 1.0 eq.), 1-(4-([1,1f-biphenyl]-4-yl)pyrido[2,3-d]pyrimidin-2-yl)-4-chloro-2-naphthonitrile (19.29 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 848 (17.53 g, yield 77%). [M+H]=700

Synthesis Example 46

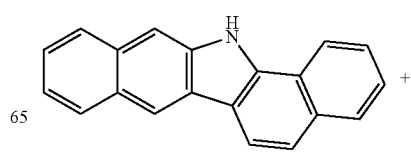

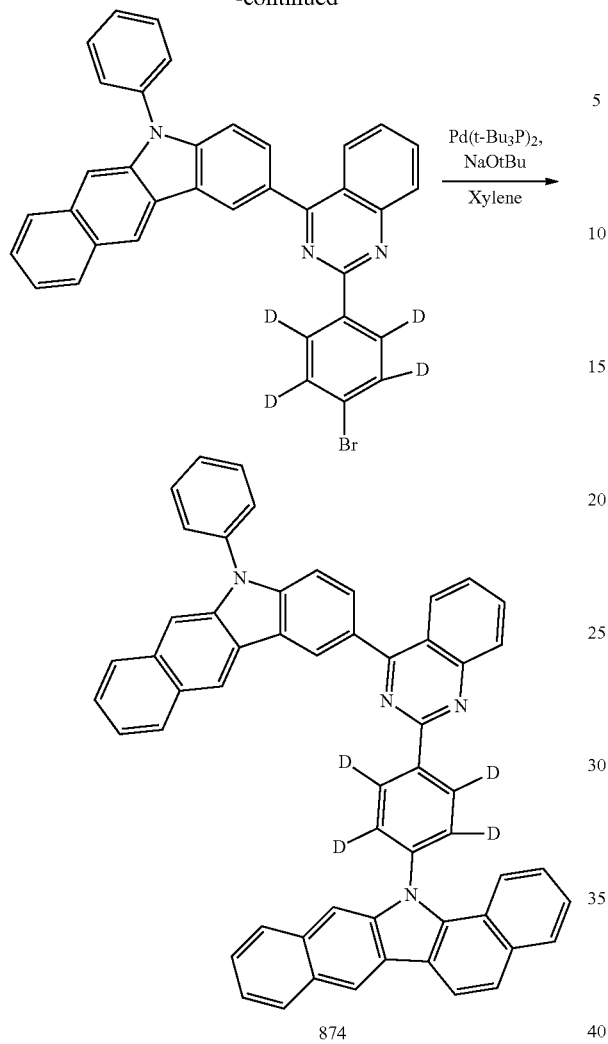

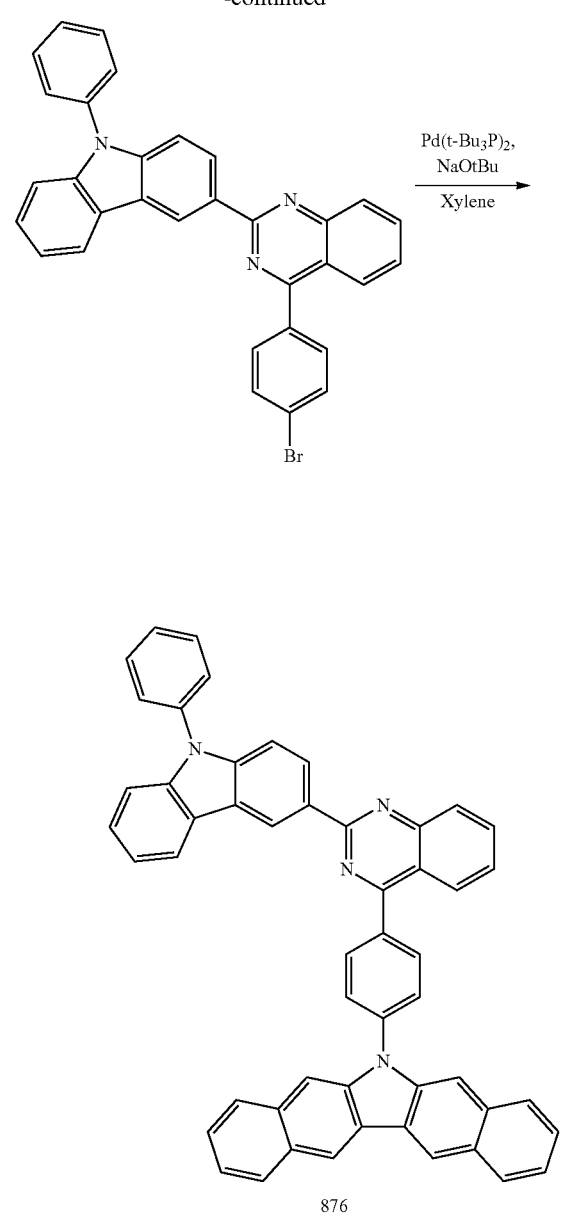

Chemical Formula d (10.0 g, 1.0 eq.), 2-(2-(4-bromophenyl-2,3,5,6-d4)quinolin-4-yl)-5-phenyl-5H-benzo[b]carbazole (23.88 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 874 (20.36 g, yield 71%). [M+H]=767

Synthesis Example 47

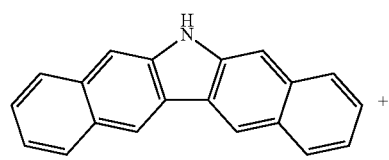 +

Chemical Formula c (10.0 g, 1.0 eq.), 3-(4-(4-bromophenyl)quinazolin-2-yl)-9-phenyl-9H-carbazole (21.66 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 876 (21.81 g, yield 74%). [M+H]=713

Synthesis Example 48

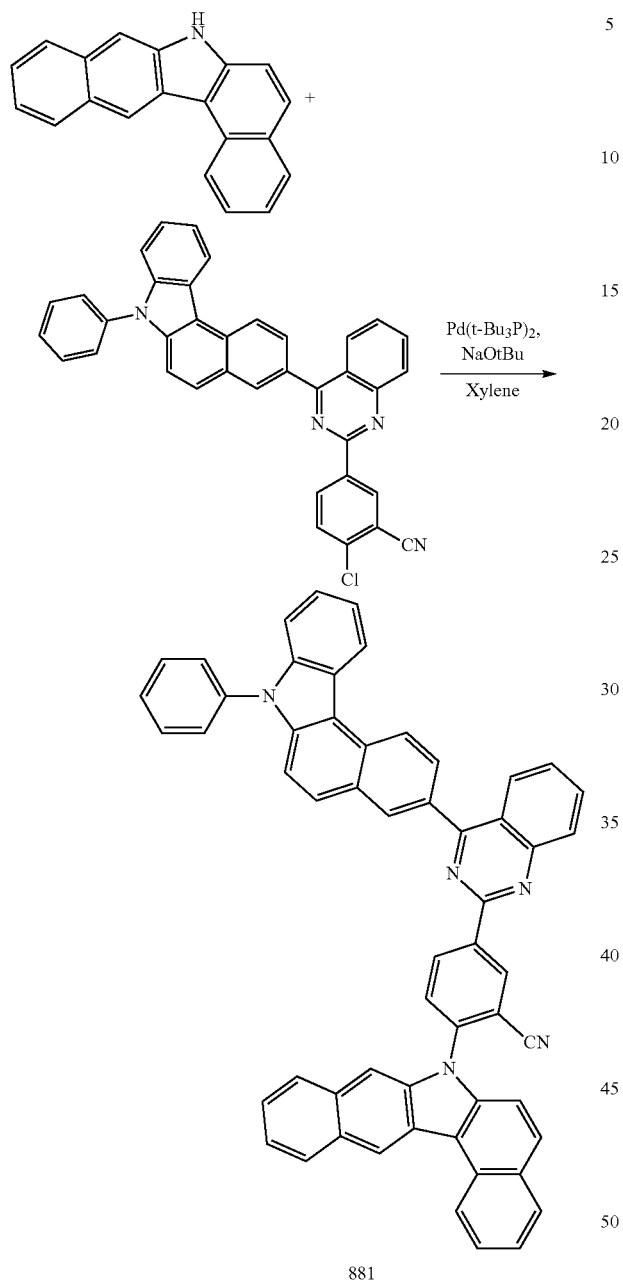

881

Chemical Formula b (10.0 g, 1.0 eq.), 2-chloro-5-(4-(7-phenyl-7H-benzo[c]carbazol-3-yl)quinazolin-2-yl)benzonitrile (22.92 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 881 (21.81 g, yield 74%). [M+H]=788

Synthesis Example 49

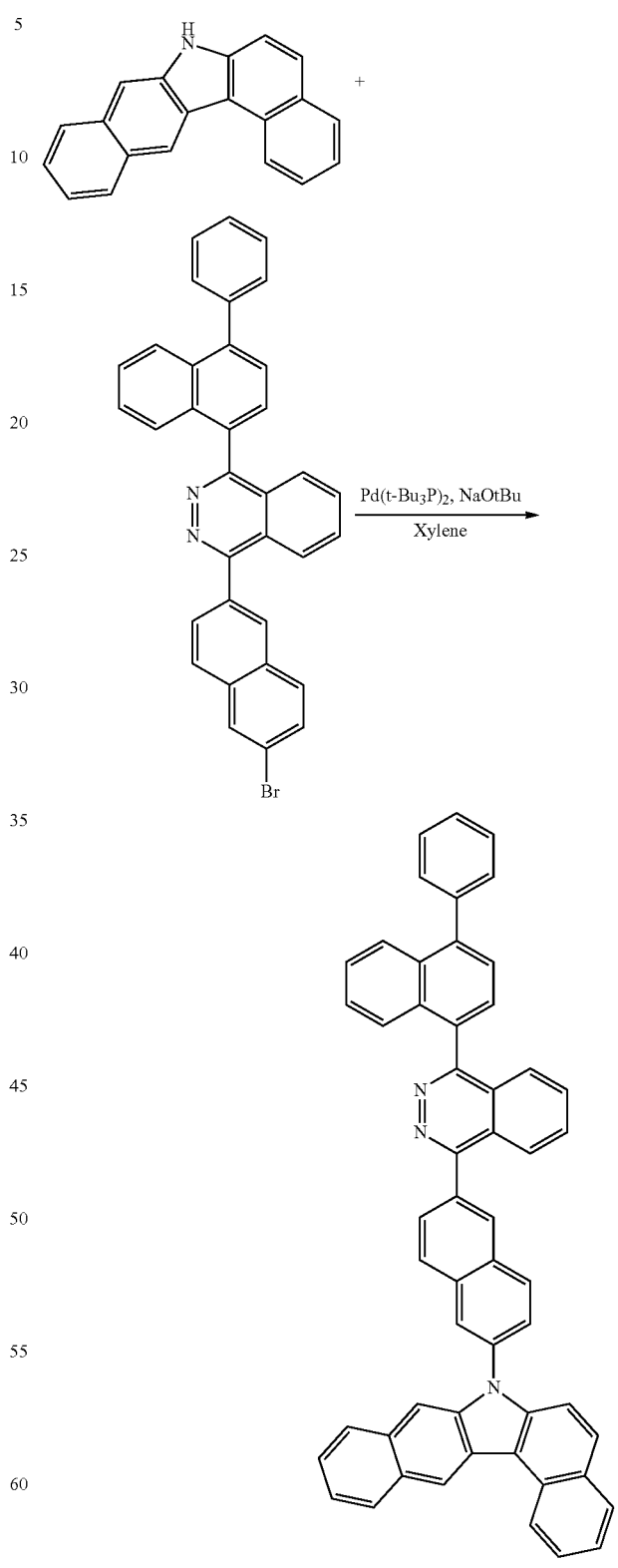

889

Chemical Formula b (10.0 g, 1.0 eq.), 1-(6-bromonaphthalen-2-yl)-4-(4-phenylnaphthalen-1-yl)phthalazine (22.11 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 889 (18.95 g, yield 70%). [M+H]=724

Synthesis Example 50

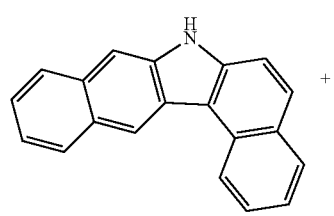
+

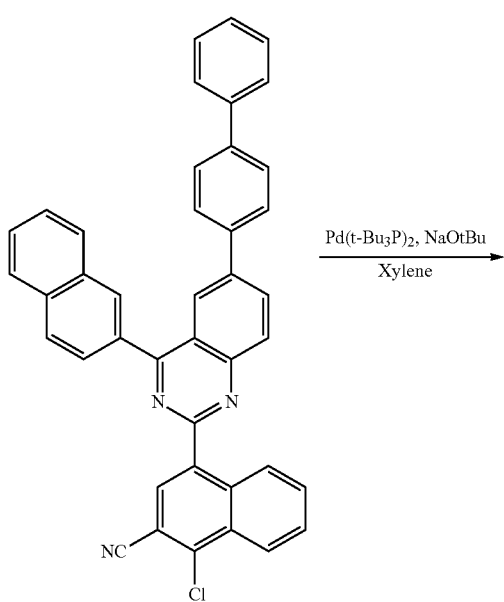

-continued

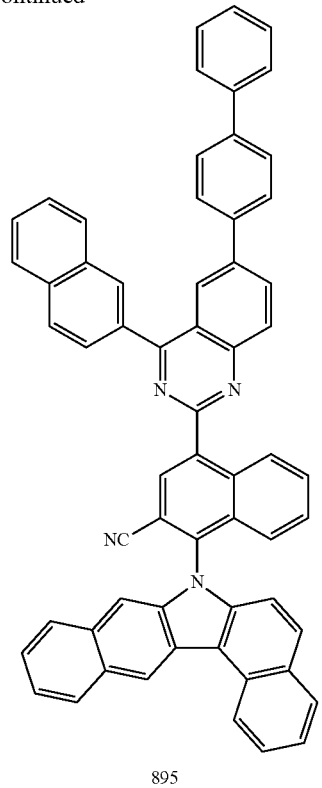

895

Chemical Formula b (10.0 g, 1.0 eq.), 4-(6-([1,1'-biphenyl]-4-yl)-4-(naphthalen-2-yl)quinolin-2-yl)-1-chloro-2-naphthonitrile (24.44 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 895 (22.21 g, yield 72%). [M+H]=825

Synthesis Example 51

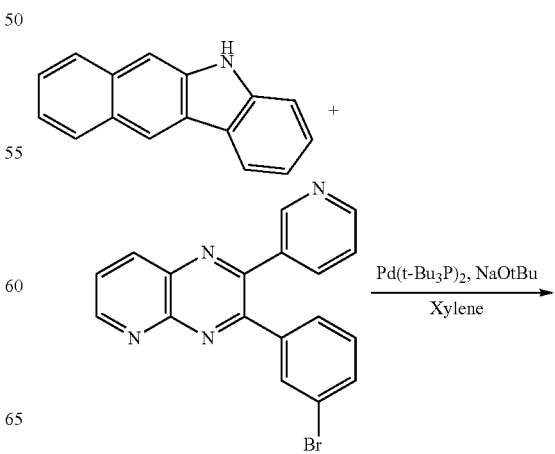

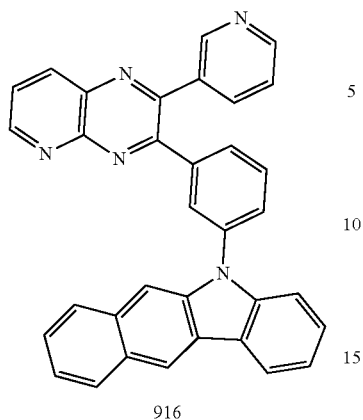

916

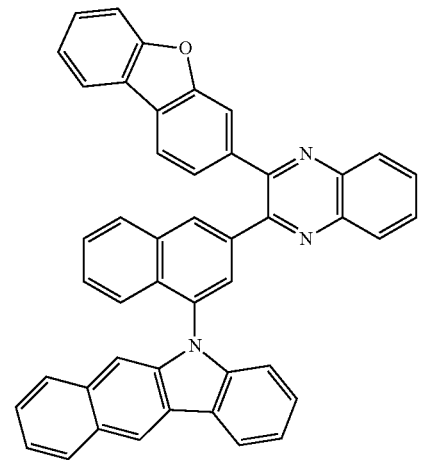

921

Chemical Formula a (10.0 g, 1.0 eq.), 3-(3-bromophenyl)-2-(pyridin-3-yl)pyrido[2,3-b]pyrazine (18.38 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 916 (16.78 g, yield 73%). [M+H]=500

Chemical Formula a (10.0 g, 1.0 eq.), 2-(4-chloronaphthalen-2-yl)-3-(dibenzo[b,d]furan-3-yl)quinoxaline (23.13 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 921 (20.54 g, yield 70%). [M+H]=638

Synthesis Example 52

Synthesis Example 53

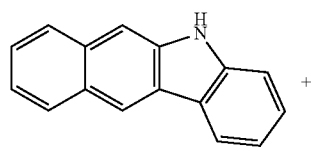 +

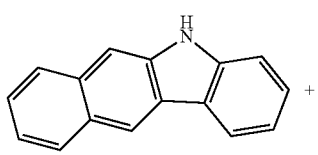 +

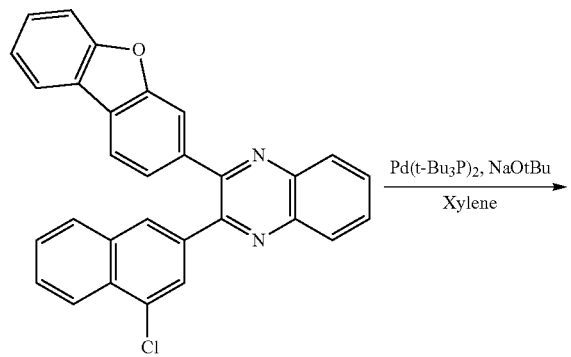 $\xrightarrow{\text{Pd(t-Bu}_3\text{P)}_2\text{, NaOtBu}}_{\text{Xylene}}$

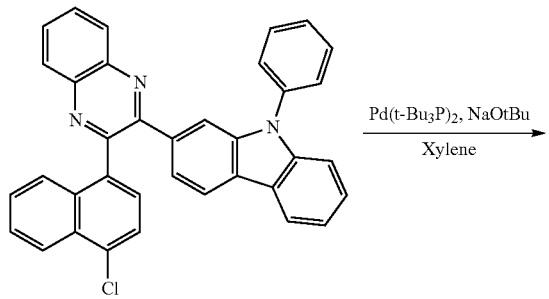 $\xrightarrow{\text{Pd(t-Bu}_3\text{P)}_2\text{, NaOtBu}}_{\text{Xylene}}$

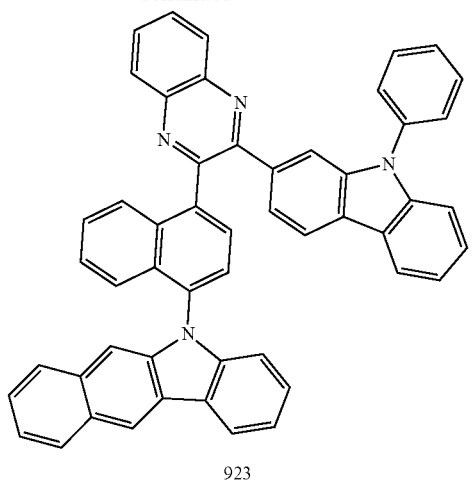

923

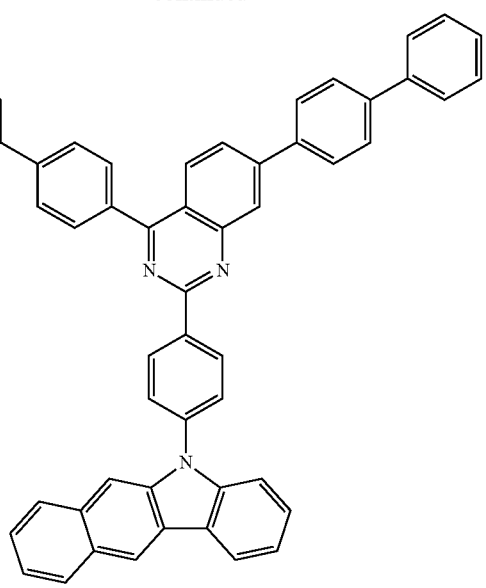

934

Chemical Formula a (10.0 g, 1.0 eq.), 2-(3-(4-chloronaphthalen-1-yl)quinoxalin-2-yl)-9-phenyl-9H-carbazole (26.93 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 923 (24.27 g, yield 74%). [M+H]=713

Synthesis Example 54

Chemical Formula a (10.0 g, 1.0 eq.), 4,7-di([1,1f-biphenyl]-4-yl)-2-(4-bromophenyl)quinazoline (29.84 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 934 (23.72 g, yield 71%). [M+H]=726

Synthesis Example 55

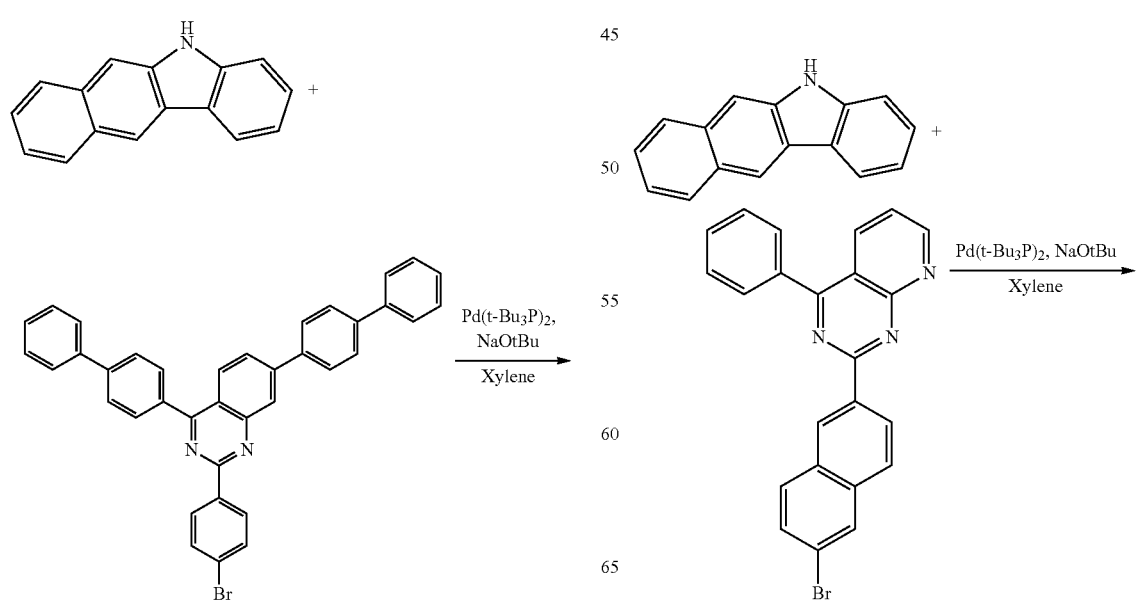

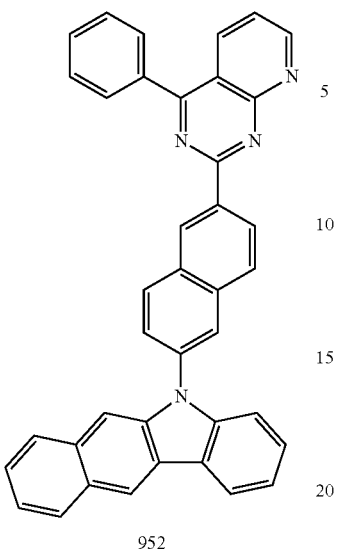

952

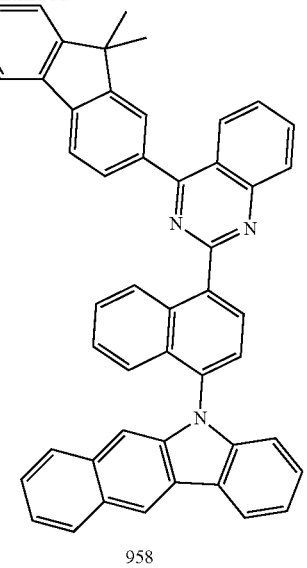

958

Chemical Formula a (10.0 g, 1.0 eq.), 2-(6-bromonaphthalen-2-yl)-4-phenylpyrido[2,3-d]pyrimidine (20.87 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 952 (19.44 g, yield 77%). [M+H]=549

Chemical Formula a (10.0 g, 1.0 eq.), 2-(4-chloronaphthalen-1-yl)-4-(9,9-dimethyl-9H-fluoren-2-yl)quinazoline (24.45 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 958 (22.60 g, yield 74%). [M+H]=664

Synthesis Example 56

Synthesis Example 57

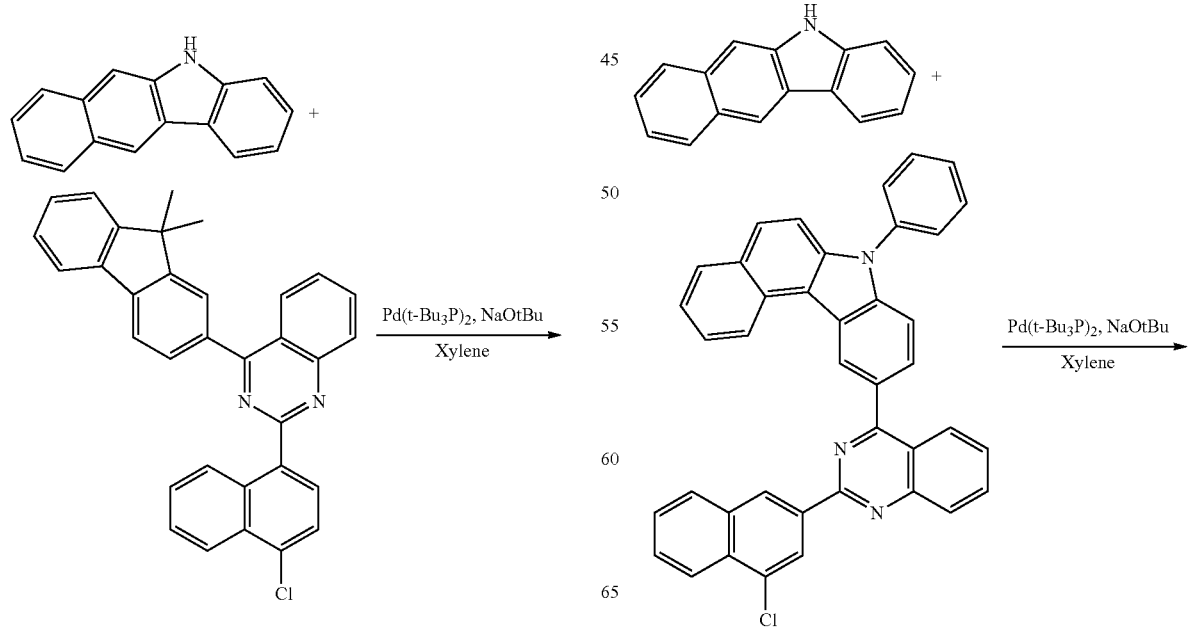

447
-continued

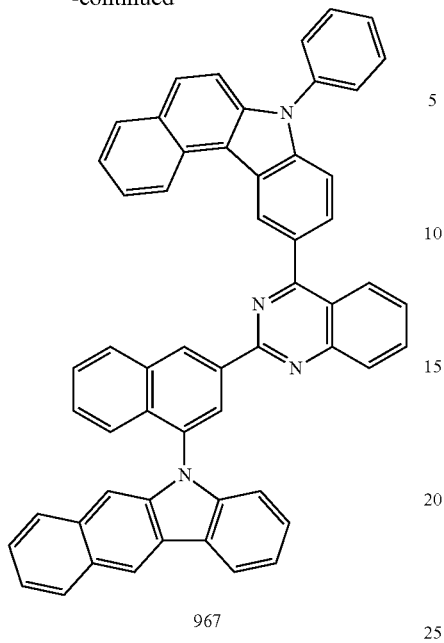

967

Chemical Formula a (10.0 g, 1.0 eq.), 10-(2-(4-chloronaphthalen-2-yl)quinazolin-4-yl)-7-phenyl-7H-benzo[c]carbazole (29.47 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 967 (25.98 g, yield 74%). [M+H]=763

Synthesis Example 58

448
-continued

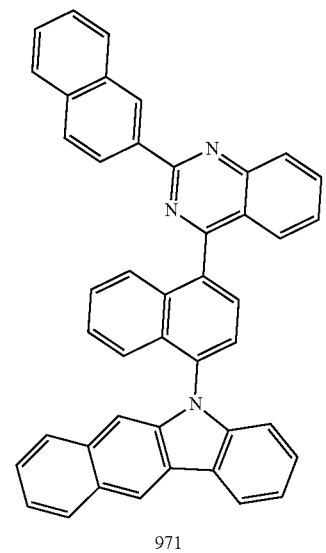

971

Chemical Formula a (10.0 g, 1.0 eq.), 4-(4-chloronaphthalen-1-yl)-2-(naphthalen-2-yl)quinazoline (21.10 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 971 (19.53 g, yield 71%). [M+H]=598

Synthesis Example 59

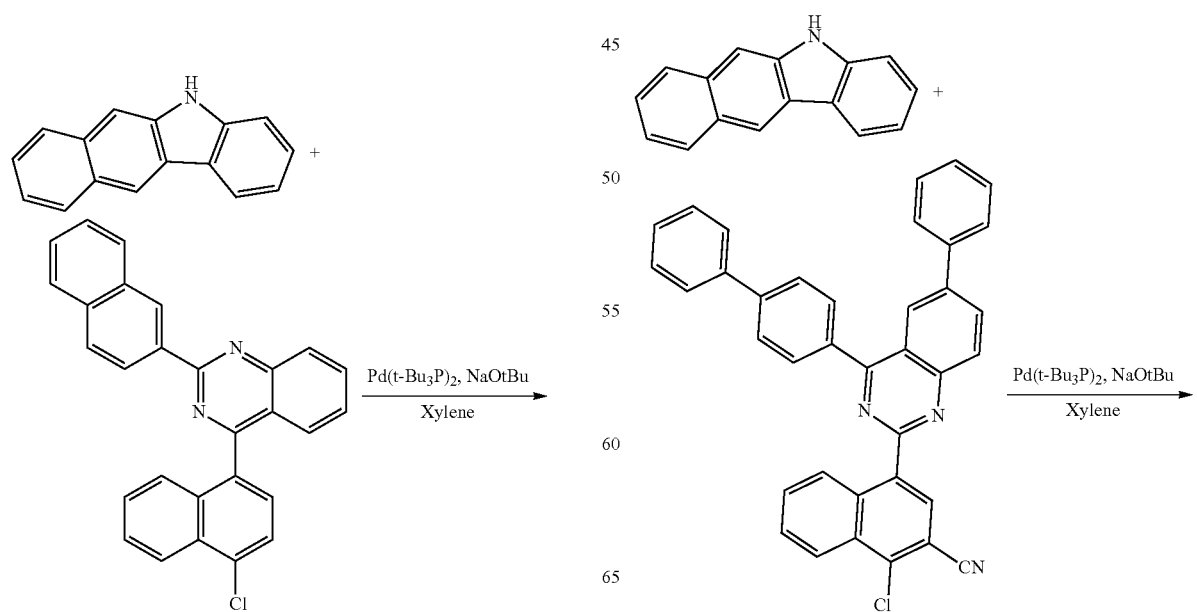

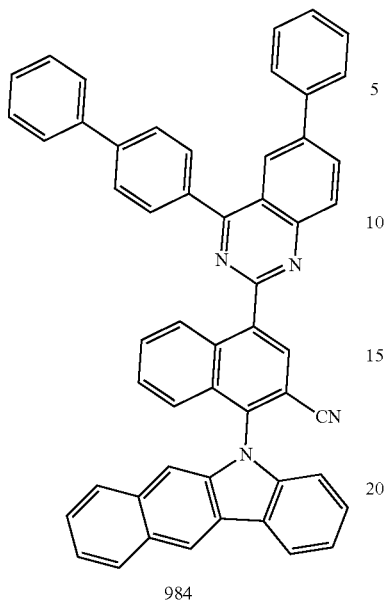

984

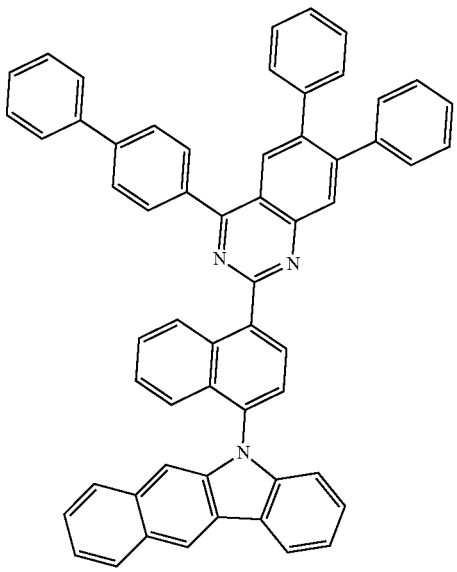

1005

Chemical Formula a (10.0 g, 1.0 eq.), 4-(4-([1,1f-biphenyl]-4-yl)-6-phenylquinazolin-2-yl)-1-chloro-2-naphthonitrile (27.54 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 984 (21.01 g, yield 63%). [M+H]=725

Synthesis Example 60

Chemical Formula a (10.0 g, 1.0 eq.), 4-([1,1'-biphenyl]-4-yl)-2-(4-chloronaphthalen-1-yl)-6,7-diphenylquinazoline (30.13 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1005 (27.49 g, yield 77%). [M+H]=776

Synthesis Example 61

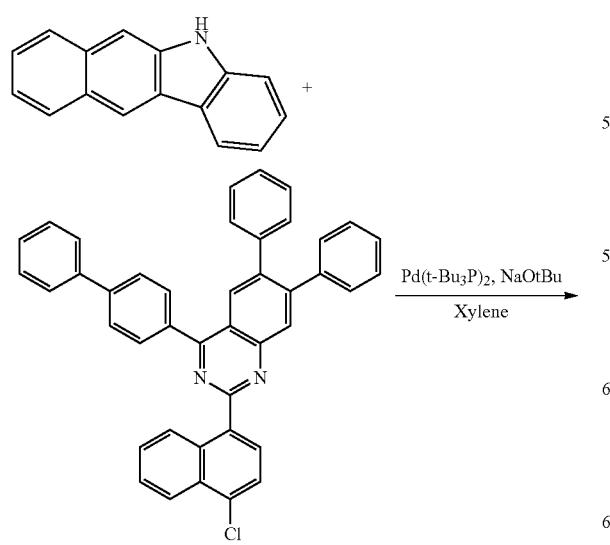

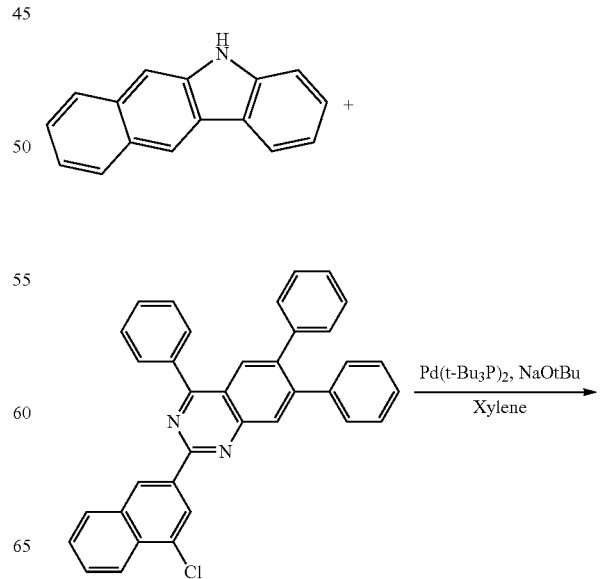

451
-continued

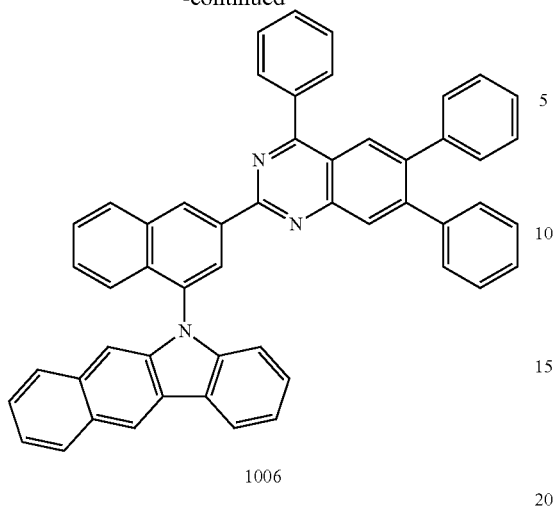

1006

Chemical Formula a (10.0 g, 1.0 eq.), 2-(4-chloronaphthalen-2-yl)-4,6,7-triphenylquinazoline (26.27 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1006 (22.87 g, yield 71%). [M+H]=700

Synthesis Example 62

452
-continued

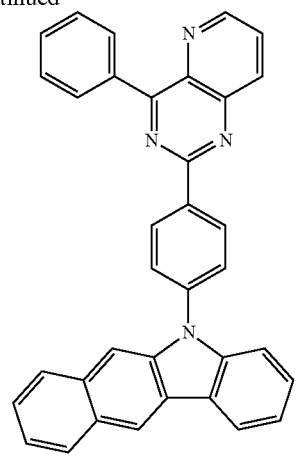

1039

Chemical Formula a (10.0 g, 1.0 eq.), 2-(4-bromophenyl)-4-phenylpyrido[3,2-d]pyrimidine (18.38 g, 1.1 eq.), NaOtBu (7.18 g, 2.0 eq.) and Pd(t-Bu₃P)₂ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl₃, washed with water, and approximately 50% of the solvent was removed under vacuum again. Under reflux again, crystals were dropped while adding ethyl acetate thereto, and the result was cooled and then filtered. This went through column chromatography to obtain Compound 1039 (18.12 g, yield 79%). [M+H]=499

Synthesis Example 63

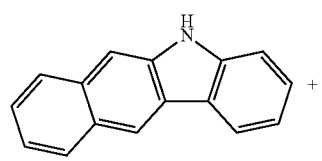

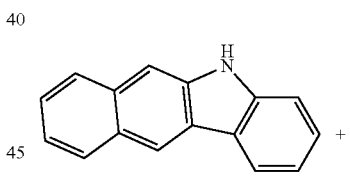

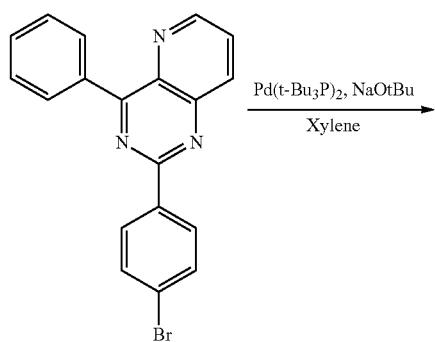

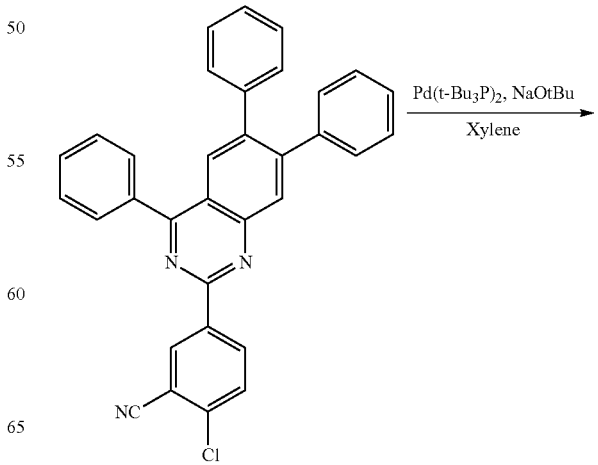

-continued

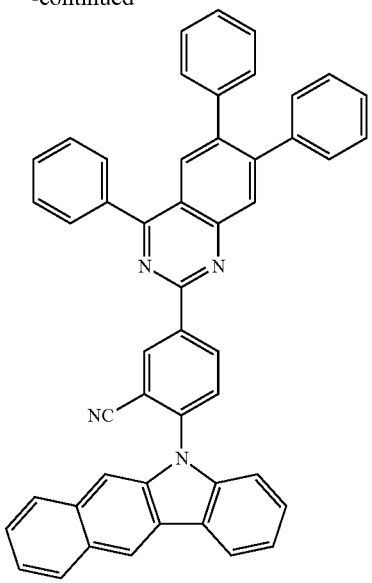

1062

Chemical Formula a (10.0 g, 1.0 eq.), 2-chloro-5-(4,6,7-triphenylquinazolin-2-yl)benzonitrile (25.00 g, 1.1 eq.), NaOtBu (7.18 g, 2.0 eq.) and Pd(t-Bu$_3$P)$_2$ (0.10 g, 0.005 eq.) were dissolved in xylene (250 ml), and the result was stirred under reflux. When the reaction was terminated after 3 hours, the solvent was removed under vacuum. After that, the result was completely dissolved in CHCl$_3$, washed with water, and approximately 50% of the solvent was removed under vacuum again. Under reflux again, crystals were dropped while adding ethyl acetate thereto, and the result was cooled and then filtered. This went through column chromatography to obtain Compound 1062 (20.80 g, yield 67%). [M+H]=675

EXPERIMENTAL EXAMPLE

Comparative Example 1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, the following HI-1 Compound was formed to a thickness of 1150 Å as a hole injection layer with the following A-1 Compound being p-doped in a concentration of 1.5%. A hole transfer layer having a film thickness of 800 Å was formed by vacuum depositing the following HT-1 Compound on the hole injection layer. Subsequently, an electron blocking layer was formed by vacuum depositing the following EB-1 Compound on the hole transfer layer to a film thickness of 150 Å. Then, on the EB-1 deposited film, a red light emitting layer having a thickness of 400 Å was formed by vacuum depositing the following RH-1 Compound and the following Dp-7 Compound in a weight ratio of 98:2. On the light emitting layer, a hole blocking layer was formed by vacuum depositing the following HB-1 Compound to a film thickness of 30 Å. Then, on the hole blocking layer, an electron injection and transfer layer was formed to a thickness of 300 Å by vacuum depositing the following ET-1 Compound and the following LiQ Compound in a weight ratio of 2:1. A cathode was formed on the electron injection and transfer layer by depositing lithium fluoride (LiF) to a thickness of 12 Å and aluminum to a thickness of 1,000 Å in consecutive order.

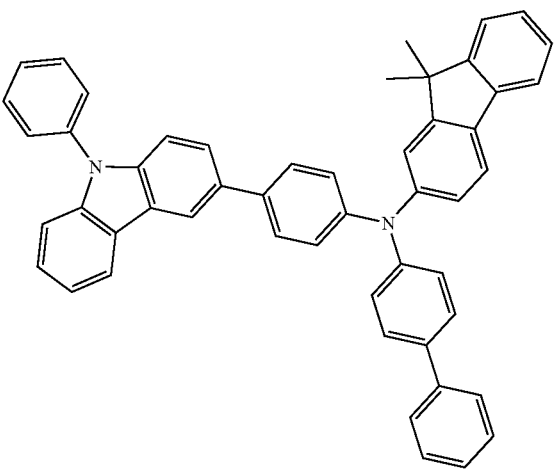

HI-1

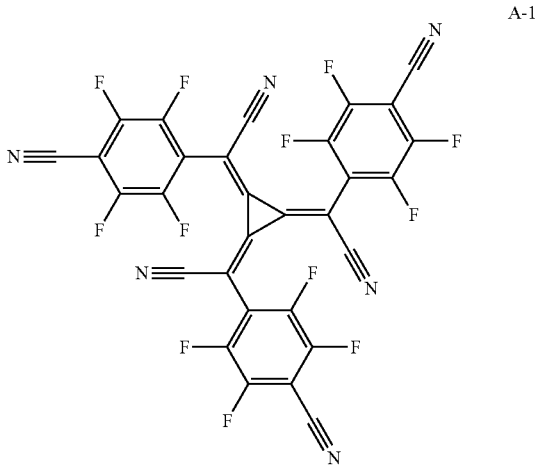

A-1

HT-1
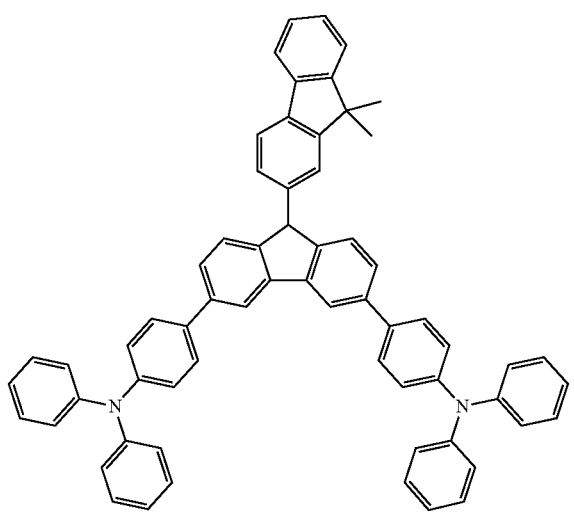
Dp-7
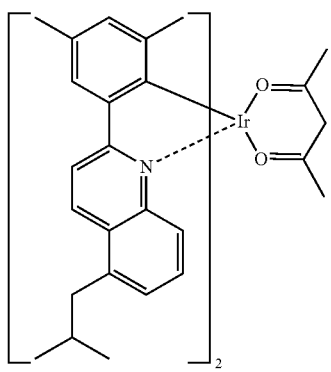
HB-1
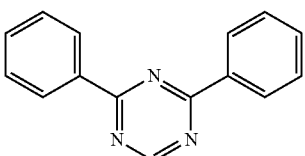
EB-1
ET-1
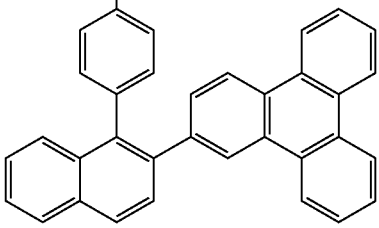
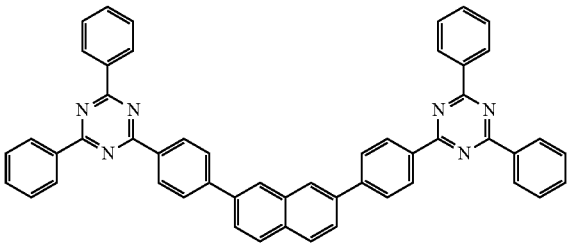
LiQ
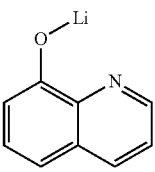
RH-1
RH-2
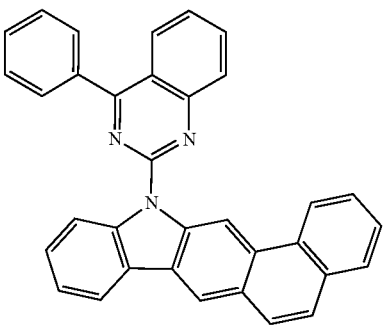

RH-3
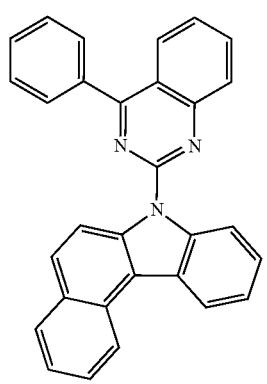
RH-4
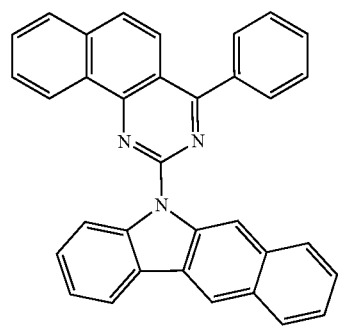
RH-5
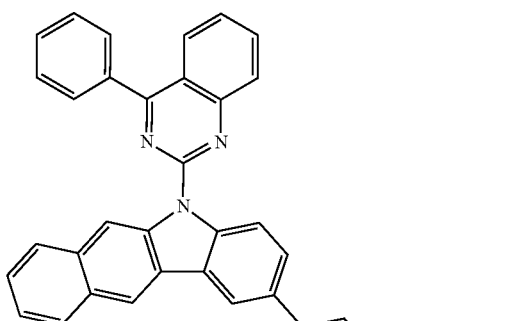
RH-6
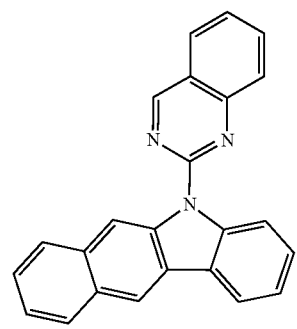
RH-7
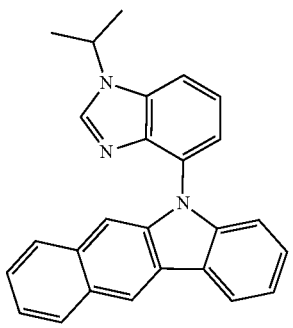
RH-8
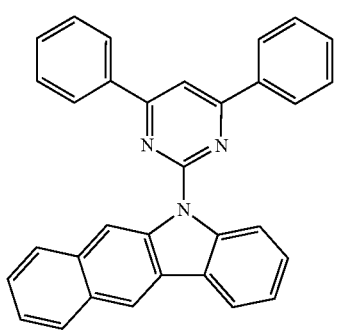
RH-9
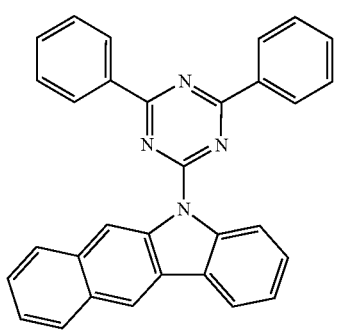
RH-10
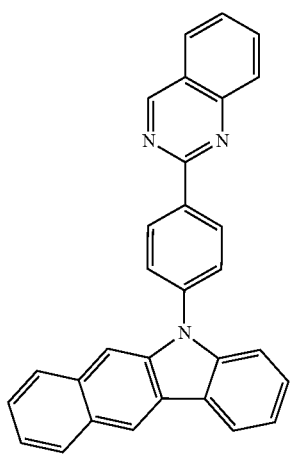

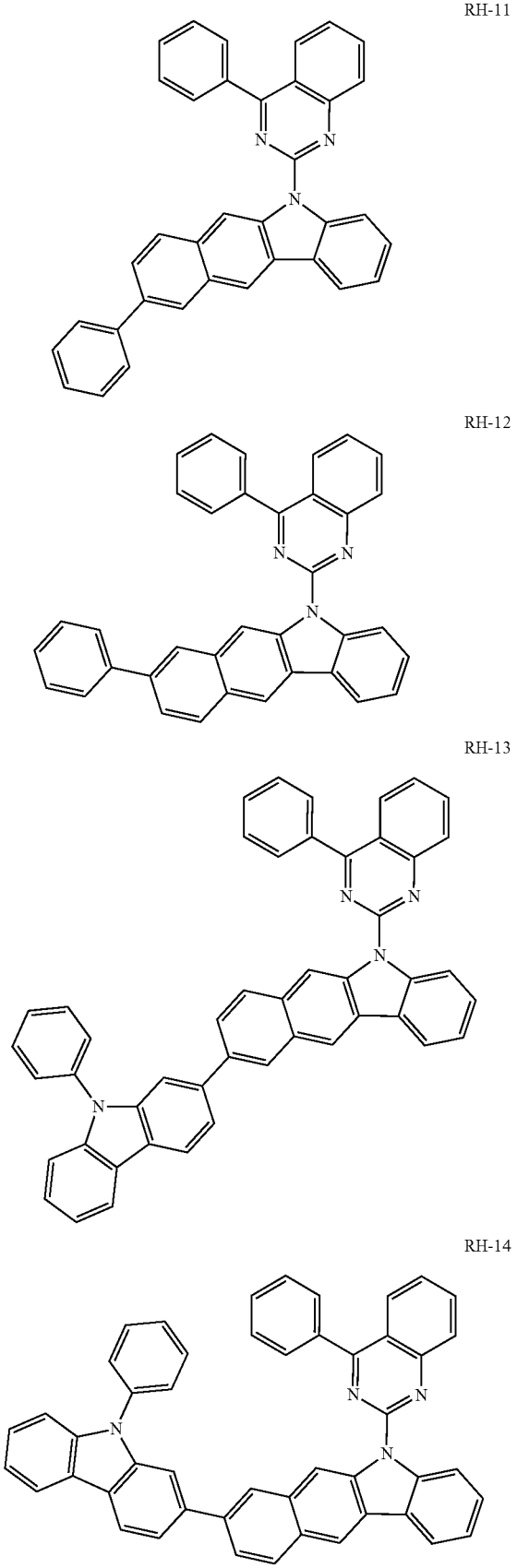

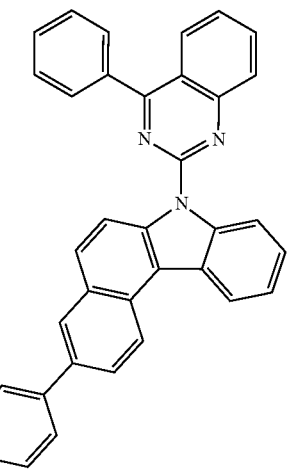

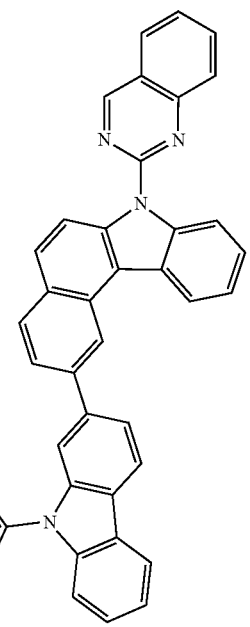

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Comparative Example 2 to Comparative Example 16

Organic light emitting devices were manufactured in the same manner as in Comparative Example 1 except that, in the organic light emitting device of Comparative Example 1, compounds described in the following Table 1 were used instead of RH-1.

Example 1 to Example 63

Organic light emitting devices were manufactured in the same manner as in Comparative Example 1 except that, in the organic light emitting device of Comparative Example 1, compounds described in the following Table 1 were used instead of RH-1.

When a current was applied to the organic light emitting devices manufactured in Example 1 to Example 63, and Comparative Example 1 to Comparative Example 16, a voltage, efficiency and a lifetime were measured, and the results are shown in the following Table 1. T95 means time taken for the luminance decreasing to 95% from its initial luminance (5000 nit).

TABLE 1

| Category | Material | Driving Voltage (V) | Efficiency (cd/A) | Lifetime T95 (hr) | Light Emitting Color |
|---|---|---|---|---|---|
| Comparative Example 1 | RH-1 | 4.51 | 33.8 | 187 | Red |
| Example 1 | Compound 11 | 4.20 | 33.5 | 263 | Red |
| Example 2 | Compound 32 | 4.34 | 35.7 | 293 | Red |
| Example 3 | Compound 65 | 3.95 | 39.8 | 351 | Red |
| Example 4 | Compound 70 | 3.89 | 40.7 | 340 | Red |
| Example 5 | Compound 91 | 3.99 | 37.1 | 317 | Red |
| Example 6 | Compound 95 | 3.97 | 37.8 | 305 | Red |
| Example 7 | Compound 102 | 4.03 | 37.6 | 285 | Red |
| Example 8 | Compound 170 | 4.12 | 38.0 | 257 | Red |
| Example 9 | Compound 182 | 4.19 | 37.9 | 271 | Red |
| Example 10 | Compound 232 | 3.91 | 39.1 | 347 | Red |
| Example 11 | Compound 258 | 4.34 | 32.1 | 220 | Red |
| Example 12 | Compound 287 | 4.42 | 32.1 | 251 | Red |
| Example 13 | Compound 382 | 3.85 | 39.4 | 279 | Red |
| Example 14 | Compound 385 | 3.87 | 40.0 | 268 | Red |
| Example 15 | Compound 389 | 4.01 | 38.7 | 270 | Red |
| Example 16 | Compound 404 | 3.93 | 37.5 | 275 | Red |
| Example 17 | Compound 418 | 3.99 | 38.1 | 239 | Red |
| Example 18 | Compound 429 | 3.95 | 38.7 | 273 | Red |
| Example 19 | Compound 437 | 3.95 | 40.3 | 289 | Red |
| Example 20 | Compound 471 | 4.07 | 38.3 | 321 | Red |
| Example 21 | Compound 522 | 3.95 | 37.1 | 254 | Red |
| Example 22 | Compound 548 | 3.98 | 38.7 | 271 | Red |
| Example 23 | Compound 572 | 4.02 | 39.3 | 285 | Red |
| Example 24 | Compound 583 | 4.07 | 38.8 | 267 | Red |
| Example 25 | Compound 597 | 4.09 | 39.3 | 304 | Red |
| Example 26 | Compound 619 | 3.70 | 37.3 | 271 | Red |
| Example 27 | Compound 630 | 4.10 | 39.3 | 317 | Red |
| Example 28 | Compound 645 | 3.80 | 42.7 | 337 | Red |
| Example 29 | Compound 649 | 3.94 | 40.3 | 323 | Red |
| Example 30 | Compound 660 | 4.11 | 42.3 | 301 | Red |
| Example 31 | Compound 684 | 3.83 | 40.8 | 220 | Red |
| Example 32 | Compound 691 | 3.89 | 41.1 | 225 | Red |
| Example 33 | Compound 714 | 3.92 | 40.9 | 299 | Red |
| Example 34 | Compound 718 | 3.88 | 41.7 | 317 | Red |
| Example 35 | Compound 732 | 3.80 | 39.1 | 263 | Red |
| Example 36 | Compound 738 | 3.76 | 37.1 | 234 | Red |
| Example 37 | Compound 743 | 4.17 | 41.0 | 310 | Red |
| Example 38 | Compound 747 | 3.95 | 42.3 | 298 | Red |
| Example 39 | Compound 758 | 3.92 | 40.1 | 293 | Red |
| Example 40 | Compound 777 | 3.87 | 41.0 | 269 | Red |
| Example 41 | Compound 790 | 3.92 | 40.4 | 272 | Red |
| Example 42 | Compound 791 | 3.94 | 36.1 | 249 | Red |
| Example 43 | Compound 801 | 3.97 | 40.9 | 303 | Red |
| Example 44 | Compound 813 | 3.90 | 42.3 | 283 | Red |
| Example 45 | Compound 848 | 3.73 | 43.3 | 260 | Red |
| Example 46 | Compound 874 | 3.77 | 42.0 | 287 | Red |
| Example 47 | Compound 876 | 3.76 | 40.3 | 271 | Red |
| Example 48 | Compound 881 | 3.81 | 43.8 | 287 | Red |
| Example 49 | Compound 889 | 4.35 | 39.3 | 227 | Red |
| Example 50 | Compound 895 | 4.20 | 37.3 | 193 | Red |
| Example 51 | Compound 916 | 4.31 | 35.3 | 199 | Red |
| Example 52 | Compound 921 | 4.40 | 35.8 | 184 | Red |
| Example 53 | Compound 923 | 3.93 | 42.3 | 281 | Red |
| Example 54 | Compound 934 | 4.07 | 40.3 | 190 | Red |
| Example 55 | Compound 952 | 4.17 | 43.3 | 237 | Red |
| Example 56 | Compound 958 | 3.90 | 41.8 | 271 | Red |
| Example 57 | Compound 967 | 4.13 | 40.7 | 305 | Red |
| Example 58 | Compound 971 | 3.99 | 42.1 | 271 | Red |
| Example 59 | Compound 984 | 3.80 | 40.4 | 203 | Red |
| Example 60 | Compound 1005 | 4.23 | 38.7 | 315 | Red |
| Example 61 | Compound 1006 | 3.93 | 41.1 | 212 | Red |
| Example 62 | Compound 1039 | 3.97 | 39.0 | 207 | Red |
| Example 63 | Compound 1062 | 3.90 | 39.4 | 215 | Red |
| Comparative Example 2 | RH-2 | 4.13 | 37.2 | 131 | Red |
| Comparative Example 3 | RH-3 | 4.81 | 34.1 | 140 | Red |
| Comparative Example 4 | RH-4 | 4.30 | 35.1 | 167 | Red |
| Comparative Example 5 | RH-5 | 4.68 | 33.0 | 79 | Red |
| Comparative Example 6 | RH-6 | 4.41 | 32.4 | 97 | Red |

TABLE 1-continued

| Category | Material | Driving Voltage (V) | Efficiency (cd/A) | Lifetime T95 (hr) | Light Emitting Color |
|---|---|---|---|---|---|
| Comparative Example 7 | RH-7 | 4.77 | 29.7 | 61 | Red |
| Comparative Example 8 | RH-8 | 4.21 | 34.0 | 103 | Red |
| Comparative Example 9 | RH-9 | 4.19 | 35.7 | 114 | Red |
| Comparative Example 10 | RH-10 | 4.71 | 31.3 | 73 | Red |
| Comparative Example 11 | RH-11 | 4.52 | 32.1 | 137 | Red |
| Comparative Example 12 | RH-12 | 4.57 | 31.1 | 130 | Red |
| Comparative Example 13 | RH-13 | 4.44 | 34.1 | 147 | Red |
| Comparative Example 14 | RH-14 | 4.49 | 34.7 | 140 | Red |
| Comparative Example 15 | RH-15 | 4.62 | 33.1 | 107 | Red |
| Comparative Example 16 | RH-16 | 4.41 | 33.4 | 118 | Red |

When applying a current to the organic light emitting devices manufactured in Examples 1 to 63 and Comparative Examples 1 to 16, results of Table 1 were obtained. The red organic light emitting device of Comparative Example 1 used materials that have been widely used in the art, and had a structure using Compound [EB-1] as an electron blocking layer and using RH-1/Dp-7 as a red light emitting layer. Comparative Examples 2 to 16 manufactured organic light emitting devices using RH-2 to RH-16 instead of RH-1. When examining the results of Table 1, it was seen that, when using the benzocarbazole-based compound of the present disclosure as a host of a red light emitting layer, energy transfer from a host to a red dopant was well achieved from the fact that a driving voltage decreased closer to as much as 30% and efficiency increased by 25% or greater compared to the materials in the comparative examples. In addition, it was seen that lifetime properties were greatly improved by a factor of two or more while maintaining high efficiency. This may ultimately be due to the fact that the compounds of the present disclosure have higher stability for electrons and holes compared to the compounds of the comparative examples. As a result, it can be identified that, when using the compound of the present disclosure as a host of a red light emitting layer, a driving voltage, light emission efficiency and lifetime properties of an organic light emitting device are improved.

DESCRIPTION OF DRAWINGS

FIG. 1 illustrates an example of an organic light emitting device formed with a substrate (1), an anode (2), a light emitting layer (3) and a cathode (4).

FIG. 2 illustrates an example of an organic light emitting device formed with a substrate (1), an anode (2), a hole injection layer (5), a hole transfer layer (6), an electron blocking layer (7), a light emitting layer (8), a hole blocking layer (9), an electron injection and transfer layer (10) and a cathode (4).

FIG. 3 shows a graph measuring 1H-NMR of Chemical Formula a.

FIG. 4 shows a graph measuring LC/MS of Chemical Formula a.

FIG. 5 shows a graph measuring 1H-NMR of Compound 747.

1: Substrate
2: Anode
3: Light Emitting Layer
4: Cathode
5: Hole Injection Layer
6: Hole Transfer Layer
7: Electron Blocking Layer
8: Light Emitting Layer
9: Hole Blocking Layer
10: Electron Injection and Transfer Layer

The invention claimed is:
1. A benzocarbazole-based compound represented by the following Chemical Formula 1:

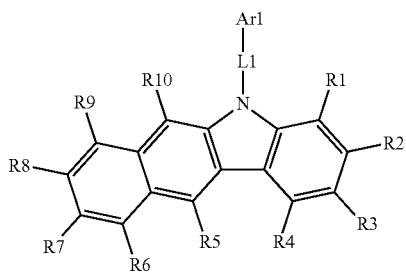

[Chemical Formula 1]

wherein in Chemical Formula 1,
R1 to R10 are each independently hydrogen or deuterium, or R1 and R2, R2 and R3, or R3 and R4 among R1 to R10 bond to each other to form a benzene ring, and the rest are each independently hydrogen or deuterium,
L1 is a direct bond; or a phenylene group unsubstituted or substituted with deuterium or a nitrile group; or a naphthylene group unsubstituted or substituted with deuterium or a nitrile group, and Ar1 is represented by the following Chemical Formula 3:

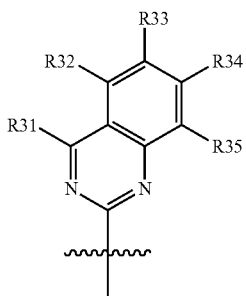

[Chemical Formula 3]

wherein in Chemical Formula 3,
R31 is a phenyl group substituted with an aryl group having 10 to 60 carbon atoms; an aryl group selected from the group consisting of a naphthyl group, a biphenyl group, a phenanthrenyl group, a triphenylene group, a terphenyl group, a fluorenyl group, a benzofluorenyl group, each of which is unsubstituted or substituted with one or more groups selected from the group consisting of deuterium, a nitrile group, an alkyl group having 1 to 30 carbon atoms, an aryl group having 6 to 60 carbon atoms, a heteroaryl group having 2 to 60 carbon atoms, and a group formed by combining two or more thereof; or a heteroaryl group selected from the group consisting of a carbazole group, a dibenzofuranyl group, a dibenzothiophenyl group, a benzocarbazole group, a naphthobenzofuranyl group, and a naphthobenzothiophenyl group, each of which is unsubstituted or substituted with one or more groups selected from the group consisting of deuterium, a nitrile group, an alkyl group having 1 to 30 carbon atoms, an aryl group having 6 to 60 carbon atoms, a heteroaryl group having 2 to 60 carbon atoms, and a group formed by combining two or more thereof, R32 to R35 are the same as or different from each other, and each independently hydrogen; an aryl group having 6 to 40 carbon atoms unsubstituted or substituted with one or more groups selected from the group consisting of deuterium, a nitrile group, an alkyl group having 1 to 30 carbon atoms, an aryl group having 6 to 60 carbon atoms, and a heteroaryl group having 2 to 60 carbon atoms, and a group formed by combining two or more thereof; or a heteroaryl group having 2 to 40 carbon atoms unsubstituted or substituted with one or more groups selected from the group consisting of deuterium, a nitrile group, an alkyl group having 1 to 30 carbon atoms, an aryl group having 6 to 60 carbon, a heteroaryl group having 2 to 60 carbon atoms, and a group formed by combining two or more thereof.

2. The benzocarbazole-based compound of claim 1, wherein Chemical Formula 1 is represented by any one of the following Chemical Formulae 19 to 22:

[Chemical Formula 19]

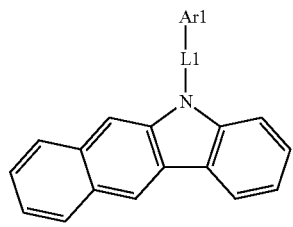

[Chemical Formula 20]

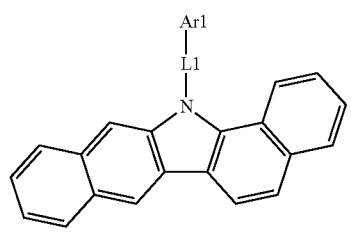

[Chemical Formula 21]

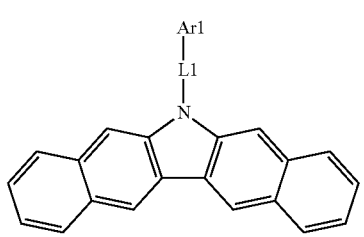

[Chemical Formula 22]

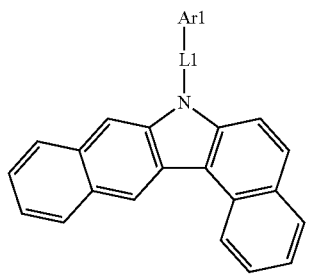

in Chemical Formulae 19 to 22,

Ar1 and L1 have the same definitions as in Chemical Formula 1.

3. The benzocarbazole-based compound of claim 1, wherein Chemical Formula 1 is represented by any one of the following compounds:

49

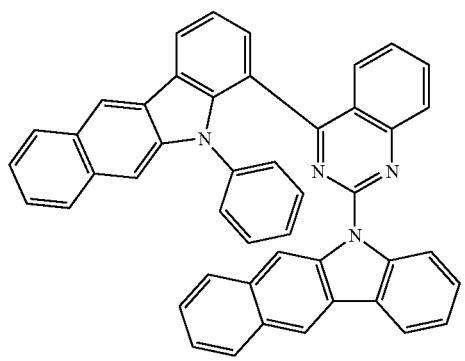

50

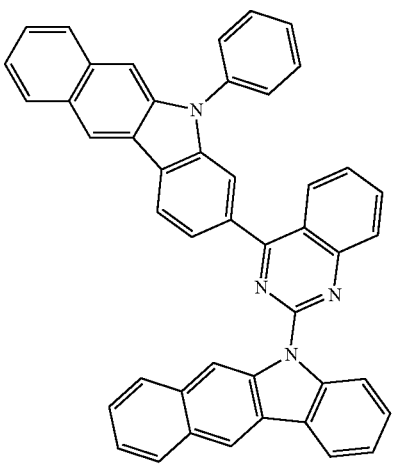

51
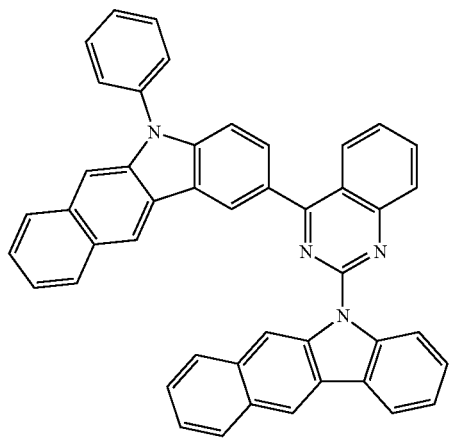
52
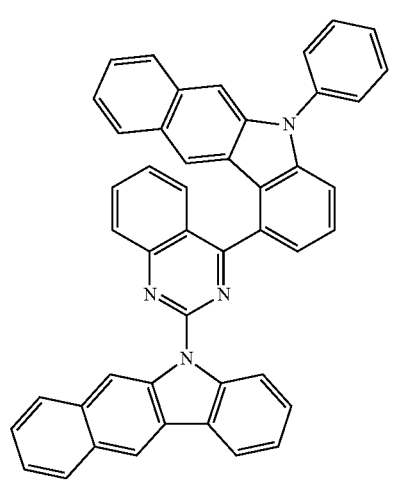
53
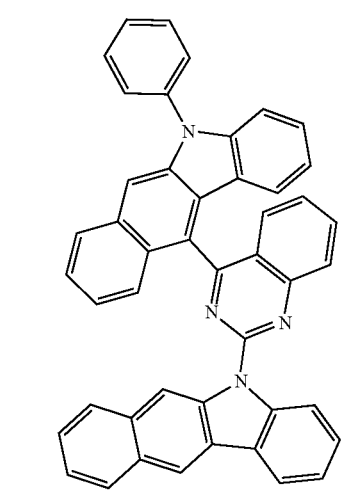
54
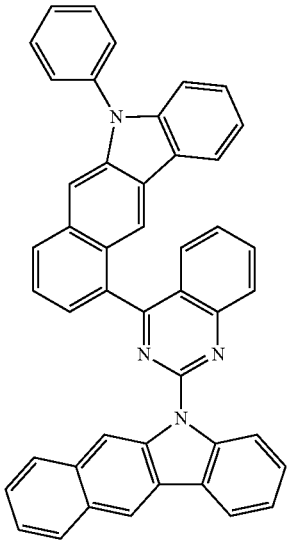
55
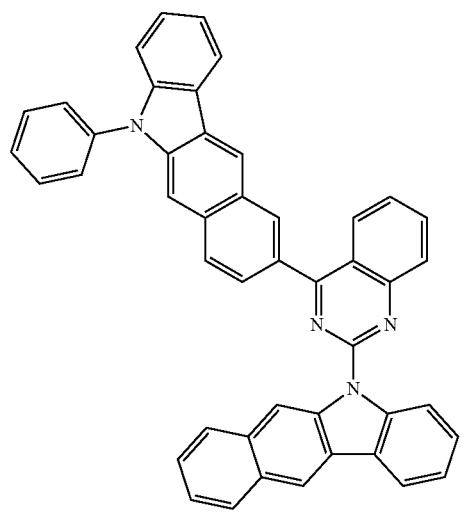
56
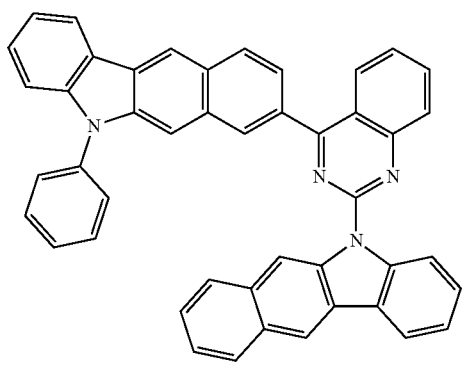

469
-continued
57
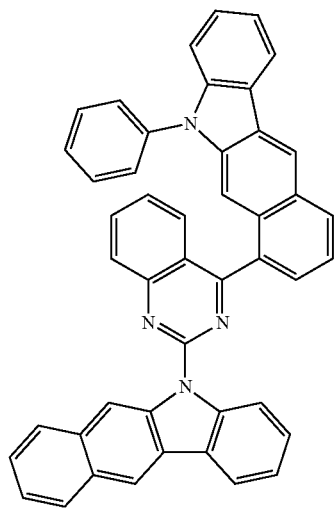
58
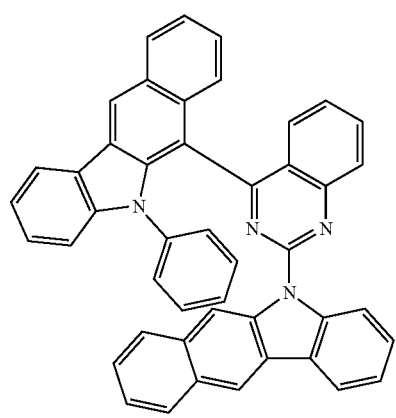
59
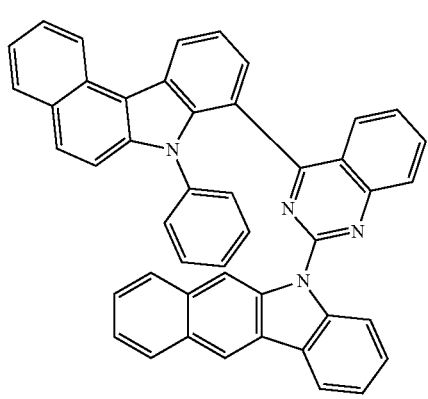
470
-continued
60
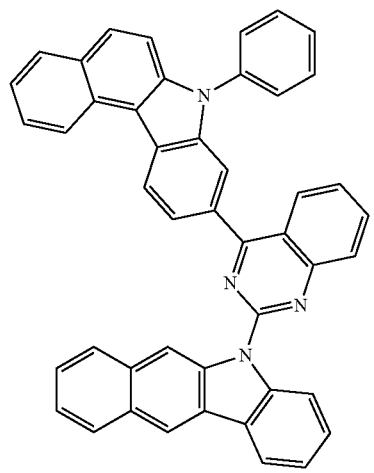
61
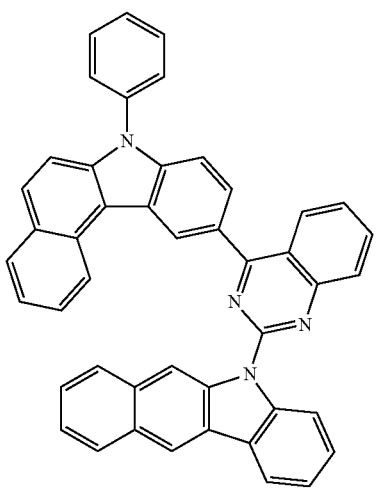
62
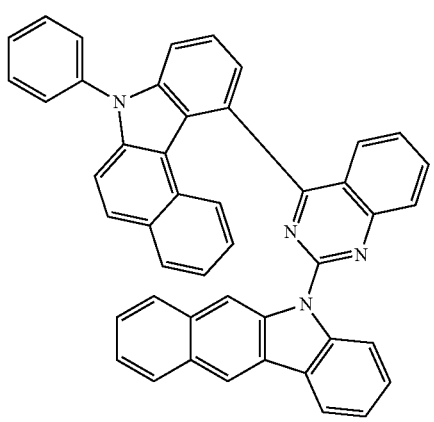

63
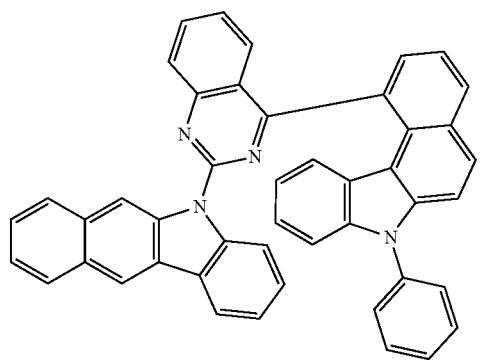
64
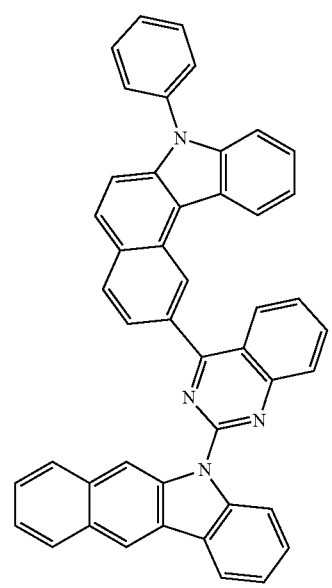
65
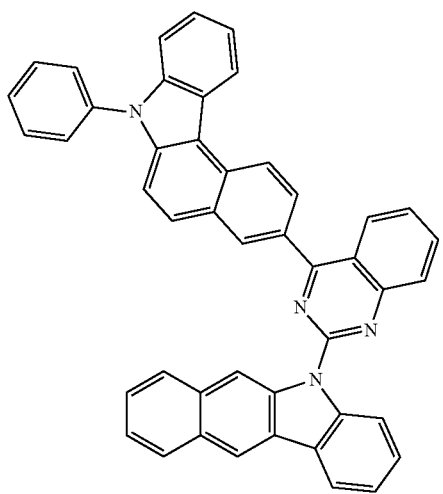
66
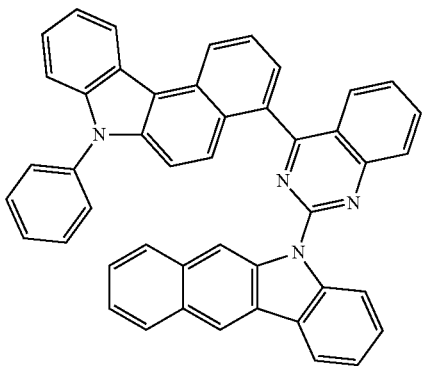
67
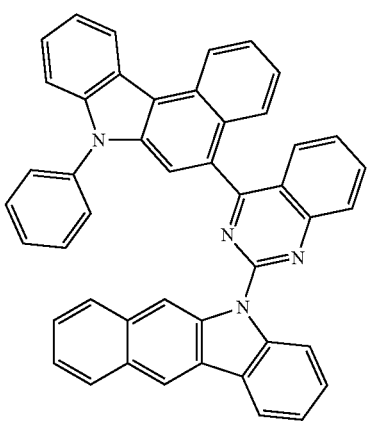
68
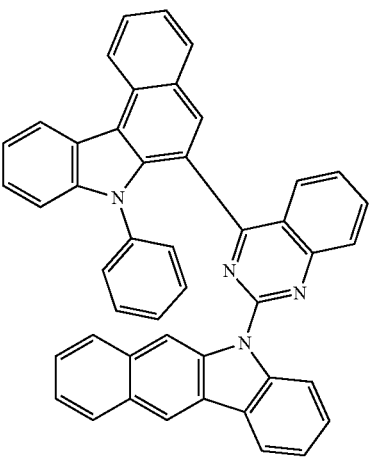
69
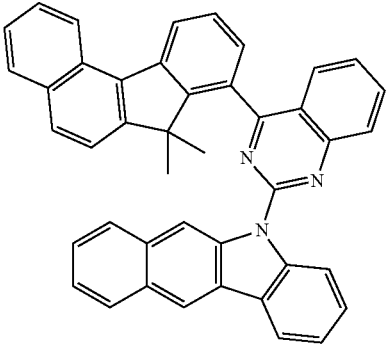

473
-continued
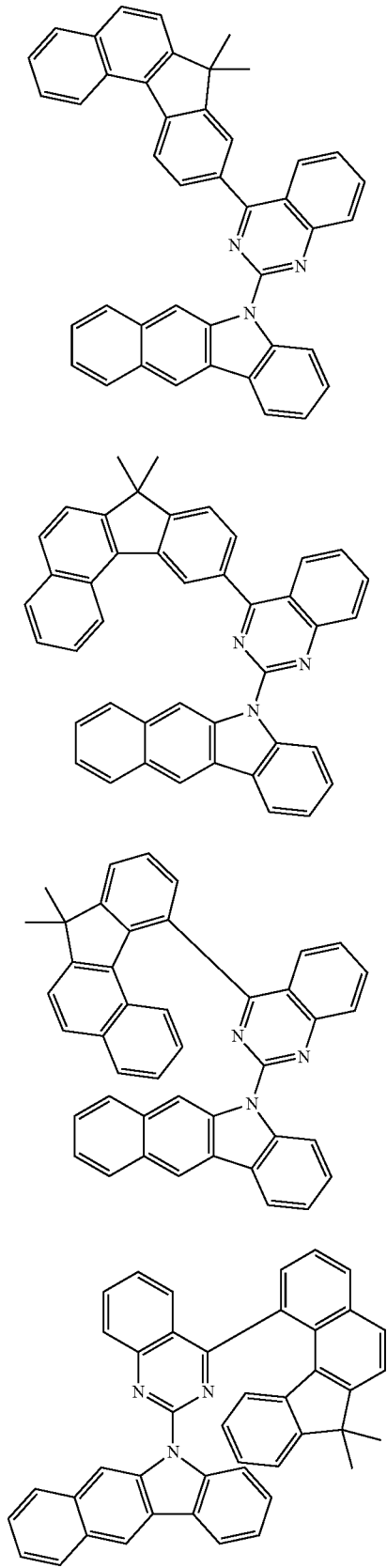
474
-continued
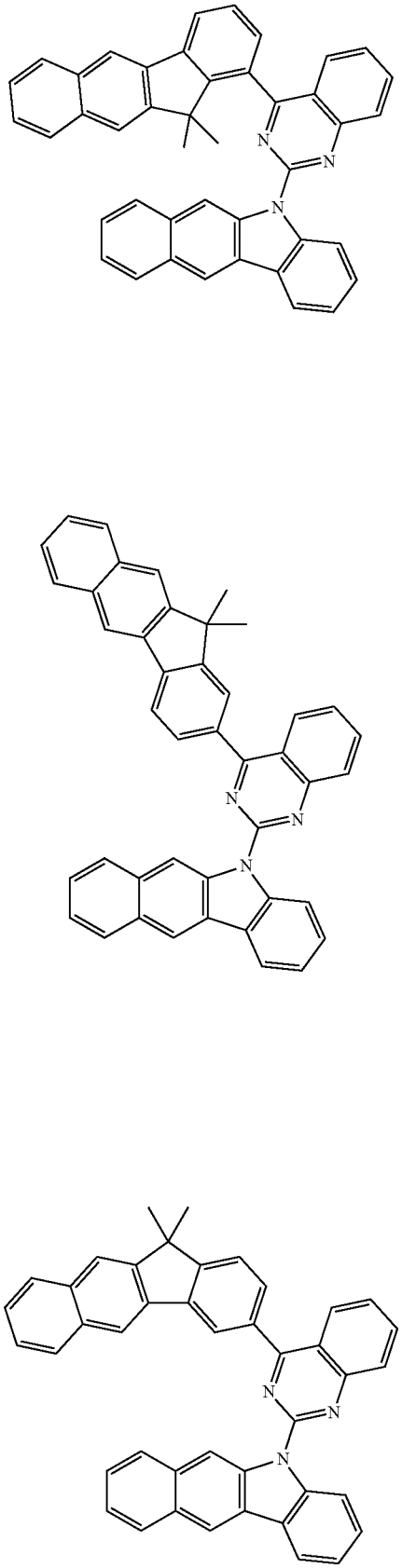

-continued
77
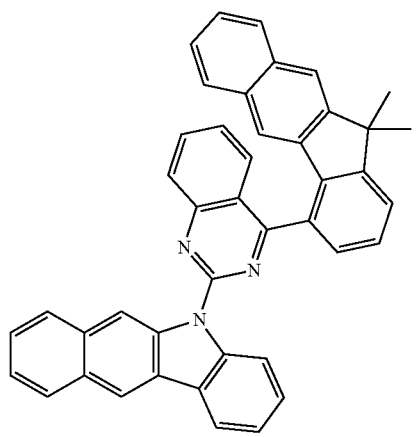
78
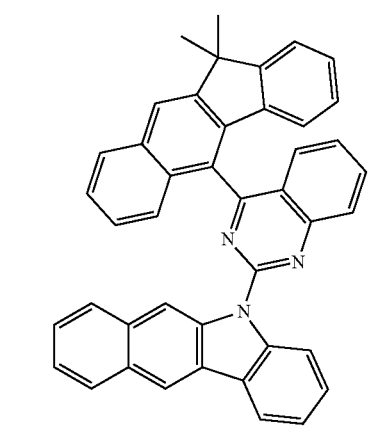
79
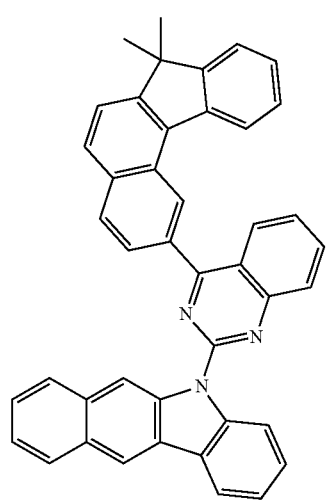
-continued
80
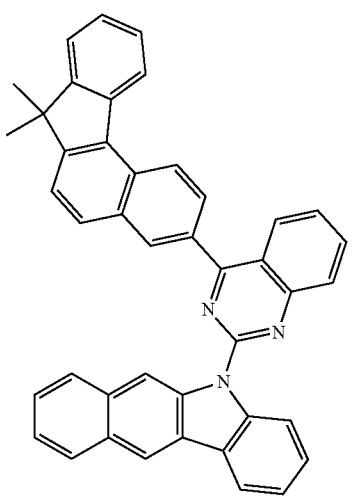
81
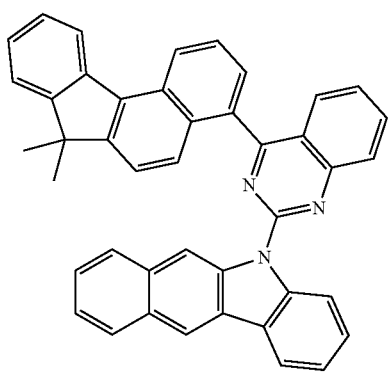
82
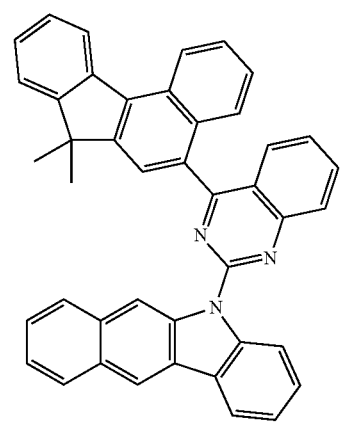

83
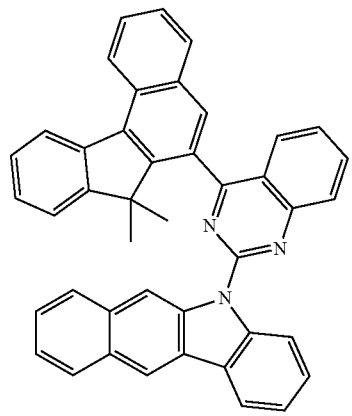
84
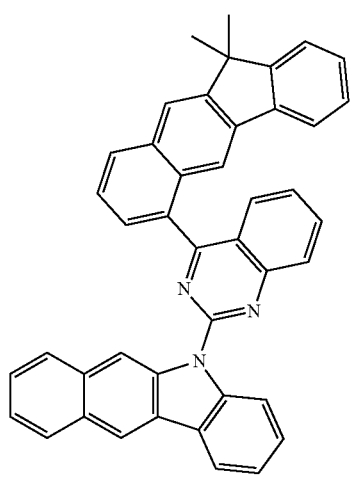
85
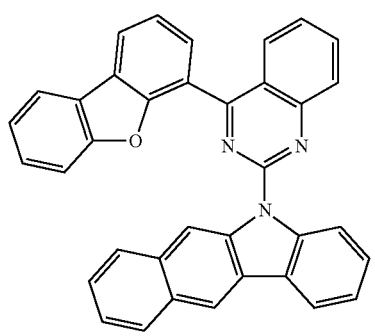
86
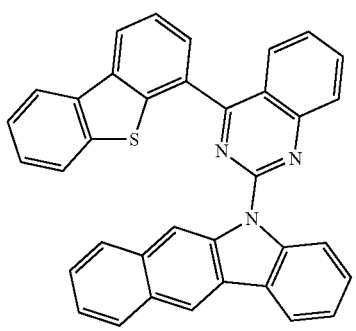
87
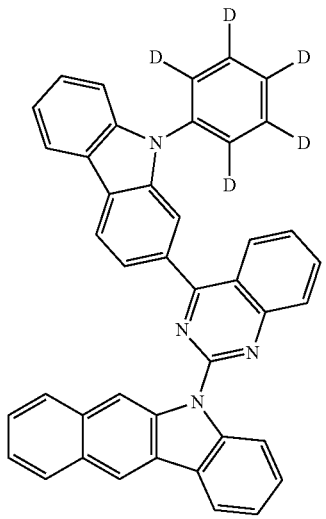
88
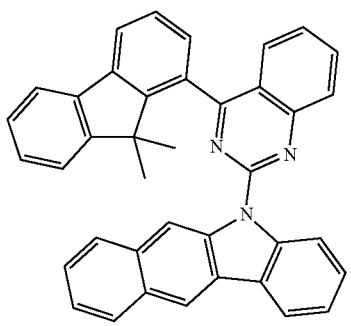
122
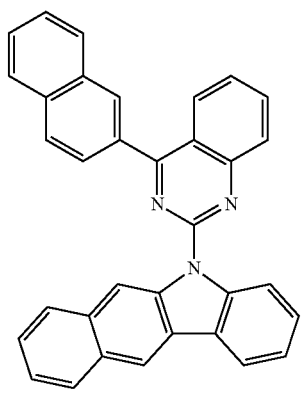
123
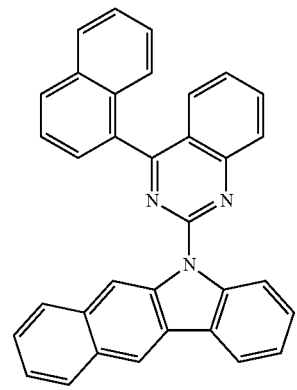

124
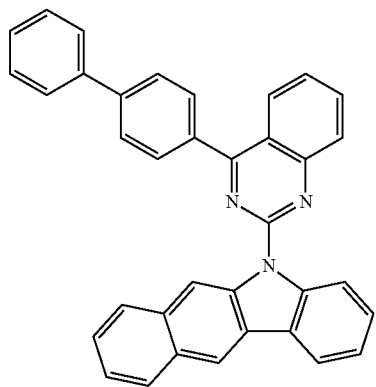
125
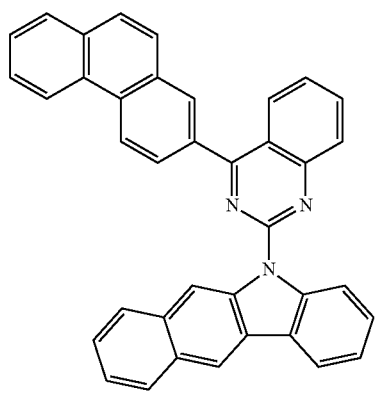
126
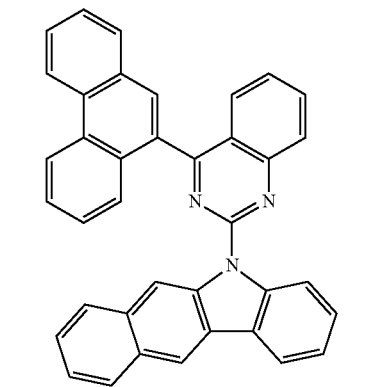
127
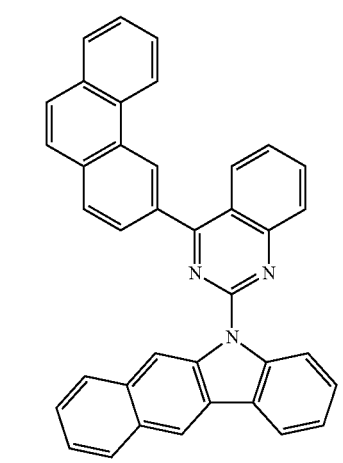
128
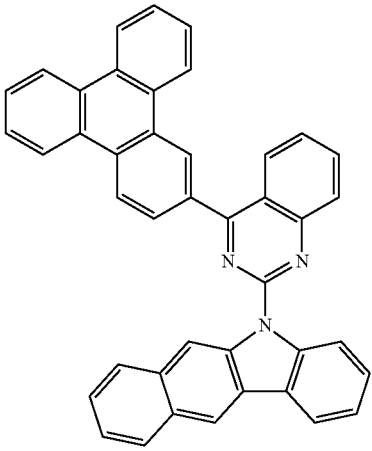
129
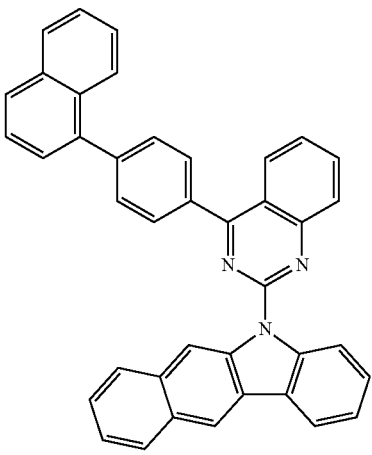
130
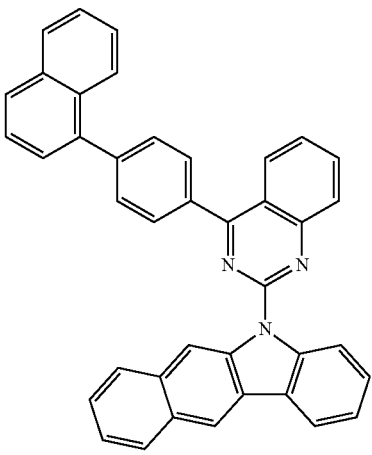

481
-continued
132
134
135
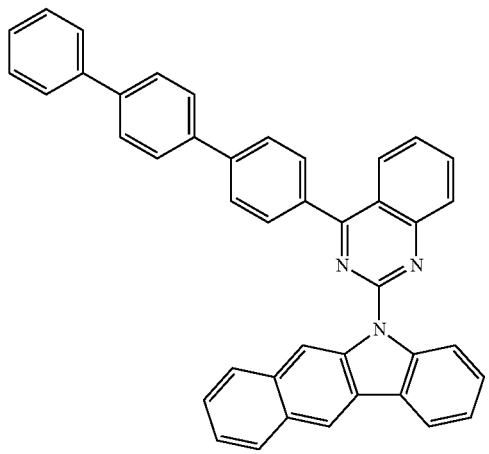
131
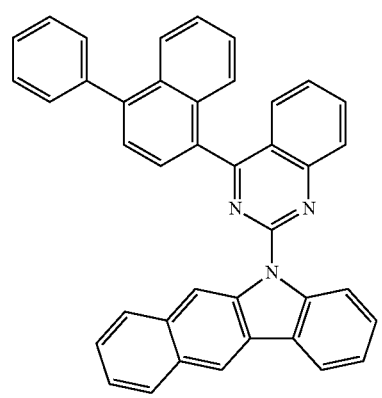
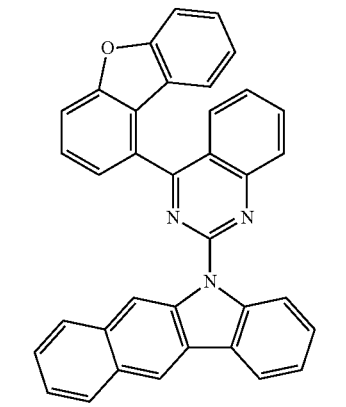
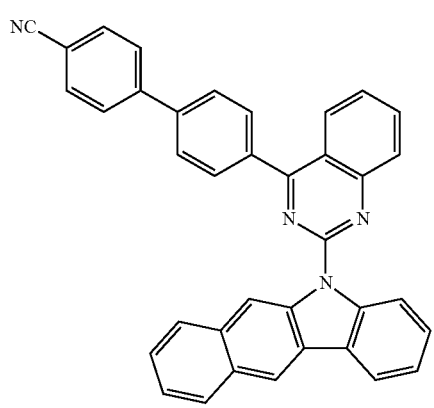
482
-continued
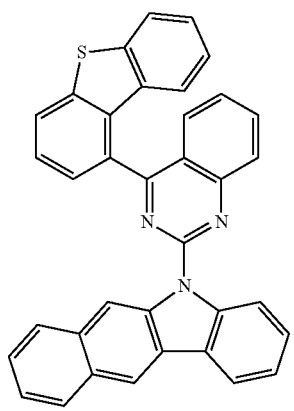
136
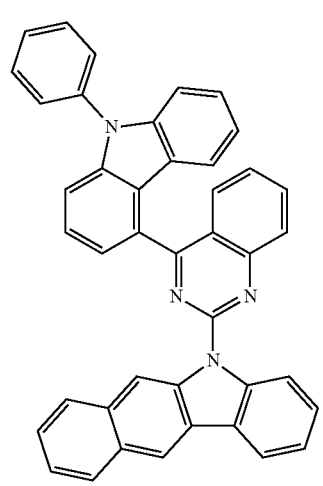
137
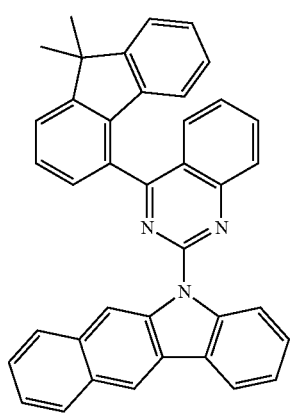
139

483
-continued
484
-continued
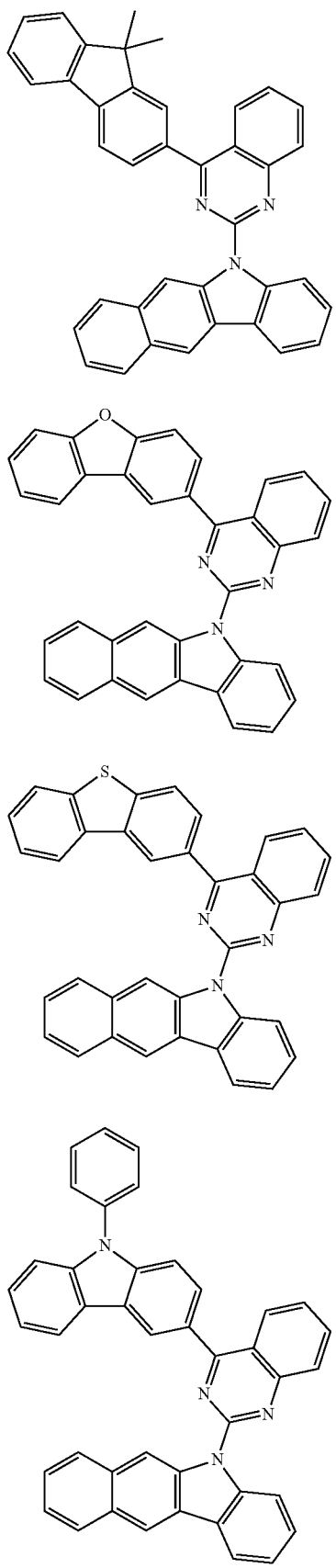
142
145
146
147
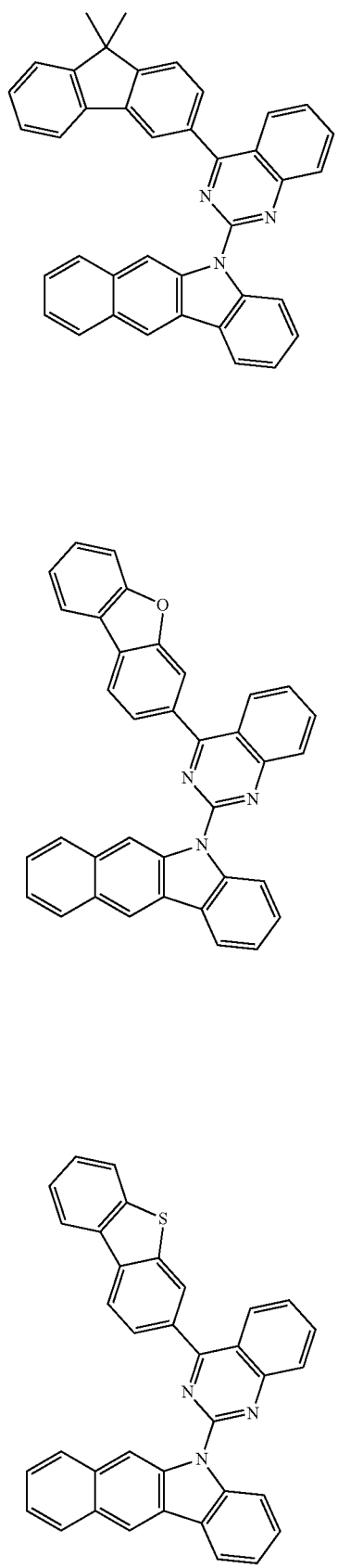
148
151
153

485
-continued
154
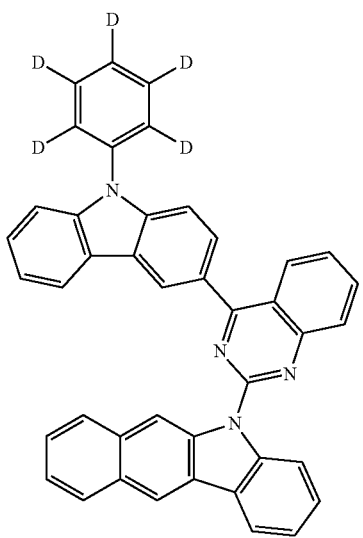
155
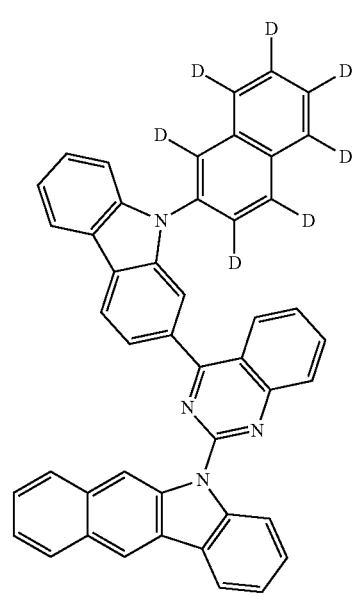
156
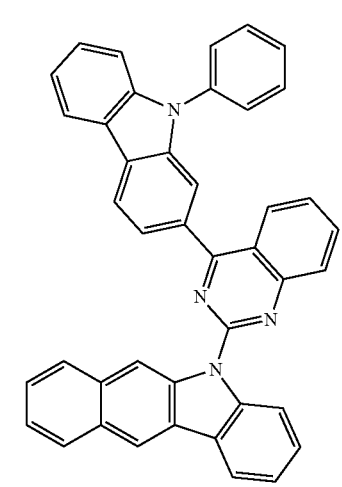
486
-continued
199
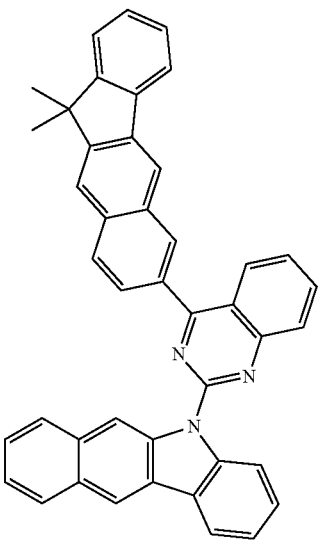
200
201

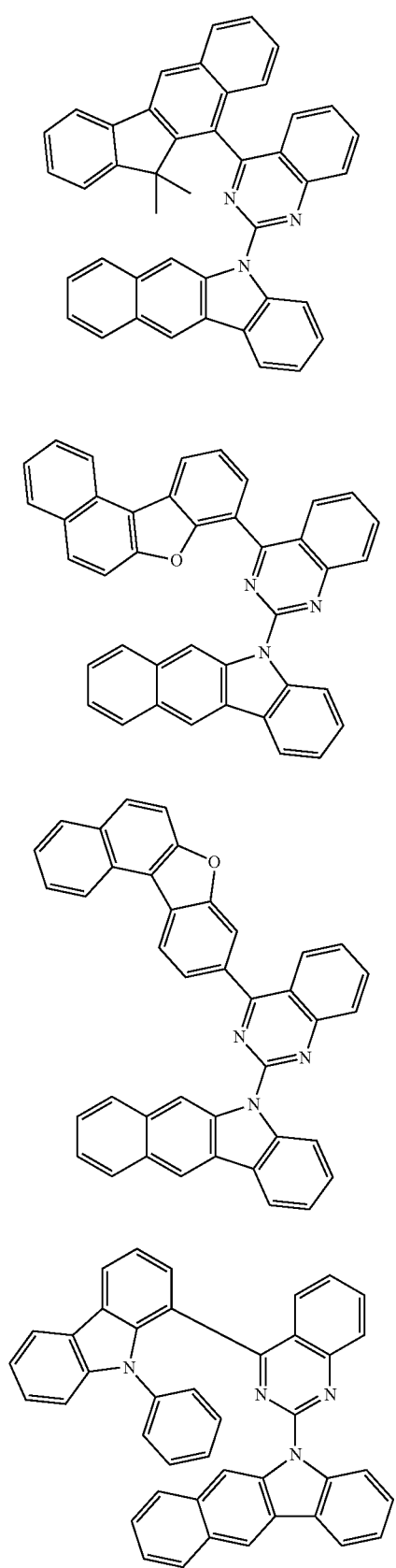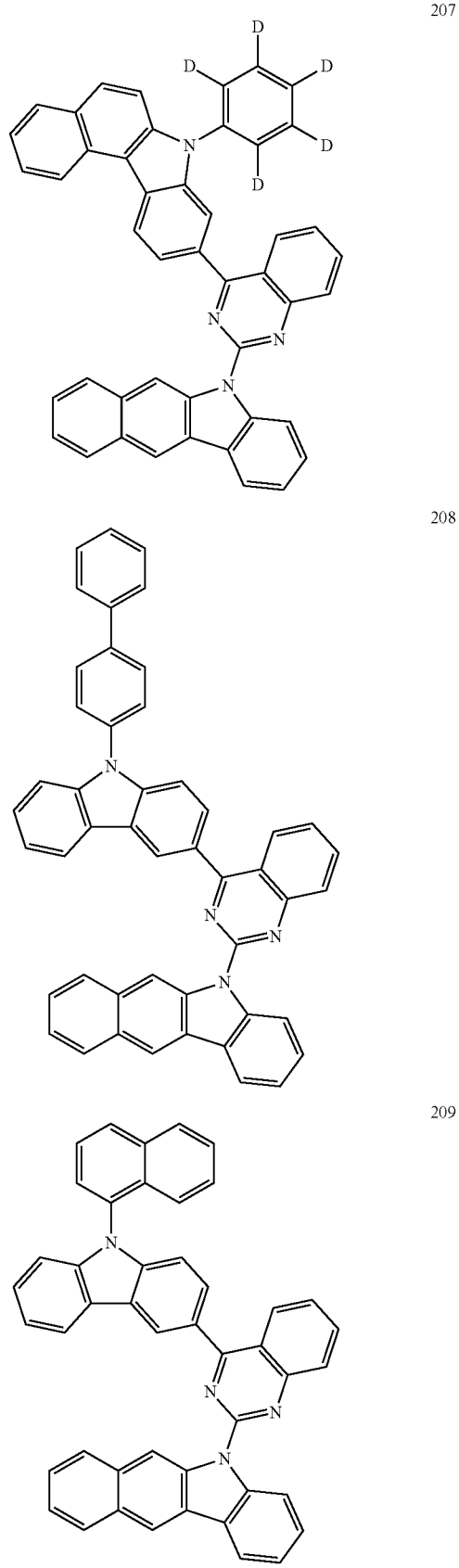

489
-continued
490
-continued
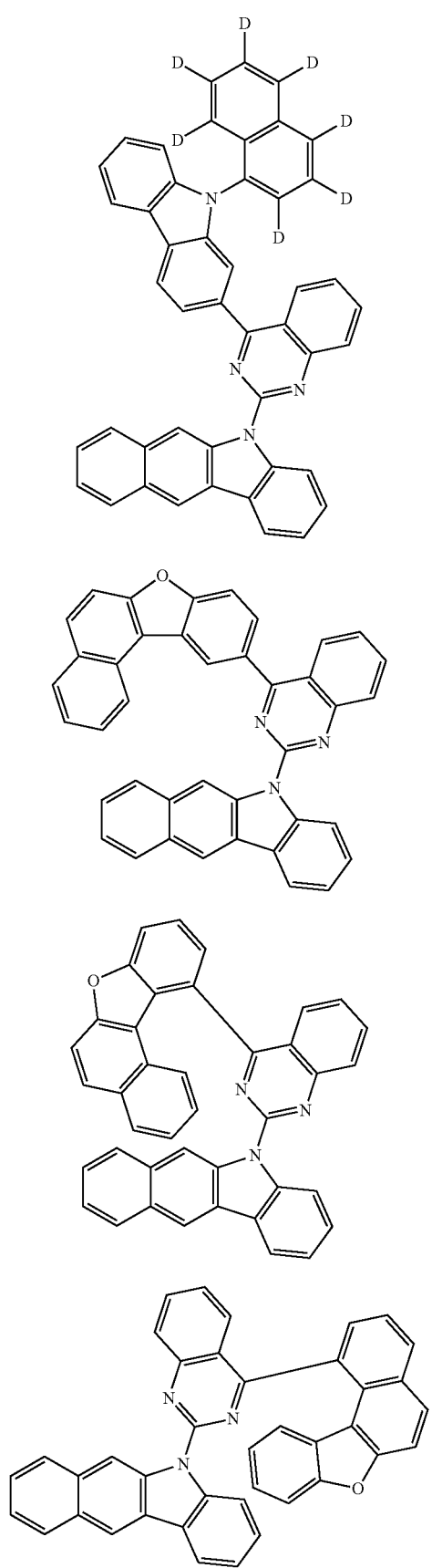
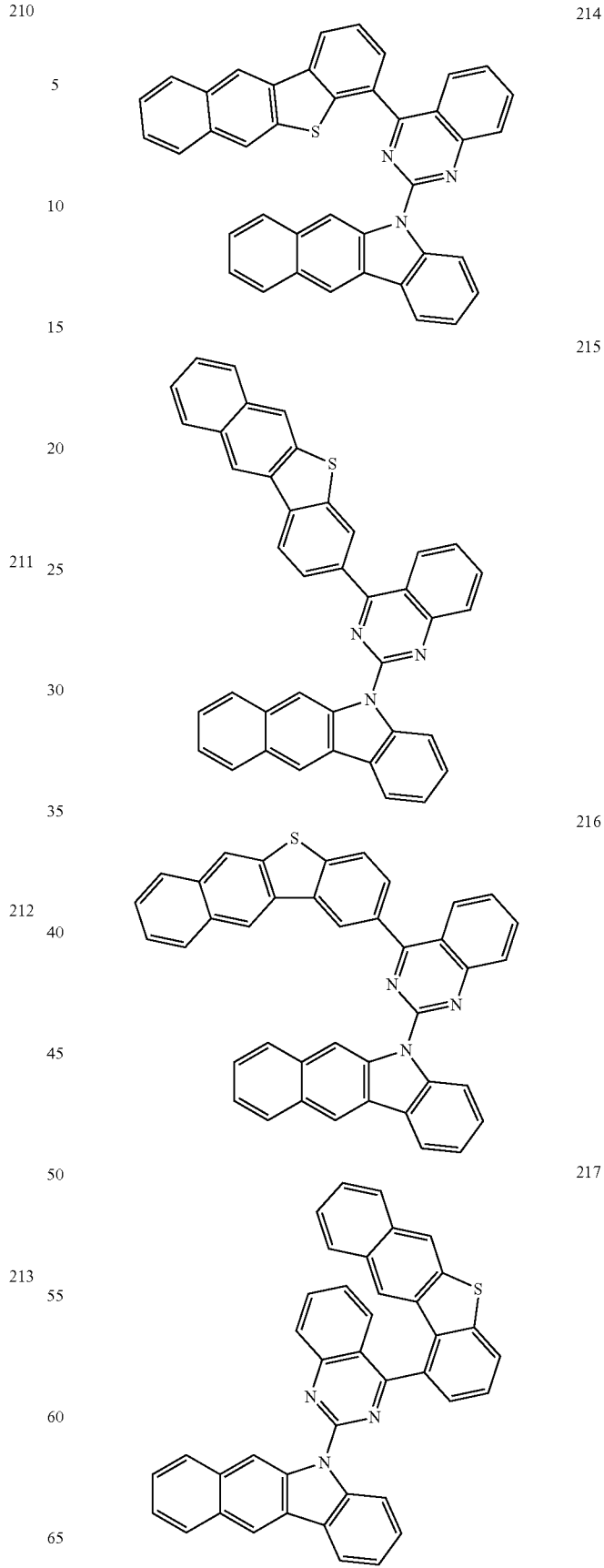

218 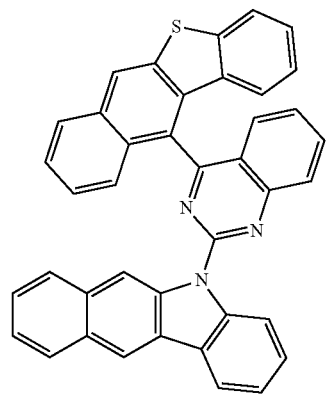
219 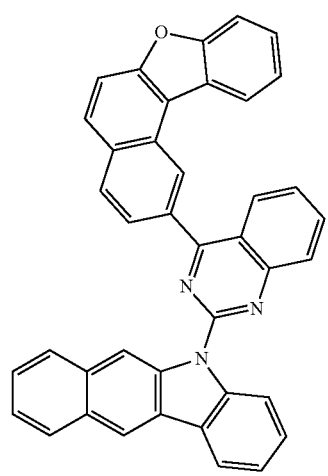
220 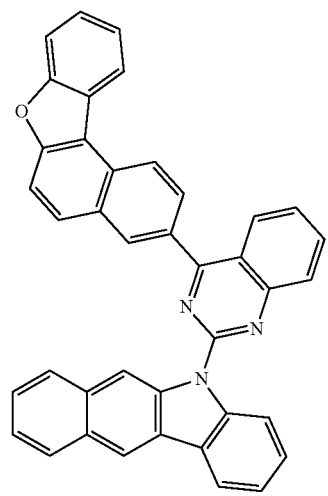
221 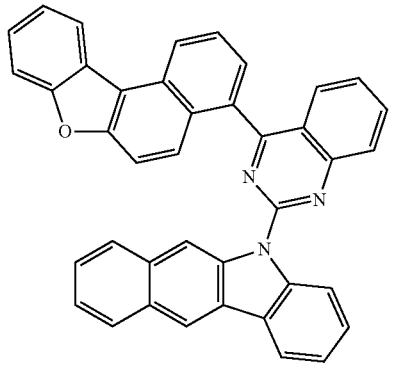
222 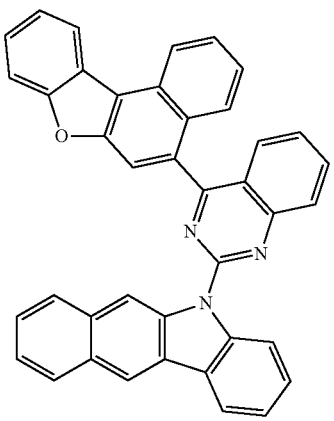
223 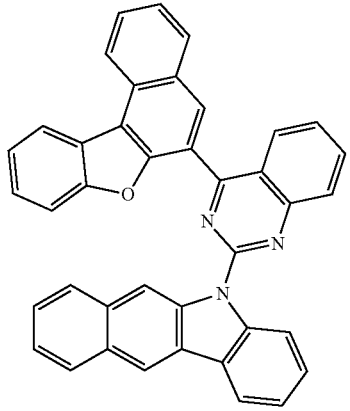
224 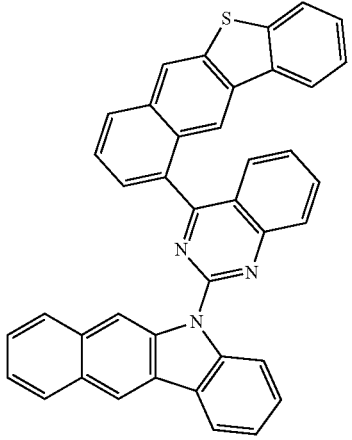

225
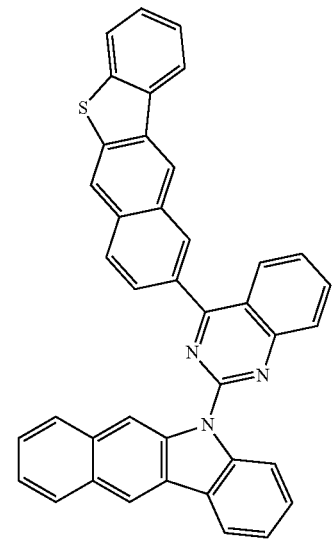
226
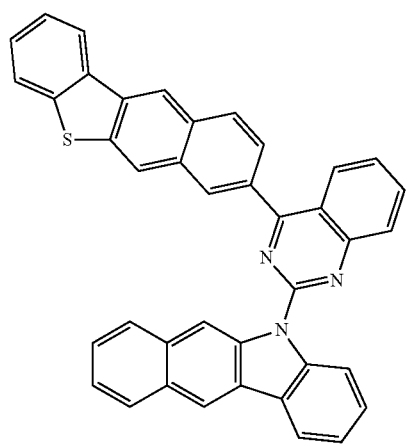
227
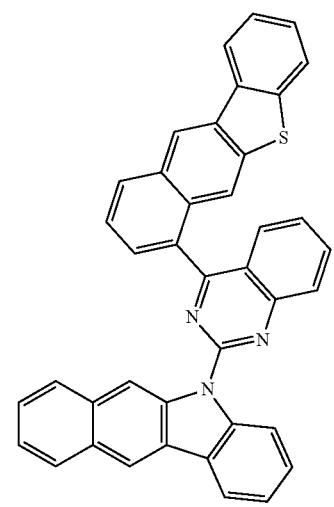
228
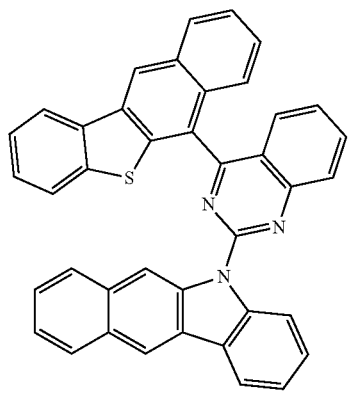
229
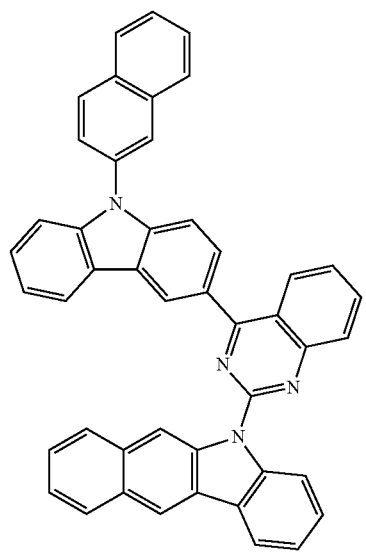
230
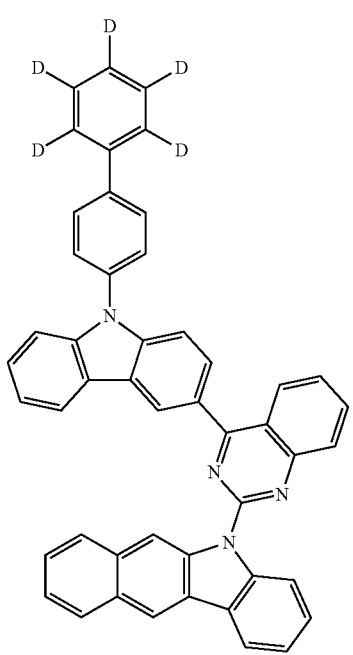

231
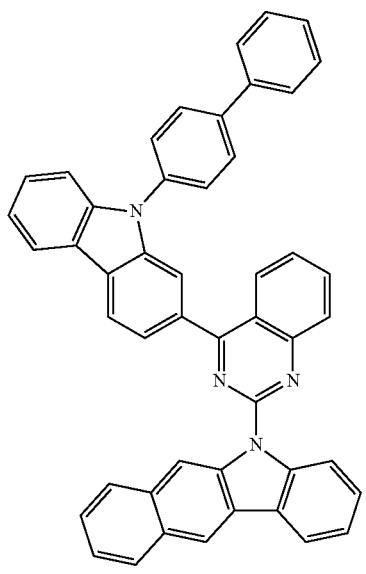
232
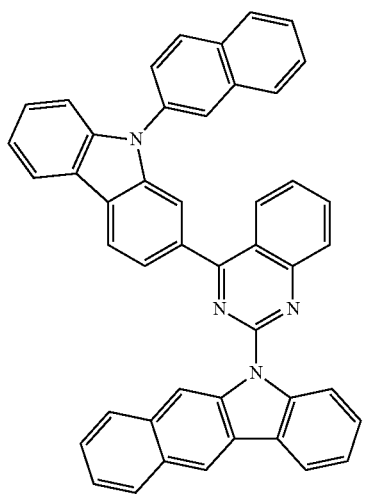
233
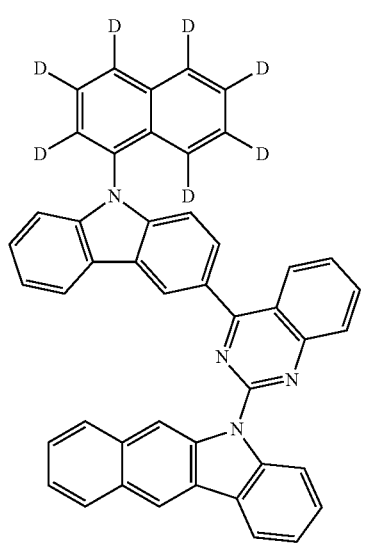
234
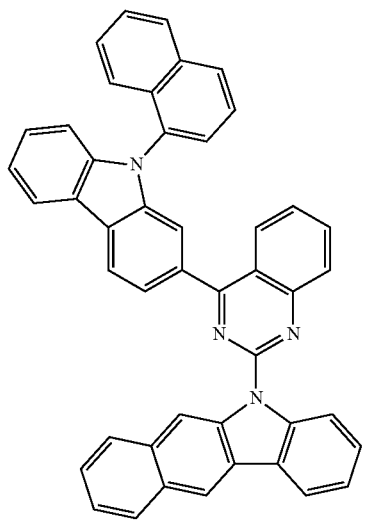
440
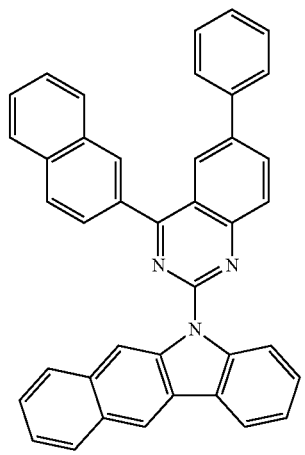
441
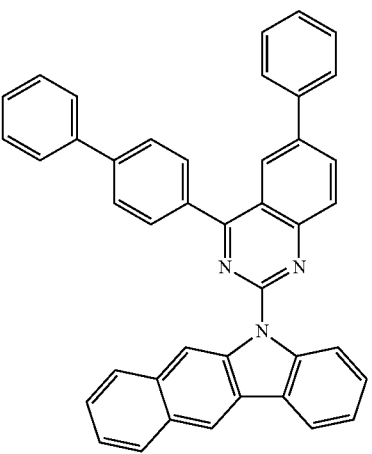

US 11,581,496 B2
| 497 | 498 |
|---|---|
| -continued | -continued |
442
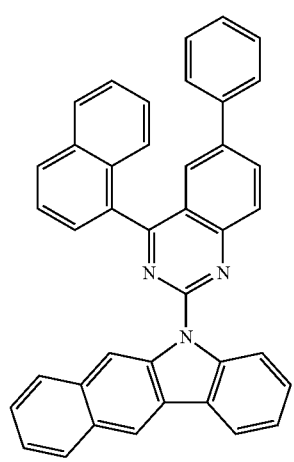
443
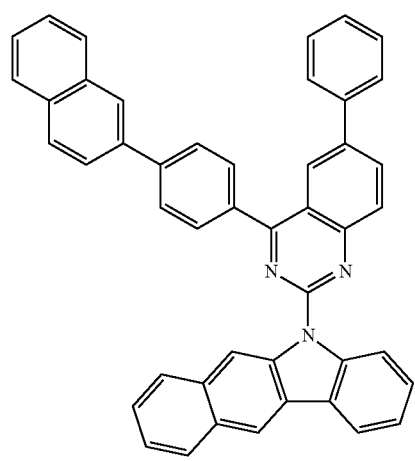
444
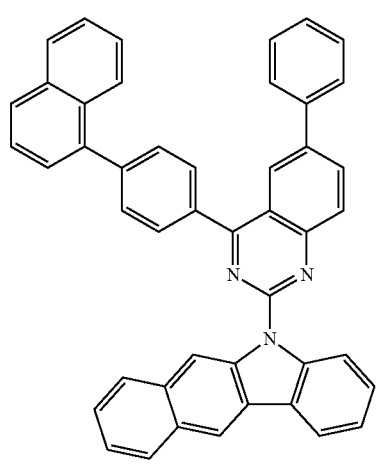
446
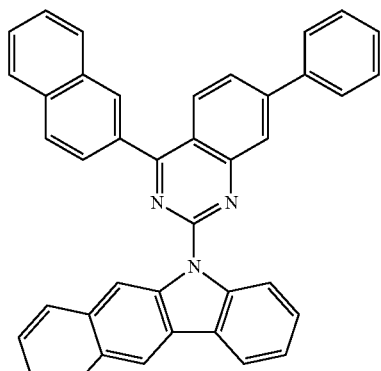
447
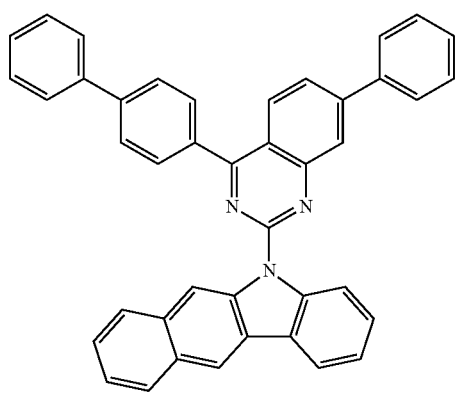
448
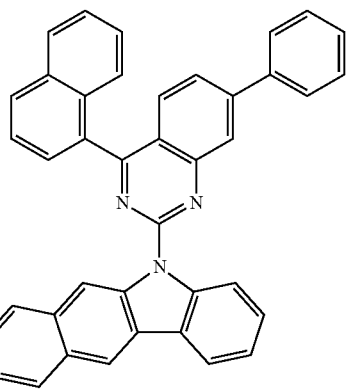
449
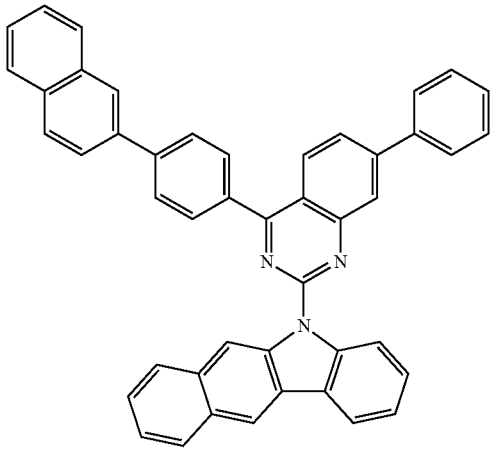

-continued
450
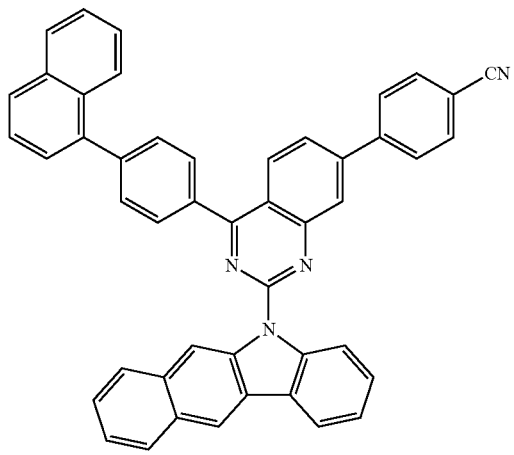
451
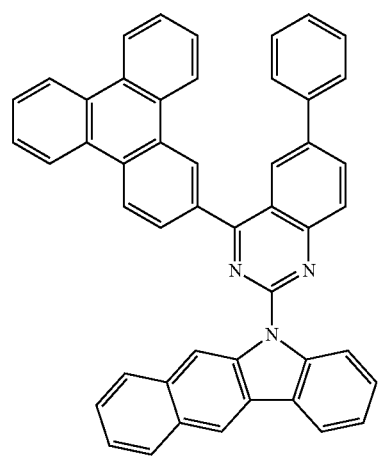
452
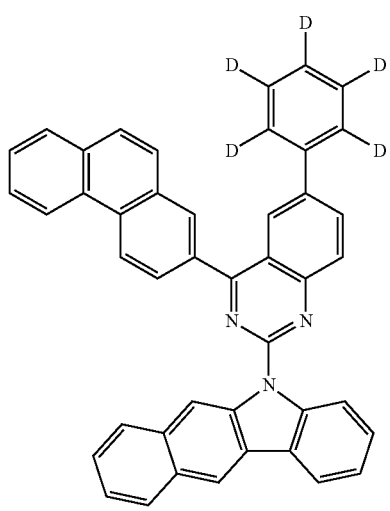
-continued
453
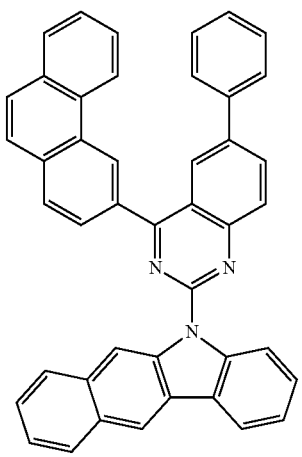
454
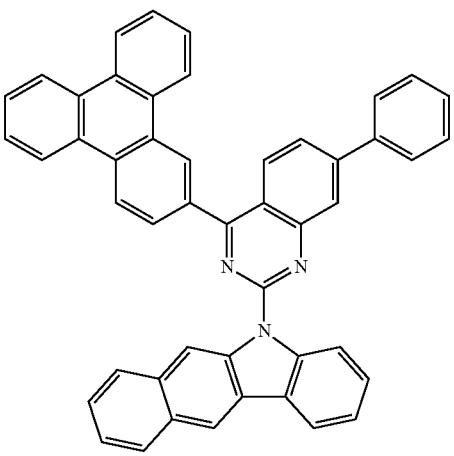
455
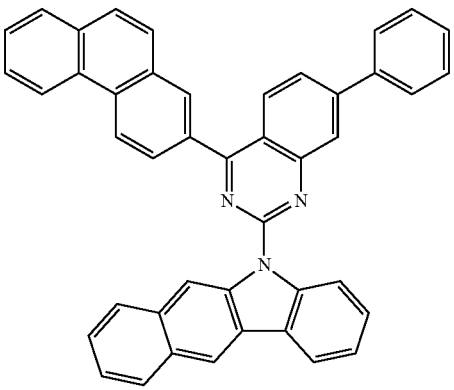

501
-continued
456
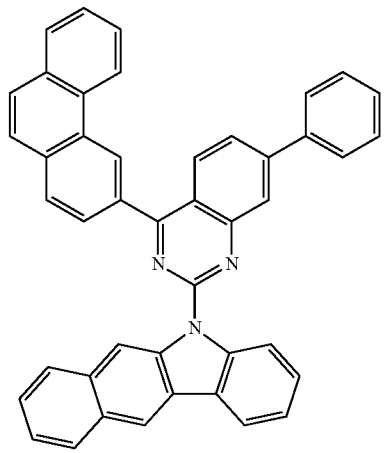
458
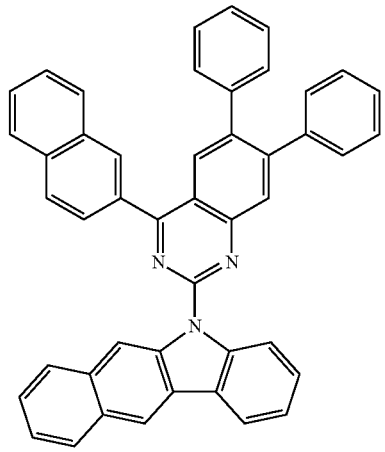
459
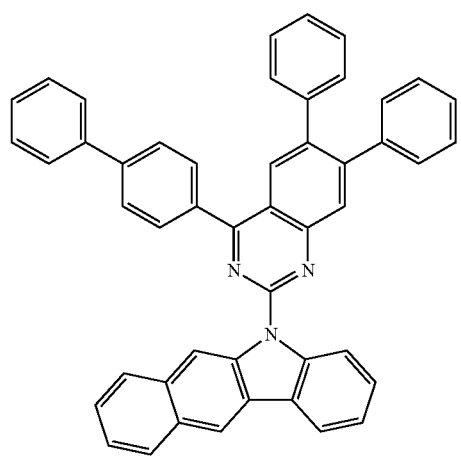
502
-continued
460
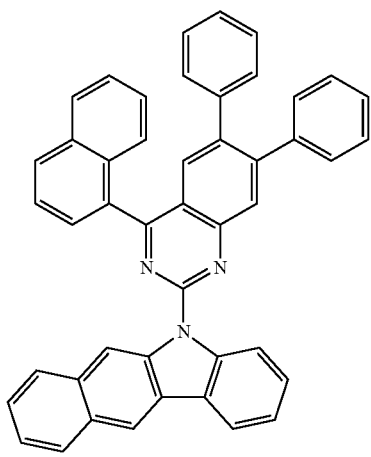
461
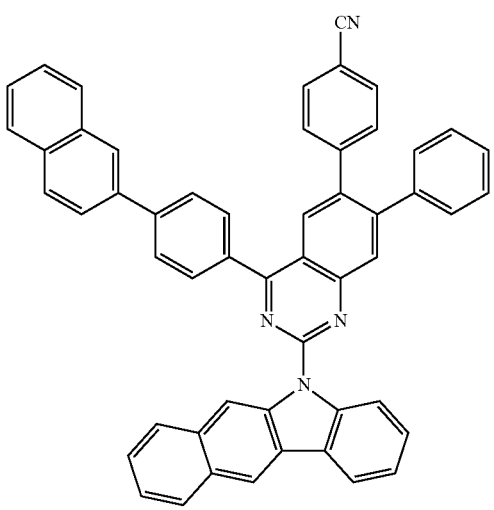
462
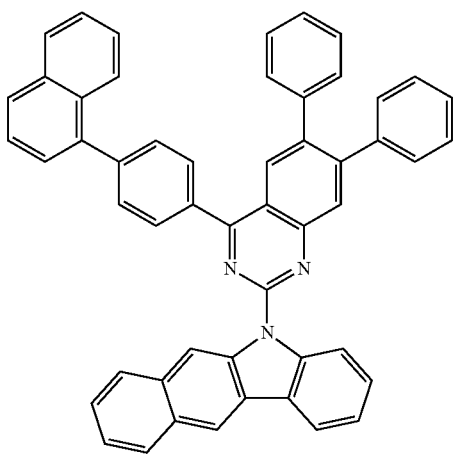

503
-continued
463
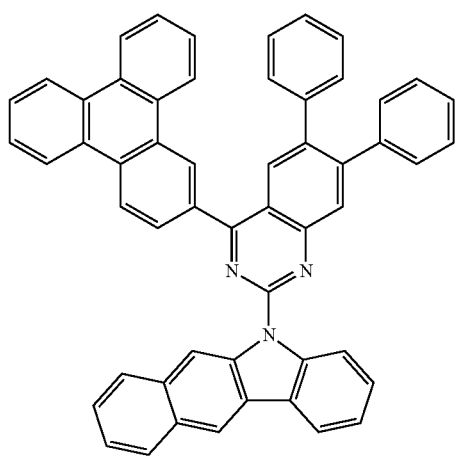
464
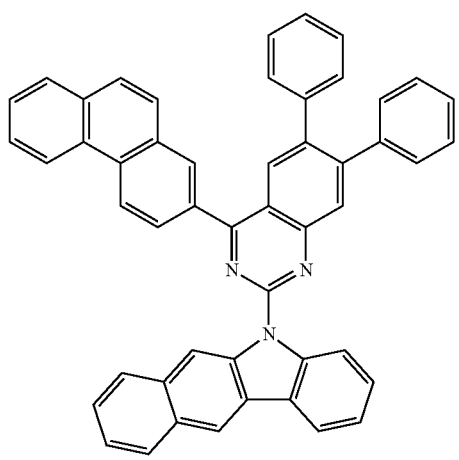
465
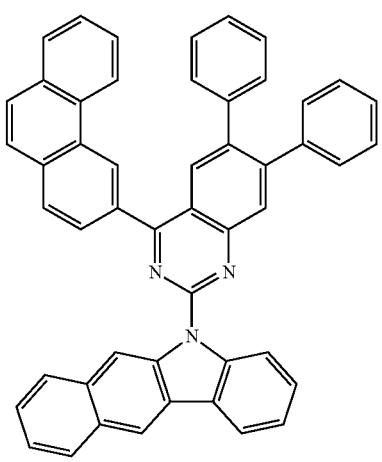
504
-continued
467
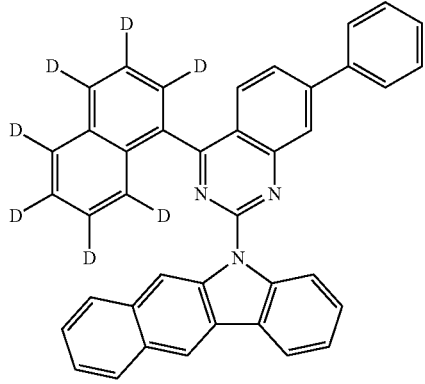
468
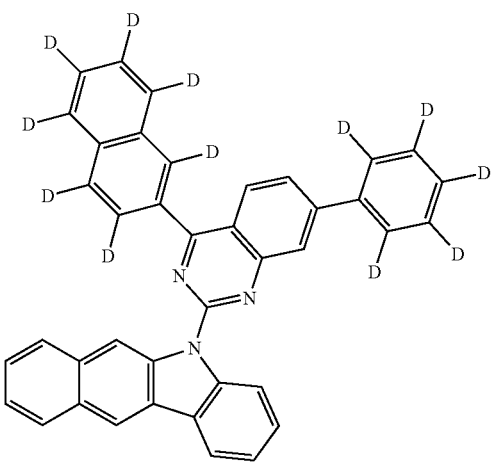
471
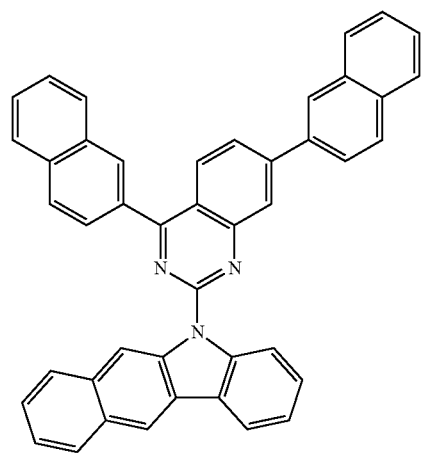

| 472 | 477 |
|---|---|
| 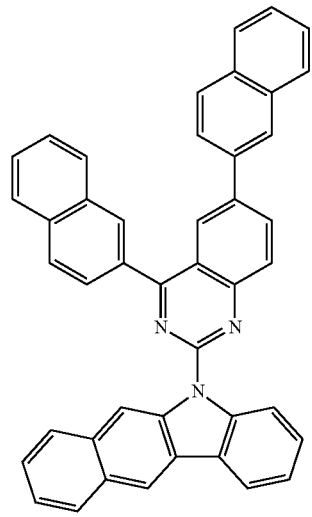 | 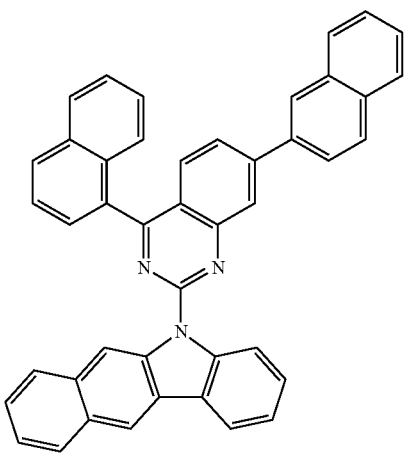 |
| 475 | 478 |
| 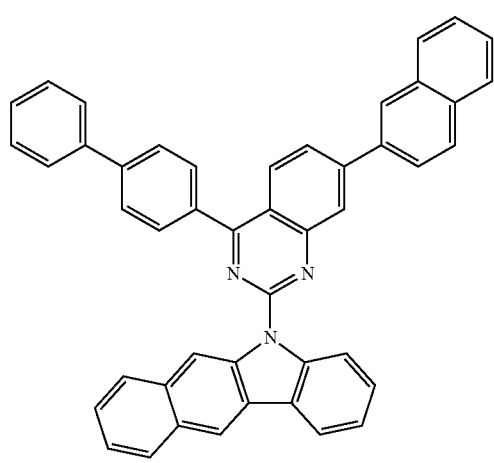 | 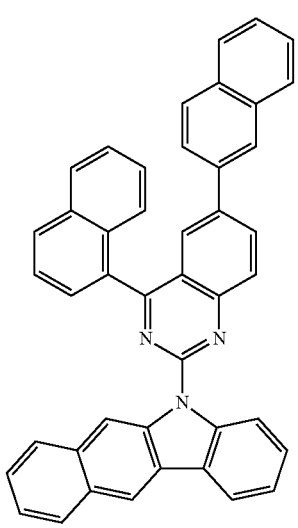 |
| 476 | 481 |
| 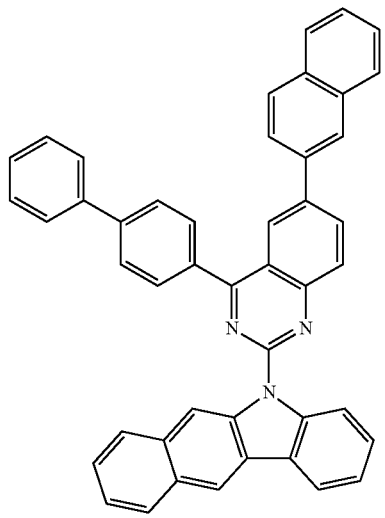 | 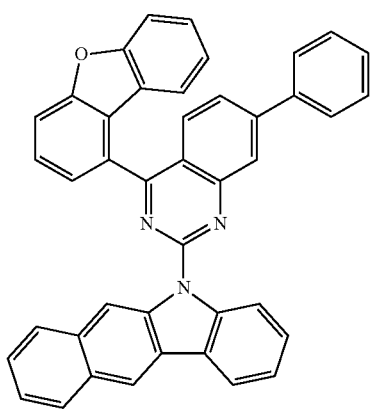 |

507
-continued
482
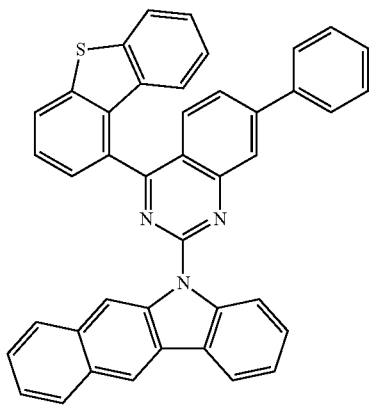
483
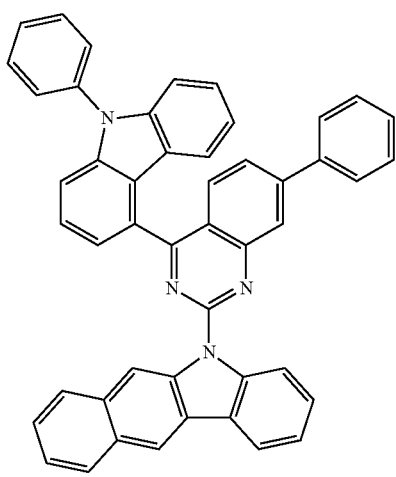
484
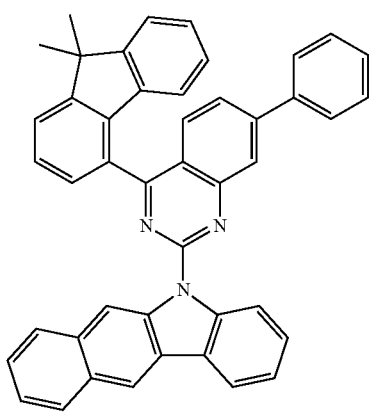
508
-continued
485
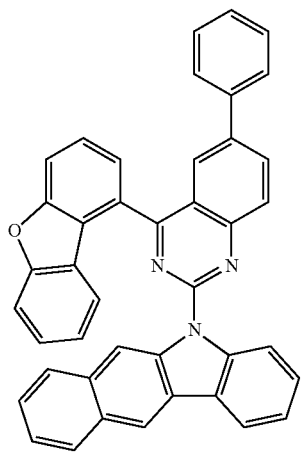
486
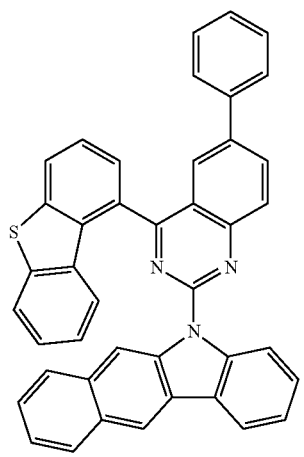
487
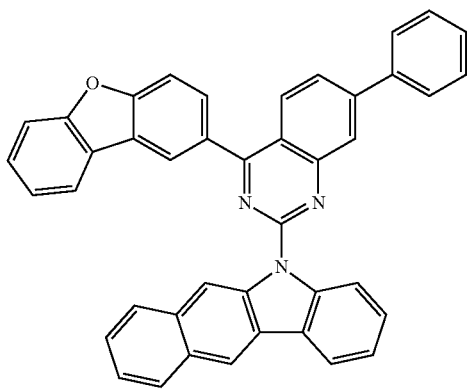

488
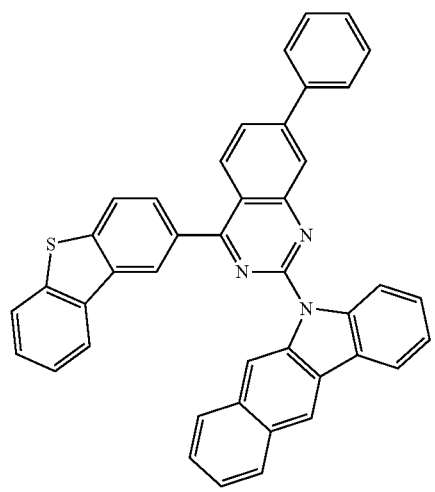
491
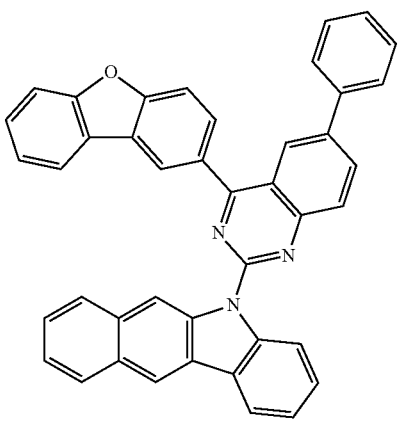
489
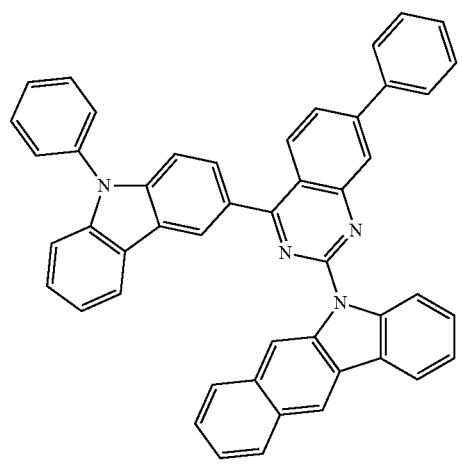
492
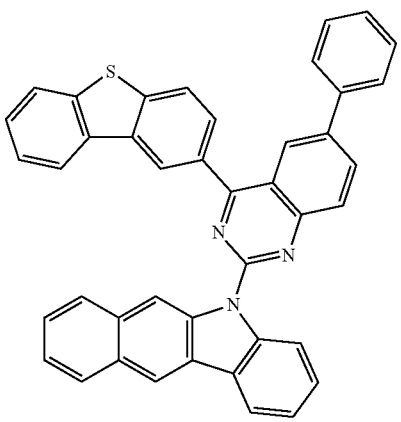
490
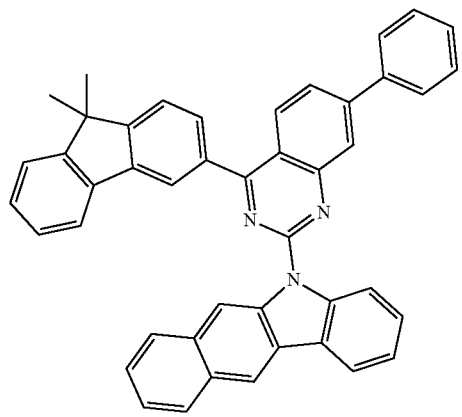
493
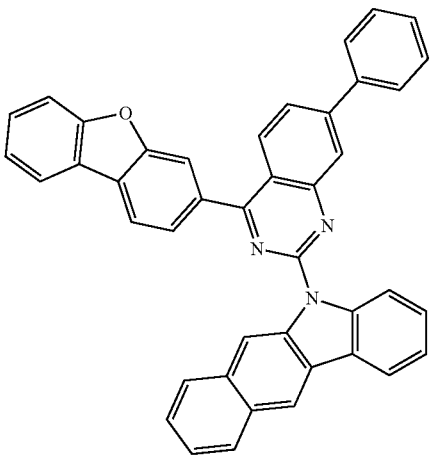

511
-continued
494
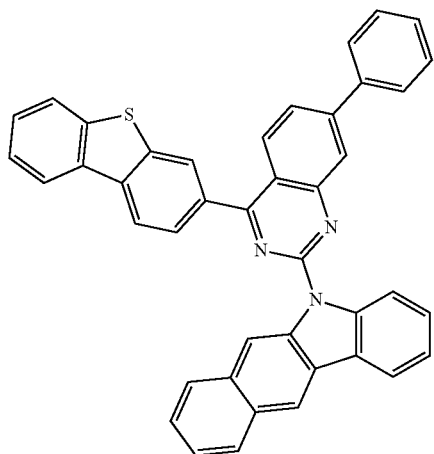
495
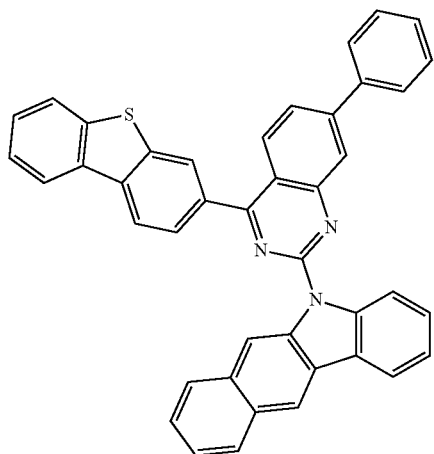
496
512
-continued
497
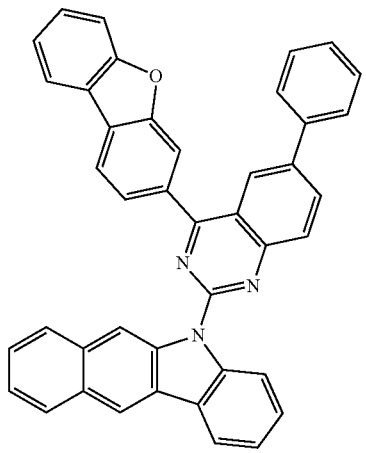
498
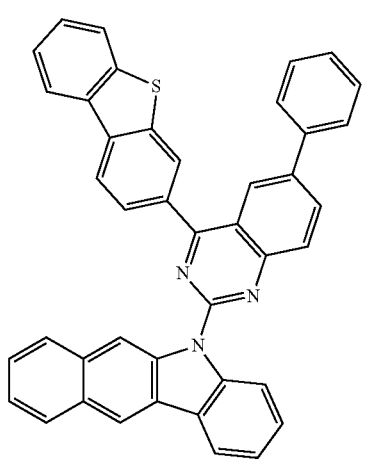
499
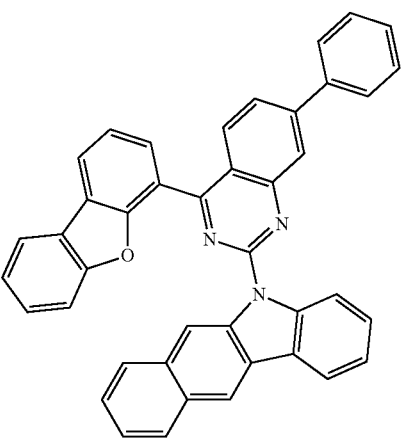

513
-continued
500
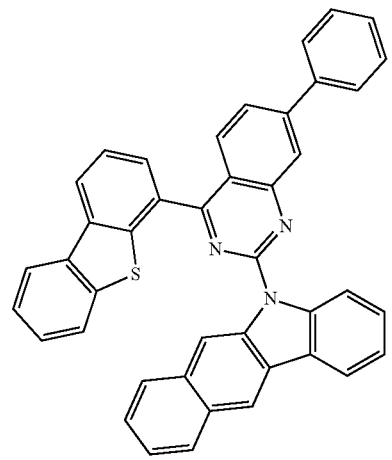
501
503
-continued
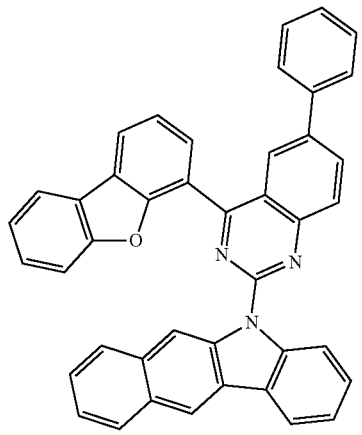
504
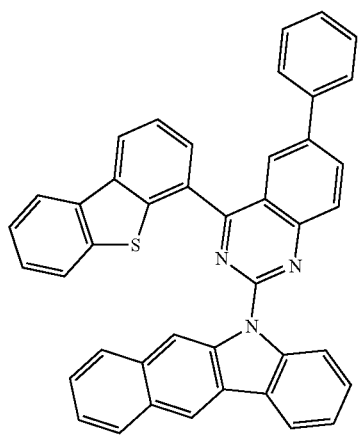
502
506
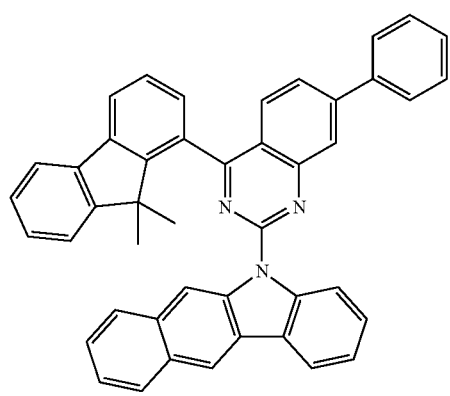
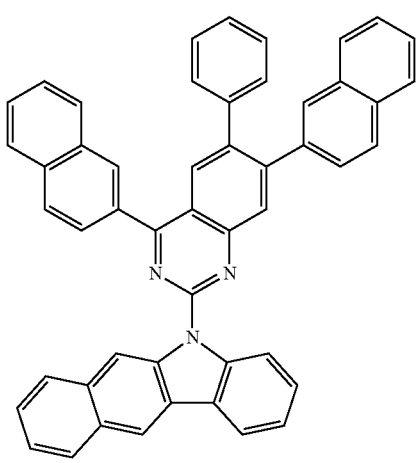

507
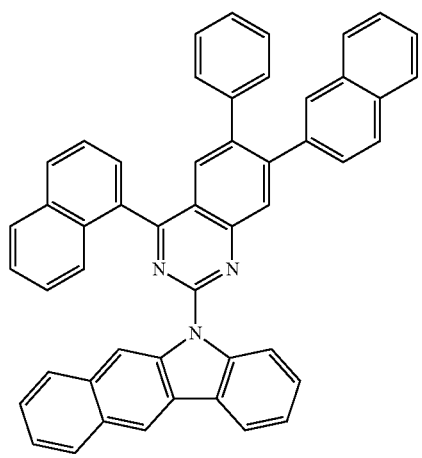
512
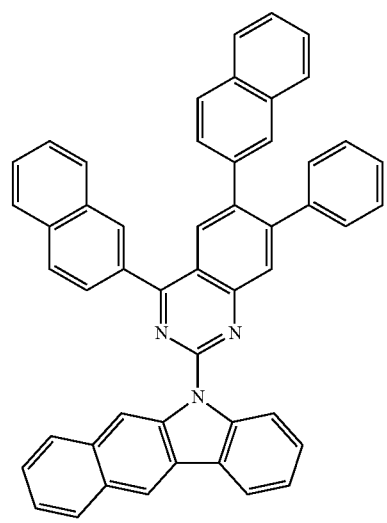
513
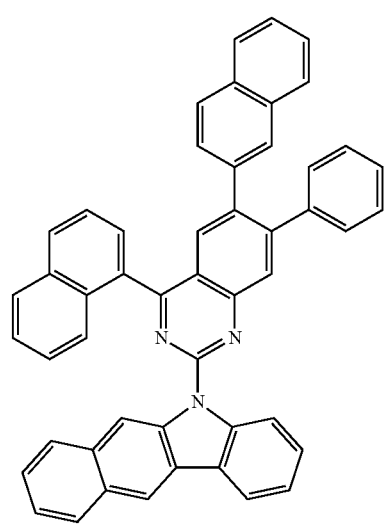
554
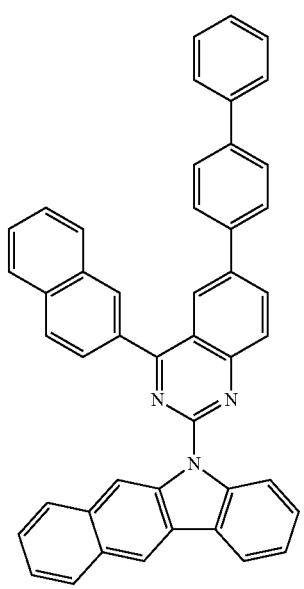
555
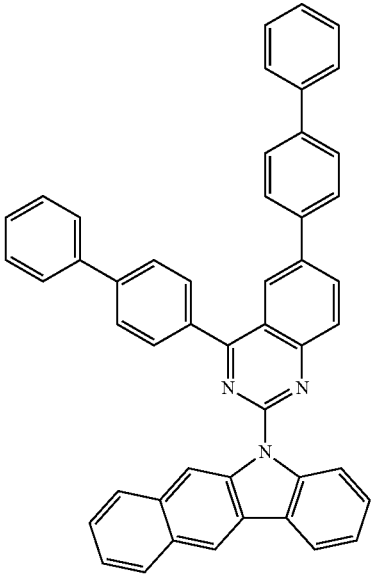

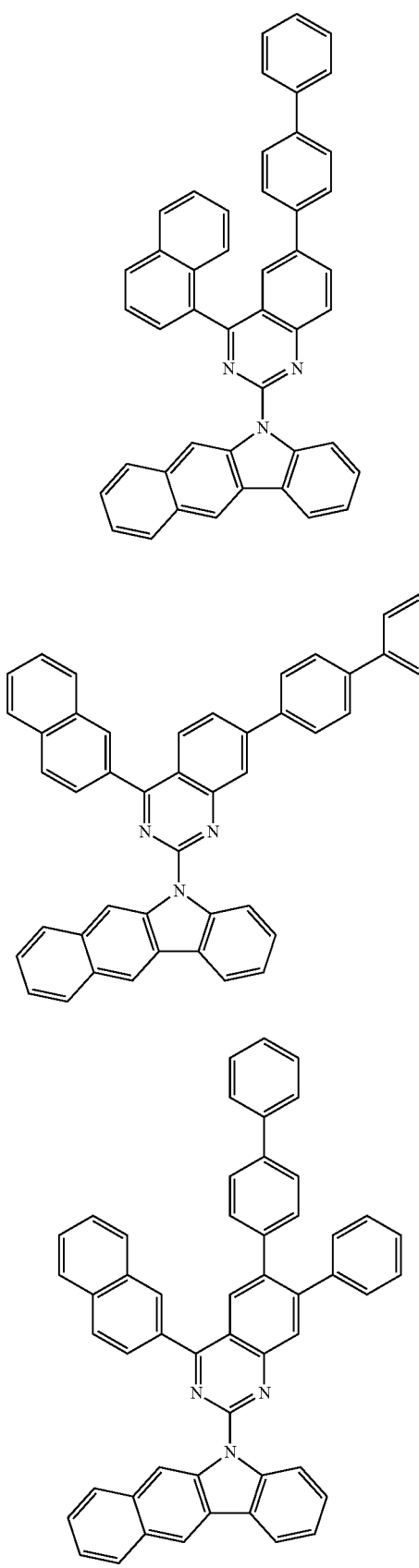
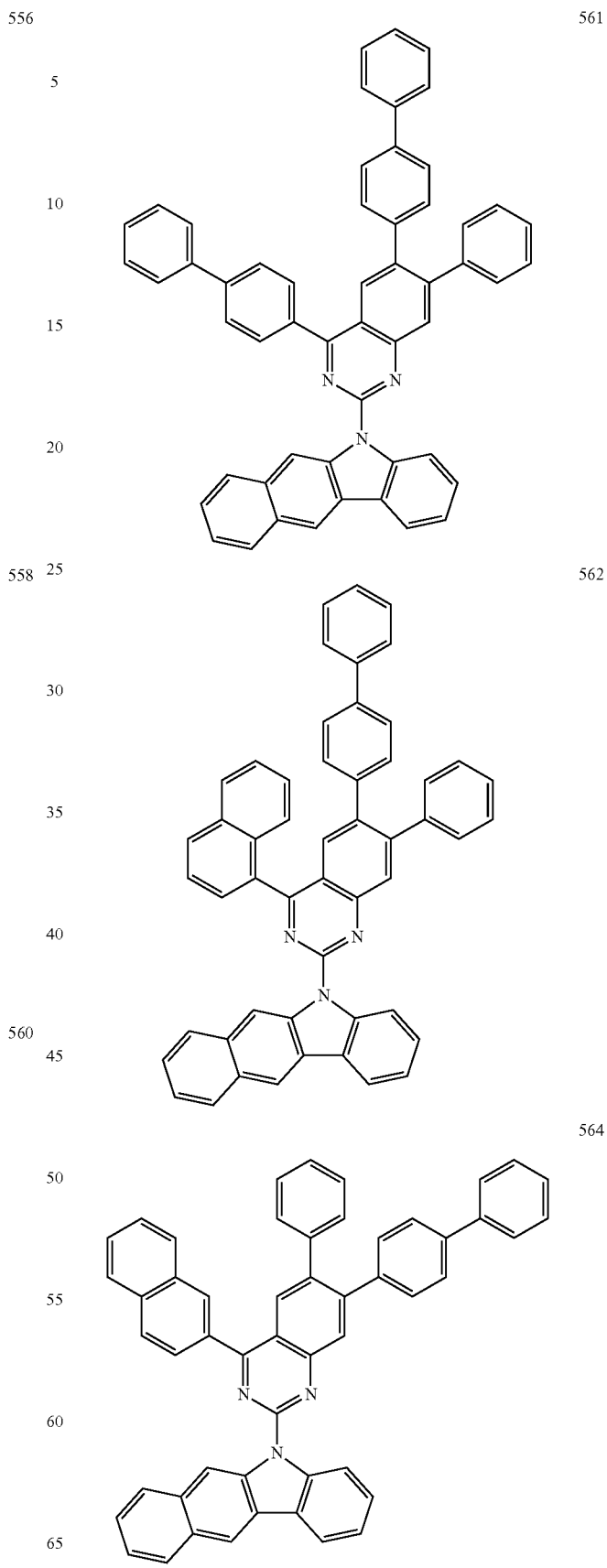

519
-continued
589
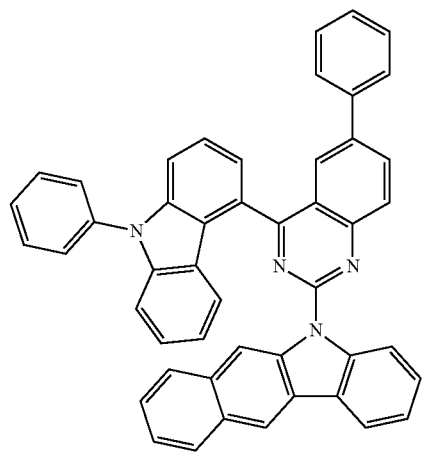
590
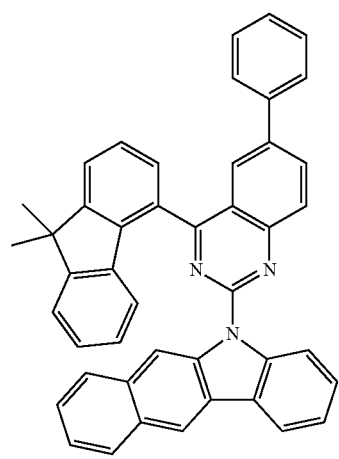
591
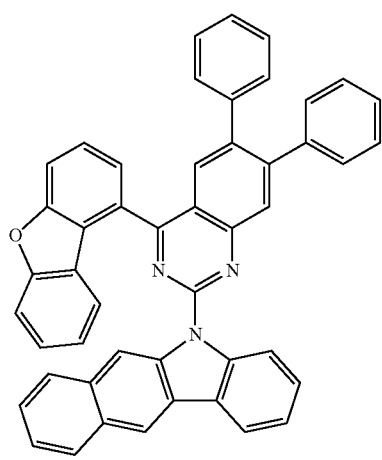
520
-continued
592
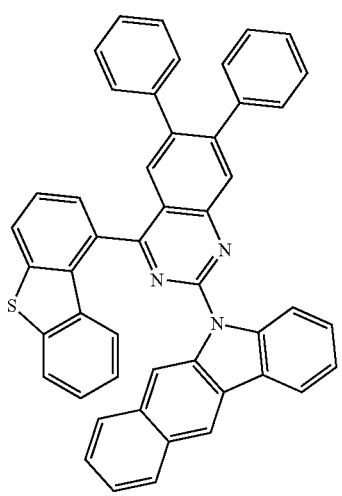
593
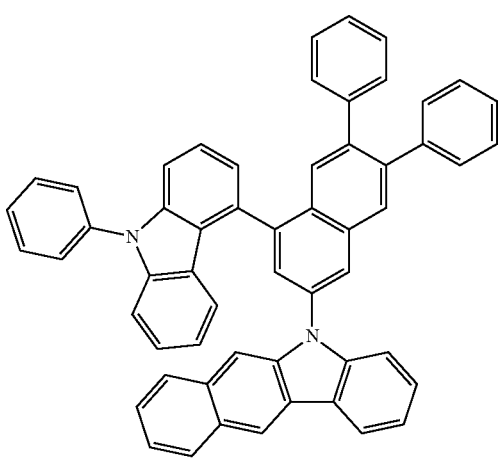
594
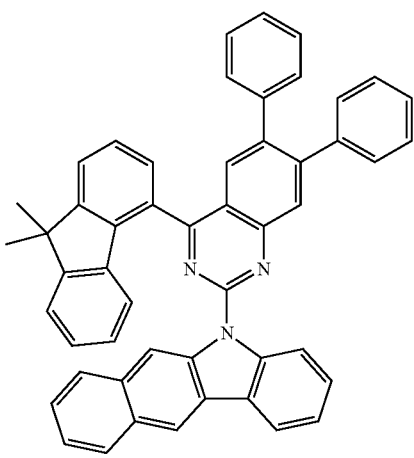

521
-continued
| | |
|---|---|
| 595 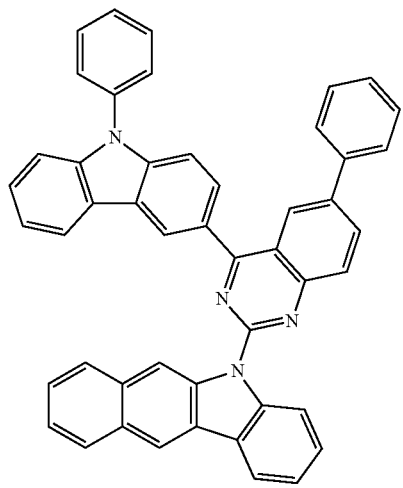 | 598 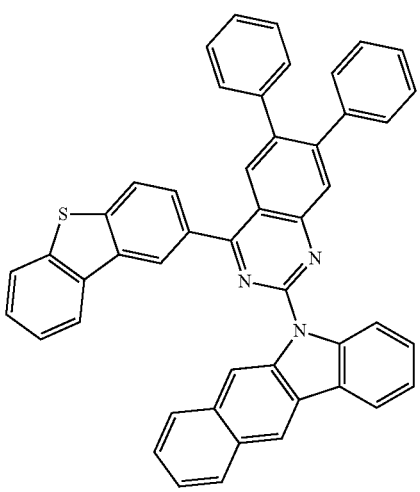 |
| 596 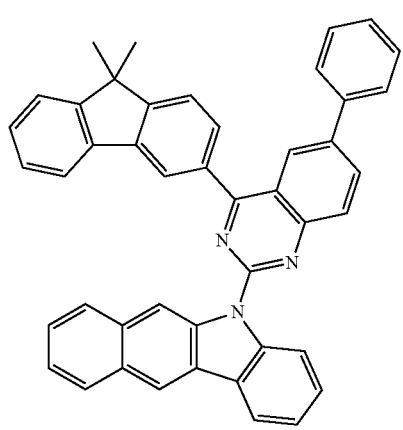 | 599 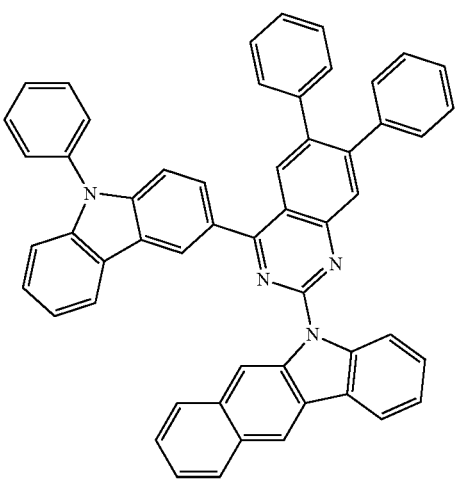 |
| 597 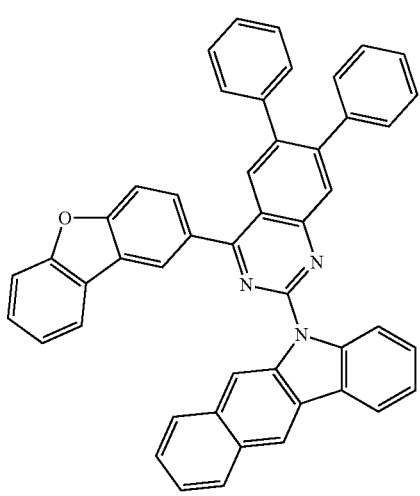 | 600 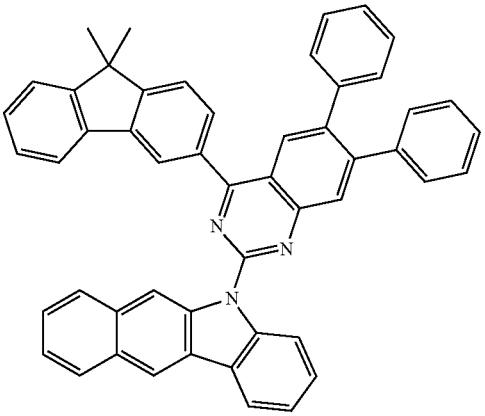 |
522
-continued 523
-continued
601
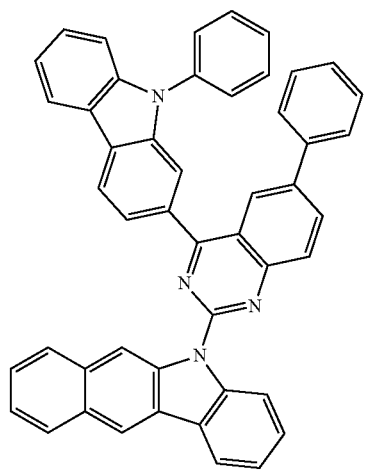
602
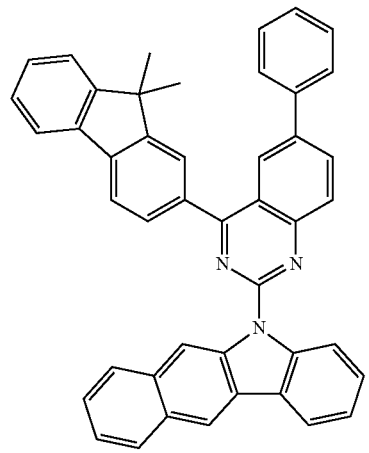
603
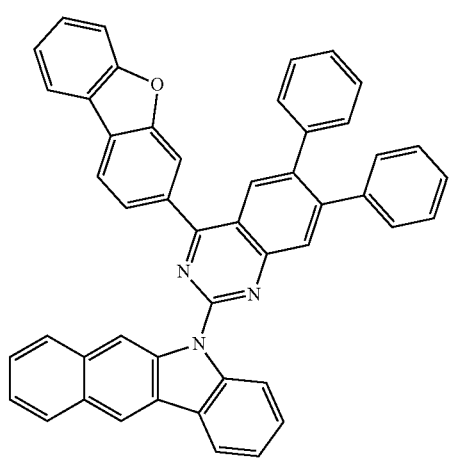
524
-continued
604
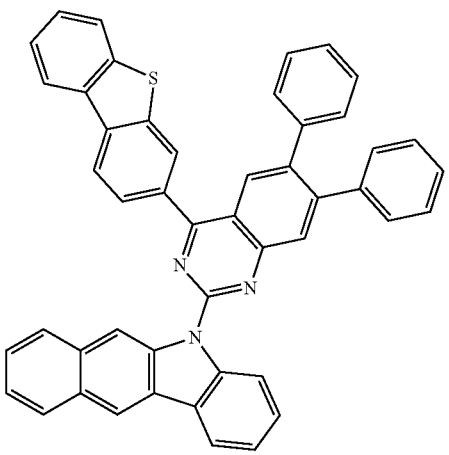
605
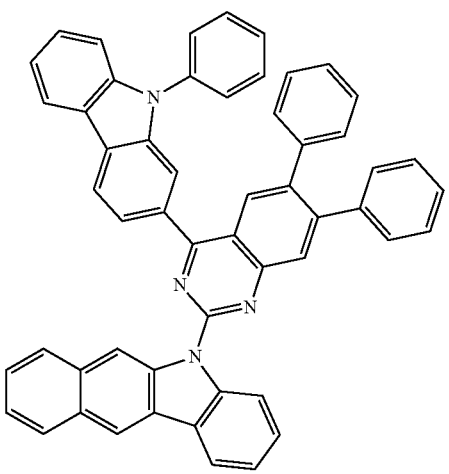
606
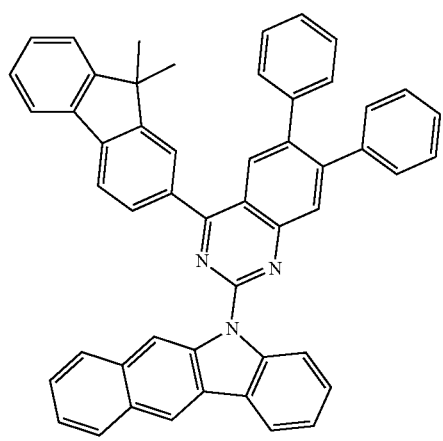

525
-continued
607
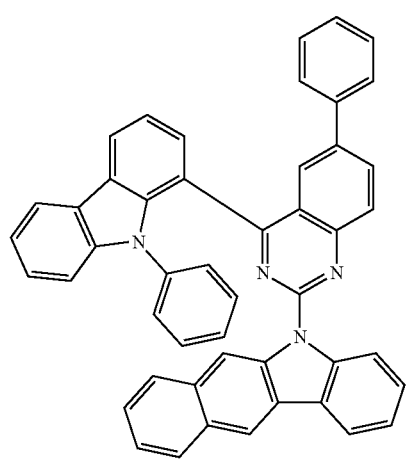
608
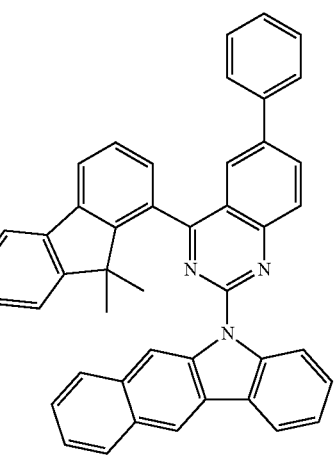
609
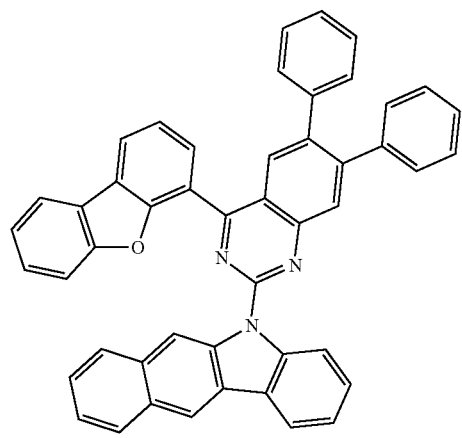
526
-continued
610
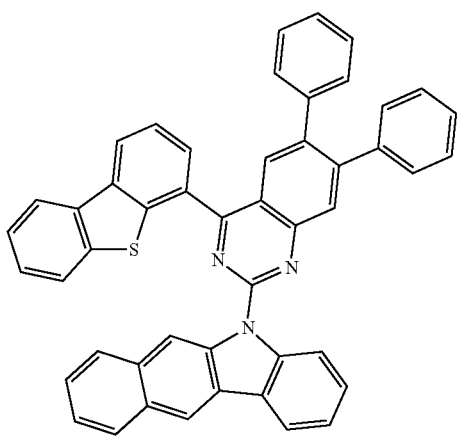
611
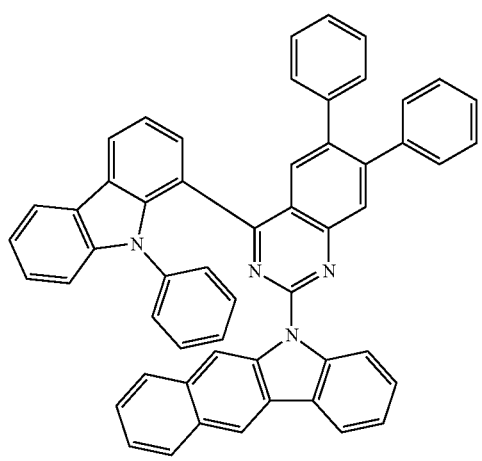
612
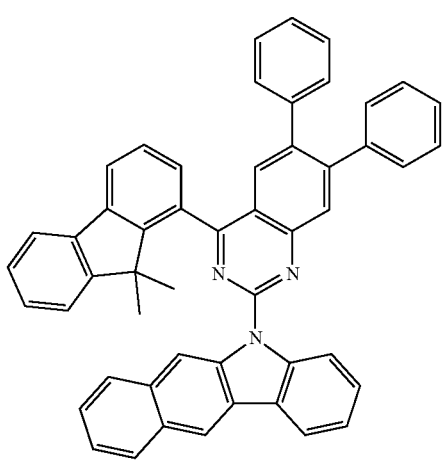

527
-continued
613
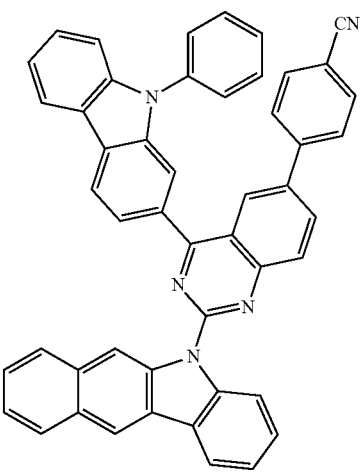
614
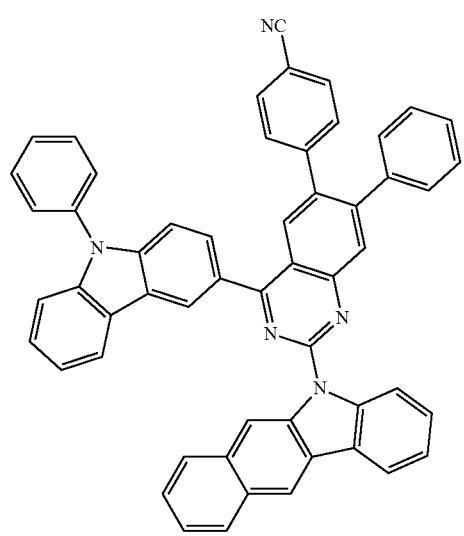
615
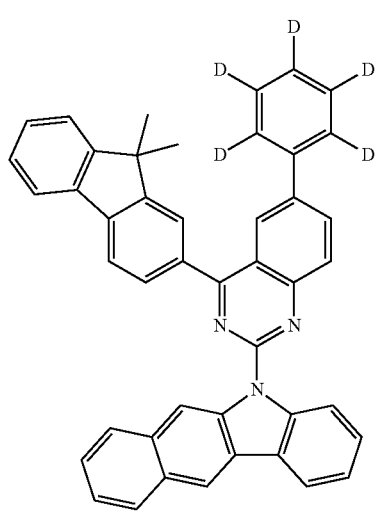
528
-continued
616
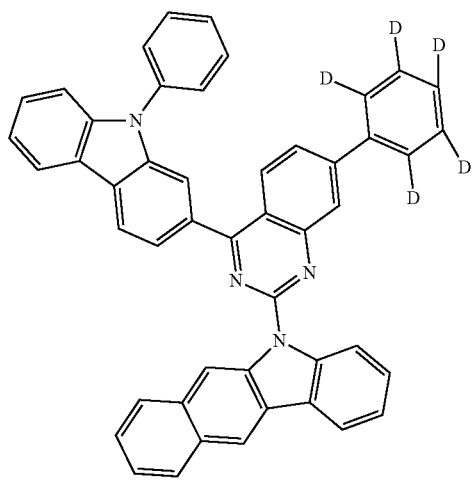
617
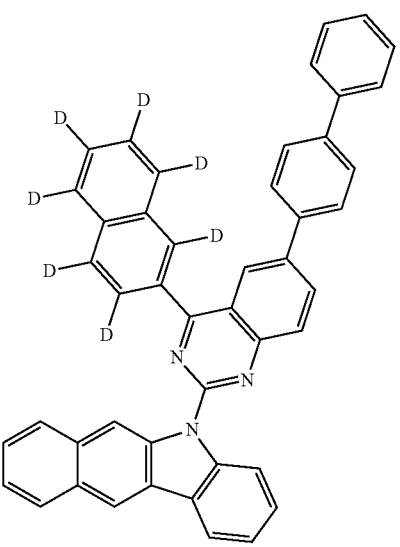
618
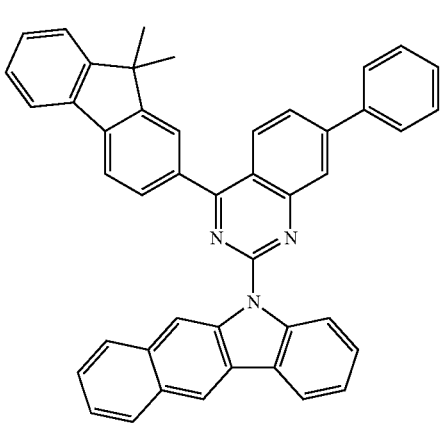

-continued
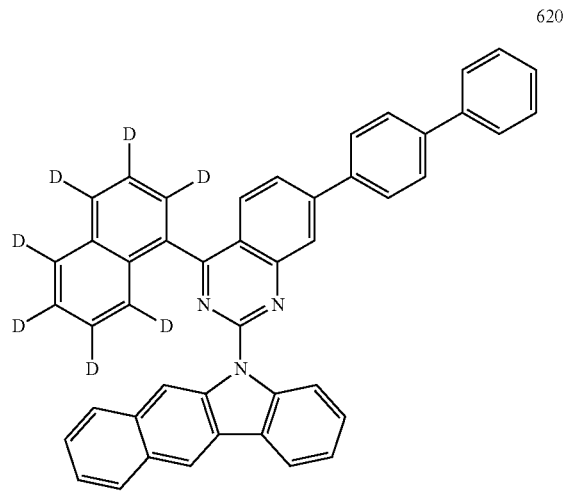
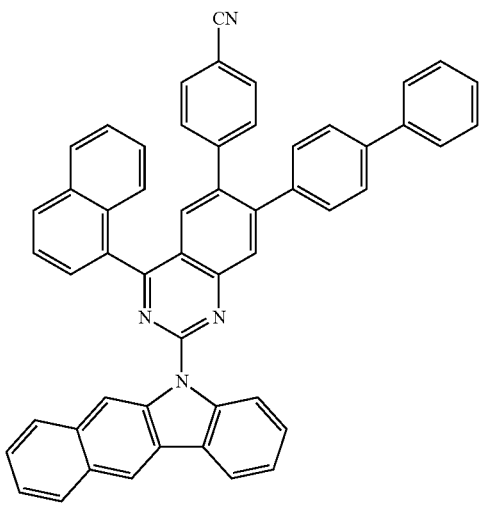
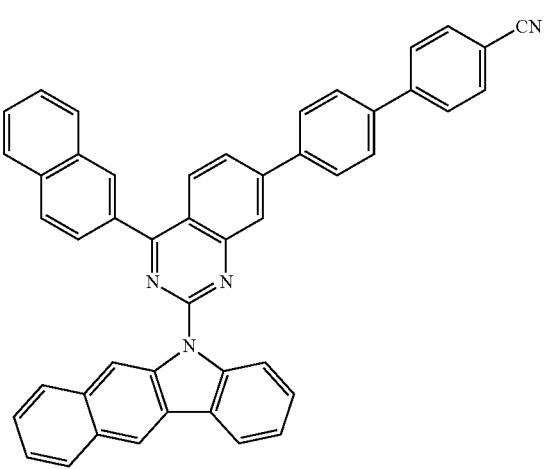
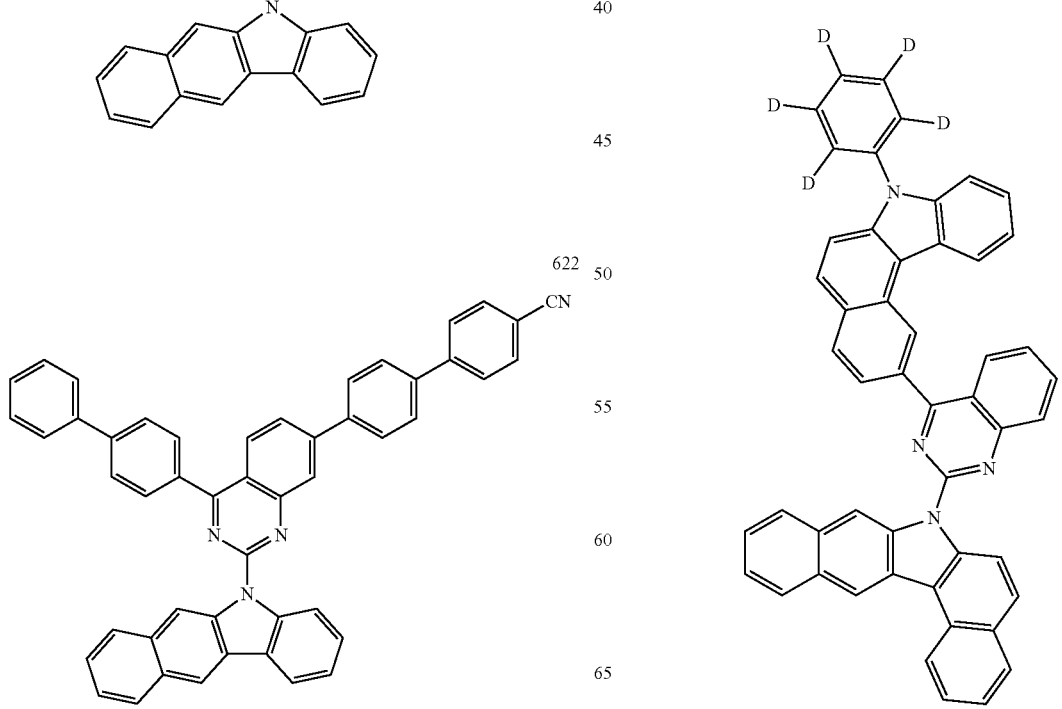

531
-continued
532
-continued
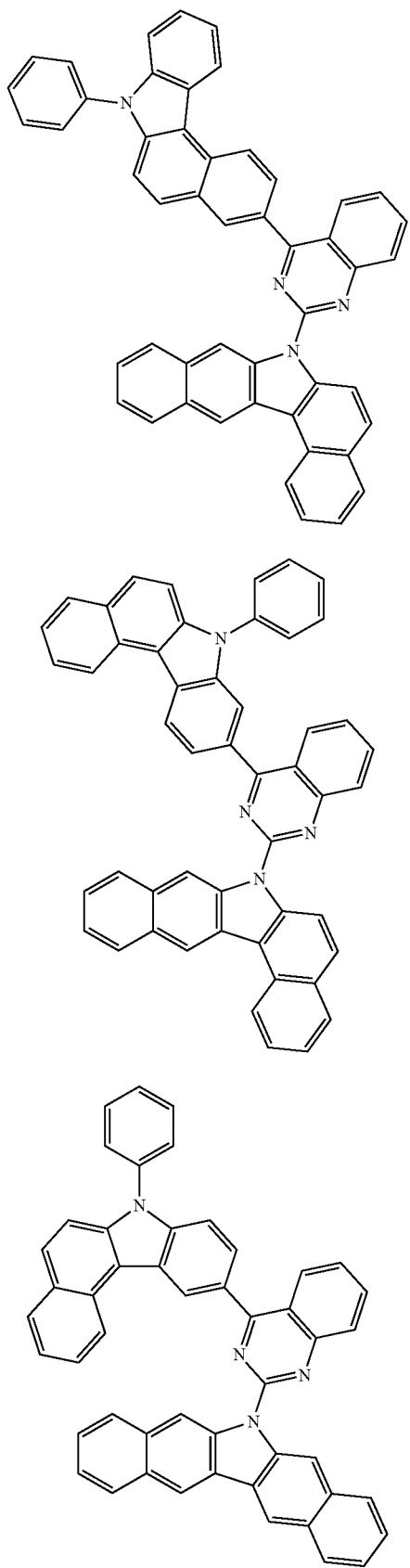
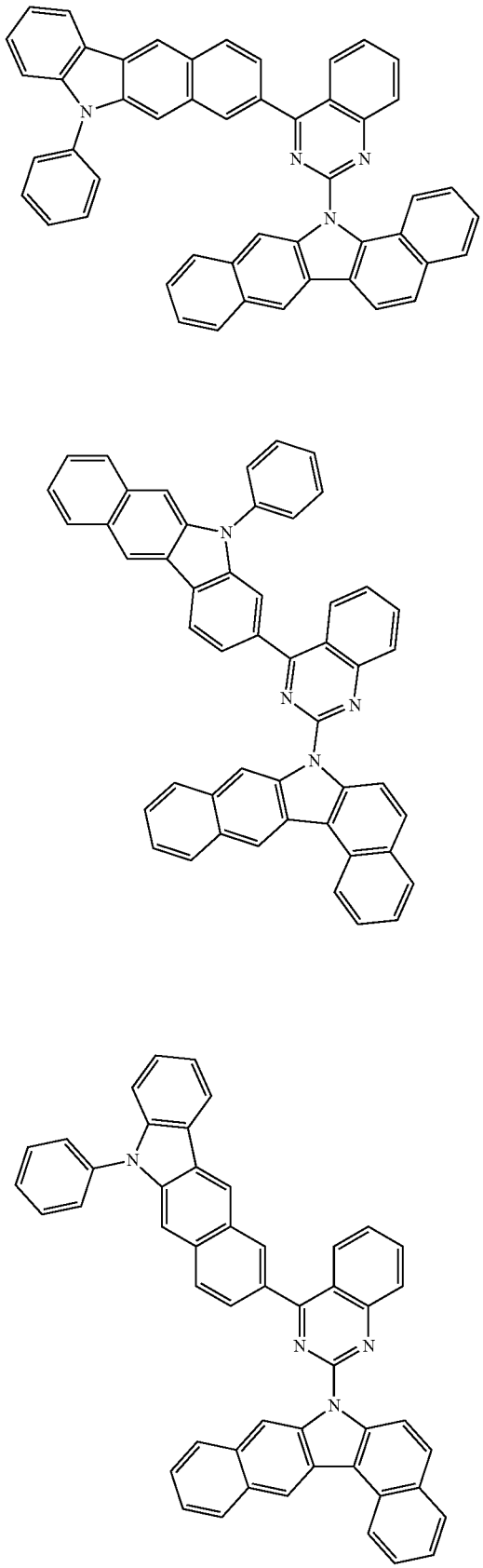

533
-continued
534
-continued
730
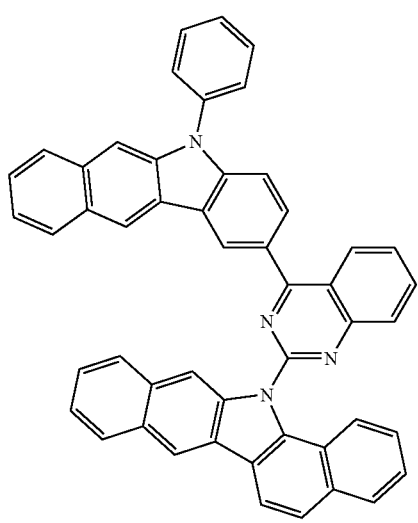
744
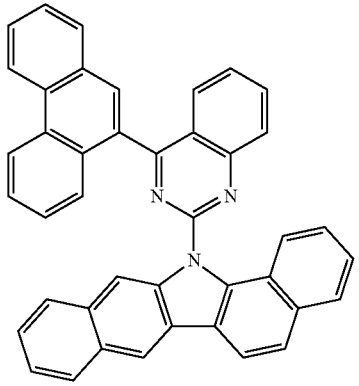
741
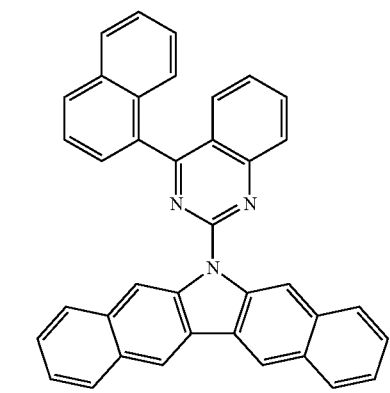
745
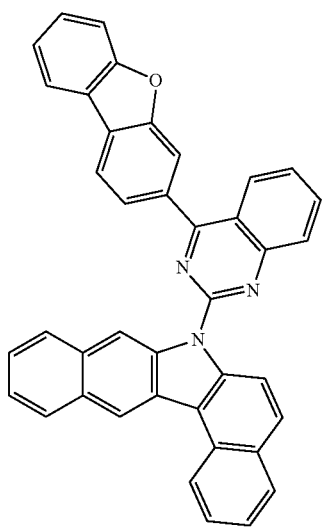
743
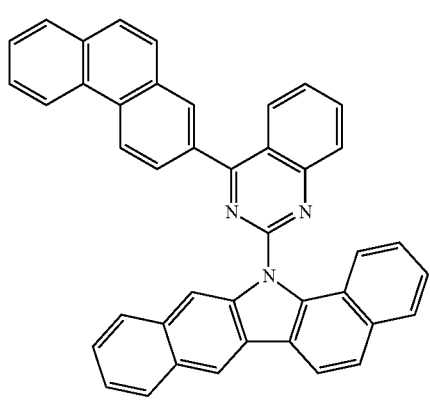
746
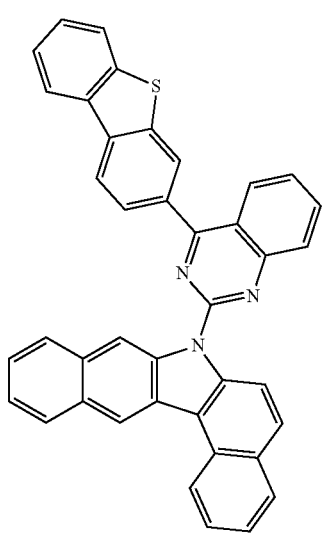

US 11,581,496 B2
535
-continued
747
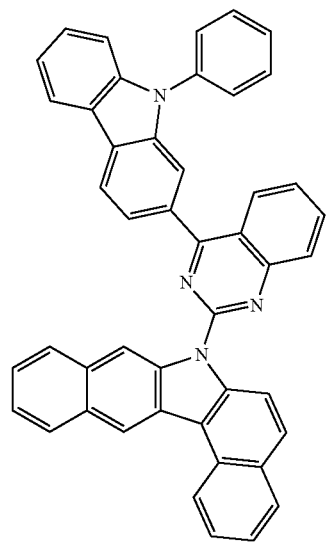
748
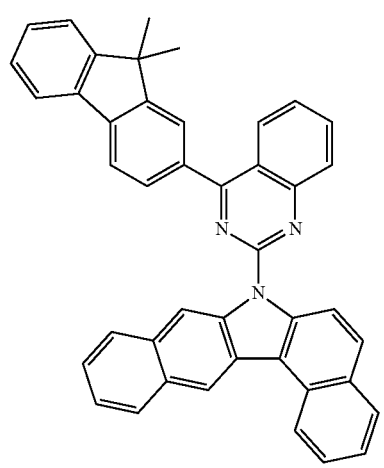
751
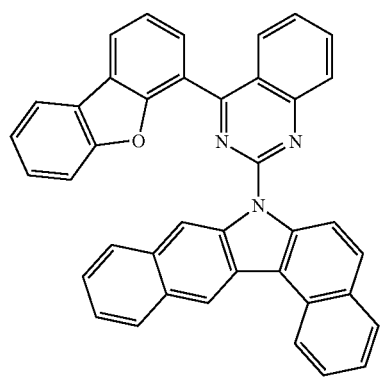
536
-continued
752
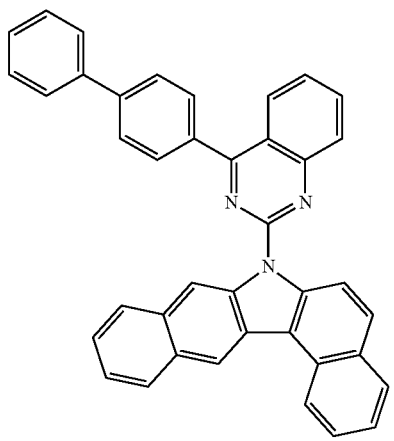
754
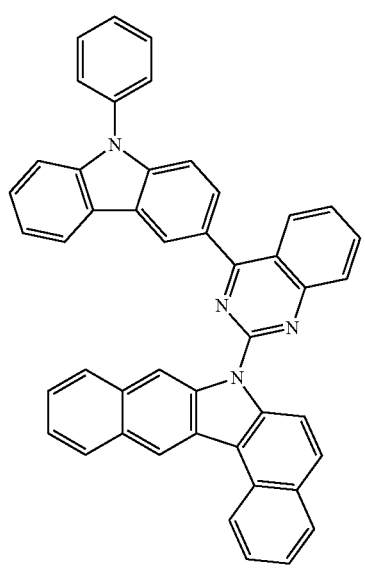
755
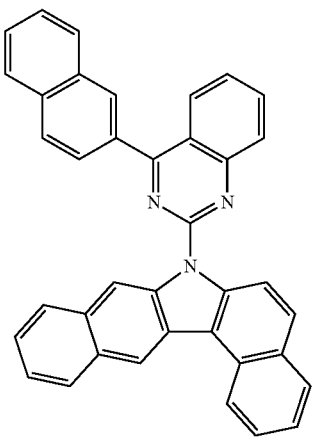

537
-continued
756
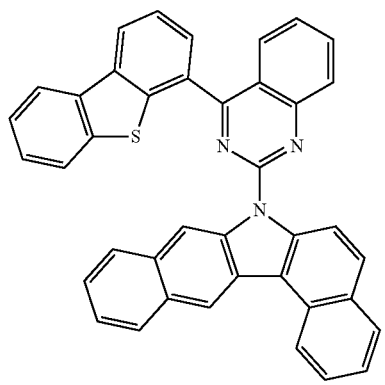
770
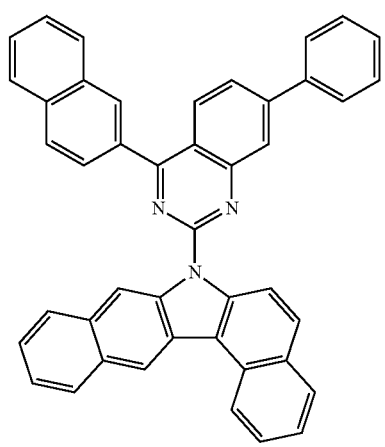
771
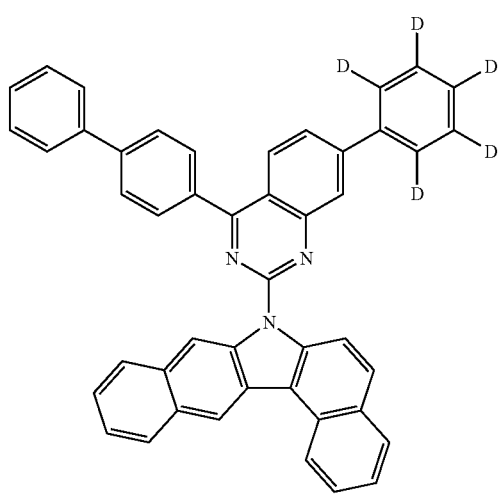
538
-continued
773
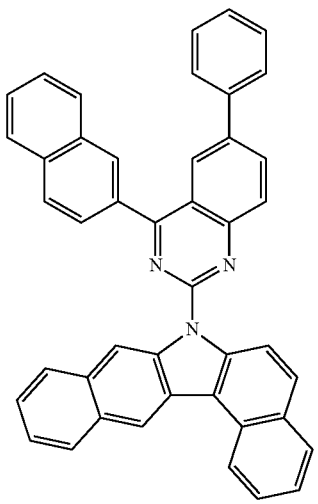
774
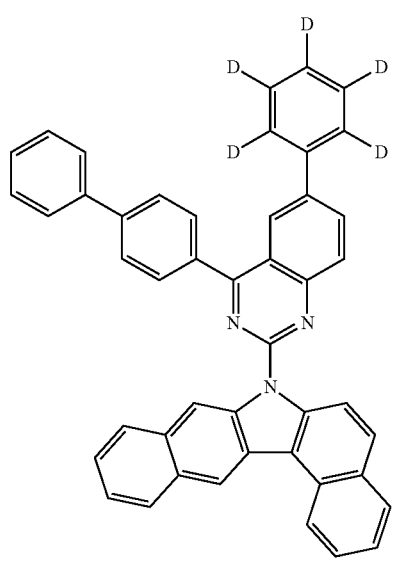
795
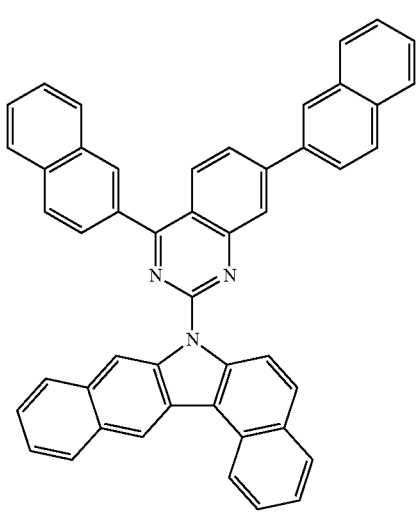

539
-continued
796
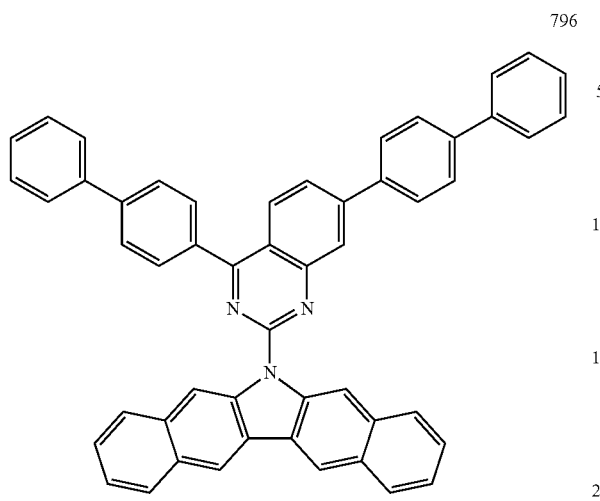
799
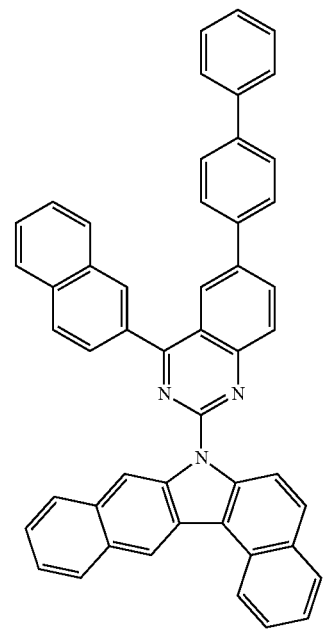
540
-continued
800
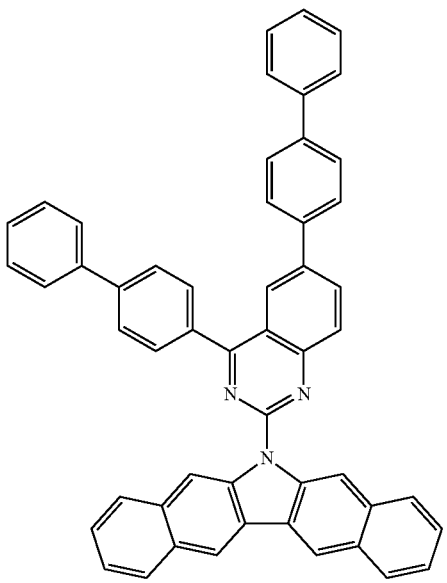
801
802
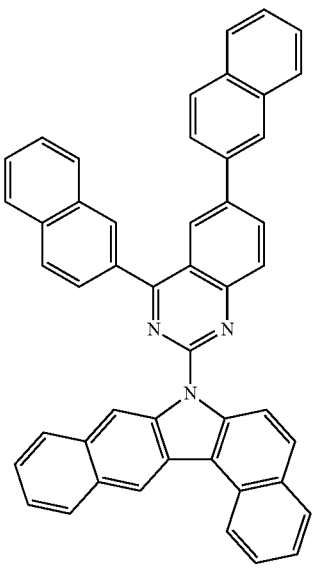

541
-continued
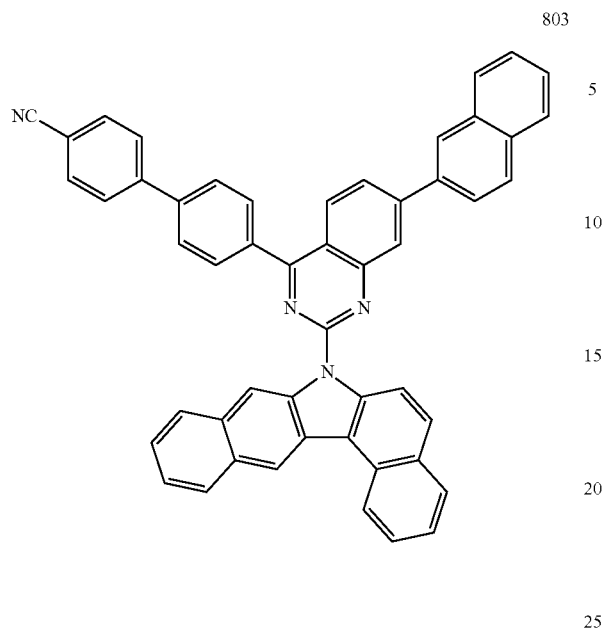
803
542
-continued
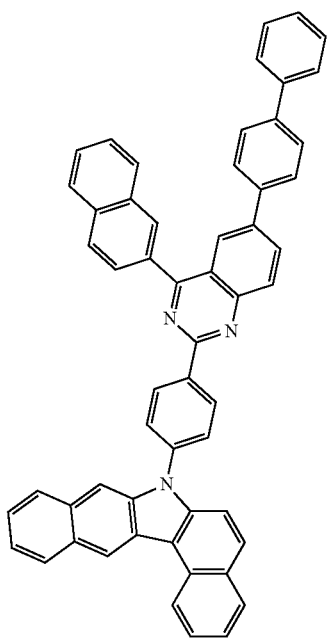
805
804
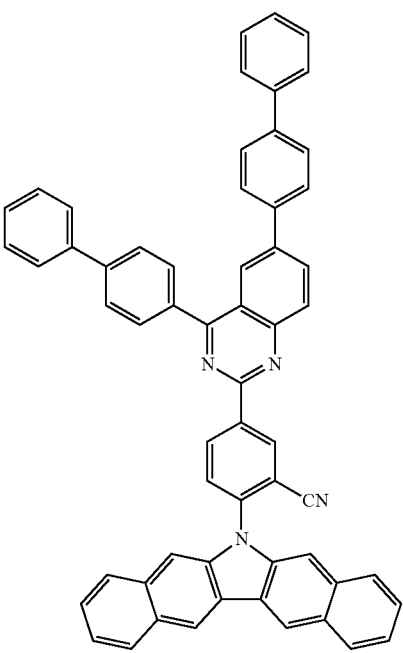
806

543
-continued
807
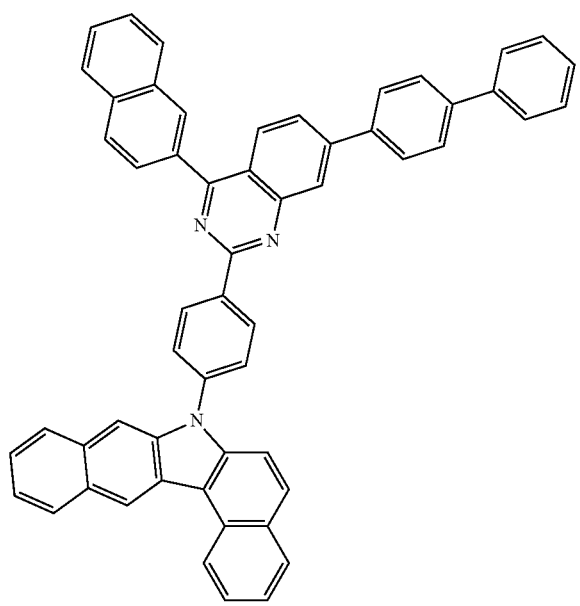
808
544
-continued
809
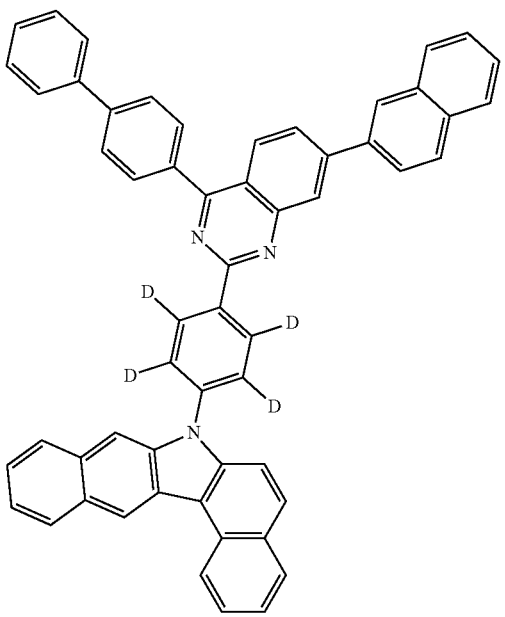
810
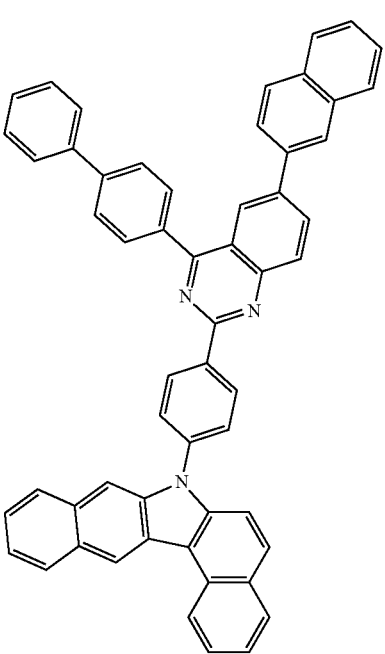

831
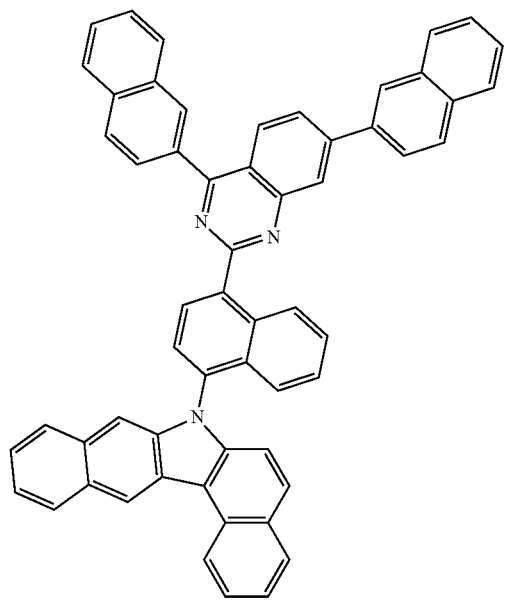
836
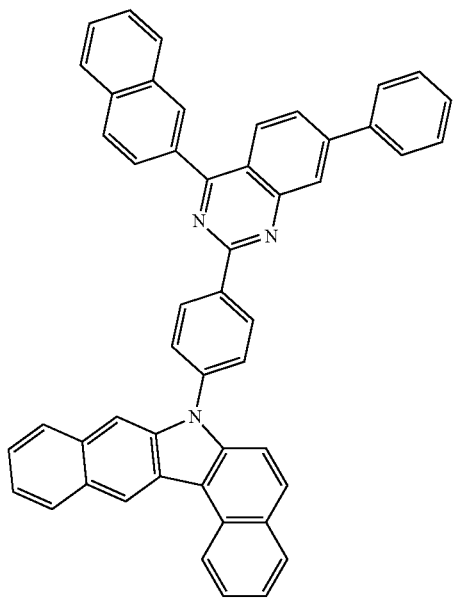
832
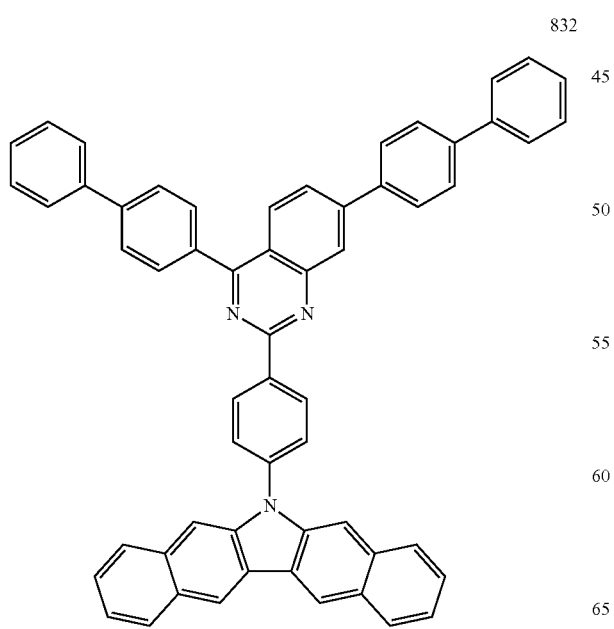
837
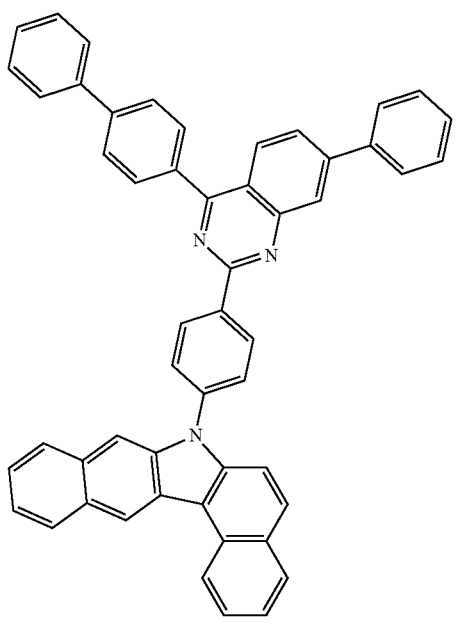

839
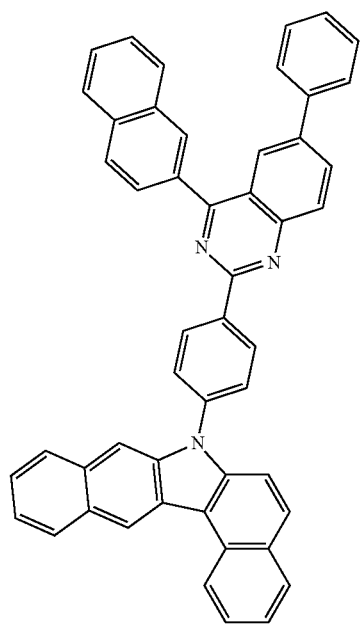
840
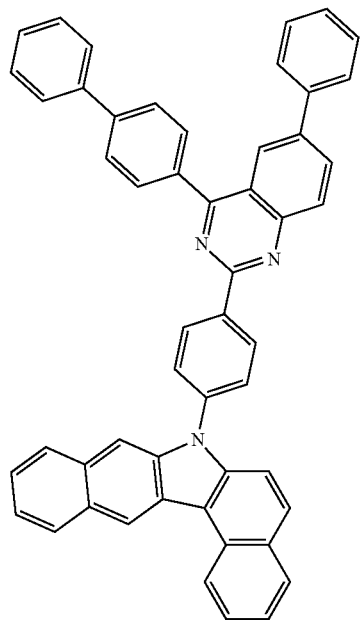
849
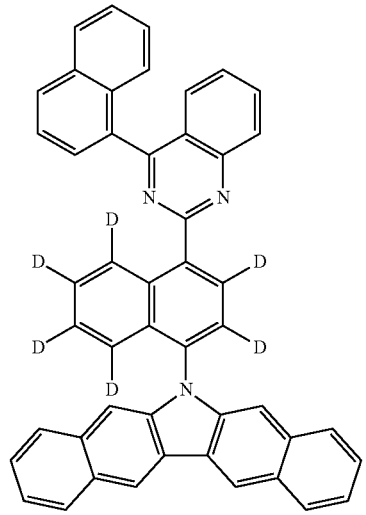
851
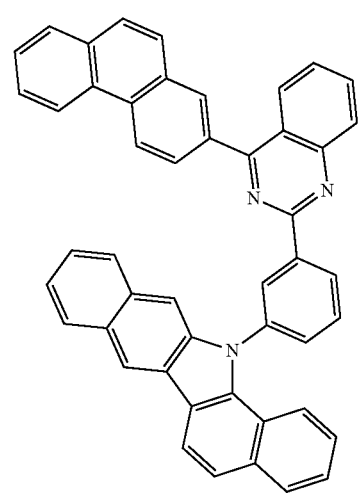
852
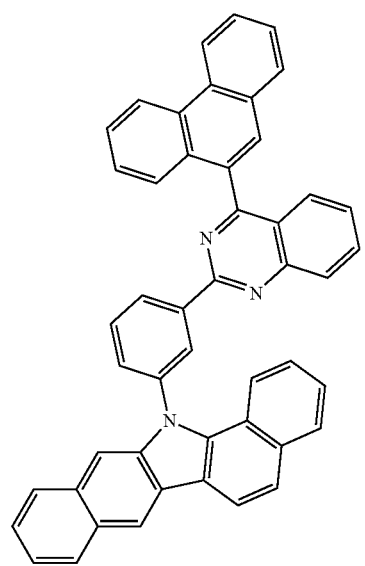

549
-continued
853
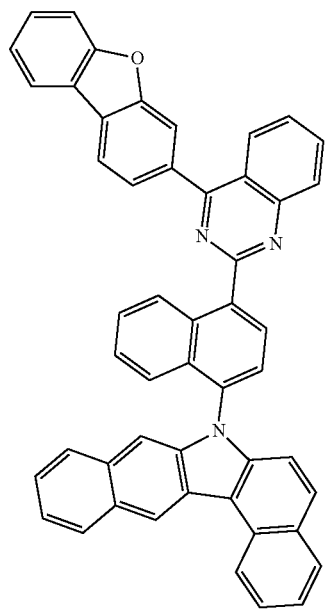
854
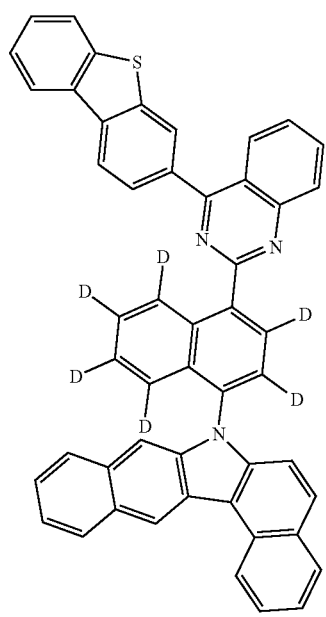
550
-continued
855
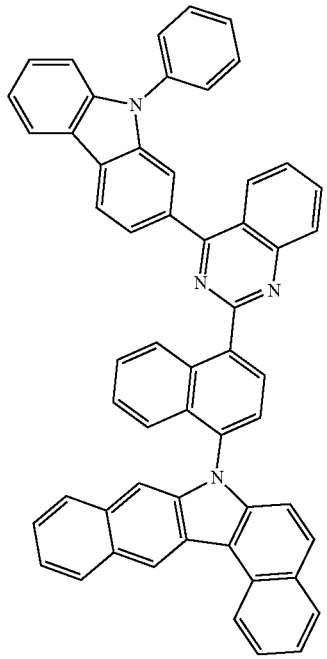
856
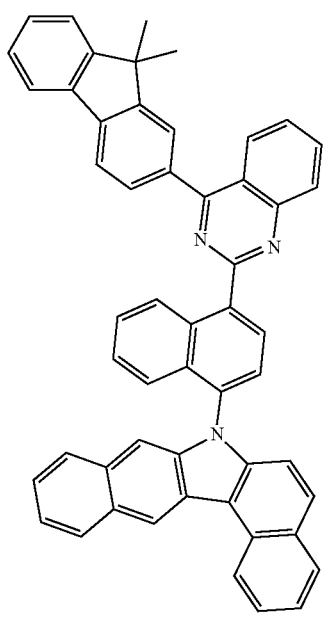

859
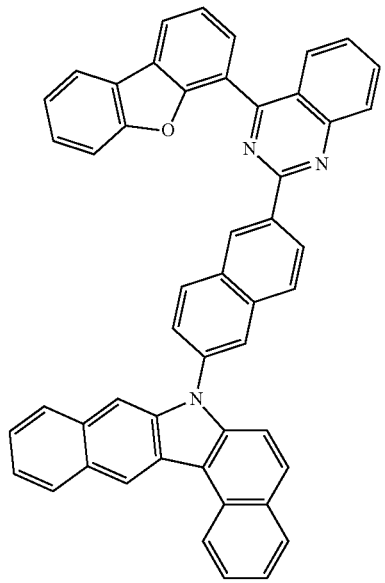
862
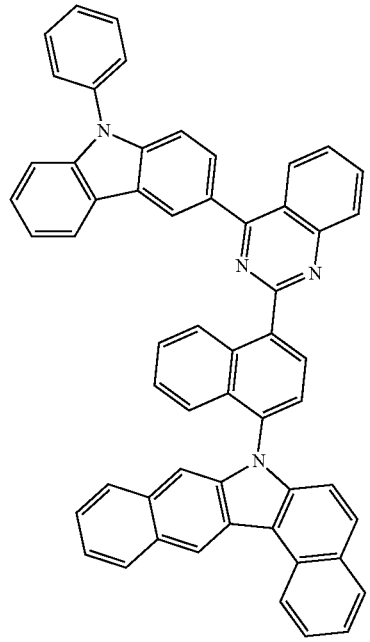
863
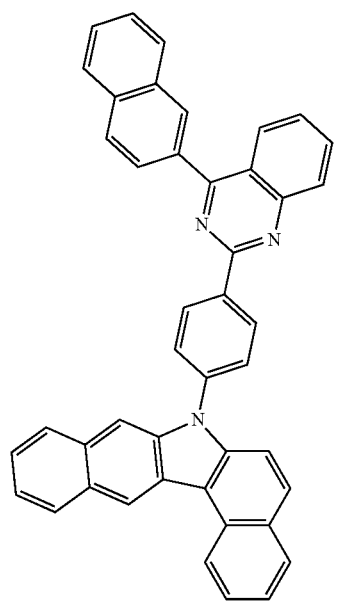
860
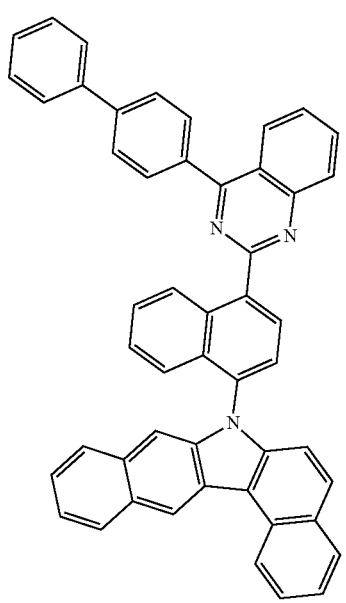
864
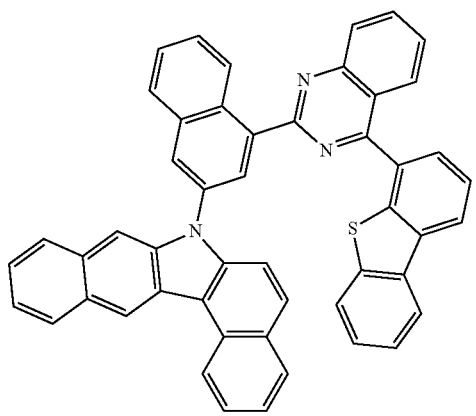

553
-continued
865
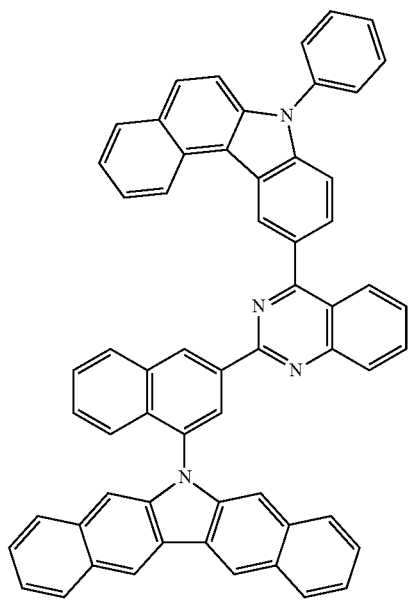
871
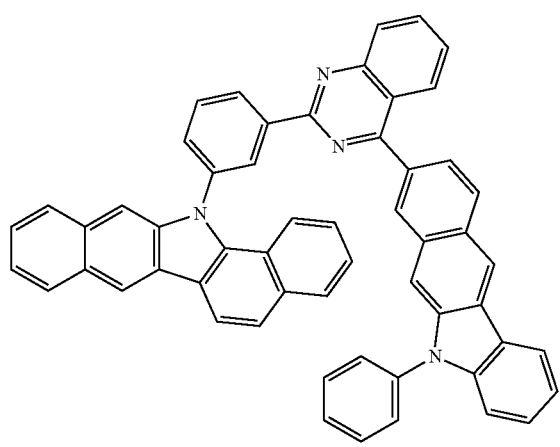
554
-continued
872
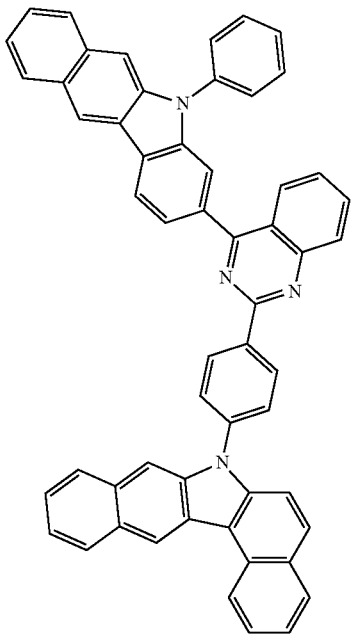
873
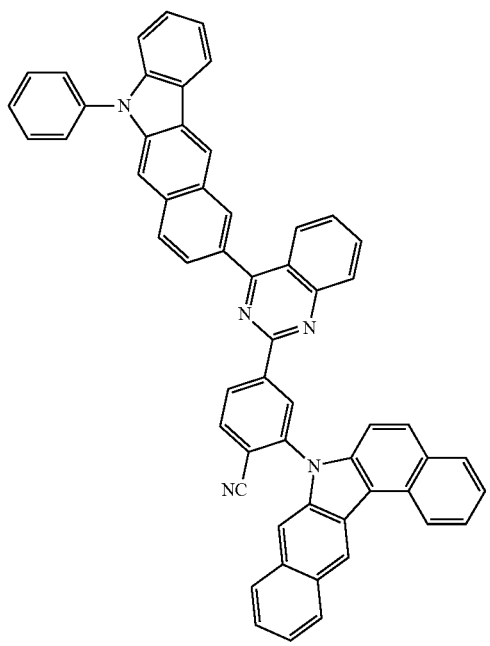

555
-continued
874
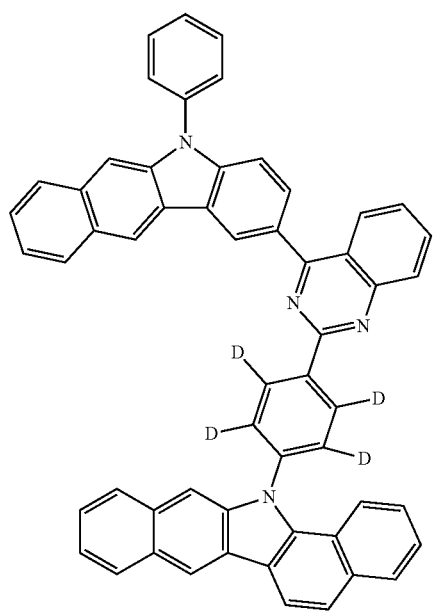
880
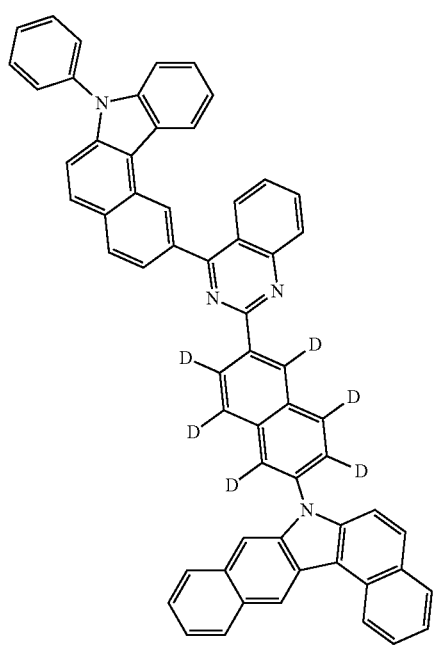
556
-continued
881
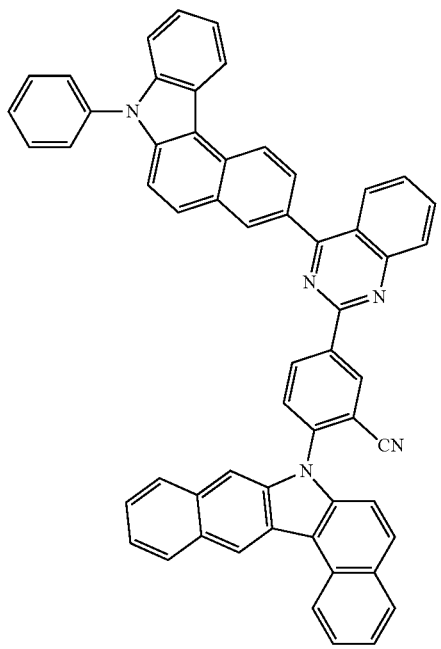
882
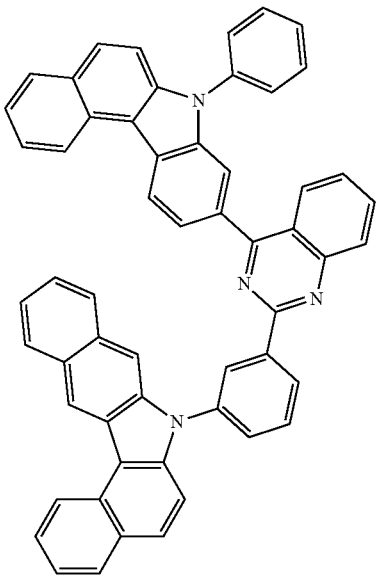

557
-continued
895
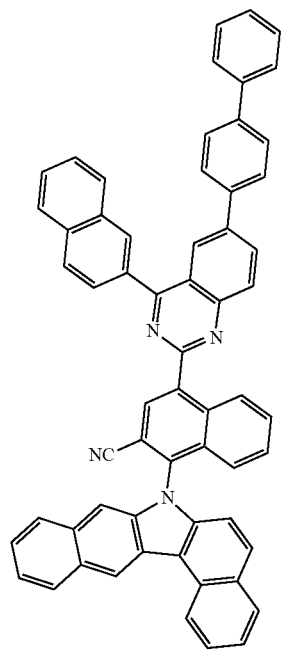
896
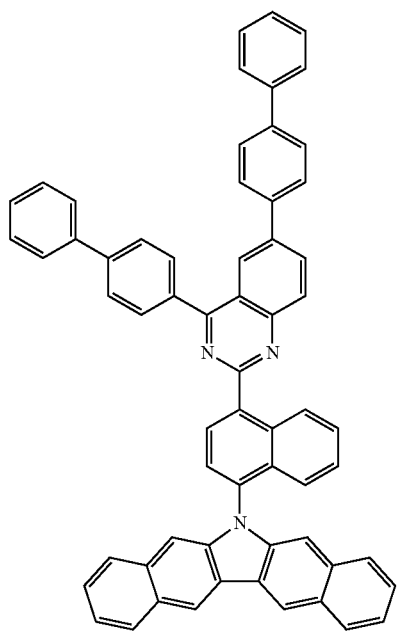
558
-continued
898
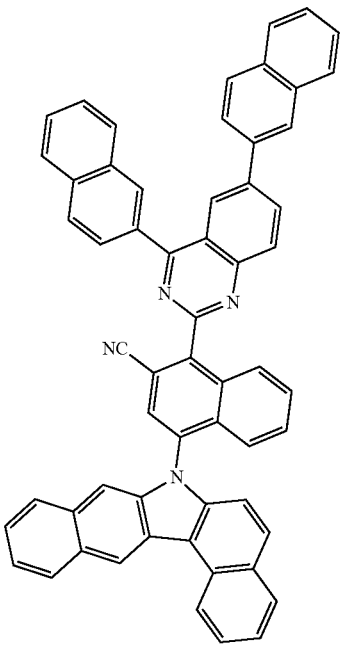
899
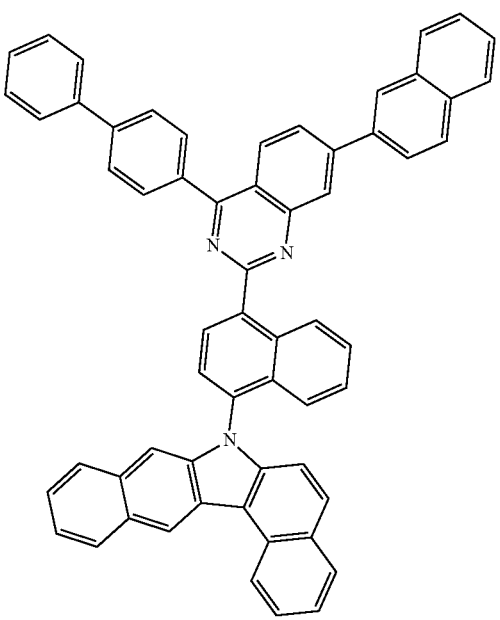

559
-continued
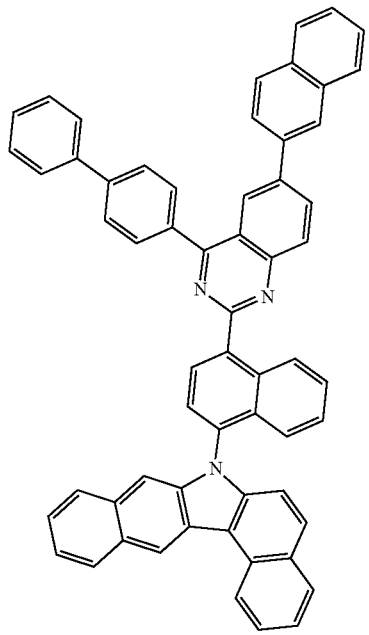
900
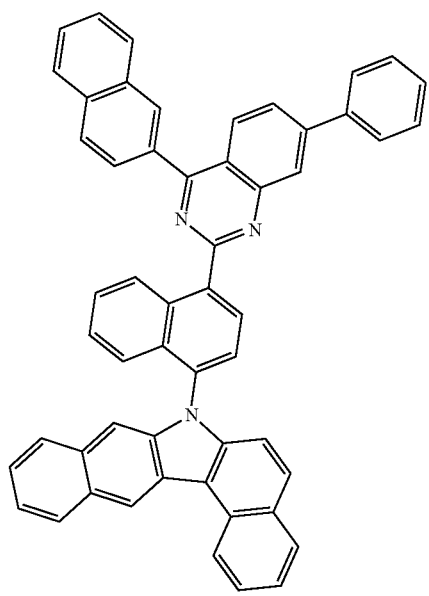
902
560
-continued
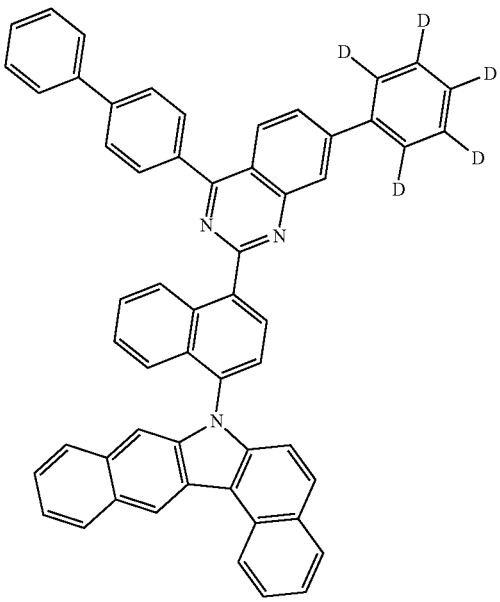
903
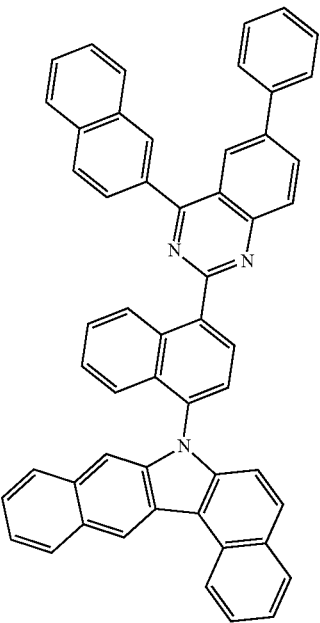
905

561
-continued
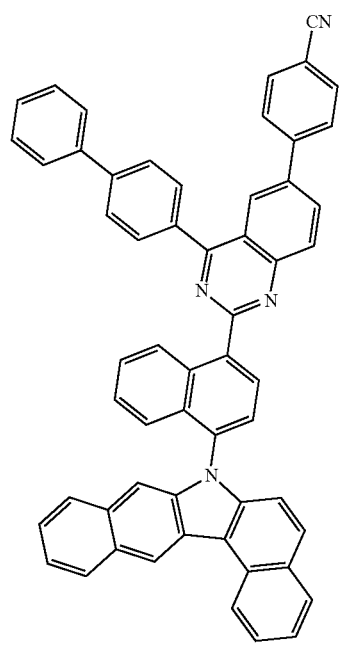
906
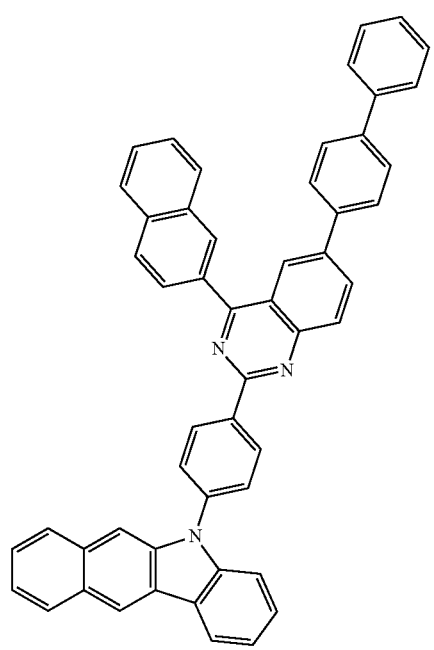
907
562
-continued
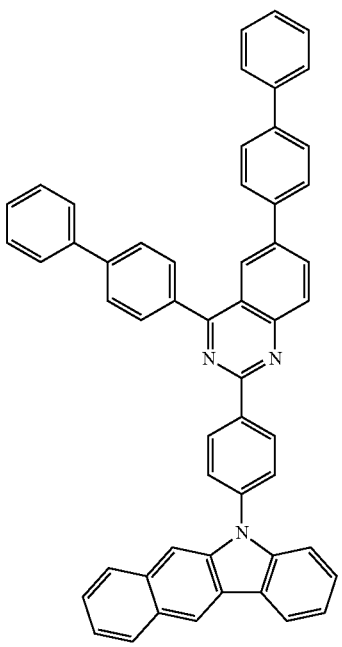
908
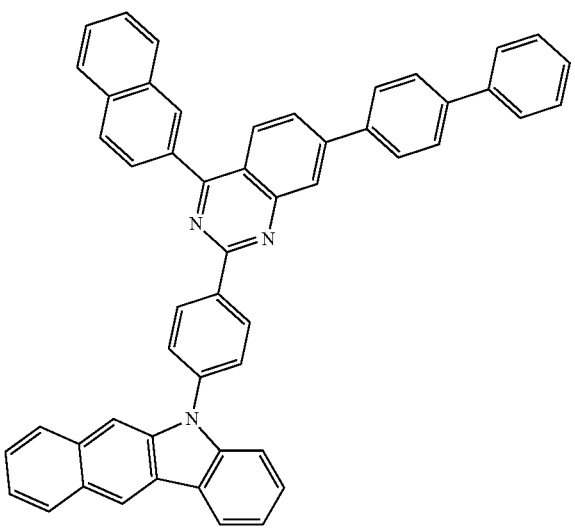
909

563
-continued
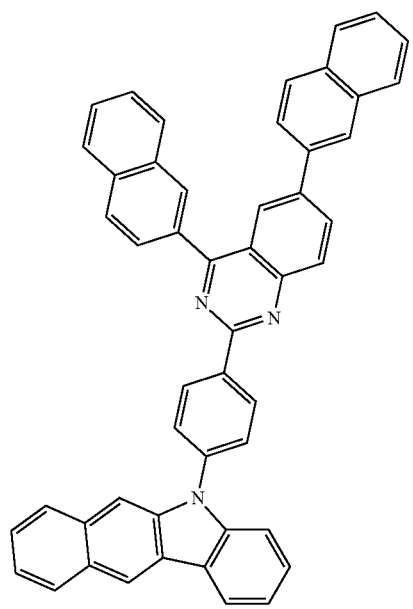
910
564
-continued
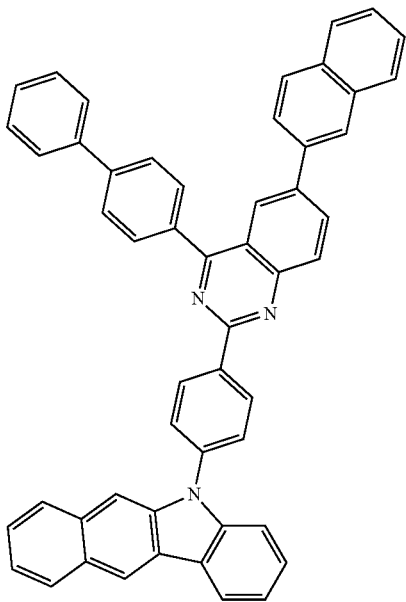
912
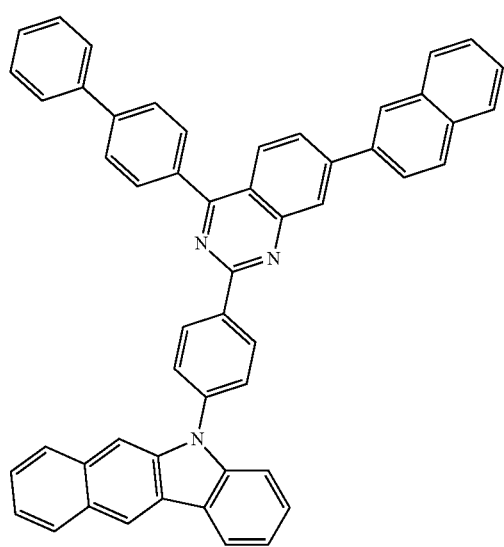
911
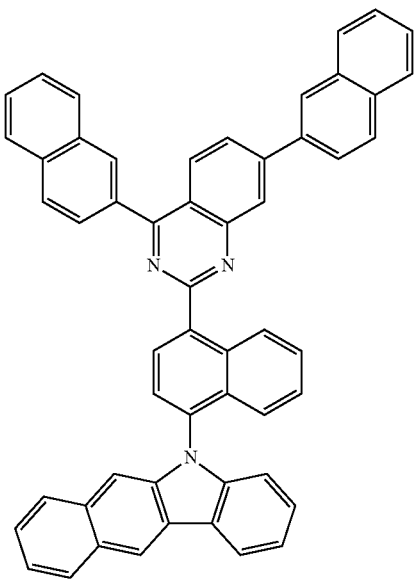
933

565
-continued
566
-continued
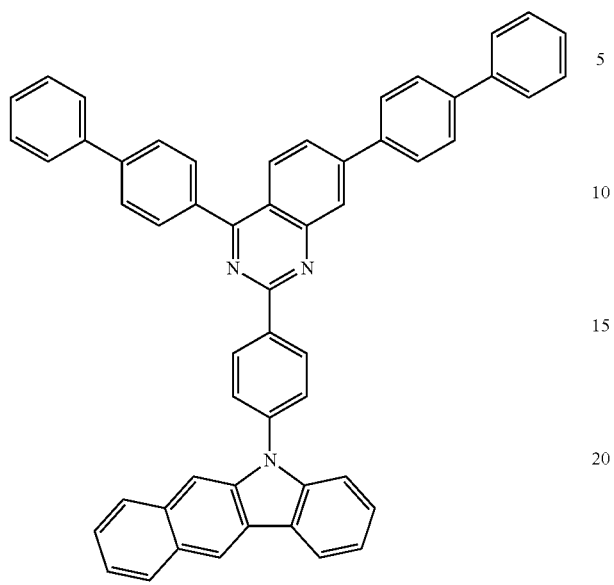
934
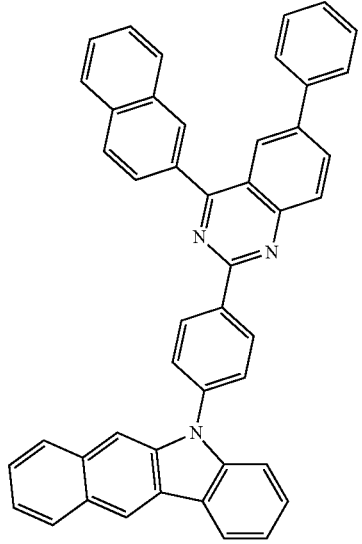
941
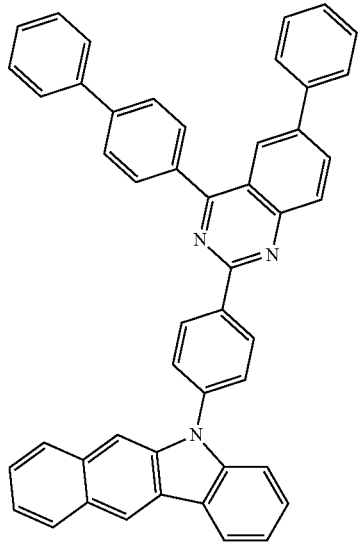
942
938
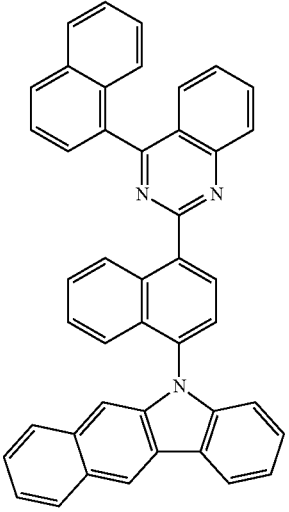
951
939

567
-continued
953
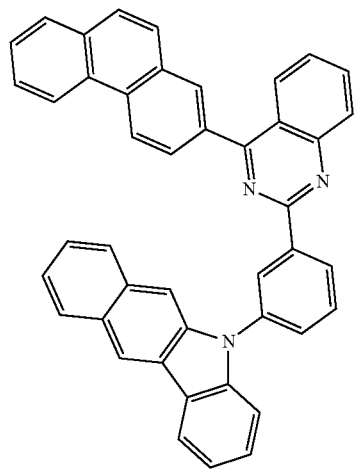
955
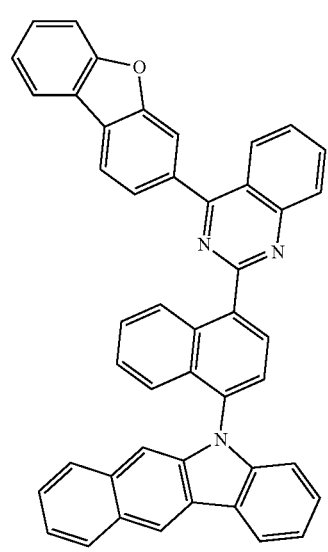
956
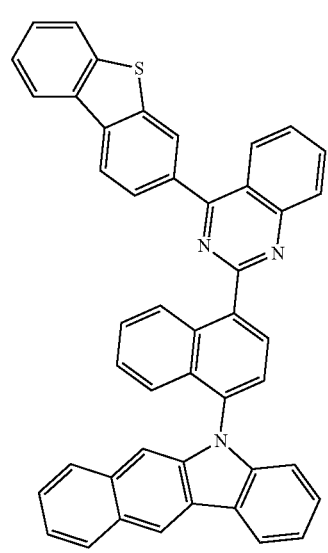
568
-continued
957
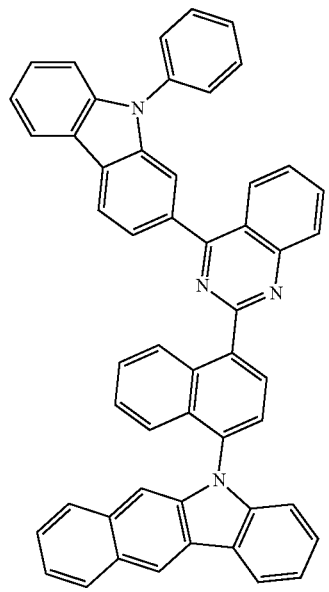
958
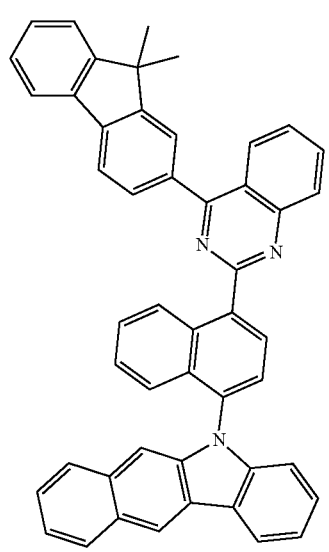
961
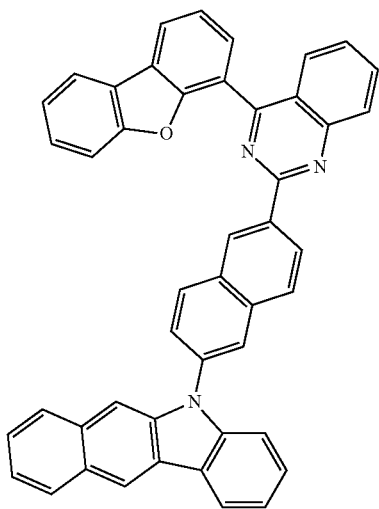

569
-continued
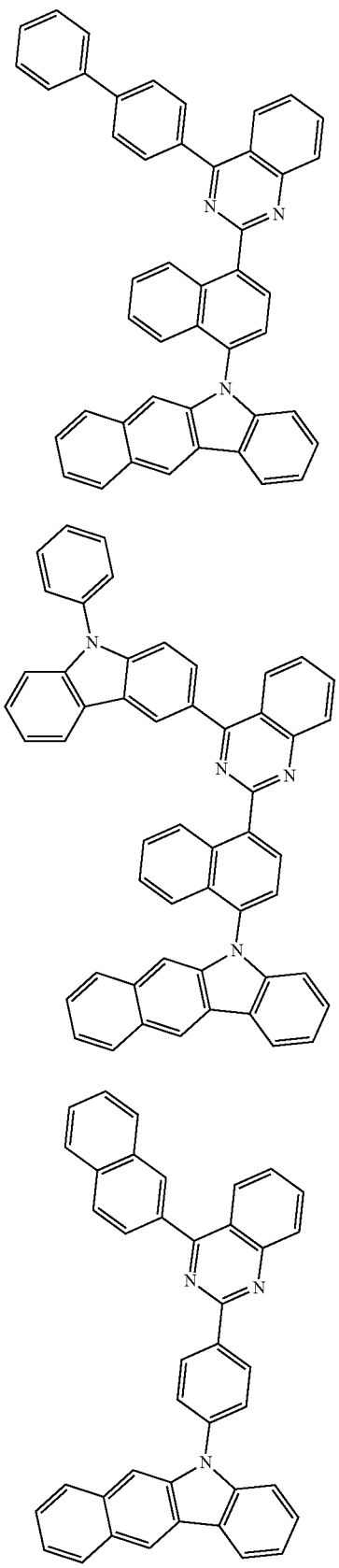
570
-continued
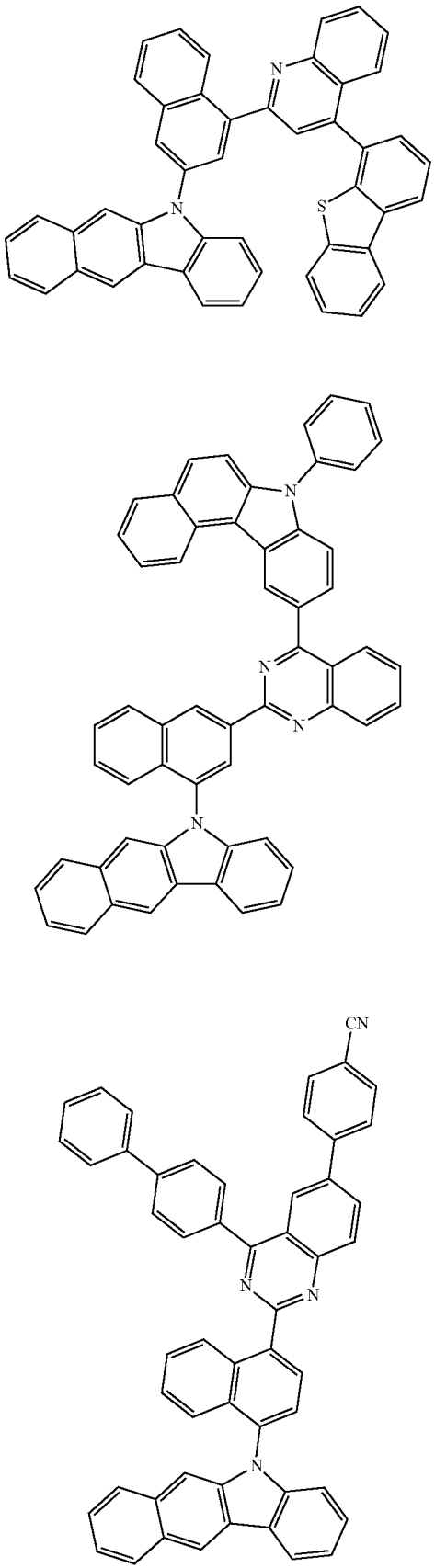

571
-continued
983
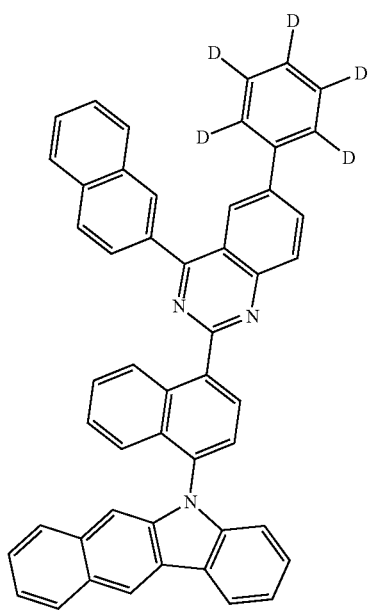
984
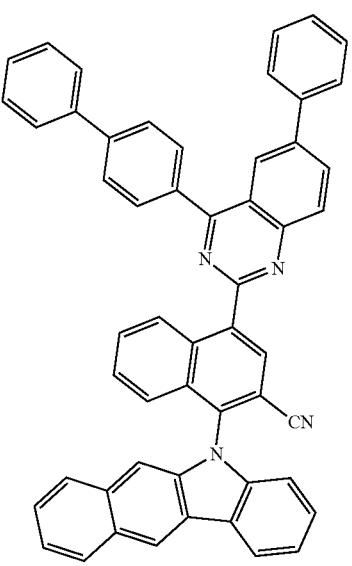
572
-continued
988
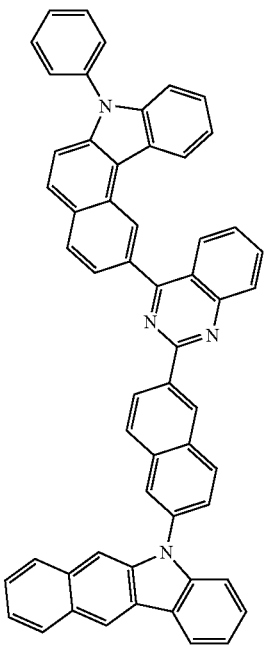
989
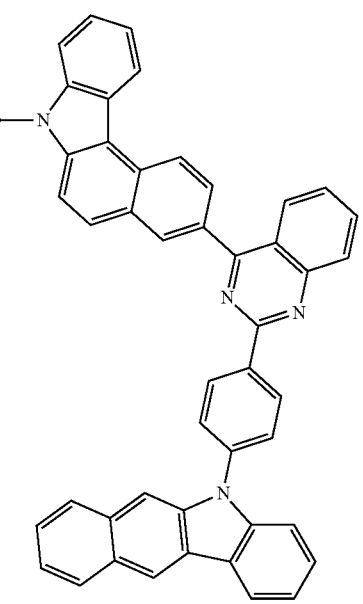

573
-continued
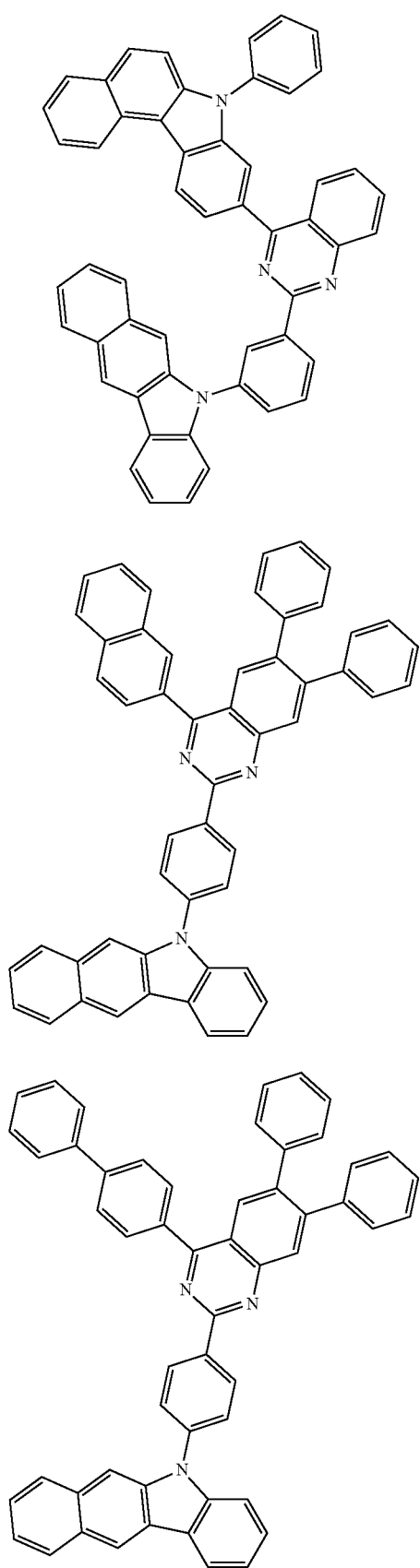
574
-continued
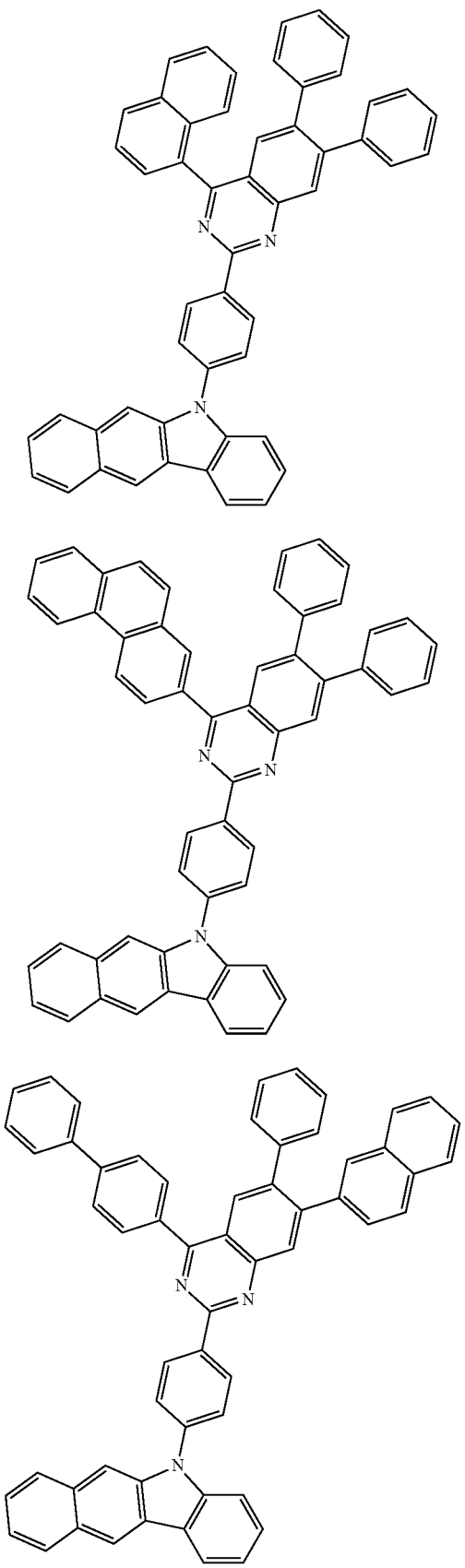

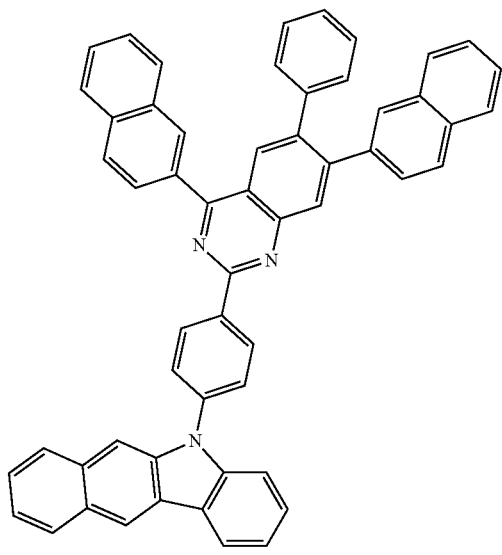
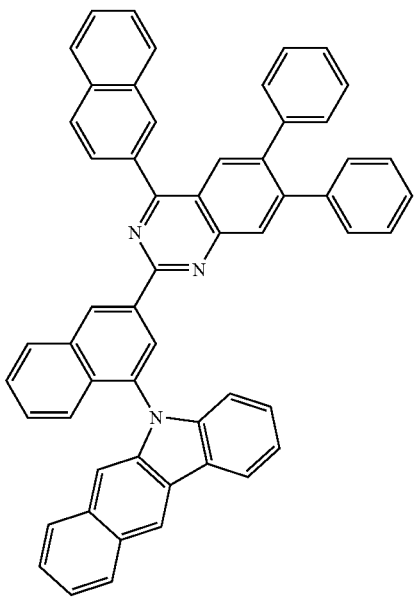

577
-continued
1009
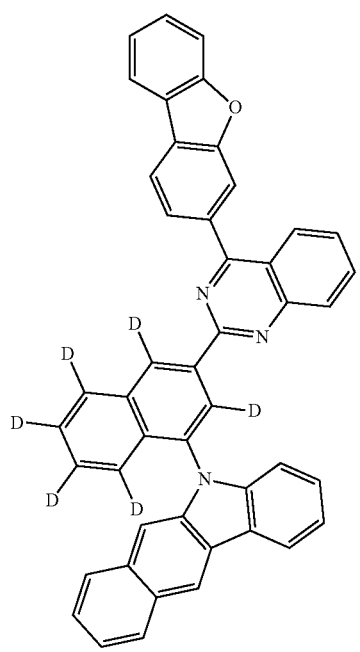
1010
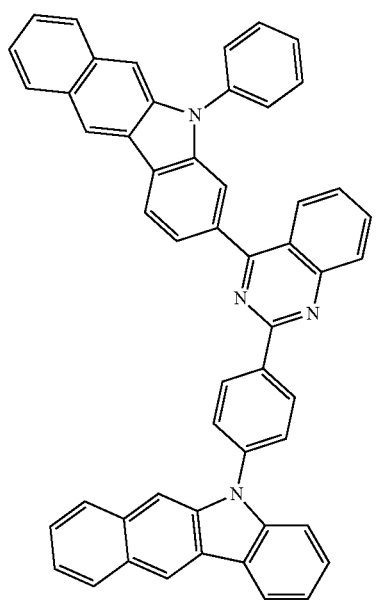
578
-continued
1011
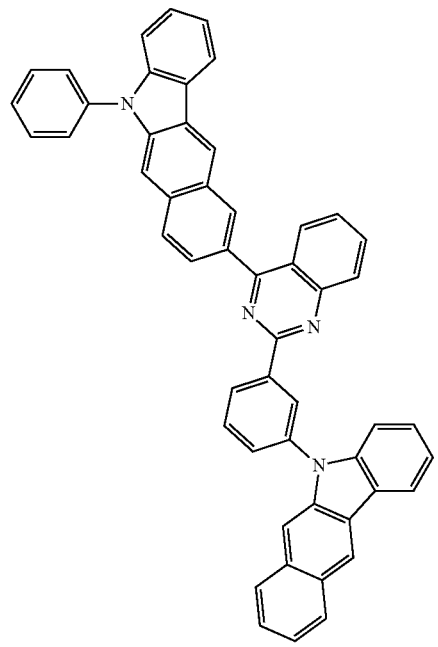
1012
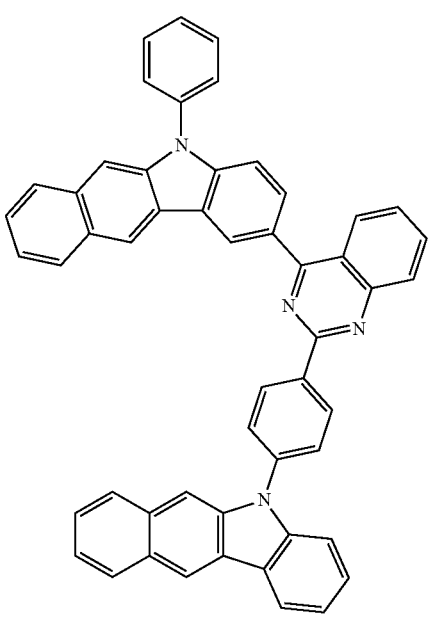

1023
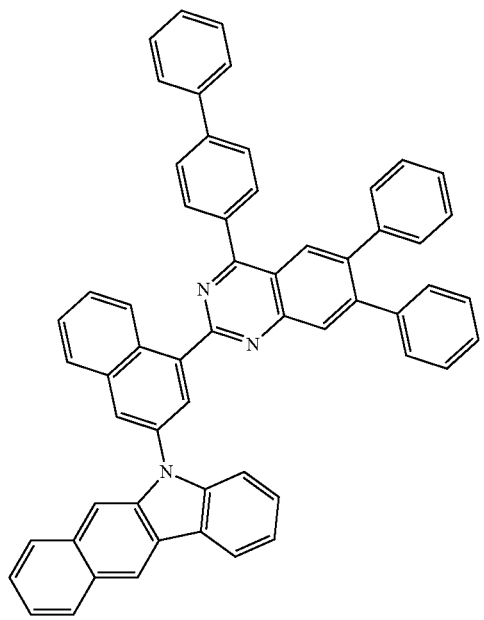
1024
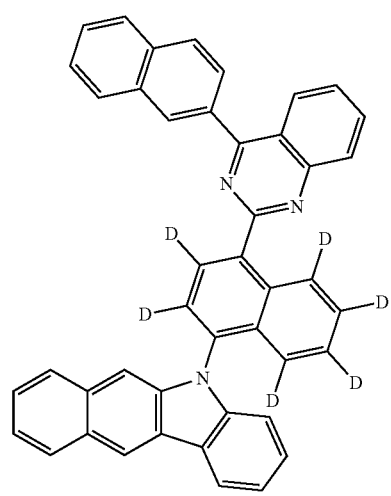
1025
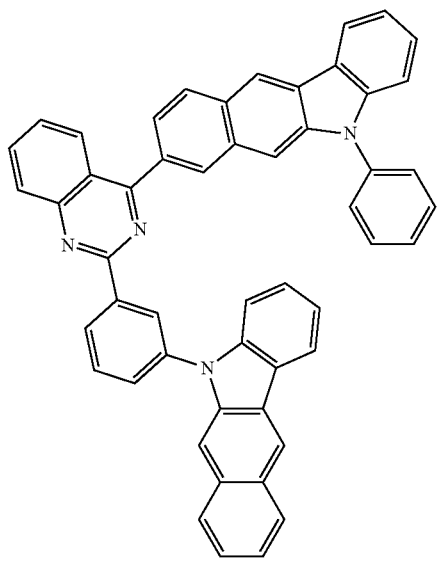
1028
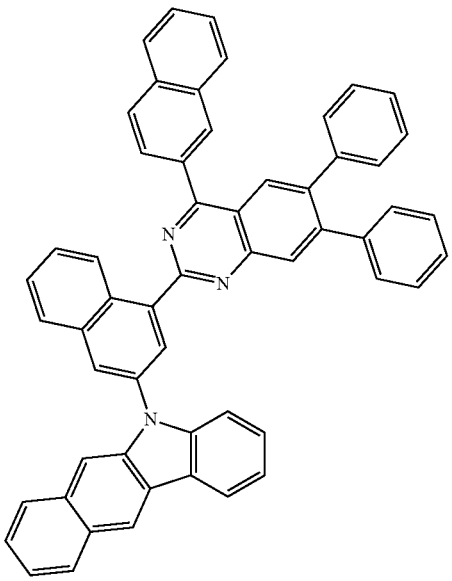

-continued
1029
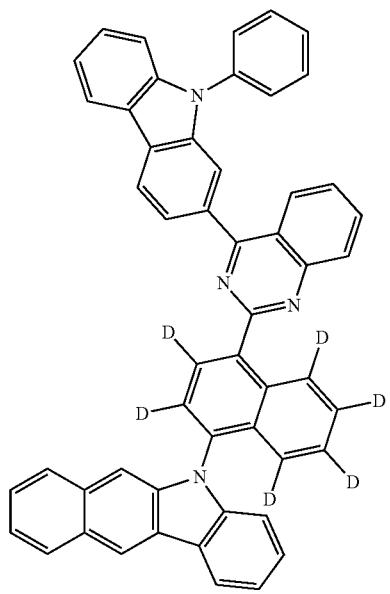
1031
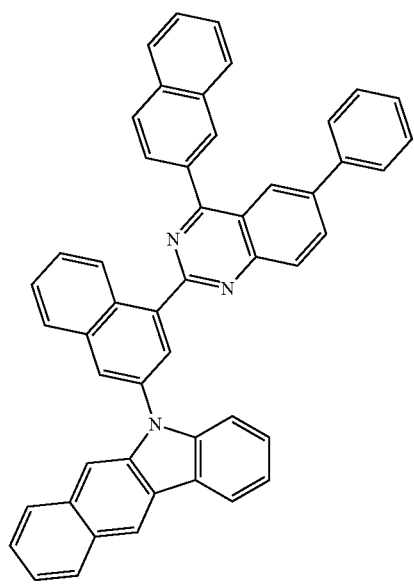
1034
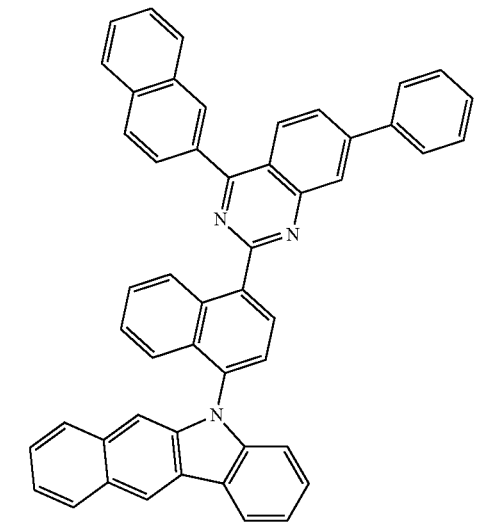
1035
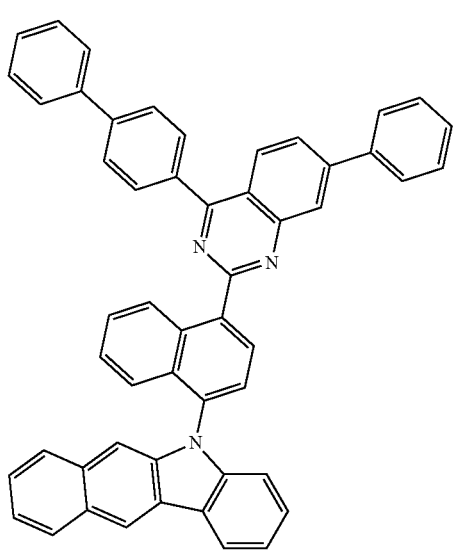
1037
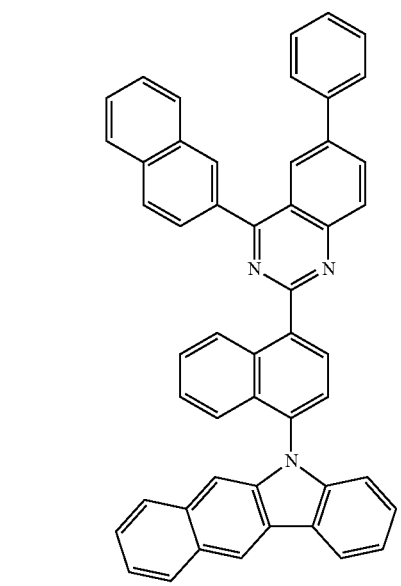

1038
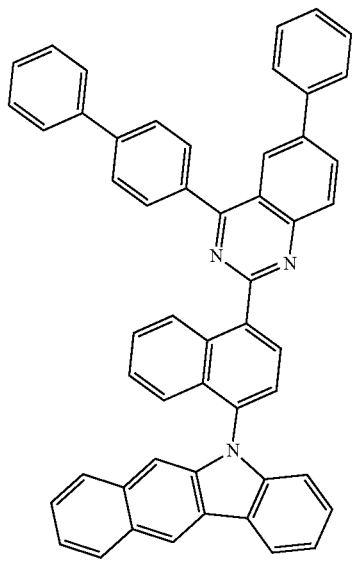
1048
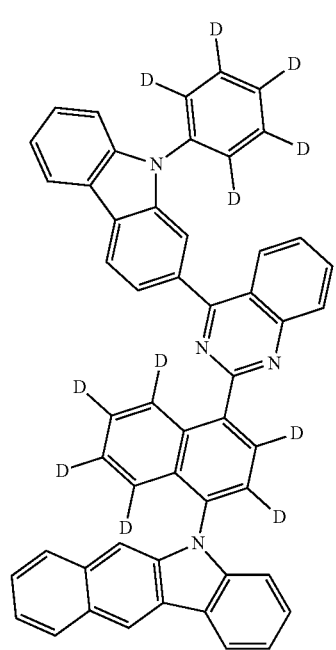
1051
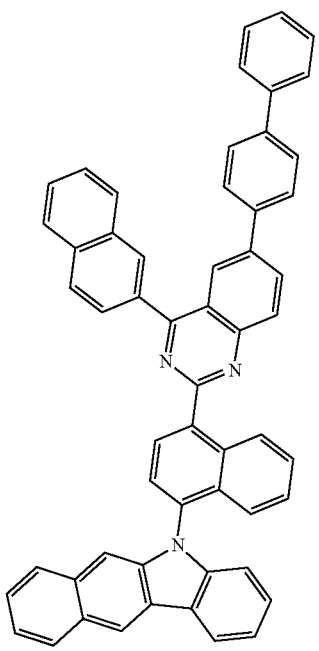
1052
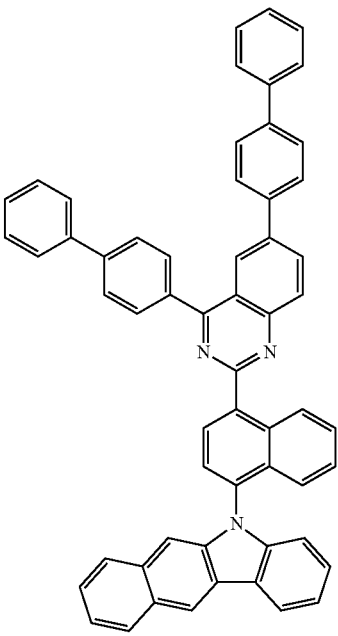

585
-continued
1053
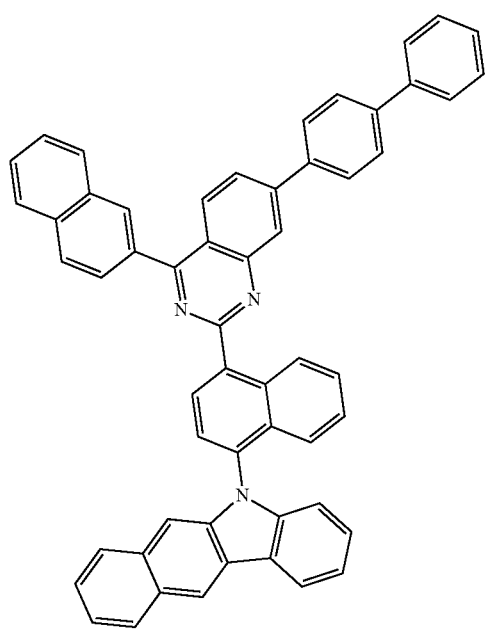
1054
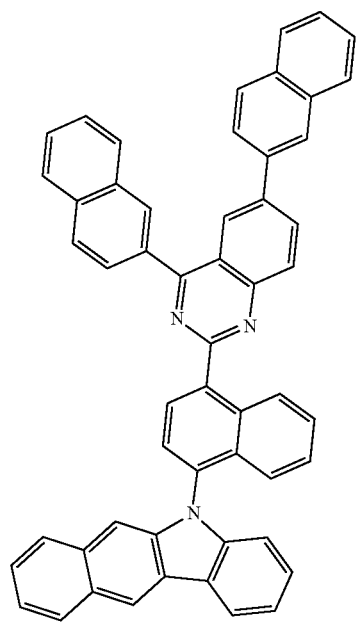
586
-continued
1055
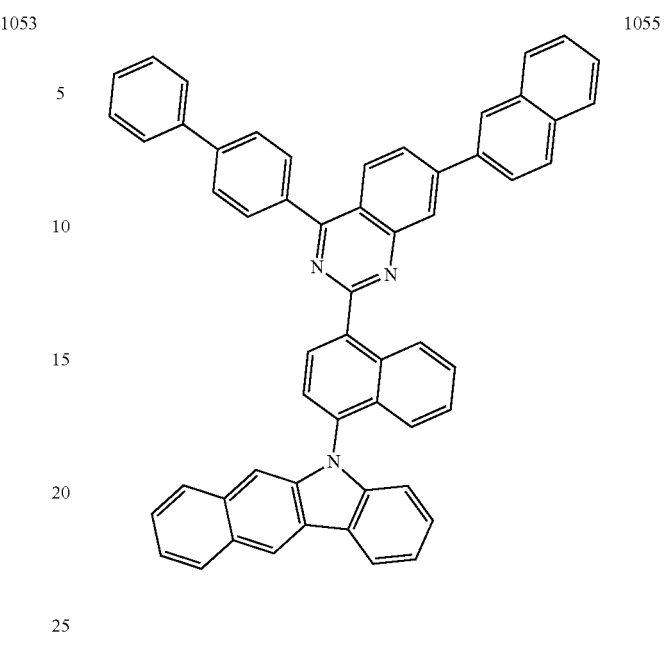
1056
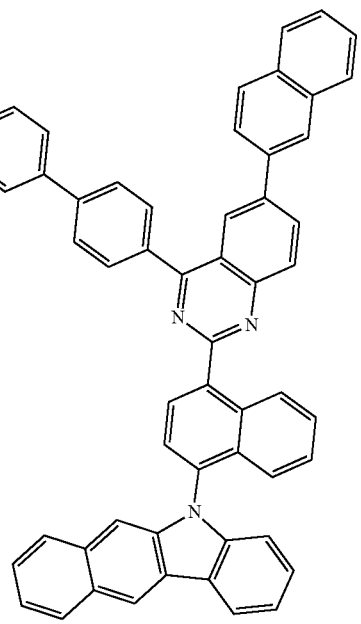

587
-continued
1059
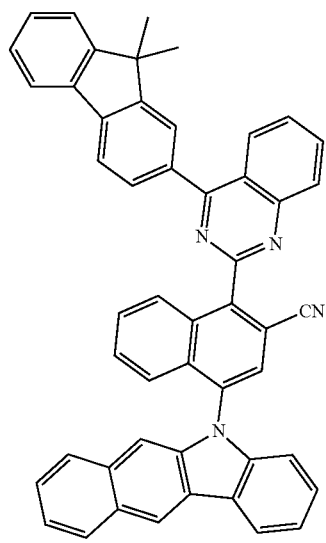
588
-continued
1063
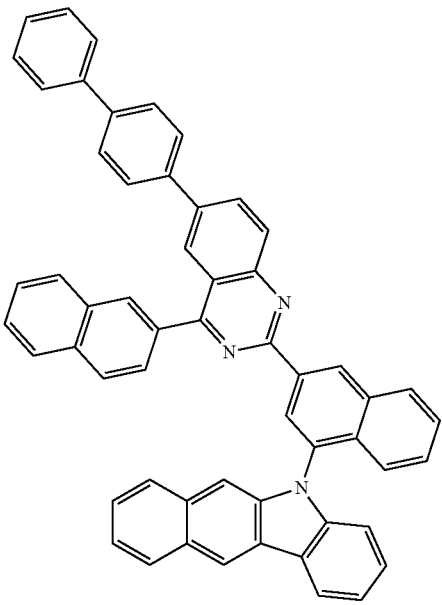
1061
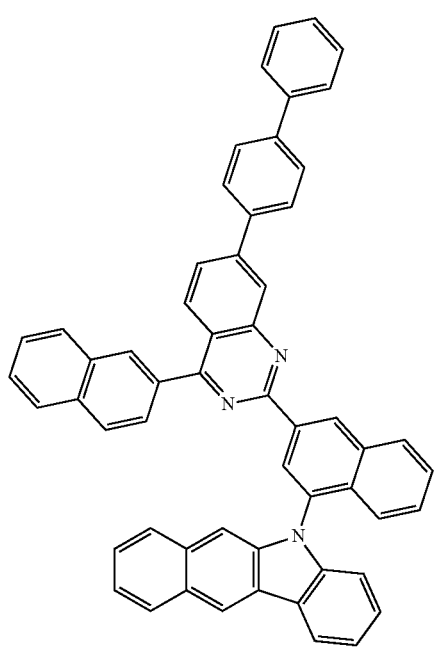
1065

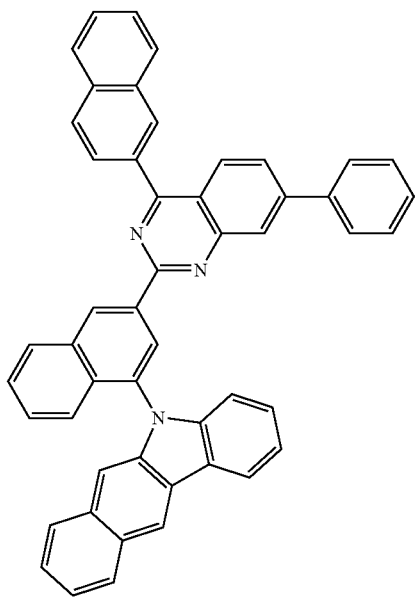
1066

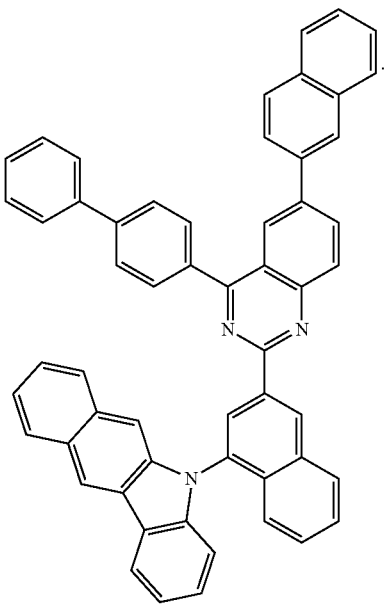
1068

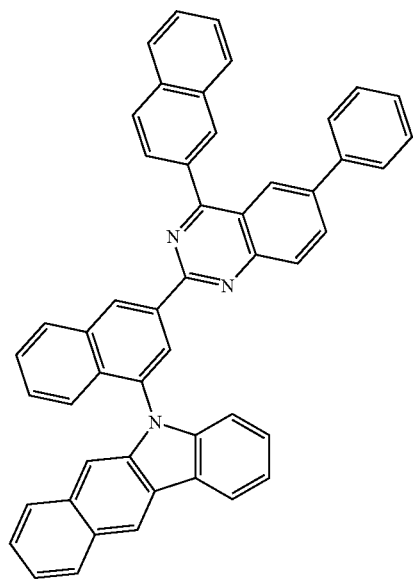
1067

4. An organic light emitting device comprising:
a first electrode;
a second electrode provided opposite to the first electrode; and
one or more organic material layers provided between the first electrode and the second electrode,
wherein one or more layers of the one or more organic material layers comprise the benzocarbazole-based compound of claim 1.

5. The organic light emitting device of claim 4, wherein the one or more organic material layers comprise a hole injection layer or a hole transfer layer, and the hole injection layer or the hole transfer layer comprises the benzocarbazole-based compound.

6. The organic light emitting device of claim 4, wherein the one or more organic material layers comprise an electron transfer layer or an electron injection layer, and the electron transfer layer or the electron injection layer comprises the benzocarbazole-based compound.

7. The organic light emitting device of claim 4, wherein the one or more organic material layers comprise a light emitting layer, and the light emitting layer comprises the benzocarbazole-based compound.

* * * * *